United States Patent
Butler et al.

(10) Patent No.: US 11,643,412 B2
(45) Date of Patent: May 9, 2023

(54) MELANOCORTIN 4 RECEPTOR ANTAGONISTS AND USES THEREOF

(71) Applicant: Pfizer Inc., New York, NY (US)

(72) Inventors: Christopher Ryan Butler, Canton, MA (US); Michelle Renee Garnsey, Medford, MA (US); Kevin Alexander Ogilvie, Gales Ferry, CT (US); Jana Polivkova, Mystic, CT (US); Matthew Forrest Sammons, Quincy, MA (US); Aaron Christopher Smith, North Providence, RI (US); Qingyi Yang, Lexington, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/341,877

(22) Filed: Jun. 8, 2021

(65) Prior Publication Data
US 2023/0019853 A1  Jan. 19, 2023

Related U.S. Application Data

(60) Provisional application No. 63/036,798, filed on Jun. 9, 2020, provisional application No. 63/167,271, filed on Mar. 29, 2021.

(51) Int. Cl.
| | | |
|---|---|---|
| *C07D 471/20* | (2006.01) | |
| *C07D 519/00* | (2006.01) | |
| *A61K 31/438* | (2006.01) | |
| *A61P 1/08* | (2006.01) | |
| *A61P 3/04* | (2006.01) | |
| *A61P 19/00* | (2006.01) | |
| *A61P 21/00* | (2006.01) | |
| *A61P 29/00* | (2006.01) | |

(52) U.S. Cl.
CPC ......... *C07D 471/20* (2013.01); *C07D 519/00* (2013.01); *C07B 2200/13* (2013.01)

(58) Field of Classification Search
CPC .. C07D 471/20; C07D 519/00; A61K 31/438; A61P 1/08; A61P 3/04; A61P 19/00; A61P 21/00; A61P 29/00
See application file for complete search history.

(56) References Cited

U.S. PATENT DOCUMENTS

| | | | |
|---|---|---|---|
| 2016/0304456 A1 | 10/2016 | Ng et al. | |
| 2016/0304462 A1 | 10/2016 | Ng et al. | |

FOREIGN PATENT DOCUMENTS

| | | |
|---|---|---|
| EP | 2003131 | 12/2008 |
| WO | 2007/041052 | 4/2007 |

OTHER PUBLICATIONS

Foster et al., "Melanocortin-4 receptor antagonists as potential therapeutics in the treatment of cachexia", Current Topics in Medicinal Chemistry, vol. 7(11), pp. 1131-1136 (2007).
PCT/IB2021/054970 International Search Report and Written Opinion of the International Searching Authority dated Aug. 9, 2021.

*Primary Examiner* — Bruck Kifle

(57) ABSTRACT

Described herein are compounds of Formula I:

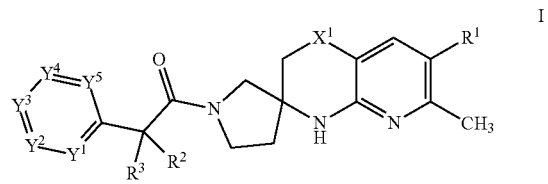

and their pharmaceutically acceptable salts, wherein $R^1$, $R^2$, $R^3$, $X^1$, $Y^1$, $Y^2$, $Y^3$, $Y^4$ and $Y^5$ are defined herein; their use as MC4R antagonists; pharmaceutical compositions containing such compounds and salts; the use of such compounds and salts to treat, for example, cachexia, anorexia, or anorexia nervosa; and intermediates and processes for preparing such compounds and salts.

20 Claims, 6 Drawing Sheets

MELANOCORTIN 4 RECEPTOR ANTAGONISTS AND USES THEREOF

This application claims the benefit of priority to U.S. Provisional Patent Application Ser. No. 63/036,798 filed Jun. 9, 2020 and to U.S. Provisional Patent Application Ser. No. 63/167,271 filed Mar. 29, 2021, the disclosure of each of which is hereby incorporated by reference in its entirety.

FIELD OF THE INVENTION

The present invention relates to new pharmaceutical compounds, pharmaceutical compositions containing the compounds, and use of the compounds as melanocortin receptor 4 (MC4R) antagonists.

BACKGROUND OF THE INVENTION

Melanocortins are peptides derived from pro-opiomelanocortins (POMC) that bind to and activate G-protein coupled receptors (GPCR's) of the melanocortin receptor family.

Melanocortins regulate a diverse number of physiological processes including sexual function and sexual behaviour, food intake and metabolism. To date, five melanocortin receptors (MCRs) have been identified in mammals, MC1R, MC2R, MC3R, MC4R, and MC5R, which are expressed in various tissues. MC1R is specifically expressed in melanocytes and melanoma cells, MC2R is the ACTH receptor and is expressed in adrenal tissue, MC3R is predominantly expressed in the brain and limbic system, MC4R is widely expressed in the brain and spinal cord, and MC5R is expressed in the brain and many peripheral tissues including skin, adipose tissue, skeletal muscle, and lymphoid tissue. See e.g., U.S. Pat. No. 8,138,188 and Saleh et al., *Front. Pharmacol.*, 2018, 9:560.

MC4R is a G-protein-coupled seven-transmembrane receptor primarily expressed in the hypothalamus, hippocampus, and thalamus (Gantz et al. 1993 *J. Biol. Chem.* 268:15174-15179). The receptor is implicated in the central regulation of body weight: MC4R is activated by α-melanocyte-stimulating hormone (MSH), which is derived from pro-opiomelanocortin and is inactivated by agouti gene-related protein (AGRP). α-MSH induces weight loss, whereas the ectopic expression of agouti protein results in obesity in the agouti mice (Fan et al. 1993 *Nature* 385:165-168; Lu et al. 1994 *Nature* 371:799-802). Additional evidence for the role of MC4R in weight regulation stems from both a knockout model in mice (Huszar et al. 1997 Cell 88:131-141) and haploinsufficiency mutations in humans (Vaisse et al. 1998 *Nat. Genet.* 20:113-114; Yeo et al. 1998 *Nat. Genet.* 20:111-112; Hinney et al. 1999 *J. Clin. Endocrinol. Metab.* 84:1483-1486). In MC4R-knockout mice, an increased body weight was discernible by age 5 wk. By age 15 wk, homozygous mutant females were, on average, twice as heavy as their wild-type littermates, whereas homozygous mutant males were ~50% heavier than wild-type controls. Mice heterozygous for the MC4R knockout showed a weight gain intermediate to that seen in wild-type and homozygous mutant littermates, thus demonstrating a gene dosage effect of MC4R ablation on body-weight regulation. The food intake of homozygous mutants was increased by ~50% in comparison to that in wild-type sibs (Huszar et al. 1997 Cell 88:131-141). [From *Am. J. Hum. Genet.*, 65:1501-1507,1999]. MC4R activation has been shown to induce penile erection in rodents and MC4R inactivation has been shown to cause obesity (reviewed in Hadley, 1999, *Ann. NY Acad. Sci.*, 885:1-21; Wikberg et al. 2000, *Pharmacol. Res.*, 42(5), 393-420; and Saleh et al., *Front. Pharmacol.*, 2018, 9:560).

In recent years, several kinds of small-molecule MC4R antagonists have been reported in the literature and patent applications [see e.g., WO2010052256; WO2010081666; U.S. Pat. No. 8,044,068; Chaki et al., *Current Topics in Medicinal Chemistry*, 2007, 7, 1145-1151; Foster et al., *Current Topics in Medicinal Chemistry*, 2007, 7, 1131-1136; Pontillo et al., *Bioorganic & Medicinal Chemistry Letters* 15 (2005) 2541-46; Vos et al., *Bioorganic & Medicinal Chemistry Letters* 16(2006) 2302-2305; Tao, *Endocrine Reviews*, 2010, 31(4):506-543; and Saleh et al., *Front. Pharmacol.*, 2018, 9: 560]. These MC4R antagonists are useful for treating and/or preventing MC4R-related conditions, diseases, or disorders, for example, cachexia [including for example, cachexia associated with a chronic illness, such as cachexia associated with cancer, cachexia associated with acquired immunodeficiency syndrome (AIDS), cachexia associated with heart failure for example cachexia associated with congestive heart failure (CHF), cachexia associated with chronic kidney disease (CKD); cachexia associated with treatment of a chronic illness, such as, cachexia associated with treatment of cancer or cachexia associated with treatment of heart failure (e.g. CHF)]; anorexia or anorexia nervosa (e.g., geriatric anorexia, anorexia associated with chemotherapy and/or radiotherapy); nausea; emesis; weight loss (e.g., involuntary weight loss); failure to thrive; sarcopenia; muscle wasting; muscle weakness; frailty; osteoporosis; bone disorders (e.g., bone loss); pain; neuropathic pain; anxiety (e.g., posttraumatic stress disorder, or PTSD); depression; hypertension; malnutrition; obesity (e.g. sarcopenia resulting from chronic obesity); sexual dysfunction; and inflammatory disease (e.g. an inflammatory disease associated with anorexia or cachexia or sarcopenia or muscle wasting).

There continues to be a need for alternative MC4R antagonists, for example, for developing new and/or improved pharmaceuticals (e.g., more effective, more selective, less toxic, and/or having improved biopharmaceutical properties such as physical stability; solubility; oral bioavailability; appropriate metabolic stability; clearance; half life) to treat or prevent MC4R-related conditions, diseases, or disorders, such as those described herein. The present invention is directed to these and other important ends.

SUMMARY OF THE INVENTION

In one embodiment (Embodiment A1), the present invention provides a compound of Formula I:

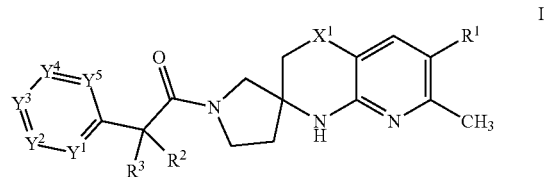

or a pharmaceutically acceptable salt thereof, wherein:
$R^1$ is H, halogen, $C_{1-4}$ alkyl, $C_{1-4}$ haloalkyl, $C_{3-6}$ cycloalkyl, 4- to 7-membered heterocycloalkyl, phenyl, or $R^{1a}$, wherein each of the $C_{3-6}$ cycloalkyl and 4- to 7-membered heterocycloalkyl is optionally substituted with 1, 2, 3, or 4 independently selected $C_{1-4}$ alkyl, and wherein the phenyl is optionally substituted with 1, 2, 3, or 4 independently selected $R^B$, wherein each $R^B$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or $R^{B1}$, or two adjacent $R^B$ together with the two ring-forming atoms of the phenyl to which they are attached form a fused 5- or 6-membered heteroaryl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;

$R^{1a}$ is 5- or 6-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, —N($C_{1-4}$ alkyl)$_2$, $R^A1$, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy; or two adjacent $R^A$ together with the two ring-forming atoms of the 5- or 6-membered heteroaryl to which they are attached form a fused benzene ring or a fused 5- or 6-membered heteroaryl or a fused 5- or 6-membered heterocycloalkyl or a fused 5- or 6-membered cycloalkyl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;

$R^{A1}$ is 5- or 6-membered heteroaryl or 5- or 6-membered heterocycloalkyl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;

$R^{B1}$ is 5- or 6-membered heteroaryl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;

$X^1$ is $C(R^X)_2$, wherein each $R^X$ is independently H or $C_{1-4}$ alkyl;

each of $R^2$ and $R^3$ is independently H, halogen, $C_{1-4}$ alkyl, $C_{1-4}$ hydroxyalkyl, $C_{1-4}$ haloalkyl, ($C_{1-4}$ alkoxy)-$C_{1-4}$ alkyl-, $C_{3-4}$ cycloalkyl, or ($C_{3-4}$ cycloalkyl)-$C_{1-4}$ alkyl, wherein each of $C_{3-4}$ cycloalkyl and ($C_{3-4}$ cycloalkyl)-$C_{1-4}$ alkyl- is optionally substituted with 1, 2, 3, 4, or 5 substituents each independently selected from halogen, —OH, $C_{1-4}$ alkyl, $C_{1-4}$ haloalkyl, $C_{1-4}$ alkoxy, and $C_{1-4}$ haloalkoxy;

or $R^2$ and $R^3$ together with the carbon atom to which they are attached form $C_{3-6}$ cycloalkyl optionally substituted with 1, 2, 3, 4, or 5 substituents each independently selected from halogen, —OH, $C_{1-4}$ alkyl, $C_{1-4}$ haloalkyl, $C_{1-4}$ alkoxy, and $C_{1-4}$ haloalkoxy;

each of $Y^1$, $Y^2$, $Y^3$, $Y^4$, and $Y^5$ is independently $CR^4$ or N, provided that no more than 3 of $Y$, $Y^2$, $Y^3$, $Y^4$, and $Y^5$ are N; and each $R^4$ is independently H, halogen, —OH, —CN, $C_{1-4}$ alkyl, $C_{1-4}$ haloalkyl, $C_{1-4}$ alkoxy, $C_{1-4}$ haloalkoxy, —N($C_{1-2}$ alkyl)$_2$, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

The present invention also provides a pharmaceutical composition having a therapeutically effective amount of the compound of Formula I or a pharmaceutically acceptable salt of the compound and a pharmaceutically acceptable carrier.

The present invention also provides a method for treating an MC4R-related condition, disease, or disorder in a mammal (e.g., a human) in need of such treatment, which method includes administering to the mammal (e.g., the human) the compound of Formula I or a pharmaceutically acceptable salt of the compound.

The present invention also provides the compound of Formula I or a pharmaceutically acceptable salt of the compound for use in treating an MC4R-related condition, disease, or disorder.

The MC4R-related condition, disease, or disorder includes one selected from cachexia [including for example, cachexia associated with a chronic illness, such as cachexia associated with cancer, cachexia associated with acquired immunodeficiency syndrome (AIDS), cachexia associated with heart failure for example cachexia associated with congestive heart failure (CHF), cachexia associated with chronic kidney disease (CKD); cachexia associated with treatment of a chronic illness, such as, cachexia associated with treatment of cancer or cachexia associated with treatment of heart failure (e.g. CHF)]; anorexia or anorexia nervosa (e.g., geriatric anorexia, anorexia associated with chemotherapy and/or radiotherapy); nausea; emesis; weight loss (e.g., involuntary weight loss); failure to thrive; sarcopenia; muscle wasting; muscle weakness [e.g. muscle weakness associated with chronic obstructive pulmonary disease (COPD)]; frailty; osteoporosis; bone disorders (e.g., bone loss); pain; neuropathic pain; anxiety (e.g., posttraumatic stress disorder, or PTSD); depression; hypertension; malnutrition; obesity (e.g. sarcopenia resulting from chronic obesity); sexual dysfunction; and inflammatory disease (e.g. an inflammatory disease associated with anorexia or cachexia or sarcopenia or muscle wasting).

The present invention also provides a method for treating a condition, disease, or disorder in a mammal (e.g., a human) in need of such treatment, which method includes administering to the mammal (e.g., the human) the compound of Formula I or a pharmaceutically acceptable salt of the compound, wherein the condition, disease, or disorder is selected from cachexia [including for example, cachexia associated with a chronic illness, such as cachexia associated with cancer, cachexia associated with acquired immunodeficiency syndrome (AIDS), cachexia associated with heart failure for example cachexia associated with congestive heart failure (CHF), cachexia associated with chronic kidney disease (CKD); cachexia associated with treatment of a chronic illness, such as, cachexia associated with treatment of cancer or cachexia associated with treatment of heart failure (e.g. CHF)]; anorexia or anorexia nervosa (e.g., geriatric anorexia, anorexia associated with chemotherapy and/or radiotherapy); nausea; emesis; weight loss (e.g., involuntary weight loss); failure to thrive; sarcopenia; muscle wasting; muscle weakness; frailty; osteoporosis; bone disorders (e.g., bone loss); pain; neuropathic pain; anxiety (e.g., posttraumatic stress disorder, or PTSD); depression; hypertension; malnutrition; obesity (e.g. sarcopenia resulting from chronic obesity); sexual dysfunction; and inflammatory disease (e.g. an inflammatory disease associated with anorexia or cachexia or sarcopenia or muscle wasting).

The present invention also provides a method for antagonizing a melanocortin-4 receptor (MC4R), which method includes contacting the MC4R with the compound of Formula I or a pharmaceutically acceptable salt of the compound.

It is to be understood that both the foregoing general description and the following detailed description are exemplary and explanatory only and are not restrictive of the invention, as claimed.

DETAILED DESCRIPTION OF THE INVENTION

Figure 1:
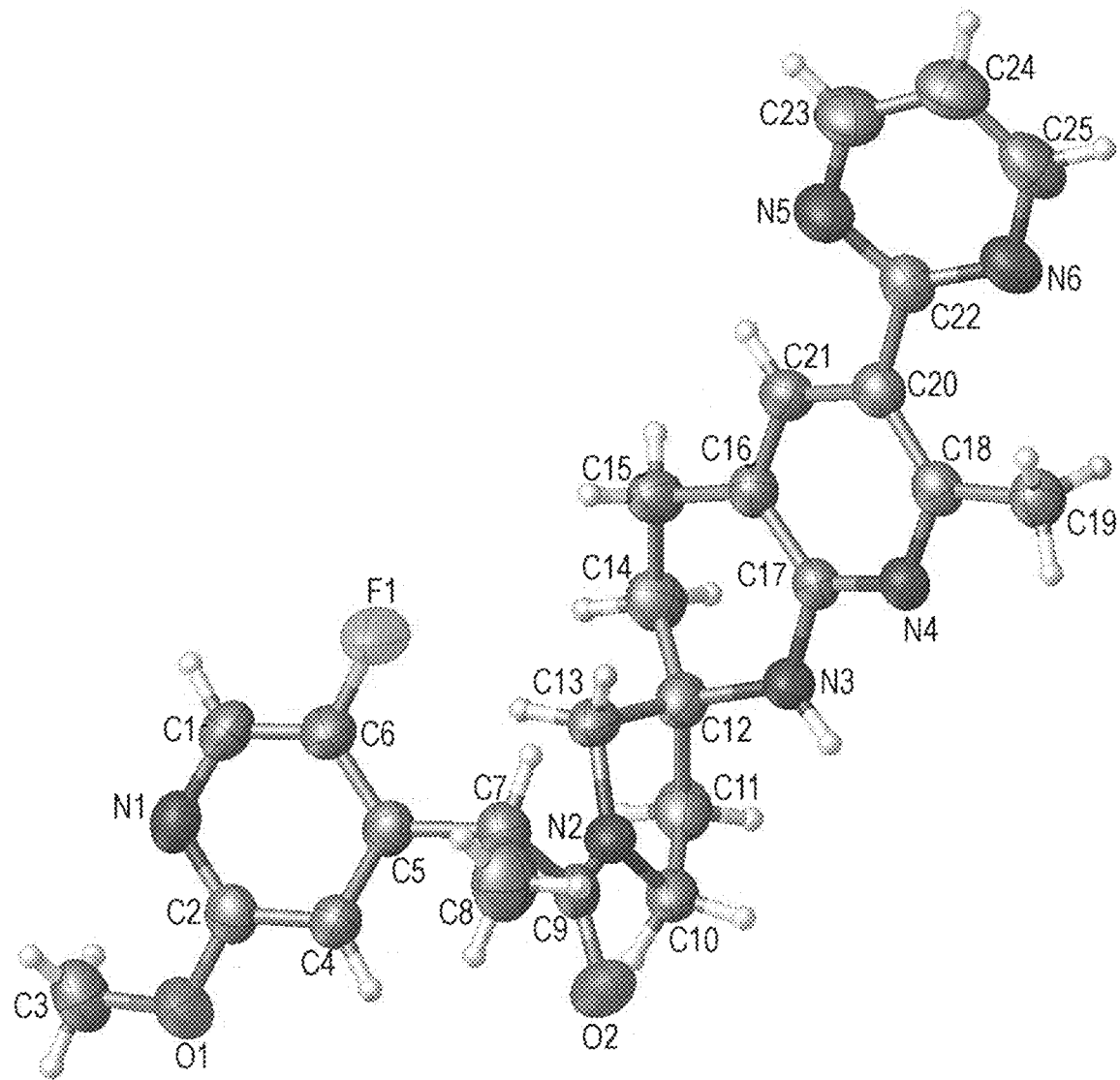
FIG. 1 shows an illustrative single crystal structure of compound Example 14.

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings: As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value to which it refers, in one embodiment, to plus or minus 5%, in another embodiment, to plus or minus 2%. For the field of this disclosure, this level of approximation is appropriate unless the value is specifically stated to require a tighter range.

"Compound" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form).

The term "alkyl" means an acyclic, saturated aliphatic hydrocarbon group which may be straight/linear or branched. Examples of such groups include, but are not limited to, methyl, ethyl, n-propyl, isopropyl, butyl, sec-butyl, isobutyl and tert-butyl. The carbon atom content of alkyl and various other hydrocarbon-containing moieties is indicated by a prefix designating a lower and upper number of carbon atoms in the moiety, that is, the prefix C; indicates a moiety of the integer "i" to the integer "j" carbon atoms, inclusive. Thus, for example, $C_{1-4}$ alkyl refers to alkyl of one to four carbon atoms, inclusive. Representative examples of $C_{1-4}$ alkyl include methyl, ethyl, n-propyl, isopropyl, n-butyl, sec-butyl, isobutyl, and tert-butyl. For another example, $C_{1-4}$ alkyl refers to alkyl of one to two carbon atoms, inclusive (i.e., methyl or ethyl). The alkyl group optionally can be substituted by 1 or more (e.g., 1 to 5) suitable substituents, when so specified.

At various places in the present specification, substituents of compounds of the invention are disclosed in groups or in ranges. It is specifically intended that the invention include each and every individual sub-combination of the members of such groups and ranges. For example, the term "$C_{1-4}$ alkyl" is specifically intended to include $C_1$ alkyl (methyl), $C_2$ alkyl (ethyl), $C_3$ alkyl, and $C_4$ alkyl. For another example, the term "4- to 7-membered heterocycloalkyl" is specifically intended to include any 4-, 5-, 6-, or 7-membered heterocycloalkyl group.

As used herein, the term "n-membered", where n is an integer, typically describes the number of ring-forming atoms in a moiety where the number of ring-forming atoms is n. For example, pyridinyl is an example of a 6-membered heteroaryl ring and pyrazolyl is an example of a 5-membered heteroaryl group.

As used herein, the term "alkoxy" or "alkyloxy" refers to an —O-alkyl group. For example, the term "$C_{1-4}$ alkoxy" or "$C_{1-4}$ alkyloxy" refers to an —O—($C_{1-4}$ alkyl) group; For another example, the term "$C_{1-2}$ alkoxy" or "$C_{1-2}$ alkyloxy" refers to an —O—($C_{1-2}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents when so specified.

The term "halo" or "halogen" as used herein, means —F, —Cl, —Br, or —I.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom); and the term "$C_{1-2}$ haloalkyl" refers to a $C_{1-2}$ alkyl group (i.e., methyl or ethyl) having one or more halogen substituents (up to perhaloalkyl, i.e., every hydrogen atom of the alkyl group has been replaced by a halogen atom). Examples of haloalkyl groups include —$CF_3$, —$CHF_2$, —$CH_2F$, —$CH_2CF_3$, —$C_2F_5$, —$CH_2Cl$ and the like.

"Fluoroalkyl" means an alkyl as defined herein substituted with one or more fluoro (—F) substituents (up to perfluoroalkyl, i.e., every hydrogen atom of the alkyl group has been replaced by a fluorine atom). The term "$C_{1-2}$ fluoroalkyl" refers to a $C_{1-2}$ alkyl group (i.e., methyl or ethyl) having one or more fluorine substituents (up to perfluoroalkyl, i.e., every hydrogen atom of the alkyl group has been replaced by a fluorine atom); and the term "$C_1$ fluoroalkyl" refers to methyl having 1, 2, or 3 fluorine substituents. Examples of $C_1$ fluoroalkyl include fluoromethyl, difluoromethyl and trifluoromethyl; some examples of $C_2$ fluoroalkyl include 1-fluoroethyl, 2-fluoroethyl, 2,2-difluoroethyl, 1,2-difluoroethyl, 2,2,2-trifluoroethyl, 1,1,2-trifluoroethyl, and the like.

As used here, the term "haloalkoxy" refers to an —O-haloalkyl group. For example, the term "$C_{1-4}$ haloalkoxy" refers to an —O—($C_{1-4}$ haloalkyl) group; and the term "$C_{1-2}$ haloalkoxy" refers to an —O—($C_{1-2}$ haloalkyl) group. For yet another example, the term "$C_1$ haloalkoxy" refers to a methoxy group having one, two, or three halogen substituents. An example of haloalkoxy is —$OCF_3$ or —$OCHF_2$.

As used here, the term "fluoroalkoxy" refers to an —O-fluoroalkyl group. For example, the term "$C_{1-2}$ fluoroalkoxy" refers to an —O—($C_{1-2}$ fluoroalkyl) group; and the term "$C_1$ fluoroalkoxy" refers to an —O—($C_1$ fluoroalkyl) group. Examples of $C_1$ fluoroalkoxy include —O—$CH_2F$, —O—$CHF_2$, and —O—$CF_3$. Some examples of $C_2$ fluoroalkoxy include —O—$CH_2CHF_2$, —O—$CH_2$—$CHF_2$, —O—$CH_2CF_3$, —O—$CF_2CH_3$, and —O—$CF_2CF_3$.

As used herein, the term "hydroxylalkyl" or "hydroxyalkyl" refers to an alkyl group having one or more (e.g., 1, 2, or 3) OH substituents. The term "$C_{1-4}$ hydroxylalkyl" or "$C_{1-4}$ hydroxyalkyl" refers to a $C_{1-4}$ alkyl group having one or more (e.g., 1, 2, or 3) OH substituents; and the term "$C_{1-2}$ hydroxylalkyl" or "$C_{1-2}$ hydroxyalkyl" refers to a $C_{1-2}$ alkyl group having one or more (e.g., 1, 2, or 3) OH substituents. An example of hydroxylalkyl is —$CH_2OH$ or —$CH_2CH_2OH$.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo [5.2.0]nonanyl, decahydronaphthalenyl, etc.). The cycloalkyl group has 3 to 15 (e.g., 3 to 14, 3 to 10, 3 to 6, 3 to 4, or 4 to 6) carbon atoms. In some embodiments the cycloalkyl may optionally contain one, two, or more non-cumulative non-aromatic double or triple bonds and/or one to three oxo groups. In some embodiments, the bicycloalkyl group has 6 to 14 carbon atoms. The term "$C_{3-4}$ cycloalkyl" as used herein, means a saturated cyclic hydrocarbon group containing from 3 to 4 carbons. Examples of $C_{3-4}$ cycloalkyl include cyclopropyl and cyclobutyl. Also included in the definition of cycloalkyl are moieties that have one or more aromatic rings (including aryl and heteroaryl) fused to the cycloalkyl ring, for example, benzo or pyridinyl derivatives of cyclopentane (a 5-membered cycloalkyl), cyclopentene, cyclohexane (a 6-membered cycloalkyl), and the like, for example, 6,7-dihydro-5H-cyclopenta[b]pyridinyl, 5,6,7,8-tetrahydroquinolinyl, or 1 5,6,7,8-tetrahydroisoquinolinyl, each of which includes a 5-membered or 6-membered cycloalkyl moiety that is fused to a heteroaryl ring (i.e. the pyridinyl ring). The cycloalkyl or $C_{3-4}$ cycoalkyl group optionally can be substituted by 1 or more (e.g., 1 to 5) suitable substituents when so specified.

The term "$C_{3-4}$ cycloalkyl-$C_{1-4}$ alkyl-" as used herein, means a $C_{3-4}$ cycloalkyl as defined herein, appended to the parent molecular moiety through a $C_{3-4}$ alkyl group, as defined herein. Some examples of $C_{3-4}$ cycloalkyl-$C_{1-4}$ alkyl- include cyclopropylmethyl, 2-cyclopropylethyl, 2-cyclopropylpropyl, 3-cyclopropylpropyl, cyclobutylmethyl, 2-cyclobutylethyl, 2-cyclobutylpropyl, and 3-cyclobutylpropyl.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 4- to 15-membered ring system (such as a 4- to 14-membered ring system, 4- to 12-membered ring system, 5- to 10-membered ring system, 4- to 7-membered ring system, 4- to 6-membered ring system, or 5- to 6-membered ring system), including 1 to 14 ring-forming carbon atoms and 1 to 10 ring-forming heteroatoms each independently selected from O, S and N (and optionally P or B when present). The heterocycloalkyl group can also optionally contain one or more oxo (i.e., =O) or thiono (i.e., =S) groups. For example, the term "4- to 7-membered heterocycloalkyl" refers to a monocyclic or polycyclic, saturated or unsaturated, non-aromatic 4- to 7-membered ring system that comprises one or more ring-forming heteroatoms each independently selected from O, S and N. For another example, the term "5- or 6-membered heterocycloalkyl" refers to a monocyclic or polycyclic, saturated or unsaturated, non-aromatic 5- or 6-membered ring system that comprises one or more ring-forming heteroatoms each independently selected from O, S and N. The heterocycloalkyl group optionally can be substituted by 1 or more (e.g., 1 to 5) suitable substituents, when so specified.

Some examples of 4- to 7-membered heterocycloalkyl include azetidinyl, oxetanyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, tetrahydrodiazinyl, and tetrahydropyranyl (also known as oxanyl). Some further examples of 4- to 7-heterocycloalkyl include tetrahydrofuran-2-yl, tetrahydrofuran-3-yl, tetrahydropyranyl (e.g., tetrahydro-2H-pyran-4-yl), imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-2-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo or thiono (i.e., =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the monocyclic heteroaryl ring; and the term "5- or 6-membered heteroaryl" refers to a monocyclic heteroaryl group as defined above with 5 or 6 ring-forming atoms in the monocyclic heteroaryl ring. A heteroaryl group optionally can be substituted by 1 or more (e.g., 1 to 5) suitable substituents, when so specified. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms.

Some examples of heteroaryl groups include pyridinyl (e.g., pyridin-2-yl, pyridin-3-yl, pyridine-4-yl), pyrazinyl, pyrimidinyl (e.g., pyrimidin-2-yl, pyrimidin-4-yl, or pyrimidin-5-yl), pyridazinyl (e.g., pyridazin-3-yl, or pyridazin-4-yl), thienyl, furyl, imidazolyl (e.g., 1H-imidazol-4-yl), pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., pyrazol-1-yl, pyrazol-3-yl, pyrazol-4-yl), tetrazolyl (e.g., 2H-tetrazol-5-yl), triazolyl (e.g., 1,2,3-triazolyl, 1,2,4-triazolyl), oxadiazolyl (e.g., 1,2,3-oxadiazolyl, 1,2,4-oxadiazolyl or 1,3,4-oxadiazolyl), thiadiazolyl (e.g., 1,3,4-thiadiazolyl, or 1,2,4-thiadiazolyl), quinolyl, isoquinolyl, benzothienyl, benzofuryl, indolyl, benzothiazolyl, 1,2-benzoxazolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyridinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyrazolo[1,5-a]pyrimidinyl, 6,7-dihydro-5H-pyrrolo[1,2-b][1,2,4]triazolyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like.

As used herein, the compound of Formula I as described herein includes optional substitutions and variables. It is understood that the normal valency of each of the designated (optionally substituted) atom or moiety is not exceeded, and that any of the optional substitution results in a stable compound. It is also understood that combinations of optional substituents and/or variables are permissible only if such combinations result in a stable compound.

As used herein, unless otherwise specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

As used herein, the point of attachment of a substituent can be specified to indicate the position where the substituent is attached to another moiety. For example, "($C_{3-4}$ cycloalkyl)-$C_{1-4}$ alkyl-" means the point of attachment occurs at the "$C_{1-4}$ alkyl" part of the "($C_{3-4}$ cycloalkyl)-$C_{1-4}$ alkyl-."

When a substituted or optionally substituted moiety is described without indicating the atom via which such moiety is bonded to a substituent, then the substituent may be bonded via any appropriate atom in such moiety. For example in a substituted "($C_{3-4}$ cycloalkyl)-$C_{1-4}$ alkyl-", a substituent on the cycloalkylalkyl [i.e., ($C_{3-4}$ cycloalkyl)-$C_{1-4}$ alkyl-] can be bonded to any carbon atom on the alkyl part or on the cycloalkyl part of the cycloalkylalkyl. Combinations of substituents and/or variables are permissible only if such combinations result in stable compounds.

As used herein, the term "adjacent" in describing the relative positions of two substituent groups on a ring structure refers to two substituent groups that are respectively attached to two ring-forming atoms of the same ring, wherein the two ring-forming atoms are directly connected through a chemical bond. For example, in each of the following structures:

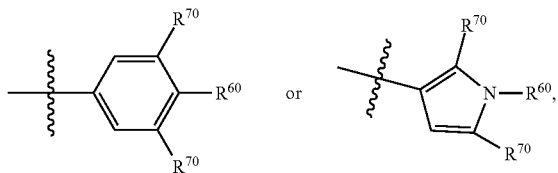

either of the two $R^{70}$ groups is an adjacent group of $R^{60}$.

"Mammals" refers to warm-blooded vertebrate animals characterized by the secretion of milk by females for the nourishment of the young, such as guinea pigs, mice, rats, gerbils, cats, rabbits, dogs, cattle, goats, sheep, horses, monkeys, chimpanzees, and humans.

The term "pharmaceutically acceptable" means the substance (e.g., the compounds of the invention) and any salt thereof, or composition containing the substance or salt of the invention that is suitable for administration to a patient.

As used herein, the expressions "reaction-inert solvent" and "inert solvent" refer to a solvent or a mixture thereof which does not interact with starting materials, reagents, intermediates or products in a manner which adversely affects the yield of the desired product.

As used herein, the term "selectivity" or "selective" refers to a greater effect of a compound in a first assay, compared to the effect of the same compound in a second assay. For example, in "gut-selective" compounds, the first assay is for the half-life of the compound in the intestine and the second assay is for the half-life of the compound in the liver.

"Therapeutically effective amount" means an amount of a compound of the present invention that (i) treats or prevents the particular disease, condition, or disorder; (ii) attenuates, ameliorates, or eliminates one or more symptoms of the particular disease, condition, or disorder; or (iii) prevents or delays the onset of one or more symptoms of the particular disease, condition, or disorder described herein.

The term "treating", "treat", or "treatment" as used herein embraces both preventative, i.e., prophylactic, and palliative treatment, including reversing, relieving, alleviating, or slowing the progression of the disease (or disorder or condition) or any tissue damage associated with one or more symptoms of the disease (or disorder or condition).

As used herein, the term "contacting" refers to the bringing together of indicated moieties in an in vitro system or an in vivo system. For example, "contacting" MC4R with a compound of the invention includes the administration of a compound of the present invention to a mammal, such as a human, having the MC4R, as well as, for example, introducing a compound of the invention into a sample containing a cellular or purified preparation containing the MC4R.

Embodiment A2 is a further embodiment of Embodiment A1, wherein the compound of Formula I or pharmaceutically acceptable salt thereof is a compound of Formula Ia:

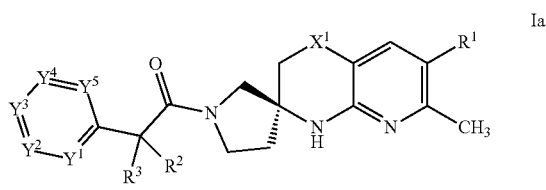

Ia or a pharmaceutically acceptable salt thereof, and wherein the variables $R^1$, $R^2$, $R^3$, $X^1$, $Y^1$, $Y^2$, $Y^3$, $Y^4$, and $Y^5$ are defined as the same as those in Embodiment A1.

Embodiment A3 is a further embodiment of Embodiment A1 or A2, wherein the compound or pharmaceutically acceptable salt thereof is a compound of Formula II:

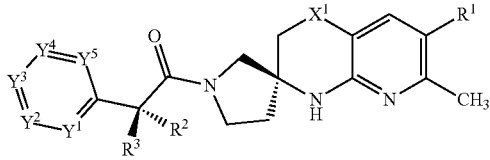

II or a pharmaceutically acceptable salt thereof, and wherein the variables $R^1$, $R^2$, $R^3$, $X^1$, $Y^1$, $Y^2$, $Y^3$, $Y^4$, and $Y^5$ are defined as the same as those in Embodiment A1.

Embodiment A4 is a further embodiment of any one of Embodiments A1 to A3, wherein the compound or pharmaceutically acceptable salt thereof is a compound of Formula III:

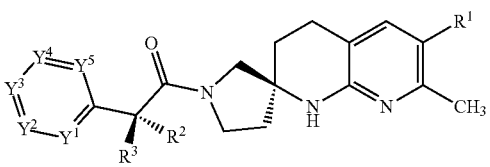

III or a pharmaceutically acceptable salt thereof, and wherein the variables $R^1$, $R^2$, $R^3$, $Y^1$, $Y^2$, $Y^3$, $Y^4$, and $Y^5$ are defined as the same as those in Embodiment A1.

Embodiment A5 is a further embodiment of any one of Embodiments A1 to A4, wherein:

$R^1$ is H, halogen, $C_{1-4}$ alkyl, $C_{1-4}$ haloalkyl, $C_{3-6}$ cycloalkyl, 4- to 7-membered heterocycloalkyl optionally substituted with 1 to 4 $C_{1-4}$ alkyl, or $R^{1a}$;

$R^{1a}$ is 5- or 6-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy; or two adjacent $R^A$ together with the two-ring atoms of the 5- or 6-membered heteroaryl to which they are attached form a fused benzene ring or a fused 5- or 6-membered heteroaryl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A6 is a further embodiment of any one of Embodiments A1 to A4, wherein $R^1$ is H, halogen, or a 4- to 7-membered heterocycloalkyl.

Embodiment A7 is a further embodiment of any one of Embodiments A1 to A4, wherein $R^1$ is H or halogen.

Embodiment A8 is a further embodiment of any one of Embodiments A1 to A4, wherein $R^1$ is H.

Embodiment A9 is a further embodiment of any one of Embodiments A1 to A4, wherein $R^1$ is halogen (e.g., Cl).

Embodiment A10 is a further embodiment of any one of Embodiments A1 to A4, wherein $R^1$ is 4- to 7-membered heterocycloalkyl (e.g., tetrahydrofuranyl, tetrahydropyranyl, pyrrolidinyl, piperidinyl, piperazinyl, or morpholino) optionally substituted with 1 to 4 $C_{1-4}$ alkyl.

Embodiment A11 is a further embodiment of any one of Embodiments A1 to A4, wherein $R^1$ is $R^{1a}$.

Embodiment A12 is a further embodiment of any one of Embodiments A1 to A4, wherein:

$R^1$ is $R^{1a}$; and $R^{1a}$ is a 5-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy; or two adjacent $R^A$ together with the two ring-atoms of the 5-membered heteroaryl to which they are attached form a fused 5- or 6-membered heteroaryl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A13 is a further embodiment of Embodiment A11 or A12, wherein $R^{1a}$ is a 5-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A14 is a further embodiment of Embodiment A11 or A12, wherein $R^{1a}$ is a 5-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl.

Embodiment A15 is a further embodiment of any one of Embodiments A12 to A14, wherein each of the ring-forming atoms of the 5-membered heteroaryl of $R^{1a}$ is a carbon or nitrogen atom.

Embodiment A16 is a further embodiment of Embodiment A11, wherein $R^{1a}$ is pyrazolyl, 1,2,4-triazolyl, 1,2,3-triazolyl, tetrazolyl, 1,2-thiazolyl, 1,3,4-thiadiazolyl, 1,2,4-thiadiazolyl, 1,3,4-oxadiazolyl, 1,2,4-oxadiazolyl, 1,3-thiazolyl, imidazoly, pyrazolo[1,5-a]pyrimidinyl, or [1,2,4]triazolo[1,5-a]pyridinyl-, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, $C_{1-4}$ haloalkoxy, and $C_{3-4}$ cycloalkyl.

Embodiment A17 is a further embodiment of Embodiment A11, wherein $R^{1a}$ is 1H-pyrazol-4-yl, 1H-1,2,4-triazol-3-yl, 2H-1,2,3-triazol-4-yl, 2H-tetrazol-5-yl, 1,2-thiazol-5-yl, 1,3,4-thiadiazol-2-yl, 1,2,4-thiadiazol-5-yl, 1,3,4-oxadiazol-2-yl, 1,2,4-oxadiazol-3-yl, 1,3-thiazol-2-yl, 1,3-thiazol-4-yl, 1H-imidazol-4-yl, pyrazolo[1,5-a]pyrimidin-3-yl, or [1,2,4]triazolo[1,5-a]pyridin-2-yl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, $C_{1-4}$ haloalkoxy, and $C_{3-4}$ cycloalkyl.

Embodiment A18 is a further embodiment of any one of Embodiments A1 to A4, wherein:

$R^1$ is $R^{1a}$; and $R^{1a}$ is a 5-membered heteroaryl substituted with 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy; or two adjacent $R^A$ together with the two ring-atoms of the 5-membered heteroaryl to which they are attached form a fused 5- or 6-membered heteroaryl or a fused 5- or 6-membered heterocycloalkyl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A19 is a further embodiment of Embodiment A18, wherein two $R^A$ are adjacent and they, together with the two ring-atoms of the 5-membered heteroaryl to which they are attached, form a fused 5- or 6-membered heteroaryl which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy; and wherein each of the rest $R^A$, if present, is independently halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A20 is a further embodiment of Embodiment A18, wherein two $R^A$ are adjacent and they, together with the two ring-atoms of the 5-membered heteroaryl to which they are attached form a fused 5- or 6-membered heterocycloalkyl which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy; and wherein each of the rest $R^A$, if present, is independently halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A21 is a further embodiment of any one of Embodiments A1 to A4, wherein:

$R^1$ is $R^{1a}$; and $R^{1a}$ is 6-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy; or two adjacent $R^A$ together with the two ring-atoms of the 6-membered heteroaryl to which they are attached form a fused benzene ring or a fused 5- or 6-membered heteroaryl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A22 is a further embodiment of Embodiment A21, wherein $R^{1a}$ is 6-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A23 is a further embodiment of Embodiment A21, wherein $R^{1a}$ is 6-membered heteroaryl optionally substituted with 1, 2, 3, or 4 independently selected $R^A$, and wherein each $R^A$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl.

Embodiment A24 is a further embodiment of any one of Embodiments A21 to A23, wherein each of the ring-forming atoms of the 6-membered heteroaryl of $R^{1a}$ is a carbon or nitrogen atom. In a further embodiment, 1, 2, or 3 of the ring-forming atoms of the 6-membered heteroaryl of $R^{1a}$ are nitrogen atoms (and the rest of the ring-forming atoms are carbon atoms).

Embodiment A25 is a further embodiment of any one of Embodiments A21 to A23, wherein $R^{1a}$ is pyridinyl, pyridazinyl, pyrazinyl, or pyrimidinyl, each of which is optionally substituted with 1, 2, or 3 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl.

Embodiment A26 is a further embodiment of any one of Embodiments A21 to A23, wherein $R^{1a}$ is pyridin-2-yl, pyridin-3-yl, pyridazin-3-yl, pyridazin-4-yl, pyrazin-2-yl, pyrimidin-2-yl, pyrimidin-4-yl, or pyrimidin-5-yl, each of which is optionally substituted with 1, 2, or 3 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl.

Embodiment A27 is a further embodiment of any one of Embodiments A21 to A23, wherein $R^{1a}$ is pyrimidinyl optionally substituted with 1, 2, or 3 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl.

Embodiment A28 is a further embodiment of any one of Embodiments A21 to A23, wherein $R^{1a}$ is pyrimidin-2-yl optionally substituted with 1 or 2 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl.

Embodiment A29 is a further embodiment of any one of Embodiments A21 to A23, wherein $R^{1a}$ is pyrimidin-2-yl.

Embodiment A30 is a further embodiment of any one of Embodiments A1 to A4, wherein $R^1$ is phenyl, wherein the phenyl is substituted with 3 or 4 independently selected $R^B$, wherein two adjacent $R^B$ together with the two ring-forming atoms of the phenyl to which they are attached form a fused 5- or 6-membered heteroaryl, each of which each is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy; and wherein each of the rest $R^B$ is independently halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl; Embodiment A31 is a further embodiment of Embodiment A30, wherein $R^1$ is 1,2-benzoxazolyl (e.g., 2-benzoxazol-6-yl) or 1,3-benzothiazolyl (e.g., 1,3-benzothiazol-5-yl), each optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

Embodiment A32 is a further embodiment of any one of Embodiments A1 to A4, wherein $R^1$ is phenyl, wherein the phenyl is substituted with $R^{B1}$ and optionally substituted with 1, 2, or 3 substituents each independently selected from halogen, —OH, —CN, $C_{1-4}$ alkyl, $C_{1-4}$ haloalkyl, $C_{1-4}$ alkoxy, $C_{1-4}$ haloalkoxy, and $C_{3-4}$ cycloalkyl.

Embodiment A33 is a further embodiment of Embodiment A32, wherein $R^{B1}$ is 1,3,4-oxadiazolyl (e.g., 1,3,4-oxadiazol-2-yl), 1,2,4-oxadiazolyl (e.g., 1,2,4-oxadiazol-3-yl), or 1,3-oxazolyl (e.g., 1,3-oxazol-5-y), each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, $C_{1-4}$ haloalkoxy, and $C_{3-4}$ cycloalkyl.

Embodiment A34 is a further embodiment of any one of Embodiments A1 to A3 and A5 to A33, wherein $X^1$ is $CH_2$.

Embodiment A35 is a further embodiment of any one of Embodiments A1 to A3 and A5 to A33, wherein $X^1$ is $CH(CH_3)$.

Embodiment A36 is a further embodiment of any one of Embodiments A1 to A35, wherein each of $R^2$ and $R^3$ is independently H, F, or $C_{1-4}$ alkyl.

Embodiment A37 is a further embodiment of any one of Embodiments A1 to A35, wherein each of $R^2$ and $R^3$ is independently H, F, or $C_{1-2}$ alkyl.

Embodiment A38 is a further embodiment of any one of Embodiments A1 to A35, wherein each of $R^2$ and $R^3$ is independently H or $C_{1-4}$ alkyl.

Embodiment A39 is a further embodiment of any one of Embodiments A1 to A35, wherein each of $R^2$ and $R^3$ is independently H or $C_{1-2}$ alkyl.

Embodiment A40 is a further embodiment of any one of Embodiments A1 to A35, wherein each of $R^2$ and $R^3$ is independently H or methyl.

Embodiment A41 is a further embodiment of any one of Embodiments A1 to A35, wherein $R^2$ is $C_{1-4}$ alkyl and $R^3$ is H.

Embodiment A42 is a further embodiment of any one of Embodiments A1 to A35, wherein $R^2$ is $C_{1-2}$ alkyl and $R^3$ is H.

Embodiment A43 is a further embodiment of any one of Embodiments A1 to A35, wherein $R^2$ is methyl and $R^3$ is H.

Embodiment A44 is a further embodiment of any one of Embodiments A1 to A43, wherein each of $Y^1$, $Y^2$, $Y^3$, $Y^4$, and $Y^5$ is independently $CR^4$.

Embodiment A45 is a further embodiment of any one of Embodiments A1 to A43, wherein one of $Y^1$, $Y^2$, $Y^3$, $Y^4$, and $Y^5$ is N, and each of the rest is independently $CR^4$.

Embodiment A46 is a further embodiment of any one of Embodiments A1 to A43, wherein $Y^3$ is N, and each of $Y^1$, $Y^2$, $Y^4$, and $Y^5$ is independently $CR^4$.

Embodiment A47 is a further embodiment of any one of Embodiments A1 to A43, wherein two of $Y^1$, $Y^2$, $Y^3$, $Y^4$, and $Y^5$ are N, and each of the rest of $Y^1$, $Y^2$, $Y^3$, $Y^4$, and $Y^5$ is independently $CR^4$.

Embodiment A48 is a further embodiment of any one of Embodiments A1 to A43, wherein $Y^1$ is N, $Y^3$ is N, and each of $Y^2$, $Y^4$, and $Y^5$ is independently $CR^4$.

Embodiment A49 is a further embodiment of any one of Embodiments A1 to A48, wherein each $R^4$ is independently H, halogen, $C_{1-2}$ alkyl, $C_{1-2}$ haloalkyl, —N($C_{1-4}$ alkyl)$_2$, $C_{1-2}$ alkoxy, or $C_{1-2}$ haloalkoxy.

Embodiment A50 is a further embodiment of any one of Embodiments A1 to A48, wherein each $R^4$ is independently H, F, Cl, —CH$_3$, $C_1$ fluoroalkyl, —OCH$_3$, or $C_1$ fluoroalkoxy.

Embodiment A51 is a further embodiment of any one of Embodiments A1 to A48, wherein each $R^4$ is independently H, halogen, or $C_{1-2}$ alkoxy.

Embodiment A52 is a further embodiment of any one of Embodiments A1 to A48, wherein each $R^4$ is independently H, F, Cl, or —OCH$_3$.

Embodiment A53 is a further embodiment of any one of Embodiments A1 to A48, wherein each $R^4$ is independently H, F, or —OCH$_3$.

Embodiment A54 is a further embodiment of any one of Embodiments A1 to A3, wherein:
  $R^1$ is $R^{1a}$;
  $R^{1a}$ is pyrazolyl, 1,2,4-triazolyl, 1,2,3-triazolyl, tetrazolyl, 1,2-thiazolyl, 1,3,4-thiadiazolyl, 1,2,4-thiadiazolyl, 1,3,4-oxadiazolyl, 1,2,4-oxadiazolyl, 1,3-thiazolyl, imidazolyl, pyrazolo[1,5-a]pyrimidinyl, or [1,2,4]triazolo[1,5-a]pyridinyl-, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, $C_{1-4}$ haloalkoxy, and $C_{3-4}$ cycloalkyl;
  $X^1$ is $CH_2$ or $CH(CH_3)$;
  $R^2$ is $C_{1-2}$ alkyl and $R^3$ is H;
  one of $Y^1$, $Y^2$, $Y^3$, $Y^4$, and $Y^5$ is N, and each of the rest of $Y^1$, $Y^2$, $Y^3$, $Y^4$, and $Y^5$ is independently $CR^4$; and
  each $R^4$ is independently H, F, C, —CH$_3$, $C_1$ fluoroalkyl, —OCH$_3$, or $C_1$ fluoroalkoxy.

Embodiment A55 is a further embodiment of any one of Embodiments A1 to A3, wherein:
  $R^1$ is $R^{1a}$;
  $R^{1a}$ is 1,2,4-triazolyl, 1,2,3-triazolyl, or tetrazolyl (e.g., 2H-tetrazol-5-yl), each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, $C_{1-4}$ haloalkoxy, and $C_{3-4}$ cycloalkyl;
  $X^1$ is $CH_2$;
  $R^2$ is $C_{1-2}$ alkyl and $R^3$ is H;
  $Y^3$ is N, and each of $Y^1$, $Y^2$, $Y^4$, and $Y^5$ is independently $CR^4$; and
  each $R^4$ is independently H, F, Cl, —CH$_3$, $C_1$ fluoroalkyl, —OCH$_3$, or $C_1$ fluoroalkoxy.

Embodiment A56 is a further embodiment of any one of Embodiments A1 to A3, wherein:
  $R^1$ is $R^{1a}$;
  $R^{1a}$ is tetrazolyl (e.g., 2H-tetrazol-5-yl) optionally substituted with 1, 2, or 3 independently selected $R^4$, wherein each $R^4$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl (e.g., $R^{1a}$ is 2H-tetrazol-5-yl substituted with $C_{1-4}$ alkyl such as methyl);
  $X^1$ is $CH_2$;
  $R^2$ is methyl and $R^3$ is H;
  $Y^3$ is N, and each of $Y^1$, $Y^2$, $Y^4$, and $Y^5$ is independently $CR^4$; and
  each $R^4$ is independently H, F, Cl, or —OCH$_3$.

Embodiment A57 is a further embodiment of any one of Embodiments A1 to A3, wherein:
  $R^1$ is $R^{1a}$;
  $R^{1a}$ is pyrazolyl (e.g., 1H-pyrazol-4-yl) optionally substituted with 1, 2, or 3 independently selected $R^4$, wherein each $R^4$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl (e.g., $R^{1a}$ is 1H-pyrazol-4-yl substituted with $C_{1-4}$ alkyl such as methyl);
  $X^1$ is $CH_2$;
  $R^2$ is methyl and $R^3$ is H;
  $Y^3$ is N, and each of $Y^1$, $Y^2$, $Y^4$, and $Y^5$ is independently $CR^4$; and
  each $R^4$ is independently H, F, C, or —OCH$_3$ (e.g., each $R^4$ is independently H, F, or —OCH$_3$).

Embodiment A58 is a further embodiment of any one of Embodiments A1 to A3, wherein:
  $R^1$ is $R^{1a}$;
  $R^{1a}$ is pyridinyl, pyridazinyl, pyrazinyl, or pyrimidinyl, each of which is optionally substituted with 1, 2, or 3 independently selected $R^4$, wherein each $R^4$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl;
$X^1$ is $CH_2$ or $CH(CH_3)$;
$R^2$ is $C_{1-2}$ alkyl and $R^3$ is H;
one of $Y^1$, $Y^2$, $Y^3$, $Y^4$, and $Y^5$ is N, and each of the rest of $Y^1$, $Y^2$, $Y^3$, $Y^4$, and $Y^5$ is independently $CR^4$; and
each $R^4$ is independently H, F, Cl, —CHF$_2$, or —OCH$_3$.

Embodiment A59 is a further embodiment of any one of Embodiments A1 to A3, wherein:
$R^1$ is $R^{1a}$;
$R^{1a}$ is pyridinyl, pyridazinyl, pyrazinyl, or pyrimidinyl, each of which is optionally substituted with 1, 2, or 3 independently selected $R^4$, wherein each $R^4$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl;
$X^1$ is $CH_2$;
$R^2$ is $C_{1-2}$ alkyl and $R^3$ is H;
$Y^3$ is N, and each of $Y^1$, $Y^2$, $Y^4$, and $Y^5$ is independently $CR^4$; and
each $R^4$ is independently H, F, or —OCH$_3$.

Embodiment A60 is a further embodiment of any one of Embodiments A1 to A3, wherein:
$R^1$ is $R^{1a}$;
$R^{1a}$ is pyrimidinyl (e.g., pyrimidin-2-yl) optionally substituted with 1, 2, or 3 independently selected $R^4$, wherein each $R^4$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl (e.g., $R^{1a}$ is unsubstituted pyrimidin-2-yl);
$X^1$ is $CH_2$;
$R^2$ is methyl and $R^3$ is H;
$Y^3$ is N, and each of $Y^1$, $Y^2$, $Y^4$, and $Y^5$ is independently $CR^4$; and
each $R^4$ is independently H, F, C, or —OCH$_3$ (e.g., each $R^4$ is independently H, F, or —OCH$_3$).

Embodiment A61 is a further embodiment of any one of Embodiments A1 to A3, wherein:
$R^1$ is $R^{1a}$;
$R^{1a}$ is [1,2,4]triazolo[1,5-a]pyridin-2-yl optionally substituted with 1, 2, or 3 independently selected $R^4$, wherein each $R^4$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl (e.g., $R^{1a}$ is unsubstituted [1,2,4]triazolo[1,5-a]pyridin-2-yl);
$X^1$ is $CH_2$;
$R^2$ is methyl and $R^3$ is H;
$Y^3$ is N, and each of $Y^1$, $Y^2$, $Y^4$, and $Y^5$ is independently $CR^4$; and
each $R^4$ is independently H, F, C, or —OCH$_3$ (e.g., each $R^4$ is independently H, F, or —OCH$_3$).

Embodiment A62 is a further embodiment of any one of Embodiments A1 to A3, wherein:
$R^1$ is $R^{1a}$;
$R^{1a}$ is pyridinyl, pyridazinyl, pyrazinyl, or pyrimidinyl, each of which is optionally substituted with 1, 2, or 3 independently selected $R^4$, wherein each $R^4$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl;
$X^1$ is $CH_2$ or $CH(CH_3)$;
$R^2$ is $C_{1-2}$ alkyl and $R^3$ is H;
each of $Y^1$, $Y^2$, $Y^3$, $Y^4$, and $Y^5$ is independently $CR^4$; and
each $R^4$ is independently H, F, Cl, —CH$_3$, —CF$_3$, —CHF$_2$, or —OCH$_3$.

Embodiment A63 is a further embodiment of any one of Embodiments A1 to A3, wherein:
$R^1$ is H;
$X^1$ is $CH_2$ or $CH(CH_3)$;
each of $R^2$ and $R^3$ is independently H or $C_{1-2}$ alkyl (e.g., each of $R^2$ and $R^3$ is H);
each of $Y^1$, $Y^2$, $Y^3$, $Y^4$, and $Y^5$ is independently $CR^4$; and
each $R^4$ is independently H, F, C, —CH$_3$, —CF$_3$, —CHF$_2$, or —OCH$_3$ (e.g., each $R^4$ is independently H or F, for example, one of $R^4$ is F and each of the remaining $R^4$ is H).

Embodiment A64 (a further embodiment of Embodiment A1) provides a compound selected from Examples 1 to 201 in the EXAMPLES section or a pharmaceutically acceptable salt thereof (or the parent compound thereof where the exemplary compound, for example, is a salt) herein described.

Embodiment A65 (a further embodiment of Embodiment A1) provides a compound selected from
2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one;
2-(6-methoxy-2-methylpyrimidin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one;
2-[6-(difluoromethoxy)pyridin-3-yl]-1-[7-methyl-6-(pyrimidin-2-yl)-3,4-dihydro-1H-spiro[1,8-naphthyridine-2,3'-pyrrolidin]-1'-yl]propan-1-one;
1-[7-methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one;
1-(4,7-dimethyl-3,4-dihydro-1H-spiro[1,8-naphthyridine-2,3'-pyrrolidin]-1'-yl)-2-(4-fluorophenyl)ethan-1-one;
2-(5-fluoro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one;
2-(5-fluoro-2-methoxypyridin-4-yl)-1-[7-methyl-6-(pyrimidin-2-yl)-3,4-dihydro-1H-spiro[1,8-naphthyridine-2,3'-pyrrolidin]-1'-yl]propan-1-one;
2-(5-chloro-2-methoxypyridin-4-yl)-1-[7-methyl-6-(pyrimidin-2-yl)-3,4-dihydro-1H-spiro[1,8-naphthyridine-2,3'-pyrrolidin]-1'-yl]propan-1-one;
2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one; and
2-(5-fluoro-2-methoxypyridin-4-yl)-1-{7-methyl-6-[(4,6-$^2$H$_2$)pyrimidin-2-yl]-3,4-dihydro-1H-spiro[1,8-naphthyridine-2,3'-pyrrolidin]-1'-yl}propan-1-one,
or pharmaceutically acceptable salt thereof.

Embodiment A66 (a further embodiment of Embodiment 1) provides a compound selected from
(2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one;
2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one;
2-[6-(difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one;
1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one;
1-(4,7-dimethyl-3,4-dihydro-1H-spiro[1,8-naphthyridine-2,3'-pyrrolidin]-1'-yl)-2-(4-fluorophenyl)ethan-1-one;
(2R)-2-(5-fluoro-2-methoxypyridin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one;
(2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one;

(2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one;
(2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one; and
(2R)-2-(5-fluoro-2-methoxypyridin-4-yl)-1-{(2S)-7-methyl-6-[(4,6-$^2$H$_2$)pyrimidin-2-yl]-3,4-dihydro-1H-spiro[1,8-naphthyridine-2,3'-pyrrolidin]-1'-yl}propan-1-one,
or pharmaceutically acceptable salt thereof.

Embodiment A67 (a further embodiment of Embodiment A1) provides a compound selected from:
(2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1;
2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1;
2-[6-(difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2;
1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one, DIAST-1;
1-(4,7-dimethyl-3,4-dihydro-1H-spiro[1,8-naphthyridine-2,3'-pyrrolidin]-1'-yl)-2-(4-fluorophenyl)ethan-1-one, DIAST-1;
(2R)-2-(5-fluoro-2-methoxypyridin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one;
(2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one;
(2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one;
(2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1; and
(2R)-2-(5-fluoro-2-methoxypyridin-4-yl)-1-{(2S)-7-methyl-6-[(4,6-$^2$H$_2$)pyrimidin-2-yl]-3,4-dihydro-1H-spiro[1,8-naphthyridine-2,3'-pyrrolidin]-1'-yl}propan-1-one,
or pharmaceutically acceptable salt thereof.

Embodiment A68 (a further embodiment of Embodiment A1) provides a compound that is (2R)-2-(5-Fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, or a pharmaceutically acceptable salt thereof.

Embodiment A69 (a further embodiment of Embodiment A1) provides a compound that is (2R)-2-(5-Fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one.

Embodiment A70 (a further embodiment of Embodiment A69) provides a crystalline form of (2R)-2-(5-Fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one. In a further embodiment of Embodiment A70, the crystalline form exhibits a powder X-ray diffraction pattern comprising at least one characteristic peak, in terms of 2θ, selected from at 8.7±0.2°; 11.1±0.2°; and 13.3±0.2°.

In a further embodiment of Embodiment A70, the crystalline form is Form I described in Example 14 herein. In some embodiments, Form I exhibits a powder X-ray diffraction pattern comprising at least one characteristic peak, in terms of 2θ, at 8.7±0.2°. In some embodiments Form I exhibits a powder X-ray diffraction pattern comprising at least one characteristic peak, in terms of 2θ, at 11.1±0.2°. In some embodiments, Form I exhibits a powder X-ray diffraction pattern comprising at least one characteristic peak, in terms of 2θ, at 13.3±0.2°. In some embodiments, Form I exhibits a powder X-ray diffraction pattern comprising at least two characteristic peaks, in terms of 2θ, selected from at 8.7±0.2°; 11.1±0.2°; and 13.3±0.2°. In some embodiments, Form I exhibits a powder X-ray diffraction pattern comprising two characteristic peaks, in terms of 2θ, selected from at 8.7±0.2°; and 11.1±0.2. In some embodiments, Form I exhibits a powder X-ray diffraction pattern comprising at least three characteristic peaks, in terms of 2θ, selected from at 8.7±0.2°; 11.1±0.2°; and 13.3±0.2°.

In some embodiments, Form I exhibits a powder X-ray diffraction pattern comprising at least two characteristic peaks, in terms of 2θ, selected from at 8.7±0.2°; 11.1±0.2°; and 26.0±0.2. In some embodiments, Form I exhibits a powder X-ray diffraction pattern comprising at least two characteristic peaks, in terms of 2θ, selected from at 8.7±0.2°; and 26.0±0.2°. In some embodiments, Form I exhibits a powder X-ray diffraction pattern comprising at least two characteristic peaks, in terms of 2θ, selected from at 11.1±0.2°; and 26.0±0.2°. In some embodiments, Form I exhibits a powder X-ray diffraction pattern comprising at least three characteristic peaks, in terms of 2θ, selected from at 8.7±0.2°; 11.1±0.2°; and 26.0±0.2°.

In some embodiments, Form I exhibits a powder X-ray diffraction pattern comprising at least two characteristic peaks, in terms of 2θ, as those listed in Table X1. In some embodiments, Form I exhibits a powder X-ray diffraction pattern comprising at least three characteristic peaks, in terms of 2θ, as those listed in Table X1. In some embodiments, Form I exhibits a powder X-ray diffraction pattern comprising at least four (e.g. 4, 5, 6, 7, 8, 9, or 10) characteristic peaks, in terms of 2θ, as those listed in Table X1.

In some embodiments, Form I exhibits a powder X-ray diffraction pattern substantially as shown in FIG. 1.

Every embodiment, Example, or pharmaceutically acceptable salt thereof may be claimed individually or grouped together in any combination with any number of each and every embodiment described herein.

The spirocyclic compound of Formula I (further including a compound of Formula Ia, II, or III) of the invention can be used in any of the pharmaceutical compositions, uses, and methods of the invention described herein.

The compound of Formula I or a pharmaceutically acceptable salt thereof of the present invention is an MC4R antagonist. Thus, the present invention further provides a method for antagonizing MC4R (either in vitro or in vivo), comprising contacting (including incubating) the MC4R with the compound of Formula I or a pharmaceutically acceptable salt thereof (such as one selected from Embodiments A1-A70 or Examples 1-201 herein) described herein.

The amount of the compound of Formula I or a pharmaceutically acceptable salt thereof used in any one of the methods (or uses) of the present invention is effective in antagonizing MC4R.

Another embodiment of the present invention includes use of a compound of Formula I or a pharmaceutically acceptable salt of the compound (such as one selected from Embodiments A1-A70 or Examples 1-201 herein) as a medicament, particularly wherein the medicament is for use in the treatment of an MC4R-related condition, disease, or disorder, including administering to a mammal, such as a human, in need of such treatment a therapeutically effective amount.

Another embodiment of the present invention includes use of a compound of Formula I or a pharmaceutically acceptable salt of the compound (such as one selected from Embodiments A1-A70 or Examples 1-201 herein) in the manufacture of a medicament in treating an MC4R-related condition, disease, or disorder, including administering to a mammal, such as a human, in need of such treatment a therapeutically effective amount.

Another embodiment of the present invention includes use of a compound of Formula I or a pharmaceutically acceptable salt of the compound (such as one selected from Embodiments A1-A70 or Examples 1-201 herein) as a medicament, particularly wherein the medicament is for use in the treatment of a condition, disease, or disorder selected from cachexia [including for example, cachexia associated with a chronic illness, such as cachexia associated with cancer, cachexia associated with acquired immunodeficiency syndrome (AIDS), cachexia associated with heart failure for example cachexia associated with congestive heart failure (CHF), cachexia associated with chronic kidney disease (CKD); cachexia associated with treatment of a chronic illness, such as, cachexia associated with treatment of cancer or cachexia associated with treatment of heart failure (e.g. CHF)]; anorexia or anorexia nervosa (e.g., geriatric anorexia, anorexia associated with chemotherapy and/or radiotherapy); nausea; emesis; weight loss (e.g., involuntary weight loss); failure to thrive; sarcopenia; muscle wasting; muscle weakness; frailty; osteoporosis; bone disorders (e.g., bone loss); pain; neuropathic pain; anxiety (e.g., posttraumatic stress disorder, or PTSD); depression; hypertension; malnutrition; obesity (e.g. sarcopenia resulting from chronic obesity); sexual dysfunction; and inflammatory disease (e.g. an inflammatory disease associated with anorexia or cachexia or sarcopenia or muscle wasting), including administering to a mammal, such as a human, in need of such treatment a therapeutically effective amount of or a pharmaceutically acceptable salt of the compound.

Another embodiment of the present invention includes use of a compound of Formula I or a pharmaceutically acceptable salt of the compound (such as one selected from Embodiments A1-A70 or Examples 1-201 herein) for the manufacture of a medicament in treating a condition, disease, or disorder selected from cachexia [including for example, cachexia associated with a chronic illness, such as cachexia associated with cancer, cachexia associated with acquired immunodeficiency syndrome (AIDS), cachexia associated with heart failure for example cachexia associated with congestive heart failure (CHF), cachexia associated with chronic kidney disease (CKD); cachexia associated with treatment of a chronic illness, such as, cachexia associated with treatment of cancer or cachexia associated with treatment of heart failure (e.g. CHF)]; anorexia or anorexia nervosa (e.g., geriatric anorexia, anorexia associated with chemotherapy and/or radiotherapy); nausea; emesis; weight loss (e.g., involuntary weight loss); failure to thrive; sarcopenia; muscle wasting; muscle weakness; frailty; osteoporosis; bone disorders (e.g., bone loss); pain; neuropathic pain; anxiety (e.g., posttraumatic stress disorder, or PTSD); depression; hypertension; malnutrition; obesity (e.g. sarcopenia resulting from chronic obesity); sexual dysfunction; and inflammatory disease (e.g. an inflammatory disease associated with anorexia or cachexia or sarcopenia or muscle wasting), including administering to a mammal, such as a human, in need of such treatment a therapeutically effective amount of a compound of Formula I or a pharmaceutically acceptable salt of the compound.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans- forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture. In the case where SFC is used, the mobile phase may consist of a supercritical fluid, typically carbon dioxide, containing 2-50% of an alcohol, such as methanol, ethanol or isopropanol.

Diastereomeric mixtures can be separated into their individual diastereoisomers on the basis of their physicochemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

In some embodiments, the compounds of the invention may have asymmetric carbon atoms. The carbon-carbon bonds of the compounds of Formula I may be depicted herein using a solid line (———), a wavy line ( ⁓⁓⁓⁓ ), a solid wedge ( ◢▬▬■ ), or a dotted wedge ( ⋯⋯ıııı ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. The use of a wavy line to depict bonds to asymmetric carbon atoms is meant to indicate that the stereochemistry is unknown (unless otherwise specified). It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations.

Valence tautomers include interconversions by reorganization of some of the bonding electrons.

Included within the scope of the claimed compounds present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I, $^{124}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically labelled compounds of Formula I, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

Isotopically labelled compounds of Formula I can generally be prepared by conventional techniques known to those skilled in the art or by processes analogous to those described in the accompanying Examples and Preparations using an appropriate isotopically labelled reagents in place of the non-labelled reagent previously employed.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately treating the compound with a suitable organic or inorganic acid and isolating the salt thus formed.

Salts encompassed within the term "pharmaceutically acceptable salts" refer to the compounds of this invention which are generally prepared by reacting the free base with a suitable organic or inorganic acid to provide a salt of the compound of the invention that is suitable for administration to a patient. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. See e.g., Berge, et al. *J. Pharm. Sci.* 66, 1-19 (1977); Handbook of Pharmaceutical Salts: Properties, *Selection, and Use by Stahl and Wermuth* (Wiley-VCH, 2002).

The compounds of Formula I, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see O. Almarsson and M. J. Zaworotko, *Chem. Commun.*, 17, 1889-1896 (2004). For a general review of multi-component complexes, see Haleblian, *J. Pharm. Sci.*, 64 (8), 1269-1288 (1975).

The compounds of the invention include compounds of Formula I or their pharmaceutically acceptable salts as hereinbefore defined, polymorphs, and isomers thereof (including optical, geometric and tautomeric isomers) as hereinafter defined and isotopically labelled compounds of Formula I or their pharmaceutically acceptable salts.

The compounds of the present invention may be administered as prodrugs. Thus certain derivatives of compounds of Formula I or their pharmaceutically acceptable salts which may have little or no pharmacological activity themselves can, when administered into or onto the body, be converted into compounds of Formula I or their pharmaceutically acceptable salts having the desired activity, for example, by hydrolytic cleavage. Such derivatives are referred to as 'prodrugs'. [Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B. Roche, American Pharmaceutical Association).]

Prodrugs can, for example, be produced by replacing appropriate functionalities present in the compounds of Formula I or their pharmaceutically acceptable salts with certain moieties known to those skilled in the art as 'promoieties' as described, for example, in "Design of Prodrugs" by H. Bundgaard (Elsevier, 1985).

Some examples of such prodrugs include:

(i) where the compound of Formula I or its pharmaceutically acceptable salt contains an alcohol functionality (—OH), an ether thereof, for example, replacement of the hydrogen with $(C_1-C_6)$alkanoyloxymethyl; or a phosphate ester (—O—$PO_3H_2$) or sulfate ester (—O—$SO_3H$) or pharmaceutically acceptable salts thereof; and (ii) an amide or carbamate of the amino functionality present in Formula (I) or (II), wherein the hydrogen of the amino NH group is replaced with $(C_1-C_{10})$alkanoyl or $(C_1-C_{10})$alkoxycarbonyl, respectively.

Also included within the scope of the invention are active metabolites of compounds of Formula I (including prodrugs) or their pharmaceutically acceptable salts, that is, compounds formed in vivo upon administration of the drug, often by oxidation or dealkylation. Some examples of metabolites in accordance with the invention include:

(i) where the compound of Formula I or its pharmaceutically acceptable salt contains a methyl group, a hydroxymethyl derivative thereof (—$CH_3$→—$CH_2OH$) and (ii) where the compound of Formula I or its pharmaceutically acceptable salt contains an alkoxy group, a hydroxy derivative thereof (—OR→—OH).

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section. Specific synthetic schemes for preparation of the compounds of Formula I or their pharmaceutically acceptable salts are outlined below. Note that tetrazoles are generally a high-energy functional group and care should be taken in the synthesis and handling of tetrazole-containing molecules.

The compounds of the present invention may be synthesized by synthetic routes that include processes analogous to those well known in the chemical arts, particularly in light of the description contained herein. The starting materials are generally available from commercial sources such as MilliporeSigma (Milwaukee, Wis.) or are readily prepared using methods well known to those skilled in the art [e.g., prepared by methods generally described in Louis F. Fieser and Mary Fieser, Reagents for Organic Synthesis, v. 1-19, Wiley, New York (1967-1999 ed.), or *Beilsteins Handbuch der Organischen Chemie*, 4, Aufl. ed. Springer-Verlag, Berlin, including supplements (also available via the *Beilstein* online database)]. Many of the compounds used herein are related to, or are derived from, compounds in which there is a large scientific interest and commercial need, and accordingly many such compounds are commercially available or are reported in the literature or are easily prepared from other commonly available substances by methods which are reported in the literature.

In the preparation of the compounds of Formula I or their salts, it is noted that some of the preparation methods described herein may require protection of remote functionality (e.g., primary amine, secondary amine, carboxyl in Formula I precursors). The need for such protection will vary depending on the nature of the remote functionality and the conditions of the preparation methods. The need of such protection is readily determined by one skilled in the art. The use of such protection/deprotection methods is also within the skill in the art. For a general description of protecting groups and their use, see T. W. Greene, *Protective Groups in Organic Synthesis*, 5$^{th}$ Edition, John Wiley & Sons, New York, 2014. For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-tert-butoxycarbonyl (Boc), benzyloxycarbonyl (Cbz), and 9-fluorenylmethoxycarbonyl (Fmoc) for amines and lower alkyl or benzyl esters for carboxylic acids) which are generally not chemically reactive under the reaction conditions described and can typically be removed without chemically altering other functionality in the Formula I compounds.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin-layer chromatography (TLC).

Compounds of Formula I, salts and intermediates thereof may be prepared according to the following reaction schemes and accompanying discussion. The reaction schemes described below are intended to provide a general description of the methodology employed in the preparation of the compounds of the present invention. Some of the compounds of the present invention contain a single chiral center with stereochemical designation (R or S) and others will contain two separate chiral centers with stereochemical designation (R or S). It will be apparent to one skilled in the art that most of the synthetic transformations can be conducted in a similar manner whether the materials are enantioenriched or racemic. Moreover, the resolution to the desired optically active material may take place at any desired point in the sequence using well known methods such as described herein and in the chemistry literature.

Unless otherwise indicated, $R^1$, $R^2$, $R^3$, $X^1$, $Y^1$, $Y^2$, $Y^3$, $Y^4$, $Y^5$, and structural Formula I (including, e.g., Ia, II) in the reaction schemes and discussion that follow are as defined herein or consistent with those described herein. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

In the Reaction Schemes that follow, the variables $X^c$, $X^2$, $X^3$, $X^4$, $X^5$, $X^6$, $X^7$, $X^8$, $X^9$, $R^5$, $R^6$, $R^7$, $R^8$, $R^9$, $R^{10}$, $R^{11}$, $R^{12}$, $R^{13}$, $R^{14}$, $LG^1$, $LG^2$, $LG^3$, $LG^4$, $PG^1$, $PG^2$, $PG^3$, $PG^4$, $PG^5$, $PG^6$, $PG^7$, and $PG^8$ are as described herein or consistent with those described in the claims of Formula I unless otherwise noted. For each of the variables, its meaning remains the same as initially described unless otherwise indicated in a later occurrence.

Scheme 1 refers to the synthesis of compounds of Formula I, Ia, and II. Acids of formula 1-1 can be reacted with amines of formula 1-2 (or salts thereof) using standard amidation conditions with coupling reagents such as 1,1'-carbonyldiimidazole, 2,4,6-tripropyl-1,3,5,2,4,6-trioxatriphosphinane 2,4,6-trioxide (T3P), O-(7-azabenzotriazol-1-yl)-N,N,N',N' tetramethyluronium hexafluorophosphate (HATU), or others to give compounds of Formula I. Alternatively, acids of formula 1-1 can reacted with amines of formula 1-3 in an analogous manner to form compounds of formula Ia. Acids of formula 1-1 can be purchased, synthesized as described in *Org. Process Res. Dev.* 1997, 1, 72, or synthesized as described herein. Amines of formula 1-2 can be synthesized as described herein. Compounds of formula I that contain mixtures of enantiomers or diastereomers may be separated using supercritical fluid chromatography or reversed-phase chromatography with a chiral column when needed to separate them into individual diastereomers or enantiomers as desired to produce compounds of Formula Ia or II.

Scheme 1

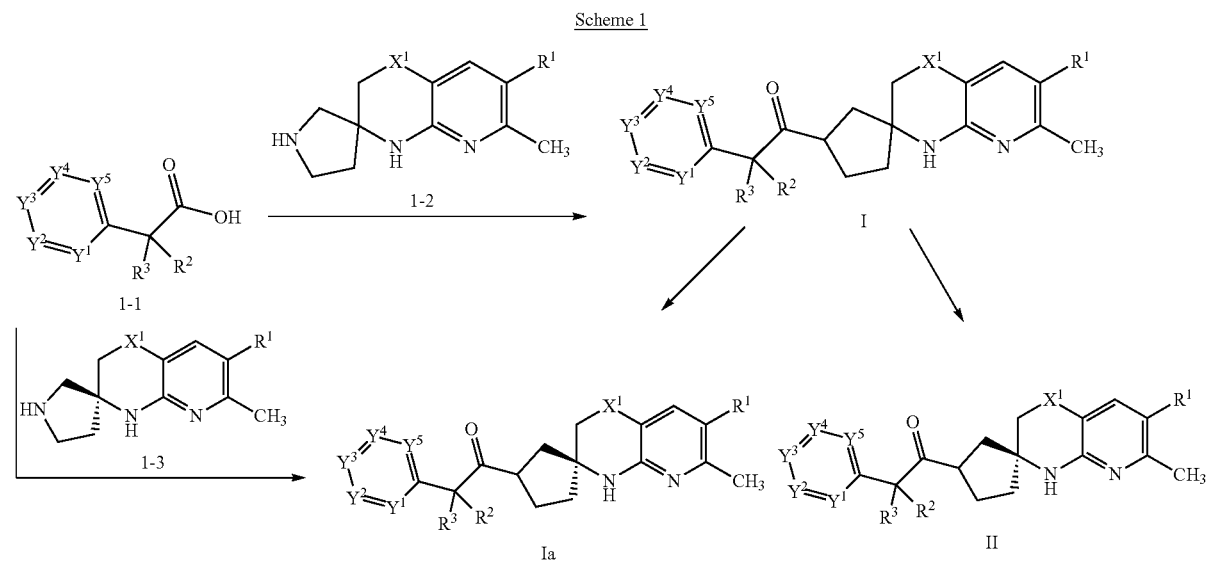

Scheme 2 describes an alternative synthesis of compounds of formula II when a single enantiomer of acids of formula 2-1 (a subtype of acids of formula 1-1) is used. Some acids of formula 2-1 can be racemized or epimerized under some general amidation conditions as described in Scheme 1. Instead, by employing lower temperatures, using solvents that aid in dissolution of the reactants, using additives such as imidazolium or pyridinium salts, or other methods as described in *Org. Process Res. Dev.* 2016, 20, 140; *Org. Lett.* 2012, 14, 1970; or *Org. Process Res. Dev.* 2009, 13, 106, or using the free base of amines of formula 1-3, high enantiomer excess could be retained throughout the reaction. Alternatively, if general conditions are used, or if epimerization or racemization occurs, the mixture of diastereomers formed may be separated using supercritical fluid or reversed-phase chromatography with a chiral column or they may be separated as a diastereomeric salt with an appropriate chiral acid under typical resolution conditions to form compounds of Formula II.

Scheme 2

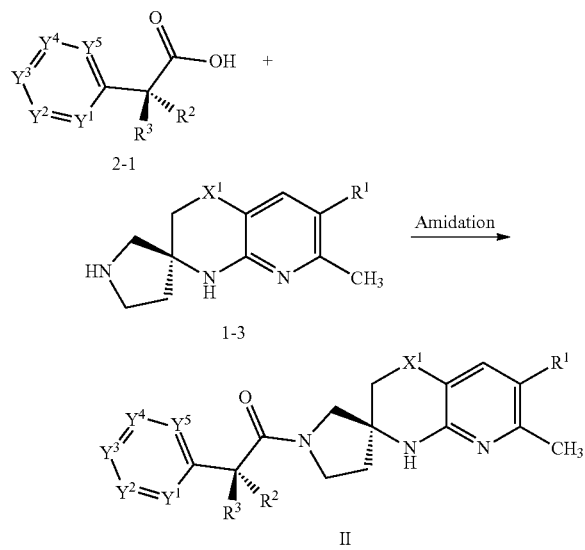

Scheme 3 describes a method to synthesize acids of formula 2-1 selectively as a single enantiomer. Acids of formula 3-1 can be purchased or synthesized using methods described in the literature or herein and reacted with a well-known chiral auxiliary ($X^c$) such as Evans-type (optically pure oxazolidinones), Myers-type (pseudoephedrine-derived), or others described in the literature to form intermediates of formula 3-2. Treatment of compounds of formula 3-2 with a strong base such as lithium diisopropylamide, lithium bis(trimethylsilyl)amide, sodium bis(trimethylsilyl)amide, potassium bis(trimethylsilyl)amide, or the like and an alkyl halide (when $R^2$ and/or $R^3$ is an alkyl group) or other electrophiles like N-fluorobenzenesulfonimide (when $R^2$ and/or $R^3$ is a fluorine) can form compounds of formula 3-3 in high diastereomeric excess. Hydrolysis conditions of the $X^c$ group in compounds of formula 3-3 depends on the individual properties but often reagents (inorganic bases) such as neat or aqueous potassium hydroxide, sodium hydroxide, lithium hydroxide with or without hydrogen peroxide and protic solvents like methanol, ethanol, or others, or aprotic solvents like tetrahydrofuran among others, can be used to form compounds of formula 2-1.

Scheme 3

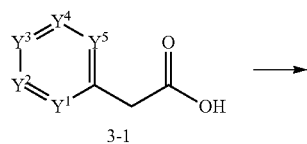

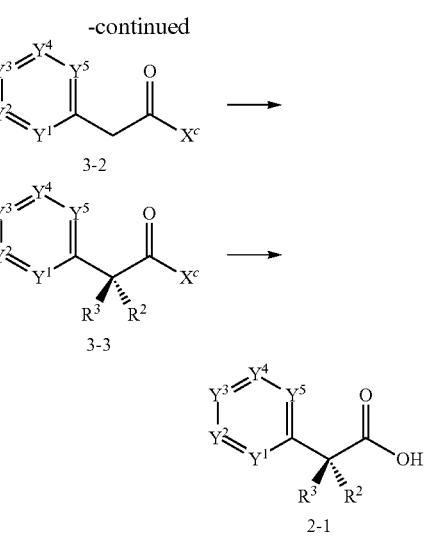

Scheme 4 describes methods that could be used to synthesize acids of formula 4-9 (a sub-type of compounds of formula 1-1), 4-7 (a sub-type of compounds of formula 2-1), or 4-8 (a sub-type of compounds of formula 2-1). Aryl or heteroaryl compounds of formula 4-1 [where $X^2$ is a halide (e.g., F, Cl, Br, or I) or a leaving group such as —OTf] can be reacted with diprotected malonates of formula 4-2 (where $PG^1$ can be methyl, ethyl, tert-butyl, benzyl, p-methoxybenzyl, or others and $PG^2$ can be an orthogonally removed protecting group selected from the same choices or could be the same protecting group) using $S_NAr$ conditions or by cross-coupling using a palladium catalyst such as palladium (II) acetate or tris(dibenzylideneacetone)dipalladium(0) [$Pd_2(dba)_3$] or others with a range of available phosphine ligands or a copper catalyst such as copper (I) iodide or an acidic ligand such as 2-picolinic acid as described in *Org. Lett.* 2007, 9, 3469 to give intermediates of formula 4-3. Compounds of formula 4-3 could be treated with an appropriate base such as sodium hydride, lithium diisopropylamide, lithium bis(trimethylsilyl)amide, sodium bis(trimethylsilyl)amide, potassium bis(trimethylsilyl)amide, potassium carbonate, cesium carbonate, or the like and subsequently alkylated with alkylating reagents such as methyl iodide, ethyl iodide, or others, fluorinating agents such as N-fluorobenzenesulfonimide, or other electrophiles to give compounds of formula 4-4. Alternatively, compounds of formula 4-1 can be reacted with compounds of formula 4-6 to directly form compounds of formula 4-4 (under similar conditions as the transformation of compounds of formula 4-1 to compounds of formula 4-3). Removal of the protecting groups of compounds of formula 4-4 can be performed using standard methods (basic or acidic hydrolysis); or when $PG^1$ or $PG^2$ is benzyl by employing palladium catalysts with hydrogen or reduction sources such as formate, trialkylsilanes, or others to form intermediates of formula 4-5. Alternatively, compounds of formula 4-4 can directly form acids of formula 4-9 under similar conditions (to those in producing compounds of formula 4-5) or those that may require elevated temperatures. The di-acids of formula 4-5 can also be mono-decarboxylated to provide racemic acids of formula 4-9 using base, acid, copper(I) oxide, by heating, or with other suitable conditions. Acids of formula 4-9 that contain mixtures of enantiomers may be separated using supercritical fluid or reversed-phase chromatography with a chiral column or they may be separated and isolated as a diastereomeric salt with an appropriate chiral acid under classical resolution conditions such as described in *Org. Process Res. Dev.* 2011, 15, 53 or one enantiomer can be selectively transformed into an ester using biocatalysis as described in *Adv. Synth. Catal.*, 2009, 351, 2333 (see also *J. Org. Chem.* 2003, 68, 7234) and separated to form acids of formula 4-7 or 4-8 in high enantiomeric excess. The di-acids of formula 4-5 can also be mono-decarboxylated using biocatalysis such as Aryl Malonate Decarboxylase (AM-Dase) enzymes to provide a single enantiomer of compounds of formula 4-7 or 4-8 in high enantiomer excess. See e.g., (a) *J. Am. Chem. Soc.* 1990, 112, 4077; (b) 0 *Eur J. Biochem.* 1992, 210, 475; (c) *Appl. Environ. Microbiol.* 2007, 73, 5676; (d) *Appl. Microbiol. Biotechnol.* 2016, 100, 8621.

similar metal-containing bases or magnesium metal and quenched with a dicarbonyl compound of formula 5-3 to give compounds of formula 5-4. Alternatively, arenes or heteroarenes of formula 5-2 can be directly deprotonated with a similar strong base or reagents such as lithium diisopropylamide, lithium 2,2,6,6-tetramethylpiperidide, bis(2,2,6,6-tetramethylpiperidinyl)zinc, or other variations of those and reacted with dicarbonyl compounds of formula 5-3 to form compounds of formula 5-4. Compounds of formula 5-4 could be treated with strong acid, such as hydrochloric acid, sulfuric acid, boron trifluoride diethyl etherate or other Bronsted or Lewis acids to form compounds of formula 5-5. Compounds of formula 5-5 could be treated with reducing agents such as silanes in the presence of acids or with hydrogen and a metal catalyst such as

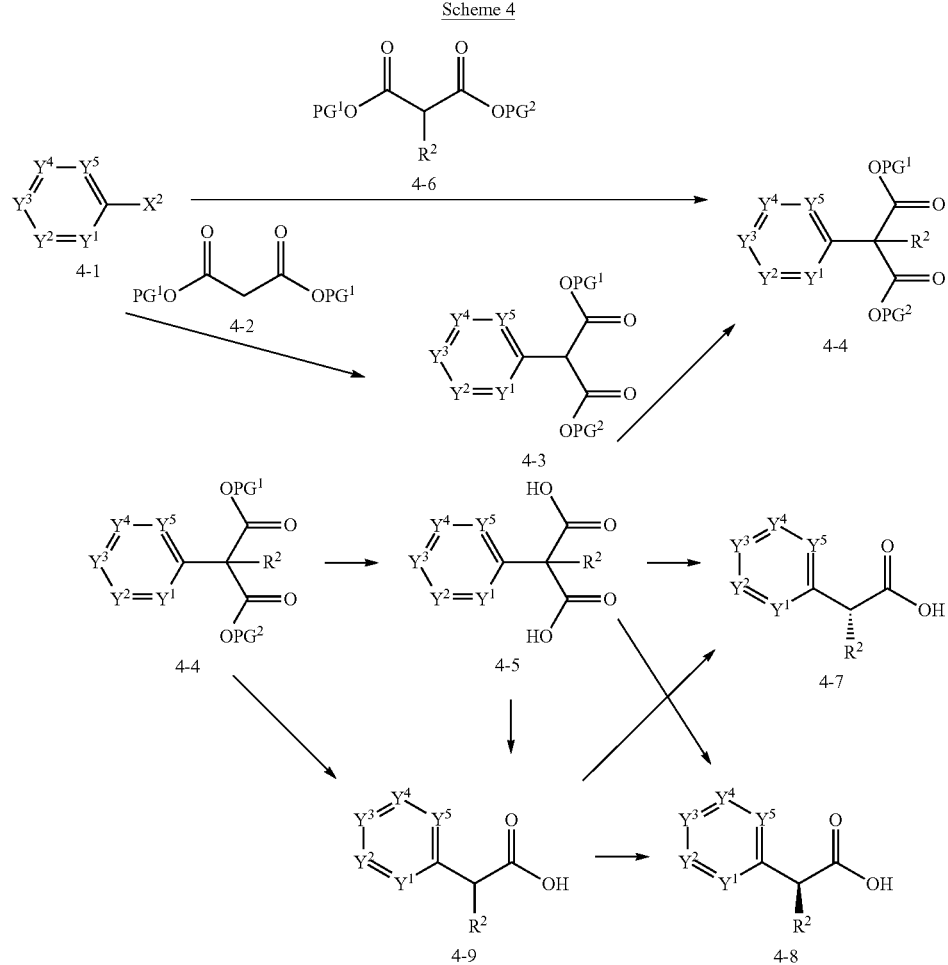

Scheme 5 refers to the synthesis of acids of formula 5-6 (a subtype of compounds of formula 1-1), 5-7 (a subtype of compounds of formula 2-1), and 5-8 (a subtype of compounds of formula 2-1) wherein $R^{2c}$ can be for example, H, alkyl, $C_{3-4}$ cycloalkyl, etc. (see definitions of $R^2$ or $R^3$). Aryl or heteroaryl halides of formula 5-1 (where $X^3$ is I, Br, or in some cases Cl) can be purchased or synthesized using methods familiar to those trained in the art of synthesis. Aryl or heteroaryl halides of formula 5-1 can be reacted with an appropriate reagent to perform a metal-halogen exchange such as n-butyllithium, isopropylmagnesium chloride or palladium to form compounds of formula 5-6. Alternatively, compounds of formula 5-4 could also be treated with similar acids in the presence of a reducing agent such as silanes or with hydrogen and a metal catalyst such as palladium to form acids of formula 5-6. Alternatively compounds of formula 5-5 could be treated with hydrogen and metals such as ruthenium or rhodium or others and a chiral ligand or many other methods such as described in *Org. Chem. Front.* 2014, 1, 155 to selectively form acids of formula 5-7 or 5-8 in high enantiomeric excess. Alternatively compounds of formula 5-5 can be transformed with a biocatalyst such as ENE-reductase (such as described in *ACS Catal.* 2018, 8, 3532) or other methods to selectively form compounds of formula 5-7 or 5-8 in high enantiomeric excess. Alternatively, compounds of formula 5-6 that contain mixtures of enantiomers may be separated using supercritical fluid or reversed-phase chromatography with a chiral column or they may be separated and isolated as a diastereomeric salt with an appropriate chiral acid under typical resolution conditions to form compounds of general formula 5-7 or 5-8.

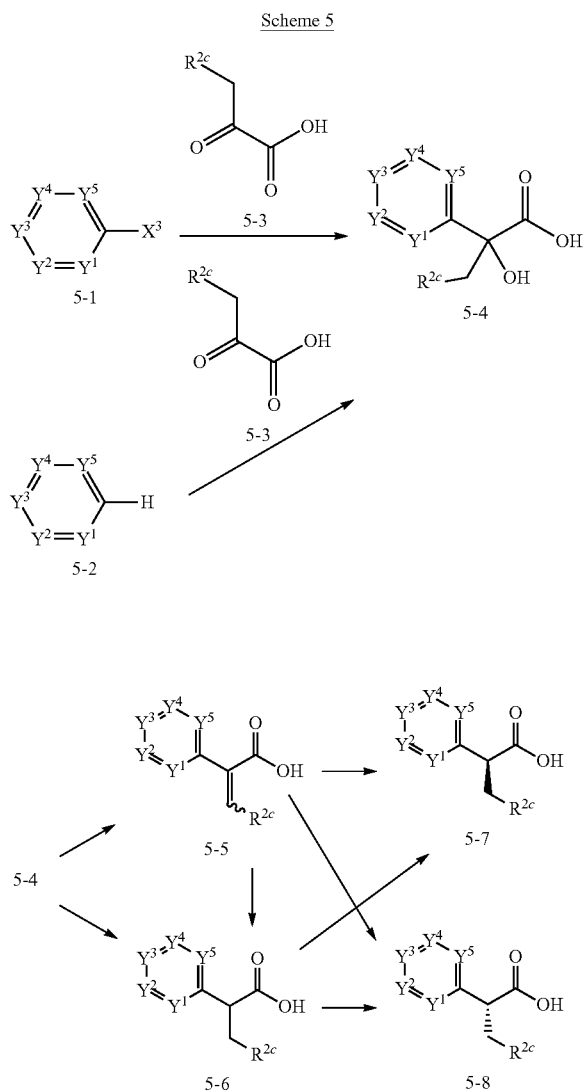

Scheme 6 describes certain other methods to synthesize acids of formulas 1-1 and 2-1. Compounds of formula 6-1 can be deprotonated with strong bases and acylated with carbon dioxide or a carbonyl compound of formula 6-2 (wherein $LG^1$ is a leaving group such as a chloride or an alkoxide and $PG^1$ is a protecting group such as previously described) to form compounds of formula 6-3. Compounds of formula 6-3 can be deprotonated with strong bases and treated with alkylating agents to form compounds of formula 6-4 in an analogous manner as described above for the transformation of compounds of formula 3-2 to compounds of formula 3-3. Compounds of 6-4 can be treated under hydrolysis conditions to form compounds of formula 1-1 in a manner analogous to that described above for the transformation of compounds of formula 3-3 to compounds of formula 2-1 or with a metal catalyst such as palladium on carbon and hydrogen when $PG^1$ is a benzylic group or with acid when $PG^1$ can leave as a stable cation or be eliminated away to form compounds of formula 1-1. Alternatively, the steps could be re-ordered such that compounds of formula 6-3 are hydrolyzed to compounds of formula 6-5 and then alkylated using similarly described conditions to form compounds of formula 1-1. Alternatively, compounds of formula 6-4 can be treated to biocatalysis conditions such as esterase enzymes to form acids of formula 2-1 in high enantiomeric excess. Alternatively, compounds of formula 6-6 can be treated with strong acid such as hydrochloric acid or sulfuric acid in the presence of an alcohol such as methanol or ethanol to form compounds of formula 6-3. Alternatively, compounds of formula 6-6 can be alkylated to form compounds of formula 6-7 using a similar method described for the transformation of compounds of formula 6-3 to compounds of formula 6-4. Alternatively, compounds of formula 6-7 can be directly hydrolyzed to acids of formula 1-1 using either strong acid such as hydrochloric acid or sulfuric acid or strong base such as sodium hydroxide, potassium hydroxide, or lithium hydroxide in the presence of water. Alternatively, compounds of formula 6-8 (where $LG^2$ is a leaving group such as Cl, Br, I, OMs, OTs, or others) can be treated with cyanide sources such as sodium cyanide, trimethylsilyl cyanide, or others to form compounds of formula 6-6. Compounds of formula 6-8 could be purchased or synthesized in a variety of ways as described in the literature or when $LG^2$ is e.g., Br or Cl by reacting compounds of formula 6-1 with a halogenating electrophile like N-bromosuccinimide, bromine, or others with a radical initiating activator such as 2,2'-azobisisobutyronitrile, light, or other reagents. Compounds of formula 6-12 (a subtype of compounds of formula 6-8 where $R^2$ is H) can be transformed into all of the analogous intermediates and compounds derived from 6-8 using similar methods. Compounds of formula 6-14 can be treated with base and alkylating agents as described for the transformation of 6-3 to 6-4 to form compounds of formula 1-1. Compounds of formula 6-11 may be purchased or synthesized using methods described in the literature. Compounds of formula 6-9 can be oxidized using an oxidizing reagent such as potassium permanganate to also form compounds of formula 6-11. Compounds of formula 6-11 can be homologated using any number of methods reported in the literature such as the Arndt-Eistert reaction (using an activating reagent such as thionyl chloride, ethyl chloroformate, or others; followed by a diazomethane reagent; a silver salt such as silver benzoate, silver oxide, or others; and a nucleophile such as water or alcohol) or other methods described in the literature such as those described in *J. Org. Chem.* 2001, 66, 5606 to form compounds of formula 6-10. Acids of formula 1-1 that contain mixtures of enantiomers may be separated using supercritical fluid or reversed-phase chromatography with a chiral column or they may be separated as a diastereomeric salt with an appropriate chiral acid under classical resolution conditions such as described in *Org. Process Res. Dev.* 2011, 15, 53 or the undesired enantiomer can be transformed into an ester using biocatalysis as described in *Adv. Synth. Catal.,* 2009, 351, 2333 (see also *J. Org. Chem.* 2003, 68, 7234) and separated to form acids of formula 2-1 in high enantiomeric excess.

Scheme 6
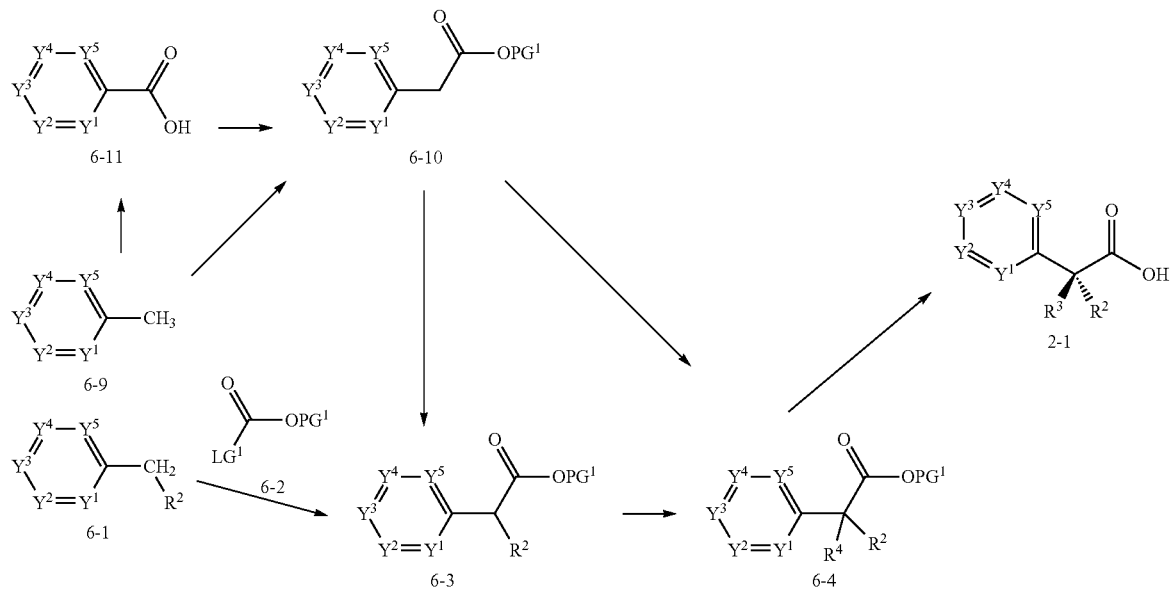
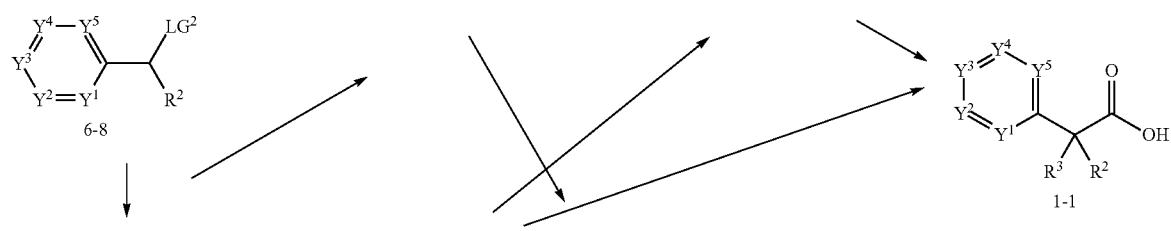
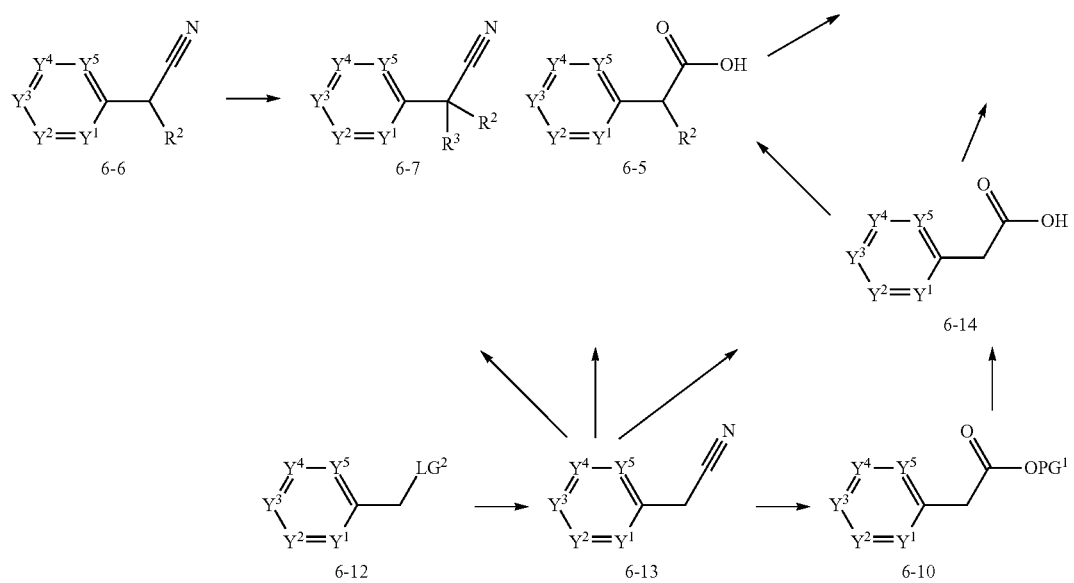

Scheme 7 describes the synthesis of compounds of formula 7-3, 7-4, 7-7, 7-8, 7-9, and 7-10 (where $Q^1$ can be any fragments of the compounds described in Formula I, Ia, II, or in Schemes 3-6), which can be used as any of the intermediates already described above when appropriate and these substituents can be installed at many points during the syntheses described in Schemes 3-6. Compounds of formula 7-1 (where $PG^1$ is already described) can be deprotected using dealkylating conditions such as trimethylsilyl iodide, sodium methanethiolate, or others, strong acids such as hydrobromic acid, boron tribromide, or when $PG^1$ is a benzyl group, palladium or related metals and hydrogen gas can be used to form compounds of formula 7-2. Compounds of formula 7-2 can be reacted with difluoromethyl sources such as difluorohaloacetates or (bromodifluoromethyl)trimethylsilane to form compounds of formula 7-3. Compounds of formula 7-2 could also be reacted with trifluoromethyl sources such as difluorohaloacetates with the addition of an electrophilic fluorine source such as Selectfluor™ trifluoromethylhalides, or via an intermediate xanthate that can be treated with XtalFluor® and an electrophilic fluorine source such as N-fluorobenzenesulfonimide or 1,3,5-trichloro-1,3,5-triazinane-2,4,6-trione (TCCA) (as described in *J. Org. Chem.* 2019, 84, 15776) or others to form compounds of formula 7-4. Compounds of formula 7-5 (where $LG^3$ can be Cl, Br, I, OTf, or others) can be treated with a nucleophilic vinyl source such as vinylboronate, vinyl stannane, or others using palladium-catalyzed cross-coupling conditions described in the literature to form compounds of formula 7-6. Compounds of formula 7-6 can be oxidatively cleaved to an aldehyde using reagents such as ozone with triphenylphosphine or dimethyl sulfide, osmium tetroxide (or ruthenium trichloride) and sodium periodate, or others to form compounds of formula 7-7. Compound of formula 7-7 can be reacted with nucleophilic difluoromethylation sources such as Deoxo-Fluor® or XtalFluor® and related reagents to form compounds of formula 7-8. Compounds of formula 7-5 can be treated with alcohols under $S_NAr$ or cross-coupling conditions using palladium and a variety of ligands to form compounds of formula 7-9 [wherein $R^8$ is, for example, $C_{1-4}$ alkyl (such as methyl) or $C_{1-4}$ haloalkyl (such as $C_1$ fluoroalkyl)]. Compounds of formula 7-5 could also be reacted with amines under similar conditions to form compounds of formula 7-10 [wherein each of $R^6$ and $R^7$ is independently $C_{1-4}$ alkyl (such as methyl), or $R^6$ and $R^7$ together with the carbon atom to which they are attached form cyclopropyl].

Scheme 7

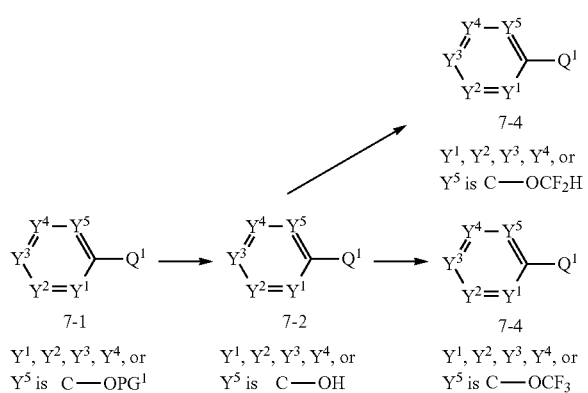

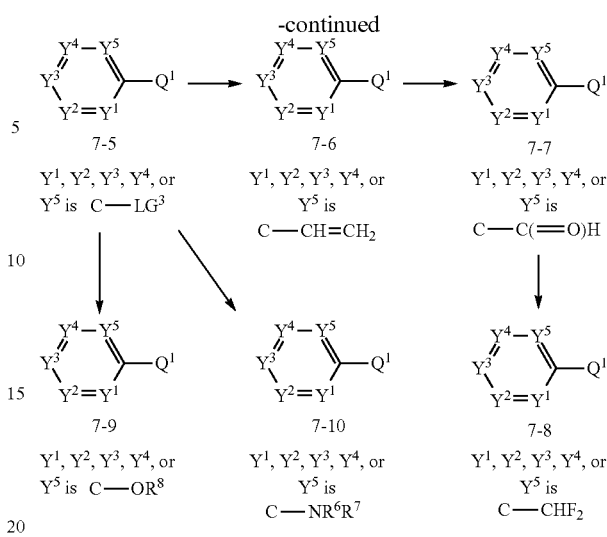

Scheme 8 describes the synthesis of compounds of formulas 1-2 and 1-3. Compounds of formula 8-1 (wherein $PG^4$ can be benzyl, p-methoxybenzyl, tert-butoxycarbonyl, benzyloxycarbonyl, acetyl, benzoyl, or other common nitrogen-protecting groups; $PG^5$ can be the same as $PG^4$ or can be any of the similar protecting groups that could be removed orthogonally) can be halogenated by electrophilic halogenation reagents such as dibromohydantoin, N-bromosuccinimide, N-chlorosuccinimide, bromine, iodine or others to form compounds of formula 8-3 (wherein $X^4$ can be Cl, Br, or I). Compounds of formula 8-3 can be reacted with a diboron source [such as tetrahydroxydiboron, bis(neopentylglycolato)diboron (5,5,5',5'-tetramethyl-2,2'-bi-1,3,2-dioxaborinane), or bis(pinacolato)diboron (4,4,4',4',5,5,5',5'-octamethyl-2,2'-bi-1,3,2-dioxaborolane)], a di-tin source such as bis(tributyltin) or others, a strong metal-containing base such as isopropylmagnesium chloride followed by a zinc source such as zinc dichloride, or others to form compounds of formula 8-2 (where $M^1$ can be a boronic acid, boronate, organotin, organozinc, or other metal capable of reacting under C—C cross-coupling conditions) and isolated if stable or telescoped into another reaction if desired. Compounds of formula 8-2 can be reacted with compounds of formula 8-9 (where $X^5$ is Cl, Br, I, OTf, or others) under C—C cross-coupling conditions such as Suzuki ($M^1$=boron), Stille ($M^1$=tin), Negishi ($M^1$=zinc halide), Kumada ($M^1$=magnesium halide) type reactions or others to form compounds of formula 8-4. Alternatively, compounds of formula 8-3 and 8-10 can be reacted in a similar manner as 8-2 and 8-9 with the nucleophile and electrophile reversed in a cross-coupling reaction to form compounds of formula 8-4. Alternatively, in some instances, compounds of formula 8-1 could also be reacted under CH activation/direct-arylation conditions with compounds of formula 8-9 to directly form compounds of formula 8-4. The $PG^4$ and $PG^5$ group of compounds of formula 8-4 can be removed using the appropriate deprotection conditions such as acid or hydrogenolysis or others to form compounds of formula 1-2. Note—if compounds of formula 8-1, 8-2, 8-3, 8-4, or 1-2 contain mixtures of stereochemistry or are racemic, they may be separated into single enantiomers using supercritical fluid or reversed-phase chromatography with a chiral column or as a diastereomeric salt with an appropriate chiral acid under classical resolution conditions and separated to form compounds of formula 8-5, 8-7, 8-6, 8-8, or 1-3 respectively in high enantiomeric excess. Alternatively compounds of formula 8-5, 8-7, 8-6, and 8-8 can be reacted under the same conditions as their analogous intermediates from this scheme without modification of conditions leading to the formation of compounds of formula 1-3.

copper and palladium catalyst to form compounds of formula 9-3. Compounds of formula 9-3 can be treated with a variety of palladium, platinum, or rhodium catalysts (on carbon or alumina or free) and hydrogen, trialkylsilanes,

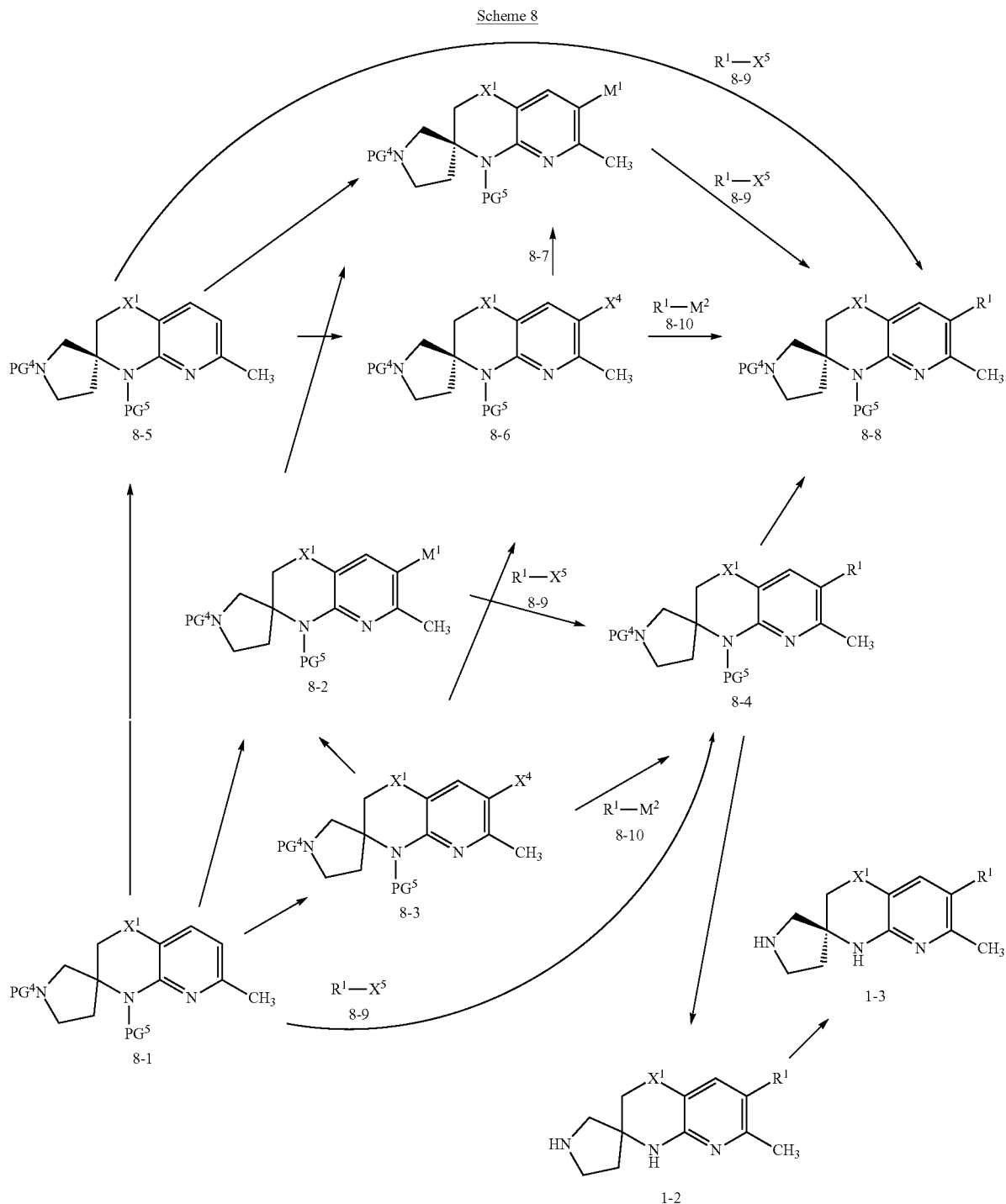

Scheme 8

Scheme 9 refers to the synthesis of the compound of formula 9-13. Compounds of formula 9-1 (where $X^7$ is more reactive than $X^6$; e.g. $X^7$=Br, $X^6$=Cl or $X^7$=I, $X^6$=Br or Cl, or other similar combinations) can be reacted with compound of formula 9-2 under Sonogashira conditions using a formic acid to form compounds of formula 9-8. Compounds of 9-8 can be treated with $S_NAr$ type conditions or with palladium or copper with appropriate ligands under common C—N cross-coupling conditions to form compounds of formulas 9-4. Under similar conditions with certain $PG^5$ groups such as carbamate and stronger base such as sodium or potassium tert-butoxide, compounds of formula 9-8 can be directly transformed into compounds of formula 9-6. Alternatively, compounds of formula 9-9 (where $R^{11}$ can be an arene such as phenyl or an alkyl group such as ethyl or butyl, or an alcohol such as ethanol, or others; and $(X^8)^-$ can be $OMs^-$, $OTs^-$, $OTf^-$, $Cl^-$, $Br^-$, $I^-$, or the like) and compounds of formula 9-10 can be reacted together under Wittig (such as described in *Tetrahedron Lett.* 2007, 48, 3359) or similar conditions with bases such as potassium carbonate, sodium tert-butoxide, n-butyllithium, or similar bases to form compounds of formula 9-11. Compounds of formula 9-11 can be transformed into compounds of formula 9-8 using analogous conditions to the transformation described for compounds of formula 9-3 to compounds of formula 9-8. Alternatively, compounds of formula 9-10 can be transformed into compounds of formula 9-12 with the appropriate methylene Wittig salt in an analogous manner to the transformation of 9-10 to 9-11. Alternatively, compounds of formula 9-11 can be reacted under photoredox isomerization conditions with catalysts such as iridium or others with appropriate ligands and blue LED light to form compounds of formula 9-7. Alternatively, the conversion of compounds of formula 9-11 can be reacted under the same photoredox conditions with a second catalyst, usually palladium, added to effect cyclization after isomerization, forming compounds of formula 9-5. Alternatively, compounds of formula 9-3 can be treated with poisoned catalysts such as Lindlar's catalyst (such as methods in *J. Org. Chem.* 2001, 66, 3634) or palladium on barium sulfate with a hydrogen source, or methods described in *Tetrahedron Lett.* 2008, 49, 2839 to form compounds of formula 9-7. Alternatively, compounds of formula 9-7 can be treated to hydrogenation conditions analogous to those described for the transformation of compounds of formula 9-11 into 9-8 to form compounds of formula 9-8. Alternatively, compounds of formulas 9-10 and 9-2 can be interconverted by using alkyne forming conditions such as Corey Fuchs or others to form compounds of formula 9-2 or treated under oxidative cleavage conditions to form compounds of formula 9-10. Alternatively, compounds of formula 9-7 can be reacted under the analogous conditions described for the transformation of compounds of formula 9-8 to compounds of formula 9-6 to form compounds of formula 9-5. Compounds of formula 9-5 can be reacted under analogous conditions to the transformation of compounds of formula 9-11 to compounds of formula 9-8 to form compounds of formula 9-4, 9-13, or 9-6 depending on the choice of protecting groups employed. Alternatively, compounds of formula 9-5 can be reacted under standard conditions to remove $PG^5$ to form compounds of formula 9-14. Compounds of formula 9-14 can then be reacted under analogous conditions to the transformation of compounds of formula 9-5 to compounds of formula 9-6 to form compounds of formula 9-6 or 9-13 depending on choice of protecting group. Alternatively, compounds of formula 9-12 can be transformed into compounds of formula 9-11 by using Heck-type cross-coupling conditions with compounds of formula 9-1. Alternatively, compounds of formula 9-12 and 9-1 can be transformed into compounds of formula 9-15 by using $S_NAr$ or C—N cross-coupling type conditions (when $X^6$ is more reactive than $X^7$, e.g., $X^7$=Cl, $X^6$=Cl or Br or $X^7$=Br, $X^6$=Br or I, or other similar combinations). Compounds of formula 9-15 can be reacted under analogous conditions to those described for the transformation of compounds of formula 9-12 to compounds of formula 9-11 to form compounds of formula 9-5.

Scheme 9

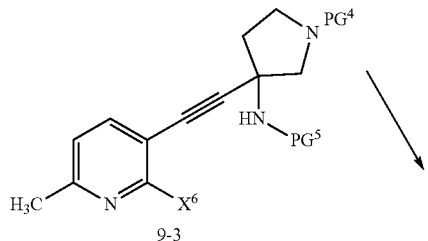

9-3

-continued
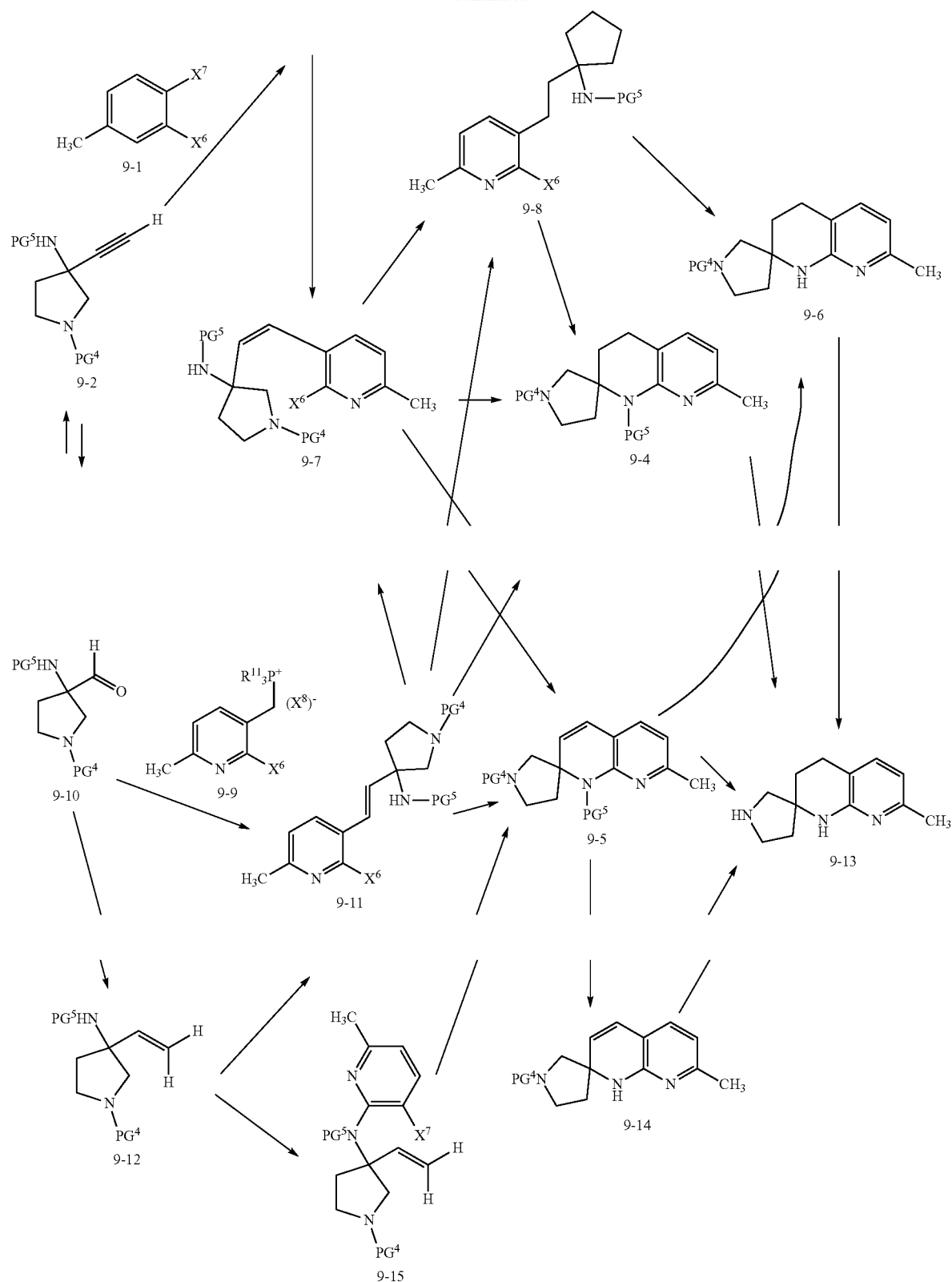
Scheme 10 describes the synthesis of the compound of formula 10-11, a sub-type of the compound of formula 9-13 wherein stereochemistry is defined. All of the transformations shown can be performed as described for the analogous compounds and intermediates described in Scheme 9 and do not require modifications or employing different conditions.

Scheme 10
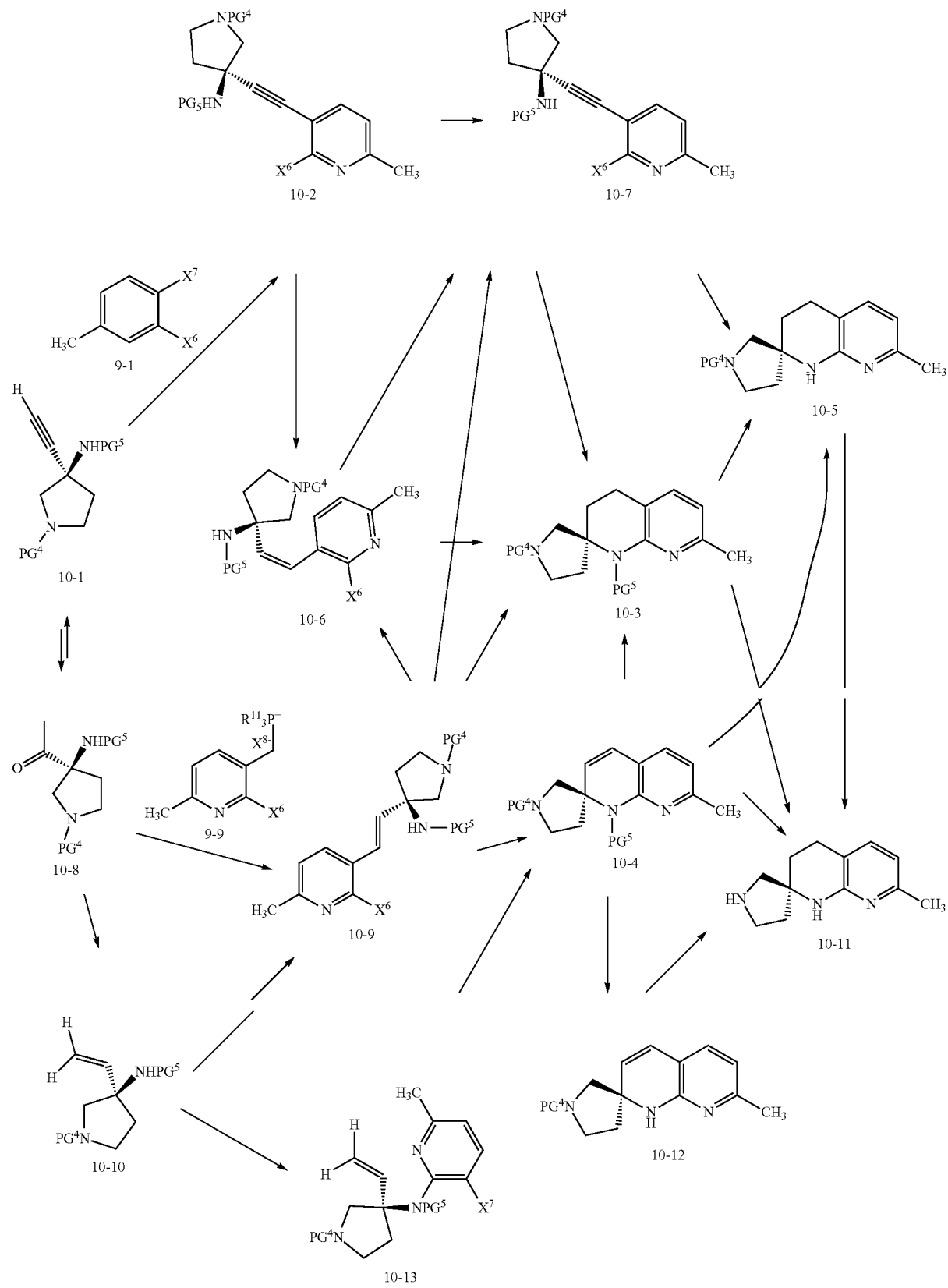

Scheme 11 describes the synthesis of compounds of formula 11-6 and 11-7 (a sub-type of compounds of formulas 9-2 and 10-1, respectively, where $PG^7$ is a protecting group that allows the adjacent nitrogen to remain nucleophilic such as benzyl, p-methoxybenzyl, or others, or possibly no protecting group). Compounds of formula 11-1 can be purchased or synthesized according to methods described in the literature and reacted with compounds of formula 11-2 (where $PG^6$ is trimethylsilyl or other appropriate alkyne protecting group) that have been deprotonated by the action of a base such as potassium tert-butoxide, lithium diisopropylamide, sodium hydride, n-butyllithium, zinc or magnesium metal, to provide compound of formula 11-3. Compounds of formula 11-3 can then be deprotected to the terminal alkyne with reagents such as tetrabutylammonium fluoride, potassium carbonate, potassium hydroxide, or others to provide compound of formula 11-4. The hydroxyl of compounds of formula 11-4 can be activated to become a leaving group $OR^9$ (wherein $R^9$ is acetyl, benzoyl, tert-butoxycarbonyl, dialkyl phosphate $[P(O)(OAlk)_2]$ or the like} with acetyl chloride, benzoyl chloride, other acyl halides, other suitably activated acids, or other activating groups such as haloformates, dialkyl halophosphates, or others and base such as triethylamine, N,N-diisopropylethylamine, pyridine, 4-(dimethylamino)pyridine, or the like, to form activated compounds of formula 11-5. Compounds of formula 11-5 can be reacted with amines protected with p-methoxybenzyl, benzyl, or others in a reaction catalyzed by copper(I) chloride, copper(I) bromide (such as in *J. Org. Chem.* 2013, 78, 5647), ruthenium catalysts (such as in *New J. Chem.* 2011, 35, 2427) and the like to form compounds of formula 11-6. If compounds of formula 11-6 contain mixtures of stereochemistry or are racemic, they may be separated into single enantiomers using supercritical fluid or reversed-phase chromatography with a chiral column or as a diastereomeric salt with an appropriate chiral acid under classical resolution conditions and separated to form compounds of formula 11-7 in high enantiomeric excess.

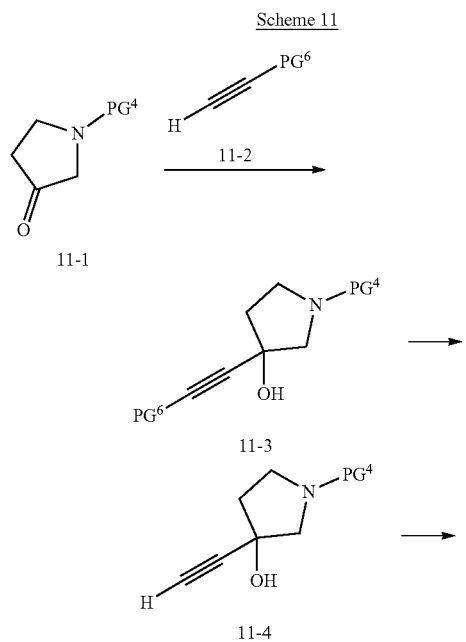

Scheme 11

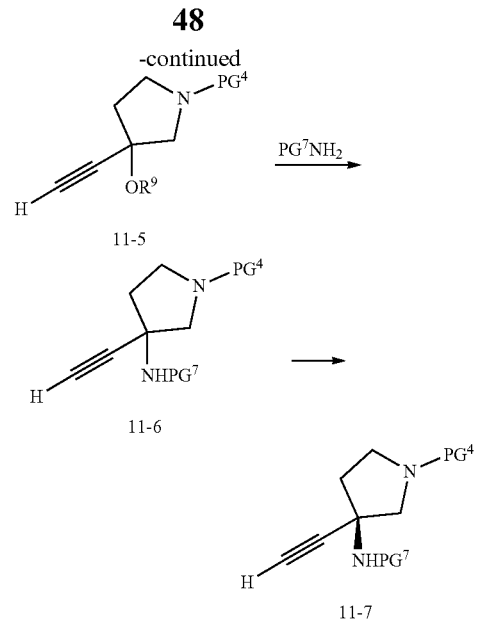

Scheme 12 describes the synthesis of compounds of formula 9-1 and 9-9 (where $R^{11}$ can be alkyl groups, aryl groups, alkoxy groups, or combinations of them or as an oxide version of these). Compounds of formula 12-1 (which can be purchased or synthesized from 12-6 or other methods described in the literature) can be treated with a reducing agent such as aluminum-based hydrides (lithium aluminum hydride, sodium bis(2-methoxyethoxy)aluminum dihydride, diisobutylaluminum hydride, or others) or borohydride-based (such as lithium borohydride, sodium borohydride, or others) to form compounds of formula 12-3. Alternatively, compounds of formula 12-2 (which can be purchased or formed from compounds of formula 12-1 using standard hydrolysis conditions or other methods described in the literature) can be transformed using the same reagents, but also by using borane or borane-derived reagents to form compounds of formula 12-3. The OH of compounds of formula 12-3 can be activated into a leaving group ($LG^4$, which can be OMs, OTs, OTf, Cl, Br, I, or others) by using the appropriate reagent such as methanesulfonyl chloride, p-toluenesulfonyl chloride, triflic anhydride, phosphorus oxychloride or thionyl chloride, phosphorus oxybromide or phosphorus tribromide, iodine with triphenylphosphine or imidazole, acids such as hydrobromic acid or hydrochloric acid, or by using a combination of methods such as methanesulfonyl chloride followed by sodium iodide, sodium chloride, sodium bromide, potassium iodide, potassium chloride, potassium bromide, or others to produce compounds of formula 12-4. Alternatively, compounds of formula 12-5 can be halogenated under radical halogenation conditions such as those described for transformation of compounds of 6-1 to 6-8 to form compounds of formula 12-4. Compound of formula 12-4 can be reacted with a compound of formula 12-9 (e.g. triphenylphosphine, triethylphosphine, triethylphosphite, or other phosphorus nucleophiles) to produce compounds of formula 9-9. Compounds of formula 12-6 can be nitrated under standard nitration conditions such as fuming nitric acid to produce compounds of formula 12-7. The nitro group of compounds of formula 12-7 can be reduced to an amine using a variety of conditions such as palladium on carbon with hydrogen, zinc or iron with acetic or hydrochloric acid, tin(II)chloride, or others to produce compounds of formula 12-8. Compounds of formula 12-8 can be treated with sodium nitrite or isoamyl nitrite with hydrobromic acid, potassium bromide, potassium iodide, or other standard Sandmeyer-type conditions to produce compounds of formula 9-1. Compounds of formula 9-1 can be treated with carbonylation conditions such as palladium with an appropriate ligand such as 1,1'-bis(diphenylphosphino)ferrocene, a carbon monoxide source, and an alcohol such as ethanol or methanol or can be treated with metal-halogen exchange conditions and quenched with an acyl source such as diethyl carbonate, carbon dioxide, ethyl chloroformate, or others to produce compounds of formula 12-1.

conditions similar to those described for the transformation of compounds of formula 12-1 to 12-3. Compounds of formula 13-5 can then be oxidized using a number of well-known reagents such as Collins chromium reagent, Dess-Martin periodinane reagents, Parikh-Doering reagent, other activated DMSO-based Swern-type reagents, or many others to provide compounds of formula 9-10. Alternatively, compounds of formula 13-8 can be treated with lithium diisopropylamide, lithium bis(trimethylsilyl)amide, n-butyllithium, or many other similar strong bases, and suitable acylating reagents such as ethyl chloroformate, ethyl cyanoformate, or diethyl carbonate to form compounds of

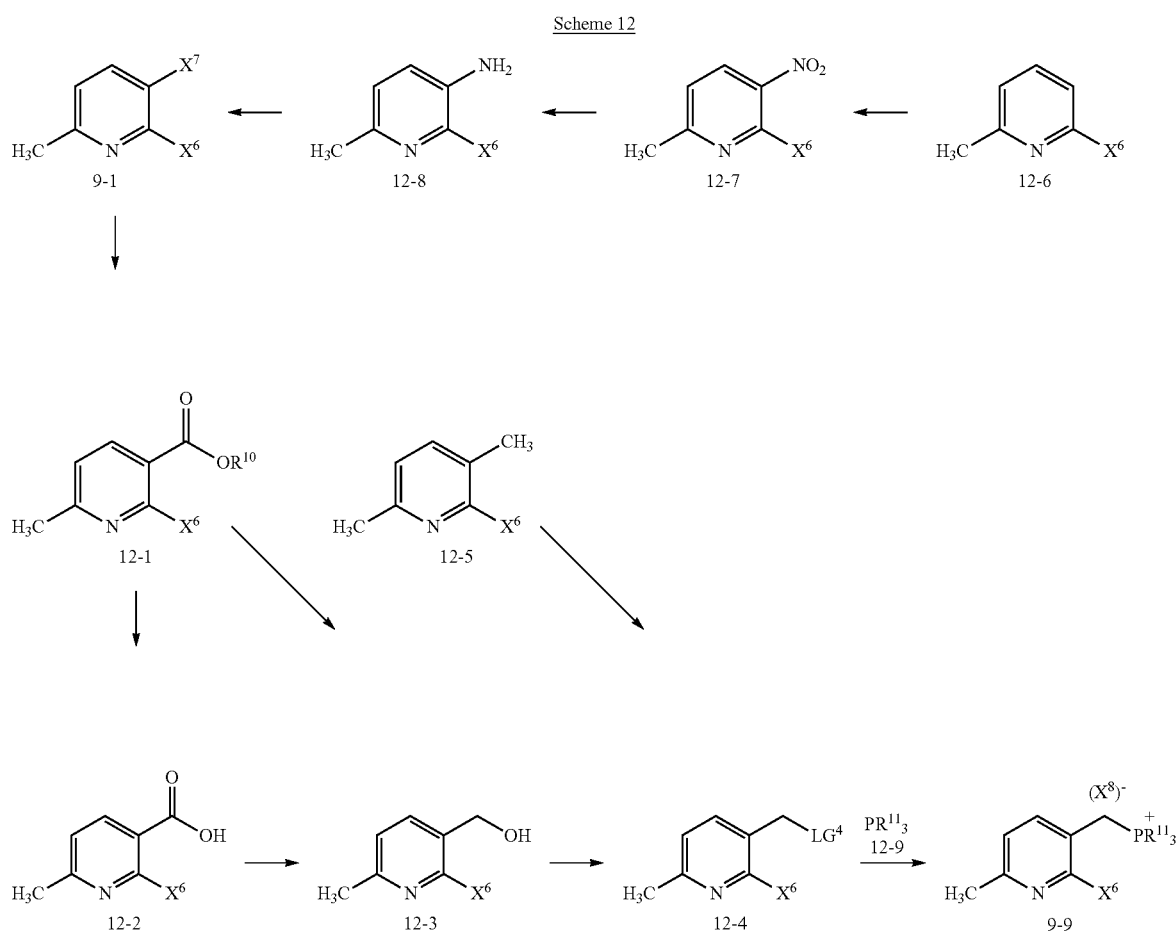

Scheme 12

Scheme 13 describes a method for synthesizing compounds of formula 9-10. Compounds of formula 13-1 (where $PG^8$ can be any C-linked alkyl or aryl, and can be purchased or synthesized using methods described in the literature) can be treated with conditions to eliminate the hydroxyl group such as with methanesulfonyl chloride or p-toluenesulfonyl chloride, as described in *Org. Lett.* 2016, 18, 1812, or other standard conditions to provide compounds of formula 13-2. Compounds of formula 13-2 can reacted in a 3+2 cycloaddition with commercially available compounds of formula 13-3 to form compounds of formula 13-4. Compounds of formula 13-4 can be reduced directly to compounds of formula 9-10 using conditions such as diisobutylaluminum hydride or other reducing agents that avoid over-reduction. Alternatively, compounds of formula 13-4 can be reduced to compounds of formula 13-5 using formula 13-9 (where $PG^9$ can be the same as $PG^8$ or can be a different alkyl or aryl group such that it can be orthogonally removed under selective conditions). Compounds of formula 13-9 can be selectively hydrolyzed using one equivalent of a base such as sodium hydroxide or lithium hydroxide, or many others, or by employing a selective $PG^9$ such as benzyl that could be removed through treatment with palladium on carbon and hydrogen to form compounds of formula 13-10. Compounds of formula 13-10 can be transformed into compounds of formula 13-4 using reactions such as a Curtius rearrangement (such as described in *Org. Biomol. Chem.* 2018, 16, 2006) or other similar reactions that rearrange an acid or related acyl group into a dehomologated amine or protected amine such as Hoffmann rearrangement, Lossen rearrangement, or Schmidt reaction.

Scheme 13

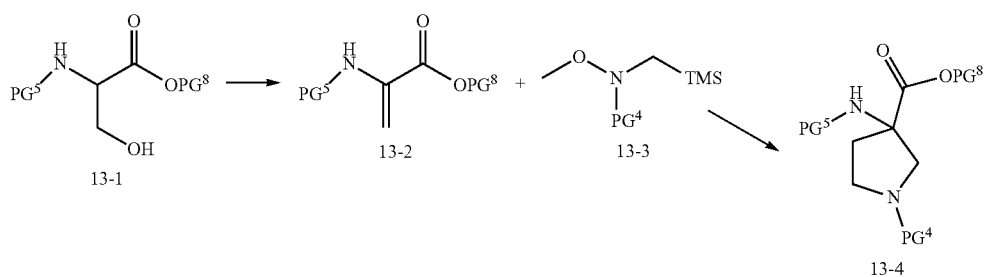

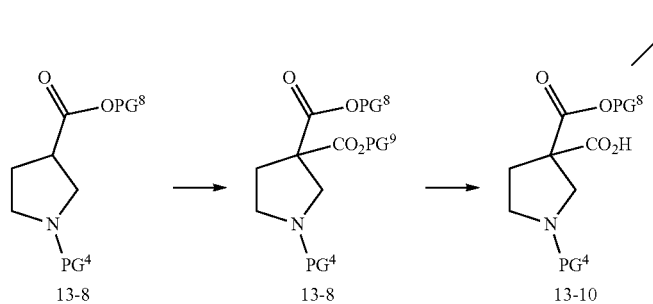

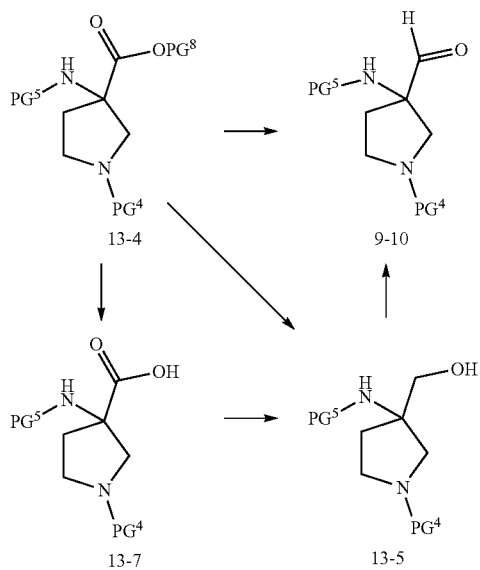

Scheme 14 describes a method for synthesizing compounds of formula 10-8 (a sub-type of 9-10 where stereochemistry is defined) and related intermediates. Racemic versions or mixtures of compounds of formula 13-4 can be separated into single enantiomers using supercritical fluid chromatography or reversed-phase chromatography with a chiral column or when $PG^4$ or $PG^5$ is a protecting group that doesn't eliminate the basicity of the nitrogen it is connected to may be also be separated using a chiral acid under classical resolution conditions to provide compounds of formula 14-4. Alternatively, compounds of formula 13-9 may be exposed to a variety of biocatalytic conditions such as Esterase ECSO3 (AB 503574) from Enzymicals or using those described in *Tetrahedron: Asymmetry* 1998, 9, 2663 to form compounds of general formula 14-1 (a sub-type of compounds of formula 13-10). Compounds of general formula 14-1 and 14-4 can be transformed to their analogous compounds described in Scheme 13 using the conditions described without any needed modifications or changes to the reaction conditions.

Scheme 14

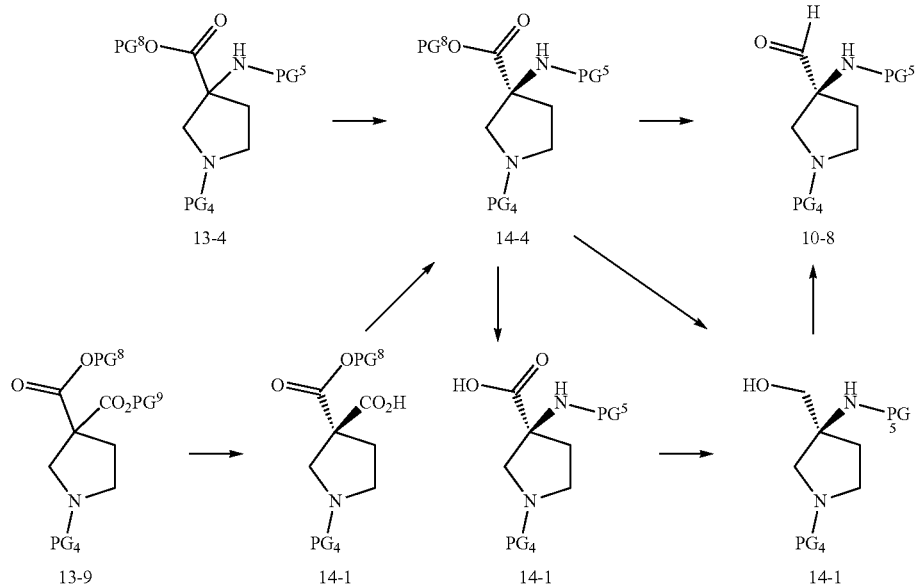

Scheme 15 describes a synthesis of 15-4 (a subtype of compounds of formula 8-4 where $X^1$ is CH—CH$_3$). Compounds of formula 11-1 can be reacted with ammonia and an allylboron reagent as described in *Chem. Commun.* 2005, 44, 5551 to form compounds of formula 15-1. Compounds of formula 15-1 can be reacted in an analogous method as described for the transformation of compounds of formulas 9-12 to 9-15 to provide compounds of formula 15-2. Compounds of 15-2 can be reacted in an analogous method to the transformation of compounds for formulas 9-15 to 9-5 to provide compounds of formula 15-3 with concomitant rearrangement to the internal olefin as shown. Compounds of formula 15-3 can be transformed into compounds of formula 15-4 using analogous methods described for the transformation of compounds of formula 9-5 to 9-4. Alternatively, compounds of formula 15-2 can be reacted with ozonolysis conditions in the presence of sodium borohydride or other oxidative cleavage conditions to provide compounds of formula 15-7. Compounds of formula 15-7 can be reacted under conditions that eliminate a hydroxyl group to an olefin such as using methanesulfonyl chloride or p-toluenesulfonyl chloride followed by a strong base, or by using Grieco elimination conditions with an arylselenocyanate in the presence of a trialkylphopshine to provide compounds of formula 15-8 (which is a sub-type of compounds of formula 9-15 where PG$^5$ is H).

Scheme 15

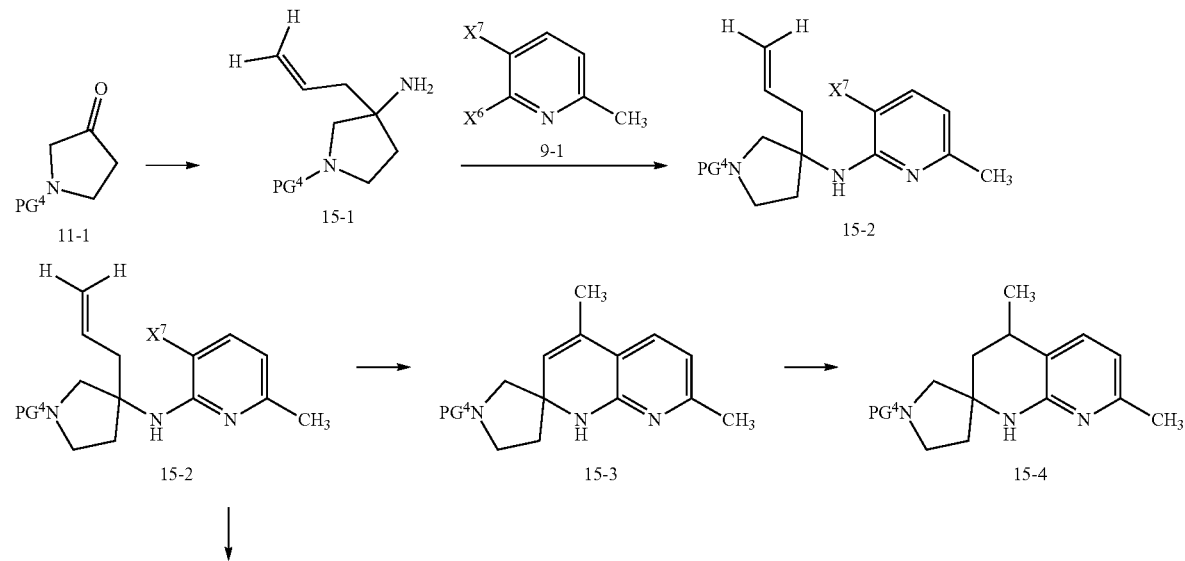

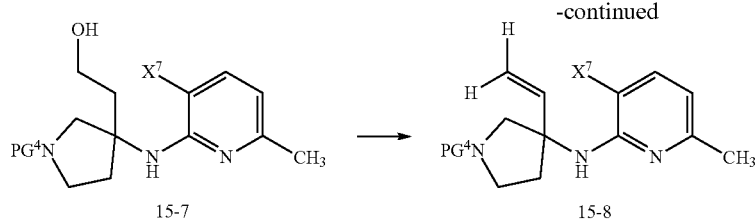

Scheme 16 describes the synthesis of compounds of formula 16-3 (where $Y^7$ is N or CH), 16-7, 16-11, and 16-14 which are all sub-types of 8-9 that may not be commercially available. Compounds of formula 16-1 can be reacted with an electrophilic halogen source in an analogous manner to the transformation of compounds of formulas 8-1 to 8-3 to form compounds of formula 16-2. Compounds of formula 16-2 can reacted under analogous conditions to the transformation of compounds of formulas 7-2 to 7-3 (when $R^{12}$ is H) or compounds of formulas 7-2 to 7-4 (when $R^{12}$ is F) to produce compounds of formula 16-3. Compounds of formula 16-4 (where $X^9$ can be a halogen that is the same as $X^5$ or can be more reactive such that $X^9$ is Br when $X^5$ is Cl, or $X^9$ is I when $X^5$ is Br or Cl) can be reacted under Chan-Lam-type conditions with cyclopropylboronic acid (when $R^{13}$ is cyclopropyl) and a copper source such as copper(II) acetate or others and appropriate ligands such as 2,2'-bipyridine, and any number of bases such as carbonates or amines and a co-oxidant like oxygen that can be added or come from the air to produce compounds of formula 16-5. Compounds of formula 16-5 (which can be purchased such as when $R^{13}$ is methyl or made as described herein or in the literature) can be reacted under metal-halogen exchange conditions such as isopropylmagnesium chloride, n-butyllithium, magnesium, or others and quenched with a carbonyl source such as N,N-dimethylformamide, morpholine-4-carbaldehyde, or others to produce compounds of formula 16-6. Compounds of formula 16-6 can be reacted under analogous conditions as the transformation of compounds of formulas 7-7 to 7-8 to produce compounds of formula 16-7. Compounds of formula 16-4 can be reacted with 4-halo-1-butene in the presence of a base such as potassium carbonate, sodium bicarbonate, sodium hydride, lithium diisopropylamide, or others to produce compounds of formula 16-8. Compounds of formula 16-8 can be reacted under Heck-like conditions as described for the transformation of compounds of formula 9-15 to 9-5 to produce compounds of formula 16-9. Compounds of formula 16-9 can be reacted through several steps in a similar manner as described for the sequence that transforms compounds of formula 7-6 to 7-7 then 7-8 to form compounds of formula 16-10 and 16-11. Compounds of formula 16-12 (where $X^{10}$ can be Cl, Br, or I, OTf, or others) can be reacted with palladium on carbon or other common catalysts and deuterium gas (or other deuteride source such as deuterated formate under transfer hydrogenation conditions) to form compounds of formula 16-13. Compounds of formula 16-13 can be reacted under similar Sandmeyer-type conditions as described for the transformation of compounds of formula 12-8 to 9-1 to produce compounds of formula 16-14. Alternatively, compounds of formula 16-15 can be reacted under similar Sandmeyer-type conditions as described for the transformation of compounds of formula 12-8 to 9-1.

Scheme 16

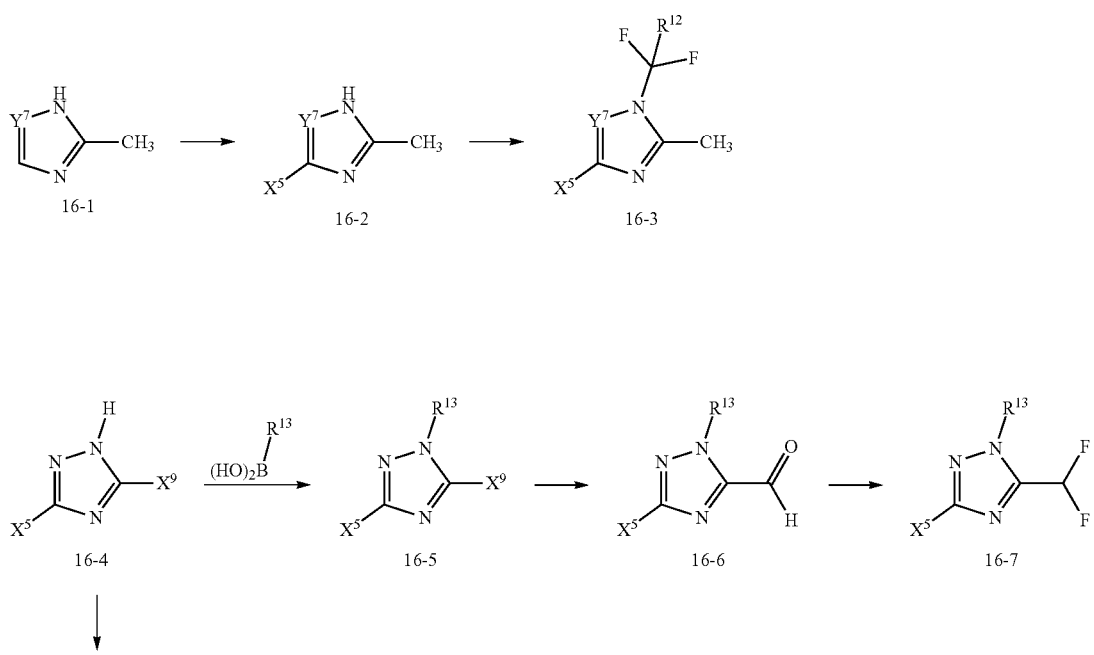

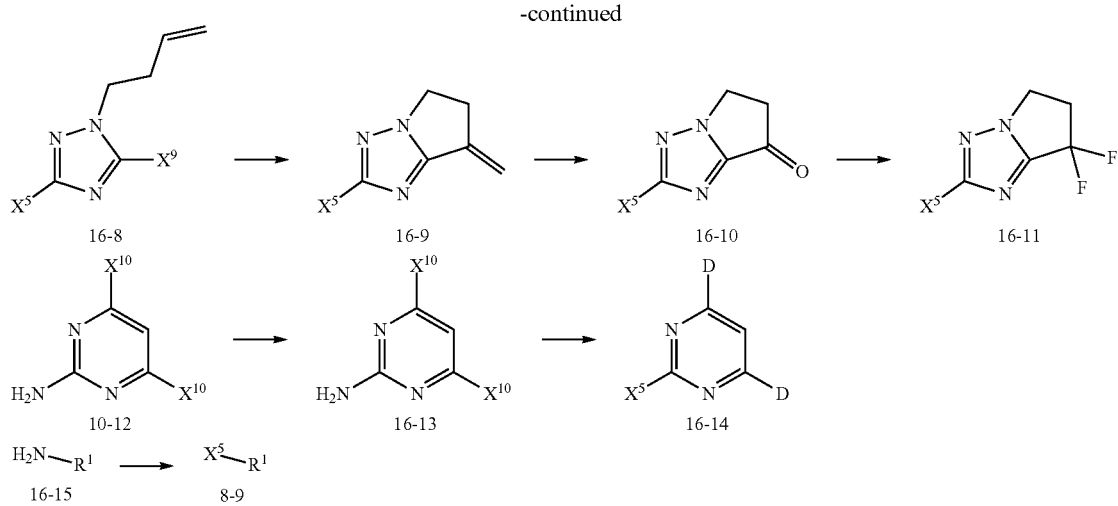

Scheme 17 describes a method of synthesis of compounds of formula 17-5 that are a sub-type of compounds of formula 8-4 where $R^1$ is a tetrazole substituted with $R^{14}$ that can be an optionally substituted alkyl or aryl group. Compounds of formula 17-1 can be reacted through an analogous transformation as described for the syntheses of compounds of formula 7-5 to 7-6 and 7-7 to form compounds of formula 17-2 and 17-3. Alternatively, compounds of formula 17-1 can be transformed to compounds of formula 17-3 directly in an analogous manner for the transformation of compounds of formula 16-5 to compounds of formula 16-6. Compounds of formula 17-3 can be reacted with substituted hydrazines under standard condensation conditions using acid or base catalysis to form compounds of formula 17-4. Compounds of formula 17-4 can be reacted with diazo compounds such as diethyl or di-tert-butyl azodicarboxylate in the presence of hypervalent iodine sources such as [bis(trifluoroacetoxy)iodo]benzene or others to produce compounds of formula 17-5.

Scheme 17

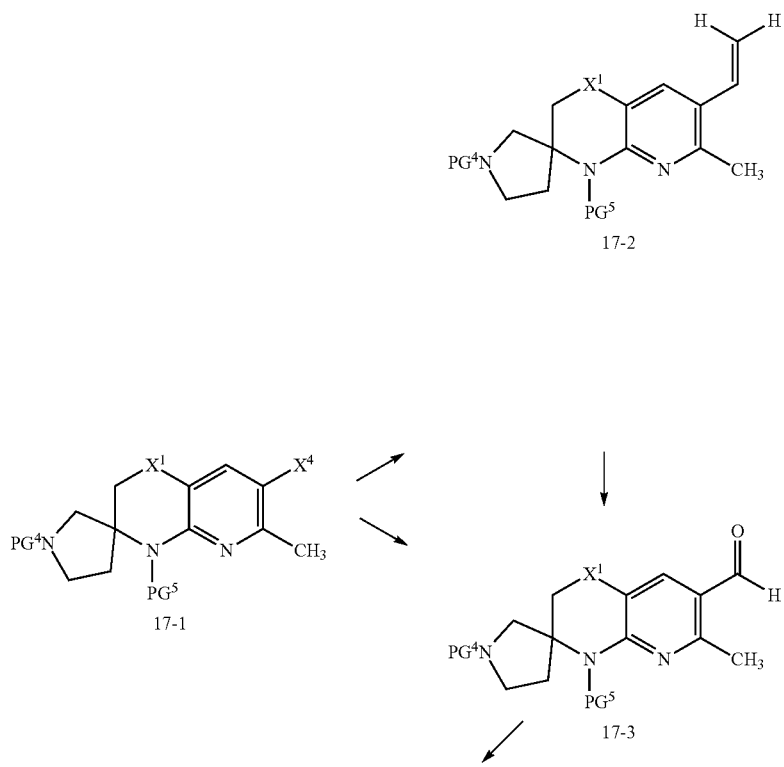

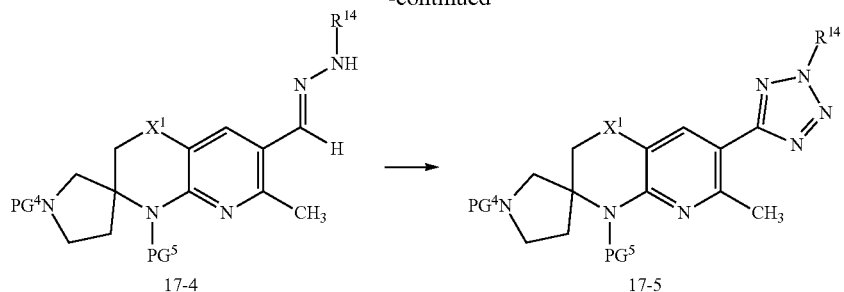

17-4 → 17-5

A detailed description of the individual reaction steps is provided in the Example section below. Those skilled in the art will appreciate that other synthetic routes may be used to synthesize the compounds. Although specific starting materials and reagents are discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

COMBINATION AGENTS

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect. The phrases "concurrent administration," "co-administration," "simultaneous administration," and "administered simultaneously" mean that the compounds are administered in combination. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/disorder/condition (e.g., cachexia, anorexia, anorexia nervosa, nausea; emesis, failure to thrive, sarcopenia, muscle wasting, frailty, osteoporosis, bone loss, pain, anxiety, depression, or hypertension).

In some embodiments, a compound of this invention may be co-administered with one or more other agents such as Orlistat, TZDs and other insulin-sensitizing agents, FGF21 analogs, Metformin, Omega-3-acid ethyl esters (e.g., Lovaza), Fibrates, HMG CoA-reductase Inhibitors, Ezetimibe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 inhibitors (including dapagliflozin, canagliflozin, empagliflozin, tofogliflozin, ertugliflozin, ASP-1941, THR1474, TS-071, ISIS388626 and LX4211 as well as those in WO2010023594), Phentermine, Topiramate, GLP-1 receptor agonists, GIP receptor agonists, dual GLP-1 receptor/glucagon receptor agonists (e.g., OPK88003, MED10382, JNJ-64565111, NN9277, BI 456906), dual GLP-1 receptor/GIP receptor agonists [e.g., Tirzepatide (LY3298176), NN9423], Angiotensin-receptor blockers, an acetyl-CoA carboxylase (ACC) inhibitor, a BCKDK inhibitor, a ketohexokinase (KHK) inhibitor, ASK1 inhibitors, branched-chain alpha-keto acid dehydrogenase kinase inhibitors (BCKDK inhibitors), inhibitors of CCR2 and/or CCR5, PNPLA3 inhibitors, DGAT1 inhibitors, DGAT2 inhibitors, an FGF21 analog, FGF19 analogs, PPAR agonists, FXR agonists, AMPK activators [e.g., ETC-1002 (bempedoic acid)], SCD1 inhibitors or MPO inhibitors.

Exemplary GLP-1 receptor agonists include liraglutide, albiglutide, exenatide, albiglutide, lixisenatide, dulaglutide, semaglutide, HM15211, LY3298176, Medi-0382, NN-9924, TTP-054, TTP-273, efpeglenatide, those described in WO2018109607, those described in PCT/IB2019/054867 filed Jun. 11, 2019, and those described in PCT/IB2019/054961 filed Jun. 13, 2019, including the following:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6- carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2;
2-[(4-{2-[(4-chloro-2-fluorobenzyl)oxy]pyridin-3-yl}piperidin-1-yl)methyl]-1-[(2S)-oxetan-2-ylmethyl]-1H-benzimidazole-6-carboxylic acid;
2-[(4-{2-[(4-chloro-2-fluorobenzyl)oxy]pyridin-3-yl}piperidin-1-yl)methyl]-1-(1,3-oxazol-2-ylmethyl)-1H-benzimidazole-6-carboxylic acid;
2-[(4-{2-[(4-cyano-2-fluorobenzyl)oxy]pyridin-3-yl}piperidin-1-yl)methyl]-1-(1,3-oxazol-2-ylmethyl)-1H-benzimidazole-6-carboxylic acid;
2-[(4-{2-[(4-cyano-2-fluorobenzyl)oxy]pyridin-3-yl}piperidin-1-yl)methyl]-1-[(2S)-oxetan-2-ylmethyl]-1H-benzimidazole-6-carboxylic acid;
2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylic acid;
2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylic acid;
2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylic acid;
2-(6-{2-[(4-chloro-2-fluorobenzyl)oxy]-5-fluoropyrimidin-4-yl}-6-azaspiro[2.5]oct-1-yl)-1-(1,3-oxazol-2-ylmethyl)-1H-benzimidazole-6-carboxylic acid;
2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylic acid;
2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylic acid;
2-[(4-{2-[(4-chloro-2-fluorobenzyl)oxy]pyrimidin-4-yl}piperidin-1-yl)methyl]-1-[(2S)-oxetan-2-ylmethyl]-1H-benzimidazole-6-carboxylic acid;
2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylic acid;
2-{[(2S)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylic acid; and
2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, and pharmaceutically acceptable salts thereof.

Exemplary ACC inhibitors include 4-(4-[(1-isopropyl-7-oxo-1,4,6,7-tetrahydro-1'H-spiro[indazole-5,4'-piperidin]-1'-yl)carbonyl]-6-methoxypyridin-2-yl)benzoic acid, gemcabene, and firsocostat (GS-0976) and pharmaceutically acceptable salts thereof.

Exemplary FXR agonists include tropifexor (2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid), cilofexor (GS-9674), obeticholic acid, LY2562175, Met409, TERN-101 and EDP-305 and pharmaceutically acceptable salts thereof.

Exemplary KHK inhibitors include [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid and pharmaceutically acceptable salts thereof.

Exemplary DGAT2 inhibitors include (S)-2-(5-((3-ethoxypyridin-2-yl)oxy)pyridin-3-yl)-N-(tetrahydrofuran-3-yl)pyrimidine-5-carboxamide [including its crystalline solid forms (Form 1 and Form 2)]. See U.S. Pat. No. 10,071,992.

Exemplary BCKDK inhibitors include those described in U.S. Ser. No. 62/868,057 filed Jun. 28, 2019 and U.S. Ser. No. 62/868,542 filed Jun. 28, 2019 including the following:
5-(5-chloro-4-fluoro 3-methylthiophen-2-yl)-1H-tetrazole;
5-(5-chloro-3-difluoromethylthiophen-2-yl)-1H-tetrazole;
5-(5-fluoro-3-methylthiophen-2-yl)-1H-tetrazole;
5-(5-chloro-3-methylthiophen-2-yl)-1H-tetrazole;
5-(3,5-dichlorothiophen-2-yl)-1H-tetrazole;
5-(4-bromo-3-methylthiophen-2-yl)-1H-tetrazole;
5-(4-bromo-3-ethylthiophen-2-yl)-1H-tetrazole;
5-(4-chloro-3-ethylthiophen-2-yl)-1H-tetrazole;
3-chloro-5-fluorothieno[3,2-b]thiophene-2-carboxylic acid;
3-bromo-5-fluorothieno[3,2-b]thiophene-2-carboxylic acid;
3-(difluoromethyl)-5-fluorothieno[3,2-b]thiophene-2-carboxylic acid;
5,6-difluorothieno[3,2-b]thiophene-2-carboxylic acid; and
3,5-difluorothieno[3,2-b]thiophene-2-carboxylic acid;
or a pharmaceutically acceptable salt thereof.

In some embodiments, a compound of this invention may be co-administered with one or more anti-diabetic agents. Suitable anti-diabetic agents include insulin, metformin, GLP-1 receptor agonists (described herein above), an acetyl-CoA carboxylase (ACC) inhibitor (described herein above), SGLT2 inhibitors (described herein above), monoacylglycerol O-acyltransferase inhibitors, phosphodiesterase (PDE)-10 inhibitors, AMPK activators [e.g., ETC-1002 (bempedoic acid)], sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, α-amylase inhibitors (e.g., tendamistat, trestatin and AL-3688), an α-glucoside hydrolase inhibitor (e.g., acarbose), α-glucosidase inhibitors (e.g., adiposine, camiglibose, emiglitate, miglitol, voglibose, pradimicin-Q, and salbostatin), PPARγ agonists (e.g., balaglitazone, ciglitazone, darglitazone, englitazone, isaglitazone, pioglitazone and rosiglitazone), PPAR α/γ agonists (e.g., CLX-0940, GW-1536, GW-1929, GW-2433, KRP-297, L-796449, LR-90, MK-0767 and SB-219994), protein tyrosine phosphatase-1B (PTP-1B) inhibitors [e.g., trodusquemine, hyrtiosal extract, and compounds disclosed by Zhang, S. et al., *Drug Discovery Today*, 12(9/10), 373-381 (2007)], SIRT-1 activators (e.g., resveratrol, GSK2245840 or GSK184072), dipeptidyl peptidase IV (DPP-IV) inhibitors (e.g., those in WO2005116014, sitagliptin, vildagliptin, alogliptin, dutogliptin, linagliptin and saxagliptin), insulin secretagogues, fatty acid oxidation inhibitors, A2 antagonists, c-jun amino-terminal kinase (JNK) inhibitors, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, insulin mimetics, glycogen phosphorylase inhibitors (e.g., GSK1362885), VPAC2 receptor agonists, glucagon receptor modulators such as those described in Demong, D. E. et al., *Annual Reports in Medicinal Chemistry* 2008, 43, 119-137, GPR119 modulators, particularly agonists, such as those described in WO2010140092, WO2010128425, WO2010128414, WO2010106457, Jones, R. M. et al., *Annual Reports in Medicinal Chemistry* 2009, 44, 149-170 (e.g., MBX-2982, GSK1292263, APD597 and PSN821), FGF21 derivatives or analogs such as those described in Kharitonenkov, A. et al., *Current Opinion in Investigational Drugs* 2009, 10(4)359-364, TGR5 (also termed GPBAR1) receptor modulators, particularly agonists, such as those described in Zhong, M., *Current Topics in Medicinal Chemistry,* 2010, 10(4), 386-396 and INT777, GPR40 agonists, such as those described in Medina, J. C., *Annual Reports in Medicinal Chemistry,* 2008, 43, 75-85, including but not limited to TAK-875, GPR120 modulators, particularly agonists, high-affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611.

Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g., SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. *Expert Opin. Ther. Pat.,* 2010, 20(12), 1627-51.

The compounds of the present invention may be co-administered with anti-heart failure agents such as ACE inhibitors (e.g., captopril, enalapril, fosinopril, lisinopril, perindopril, quinapril, ramipril, trandolapril), Angiotensin II receptor blockers (e.g., candesartan, losartan, valsartan), Angiotensin-receptor neprilysin inhibitors (sacubitril/valsartan), I$_f$ channel blocker Ivabradine, Beta-Adrenergic blocking agents (e.g., bisoprolol, metoprolol succinate, carvedilol), Aldosterone antagonists (e.g., spironolactone, eplerenone), hydralazine and isosorbide dinitrate, diuretics (e.g., furosemide, bumetanide, torsemide, chlorothiazide, amiloride, hydrochlorothiazide, Indapamide, Metolazone, Triamterene), or digoxin.

The compounds of the present invention may also be co-administered with cholesterol or lipid lowering agents including the following exemplary agents: HMG CoA reductase inhibitors (e.g., pravastatin, pitavastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates (e.g., gemfibrozil, pemafibrate, fenofibrate, clofibrate); bile acid sequestrants (such as questran, colestipol, colesevelam); ACAT inhibitors; MTP inhibitors; lipooxygenase inhibitors; cholesterol absorption inhibitors (e.g., ezetimibe); nicotinic acid agents (e.g., niacin, niacor, slo-niacin); omega-3 fatty acids (e.g., epanova, fish oil, eicosapentaenoic acid); cholesteryl ester transfer protein inhibitors (e.g., obicetrapib) and PCSK9 modulators [e.g., alirocumab, evolocumab, bococizumab, ALN-PCS (inclisiran)].

The compounds of the present invention may also be used in combination with antihypertensive agents and such antihypertensive activity is readily determined by those skilled in the art according to standard assays (e.g., blood pressure measurements). Examples of suitable anti-hypertensive agents include: alpha-adrenergic blockers; beta-adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a compound of invention may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of the invention may be co-administered with a loop diuretic. In still another embodiment, the loop diuretic is selected from furosemide and torsemide. In still another embodiment, one or more compounds of Formula I or their pharmaceutically acceptable salts may be co-administered with furosemide. In still another embodiment, one or more compounds of Formula I or their pharmaceutically acceptable salts may be co-administered with torsemide which may optionally be a controlled or modified release form of torsemide.

In another embodiment, a compound of the invention may be co-administered with a thiazide-type diuretic. In still another embodiment, the thiazide-type diuretic is selected from the group consisting of chlorothiazide and hydrochlorothiazide. In still another embodiment, one or more compounds of Formula I or their pharmaceutically acceptable salts may be co-administered with chlorothiazide. In still another embodiment, one or more compounds of Formula I or their pharmaceutically acceptable salts may be co-administered with hydrochlorothiazide.

In another embodiment, one or more compounds of Formula I or their pharmaceutically acceptable salts may be co-administered with a phthalimidine-type diuretic. In still another embodiment, the phthalimidine-type diuretic is chlorthalidone.

Examples of suitable mineralocorticoid receptor antagonists include sprionolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCl, stenting, drug-eluting stents, stem cell therapy and medical devices such as implanted pacemakers, defibrillators, or cardiac resynchronization therapy.

Particularly when provided as a single dosage unit, the potential exists for a chemical interaction between the combined active ingredients. For this reason, when a compound of this invention and a second therapeutic agent are combined in a single dosage unit they are formulated such that although the active ingredients are combined in a single dosage unit, the physical contact between the active ingredients is minimized (that is, reduced). For example, one active ingredient may be enteric-coated. By enteric-coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained release throughout the gastrointestinal tract and also serves to minimize physical contact between the combined active ingredients. Furthermore, the sustained-released component can be additionally enteric-coated such that the release of this component occurs only in the intestine. Still another approach would involve the formulation of a combination product in which the one component is coated with a sustained and/or enteric-release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In combination therapy treatment, both the compounds of this invention and the other drug therapies are administered to mammals (e.g., humans, male or female) by conventional methods. A compound of Formula I or a salt thereof is adapted to therapeutic use as agents that antagonize (including inhibit) MC4R in mammals, particularly humans, and thus are useful for the treatment of the various conditions (e.g., those described herein) in which such action is implicated.

The disease/disorder/condition that can be treated in accordance with the present invention include, but are not limited to cachexia (e.g., cachexia associated with cancer, AIDS, CHF, and/or CKD); anorexia/anorexia nervosa (e.g., geriatric anorexia, anorexia associated with chemotherapy and/or radiotherapy); nausea; emesis; weight loss (e.g., involuntary weight loss); failure to thrive; sarcopenia; muscle wasting; frailty; osteoporosis; bone disorders (e.g., bone loss); pain; neuropathic pain; anxiety; depression; hypertension; malnutrition; obesity; sexual dysfunction; and inflammatory disease.

Administration of the compounds of this invention can be via any method which delivers a compound of this invention systemically and/or locally. These methods include oral routes, parenteral, intraduodenal routes, buccal, intranasal, etc. Generally, the compounds of this invention are administered orally, but parenteral administration (e.g., intravenous, intramuscular subcutaneous or intramedullary) may be utilized, for example, where oral administration is inappropriate for the target or where the patient is unable to ingest the drug.

For administration to human patients, an oral daily dose of the compounds herein may be, for example, in the range 0.01 mg to 5000 mg depending, of course, on the mode of and frequency of administration, the disease state, and the age and condition of the patient, etc. An oral daily dose is in the range of 1 mg to 2000 mg (e.g 3 mg to 2000 mg) may be used. A further oral daily dose is in the range of 5 mg to 1000 mg. For convenience, the compounds of the present invention can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 300, 500, or 1000 mg of the compound of the present invention.

The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

According to the methods of treatment of the invention, a compound of the present invention or a combination of a compound of the present invention and at least one additional pharmaceutical agent (referred to herein as a "combination") is administered to a subject in need of such treatment, preferably in the form of a pharmaceutical composition. In the combination aspect of the invention, the compound of the present invention and at least one other pharmaceutical agent (e.g., another anti-cachexia or anti-anorexia agent) may be administered either separately or in a pharmaceutical composition comprising both. It is generally preferred that such administration be oral.

When a combination of a compound of the present invention and at least one other pharmaceutical agent are administered together, such administration may be sequential in time or simultaneous. In some embodiments, simultaneous administration of drug combinations is used. For separate or sequential administration, a compound of the present invention and the additional pharmaceutical agent may be administered in any order and each of them can be administered in an independent frequency or dose regimen. In some embodiments, such administration be oral. In some embodiments, such administration can be oral and simultaneous. When a compound of the present invention and the additional pharmaceutical agent are administered sequentially, the administration of each may be by the same or by different methods.

According to the methods of the invention, a compound of the present invention or a combination can be administered in the form of a pharmaceutical composition. Accordingly, a compound of the present invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone or be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington, J. P., The Science and Practice of Pharmacy, Lippincott Williams and Wilkins, Baltimore, Md. $20^{th}$ ed., 2000.

Compositions suitable for parenteral injection generally include pharmaceutically acceptable, sterile, aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or one or more lubricants (e.g., talc, calcium stearate, magnesium stearate, stearic acid, polyoxyl stearate, cetanol, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyol® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate, i.e., triacetin, from Abitec), Capmul™ MCM (medium chain mono- and diglycerides, from Abitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium-chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Some of the present compounds may be poorly soluble in water, e.g., less than about 1 μg/mL. Therefore, liquid compositions in solubilizing, non-aqueous solvents such as the medium-chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder X-ray diffraction (PXRD) crystallography, solid-state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g., 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high-temperature fusion, solvent-modified fusion and melt-congeal processes; and solvent processes including non-solvent precipitation, spray coating and spray drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoa.sup.(R)-LF, Aqoat.sup.(R)-MF and Aqoat.sup.(R)-HF respectively from Shin-Etsu Chemical Co., LTD, Tokyo, Japan. The higher MF and HF grades are generally preferred.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjuction with the Formula I compounds or their salts is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The present invention further comprises use of a compound of Formula I or its pharmaceutically acceptable salt for use as a medicament (such as a unit dosage tablet or unit dosage capsule). In another embodiment, the present invention comprises the use of a compound of Formula I or its pharmaceutically acceptable salt for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the compound of the invention, which matrices are in the form of shaped articles, e.g., films, or microcapsules. Examples of sustained-release matrices include polyesters, hydrogels [for example, poly(2-hydroxyethyl-methacrylate), or 'poly(vinylalcohol)], polylactides (U.S. Pat. No. 3,773,919), copolymers of L-glutamic acid and ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

The compounds herein may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see Remington, The Science and Practice of Pharmacy, 20th Edition (Lippincott Williams & Wilkins, 2000).

Pharmaceutical compositions according to the invention may contain 0.1% to 95% of the compound(s) of this invention, preferably 1% to 70%. In any event, the composition to be administered will contain a quantity of a compound(s) according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I or its pharmaceutically acceptable salt or a prodrug thereof or a salt of such compound or prodrug and a second compound as described above. The kit comprises a means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Also, as the present invention has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

The active ingredient may be formulated as a solid dispersion or as a self-emulsified drug delivery system (SEDDS) with pharmaceutically acceptable excipients.

The active ingredient may be formulated as an immediate release or controlled (e.g. suspended, delayed, or extended) release tablet or capsule. Alternatively, the active ingredient may be delivered as the active ingredient alone within a capsule shell, without additional excipients.

EXAMPLES

The following illustrate the synthesis of various compounds of the present invention. Additional compounds within the scope of this invention may be prepared using the methods illustrated in these Examples, either alone or in combination with techniques generally known in the art. All starting materials in these Preparations and Examples are either commercially available or can be prepared by methods known in the art or as described herein.

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. In some cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Other commercial solvents and reagents were used without further purification. For syntheses referencing procedures in other Examples or Methods, reaction conditions (reaction time and temperature) may vary. Products were generally dried under vacuum before being carried on to further reactions or submitted for biological testing.

When indicated, reactions were heated by microwave irradiation using Biotage Initiator or Personal Chemistry Emrys Optimizer microwaves. Reaction progress was monitored using thin-layer chromatography (TLC), liquid chromatography-mass spectrometry (LCMS), high-performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with iodine, potassium permanganate, cobalt(II) chloride, phosphomolybdic acid, and/or ceric ammonium molybdate stains. LCMS data were acquired on an Agilent 1100 Series instrument with a Leap Technologies autosampler, Gemini C18 columns, acetonitrile/water gradients, and either trifluoroacetic acid, formic acid, or ammonium hydroxide modifiers. The column eluent was analyzed using a Waters ZQ mass spectrometer scanning in both positive and negative ion modes from 100 to 1200 Da. Other similar instruments were also used. HPLC data were generally acquired on an Agilent 1100 Series instrument, using the columns indicated, acetonitrile/water gradients, and either trifluoroacetic acid or ammonium hydroxide modifiers. GCMS data were acquired using a Hewlett Packard 6890 oven with an HP 6890 injector, HP-1 column (12 m×0.2 mm×0.33 µm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC), generally using Berger or Thar instruments; columns such as ChiralPAK-AD, -AS, -IC, Chiralcel-OD, or -OJ columns; and $CO_2$ mixtures with methanol, ethanol, 2-propanol, or acetonitrile, alone or modified using trifluoroacetic acid or propan-2-amine. UV detection was used to trigger fraction collection. For syntheses referencing procedures in other Examples or Methods, purifications may vary: in general, solvents and the solvent ratios used for eluents/gradients were chosen to provide appropriate $R_f$s or retention times.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy ($^1$H NMR) chemical shifts are given in parts per million downfield from tetramethylsilane and were recorded on 300, 400, 500, or 600 MHz Varian, Bruker, or Jeol spectrometers. Chemical shifts are expressed in parts per million (ppm, δ) referenced to the deuterated solvent residual peaks (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). The peak shapes are described as follows: s, singlet; d, doublet; t, triplet; q, quartet; quin, quintet; m, multiplet; br s, broad singlet; app, apparent. Analytical SFC data were generally acquired on a Berger analytical instrument as described above. Optical rotation data were acquired on a PerkinElmer model 343 polarimeter using a 1 dm cell. Microanalyses were performed by Quantitative Technologies Inc. and were within 0.4% of the calculated values.

Unless otherwise noted, chemical reactions were performed at room temperature (about 23 degrees Celsius).

Unless noted otherwise, all reactants were obtained commercially and used without further purification, or were prepared using methods known in the literature.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. The term "TLC" refers to thin-layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra-performance liquid chromatography and "HPLC" refers to high-performance liquid chromatography, "SFC" refers to supercritical fluid chromatography.

Hydrogenation may be performed in a Parr shaker under pressurized hydrogen gas, or in Thales-nano H-Cube flow hydrogenation apparatus at full hydrogen and a flow rate between 1-2 mL/min at specified temperature.

HPLC, UPLC, LCMS, GCMS, and SFC retention times were measured using the methods noted in the procedures.

In some examples, chiral separations were carried out to separate enantiomers or diastereomers of certain compounds of the invention (in some examples, the separated enantiomers are designated as ENT-1 and ENT-2, according to their order of elution; similarly, separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

The compounds and intermediates described below were named using the naming convention provided with ACD/ChemSketch 2017.2.1, File Version C40H41, Build 99535

(Advanced Chemistry Development, Inc., Toronto, Ontario, Canada). The naming convention provided with ACD/ChemSketch 2017.2.1 is well known by those skilled in the art and it is believed that the naming convention provided with ACD/ChemSketch 2017.2.1 generally comports with the IUPAC (International Union for Pure and Applied Chemistry) recommendations on Nomenclature of Organic Chemistry and the CAS Index rules.

The $^1$H NMR spectra of many of the compounds herein indicate a mixture of rotamers, due to the presence of amide and/or carbamate functionality, and have been tabulated to reflect the presence of more than one rotamer.

PREPARATIONS

Preparations P1-P33 describe preparations of some starting materials or intermediates used for preparation of certain compounds of the invention.

Preparation P1
2-(5-Chloro-2-methoxypyridin-4-yl)propanoic acid (P1)

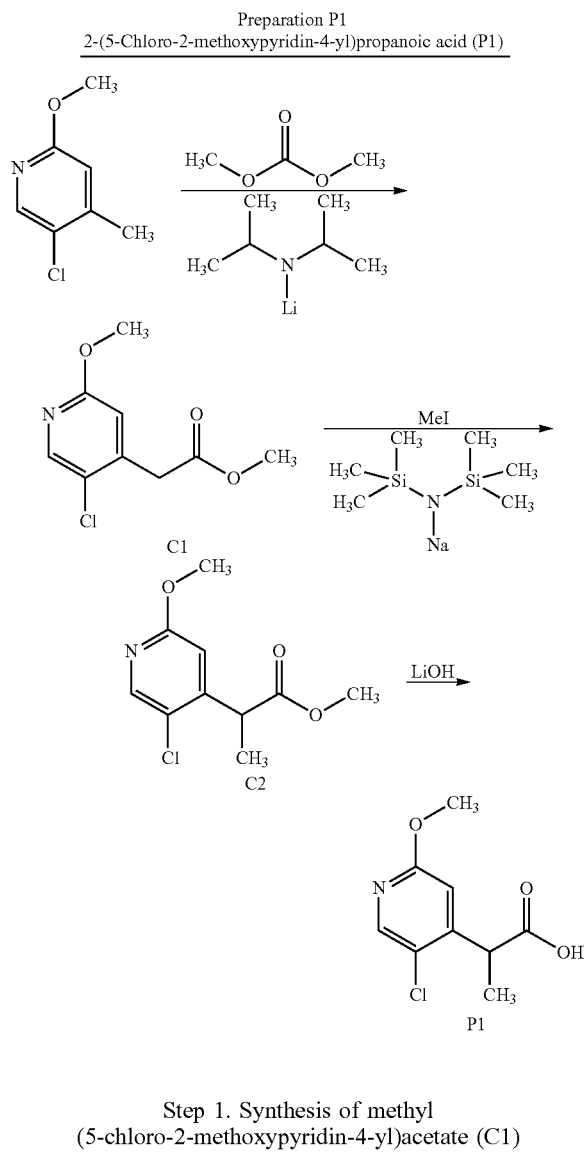

Step 1. Synthesis of methyl (5-chloro-2-methoxypyridin-4-yl)acetate (C1)

A solution of lithium diisopropylamide in tetrahydrofuran (2 M; 1.9 L, 3.8 mol) was added in a drop-wise manner to a −30° C. solution of 5-chloro-2-methoxy-4-methylpyridine (197 g, 1.25 mol) in tetrahydrofuran (1.4 L). After the reaction mixture had been stirred at −30° C. for 1 hour, dimethyl carbonate (338 g, 3.75 mol) was added drop-wise; at the end of the addition, the reaction mixture was warmed to 25° C. and stirred for 1 hour. It was then poured into hydrochloric acid (0.5 M, 7 L, 3.5 mol) and extracted with ethyl acetate (2×1.5 L); the combined organic layers were washed with saturated aqueous sodium chloride solution, dried over sodium sulfate, filtered, and concentrated in vacuo. Purification via silica gel chromatography (Gradient: 0% to 20% ethyl acetate in petroleum ether) provided C1 as a yellow oil. Yield: 203 g, 0.941 mol, 75%. LCMS m/z 216.1 (chlorine isotope pattern observed) [M+H]$^+$. $^1$H NMR (400 MHz, methanol-d$_4$) δ 8.10 (s, 1H), 6.82 (s, 1H), 3.90 (s, 3H), 3.79 (s, 2H), 3.71 (s, 3H).

Step 2. Synthesis of methyl 2-(5-chloro-2-methoxypyridin-4-yl)propanoate (C2)

To a −78° C. solution of C1 (175 g, 0.812 mol) in tetrahydrofuran (1.2 L) was added a solution of sodium bis(trimethylsilyl)amide in tetrahydrofuran (2 M; 455 mL, 0.910 mol) in a drop-wise manner. The reaction mixture was stirred at −78° C. for 1 hour, whereupon a solution of iodomethane (172.6 g, 1.216 mol) in tetrahydrofuran (100 mL) was added drop-wise at −78° C., and stirring was continued at this temperature for 2 hours. The reaction mixture was then poured into saturated aqueous ammonium chloride solution (500 mL) and extracted with ethyl acetate (2×100 mL); the combined organic layers were washed with saturated aqueous sodium chloride solution, dried over sodium sulfate, filtered, and concentrated in vacuo to provide C2 as a brown oil. By NMR and LCMS analysis, this material was contaminated with some of the dimethylated side product methyl 2-(5-chloro-2-methoxypyridin-4-yl)-2-methylpropanoate. Yield: 136 g, 50.592 mol, 573%. LCMS m/z 230.1 (chlorine isotope pattern observed) [M+H]$^+$. $^1$H NMR (400 MHz, methanol-d$_4$), product peak only: δ 8.10 (s, 1H), 6.76 (s, 1H), 4.10 (q, J=7.2 Hz, 1H), 3.89 (s, 3H), 3.69 (s, 3H), 1.48 (d, J=7.2 Hz, 3H).

Step 3. Synthesis of 2-(5-chloro-2-methoxypyridin-4-yl)propanoic acid (P1)

To a 25° C. solution of C2 (168 g, 0.732 mol) in tetrahydrofuran (1 L) was added, in a drop-wise manner, a solution of lithium hydroxide monohydrate (61.4 g, 0.146 mol) in water (300 mL) at 25° C. The mixture was stirred for 2 hours, whereupon it was concentrated in vacuo. The aqueous residue was poured into water (500 mL) and washed with tert-butyl methyl ether (2×500 mL). The aqueous layer was then adjusted to pH 4 by addition of 3 M hydrochloric acid and extracted with ethyl acetate (2×500 mL); the combined ethyl acetate layers were washed with saturated aqueous sodium chloride solution, dried over sodium sulfate, filtered, and concentrated under reduced pressure to provide P1 as a white solid. Yield: 122 g, 0.566 mol, 77%. LCMS m/z 216.1 (chlorine isotope pattern observed) [M+H]$^+$. $^1$H NMR (400 MHz, methanol-d$_4$) δ 8.10 (s, 1H), 6.79 (s, 1H), 4.06 (q, J=7.1 Hz, 1H), 3.89 (s, 3H), 1.48 (d, J=7.2 Hz, 3H).

Preparations P2 and P3
(2R)-2-(5-Chloro-2-methoxypyridin-4-yl)propanoic acid (P2) and (2S)-2-(5-Chloro-2-methoxypyridin-4-yl)propanoic acid (P3)

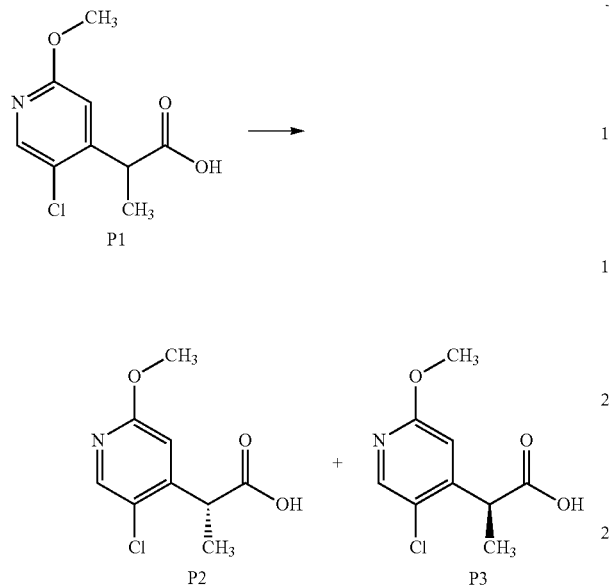

Separation of P1 (5.00 g, 23.2 mmol) into its component enantiomers was carried out via supercritical fluid chromatography (Column: Chiral Technologies Chiralpak IG, 30×250 mm, 5 μm; Mobile phase: 95:5 carbon dioxide/methanol; Flow rate: 80 mL/minute; Back pressure: 120 bar). The first-eluting enantiomer, an oil which solidified on standing, was designated as P2, and the second-eluting enantiomer as P3.

The indicated absolute stereochemistry was assigned via X-ray crystal structure determination of 15, which was synthesized using this lot of P2 (see below, Example 15, Alternate Step 3).

P2—Yield: 2.4 g, 11.1 mmol, 48%. $^1$H NMR (400 MHz, chloroform-d) δ 8.13 (s, 1H), 6.75 (s, 1H), 4.12 (q, J=7.2 Hz, 1H), 3.91 (s, 3H), 1.53 (d, J=7.2 Hz, 3H). Retention time: 3.98 minutes (Analytical conditions. Column: Chiral Technologies Chiralpak IG, 4.6×250 mm, 5 μm; Mobile phase A: carbon dioxide; Mobile phase B: methanol; Gradient: 5% B for 1.00 minute, then 5% to 60% B over 8 minutes; Flow rate: 3.0 mL/minute; Back pressure: 120 bar).

P3-Yield: 2.4 g, 11.1 mmol, 48%. Retention time: 4.22 minutes (Analytical conditions identical to those used for P2).

Preparations P4
Lithium 2-(6-methoxy-2-methylpyrimidin-4-yl)propanoate (P4)

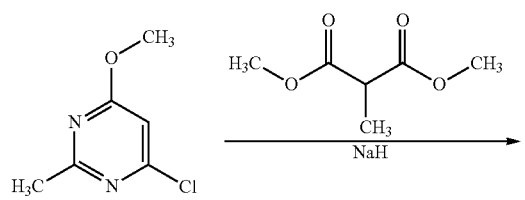

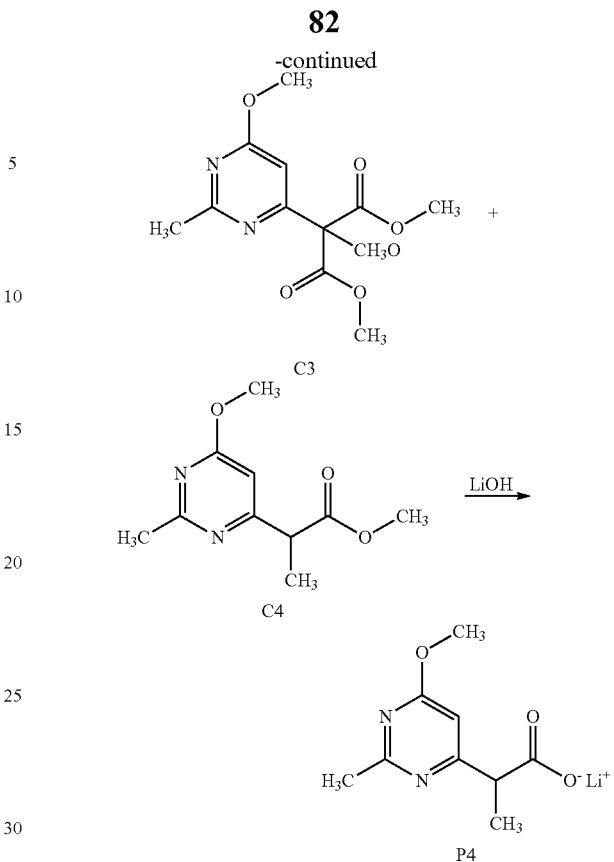

Step 1. Synthesis of dimethyl (6-methoxy-2-methylpyrimidin-4-yl)(methyl)propanedioate (C3) and methyl 2-(6-methoxy-2-methylpyrimidin-4-yl)propanoate (C4)

Sodium hydride (60% in mineral oil; 1.14 g, 28.5 mmol) was added to a solution of dimethyl methylpropanedioate (5.53 g, 37.8 mmol) in N,N-dimethylformamide (25 mL). After 30 minutes, 4-chloro-6-methoxy-2-methylpyrimidine (3.00 g, 18.9 mmol) was added, whereupon the reaction mixture was heated at 100° C. for 16 hours. It was then diluted with water (150 mL) and extracted with ethyl acetate (3×50 mL); the combined organic layers were washed with saturated aqueous sodium chloride solution, dried over sodium sulfate, filtered, concentrated in vacuo, and purified via silica gel chromatography (Gradient: 0% to 10% ethyl acetate in petroleum ether), affording the product (2.60 g) as a yellow oil. On the basis of NMR and LCMS analysis, this was judged to be an impure mixture of C3 and C4, which was taken directly into the following step. LCMS m/z 211.1 and 269.2 [M+H]$^+$. $^1$H NMR (400 MHz, methanol-d$_4$), characteristic peaks: δ 6.68 (s), 6.60 (s), 3.96 (s), 3.94 (s), 3.81 (q, J=7.2 Hz), 3.75 (s), 3.68 (s), 2.54 (s), 2.52 (s), 1.79 (s), 1.47 (d, J=7.3 Hz).

Step 2. Synthesis of lithium 2-(6-methoxy-2-methylpyrimidin-4-yl)propanoate (P4)

A solution of C3 and C4 (from the previous step; 2.60 g, 518.9 mmol) and lithium hydroxide monohydrate (1.22 g, 29.1 mmol) in a mixture of tetrahydrofuran (45 mL) and water (15 mL) was stirred at 45° C. for 3 hours. After the reaction mixture had been concentrated in vacuo, the residue was subjected to lyophilization, providing P4 as a white solid. Yield: 2.3 g, 11 mmol, 58% over 2 steps. LCMS m/z 197.1 [M+H]$^+$. $^1$H NMR (400 MHz, methanol-d$_4$) δ 6.66 (s, 1H), 3.94 (s, 3H), 3.61 (q, J=7.3 Hz, 1H), 2.53 (s, 3H), 1.44 (d, J=7.2 Hz, 3H).

Preparations P5
2-[6-(Difluoromethoxy)pyridin-3-yl]propanoic acid (P5)

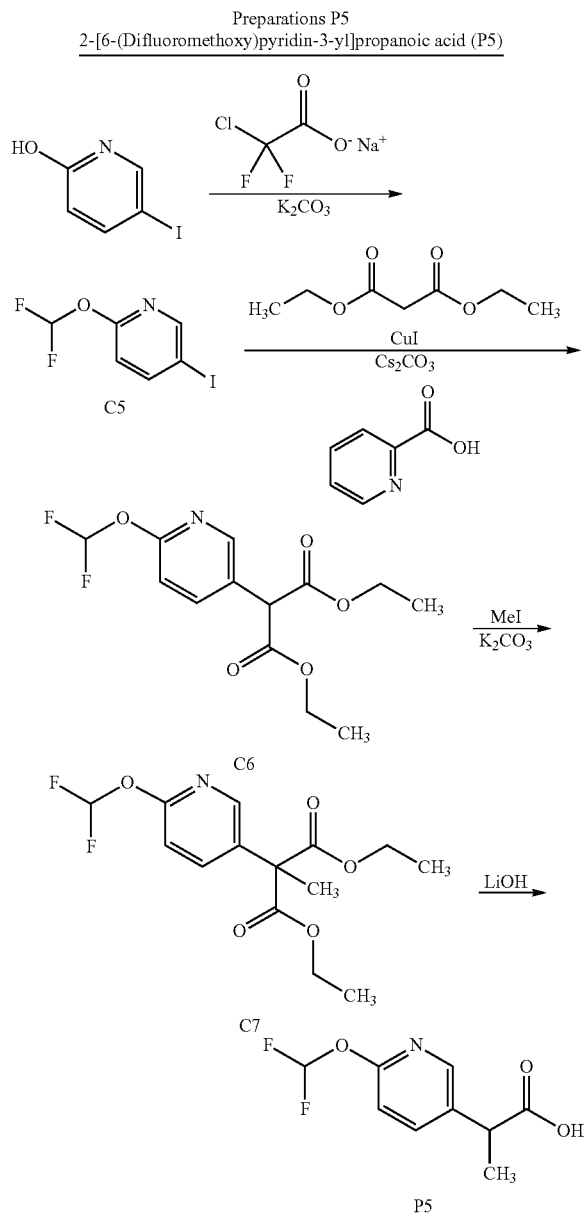

Step 1. Synthesis of
2-(difluoromethoxy)-5-iodopyridine (C5)

Sodium chloro(difluoro)acetate (4.62 g, 30.3 mmol) and potassium carbonate (5.58 g, 40.4 mmol) were added to a 25° C. solution of 5-iodopyridin-2-ol (4.46 g, 20.2 mmol) in N,N-dimethylformamide (100 mL), and the reaction mixture was stirred at 50° C. for 16 hours. It was then diluted with water (500 mL) and extracted with ethyl acetate (3×100 mL), and the combined organic layers were washed with saturated aqueous sodium chloride solution, dried over sodium sulfate, filtered, and concentrated in vacuo. Chromatography on silica gel (Gradient: 0% to 8% ethyl acetate in petroleum ether) provided C5 as an oil. Yield: 2.10 g, 7.75 mmol, 38%. $^1$H NMR (400 MHz, chloroform-d) δ 8.39 (br d, J=2.2 Hz, 1H), 7.97 (dd, J=8.6, 2.3 Hz, 1H), 7.40 (t, J$_{HF}$=72.6 Hz, 1H), 6.74 (br d, J=8.6 Hz, 1H).

Step 2. Synthesis of diethyl [6-(difluoromethoxy)pyridin-3-yl]propanedioate (C6)

A mixture of C5 (1.9 g, 7.0 mmol), diethyl propanedioate (1.68 g, 10.5 mmol), copper(I) iodide (133 mg, 0.698 mmol), pyridine-2-carboxylic acid (172 mg, 1.40 mmol), and cesium carbonate (7.42 g, 22.8 mmol) in tetrahydrofuran (50 mL) was stirred at 80° C. for 16 hours, whereupon the reaction mixture was diluted with ethyl acetate (100 mL) and washed with aqueous ammonium chloride solution (100 mL). The aqueous layer was extracted with ethyl acetate (2×50 mL), and the combined organic layers were dried over sodium sulfate, filtered, and concentrated in vacuo. Purification using silica gel chromatography (Gradient: 0% to 15% ethyl acetate in petroleum ether) afforded C6 as a colorless oil (2.4 g). By $^1$H NMR analysis, this material contained residual diethyl propanedioate; a portion of this sample was taken directly to the following step. LCMS m/z 304.0 [M+H]$^+$. $^1$H NMR (400 MHz, chloroform-d), product peaks only: δ 8.14 (br s, 1H), 7.90 (br d, J=8.4 Hz, 1H), 7.45 (t, J$_{HF}$=72.9 Hz, 1H), 6.92 (d, J=8.4 Hz, 1H), 4.59 (s, 1H), 4.26-4.17 (m, 4H, assumed; partially obscured by residual diethyl propanedioate), 1.31-1.24 (m, 6H, assumed; partially obscured by residual diethyl propanedioate).

Step 3. Synthesis of diethyl [6-(difluoromethoxy)pyridin-3-yl](methyl)propanedioate (C7)

To a solution of C6 (from the previous step; 750 mg, 52.2 mmol) in N,N-dimethylformamide (15 mL) was added potassium carbonate (1.03 g, 7.45 mmol). Iodomethane (527 mg, 3.71 mmol) was added drop-wise, and the reaction mixture was stirred at 25° C. for 4 hours. It was then combined with a similar reaction carried out using C6 (250 mg, 50.73 mmol), poured into water (200 mL), and extracted with ethyl acetate (2×50 mL). The combined organic layers were washed with saturated aqueous sodium chloride solution, dried over sodium sulfate, and concentrated in vacuo; chromatography on silica gel (Gradient: 0% to 15% ethyl acetate in petroleum ether) provided C7 as an oil. Combined yield: 738 mg, 2.33 mmol, 80% over 2 steps. LCMS m/z 318.2 [M+H]$^+$. $^1$H NMR (400 MHz, chloroform-d) δ 8.20 (br s, 1H), 7.81 (br d, J=8.7 Hz, 1H), 7.45 (t, J$_{HF}$=72.9 Hz, 1H), 6.90 (d, J=8.7 Hz, 1H), 4.30-4.18 (m, 4H), 1.87 (s, 3H), 1.27 (t, J=7.1 Hz, 6H).

Step 4. Synthesis of 2-[6-(difluoromethoxy)pyridin-3-yl]propanoic acid (P5)

To a 25° C. solution of C7 (738 mg, 2.33 mmol) in tetrahydrofuran (10 mL) was added a solution of lithium hydroxide (279 mg, 11.6 mmol) in water (3 mL). The reaction mixture was stirred at 25° C. for 16 hours, whereupon it was diluted with water (100 mL) and washed with dichloromethane (3×50 mL). These organic layers were discarded. After the aqueous layer had been adjusted to pH 5 by addition of 5 M hydrochloric acid, it was extracted with dichloromethane (3×50 mL); the combined organic layers were concentrated in vacuo to afford P5 as a solid. Yield: 337 mg, 1.55 mmol, 67%. LCMS m/z 218.1 [M+H]$^+$. $^1$H NMR (400 MHz, methanol-$d_4$) δ 8.15 (d, J=2.5 Hz, 1H), 7.83 (dd, J=8.5, 2.5 Hz, 1H), 7.51 (t, $J_{HF}$=73.2 Hz, 1H), 6.94 (d, J=8.5 Hz, 1H), 3.78 (q, J=7.2 Hz, 1H), 1.49 (d, J=7.2 Hz, 3H).

Preparations P6
2-[5-(5-Fluoro-2-methoxypyridin-4-yl)propanoic acid (P6)

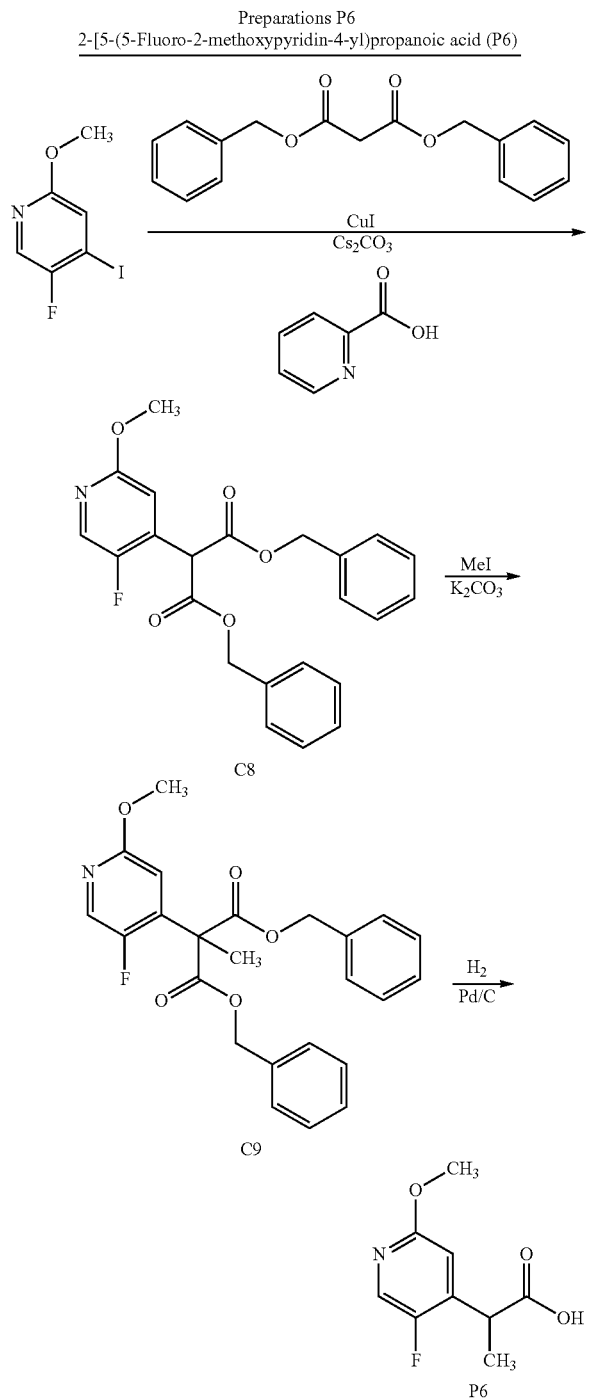

Step 1. Synthesis of dibenzyl (5-fluoro-2-methoxypyridin-4-yl)propanedioate (C8)

This reaction was carried out in three parallel batches. To a 25° C. solution of dibenzyl propanedioate (607 g, 2.13 mol) in tetrahydrofuran (1.5 L) was added pyridine-2-carboxylic acid (35.0 g, 284 mmol), followed by copper(I) iodide (27.1 g, 142 mmol), and then freshly ground cesium carbonate (1.39 kg, 4.27 mol). After the reaction mixture had been heated to 70° C., it was treated in a drop-wise manner with a solution of 5-fluoro-4-iodo-2-methoxypyridine (360 g, 1.42 mol) in tetrahydrofuran (800 mL), whereupon stirring was continued for 16 hours at 70° C. The three reaction mixtures were combined at this point, cooled to 25° C., and filtered through diatomaceous earth. The filter pad was rinsed with ethyl acetate (3×500 mL), and the combined filtrates were concentrated in vacuo, while keeping the internal temperature below 40° C. The residue was dissolved in ethyl acetate (2 L), washed sequentially with saturated aqueous ammonium chloride solution (500 mL) and saturated aqueous sodium chloride solution (500 mL), dried over sodium sulfate, filtered, and concentrated under reduced pressure at 40° C. Chromatography on silica gel (Gradient: 1% to 8% ethyl acetate in petroleum ether) afforded C8 (1.87 kg) as a yellow oil. By $^1$H NMR analysis, this material was contaminated with dibenzyl propanedioate; a portion of it was used in the following step. LCMS m/z 410.1 [M+H]$^+$. $^1$H NMR (400 MHz, chloroform-d), product peaks only: δ 8.01 (d, J=1.3 Hz, 1H), 7.40-7.25 (m, 10H, assumed; partially obscured by residual dibenzyl propanedioate), 6.83 (d, J=4.8 Hz, 1H), 5.20 (AB quartet, $J_{AB}$=12.2 Hz, $Δv_{AB}$=11.9 Hz, 4H), 5.00 (s, 1H), 3.89 (s, 3H).

Step 2. Synthesis of dibenzyl (5-fluoro-2-methoxypyridin-4-yl)(methyl)propanedioate (C9)

This reaction was carried out in two parallel batches. A solution of C8 (from the previous step; 575 g, ≤1.31 mol) in acetonitrile (1.5 L) was stirred in an ice-water bath for 20 minutes, whereupon potassium carbonate (582 g, 4.21 mol) was added. Stirring was continued for an additional 10 minutes. Iodomethane (302 g, 2.13 mol) was then added to the reaction mixture at 0° C., and the reaction was allowed to proceed until LCMS analysis indicated conversion to C9. After the two reaction mixtures had been combined, they were filtered through diatomaceous earth, and the filter cake was washed with acetonitrile (2×1 L). The combined filtrates were concentrated at 40° C. and the residue was partitioned between ethyl acetate (2 L) and water (500 mL). The aqueous layer was extracted with ethyl acetate (2×1 L), and the combined organic layers were washed with saturated aqueous sodium chloride solution (1 L), dried over sodium sulfate, filtered, and concentrated under reduced pressure at 40° C. The resulting crude product was dissolved in petroleum ether (1.5 L) and stirred at 0° C. for 2 hours; a solid was collected via filtration. The filtrate was concentrated in vacuo, and the residue was taken up in petroleum ether (500 mL), then cooled to 0° C. to provide additional solid, which was isolated via filtration. The two solids were combined, suspended in petroleum ether (800 mL), and stirred at 20° C. for 16 hours. Subsequent collection via filtration afforded C9 as a yellow solid. Yield: 670 g, 1.58 mol, 60% over 2 steps. LCMS m/z 423.8 [M+H]$^+$. $^1$H NMR (400 MHz, chloroform-d) δ 7.94 (d, J=2.6 Hz, 1H), 7.36-7.20 (m, 10H), 6.54 (d, J=5.1 Hz, 1H), 5.18 (s, 4H), 3.87 (s, 3H), 1.85 (s, 3H).

Step 3. Synthesis of 2-(5-fluoro-2-methoxypyridin-4-yl)propanoic acid (P6)

This reaction was carried out in four parallel batches. To a 25° C. solution of C9 (200 g, 472 mmol) in ethyl acetate (1 L) was added 10% palladium on carbon (wet; 40 g). The mixture was degassed under vacuum and then purged with nitrogen; this evacuation-purge cycle was carried out a total of three times. The mixture was again degassed under vacuum and then purged with hydrogen; this evacuation-purge cycle was also carried out a total of three times. The mixture was hydrogenated (30 psi) at 50° C. for 16 hours. The four reaction mixtures were combined and filtered through a pad of diatomaceous earth, and the filtrate was concentrated in vacuo at 45° C. Chromatography on silica gel (Gradient: 10% to 20% ethyl acetate in petroleum ether) provided P6 as a white solid. Combined yield: 270 g, 1.36 mmol, 72%. LCMS m/z 199.7 [M+H]+. 1H NMR (400 MHz, chloroform-d) δ 7.98 (d, J=1.7 Hz, 1H), 6.70 (d, J=4.9 Hz, 1H), 3.97 (q, J=7.3 Hz, 1H), 3.89 (s, 3H), 1.53 (d, J=7.3 Hz, 3H).

Preparations P7 and P8
(2R)-2-(5-Fluoro-2-methoxypyridin-4-yl)propanoic acid (P7) and (2S)-2-(5-Flouro-2-methoxypyridin-4-yl)propanoic acid (P8)

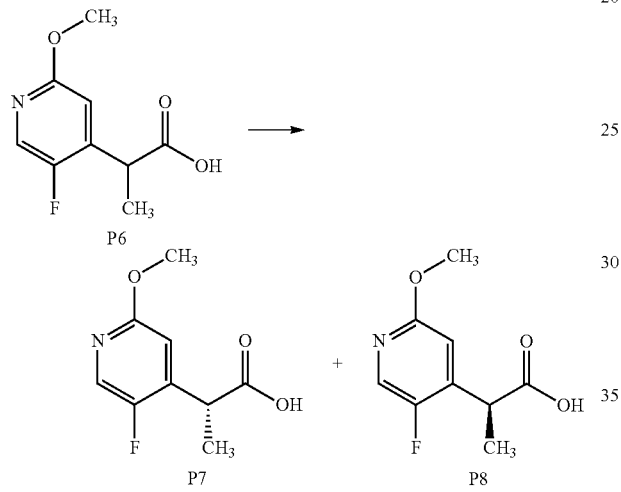

Separation of P6 (700 g, 3.51 mol) into its component enantiomers was carried out by supercritical fluid chromatography (Column: Chiral Technologies Chiralpak AD-H, 50×250 mm, 5 μm; Mobile phase: 9:1 carbon dioxide/2-propanol; Flow rate: 250 mL/minute; Back pressure: 120 bar). The first-eluting enantiomer was designated as P7, and the second-eluting enantiomer as P8; both were isolated as solids.

P7—Yield: 260 g, 1.30 mol, 37%. Retention time: 3.17 minutes (Analytical conditions. Column: Chiral Technologies Chiralpak AD-H, 4.6×250 mm, 5 μm; Mobile phase A: carbon dioxide; Mobile phase B: 2-propanol; Gradient: 5% B for 1.00 minute, then 5% to 60% B over 8 minutes; Flow rate: 3.0 mL/minute; Back pressure: 120 bar).

P8—Yield: 400 g, 2.01 mol, 57%. Retention time: 3.36 minutes (Analytical conditions identical to those used for P7).

The indicated absolute stereochemistries for P7 and P8 were assigned on the basis of comparison to the sample of P7 synthesized in Alternate Preparation (#1) of P7; the configuration of that material was established via X-ray crystallographic study of the derived compound 14 (see below).

Retention time for P7 from Preparations P7 and P8: 2.86 minutes.

Retention time for P7 from Alternate Preparation (#1) of P7: 2.86 minutes.

Retention times for a racemic mixture of P7 and P8: 2.87 and 3.16 minutes.

These three analyses were run using the same analytical method: [Column: Chiral Technologies Chiralpak IG, 4.6× 250 mm, 5 μm; Mobile phase A: carbon dioxide; Mobile phase B: methanol; Gradient: 5% B for 1 minute, then 5% to 60% B over 7 minutes; Flow rate: 3 mL/minute; Back pressure: 120 bar].

Alternate Preparation (#1) P7
(2R)-2-(5-Fluoro-2-methoxypyridin-4-yl)propanoic acid (P7)

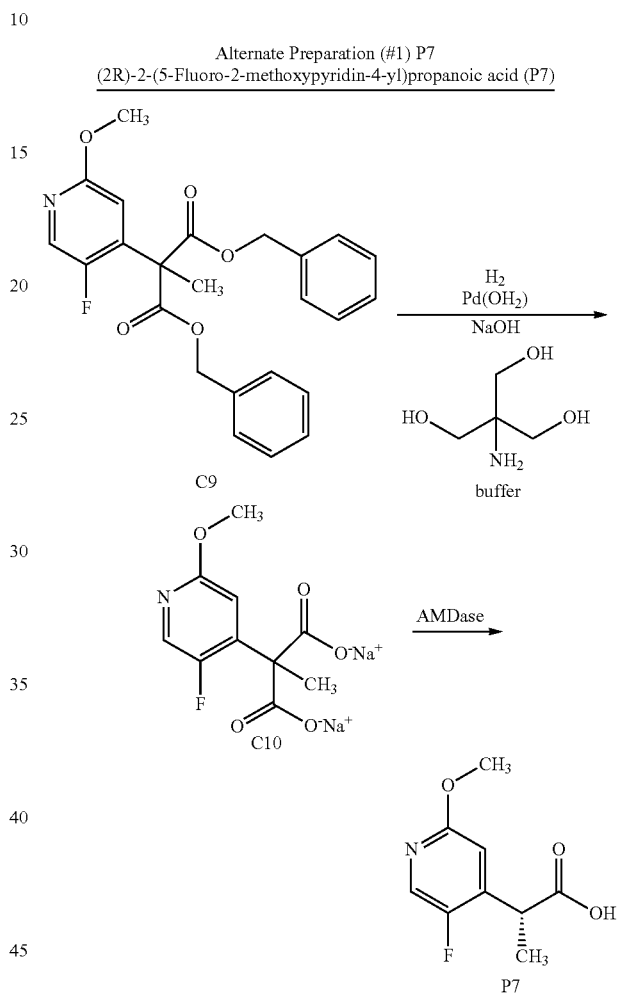

Step 1. Synthesis of disodium (5-fluoro-2-methoxy-pyridin-4-yl)(methyl)propanedioate (C10)

A 1.0 M, pH 8.0 buffer solution was prepared in the following manner: a solution of 2-amino-2-(hydroxymethyl)propane-1,3-diol (Tris; 121 g, 1.00 mol) in water (900 mL) was adjusted to pH 8.0 by addition of hydrochloric acid (37.5 weight %, approximately 40 mL), and then brought to a volume of 1 L by addition of water.

A hydrogenation reactor was charged with palladium hydroxide on carbon (10%; 5.00 g). To this was added a solution of C9 (50.0 g, 118 mmol) in toluene (50 mL, 1 volume); additional toluene (50 mL) was used to rinse the flask, and this was also added to the reaction mixture. A mixture of aqueous sodium hydroxide solution (2.0 M, 118 mL, 236 mmol), the pH 8.0 buffer solution described above (1.0 M; 250 mL, 250 mmol), and water (132 mL) was added, and the resulting mixture was purged with nitrogen (3.5 bar)

followed by hydrogen (3.5 bar); this purging process was carried out a total of three times. After the mixture had been brought to 20° C., stirring at 100 rpm, it was pressurized with hydrogen to 3.45 bar, whereupon the rate of stirring was increased to 750 rpm. After the hydrogenation had proceeded for 4 hours at 20° C., the stirring rate was decreased to 250 rpm and the reaction was purged three times with nitrogen (3.5 bar). The catalyst was removed via filtration, and the reactor was rinsed with water (100 mL), which was then used to wash the filter cake. The aqueous phase of the combined filtrates (590 mL, pH 8.2), containing C10, was progressed directly to the following step. LCMS m/z 244.2 [M+H]$^+$.

Step 2. Synthesis of (2R)-2-(5-fluoro-2-methoxy-pyridin-4-yl)propanoic acid (P7)

A 2 L jacketed vessel (set to a 20° C. jacket temperature) with overhead stirrer was charged with C10 (aqueous solution from the previous step; ≤118 mmol), and the stirring rate was set at 200 rpm. A solution of *Bordetella bronchiseptica* AMDase lyophilized cell-free extract powder (1.75 gm) [This aryl malonate decarboxylase (AMDase) from *Bordetella bronchiseptica* is a wild-type enzyme described in the literature with accession number Q05115, which was recombinantly expressed in *E. coli* and charged as a lyophilized cell-free extract powder. Literature references: S. K. Gaßmeyer et al., *ChemCatChem*, 2016, 8, 916-921; K. Okrasa et al., *Angew. Chem. Int. Ed.* 2009, 48, 7691-7694] in water (17.5 mL) was then charged to the reactor, along with a water rinse of the enzyme vessel (5 mL). After 15 hours, the stirring speed was lowered to 100 rpm, and the pH of the reaction mixture was adjusted to pH 6.0 by sequential additions of hydrochloric acid (4.0 M, 5 mL portions, 38 mL). At this point, the mixture was stirred for 1.5 hours to allow off-gassing to subside, whereupon it was acidified to a pH of ≤2.0 via further addition of hydrochloric acid (4.0 M, total of 85 mL). tert-Butyl methyl ether (300 mL) was added and stirring was continued at 200 rpm for 15 minutes. The mixture was then filtered through diatomaceous earth (25 g), using a Buchner funnel and filter paper; the reactor was rinsed with tert-butyl methyl ether (100 mL), which was then used to wash the filter cake. The aqueous layer of the combined filtrates was extracted in the same manner with tert-butyl methyl ether (300 mL). The combined organic layers were dried over sodium sulfate (50 g) and filtered; the filter cake was washed with tert-butyl methyl ether (25 mL). The combined filtrates were concentrated in vacuo at 30° C. to provide an oil, which solidified under vacuum drying overnight to afford P7 as an off-white solid. Yield: 18.88 g, 94.8 mmol, 80% over 2 steps. $^1$H NMR (400 MHz, chloroform-d) δ 11.4-10.3 (br s, 1H), 7.98 (d, J=1.6 Hz, 1H), 6.70 (d, J=4.9 Hz, 1H), 3.97 (q, J=7.2 Hz, 1H), 3.89 (s, 3H), 1.53 (d, J=7.2 Hz, 3H).

Combination of P7 from the previous step (18.6 g, 93.4 mmol) and P7 (24.9 g, 125 mmol) from a similar reaction of C10 with AMDase afforded a slightly pink solid, with an enantiomeric excess of 98.5%. $^1$H NMR (400 MHz, methanol-d$_4$) δ 7.94 (d, J=1.9 Hz, 1H), 6.74 (d, J=5.0 Hz, 1H), 3.93 (q, J=7.3 Hz, 1H), 3.87 (s, 3H), 1.48 (d, J=7.3 Hz, 3H). Retention time: 2.86 minutes [Column: Chiral Technologies Chiralpak IG, 4.6×250 mm, 5 μm; Mobile phase A: carbon dioxide; Mobile phase B: methanol; Gradient: 5% B for 1 minute, then 5% to 60% B over 7 minutes; Flow rate: 3 mL/minute; Back pressure: 120 bar].

The indicated absolute stereochemistry of P7 was assigned on the basis of conversion of this lot of P7 to Example 14; the absolute stereochemistry of 14 was established via single-crystal X-ray analysis (see below).

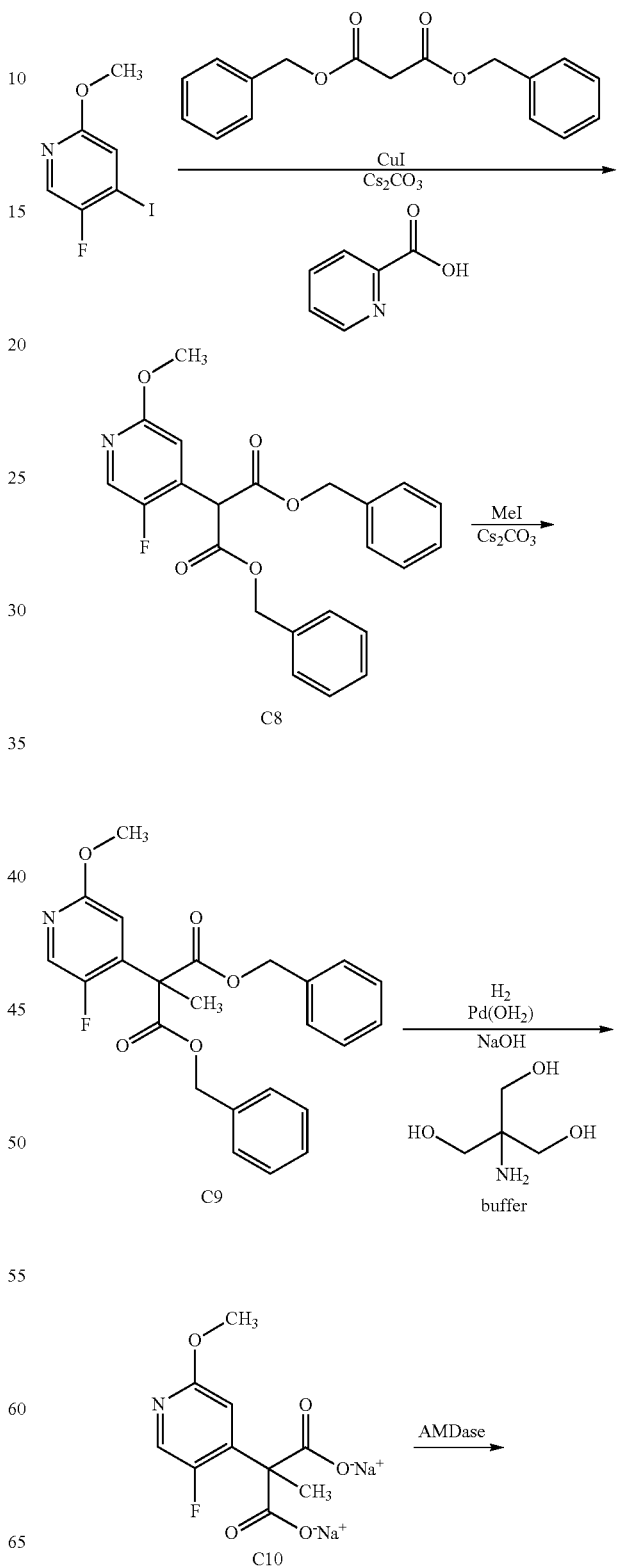

-continued

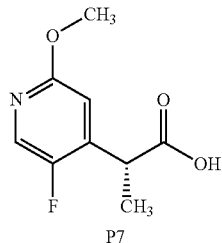

P7

Step 1. Synthesis of dibenzyl (5-fluoro-2-methoxypyridin-4-yl)propanedioate (C8)

A mixture of pyridine-2-carboxylic acid (24.6 g, 0.200 mol), copper(I) iodide (19.1 g, 0.100 mol), and cesium carbonate (977 g, 3.00 mol) in tetrahydrofuran (1.26 L; 5 volumes), was heated to an internal temperature of 60° C. to 70° C., whereupon a solution of 5-fluoro-4-iodo-2-methoxypyridine (253 g, 1.00 mol) and dibenzyl propanedioate (426 g, 1.50 mol) in tetrahydrofuran (250 mL, 1 volume) was added. After the reaction mixture had been heated at 60° C. to 70° C. for approximately 3 to 6 hours, it was allowed to cool to 15° C. to 30° C. and filtered through diatomaceous earth (250 g). The filter cake was washed with tetrahydrofuran (500 mL, 2 volumes) and the combined filtrates, containing C8, were used directly in the following step. Representative $^1$H NMR (500 MHz, chloroform-d) δ 8.00 (d, J=1.3 Hz, 1H), 7.40-7.24 (m, 10H, assumed; partially obscured by residual dibenzyl propanedioate), 6.82 (d, J=4.8 Hz, 1H), 5.20 (AB quartet, $J_{AB}$=12.3 Hz, $\Delta v_{AB}$=14.9 Hz, 4H), 4.99 (s, 1H), 3.88 (s, 3H).

Step 2. Synthesis of dibenzyl (5-fluoro-2-methoxypyridin-4-yl)(methyl)propanedioate (C9)

Iodomethane (284 g, 2.00 mol) was slowly added to a 10° C. to 20° C. mixture of cesium carbonate (977 g, 3.00 mol) and a solution of C8 (from the previous step, solution in tetrahydrofuran; 51.00 mol). After the reaction mixture had been stirred at 10° C. to 20° C. for approximately 10 to 12 hours, it was filtered through diatomaceous earth (250 g). The filter cake was washed with tetrahydrofuran (500 mL, 1.2 volumes), and the combined filtrates were concentrated to 1 to 2 volumes. The resulting mixture was diluted with propan-2-yl acetate (1.25 L, 3.1 volumes), washed sequentially with water (750 mL, 1.8 volumes), aqueous ammonium chloride solution (20%; 750 mL), and aqueous sodium chloride solution (20%; 750 mL), and concentrated in vacuo. The remaining solvent was exchanged with heptane, and precipitation was allowed to proceed from heptane (2 to 3 volumes) at 15° C. to 25° C. The resulting solid was collected via filtration and triturated with a mixture of heptane (450 mL) and propan-2-yl acetate (50 mL) to afford C9 as a solid. Three batches of the chemistry in steps 1 and 2 were carried out, and the final lots of C9 were combined. Yield: 675 g, 1.59 mol, approximately 53% over 2 steps. Representative $^1$H NMR (500 MHz, DMSO-$d_6$) δ 8.15 (d, J=2.0 Hz, 1H), 7.39-7.21 (m, 10H), 6.75 (d, J=5.0 Hz, 1H), 5.21 (s, 4H), 3.81 (s, 3H), 1.81 (s, 3H).

Step 3. Synthesis of disodium (5-fluoro-2-methoxypyridin-4-yl)(methyl)propanedioate (C10)

A buffer solution [pH 8.0; 2-amino-2-(hydroxymethyl)propane-1,3-diol (Tris; 121 g, 1.00 mol), and concentrated hydrochloric acid (46 mL, 0.23 volumes) in water (1 L, 5 volumes)], and palladium hydroxide on carbon (10%, 20 g) were added to a 15° C. to 25° C. mixture of C9 (200 g, 0.472 mol) in toluene (400 mL, 2 volumes). A solution of sodium hydroxide (38.8 g, 0.970 mol) in water (1 L, 5 volumes), was added, whereupon the mixture was stirred for approximately 10 to 20 minutes. After the reactor had been purged with nitrogen, then purged with hydrogen, the reaction mixture was stirred at 15° C. to 30° C. under a bag of hydrogen (approximately 10 L), until HPLC analysis indicated 50.5% of C9 was present (approximately 22 hours) (Retention time: 11.44 minutes. HPLC conditions. Column: Agilent Technologies ZORBAX Eclipse Plus C18, 4.6×100 mm, 3.5 μm; Mobile phase A: 0.1% phosphoric acid in water; Mobile phase B: acetonitrile; Gradient: 5% B for 3 minutes, then 5% to 100% B over 9 minutes, then 100% B for 3 minutes; Flow rate: 1.5 mL/minute). The reaction mixture was filtered, and the filter cake was washed with water (2.6 volumes); the aqueous layer of the filtrate, containing C10, was taken directly to the following step.

Step 4. Synthesis of (2R)-2-(5-fluoro-2-methoxypyridin-4-yl)propanoic acid (P7)

A mixture of AMDase (7 g) in water (70 mL, 0.35 volumes) and C10 (from the previous step, as a solution in water, 50.472 mol) was stirred at 15° C. to 30° C. until HPLC analysis indicated that 50.5% of C10 was present (approximately 16 hours) [Retention time: 5.80 minutes. HPLC conditions identical to those described in Step 3, Synthesis of disodium (5-fluoro-2-methoxypyridin-4-yl)(methyl)propanedioate (C10)]. Hydrochloric acid (4.0 M) was then slowly added until the pH of the reaction mixture reached 6.0, whereupon stirring was continued for 1.5 hours. The pH was then adjusted to ≤2.0 (range, 1.5 to 2.0) by further addition of hydrochloric acid (4.0 M). After addition of tert-butyl methyl ether (1.2 L, 6 volumes), the mixture was filtered through diatomaceous earth (100 g), and the aqueous phase of the filtrate was extracted with tert-butyl methyl ether (800 mL, 4 volumes). The combined organic layers were washed with aqueous sodium chloride solution (15%; 600 mL, 3 volumes), and concentrated to 2 to 2.5 volumes at a temperature of ≤45° C. and a pressure of ≤−0.08 MPa. n-Heptane (600 mL, 3 volumes) was added, and the mixture was concentrated to 3 to 5 volumes at a temperature of ≤45° C. and a pressure of ≤−0.08 MPa; this heptane dilution/concentration was carried out a total of 3 times. After the resulting mixture had been stirred at 0° C. to 10° C. for approximately 1 to 2 hours, the precipitate was collected via filtration, providing P7 as an off-white solid with an enantiomeric excess of 99.8%. Yield: 80.0 g, 0.402 mol, 85% over 2 steps. Representative $^1$H NMR (500 MHz, chloroform-d) δ 11.68 (v br s, 1H), 7.99 (br s, 1H), 6.70 (d, J=4.9 Hz, 1H), 3.97 (q, J=7.2 Hz, 1H), 3.88 (s, 3H), 1.52 (d, J=7.3 Hz, 3H).

Preparation P9
2[5-(Difluoromethyl)-2-methoxypyridin-4-yl]propanoic acid (P9)

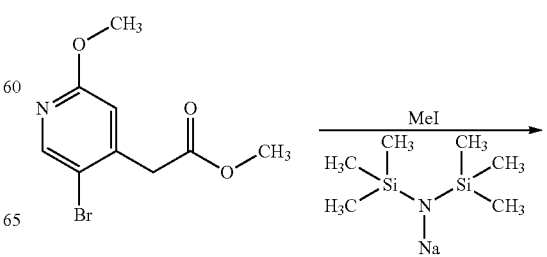

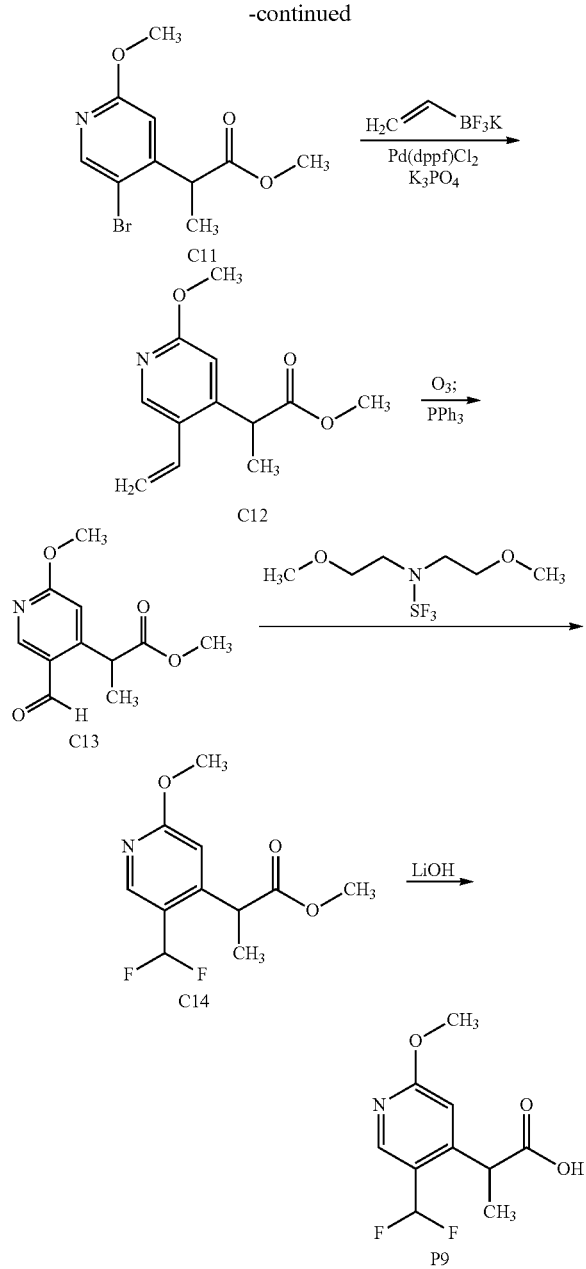

Step 1. Synthesis of methyl 2-(5-bromo-2-methoxypyridin-4-yl)propanoate (C11)

A solution of sodium bis(trimethylsilyl)amide in tetrahydrofuran (2 M; 1 mL, 2 mmol) was added drop-wise to a −78° C. solution of methyl (5-bromo-2-methoxypyridin-4-yl)acetate (415 mg, 1.60 mmol) in tetrahydrofuran (50 mL). After the reaction mixture had been stirred at −78° C. for 1 hour, a solution of iodomethane (0.5 mL, 8 mmol) was added drop-wise. At the completion of the addition, the reaction mixture was warmed to −30° C. and allowed to stir at that temperature for 3 hours, whereupon it was diluted with aqueous ammonium chloride solution and extracted with ethyl acetate (3×50 mL). The combined organic layers were washed with saturated aqueous sodium chloride solution, dried over sodium sulfate, filtered, and concentrated in vacuo while keeping the temperature below 45° C. Purification via silica gel chromatography (Eluent: 1:3 ethyl acetate/petroleum ether) provided C11 as a colorless oil. Yield: 376 mg, 1.37 mmol, 86%. LCMS m/z 276.0 (bromine isotope pattern observed) [M+H]$^+$. $^1$H NMR (400 MHz, methanol-d$_4$) δ 8.23 (s, 1H), 6.76 (s, 1H), 4.10 (q, J=7.1 Hz, 1H), 3.89 (s, 3H), 3.69 (s, 3H), 1.48 (d, J=7.2 Hz, 3H).

Step 2. Synthesis of methyl 2-(5-ethenyl-2-methoxypyridin-4-yl)propanoate (C12)

A mixture of C11 (376 mg, 1.37 mmol), potassium vinyltrifluoroborate (460 mg, 3.43 mmol), [1,1'-bis(diphenylphosphino)ferrocene]dichloropalladium(II) (201 mg, 0.275 mmol), and potassium phosphate (872 mg, 4.11 mmol) in N,N-dimethylformamide (20 mL) was stirred at 100° C. for 16 hours. The reaction mixture was then filtered; the filtrate was poured into water and extracted with ethyl acetate (2×30 mL). The combined organic layers were washed with saturated aqueous sodium chloride solution, dried over sodium sulfate, filtered, concentrated in vacuo, and purified via chromatography on silica gel (Gradient: 0% to 30% ethyl acetate in petroleum ether) to afford C12 as a colorless oil. Yield: 188 mg, 0.850 mmol, 62%. LCMS m/z 222.1 [M+H]$^+$. $^1$H NMR (400 MHz, chloroform-d) δ 8.21 (s, 1H), 6.81 (dd, J=17.3, 10.9 Hz, 1H), 6.63 (s, 1H), 5.56 (br d, J=17.3 Hz, 1H), 5.32 (br d, J=10.8 Hz, 1H), 3.95-3.87 (m, 1H), 3.93 (s, 3H), 3.67 (s, 3H), 1.46 (d, J=7.1 Hz, 3H).

Step 3. Synthesis of methyl 2-(5-formyl-2-methoxypyridin-4-yl)propanoate (C13)

A solution of C12 (195 mg, 0.881 mmol) in dichloromethane (10 mL) was cooled to −78° C., and then treated with a stream of ozone-enriched oxygen until a blue color persisted. After 5 minutes, a stream of dry nitrogen was bubbled through the reaction mixture until the blue color had disappeared, whereupon triphenylphosphine (439 mg, 1.67 mmol) was added. The resulting mixture was warmed to 25° C. and stirred for 2 hours, at which point it was combined with a similar reaction carried out using C12 (63 mg, 0.28 mmol) and concentrated in vacuo. The residue was purified using silica gel chromatography (Gradient: 0% to 30% ethyl acetate in petroleum ether) to provide C13 as a colorless oil. Combined yield: 124 mg, 0.555 mmol, 48%. LCMS m/z 224.0 [M+H]$^+$.

Step 4. Synthesis of methyl 2-[5-(difluoromethyl)-2-methoxypyridin-4-yl]propanoate (C14)

To a solution of C13 (124 mg, 0.555 mmol) in dichloromethane (5 mL) was added [bis(2-methoxyethyl)amino]sulfur trifluoride (614 mg, 2.78 mmol). After the reaction mixture had been stirred at 25° C. for 16 hours, it was poured into saturated aqueous sodium bicarbonate solution (50 mL) and extracted with dichloromethane (50 mL). The organic layer was washed with saturated aqueous sodium chloride solution, dried over sodium sulfate, filtered, and concentrated in vacuo. Silica gel chromatography (Gradient: 0% to 20% ethyl acetate in petroleum ether) provided C14 as a colorless oil. Yield: 110 mg, 0.449 mmol, 81%. LCMS m/z 246.1 [M+H]$^+$. $^1$H NMR (400 MHz, chloroform-d) δ 8.28 (s, 1H), 6.87 (s, 1H), 6.76 (t, $J_{HF}$=54.5 Hz, 1H), 4.11 (q, J=6.9 Hz, 1H), 4.03 (s, 3H), 3.69 (s, 3H), 1.52 (d, J=7.0 Hz, 3H).

Step 5. Synthesis of 2-[5-(difluoromethyl)-2-methoxypyridin-4-yl]propanoic acid (P9)

To a solution of C14 (145 mg, 0.591 mmol) in methanol (10 mL) was added a solution of lithium hydroxide (43 mg, 1.8 mmol) in water (4 mL), and the reaction mixture was stirred at 20° C. for 4 hours, whereupon it was concentrated in vacuo and washed with tert-butyl methyl ether (2×5 mL). The aqueous layer was adjusted to pH 5 by addition of 2 M hydrochloric acid and then extracted with ethyl acetate (3×10 mL). The combined ethyl acetate layers were washed with water (3×10 mL) and with saturated aqueous sodium chloride solution (20 mL), dried over sodium sulfate, filtered, and concentrated under reduced pressure to provide P9 as a yellow oil. Yield: 132 mg, 0.571 mmol, 97%. LCMS m/z 232.1 [M+H]+. 1H NMR (400 MHz, methanol-d4) δ 8.26 (s, 1H), 6.96 (t, $J_{HF}$=54.4 Hz, 1H), 6.84 (s, 1H), 4.12 (q, J=7.2 Hz, 1H), 3.94 (s, 3H), 1.48 (d, J=7.2 Hz, 3H).

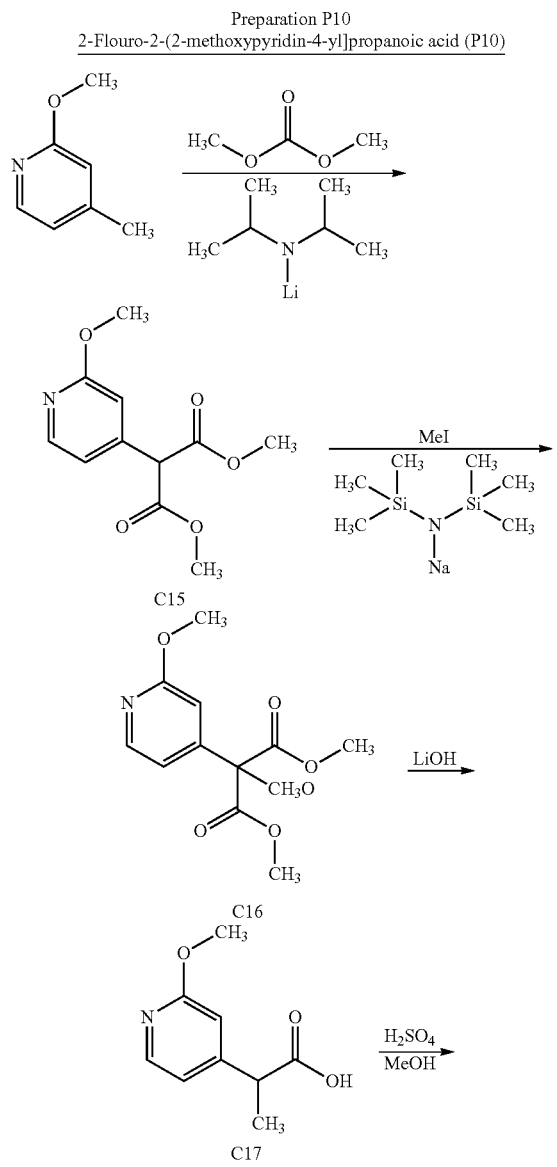

Preparation P10
2-Flouro-2-(2-methoxypyridin-4-yl)propanoic acid (P10)

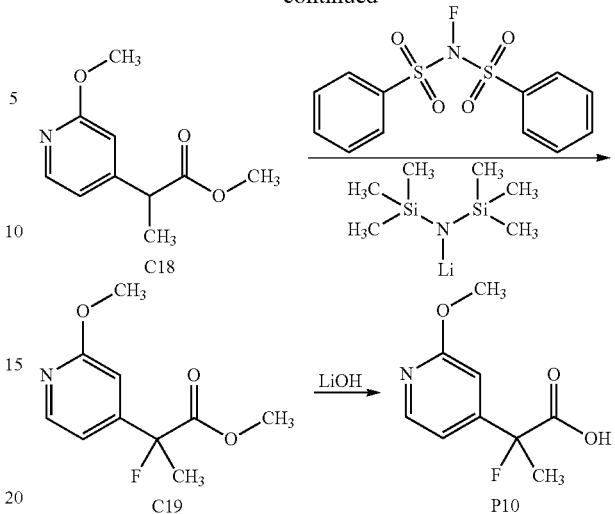

Step 1. Synthesis of dimethyl (2-methoxypyridin-4-yl)propanedioate (C15)

To a −10° C. solution of 2-methoxy-4-methylpyridine (5.00 g, 40.6 mmol) in tetrahydrofuran (30 mL) was added lithium diisopropylamide (2 M solution in tetrahydrofuran; 81.2 mL, 162 mmol). After the reaction mixture had been stirred at −10° C. for 1.5 hours, dimethyl carbonate (14.6 g, 162 mmol) was added and stirring was continued at −10° C. for 1.5 hours. The reaction mixture was then warmed to 25° C. and allowed to stir for 16 hours, whereupon it was quenched by addition of aqueous ammonium chloride solution. The resulting mixture was extracted with ethyl acetate (3×30 mL), and the combined organic layers were dried over sodium sulfate, filtered, and concentrated in vacuo. Purification via chromatography on silica gel (Gradient: 0% to 20% ethyl acetate in petroleum ether) provided C15 as a yellow oil. Yield: 4.92 g, 20.6 mmol, 51%. LCMS m/z 240.1 [M+H]+. 1H NMR (400 MHz, chloroform-d) δ 8.17 (d, J=5.0 Hz, 1H), 6.95 (d, J=4.8 Hz, 1H), 6.80 (s, 1H), 4.59 (s, 1H), 3.96 (s, 3H), 3.77 (s, 6H).

Also obtained from the chromatographic purification was the product of mono-acylation, methyl (2-methoxypyridin-4-yl)acetate. Yield: 1.29 g, 7.12 mmol, 18%. LCMS m/z 182.1 [M+H]+. 1H NMR (400 MHz, chloroform-d) δ 8.11 (br d, J=5.3 Hz, 1H), 6.81 (dd, J=5.4, 1.5 Hz, 1H), 6.68-6.66 (m, 1H), 3.93 (s, 3H), 3.71 (s, 3H), 3.57 (s, 2H).

Step 2. Synthesis of dimethyl (2-methoxypyridin-4-yl)(methyl)propanedioate (C16)

Sodium bis(trimethylsilyl)amide (2 M solution in tetrahydrofuran; 14.0 mL, 28.0 mmol) was added to a −78° C. solution of C15 (4.47 g, 18.7 mmol) in tetrahydrofuran (30 mL). After the reaction mixture had been stirred at −78° C. for 1 hour, iodomethane (1.40 mL, 22.5 mmol) was added. The reaction mixture was then warmed to −40° C., stirred for 2 hours, warmed to 25° C., and stirred for a further 16 hours, whereupon it was quenched with aqueous ammonium chloride solution. The resulting mixture was extracted with ethyl acetate (2×30 mL), and the combined organic layers were dried over sodium sulfate, filtered, and concentrated in vacuo. Silica gel chromatography (Gradient: 0% to 10% ethyl acetate in petroleum ether) afforded C16 as a yellow oil. Yield: 3.29 g, 13.0 mmol, 70%. LCMS m/z 254.1 [M+H]$^+$. $^1$H NMR (400 MHz, chloroform-d) δ 8.15 (d, J=5.5 Hz, 1H), 6.88 (br d, J=5.5 Hz, 1H), 6.74 (br s, 1H), 3.95 (s, 3H), 3.78 (s, 6H), 1.83 (s, 3H).

Step 3. Synthesis of 2-(2-methoxypyridin-4-yl)propanoic acid (C17)

A solution of C16 (3.28 g, 13.0 mmol) and lithium hydroxide (1.24 g, 51.8 mmol) in a mixture of tetrahydrofuran (20 mL) and water (10 mL) was stirred at 45° C. for 5 hours. LCMS analysis indicated conversion to C17: LCMS m/z 182.1 [M+H]$^+$, and the reaction mixture was concentrated in vacuo, providing C17 as a white solid (2.40 g). This material was used directly in the following step.

Step 4. Synthesis of methyl 2-(2-methoxypyridin-4-yl)propanoate (C18)

A mixture of C17 (from the previous step; 2.40 g, 513.0 mmol) and sulfuric acid (2.5 mL) in methanol (25 mL) was stirred at 60° C. for 16 hours. The reaction mixture was then concentrated in vacuo, washed with aqueous sodium bicarbonate solution, and extracted with ethyl acetate (2×20 mL). The combined organic layers were dried over sodium sulfate, filtered, and concentrated under reduced pressure to afford C18 as a colorless oil. Yield: 1.56 g, 7.99 mmol, 61% over 2 steps. LCMS m/z 196.2 [M+H]$^+$. $^1$H NMR (400 MHz, chloroform-d) δ 8.10 (d, J=5.4 Hz, 1H), 6.81 (dd, J=5.4, 1.5 Hz, 1H), 6.67 (br s, 1H), 3.93 (s, 3H), 3.67 (s, 3H), 3.66 (q, J=7.1 Hz, 1H), 1.47 (d, J=7.2 Hz, 3H).

Step 5. Synthesis of methyl 2-fluoro-2-(2-methoxypyridin-4-yl)propanoate (C19)

To a −78° C. solution of C18 (500 mg, 2.56 mmol) in tetrahydrofuran (13 mL) was added lithium bis(trimethylsilyl)amide (1 M solution in tetrahydrofuran 3.33 mL, 3.33 mmol). After the reaction mixture had been stirred at −78° C. for 30 minutes, a solution of N-(benzenesulfonyl)-N-fluorobenzenesulfonamide (969 mg, 3.07 mmol) in tetrahydrofuran (2 mL) was added. The reaction mixture was stirred at −10° C. for 3 hours, whereupon it was quenched with aqueous ammonium chloride solution and extracted with ethyl acetate (3×20 mL). The combined organic layers were dried over sodium sulfate, filtered, and concentrated in vacuo; silica gel chromatography (Gradient: 0% to 10% ethyl acetate in petroleum ether) afforded C19 as a yellow oil. Yield: 400 mg, 1.88 mmol, 73%. LCMS m/z 214.1 [M+H]$^+$. $^1$H NMR (400 MHz, chloroform-d) δ 8.18 (d, J=5.4 Hz, 1H), 7.00 (dd, J=5.5, 1.6 Hz, 1H), 6.88 (br d, J=1.5 Hz, 1H), 3.96 (s, 3H), 3.78 (s, 3H), 1.89 (d, J$_{HF}$=22.3 Hz, 3H).

Step 6. Synthesis of 2-fluoro-2-(2-methoxypyridin-4-yl)propanoic acid (P10)

A solution of C19 (400 mg, 1.88 mmol) and lithium hydroxide (89.9 mg, 3.75 mmol) in a mixture of tetrahydrofuran (10 mL) and water (2 mL) was stirred at 45° C. for 4 hours. The reaction mixture was then concentrated in vacuo, diluted with water (12 mL), and adjusted to pH 6 by addition of 3 M hydrochloric acid. The resulting mixture was extracted with ethyl acetate (2×20 mL), and the combined organic layers were dried over sodium sulfate, filtered, and concentrated under reduced pressure to provide P10 as a yellow oil. Yield: 300 mg, 1.51 mmol, 80%. LCMS m/z 200.1 [M+H]$^+$. $^1$H NMR (400 MHz, chloroform-d) δ 9.9-9.4 (br s, 1H), 8.21 (d, J=5.6 Hz, 1H), 7.08 (dd, J=5.6, 1.6 Hz, 1H), 6.95 (br s, 1H), 3.95 (s, 3H), 1.92 (d, J$_{HF}$=22.2 Hz, 3H).

Preparation P11
2-[3-(Difluoromethyoxy)-5-methoxyphenyl]propanoic acid (P11)

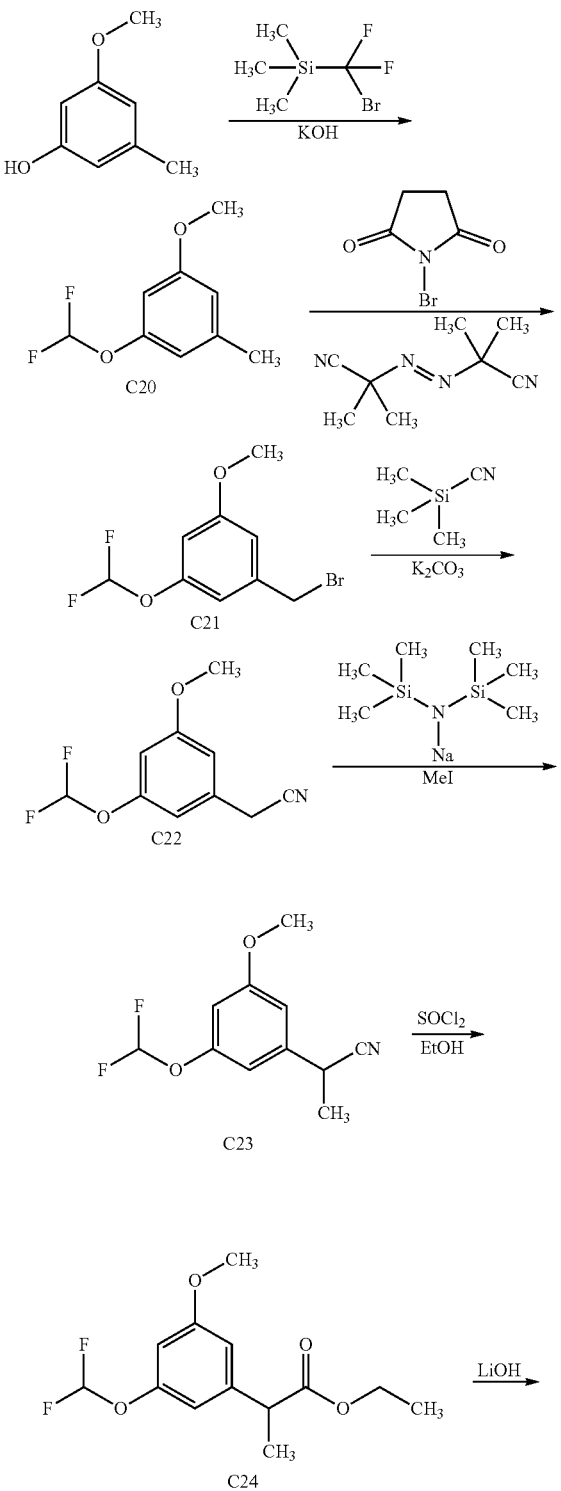

-continued

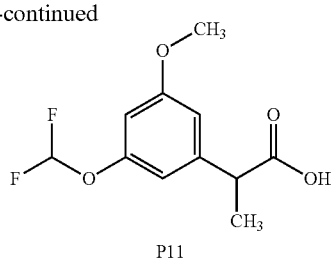

P11

Step 1. Synthesis of 1-(difluoromethoxy)-3-methoxy-5-methylbenzene (C20)

Aqueous potassium hydroxide solution (20% solution; 60.9 g, 217 mmol) and [bromo(difluoro)methyl](trimethyl)silane (11.3 mL, 72.7 mmol) were sequentially added to a 0° C. solution of 3-methoxy-5-methylphenol (5.00 g, 36.2 mmol) in dichloromethane (50 mL). After the reaction mixture had been stirred at 0° C. for 4.5 hours, it was diluted with water (50 mL) and extracted with dichloromethane (3×100 mL). The combined organic layers were washed with saturated aqueous sodium chloride solution, dried over sodium sulfate, filtered, concentrated in vacuo, and purified via chromatography on silica gel (Gradient: 0% to 5% ethyl acetate in petroleum ether), affording C20 as a colorless oil. Yield: 6.27 g, 33.3 mmol, 92%. $^1$H NMR (400 MHz, methanol-$d_4$) δ 6.76 (t, $J_{HF}$=74.4 Hz, 1H), 6.60 (br s, 1H), 6.53 (br s, 1H), 6.49-6.46 (m, 1H), 3.76 (s, 3H), 2.30 (s, 3H).

Step 2. Synthesis of 1-(bromomethyl)-3-(difluoromethoxy)-5-methoxybenzene (C21)

A mixture of C20 (3.00 g, 15.9 mmol), 2,2'-azobisisobutyronitrile (262 mg, 1.60 mmol), and N-bromosuccinimide (2.84 g, 15.9 mmol) in tetrachloromethane (90 mL) was stirred at 80° C. for 8 hours. Concentration in vacuo provided C21 as a yellow oil. Yield: 4.0 g, 15 mmol, 94%. $^1$H NMR (400 MHz, methanol-$d_4$), product peaks only, characteristic peaks: δ 6.84 (s, 1H), 6.77 (s, 1H), 6.63-6.60 (m, 1H), 4.50 (s, 2H), 3.81 (s, 3H).

Step 3. Synthesis of [3-(difluoromethoxy)-5-methoxyphenyl]acetonitrile (C22)

To a solution of C21 (4.0 g, 15 mmol) in acetonitrile (150 mL) were sequentially added potassium carbonate (3.11 g, 22.5 mmol) and trimethylsilyl cyanide (2.2 g, 22 mmol). The resulting mixture was stirred at 80° C. for 16 hours, at which time LCMS analysis indicated the presence of C22: LCMS m/z 214.1 [M+H]$^+$. The reaction mixture was concentrated under reduced pressure, diluted with water (50 mL), and extracted with ethyl acetate (3×50 mL). The combined organic layers were washed with saturated aqueous sodium chloride solution, dried over sodium sulfate, concentrated in vacuo, and purified using silica gel chromatography (Gradient: 0% to 30% ethyl acetate in petroleum ether) to afford C22 as a yellow oil. Yield: 1.20 g, 5.63 mmol, 38%. $^1$H NMR (400 MHz, methanol-$d_4$) δ 6.84 (t, $J_{HF}$=73.9 Hz, 1H), 6.81 (br s, 1H), 6.73 (br s, 1H), 6.68-6.66 (m, 1H), 3.89 (s, 2H), 3.82 (s, 3H).

Step 4. Synthesis of 2-[3-(difluoromethoxy)-5-methoxyphenyl]propanenitrile (C23)

Conversion of C22 (3.00 g, 14.1 mmol) to C23 was carried out using the procedure described for synthesis of C16 from C15 in Preparation P10. Silica gel chromatography (Gradient: 0% to 5% ethyl acetate in petroleum ether) provided C23 as a yellow oil. Yield: 1.00 g, 4.40 mmol, 31%. LCMS m/z 228.1 [M+H]$^+$. $^1$H NMR (400 MHz, methanol-$d_4$) δ 6.85 (t, $J_{HF}$=73.9 Hz, 1H), 6.84-6.82 (m, 1H), 6.77-6.74 (m, 1H), 6.69-6.66 (m, 1H), 4.11 (q, J=7.2 Hz, 1H), 3.82 (s, 3H), 1.60 (d, J=7.3 Hz, 3H).

Step 5. Synthesis of ethyl 2-[3-(difluoromethoxy)-5-methoxyphenyl]propanoate (C24)

Thionyl chloride (5.3 mL, 73 mmol) was added in a drop-wise manner to a 0° C. solution of C23 (900 mg, 3.96 mmol) in ethanol (40 mL). The reaction mixture was stirred at 85° C. for 16 hours, whereupon it was diluted with water (50 mL) and extracted with ethyl acetate (3×30 mL). The combined organic layers were washed with saturated aqueous sodium chloride solution, dried over sodium sulfate, filtered, and concentrated in vacuo. Silica gel chromatography (Gradient: 0% to 6% ethyl acetate in petroleum ether) provided C24 (700 mg, 2.55 mmol, 64%) as a yellow oil. Yield: 700 mg, 2.55 mmol, 64%. LCMS m/z 275.1 [M+H]$^+$. $^1$H NMR (400 MHz, methanol-$d_4$) δ 6.80 (t, $J_{HF}$=74.2 Hz, 1H), 6.74-6.71 (m, 1H), 6.65 (br s, 1H), 6.59 (dd, J=2.2, 2.2 Hz, 1H), 4.19-4.05 (m, 2H), 3.79 (s, 3H), 3.72 (q, J=7.2 Hz, 1H), 1.44 (d, J=7.2 Hz, 3H), 1.20 (t, J=7.1 Hz, 3H).

Step 6. Synthesis of 2-[3-(difluoromethoxy)-5-methoxyphenyl]propanoic acid (P11)

To a solution of C24 (700 mg, 2.55 mmol) in tetrahydrofuran (30 mL) was added a solution of lithium hydroxide monohydrate (535 mg, 12.8 mmol) in water (10 mL). After the reaction mixture had been stirred at 25° C. for 16 hours, it was concentrated in vacuo, diluted with water (20 mL), and washed with dichloromethane (3×25 mL). These organic layers were discarded. The aqueous layer was adjusted to a pH of approximately 2 using 2 M hydrochloric acid; it was then extracted with dichloromethane (3×25 mL). The combined organic layers were washed with saturated aqueous sodium chloride solution (10 mL), dried over sodium sulfate, filtered, and concentrated under reduced pressure, affording P11 as a yellow oil. Yield: 628 mg, 2.55 mmol, quantitative. LCMS m/z 247.1 [M+H]$^+$. $^1$H NMR (400 MHz, methanol-$d_4$) δ 6.79 (t, $J_{HF}$=74.2 Hz, 1H), 6.77-6.73 (m, 1H), 6.69-6.66 (m, 1H), 6.59 (dd, J=2.2, 2.2 Hz, 1H), 3.79 (s, 3H), 3.69 (q, J=7.2 Hz, 1H), 1.44 (d, J=7.2 Hz, 3H).

Preparation P12
2-[5-Fluoro-2-(trifluoromethyoxy)pyridin-4-yl]propanoic acid (P12)

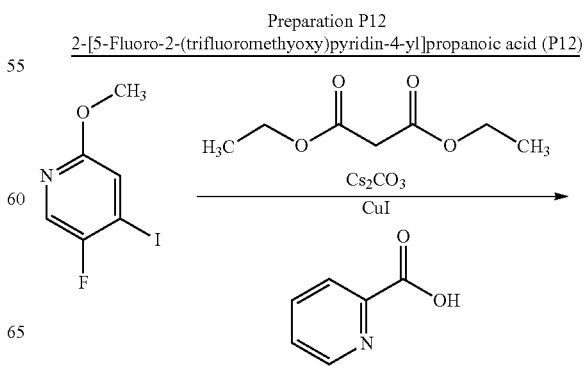

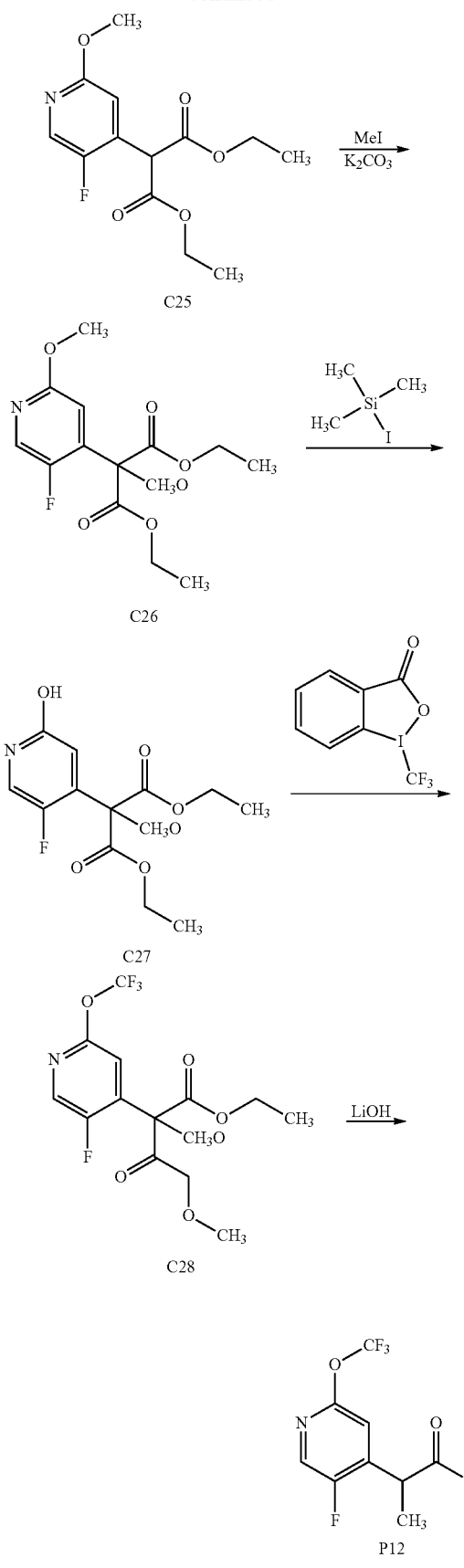

Step 1. Synthesis of diethyl (5-fluoro-2-methoxypyridin-4-yl)propanedioate (C25)

Reaction of 5-fluoro-4-iodo-2-methoxypyridine (3.45 g, 13.6 mmol) with diethyl propanedioate (3.28 g, 20.5 mmol) was carried using the method described for synthesis of C6 from C5 in Preparation P5. Purification using silica gel chromatography (Gradient: 0% to 15% ethyl acetate in petroleum ether) afforded C25 as a colorless oil. Yield: 2.80 g, 9.82 mmol, 72%. LCMS m/z 286.1 [M+H]$^+$. $^1$H NMR (400 MHz, chloroform-d) δ 8.00 (br s, 1H), 6.84 (br d, J=4.8 Hz, 1H), 4.87 (s, 1H), 4.30-4.21 (m, 4H), 3.90 (s, 3H), 1.28 (t, J=7.1 Hz, 6H).

Step 2. Synthesis of diethyl (5-fluoro-2-methoxy-pyridin-4-yl)(methyl)propanedioate (C26)

To a solution of C25 (2.80 g, 9.82 mmol) in acetonitrile (100 mL) was added potassium carbonate (4.07 g, 29.4 mmol), followed by drop-wise addition of iodomethane (2.09 g, 14.7 mmol). The reaction mixture was stirred at 25° C. for 2 days, whereupon LCMS analysis indicated conversion to C26: LCMS m/z 300.1 [M+H]$^+$. The reaction mixture was poured into water (1 L) and extracted with ethyl acetate (2×100 mL); the combined organic layers were washed with saturated aqueous sodium chloride solution, dried over sodium sulfate, filtered, and concentrated in vacuo to provide C26 as a yellow oil. Yield: 2.25 g, 7.52 mmol, 77%. $^1$H NMR (400 MHz, chloroform-d) δ 7.95 (d, J=2.7 Hz, 1H), 6.58 (d, J=5.2 Hz, 1H), 4.30-4.22 (m, 4H), 3.90 (s, 3H), 1.81 (s, 3H), 1.27 (t, J=7.1 Hz, 6H).

Step 3. Synthesis of diethyl (5-fluoro-2-hydroxy-pyridin-4-yl)(methyl)propanedioate (C27)

Trimethylsilyl iodide (7.52 g, 37.6 mmol) was added in a drop-wise manner to a solution of C26 (2.25 g, 7.52 mmol) in acetonitrile (100 mL), and the reaction mixture was stirred at 100° C. for 4 hours, at which time LCMS analysis indicated conversion to C27: LCMS m/z 286.1 [M+H]$^+$. The reaction mixture was poured into aqueous sodium bicarbonate solution (100 mL), and the resulting mixture was extracted with ethyl acetate (3×100 mL). The combined organic layers were washed with aqueous sodium dithionite solution (200 mL), filtered, concentrated in vacuo, and purified by silica gel chromatography (Gradient: 0% to 15% methanol in dichloromethane), providing C27 as a white solid. Yield: 685 mg, 2.40 mmol, 32%. $^1$H NMR (400 MHz, chloroform-d) δ 7.29-7.26 (m, 1H, assumed; partially obscured by solvent peak), 6.43 (d, J=6.4 Hz, 1H), 4.35-4.19 (m, 4H), 1.80 (s, 3H), 1.27 (t, J=7.1 Hz, 6H).

Step 4. Synthesis of diethyl [5-fluoro-2-(trifluoromethoxy)pyridin-4-yl](methyl)propanedioate (C28)

A solution of 1-trifluoromethyl-1,2-benziodoxol-3-(1H)-one (759 mg, 2.40 mmol) and C27 (685 mg, 2.40 mmol) in nitromethane (20 mL) was stirred at 100° C. for 16 hours. After removal of solvent in vacuo, the residue was purified via chromatography on silica gel (Gradient: 0% to 20% ethyl acetate in petroleum ether) to afford C28 as a colorless oil. Yield: 283 mg, 0.801 mmol, 33%. LCMS m/z 354.0 [M+H]$^+$. $^1$H NMR (400 MHz, chloroform-d) δ 8.13 (d, J=2.3 Hz, 1H), 6.93 (d, J=5.0 Hz, 1H), 4.34-4.22 (m, 4H), 1.85 (s, 3H), 1.28 (t, J=7.1 Hz, 6H).

Step 5. Synthesis of 2-[5-fluoro-2-(trifluoromethoxy)pyridin-4-yl]propanoic acid (P12)

To a solution of C28 (300 mg, 0.849 mmol) in tetrahydrofuran (10 mL) was added a solution of lithium hydroxide (102 mg, 4.26 mmol) in water (3 mL) at 25° C. After the reaction mixture had been stirred at 25° C. for 16 hours, it was combined with a similar reaction carried out using C28 (50 mg, 0.14 mmol), diluted with water (100 mL), and washed with dichloromethane (3×50 mL). These organic layers were discarded. The aqueous layer was adjusted to pH 5 by addition of 5 M hydrochloric acid and extracted with dichloromethane (3×50 mL); the combined dichloromethane layers were concentrated in vacuo to provide P12 as a white solid. Combined yield: 230 mg, 0.909 mmol, 92%. LCMS m/z 254.0 [M+H]$^+$. $^1$H NMR (400 MHz, methanol-d$_4$) δ 8.17 (d, J=1.5 Hz, 1H), 7.20 (d, J=4.8 Hz, 1H), 4.05 (q, J=7.3 Hz, 1H), 1.53 (d, J=7.3 Hz, 3H).

Preparation P13
2-[2-(Difluoromethoxy)-5-fluoropyridin-4-yl]propanoic acid (P13)

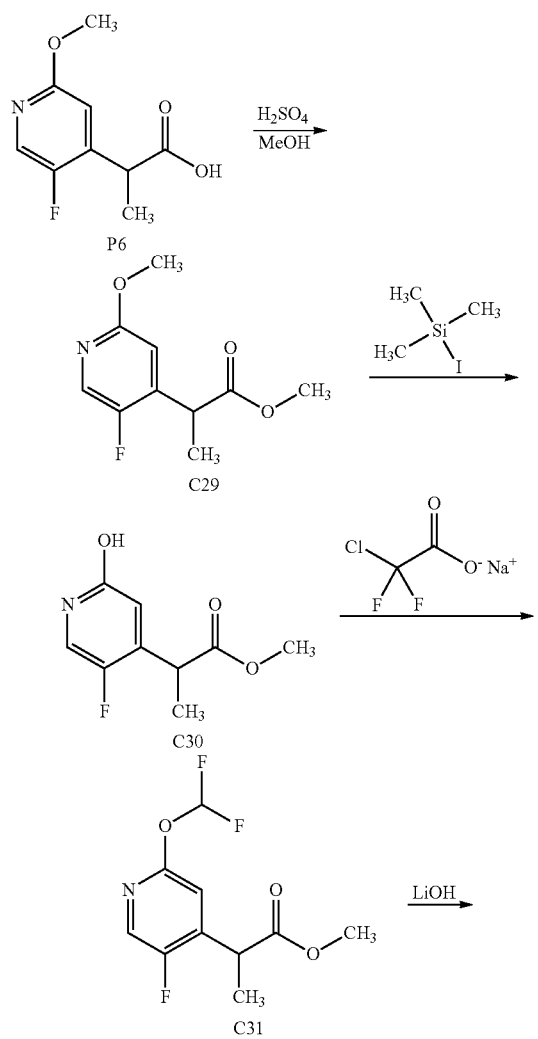

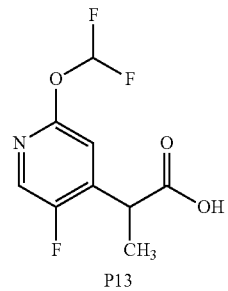

P13

Step 1. Synthesis of methyl 2-(5-fluoro-2-methoxypyridin-4-yl)propanoate (C29)

Sulfuric acid (0.2 mL) was added to a solution of a solution of P6 (1.80 g, 9.04 mmol) in methanol (20 mL), and the reaction mixture was stirred at 70° C. for 12 hours, whereupon it was concentrated under reduced pressure. The residue was treated with saturated aqueous sodium bicarbonate solution (30 mL) until the pH reached 8, and it was then extracted with ethyl acetate (3×30 mL). The combined organic layers were washed with saturated aqueous sodium chloride solution, dried over sodium sulfate, filtered, and concentrated in vacuo to provide C29 as a colorless oil. Yield: 1.85 g, 8.68 mmol, 96%. LCMS m/z 214.1 [M+H]$^+$. $^1$H NMR (400 MHz, chloroform-d) δ 7.94 (br s, 1H), 6.65 (d, J=5.0 Hz, 1H), 3.93 (q, J=7.3 Hz, 1H), 3.89 (s, 3H), 3.69 (s, 3H), 1.49 (d, J=7.3 Hz, 3H).

Step 2. Synthesis of methyl 2-(5-fluoro-2-hydroxypyridin-4-yl)propanoate (C30)

A solution of C29 (700 mg, 3.28 mmol) and trimethylsilyl iodide (1.97 g, 9.85 mmol) in acetonitrile (10 mL) was stirred at 80° C. for 4 hours. After the reaction mixture had been concentrated in vacuo, the residue was purified using silica gel chromatography (Gradient: 0% to 10% methanol in dichloromethane), affording C30 as a pale brown oil. Yield: 550 mg, 2.76 mmol, 84%. LCMS m/z 200.1 [M+H]$^+$. $^1$H NMR (400 MHz, chloroform-d) δ 7.99 (d, J=3.5 Hz, 1H), 6.93 (d, J=5.8 Hz, 1H), 3.99 (q, J=7.2 Hz, 1H), 3.75 (s, 3H), 1.58 (d, J=7.2 Hz, 3H).

Step 3. Synthesis of methyl 2-[2-(difluoromethoxy)-5-fluoropyridin-4-yl]propanoate (C31)

A mixture of C30 (580 mg, 2.91 mmol) and sodium chloro(difluoro)acetate (888 mg, 5.82 mmol) in acetonitrile (10.0 mL) was stirred at 100° C. for 12 hours. The reaction mixture was then concentrated in vacuo and subjected to silica gel chromatography (Gradient: 0% to 30% ethyl acetate in petroleum ether), providing C31 as a colorless oil. Yield: 550 mg, 2.21 mmol, 76%. LCMS m/z 250.1 [M+H]$^+$. $^1$H NMR (400 MHz, chloroform-d) δ 7.99 (d, J=1.3 Hz, 1H), 7.36 (t, J$_{HF}$=72.9 Hz, 1H), 6.86 (d, J=4.8 Hz, 1H), 3.99 (q, J=7.3 Hz, 1H), 3.72 (s, 3H), 1.53 (d, J=7.3 Hz, 3H).

Step 4. Synthesis of 2-[2-(difluoromethoxy)-5-fluoropyridin-4-yl]propanoic acid (P13)

A solution of lithium hydroxide monohydrate (455 mg, 10.8 mmol) in water (5 mL) was added to a solution of C31 (1.00 g, 4.01 mmol) in tetrahydrofuran (10 mL). The reaction mixture was stirred at 25° C. for 10 hours, whereupon it was concentrated under reduced pressure, and the aqueous residue was washed with dichloromethane (3×10 mL). The aqueous layer was then adjusted to pH 7 by addition of 1 M hydrochloride acid, and the resulting mixture was extracted with ethyl acetate (3×30 mL). The combined ethyl acetate layers were concentrated in vacuo, providing P13 as a colorless oil. Yield: 830 mg, 3.53 mmol, 88%. LCMS m/z 236.1 [M+H]⁺. ¹H NMR (400 MHz, chloroform-d) δ 7.99 (br s, 1H), 7.35 (t, $J_{HF}$=72.8 Hz, 1H), 6.86 (d, J=4.8 Hz, 1H), 3.98 (q, J=7.2 Hz, 1H), 1.52 (d, J=7.3 Hz, 3H).

Preparation P14
2-[2-(Dimethylamino)-5-fluoropyridin-4-yl]propanoic acid (P14)

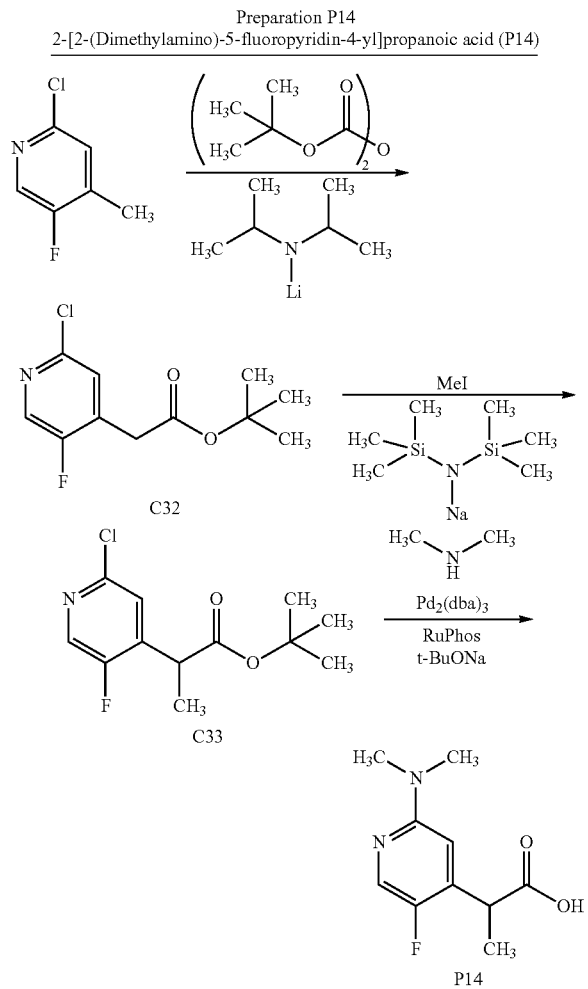

Step 1. Synthesis of tert-butyl (2-chloro-5-fluoropyridin-4-yl)acetate (C32)

Lithium diisopropylamide (2 M solution in tetrahydrofuran; 50.5 mL, 101 mmol) was added to a −78° C. solution of 2-chloro-5-fluoro-4-methylpyridine (4.90 g, 33.7 mmol) in tetrahydrofuran (200 mL). After the reaction mixture had been stirred at −50° C. for 1 hour, it was cooled to −78° C., and a solution of di-tert-butyl dicarbonate (8.51 mL, 37.0 mmol) in tetrahydrofuran (30 mL) was added. The reaction mixture was then warmed to −30° C., stirred for 2 hours, and diluted with water (100 mL). The resulting mixture was extracted with ethyl acetate (3×50 mL); the combined organic layers were washed with saturated aqueous sodium chloride solution, dried over sodium sulfate, filtered, and concentrated in vacuo. Silica gel chromatography (Gradient: 0% to 10% ethyl acetate in petroleum ether) provided C32 as an oil. Yield: 4.90 g, 19.9 mmol, 59%. LCMS m/z 246.1 (chlorine isotope pattern observed) [M+H]⁺. ¹H NMR (400 MHz, chloroform-d) δ 8.21 (br s, 1H), 7.29 (d, J=5.2 Hz, 1H), 3.59 (s, 2H), 1.46 (s, 9H).

Step 2. Synthesis of tert-butyl 2-(2-chloro-5-fluoropyridin-4-yl)propanoate (C33)

Conversion of C32 (4.60 g, 18.7 mmol) to C33 was carried out using the method described for synthesis of C16 from C15 in Preparation P10. Silica gel chromatography (Gradient 0% to 20% ethyl acetate in petroleum ether) provided C33 as an oil. Yield: 4.40 g, 16.9 mmol, 90%. LCMS m/z 262.1 (chlorine isotope pattern observed) [M+H]⁺. ¹H NMR (400 MHz, chloroform-d) δ 8.19 (br s, 1H), 7.28 (d, J=5.1 Hz, 1H), 3.87 (q, J=7.3 Hz, 1H), 1.48 (d, J=7.2 Hz, 3H), 1.42 (s, 9H).

Step 3. Synthesis of 2-[2-(dimethylamino)-5-fluoropyridin-4-yl]propanoic acid (P14)

A mixture of C33 (3.00 g, 11.6 mmol), dimethylamine (2 M solution in tetrahydrofuran; 8.66 mL, 17.3 mmol), tris(dibenzylideneacetone)dipalladium(0) (1.06 g, 1.16 mmol), 2-dicyclohexylphosphino-2',6'-diisopropoxybiphenyl (RuPhos; 1.08 g, 2.31 mmol), and sodium tert-butoxide (3.33 g, 34.7 mmol) in toluene (100 mL) was stirred at 100° C. for 16 hours. After the reaction mixture had been concentrated in vacuo, it was diluted with water and washed with dichloromethane (3×30 mL). The aqueous layer was then adjusted to pH 5 by addition of 5 M hydrochloric acid, and extracted with ethyl acetate (2×50 mL). The combined ethyl acetate layers were dried over sodium sulfate, filtered, and concentrated in vacuo. Chromatography on silica gel (Gradient: 0% to 10% methanol in dichloromethane) afforded P14 as a gray solid. Yield: 700 mg, 3.30 mmol, 28%. LCMS m/z 213.1 [M+H]⁺. ¹H NMR (400 MHz, methanol-d₄) δ 7.87 (d, J=2.1 Hz, 1H), 6.57 (d, J=4.9 Hz, 1H), 3.90 (q, J=7.2 Hz, 1H), 3.04 (s, 6H), 1.48 (d, J=7.2 Hz, 3H).

Preparation P15
Lithium 2-(5-chloro-2-methyoxypyrmidin-4-yl)propanate (P15)

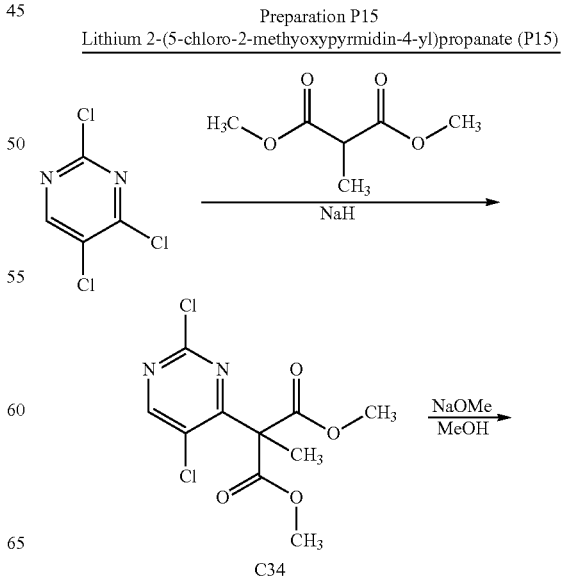

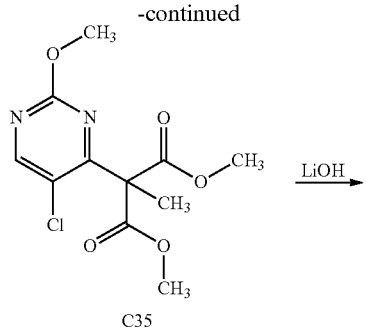

Step 1. Synthesis of dimethyl (2,5-dichloropyrimidin-4-yl)(methyl)propanedioate (C34)

Sodium hydride (60% dispersion in mineral oil; 1.31 g, 33 mmol) was slowly added to a 0° C. solution of dimethyl methylpropanedioate (4.78 g, 32.7 mmol) in tetrahydrofuran (40 mL). The reaction mixture was stirred at 0° C. for 30 minutes, whereupon a solution of 2,4,5-trichloropyrimidine (5.00 g, 27.3 mmol) in tetrahydrofuran (10 mL) was added drop-wise at 0° C. Stirring was continued at 0° C. for 30 minutes, at which point the reaction mixture was slowly warmed to 25° C. and allowed to stir at that temperature for 30 minutes. After addition of saturated aqueous ammonium chloride solution (100 mL), the mixture was extracted with ethyl acetate (3×100 mL). The combined organic layers were washed sequentially with water and with saturated aqueous sodium chloride solution, then combined with the organic layer from a similar reaction carried out using 2,4,5-trichloropyrimidine (500 mg, 2.73 mmol), dried over sodium sulfate, filtered, and concentrated in vacuo while keeping the temperature below 40° C. Silica gel chromatography (Gradient: 10% to 13% ethyl acetate in petroleum ether) provided C34 as a colorless oil. Combined yield: 6.82 g, 23.3 mmol, 78%. LCMS m/z 293.0 (dichloro isotope pattern observed) [M+H]$^+$. $^1$H NMR (400 MHz, methanol-d$_4$) δ 8.74 (s, 1H), 3.79 (s, 6H), 1.90 (s, 3H).

Step 2. Synthesis of dimethyl (5-chloro-2-methoxypyrimidin-4-yl)(methyl)propanedioate (C35)

A solution of sodium methoxide in methanol (30% solution; 4.66 g, 26 mmol) was added drop-wise to a solution of C34 (6.32 g, 21.6 mmol) in methanol (120 mL). After the reaction mixture had been stirred at 25° C. for 2 hours, it was concentrated in vacuo while keeping the temperature below 40° C., diluted with water (50 mL), and extracted with ethyl acetate (2×100 mL). The organic layers were combined with those from a similar reaction carried out using C34 (500 mg, 1.71 mmol), washed sequentially with water and with saturated aqueous sodium chloride solution, dried over sodium sulfate, filtered, and concentrated in vacuo. Silica gel chromatography (Gradient: 11% to 15% ethyl acetate in petroleum ether) afforded C35 as a colorless oil. Combined yield: 4.00 g, 13.9 mmol, 60%. LCMS m/z 289.0 (chlorine isotope pattern observed) [M+H]$^+$. $^1$H NMR (400 MHz, methanol-d$_4$) δ 8.53 (s, 1H), 3.95 (s, 3H), 3.79 (s, 6H), 1.88 (s, 3H).

Step 3. Synthesis of lithium 2-(5-chloro-2-methoxypyrimidin-4-yl)propanoate (P15)

A solution of lithium hydroxide monohydrate (1.65 g, 39.3 mmol) in water (20 mL) was added drop-wise to a solution of C35 (3.78 g, 13.1 mmol) in tetrahydrofuran (60 mL). The reaction mixture was stirred at 35° C. for 3 hours, whereupon it was concentrated in vacuo. The resulting aqueous mixture was washed with dichloromethane and then purified via reversed-phase chromatography (Column: C18; Gradient: 0% to 10% acetonitrile in water), providing P15 as a white solid. Yield: 1.87 g, 8.40 mmol, 64%. LCMS m/z 217.1 [M+H]$^+$. $^1$H NMR (400 MHz, methanol-d$_4$) δ 8.37 (s, 1H), 4.05 (q, J=7.2 Hz, 1H), 4.00 (s, 3H), 1.55 (d, J=7.2 Hz, 3H).

Preparation P16
2-[2-(Difluoromethyoxy)-6-methyoxypyridin-4-yl]propanioc acid (P16)

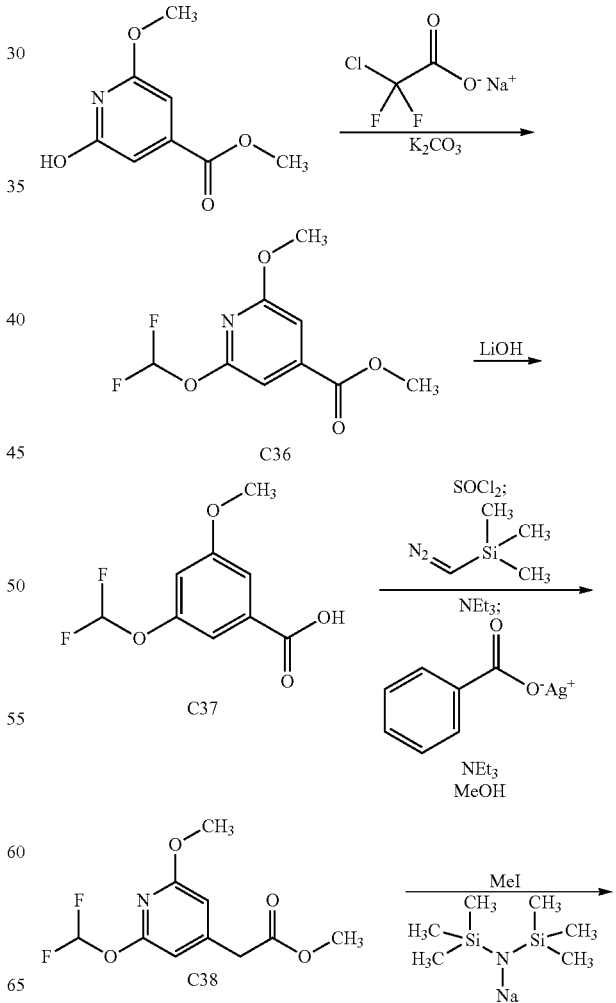

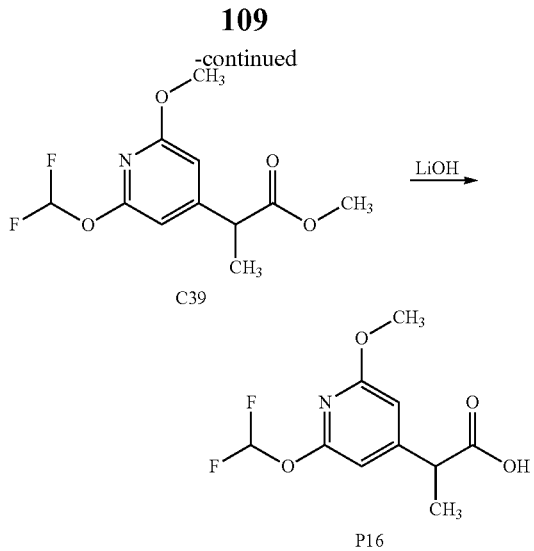

Step 1. Synthesis of methyl 2-(difluoromethoxy)-6-methoxypyridine-4-carboxylate (C36).

Methyl 2-hydroxy-6-methoxypyridine-4-carboxylate (900 mg, 4.91 mmol) was converted to C36 using the method described for synthesis of C5 from 5-iodopyridin-2-ol in Preparation P5. Chromatography on silica gel (Gradient: 0% to 8% ethyl acetate in petroleum ether) provided C36 as a colorless oil. Yield: 720 mg, 3.09 mmol, 63%. LCMS m/z 234.1 [M+H]$^+$. $^1$H NMR (400 MHz, chloroform-d) δ 7.39 (t, $J_{HF}$=73.0 Hz, 1H), 7.10 (br s, 1H), 7.00 (br s, 1H), 3.94 (s, 3H), 3.93 (s, 3H).

Step 2. Synthesis of 2-(difluoromethoxy)-6-methoxypyridine-4-carboxylic acid (C37)

Using the method described for synthesis of P11 from C24 in Preparation P11, C36 (1.10 g, 4.72 mmol) was hydrolyzed, affording C37 as a white solid. Yield: 980 mg, 4.47 mmol, 95%. LCMS m/z 220.1 [M+H]$^+$. $^1$H NMR (400 MHz, chloroform-d) δ 7.41 (t, $J_{HF}$=72.8 Hz, 1H), 7.15 (d, J=1.1 Hz, 1H), 7.05 (d, J=1.0 Hz, 1H), 3.95 (s, 3H).

Step 3. Synthesis of methyl [2-(difluoromethoxy)-6-methoxypyridin-4-yl]acetate (C38)

A solution of C37 (980 mg, 4.47 mmol) in thionyl chloride (6.49 mL, 89.0 mmol) was stirred at 70° C. for 2.5 hours, whereupon it was concentrated under reduced pressure. After the resulting acyl chloride had been dissolved in a mixture of tetrahydrofuran (8 mL) and acetonitrile (8 mL), it was cooled to 0° C. and treated with freshly distilled triethylamine (0.87 mL, 6.2 mmol), followed by (diazomethyl)(trimethyl)silane (2 M solution in diethyl ether; 3.35 mL, 6.70 mmol). The reaction mixture was stirred at 0° C. for 8 hours, whereupon it was diluted with diethyl ether (25 mL) and washed sequentially with 10% aqueous citric acid solution (5 mL), saturated aqueous sodium bicarbonate solution (15 mL), and saturated aqueous sodium chloride solution (25 mL). The organic layer was dried over sodium sulfate, filtered, and concentrated under reduced pressure to provide the crude diazoketone. This material was suspended in methanol (10 mL) in an ultrasonic bath; a solution of silver benzoate (512 mg, 2.24 mmol) in triethylamine (1.86 mL, 13.3 mmol) was gradually added at room temperature while the reaction mixture was sonicated. After 30 minutes, volatiles were removed in vacuo, and the residue was purified using chromatography on silica gel (Gradient: 0% to 10% ethyl acetate in petroleum ether) to provide C38 as a colorless oil. Yield: 340 mg, 1.38 mmol, 31%. LCMS m/z 248.0 [M+H]$^+$. $^1$H NMR (400 MHz, chloroform-d) δ 7.40 (t, $J_{HF}$=73.4 Hz, 1H), 6.45 (br s, 1H), 6.40 (br s, 1H), 3.88 (s, 3H), 3.71 (s, 3H), 3.57 (s, 2H).

Step 4. Synthesis of methyl 2-[2-(difluoromethoxy)-6-methoxypyridin-4-yl]propanoate (C39)

To a −78° C. solution of C38 (230 mg, 0.930 mmol) in tetrahydrofuran (20 mL) was added sodium bis(trimethylsilyl)amide (2 M solution in tetrahydrofuran; 0.56 mL, 1.1 mmol), and the reaction mixture was stirred at −78° C. for 1 hour. Iodomethane (57.9 µL, 0.93 mmol) was then added and stirring was continued for 2 hours at −78° C. After addition of saturated aqueous ammonium chloride solution (10 mL), the mixture was combined with a similar reaction carried out using C38 (100 mg, 0.405 mmol) and extracted with ethyl acetate (3×20 mL). The combined organic layers were washed with saturated aqueous sodium chloride solution, dried over sodium sulfate, filtered, and concentrated in vacuo; silica gel chromatography (Gradient: 0% to 4% ethyl acetate in petroleum ether) afforded C39 as a colorless oil. Combined yield: 150 mg, 0.574 mmol, 43%. LCMS m/z 262.1 [M+H]$^+$. $^1$H NMR (400 MHz, methanol-d$_4$) δ 7.51 (t, $J_{HF}$=73.3 Hz, 1H), 6.50 (br d, J=1 Hz, 1H), 6.43 (br d, J=1 Hz, 1H), 3.88 (s, 3H), 3.78 (q, J=7.2 Hz, 1H), 3.68 (s, 3H), 1.44 (d, J=7.2 Hz, 3H).

Step 5. Synthesis of 2-[2-(difluoromethoxy)-6-methoxypyridin-4-yl]propanoic acid (P16)

Hydrolysis of C39 (130 mg, 0.498 mmol) was carried out using the method described for synthesis of P12 from C28 in Preparation P12, providing P16 as a colorless oil. Yield: 101 mg, 0.409 mmol, 82%. LCMS m/z 248.0 [M+H]$^+$. $^1$H NMR (400 MHz, methanol-d$_4$) δ 7.51 (t, $J_{HF}$=73.3 Hz, 1H), 6.53 (br d, J=1.1 Hz, 1H), 6.46 (br d, J=1.1 Hz, 1H), 3.88 (s, 3H), 3.72 (q, J=7.1 Hz, 1H), 1.44 (d, J=7.2 Hz, 3H).

Preparations P17 and P18
tert-Butyl 7-methyl-3,4-dihydro-1H-spiro[1,8-napthyridine-2,3′-pyrrolidine]-1′-carboxylate (P17) and Di-tert-butyl 7-methyl-3,4-dihydro-1H-spiro[1,8-napthyridine-2,3′-pyrrolidine]-1,1′-dicarboxylate (P18)

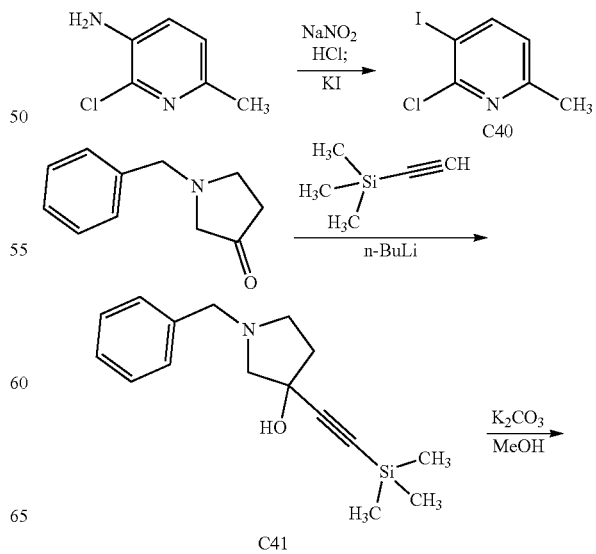

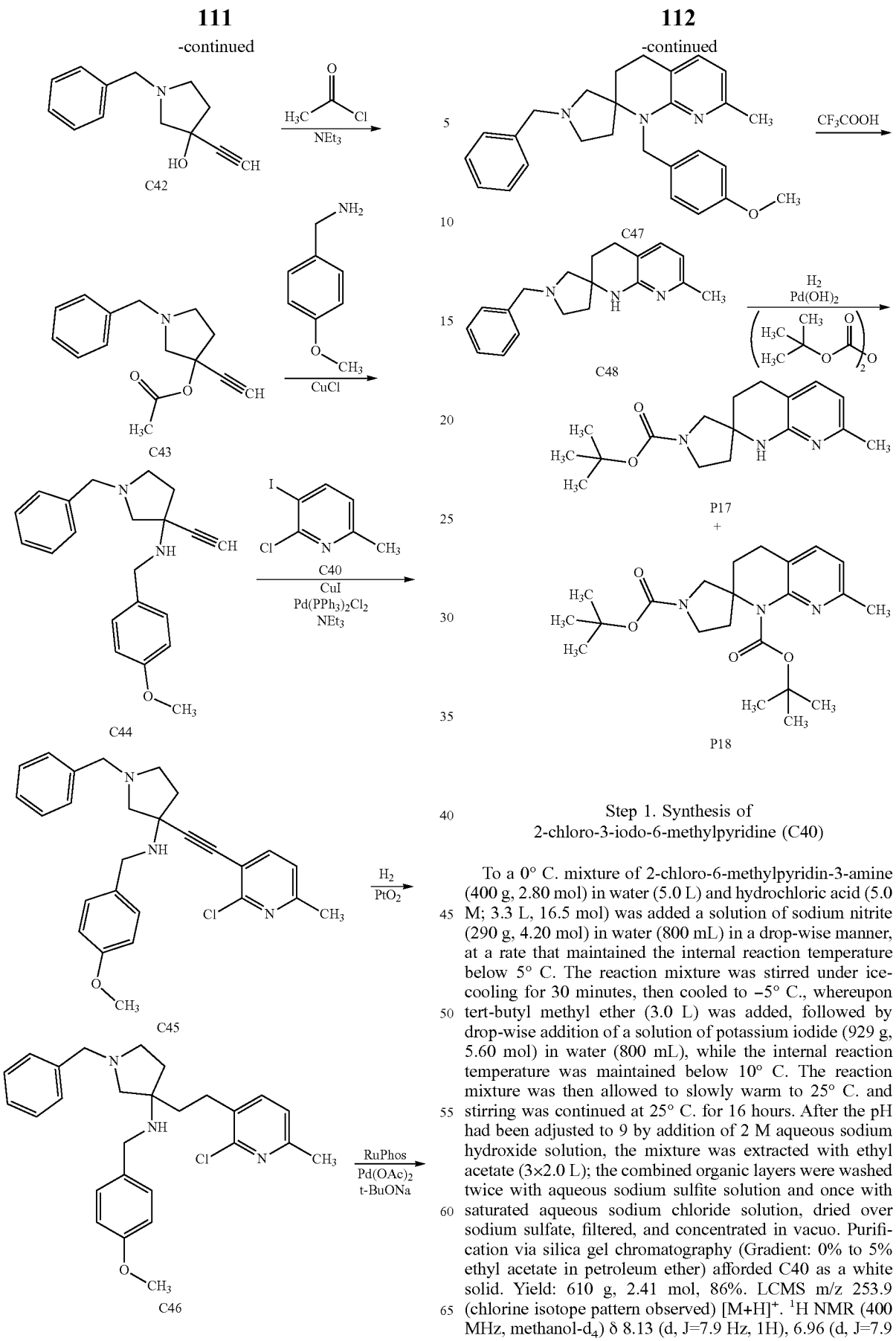

Step 1. Synthesis of
2-chloro-3-iodo-6-methylpyridine (C40)

To a 0° C. mixture of 2-chloro-6-methylpyridin-3-amine (400 g, 2.80 mol) in water (5.0 L) and hydrochloric acid (5.0 M; 3.3 L, 16.5 mol) was added a solution of sodium nitrite (290 g, 4.20 mol) in water (800 mL) in a drop-wise manner, at a rate that maintained the internal reaction temperature below 5° C. The reaction mixture was stirred under ice-cooling for 30 minutes, then cooled to −5° C., whereupon tert-butyl methyl ether (3.0 L) was added, followed by drop-wise addition of a solution of potassium iodide (929 g, 5.60 mol) in water (800 mL), while the internal reaction temperature was maintained below 10° C. The reaction mixture was then allowed to slowly warm to 25° C. and stirring was continued at 25° C. for 16 hours. After the pH had been adjusted to 9 by addition of 2 M aqueous sodium hydroxide solution, the mixture was extracted with ethyl acetate (3×2.0 L); the combined organic layers were washed twice with aqueous sodium sulfite solution and once with saturated aqueous sodium chloride solution, dried over sodium sulfate, filtered, and concentrated in vacuo. Purification via silica gel chromatography (Gradient: 0% to 5% ethyl acetate in petroleum ether) afforded C40 as a white solid. Yield: 610 g, 2.41 mol, 86%. LCMS m/z 253.9 (chlorine isotope pattern observed) [M+H]$^+$. $^1$H NMR (400 MHz, methanol-d$_4$) δ 8.13 (d, J=7.9 Hz, 1H), 6.96 (d, J=7.9 Hz, 1H), 2.44 (s, 3H).

Step 2. Synthesis of 1-benzyl-3-[(trimethylsilyl)ethynyl]pyrrolidin-3-ol (C41)

A solution of n-butyllithium in tetrahydrofuran (2.5 M; 3.75 L, 9.4 mol) was added in a drop-wise manner to a −78° C. solution of ethynyl(trimethyl)silane (1.01 kg, 10.3 mol) in tetrahydrofuran (4.0 L). The reaction mixture was stirred at −78° C. for 1 hour, whereupon a solution of 1-benzylpyrrolidin-3-one (1.50 kg, 8.56 mol) in tetrahydrofuran (1.5 L) was added drop-wise. After completion of the addition, the reaction mixture was warmed to 20° C., stirred at 20° C. for 16 hours, and subsequently poured into aqueous ammonium chloride solution. The resulting mixture was extracted with ethyl acetate (2×2.0 L), and the combined organic layers were washed with saturated aqueous sodium chloride solution, dried over sodium sulfate, filtered, and concentrated in vacuo to provide C41 as a yellow oil. Yield: 2.25 kg, 8.23 mol, 96%. LCMS m/z 274.2 [M+H]$^+$. $^1$H NMR (400 MHz, methanol-$d_4$) δ 7.37-7.28 (m, 4H), 7.28-7.22 (m, 1H), 3.66 (AB quartet, $J_{AB}$=12.7 Hz, $\Delta v_{AB}$=12.2 Hz, 2H), 2.89-2.77 (m, 3H), 2.65 (ddd, J=9.4, 7.9, 5.5 Hz, 1H), 2.30-2.21 (m, 1H), 2.12-2.03 (m, 1H), 0.14 (s, 9H).

Step 3. Synthesis of 1-benzyl-3-ethynylpyrrolidin-3-ol (C42)

A mixture of C41 (2.77 kg, 10.1 mol) and potassium carbonate (2.80 kg, 20.3 mol) in methanol (10 L) was stirred at 25° C. for 3 hours, whereupon the reaction mixture was filtered, and the filtrate was concentrated in vacuo. After the residue had been diluted with ethyl acetate (10 L), it was filtered. Concentration of this filtrate under reduced pressure afforded C42 as a black oil (2.30 kg). This material was taken directly to the following step. LCMS m/z 202.2 [M+H]$^+$. $^1$H NMR (400 MHz, methanol-$d_4$), characteristic peaks: δ 7.37-7.28 (m, 4H), 7.28-7.22 (m, 1H), 3.66 (AB quartet, $J_{AB}$=12.7 Hz, $\Delta v_{AB}$=12.7 Hz, 2H), 2.89-2.78 (m, 3H), 2.65 (ddd, J=9.4, 7.9, 5.7 Hz, 1H), 2.27 (ddd, J=13.3, 7.9, 6.8 Hz, 1H), 2.14-2.04 (m, 1H).

Step 4. Synthesis of 1-benzyl-3-ethynylpyrrolidin-3-yl acetate (C43)

To a 0° C. solution of C42 (from the previous step; 2.30 kg, 510.1 mol) and triethylamine (3.17 L, 22.7 mol) in dichloromethane (10 L) was added acetyl chloride (1.35 kg, 17.2 mol) in a drop-wise manner. The reaction mixture was then stirred at 25° C. for 30 minutes, whereupon water (10 L) was added. The resulting mixture was extracted with dichloromethane (2×3.0 L), and the combined organic layers were washed with saturated aqueous sodium chloride solution, dried over sodium sulfate, filtered, and concentrated in vacuo to provide C43 as a brown oil (2.82 kg). A portion of this material was used in the following step. LCMS m/z 244.2 [M+H]$^+$. $^1$H NMR (400 MHz, methanol-$d_4$) δ 7.38-7.23 (m, 5H), 3.65 (s, 2H), 3.05 (s, 2H), 3.03 (s, 1H), 2.77 (ddd, J=9.5, 7.4, 6.1 Hz, 1H), 2.66 (ddd, J=9.5, 7.4, 6.5 Hz, 1H), 2.46 (ddd, J=13.6, 7.4, 6.1 Hz, 1H), 2.40-2.31 (m, 1H), 2.02 (s, 3H).

Step 5. Synthesis of 1-benzyl-3-ethynyl-N-[(4-methoxyphenyl)methyl]pyrrolidin-3-amine (C44)

A mixture of C43 (from the previous step; 1.20 kg, 54.30 mol), 1-(4-methoxyphenyl)methanamine (1.35 kg, 9.84 mmol), and copper(I) chloride (48.8 g, 0.493 mol) in tetrahydrofuran (6.0 L) was degassed under vacuum and then purged with nitrogen; this evacuation-purge cycle was carried out a total of three times. The reaction mixture was then stirred at reflux for 45 minutes, whereupon it was concentrated in vacuo. This material was combined with that from three similar reactions carried out using C43 (from the previous step; 900 g of C43 employed in the three reactions, 53.2 mol) and purified by chromatography on silica gel (Gradient: 0% to 50% ethyl acetate in petroleum ether) to provide C44 as a brown oil. Combined yield: 620 g, 1.93 mol, 26% over 3 steps. LCMS m/z 321.3 [M+H]$^+$. $^1$H NMR (400 MHz, methanol-$d_4$) δ 7.36-7.21 (m, 7H), 6.85 (br d, J=8.7 Hz, 2H), 3.81-3.69 (m, 2H), 3.77 (s, 3H), 3.65 (AB quartet, $J_{AB}$=12.7 Hz, $\Delta v_{AB}$=9.9 Hz, 2H), 2.88 (s, 1H), 2.82-2.67 (m, 2H), 2.79 (AB quartet, $J_{AB}$=9.8 Hz, $\Delta v_{AB}$=37.8 Hz, 2H), 2.27 (ddd, J=13.4, 7.7, 6.0 Hz, 1H), 2.09-2.01 (m, 1H).

Step 6. Synthesis of 1-benzyl-3-[(2-chloro-6-methylpyridin-3-yl)ethynyl]-N-[(4-methoxyphenyl)methyl]pyrrolidin-3-amine (C45)

A mixture of C44 (426 g, 1.33 mol), C40 (303 g, 1.20 mmol), dichlorobis(triphenylphosphine)palladium(II) (46.6 g, 66.4 mmol), and copper(I) iodide (12.6 g, 66.2 mmol) in triethylamine (2.0 L) was degassed under vacuum and then purged with nitrogen; this evacuation-purge cycle was carried out a total of three times. The reaction mixture was stirred at reflux for 16 hours, whereupon it was filtered; the filtrate was concentrated in vacuo and combined with material from two similar reactions carried out using C40 (12.17 g, 48.0 mmol; 146 g, 0.576 mol). The resulting mixture was purified via silica gel chromatography (Gradient: 20% to 50% ethyl acetate in petroleum ether), affording C45 as a black oil. Combined yield: 420 g, 0.942 mol, 52%. LCMS m/z 446.2 [M+H]$^+$. $^1$H NMR (400 MHz, methanol-$d_4$) δ 7.80 (d, J=7.8 Hz, 1H), 7.39-7.20 (m, 8H), 6.86 (d, J=8.6 Hz, 2H), 3.87 (AB quartet, $J_{AB}$=12.0 Hz, $\Delta v_{AB}$=29.6 Hz, 2H), 3.76 (s, 3H), 3.70 (AB quartet, $J_{AB}$=13.0 Hz, $\Delta v_{AB}$=9.3 Hz, 2H), 3.00 (d, component of AB quartet, J=9.9 Hz, 1H), 2.87-2.77 (m, 3H), 2.51 (s, 3H), 2.44-2.33 (m, 1H), 2.21-2.10 (m, 1H).

Step 7. Synthesis of 1-benzyl-3-[2-(2-chloro-6-methylpyridin-3-yl)ethyl]-N-[(4-methoxyphenyl)methyl]pyrrolidin-3-amine (C46)

A mixture of C45 (40.0 g, 89.7 mmol) and platinum(IV) oxide (4.09 g, 18.0 mmol) in methanol (400 mL) was hydrogenated (60 psi) at 25° C. for 3 hours. The reaction mixture was then filtered, and the filtrate was concentrated in vacuo to provide C46 as a black oil. Yield: 40.5 g, assumed quantitative. LCMS m/z 450.3 [M+H]$^+$. $^1$H NMR (400 MHz, methanol-$d_4$), characteristic peaks: δ 7.61 (d, J=7.7 Hz, 1H), 7.38-7.23 (m, 7H), 7.17 (d, J=7.7 Hz, 1H), 6.88 (br d, J=8.7 Hz, 2H), 3.78 (s, 3H), 3.64 (AB quartet, $J_{AB}$=12.0 Hz, $\Delta v_{AB}$=21.6 Hz, 2H), 3.64 (s, 2H), 2.46 (s, 3H).

Step 8. Synthesis of 1'-benzyl-1-[(4-methoxyphenyl)methyl]-7-methyl-3,4-dihydro-1H-spiro[1,8-naphthyridine-2,3'-pyrrolidine] (C47)

A mixture of C46 (400 g, 0.89 mol), palladium(II) acetate (9.97 g, 44.4 mmol), 2-dicyclohexylphosphino-2',6'-diisopropoxybiphenyl (RuPhos; 41.5 g, 88.9 mmol) and sodium tert-butoxide (170 g, 1.77 mol) in 1,4-dioxane (4.0 L) was stirred at 90° C. for 10 hours, whereupon the reaction mixture was filtered, and the filtrate was concentrated in vacuo. After the residue had been partitioned between ethyl acetate (2 L) and water (2 L), the aqueous layer was extracted with ethyl acetate (1 L). The combined organic layers were washed with saturated aqueous sodium chloride solution, dried over sodium sulfate, filtered, concentrated in vacuo, and subjected to silica gel chromatography (Gradient: 0% to 10% ethyl acetate in petroleum ether), affording C47 as a white solid. Yield: 195 g, 0.472 mol, 53%. LCMS m/z 414.3 [M+H]⁺. ¹H NMR (400 MHz, chloroform-d) δ 7.38-7.21 (m, 5H, assumed; partially obscured by solvent peak), 7.17 (d, J=8.2 Hz, 2H), 7.03 (d, J=7.2 Hz, 1H), 6.77 (d, J=8.2 Hz, 2H), 6.32 (d, J=7.3 Hz, 1H), 5.07-4.92 (m, 2H), 3.77 (s, 3H), 3.54 (br AB quartet, J$_{AB}$=13 Hz, Δv$_{AB}$=40 Hz, 2H), 2.95 (d, J=10.2 Hz, 1H), 2.92-2.83 (m, 1H), 2.83-2.73 (m, 1H), 2.73-2.63 (m, 1H), 2.43-2.31 (m, 1H), 2.29-2.08 (m, 2H), 2.23 (s, 3H), 2.03-1.73 (m, 3H).

Step 9. Synthesis of 1'-benzyl-7-methyl-3,4-dihydro-1H-spiro[1,8-naphthyridine-2,3'-pyrrolidine] (C48)

To a 0° C. solution of C47 (190 g, 0.459 mol) in dichloromethane (1.5 L) was added trifluoroacetic acid (523 g, 4.59 mol), and the reaction mixture was stirred at 25° C. for 3 hours. It was then concentrated in vacuo; the residue was diluted with ethyl acetate (1.5 L) and washed with saturated aqueous sodium carbonate solution (1.0 L), and this aqueous layer was extracted with ethyl acetate (2×300 mL). The combined organic layers were concentrated in vacuo and purified via silica gel chromatography (Gradient: 0% to 10% methanol in dichloromethane) to afford C48 as a brown oil (179 g). This material was progressed directly to the following step. LCMS m/z 294.3 [M+H]⁺. ¹H NMR (400 MHz, chloroform-d) δ 9.1-8.3 (br s, 1H), 7.41-7.35 (m, 2H), 7.35-7.28 (m, 2H), 7.28-7.22 (m, 2H, assumed; partially obscured by solvent peak), 6.35 (d, J=7.3 Hz, 1H), 3.72 (s, 2H), 2.96-2.85 (m, 1H), 2.80-2.62 (m, 5H), 2.42 (s, 3H), 2.05 (ddd, J=13.1, 8.1, 5.0 Hz, 1H), 1.98-1.81 (m, 3H).

Step 10. Synthesis of tert-butyl 7-methyl-3,4-dihydro-1H-spiro[1,8-naphthyridine-2,3'-pyrrolidine]-1'-carboxylate (P17) and di-tert-butyl 7-methyl-3,4-dihydro-1H-spiro[1,8-naphthyridine-2,3'-pyrrolidine]-1,1'-dicarboxylate (P18)

A mixture of C48 (from the previous step; 179 g, 50.459 mol), di-tert-butyl dicarbonate (199.7 g, 915 mmol), and palladium hydroxide (17.9 g, 127 mmol) in methanol (2.0 L) and ethyl acetate (2.0 L) was hydrogenated at 55 psi and 25° C. for 18 hours. The reaction mixture was then filtered through a pad of diatomaceous earth and the filtrate was concentrated in vacuo. Silica gel chromatography (Gradient: 0% to 50% dichloromethane in ethyl acetate) provided P17 and P18, both as white solids.

P17—Yield: 101 g, 0.333 mol, 73% over 2 steps. LCMS m/z 304.3 [M+H]⁺. ¹H NMR (400 MHz, methanol-d₄) δ 7.20 (d, J=7.3 Hz, 1H), 6.44 (d, J=7.4 Hz, 1H), 3.62-3.44 (m, 2H), 3.37-3.3 (m, 2H, assumed; partially obscured by solvent peak), 2.84-2.66 (m, 2H), 2.27 (s, 3H), 2.05-1.92 (m, 2H), 1.92-1.76 (m, 2H), [1.48 (s) and 1.46 (s), total 9H].

P18—Yield: 21.3 g, 52.8 mmol, 12% over 2 steps. LCMS m/z 404.3 [M+H]⁺. ¹H NMR (400 MHz, methanol-d₄) δ 7.49 (d, J=7.7 Hz, 1H), 7.02 (br d, J=7.7 Hz, 1H), [3.85 (d, J=11.3 Hz) and 3.75 (d, J=11.2 Hz), total 1H], 3.62-3.47 (m, 2H), 3.40-3.24 (m, 1H, assumed; partially obscured by solvent peak), 2.89-2.73 (m, 2H), 2.54-2.27 (m, 1H), 2.44 (s, 3H), 2.13-1.82 (m, 3H), 1.46 (s, 9H), [1.43 (s) and 1.43 (s), total 9H].

Preparations P19 and P20
tert-Butyl (2S)-7-methyl-3,4-dihydro-1H-spiro[1,8-napthyridine-2,3'-pyrrolidine]-1'-carboxylate (P19) and tert-butyl (2R)-7-methyl-3,4-dihydro-1H-spiro[1,8-napthyridine-2,3'-pyrrolidine]-1'-carboxylate (P20)

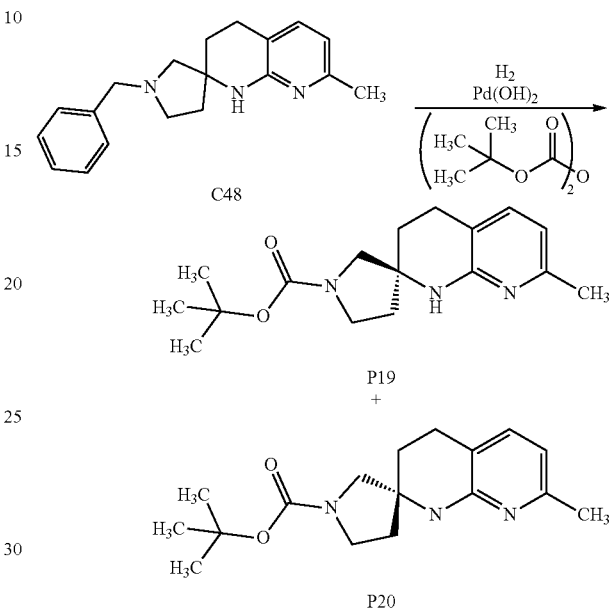

Di-tert-butyl dicarbonate (3.97 g, 18.2 mmol) was added to a solution of C48 (4.45 g, 15.2 mmol) in a mixture of methanol (20 mL) and ethyl acetate (25 mL). After addition of palladium hydroxide on carbon (900 mg), the reaction mixture was hydrogenated at 80 psi for 18 hours, at which time LCMS analysis indicated complete conversion to P19/P20: LCMS m/z 304.2 [M+H]⁺. The reaction mixture was filtered, and the filtrate was concentrated under reduced pressure; the residue was dissolved in ethyl acetate, washed sequentially with saturated sodium bicarbonate solution and saturated aqueous sodium chloride solution, dried over magnesium sulfate, filtered, and concentrated in vacuo. Separation of the component enantiomers was carried out via supercritical fluid chromatography {Column: Chiral Technologies Chiralpak IB, 30×250 mm, 5 µm; Mobile phase 9:1 carbon dioxide/[ethanol containing 0.2% (7 M ammonia in methanol)]; Flow rate: 80 mL/minute; Back pressure: 100 bar}. The first-eluting enantiomer was designated as P19 and the second-eluting enantiomer as P20. Both were isolated as solids.

P19—Yield: 1.60 g, 5.27 mmol, 35%. Retention time: 3.75 minutes [Analytical conditions. Column: Chiral Technologies Chiralpak IB, 4.6×250 mm, 5 µm; Mobile phase A: carbon dioxide; Mobile phase B: ethanol containing 0.2% (7 M ammonia in methanol); Gradient: 5% B for 1 minute, then 5% to 60% B over 8 minutes; Flow rate: 3.0 mL/minute; Back pressure: 120 bar].

P20—Yield: 1.50 g, 4.94 mmol, 32%. Retention time: 3.96 minutes (Analytical conditions identical to those used for P19).

The indicated absolute stereochemistries were assigned based on the conversion of this batch of P19 to P23 in Alternate Preparation (#1) of P23 below. The absolute configuration of P23 was established via its use in the synthesis of 14, which was analyzed via single-crystal X-ray crystallography (see below).

Preparation P21
Di-tert-butyl 6-bromo-7-methyl-3,4-dihydro-1H-spiro[1,8-napthyridine-2,3'-pyrrolidine]-1,1'-dicarboxylate (P21)

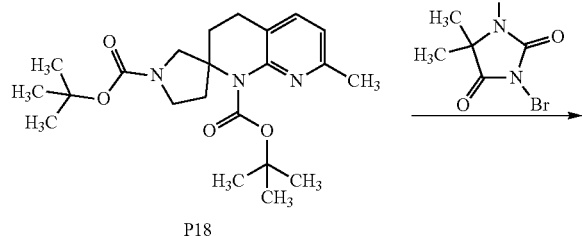

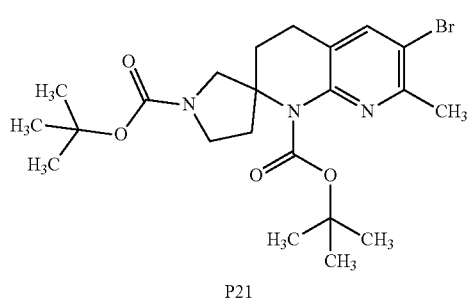

To a 0° C. solution of P18 (20 g, 50 mmol) in dichloromethane (200 mL) was added 1,3-dibromo-5,5-dimethyl-imidazolidine-2,4-dione (7.09 g, 24.8 mmol) in six portions over 30 minutes. The reaction mixture was stirred at 0° C. for 1 hour, whereupon it was treated with saturated aqueous sodium sulfite solution (200 mL) and extracted with dichloromethane (3×100 mL). The combined organic layers were washed with saturated aqueous sodium bicarbonate solution, dried over sodium sulfate, filtered, and concentrated in vacuo. Silica gel chromatography (Gradient: 0% to 40% ethyl acetate in petroleum ether) provided P21 as a white solid. Yield: 22.8 g, 47.2 mmol, 94%. LCMS m/z 384.1 (bromine isotope pattern observed) {[M-(2-methylprop-1-ene and CO$_2$)]+H}$^+$. $^1$H NMR (400 MHz, chloroform-d) δ 7.51 (br s, 1H), [3.89 (d, J=11.0 Hz) and 3.73 (d, J=11.0 Hz), total 1H], 3.65-3.51 (m, 1H), 3.46 (d, J=11.0 Hz, 1H), 3.38-3.26 (m, 1H), [2.87-2.56 (m) and 2.15-1.70 (m), total 6H], 2.57 (s, 3H), [1.46 (s) and 1.45 (s), total 18H].

Preparation P22
tert-butyl 6-bromo-7-methyl-3,4-dihydro-1H-spiro[1,8-napthyridine-2,3'-pyrrolidine]-1'-carboxylate (P22)

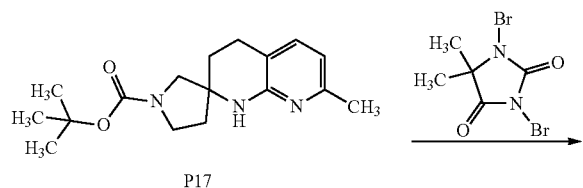

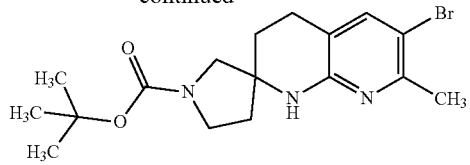

1,3-Dibromo-5,5-dimethylimidazolidine-2,4-dione (2.47 g, 8.64 mmol) was added in portions over 20 minutes to a 0° C. solution of P17 (5.25 g, 17.3 mmol) in dichloromethane (69 mL). After the reaction mixture had been stirred at 0° C. for 45 minutes, LCMS analysis indicated conversion to P22: LCMS m/z 384.3 (bromine isotope pattern observed) [M+H]$^+$. After 1 hour at 0° C., the reaction mixture was treated with saturated aqueous sodium sulfite solution (100 mL), and the mixture was extracted with dichloromethane. The organic layer was washed sequentially with saturated aqueous sodium bicarbonate solution and saturated aqueous sodium chloride solution, dried over magnesium sulfate, filtered, and concentrated in vacuo to provide P22 as a solid. Yield: 6.60 g, 17.3 mmol, quantitative. $^1$H NMR (400 MHz, methanol-d$_4$) δ 7.40 (br s, 1H), 3.61-3.43 (m, 2H), 3.37-3.3 (m, 2H, assumed; largely obscured by water peak), 2.85-2.67 (m, 2H), 2.37 (s, 3H), 2.06-1.92 (m, 2H), 1.92-1.75 (m, 2H), [1.47 (s) and 1.46 (s), total 9H].

Preparations of P23 and P24
tert-Butyl (2S)-6-bromo-7-methyl-3,4-dihydro-1H-spiro[1,8-napthyridine-2,3'-pyrrolidine]-1'-carboxylate (P23) and tert-Butyl (2R)-6-bromo-7-methyl-3,4-dihydro-1H-spiro[1,8-napthyridine-2,3'-pyrrolidine]-1'-carboxylate (P24)

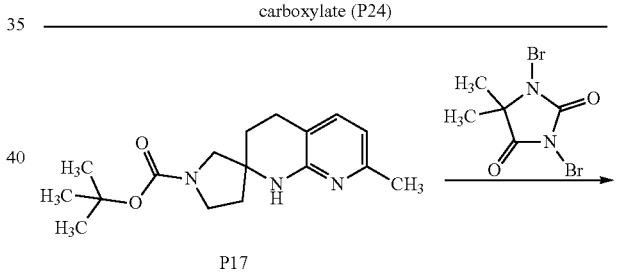

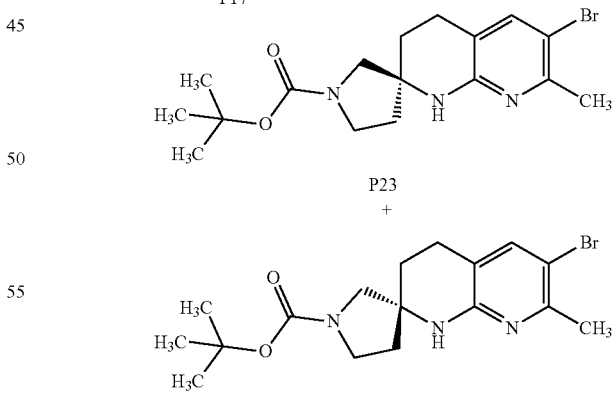

1,3-Dibromo-5,5-dimethylimidazolidine-2,4-dione (5.65 g, 19.8 mmol) was added in portions to a 0° C. solution of P17 (10.0 g, 32.9 mmol) in dichloromethane (150 mL), and the reaction mixture was stirred at 0° C. to 5° C. for 1 hour, at which time LCMS analysis indicated that bromination had occurred: LCMS m/z 382.3 [M+H]$^+$. Saturated aqueous sodium sulfite solution (20 mL) was added, followed by water (50 mL); the resulting aqueous layer was extracted with dichloromethane (2×50 mL). The combined organic layers were washed with saturated aqueous sodium chloride solution, dried over magnesium sulfate, filtered, and concentrated in vacuo; silica gel chromatography (Gradient: 0% to 100% ethyl acetate in heptane) afforded a racemic mixture of P23 and P24 as a light-yellow foam (11.8 g). This was combined with the product of a similar reaction carried out using P17 (7.40 g, 24.4 mmol) to provide a light-yellow foam (20.9 g, 54.6 mmol, combined yield 95%), and separated into its component enantiomers via supercritical fluid chromatography [Column: Chiral Technologies Chiralcel OJ, 50×250 mm, 5 μm; Mobile phase 4:1 carbon dioxide/ (1:1 methanol/acetonitrile); Flow rate: 250 mL/minute; Back pressure: 120 bar]. The first-eluting enantiomer was designated as P23, and the second-eluting enantiomer was designated as P24.

The indicated absolute stereochemistry was assigned on the basis of conversion of this batch of P23 to P28 (see Preparation P28) and then to Example 14; the absolute stereochemistry of 14 was established via single-crystal X-ray analysis (see below).

P23, isolated as a yellow oil that solidified on standing— Combined yield: 9.37 g, 24.5 mmol, 43%. $^1$H NMR (400 MHz, DMSO-$d_6$) δ 7.37 (s, 1H), 7.02-6.96 (m, 1H), [3.55-3.40 (m), 3.36-3.26 (m, assumed; partially obscured by water peak), and 3.24-3.13 (m), total 4H], 2.75-2.55 (m, 2H), 2.31 (s, 3H), 1.95-1.78 (m, 2H), 1.76-1.60 (m, 2H), [1.40 (s) and 1.38 (s), total 9H].

Retention time: 4.01 minutes [Analytical conditions. Column: Chiral Technologies Chiralcel OJ-H, 4.6×250 mm, 5 μm; Mobile phase A: carbon dioxide; Mobile phase B: methanol containing 0.2% (7 M ammonia in methanol); Gradient: 5% B for 1 minute, then 5% to 60% B over 8 minutes; Flow rate: 3.0 mL/minute; Back pressure: 120 bar].

P24—Combined yield: 11.8 g, which contained ethanol; corrected estimate: 28.4 mmol, 50%. $^1$H NMR (400 MHz, DMSO-$d_6$), characteristic peaks: δ 7.37 (s, 1H), 7.01-6.96 (m, 1H), 2.75-2.55 (m, 2H), 2.31 (s, 3H), 1.95-1.78 (m, 2H), 1.76-1.60 (m, 2H), [1.40 (s) and 1.38 (s), total 9H]. Retention time: 4.32 minutes (Analytical conditions identical to those used for P23).

1,3-Dibromo-5,5-dimethylimidazolidine-2,4-dione (625 mg, 2.19 mmol) was added in portions to a 0° C. solution of P19 (material from Preparations P19 and P20; 1.10 g, 3.63 mmol) in dichloromethane (20 mL). After the reaction mixture had been stirred at room temperature for 1 hour, LCMS analysis indicated conversion to P23: LCMS m/z 384.2 (bromine isotope pattern observed) [M+H]$^+$. Saturated aqueous sodium sulfite solution was then added, and the resulting mixture was extracted with dichloromethane. The organic layer was washed with saturated aqueous sodium chloride solution, dried over magnesium sulfate, filtered, concentrated in vacuo, and purified using silica gel chromatography (Gradient: 10% to 40% ethyl acetate in heptane) to afford P23 as a white solid. Yield: 1.25 g, 3.27 mmol, 90%. $^1$H NMR (400 MHz, chloroform-d) δ 7.33 (s, 1H), 5.15-5.01 (br s, 1H), 3.59-3.45 (m, 2H), 3.43-3.25 (m, 2H), 2.81-2.66 (m, 2H), 2.43 (s, 3H), 2.01-1.74 (m, 4H), 1.48-1.43 (br s, 9H).

The absolute stereochemistry of this sample of P23 was assigned as indicated, via comparison with samples from Preparations P23 and P24:

Retention time of P23 from Alternate Preparation (#1) of P23: 4.08 minutes

Retention times of a racemic mixture of P23 and P24: 4.07 and 4.36 minutes.

Retention time of P23 from Preparations P23 and P24: 4.01 minutes

Retention time of P24 from Preparations P23 and P24: 4.32 minutes

These four analyses were run using the same analytical method: [Column: Chiral Technologies Chiralcel OJ-H, 4.6× 100 mm, 5 μm; Mobile phase A: carbon dioxide; Mobile phase B: methanol containing 0.2% (7 M ammonia in methanol); Gradient: 5% B for 1 minute, then 5% to 60% B over 8 minutes; Flow rate: 3.0 mL/minute].

Alternate Preparation (#1) of P23
tert-Butyl (2S)-6-bromo-7-methyl-3,4-dihydro-1H-spiro[1,8-napthyridine-2,3'-pyrrolidine]-1'-carboxylate (P23)

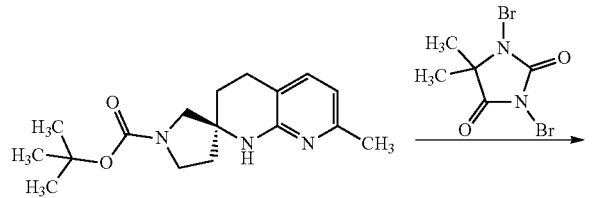

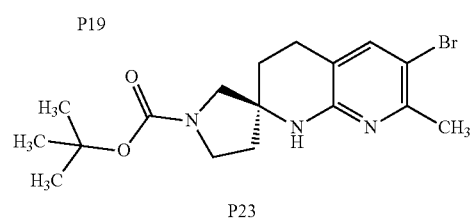

Alternate Preparation (#2) of P23
tert-Butyl (2S)-6-bromo-7-methyl-3,4-dihydro-1H-spiro[1,8-naphthyridine--2,3'-pyrrolidine]-1'-carboxylate (P23)

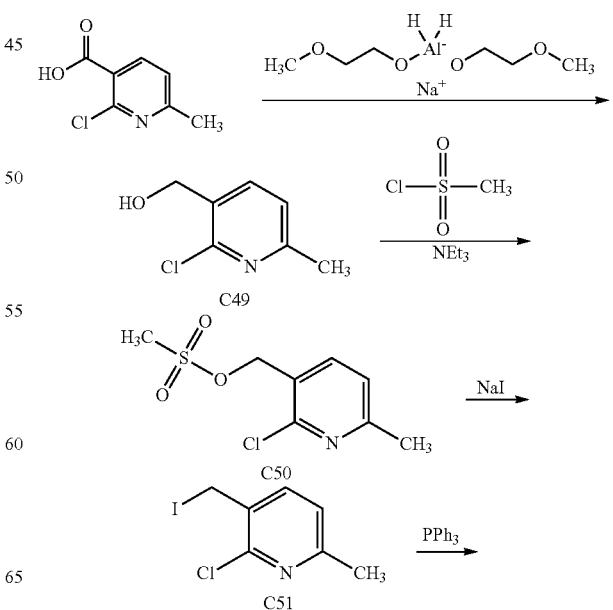

121
-continued
122
-continued
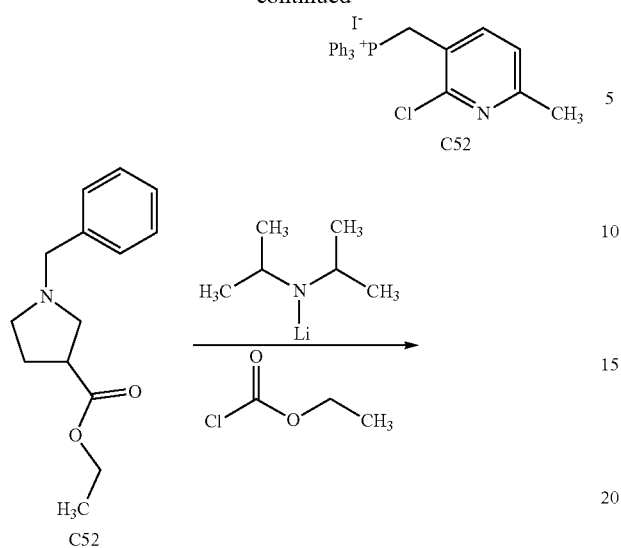
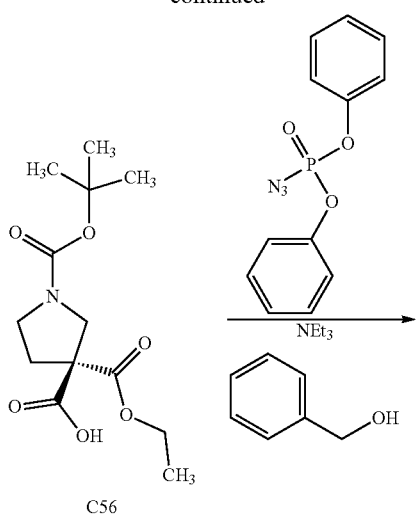

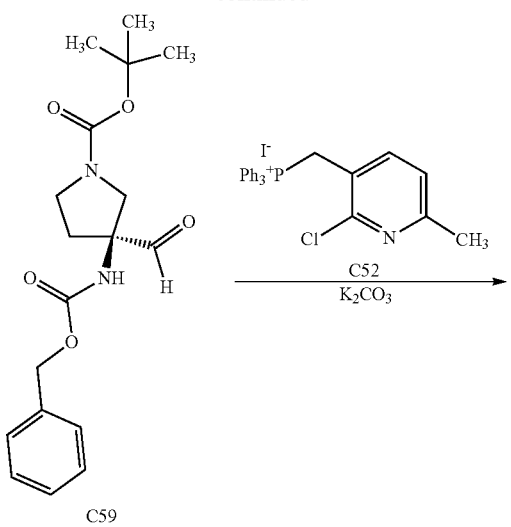

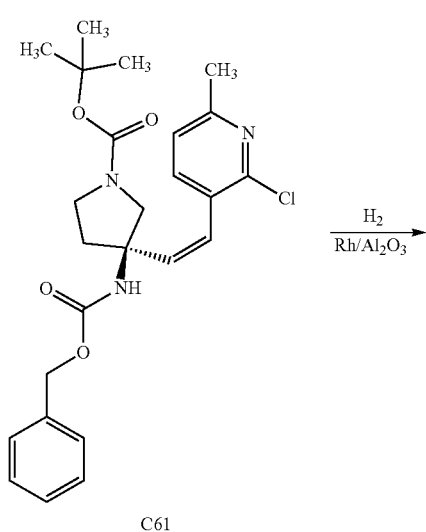

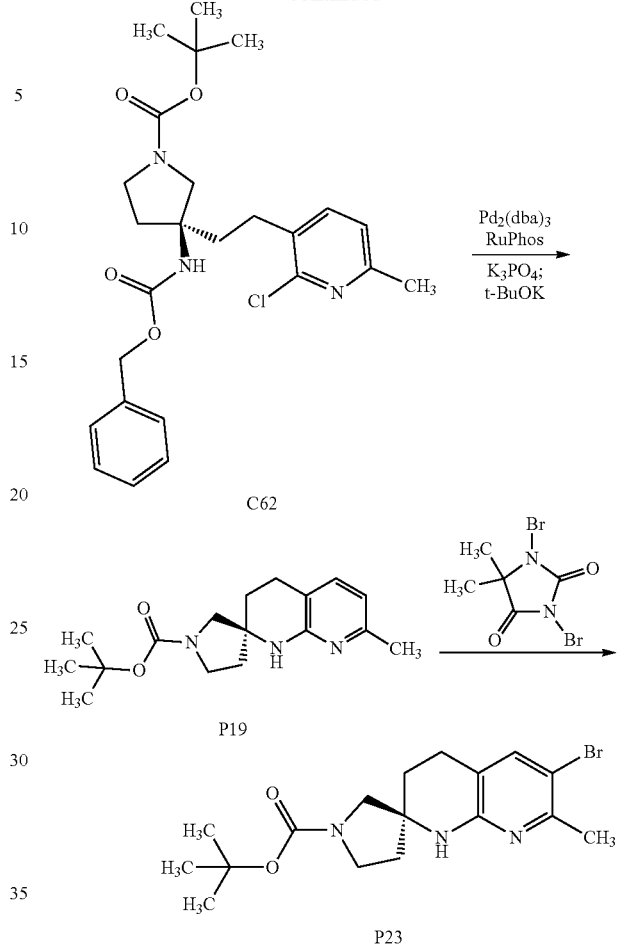

Step 1. Synthesis of (2-chloro-6-methylpyridin-3-yl)methanol (C49)

Sodium bis(2-methoxyethoxy)aluminum hydride solution (70%; 1.05 kg, 2.5 eq) was added to a −5° C. to 5° C. solution of 2-chloro-6-methylpyridine-3-carboxylic acid (250 g, 1.46 mol) in toluene (2.5 L). After the reaction mixture had been stirred at −5° C. to 5° C. for 19 hours, it was treated with a solution of sodium hydroxide (145.7 g, 3.642 mol, 2.50 eq) in water (1.25 L), while the internal temperature was maintained below 0° C. to 10° C. The resulting mixture was then warmed to 25° C.; after 15 minutes, the aqueous layer was extracted with propan-2-yl acetate (2×1.25 L). These two extracts were combined with the toluene layer and filtered through silica gel (125 g). The filter cake was rinsed with propan-2-yl acetate (125 mL), and the combined filtrates were concentrated to 8 volumes at a temperature of 40° C. to 45° C., affording C49 as a solution in toluene (1.602 kg, 11.2% C49 by weight); the bulk of this solution was used in the following step. Estimated yield: 179.4 g, 1.138 mol, 78%. $^1$H NMR (400 MHz, DMSO-$d_6$) δ 7.81 (d, J=7.8 Hz, 1H), 7.29 (d, J=7.7 Hz, 1H), 5.48 (t, J=5.6 Hz, 1H), 4.50 (d, J=5.6 Hz, 2H), 2.43 (s, 3H).

Step 2. Synthesis of (2-chloro-6-methylpyridin-3-yl)methyl methanesulfonate (C50)

Triethylamine (134.2 g, 1.326 mol) was added to a solution of C49 in toluene (from the previous step; 1.537 kg, containing 11.2% C49, 172.1 g, 1.09 mol). The solution was cooled to −5° C. to 5° C., and then treated in a drop-wise manner with methanesulfonyl chloride (128.5 g, 1.122 mol), while maintaining the internal temperature at −5° C. to 5° C. After the reaction mixture had been stirred at this temperature for 2 hours, triethylamine (22.7 g, 0.224 mol) was again added, followed by drop-wise addition of methanesulfonyl chloride (25.7 g, 0.224 mol). Stirring was continued at −5° C. to 5° C. for 1 hour, whereupon the reaction mixture was treated with water (805 mL) while the internal temperature was maintained below 25° C., and then stirred for 15 minutes at 25° C. The organic layer was washed with water (805 mL) and concentrated to provide C50 as a solution in toluene (861 g). This solution was used directly in the following step. $^1$H NMR (400 MHz, DMSO-$d_6$) δ 7.92 (d, J=7.7 Hz, 1H), 7.36 (d, J=7.7 Hz, 1H), 5.30 (s, 2H), 3.29 (s, 3H), 2.48 (s, 3H).

Step 3. Synthesis of 2-chloro-3-(iodomethyl)-6-methylpyridine (C51)

Sodium iodide (230 g, 1.53 mol) was dissolved in acetone (1.13 kg) at 25° C.; to this solution was added a solution of C50 in toluene (from the previous step; 861 g, ≤1.09 mol of C50). After the reaction mixture had been stirred at 25° C. for 1 hour, a solution of sodium metabisulfite (57.86 g, 0.3044 mol) in water (1.45 L) was added and stirring was continued for 30 minutes. The organic layer was separated, diluted with toluene (417 mL), and concentrated to 5 volumes, providing C51 as a solution in toluene (1.110 kg, 22.93% C51 by weight). This solution was used directly in the following step. Estimated yield: 254.5 g, 0.9514 mol, 87% over 2 steps. $^1$H NMR (400 MHz, DMSO-$d_6$) δ 7.90 (d, J=7.7 Hz, 1H), 7.26 (d, J=7.8 Hz, 1H), 4.55 (s, 2H), 2.41 (s, 3H).

Step 4. Synthesis of [(2-chloro-6-methylpyridin-3-yl)methyl](triphenyl)phosphonium iodide (C52)

A solution of C51 in toluene (from the previous step; 1.110 kg, 22.93% C51 by weight, 254.5 g, 0.9514 mol) was diluted with acetonitrile (1.29 L) and treated with triphenylphosphine (262 g, 0.999 mol). After the reaction mixture had been stirred for 4 hours at 25° C., it was cooled to 10° C., stirred at that temperature for 16 hours, and filtered. The filter cake was washed with toluene (255 mL) and dried at 45° C. for 4 hours, affording C52 as a solid. Yield: 412.6 g, 0.7788 mol, 56% over 4 steps. Purity: 99.7% by HPLC. $^1$H NMR (400 MHz, DMSO-$d_6$) δ 7.97-7.90 (m, 3H), 7.80-7.71 (m, 8H), 7.71-7.66 (m, 4H), 7.44 (dd, J=7.8, 2.4 Hz, 1H), 7.20 (d, J=7.8 Hz, 1H), 5.15 (d, $J_{HP}$=15.0 Hz, 2H), 2.40 (d, J=2.4 Hz, 3H).

Step 5. Synthesis of diethyl 1-benzylpyrrolidine-3,3-dicarboxylate (C53)

A solution of ethyl 1-benzylpyrrolidine-3-carboxylate (700 g, 3.00 mol) in tetrahydrofuran (4.20 L) was added in a drop-wise manner over 5 hours to a −80° C. to −70° C. solution of lithium diisopropylamide (2.0 M, 2.40 L, 4.80 mol). Stirring was continued at −80° C. to −70° C. for 2 hours, whereupon ethyl chloroformate (423.5 g, 3.90 mol) was added over 3 hours, while the reaction temperature was maintained at −80° C. to −70° C. After the reaction mixture had been stirred for 2 hours at −80° C. to −70° C., the temperature was adjusted to −50° C. to −40° C., and the reaction was quenched by addition of a solution of acetic acid (288 g, 4.80 mol) in tetrahydrofuran (1.40 L), while the temperature was kept at −50° C. to −40° C. The resulting mixture was warmed to 15° C. to 25° C. and partitioned between water (3.50 L) and 2-methyltetrahydrofuran (7.0 L). After this mixture had been stirred for 30 minutes at 15° C. to 25° C., the aqueous layer was extracted with 2-methyltetrahydrofuran (7.0 L), and the combined organic layers were washed with a solution of acetic acid (288 g, 4.80 mol) in water (4.2 L) and then with an aqueous solution of sodium sulfate (10%; 2×3.50 kg). The organic layers were concentrated in vacuo to 2 to 3 volumes, while keeping the temperature below 50° C. Ethanol (4.90 L, 7 volumes) was added, and the solution was again concentrated in vacuo to 2 to 3 volumes, while keeping the temperature below 50° C. This ethanol addition/concentration was carried out a total of three times, with the final round employing 2.80 L of ethanol, followed by concentration to 4 to 5 volumes. This provided C53 as a solution in ethanol (3.148 kg, 24.23% C53 by weight). A portion of this solution was used in the following step. Estimated yield: 762.8 g, 2.498 mol, 83%. $^1$H NMR (400 MHz, DMSO-$d_6$) δ 7.35-7.20 (m, 5H), 4.12 (q, J=7.1 Hz, 4H), 3.57 (s, 2H), 2.90 (s, 2H), 2.55 (t, J=6.9 Hz, 2H), 2.29 (t, J=6.8 Hz, 2H), 1.14 (t, J=7.1 Hz, 6H).

Step 6. Synthesis of diethyl pyrrolidine-3,3-dicarboxylate, L-tartrate salt (C54)

Ethanol (720 mL, 6 volumes) was added to a solution of C53 (120 g, 0.393 mol) in ethanol (from the previous step; approximately 500 mL). After addition of wet palladium on carbon (10%; 12 g), the reaction vessel was evacuated and charged with argon three times, and then evacuated and charged with hydrogen three times. Hydrogenation was then carried out at 40 to 50 psi and 40° C. to 50° C. for 24 hours. The resulting mixture was filtered through diatomaceous earth (50 g); the filter cake was washed with ethanol (240 mL, 2 volumes), and the combined filtrates were concentrated in vacuo to 2.5 to 3.5 volumes while keeping the temperature at or below 45° C. This solution was added, over 2 hours, to a 40° C. to 50° C. solution of L-tartaric acid (76.7 g, 0.511 mol) in water (85 mL, 0.7 volumes) and ethanol (465 mL). After the mixture had been stirred at 40° C. to 50° C. for 1 hour, a seed of C54 (0.4 g; see below) was added at 45° C. The mixture was cooled to 10° C. over 6 hours, and then stirred at 10° C. for 4 hours; filtration provided a filter cake, which was washed with ethanol (2 volumes) and dried at 40° C. for 20 hours to afford C54 as a solid. Yield: 127.4 g, 0.3487 mol, 89%. HPLC purity: 99.1%. $^1$H NMR (400 MHz, DMSO-$d_6$) δ 4.16 (q, J=7.1 Hz, 4H), 4.03 (s, 2H), 3.49 (s, 2H), 3.08 (t, J=7.1 Hz, 2H), 2.32 (t, J=7.1 Hz, 2H), 1.18 (t, J=7.1 Hz, 6H).

The seed material used above was obtained from another run of the same synthesis of C54, in which solid C54 formed directly upon cooling.

Step 7. Synthesis of 1-tert-butyl 3,3-diethyl pyrrolidine-1,3,3-tricarboxylate (C55)

Di-tert-butyl dicarbonate (19.7 g, 90.3 mmol) was added in a drop-wise manner to a 20° C. to 30° C. mixture of C54 (88.12 g, 0.2412 mol) and triethylamine (73.33 g, 0.7247 mol) in dichloromethane (881 mL, 10 volumes). Additional di-tert-butyl dicarbonate (19.2 g, 88.0 mmol and 19.3 g, 88.4 mmol) was added drop-wise after periodic HPLC analysis. After the reaction mixture had been stirred at 20° C. to 30° C. for 18 hours, the pH was adjusted to 7 by addition of hydrochloric acid (1 M; 309 g), and stirring was continued for 15 minutes. The organic layer was stirred with aqueous sodium sulfate solution (10%; 485.30 g) at 20° C. to 30° C. for 15 minutes, and then the organic layer was concentrated in vacuo to 1 to 2 volumes while the temperature was maintained below 40° C. Dimethyl sulfoxide (71.7 g) was added to afford C55 as a solution in dimethyl sulfoxide (154.2 g, 48.9% C55 by weight). The bulk of this material was progressed to the following step. Estimated yield: 75.4 g, 0.239 mol, 99%. $^1$H NMR (400 MHz, DMSO-$d_6$) δ 4.16 (q, J=7.1 Hz, 4H), 3.67 (br s, 2H), 3.34-3.26 (m, 2H), 2.37-2.28 (m, 2H), 1.39 (s, 9H), 1.17 (br t, J=7.1 Hz, 6H).

Step 8. Synthesis of (3R)-1-(tert-butoxycarbonyl)-3-(ethoxycarbonyl)pyrrolidine-3-carboxylic acid (C56)

ECS-Esterase 03 enzyme [*Bacillus stearothermophilus*, recombinant from *Escherichia coli*, (EC 3.1.1.1); 0.540 g] was added to phosphate buffer (0.1 M; pH=6.92, 580 mL, 8.2 volumes) at 20° C. to 30° C. A solution of C55 (72.2 g, 0.229 mol) in dimethyl sulfoxide (from the previous step; approximately 148 g) was added; additional dimethyl sulfoxide (9 mL) was used to rinse the initial vessel, and this was also added to the reaction mixture. The initial reaction pH was 7.08; after stirring at 20° C. to 30° C. for 1 hour, the pH decreased to 6.58. A pH autotitrator was used to maintain the pH at 7.5 by addition of aqueous sodium hydroxide solution (2 M; 121 mL, 0.242 mol) over 24 hours. Hydrochloric acid (6 M; 52 mL, 0.312 mol) was added, bringing the pH to 2.39; ethyl acetate (435 mL, 6.0 volumes) was then added, and the mixture was stirred for 30 minutes at 20° C. to 30° C. Filtration through diatomaceous earth (18.0 g) provided a filter cake, which was rinsed with ethyl acetate (2×75 mL). The combined filtrates were stirred at 20° C. to 30° C. for 30 minutes, and then the aqueous layer was stirred with ethyl acetate (217 mL, 3.0 volumes) for 30 minutes. The combined organic layers were washed twice with water (360 mL, 5.0 volumes) by stirring for 30 minutes. The resulting solution was concentrated in vacuo to 1 to 2 volumes, while maintaining the temperature below 40° C., then diluted with toluene (360 mL); this concentration/dilution procedure was carried out a total of three times, providing C56 as a solution in toluene (418.3 g, 15.67% C56 by weight). Estimated yield: 65.6 g, 0.228 mol, quantitative. $^1$H NMR (400 MHz, chloroform-d) δ 7.99 (v br s, 1H), 4.22 (q, J=7.1 Hz, 2H), [3.88 (br s) and 3.83 (br s), total 2H], 3.51-3.38 (m, 2H), 2.41 (t, J=7.1 Hz, 2H), 1.44 (s, 9H), 1.26 (br t, J=7 Hz, 3H).

Step 9. Synthesis of 1-tert-butyl 3-ethyl (3S)-3-{[(benzyloxy)carbonyl]amino}pyrrolidine-1,3-dicarboxylate (C57)

Toluene (170 mL, 1.2 volumes) was added to a solution of C56 in toluene (3.8 volumes, containing 28.9% by weight of C56, 146.4 g, 0.5096 mol); the solution was heated to 80° C. to 90° C. To this was slowly added, over 2 hours, a mixture of triethylamine (77.4 g, 0.765 mol) and diphenyl phosphorazidate (140.3 g, 0.5098 mol) in toluene (732 mL, 5 volumes). The reaction mixture was stirred at 80° C. to 90° C. for 3 hours, whereupon it was cooled to 50° C. and treated drop-wise, over 2 hours, with a solution of benzyl alcohol (55.12 g, 0.5097 mol) in toluene (290 mL, 2 volumes). After the reaction mixture had been stirred at 100° C. for 16 hours, it was cooled to 15° C. to 25° C. and partitioned between toluene (1.46 L, 10 volumes) and water (2.20 L, 15 volumes) by stirring for 30 minutes. The organic layer was washed sequentially with aqueous potassium carbonate solution (10%; 3×1.46 L) and with water (2×750 mL). It was then concentrated in vacuo to 1 to 2 volumes, while the temperature was maintained below 50° C., and diluted with tetrahydrofuran (1.0 L); this concentration/dilution procedure was carried out a total of three times, whereupon the mixture was concentrated in vacuo to 4 to 5 volumes while maintaining the temperature below 50° C. This afforded C57 as a solution in tetrahydrofuran (595.8 g, 19.14% C57 by weight). Estimated yield: 114 g, 0.290 mol, 57%. $^1$H NMR (400 MHz, chloroform-d) δ 7.40-7.28 (m, 5H), 5.25 (v br s, 1H), 5.10 (br s, 2H), 4.28-4.12 (m, 2H), 3.91-3.76 (m, 1H), 3.71-3.38 (m, 3H), 2.54-2.15 (m, 2H), 1.45 (s, 9H), 1.27-1.16 (m, 3H).

Step 10. Synthesis of tert-butyl (3S)-3-{[(benzyloxy)carbonyl]amino}-3-(hydroxymethyl)pyrrolidine-1-carboxylate (C58)

A solution of lithium borohydride in tetrahydrofuran (2 M; 511 mL, 1.02 mol) was added over 2 hours to a 0° C. to 10° C. solution of C57 in tetrahydrofuran (835.6 g, containing 19.20% C57 by weight, 160.4 g, 0.4087 mol). After the reaction mixture had been stirred at 0° C. to 10° C. for 15 hours, it was cooled to −5° C. to 5° C. and treated in a drop-wise manner with hydrochloric acid (0.5 M; 2.08 L, 1.04 mol, 13 volumes), to a pH of 7. The mixture was then warmed to 20° C. to 30° C., diluted with ethyl acetate (1.60 L, 10 volumes) and stirred for 10 minutes, whereupon the organic layer was concentrated in vacuo to 2 to 3 volumes while maintaining the temperature at or below 50° C. The resulting mixture was diluted with acetonitrile (880 mL) and concentrated in vacuo to 2 to 3 volumes while maintaining the temperature at or below 50° C.; this dilution/concentration procedure was carried out a total of three times. The mixture was then heated to 40° C. to 50° C. and stirred for 1 hour, whereupon it was cooled over 4 hours to 15° C. to 25° C. Water (164 mL) was added drop-wise over 2 hours at 15° C. to 25° C., and the mixture was stirred at 15° C. to 25° C. for 12 hours. The resulting solid was collected via filtration and dried in vacuo for 40 hours, at a temperature at or below 50° C., to afford C58 as a solid. Yield: 123.2 g, 0.3516 mol, 86%. HPLC purity: 99.8%. $^1$H NMR (400 MHz, DMSO-$d_6$) δ 7.40-7.27 (m, 5H), 4.99 (s, 2H), 4.93 (t, J=5.8 Hz, 1H), 3.58-3.45 (m, 3H), 3.31-3.21 (m, 3H), 2.10-1.85 (m, 2H), 1.38 (s, 9H).

Step 11. Synthesis of tert-butyl (3S)-3-{[(benzyloxy)carbonyl]amino}-3-formylpyrrolidine-1-carboxylate (C59)

A solution of C58 (125 g, 0.357 mol) and dimethyl sulfoxide (144.5 g, 1.849 mol) in dichloromethane (2.02 L) was stirred for 2 hours at 35° C. to 45° C.; Karl Fischer analysis indicated a water content of 0.029%. The solution was concentrated in vacuo to 3 to 4 volumes at 35° C. to 45° C., and then diluted with dichloromethane (1.80 L). Another Karl Fischer analysis revealed a water content of 0.034%. The solution was concentrated in vacuo at 35° C. to 45° C. to 6 to 7 volumes, whereupon triethylamine (112.3 g, 1.110 mol) was added at 20° C. to 30° C., and the reaction mixture was cooled to −5° C. to 0° C. and stirred at that temperature for 15 minutes. Sulfur trioxide pyridine complex (141.3 g, 0.8878 mol) was added in portions over 2 hours; stirring was then continued at −5° C. to 0° C. for 16 hours, at which time the reaction mixture was warmed to 35° C. to 45° C. and concentrated to 2 to 3 volumes. After the mixture had cooled to 20° C. to 30° C., it was partitioned between ethyl acetate (945 mL) and water (675 mL), and the aqueous layer was extracted with ethyl acetate (675 mL). The combined organic layers were washed sequentially with hydrochloric acid (1 M; 675 mL), water (675 mL), and saturated aqueous sodium bicarbonate solution (675 mL), then concentrated to dryness at 30° C. to 40° C., providing C59 as an oil. Yield: 118.7 g, 0.3407 mol, 95%. HPLC purity: 91.2%. $^1$H NMR (400 MHz, chloroform-d) δ 9.59 (s, 1H), 7.42-7.29 (m, 5H), 5.39 (br s, 1H), 5.12 (s, 2H), 3.85-3.70 (m, 1H), 3.63-3.43 (m, 3H), 2.44-2.04 (m, 2H), 1.45 (s, 9H).

Step 12. Synthesis of tert-butyl (3R)-3-{[(benzyloxy)carbonyl]amino}-3-[(E)-2-(2-chloro-6-methylpyridin-3-yl)ethenyl]pyrrolidine-1-carboxylate (C60) and tert-butyl (3R)-3-{[(benzyloxy)carbonyl]amino}-3-[(Z)-2-(2-chloro-6-methylpyridin-3-yl)ethenyl]pyrrolidine-1-carboxylate (C61)

A mixture of C59 (237.1 g, 0.6805 mol) and C52 (393.6 g, 0.7429 mol) in dimethyl sulfoxide (2.40 L, 10 volumes) was treated with potassium carbonate (188.7 g, 1.365 mol) and heated at 60° C. for 2 hours. Propan-2-yl acetate (1.54 L, 6.5 volumes), water (6.40 L, 27 volumes), and aqueous sodium sulfate solution (10%; 710 mL, 3.0 volumes) were then added, and the mixture was stirred for 20 minutes at 25° C. The organic layer was washed three times with aqueous sodium sulfate solution (10%; 1.30 L, 5.5 volumes) by stirring each mixture for 20 minutes before separation. It was then washed with aqueous sodium bicarbonate solution (7%; 1.30 L, 5.5 volumes) in the same manner, and concentrated in vacuo to 1 to 2 volumes at a temperature at or below 50° C. Propan-2-yl acetate (1.06 L) was added, and the mixture was concentrated in vacuo to 1 to 2 volumes at a temperature at or below 50° C. Propan-2-yl acetate (480 mL) was added, followed by drop-wise addition of methylcyclohexane (1.66 L) at 20° C. to 30° C. After the resulting mixture had been stirred at 20° C. to 30° C. for 1 hour, it was cooled to −15° C. to −5° C. and stirred at that temperature for 16 hours. Filtration of the slurry was carried out at −15° C. to −5° C., and the filter cake was washed with a mixture of propan-2-yl acetate and methylcyclohexane (3:7 ratio, 710 mL) at −15° C. to −5° C. The combined filtrates were concentrated in vacuo, diluted with methylcyclohexane (20 volumes) and subjected to silica gel chromatography (Gradient: 14% to 25% ethyl acetate in methylcyclohexane) to afford a mixture of C60 and C61 as an oil. This material was judged by $^1$H NMR analysis to consist of 3 to 4 isomers/rotamers. Yield: 268.1 g, 0.5680 mol, 83%. HPLC purity: ≥99.7%. $^1$H NMR (400 MHz, DMSO-d$_6$), characteristic peaks: S [8.00 (d, J=7.9 Hz) and 7.59 (d, J=7.6 Hz), total 1H], [7.85 (s) and 7.41 (s), total 1H], [7.38-7.25 (m), 7.22 (br d, J=7.2 Hz), and 7.16 (d, J=7.7 Hz), total 6H], [6.62 (d, component of AB quartet, J=16.1 Hz) and 6.34 (d, J=12.3 Hz), total 1H], [6.49 (br d, component of AB quartet, J=16.0 Hz), 5.88 (d, J=12.3 Hz), and 5.87 (d, J=12.3 Hz), total 1H], [5.04 (AB quartet, J$_{AB}$=12.7 Hz, Δv$_{AB}$=16.4 Hz), 4.74 (d, component of AB quartet, J=12.4 Hz), and 4.70-4.62 (m), total 2H], 3.83-3.68 (m, 1H), 3.32-3.16 (m, 3H), [2.43 (s) and 2.36 (s), total 3H], 2.27-2.12 (m, 1H), 2.00-1.85 (m, 1H), [1.40 (s), 1.39 (s), 1.37 (s), and 1.34 (s), total 9H].

Step 13. Synthesis of tert-butyl (3S)-3-{[(benzyloxy)carbonyl]amino}-3-[2-(2-chloro-6-methylpyridin-3-yl)ethyl]pyrrolidine-1-carboxylate (C62)

A reaction vessel containing a mixture of C60 and C61 (283.0 g, 0.5996 mol) and rhodium on alumina (5%; 14.15 g) in methanol (1.98 L) was evacuated and charged with argon three times, then evacuated and charged with hydrogen three times. Hydrogenation was then carried out for 40 hours at 30 to 40 psi and 20° C. to 25° C. After the reaction mixture had been filtered through diatomaceous earth (424 g), the filter cake was washed with methanol (5 volumes); the combined filtrates were concentrated in vacuo at 35° C. to 45° C. The resulting material was treated with toluene (5 volumes) and concentrated in vacuo at 50° C. to 60° C.; this toluene addition/concentration procedure was carried out a total of three times, providing C62. Yield: 254.4 g, 0.5367 mol, 90%. HPLC purity: 97.1%. $^1$H NMR (400 MHz, chloroform-d) δ 7.41-7.28 (m, 6H), 6.99 (br d, J=7.6 Hz, 1H), 5.06 (s, 2H), 4.91-4.79 (m, 1H), 3.62 (d, J=11.7 Hz, 1H), 3.57-3.36 (m, 2H), 3.36-3.26 (m, 1H), 2.74-2.55 (m, 2H), 2.48 (s, 3H), [2.48-2.40 (m), 2.39-2.07 (m) and 2.05-1.82 (m), total 4H], 1.45 (br s, 9H).

Step 14. Synthesis of tert-butyl (2S)-7-methyl-3,4-dihydro-1H-spiro[1,8-naphthyridine-2,3'-pyrrolidine]-1'-carboxylate (P19)

A solution of C62 in toluene (947.73 g, containing 19% C62 by weight, 180 g, 0.380 mol) was diluted with toluene (1.17 L, 6.5 volumes) and treated sequentially with 2-dicyclohexylphosphino-2',6'-diisopropoxybiphenyl (RuPhos; 35.44 g, 75.95 mmol) and potassium phosphate (145.1 g, 0.6836 mol). The resulting mixture was purged three times with nitrogen, whereupon tris(dibenzylideneacetone)dipalladium(0) (34.78 g, 37.98 mmol) was added, and three additional rounds of purging with nitrogen were carried out. The reaction mixture was stirred for 24 hours at 75° C. to 85° C. Potassium phosphate (16.2 g, 0.117 mol) was added, and stirring was continued at 75° C. to 85° C. for an additional 16 hours. After the reaction mixture had been cooled to 20° C. to 30° C., potassium tert-butoxide (76.7 g, 0.684 mol) was added, and the reaction mixture was stirred for 2 hours at 75° C. to 85° C. It was then cooled and partitioned between water (2.25 L) and ethyl acetate (2.25 L); after being stirred for 30 minutes at 20° C. to 30° C., the mixture was filtered through diatomaceous earth (180 g) and the filter cake was washed with ethyl acetate (1.80 L). The organic layer of the combined filtrates was washed sequentially with water (2×2.25 L) and aqueous sodium sulfate solution (10%; 2.25 L), then extracted three times with aqueous citric acid solution (0.5 M; 1.072 kg, 1.4 eq.). The combined citric acid layers were washed with ethyl acetate (2×1.07 L), then adjusted to pH 7 by addition of aqueous sodium hydroxide solution (30%; 596 g) at 20° C. to 30° C. Extraction of the aqueous layer with ethyl acetate (3×1.07 L), followed by combination of these three organic layers, provided P19 as a solution in ethyl acetate (3.218 kg, 2.7% P19 by weight); The bulk of this material was progressed to the following step. Estimated yield: 86.9 g, 0.286 mol, 75%. HPLC purity: 98.9%. $^1$H NMR (400 MHz, chloroform-d) δ 7.11 (d, J=7.3 Hz, 1H), 6.41 (d, J=7.4 Hz, 1H), 4.90 (br s, 1H), 3.59-3.43 (m, 2H), [3.40 (d, component of AB quartet, J=11.1 Hz) and 3.36-3.25 (m), total 2H], 2.80-2.65 (m, 2H), 2.31 (s, 3H), 2.00-1.75 (m, 4H), [1.45 (s) and 1.44 (s), total 9H].

Step 15. Synthesis of tert-butyl (2S)-6-bromo-7-methyl-3,4-dihydro-1H-spiro[1,8-naphthyridine-2,3'-pyrrolidine]-1'-carboxylate (P23)

1,3-Dibromo-5,5-dimethylimidazolidine-2,4-dione (45.60 g, 0.1595 mol) was added to a 0° C. to 5° C. solution of P19 in ethyl acetate (from the previous step; 2986 g, containing 2.7% P19, 80.6 g, 0.266 mol). After the reaction mixture had been stirred for 1 hour at 0° C. to 5° C., it was quenched by addition of aqueous sodium sulfite solution (10%; 203 g) and water (456 mL), and the resulting mixture was stirred at 10° C. to 20° C. for 20 minutes. The aqueous layer was extracted twice with ethyl acetate (415 mL, 5.1 volumes) by stirring at 10° C. to 20° C. for 20 minutes; the combined organic layers were then stirred for 20 minutes with aqueous sodium sulfate solution (10%; 456 g). Concentration of the organic layer to 1 to 2 volumes in vacuo below 50° C. was followed by dilution with methanol (480 mL, 6 volumes). This concentration/dilution procedure was carried out a total of three times, and the final solution was concentrated in vacuo, below 50° C., to 5 to 6 volumes. The resulting solution was cooled to 15° C. to 25° C. and water (415 mL) was slowly added, over 2 hours at 15° C. to 25° C., and then stirring was carried out for 14 hours at 15° C. to 25° C. Filtration provided a filter cake, which was washed with a mixture of methanol and water (1:1, 2×200 mL) and then dried under vacuum at 45° C. for 48 hours to afford P23 as a solid. Yield: 99.50 g, 0.2603 mol, 98%. HPLC purity: 99.7%. LCMS m/z 384.1 (bromine isotope pattern observed) [M+H]$^+$. $^1$H NMR (400 MHz, DMSO-d$_6$) δ 7.37 (s, 1H), 7.03-6.97 (m, 1H), 3.55-3.43 (m, 1H), 3.3-3.25 (m, 1H, assumed; partially obscured by water peak), 3.24-3.13 (m, 2H), 2.75-2.55 (m, 2H), 2.30 (s, 3H), 1.95-1.77 (m, 2H), 1.76-1.59 (m, 2H), [1.40 (s) and 1.38 (s), total 9H].

Acquisition of Powder X-ray Diffraction (PXRD) Data for Crystalline P23

A sample of P23 [prepared as described in Step 15 of Alternate Preparation (#2) hereinabove] was submitted for Powder X-ray diffraction (PXRD) analysis and found to be a crystalline material.

Powder X-ray diffraction analysis was conducted using a Bruker AXS D8 Endeavor diffractometer equipped with a copper (Cu) radiation source. The divergence slit was set at 15 mm continuous illumination. Diffracted radiation was detected by a PSD-Lynx Eye detector, with the detector PSD opening set at 4.123 degrees. The X-ray tube voltage and amperage were set to 40 kV and 40 mA, respectively. In addition, the energy dispersive detector, a nickel filter was used. Data was collected in the Theta-Theta goniometer at the Cu wavelength from 3.0 to 40.0 degrees 2-Theta using a step size of 0.0100 degrees and a step time of 1.0 second. The antiscatter screen was set to a fixed distance of 1.5 mm. Samples were prepared by placing them in a silicon low background sample holder and rotated at 15 revolutions/min during collection. Data were collected using Bruker DIF-FRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of 3% were generally chosen. Typically, the peaks which were not resolved or were consistent with noise were not selected. A typical error associated with the peak position from PXRD stated in USP up to +/−0.2° 2-Theta (USP-941).

Figure 3:
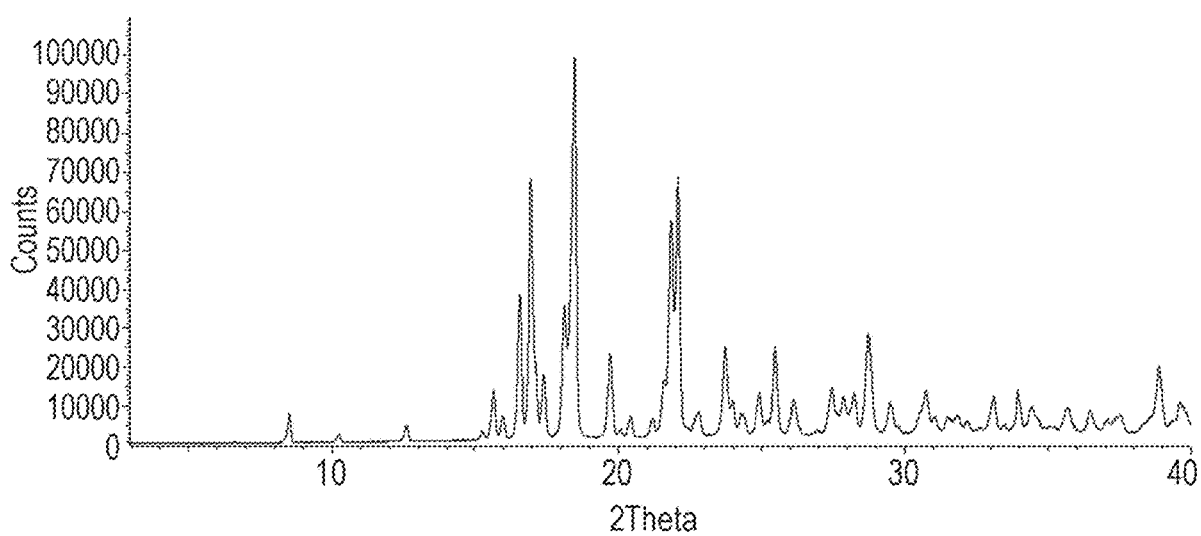
FIG. 3 shows an observed, representative powder X-ray diffraction pattern of a crystalline form of P23.

One representative diffraction pattern was observed for the crystalline form of P23 and is provided in FIG. 3. A list of diffraction peaks expressed in terms of the degree 2θ and relative intensities with a relative intensity of 3.0% of a PXRD from the sample of crystalline P23 are shown in Table X-P23 below.

TABLE X-P23

PXRD peak list for the Crystalline form of P23

| Angle (2-Theta) | Relative Intensity (%) |
|---|---|
| 8.5 | 7.2 |
| 12.6 | 4.0 |
| 15.7 | 13.2 |
| 16.0 | 5.9 |
| 16.6 | 37.6 |
| 17.0 | 67.2 |
| 17.4 | 16.6 |
| 18.1 | 34.2 |
| 18.5 | 100.0 |
| 19.7 | 21.8 |
| 20.5 | 5.3 |
| 21.2 | 4.6 |
| 21.9 | 55.9 |
| 22.1 | 67.0 |
| 22.8 | 6.4 |
| 23.7 | 22.6 |
| 24.3 | 5.5 |
| 25.0 | 11.0 |
| 25.2 | 3.6 |
| 25.5 | 22.2 |
| 26.2 | 9.2 |
| 27.5 | 11.9 |
| 27.9 | 9.5 |
| 28.3 | 10.8 |
| 28.8 | 25.8 |
| 29.5 | 8.3 |
| 30.8 | 10.8 |
| 31.1 | 4.3 |
| 31.5 | 3.8 |
| 31.8 | 4.4 |
| 33.1 | 9.0 |
| 34.0 | 10.8 |
| 34.4 | 6.6 |
| 35.7 | 6.1 |
| 36.5 | 5.7 |
| 37.1 | 3.2 |
| 37.5 | 4.2 |
| 38.9 | 16.7 |
| 39.6 | 6.6 |

In some embodiments, the present invention provide a compound that is tert-butyl (2S)-6-bromo-7-methyl-3,4-dihydro-1H-spiro[1,8-naphthyridine-2,3'-pyrrolidine]-1'-carboxylate or a salt thereof. In some embodiments, the present invention provide a compound that is tert-butyl (2S)-6-bromo-7-methyl-3,4-dihydro-1H-spiro[1,8-naphthyridine-2,3'-pyrrolidine]-1'-carboxylate. In some further embodiments, the present invention provide a crystalline form of tert-butyl (2S)-6-bromo-7-methyl-3,4-dihydro-1H-spiro[1,8-naphthyridine-2,3'-pyrrolidine]-1'-carboxylate. In some further embodiments, the crystalline form of tert-butyl (2S)-6-bromo-7-methyl-3,4-dihydro-1H-spiro[1,8-naphthyridine-2,3'-pyrrolidine]-1'-carboxylate exhibits a powder X-ray diffraction pattern comprising at least one characteristic peak, in terms of 2θ, as those listed in Table X-P23.

In some embodiments, the crystalline form of tert-butyl (2S)-6-bromo-7-methyl-3,4-dihydro-1H-spiro[1,8-naphthyridine-2,3'-pyrrolidine]-1'-carboxylate exhibits a powder X-ray diffraction pattern comprising at least two characteristic peaks, in terms of 2θ, as those listed in Table X-P23. In some embodiments, the crystalline form of tert-butyl (2S)-6-bromo-7-methyl-3,4-dihydro-1H-spiro[1,8-naphthyridine-2,3'-pyrrolidine]-1'-carboxylate exhibits a powder X-ray diffraction pattern comprising at least three characteristic peaks, in terms of 2θ, as those listed in Table X-P23.

In some embodiments, the crystalline form of tert-butyl (2S)-6-bromo-7-methyl-3,4-dihydro-1H-spiro[1,8-naphthyridine-2,3'-pyrrolidine]-1'-carboxylate exhibits a powder X-ray diffraction pattern comprising at least four (e.g. 4, 5, 6, 7, 8, 9, or 10) characteristic peaks, in terms of 2θ, as those listed in Table X-P23. In some embodiments, the crystalline form of tert-butyl (2S)-6-bromo-7-methyl-3,4-dihydro-1H-spiro[1,8-naphthyridine-2,3'-pyrrolidine]-1'-carboxylate exhibits a powder X-ray diffraction pattern substantially as shown in FIG. 3.

Preparation P25
Di-tert-butyl 7-methyl-6-(2-methyl-2H-tetrazol-5-yl)-3,4-dihydro-1H-spiro[1,8-napthyridine-2,3'-pyrrolidine]-1,-1'-dicarboxylate (P25)

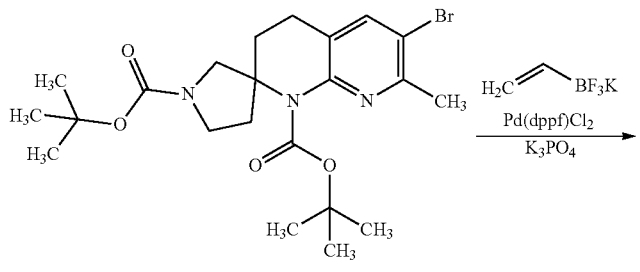

P21

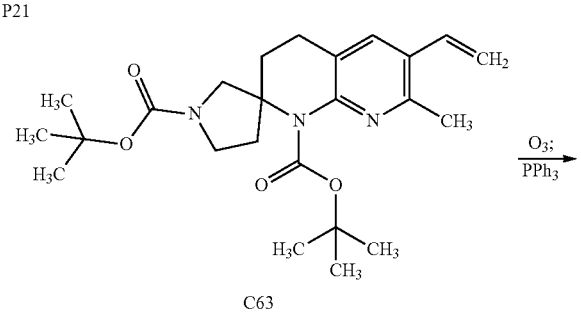

C63

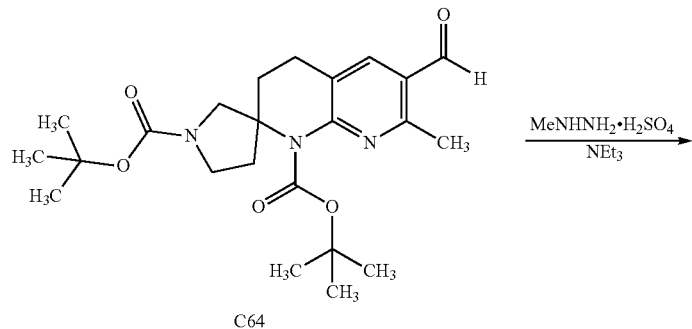

C64

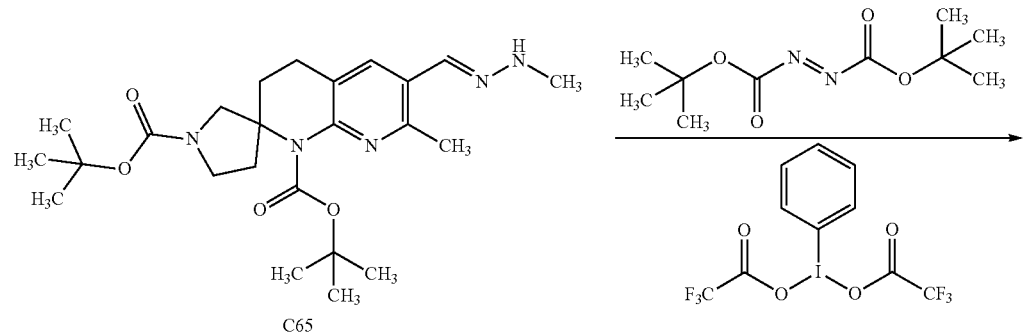

C65

-continued

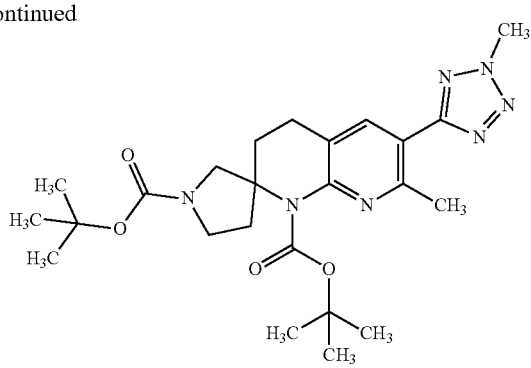

P25

Step 1. Synthesis of di-tert-butyl 6-ethenyl-7-methyl-3,4-dihydro-1H-spiro[1,8-naphthyridine-2,3'-pyrrolidine]-1,1'-dicarboxylate (C63)

A mixture of P21 (15.0 g, 31.1 mmol), potassium vinyltrifluoroborate (10.4 g, 77.6 mmol), [1,1'-bis(diphenylphosphino)ferrocene]dichloropalladium(II) (2.27 g, 3.10 mmol), and potassium phosphate (19.8 g, 93.3 mmol) in N,N-dimethylformamide (500 mL) was stirred at 95° C. for 16 hours, whereupon the reaction mixture was filtered; the filtrate was poured into water (4 L) and extracted with ethyl acetate (2×800 mL). The combined organic layers were washed with saturated aqueous sodium chloride solution, dried over sodium sulfate, filtered, and concentrated in vacuo. After the residue had been combined with the product of a similar reaction carried out using P21 (5.00 g, 10.4 mmol), it was purified via chromatography on silica gel (Gradient: 0% to 20% ethyl acetate in petroleum ether), affording C63 as a white solid. Combined yield: 17.1 g, 38.9 mmol, 94%. LCMS m/z 430.3 [M+H]$^+$. $^1$H NMR (400 MHz, chloroform-d) δ 7.46 (br s, 1H), 6.83 (dd, J=17.4, 11.1 Hz, 1H), 5.59 (br d, J=17.4 Hz, 1H), 5.37-5.24 (m, 1H), [3.90 (d, J=11.0 Hz) and 3.72 (d, J=11.0 Hz), total 1H], 3.64-3.41 (m, 2H), 3.38-3.24 (m, 1H), [2.86-2.64 (m), 2.62-2.39 (m), and 2.16-1.72 (m), total 9H], 1.45 (s, 18H).

Step 2. Synthesis of di-tert-butyl 6-formyl-7-methyl-3,4-dihydro-1H-spiro[1,8-naphthyridine-2,3'-pyrrolidine]-1,1'-dicarboxylate (C64)

A solution of C63 (17.0 g, 39.6 mmol) in dichloromethane (200 mL) was cooled to −78° C., and a stream of ozone-enriched oxygen was introduced until a blue color persisted. After an additional 5 minutes, a stream of dry nitrogen was bubbled through the reaction mixture until the blue color disappeared, whereupon triphenylphosphine (20.7 g, 78.9 mmol) was added. The resulting mixture was warmed to 25° C. and stirred for 2 hours, at which point LCMS analysis indicated the presence of C64: LCMS m/z 454.3 [M+Na$^+$]. After the reaction mixture had been concentrated in vacuo, the residue was purified using silica gel chromatography (Gradient: 0% to 50% ethyl acetate in petroleum ether) to provide C64 as a colorless gum. Yield: 9.98 g, 23.1 mmol, 58%.

Step 3. Synthesis of di-tert-butyl 7-methyl-6-[(2-methylhydrazinylidene)methyl]-3,4-dihydro-1H-spiro[1,8-naphthyridine-2,3'-pyrrolidine]-1,1'-dicarboxylate (C65)

A solution of methylhydrazine sulfate (3.20 g, 22.2 mmol) and triethylamine (7.78 mL, 55.8 mmol) in methanol (50 mL) was stirred at 25° C. for 5 minutes, whereupon a solution of C64 (7.98 g, 18.5 mmol) in methanol (20 mL) was added. After the reaction mixture had been stirred at 25° C. for 1 hour, collection of the precipitate via filtration afforded C65 as a white solid. Yield: 7.60 g, 16.5 mmol, 89%. LCMS m/z 460.3 [M+H]$^+$.

Step 4. Synthesis of di-tert-butyl 7-methyl-6-(2-methyl-2H-tetrazol-5-yl)-3,4-dihydro-1H-spiro[1,8-naphthyridine-2,3'-pyrrolidine]-1,1'-dicarboxylate (P25)

To a solution of C65 (6.70 g, 14.6 mmol) in a mixture of 2,2,2-trifluoroethanol (35 mL) and dichloromethane (35 mL) was added di-tert-butyl azodicarboxylate (4.36 g, 18.9 mmol), followed by [bis(trifluoroacetoxy)iodo]benzene (33.2 g, 77.2 mmol). The reaction mixture was stirred at 25° C. for 30 minutes, whereupon it was poured into saturated aqueous sodium sulfite solution (300 mL) and extracted with dichloromethane (2×100 mL). The combined organic layers were washed with saturated aqueous sodium chloride solution, dried over sodium sulfate, filtered, and concentrated in vacuo; silica gel chromatography (Gradient: 0% to 20% ethanol in dichloromethane) provided P25 as a white solid. Yield: 2.10 g, 4.32 mmol, 30%. LCMS m/z 508.3 [M+Na$^+$]. $^1$H NMR (400 MHz, methanol-d$_4$) δ 8.11 (s, 1H), 4.44 (s, 3H), [3.93 (d, J=11.3 Hz) and 3.86 (d, J=11.1 Hz), total 1H], 3.68-3.56 (m, 1H), 3.56-3.46 (m, 1H), 3.46-3.3 (m, 1H, assumed; partially obscured by solvent peak), 2.92-2.81 (m, 2H), 2.73 (s, 3H), [2.69-2.58 (m) and 2.58-2.47 (m), total 1H], 2.15-1.88 (m, 3H), 1.48 (br s, 18H).

Preparation P26
(2S)-7-Methyl-6-(2-methyl-2H-tetrazol-5-yl)-3,4-dihydro-1H-spiro[1,8-napthyridine-2,3'-pyrrolidine], dihydrochloride salt (P26)

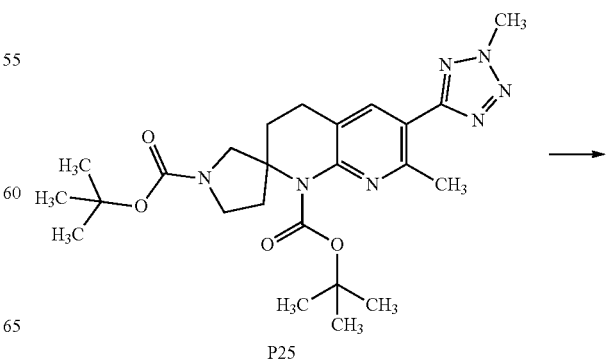

P25

-continued

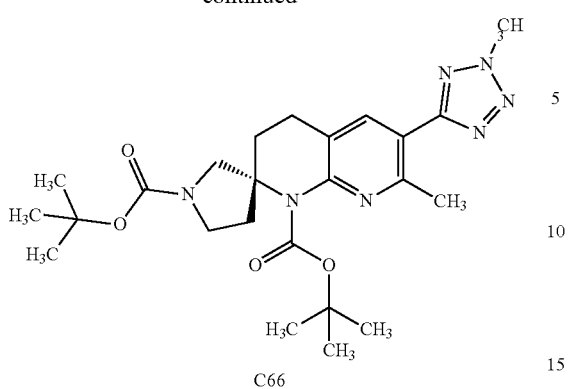
C66

+

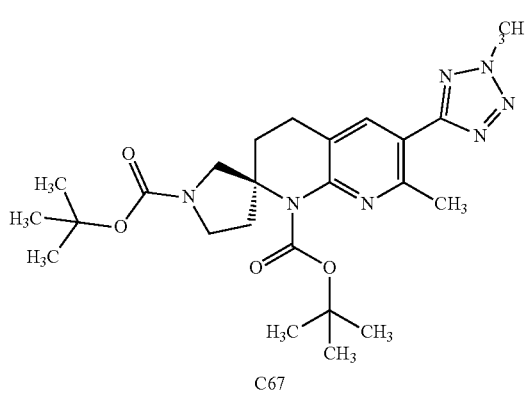
C67

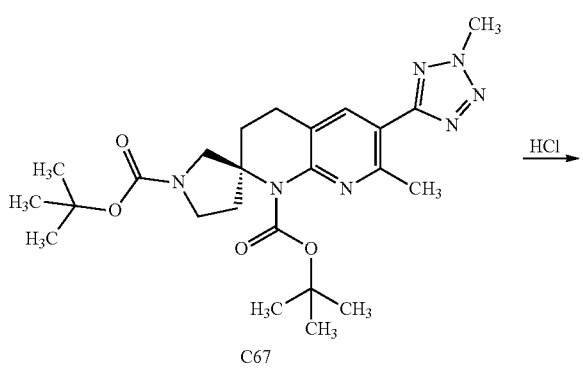
C67

-continued

P26 · 2 HCl

Step 1. Separation of di-tert-butyl (2R)-7-methyl-6-(2-methyl-2H-tetrazol-5-yl)-3,4-dihydro-1H-spiro[1,8-naphthyridine-2,3'-pyrrolidine]-1,1'-dicarboxylate (C66) and di-tert-butyl (2S)-7-methyl-6-(2-methyl-2H-tetrazol-5-yl)-3,4-dihydro-1H-spiro[1,8-naphthyridine-2,3'-pyrrolidine]-1,1'-dicarboxylate (C67)

Separation of P25 (2.37 g, 4.88 mmol) into its component diastereomers was carried out using supercritical fluid chromatography {Column: Chiral Technologies Chiralcel OJ-H, 21.2×250 mm, 5 µm; Mobile phase 9:1 carbon dioxide/[methanol containing 0.2% (7 M ammonia in methanol)]; Flow rate: 80 mL/minute; Back pressure: 120 bar}. The first-eluting diastereomer was designated as C66, and the second-eluting diastereomer was designated as C67.

C66 was isolated as a solid. Yield: 1.01 g, 2.08 mmol, 43%. Retention time: 2.68 minutes [Analytical conditions. Column: Chiral Technologies Chiralcel OJ-H, 4.6×250 mm, 5 µm; Mobile phase A: carbon dioxide; Mobile phase B: methanol containing 0.2% (7 M ammonia in methanol); Gradient: 5% B for 1.0 minute, then 5% to 60% B over 8.0 minutes; Flow rate: 3.0 mL/minute; Back pressure: 120 bar].

C67 was isolated as an oil. Yield: 1.00 g, 2.06 mmol, 42%. Retention time: 3.33 minutes (Analytical conditions identical to those used for C66).

See below for assignment of absolute stereochemistry.

Step 2. Synthesis of (2S)-7-methyl-6-(2-methyl-2H-tetrazol-5-yl)-3,4-dihydro-1H-spiro[1,8-naphthyridine-2,3'-pyrrolidine], dihydrochloride salt (P26)

A solution of C67 (150 mg, 0.309 mmol) in a mixture of dichloromethane (1.0 mL) and 1,1,1,3,3,3-hexafluoropropan-2-ol (1.0 mL) was treated with a solution of hydrogen chloride in 1,4-dioxane (4 M; 0.309 mL, 1.24 mmol). After the reaction mixture had been stirred at room temperature for 2 hours, LCMS analysis indicated conversion to P26: LCMS m/z 286.3 [M+H]$^+$. Concentration of the reaction mixture in vacuo afforded P26 as a solid. Yield: 105 mg, 0.293 mmol, 95%.

The indicated absolute stereochemistry was established in the following manner. This batch of P26 was used to prepare 3 and 4 in Alternate Synthesis of Examples 3 and 4. Correlation between those batches of 3 and 4 with the same compounds prepared from a precursor of known absolute stereochemistry (see Examples 3 and 4) is provided in Alternate Synthesis of Examples 3 and 4.

Alternate Preparation of P26
(2S)-7-Methyl-6-(2-methyl-2H-tetrazol-5-yl)-3,4-dihydro-1H-spiro[1,8-napthyridine-2,3'-pyrrolidine], dihydrochloride salt (P26)

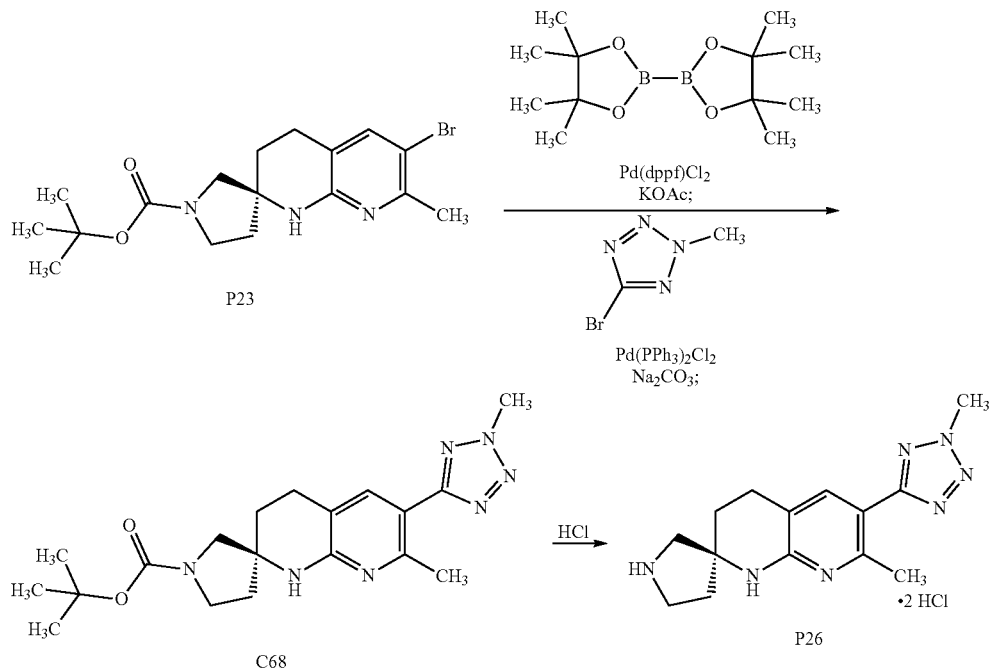

Step 1. Synthesis of tert-butyl (2S)-7-methyl-6-(2-methyl-2H-tetrazol-5-yl)-3,4-dihydro-1H-spiro[1,8-naphthyridine-2,3'-pyrrolidine]-1'-carboxylate (C68)

A mixture of 4,4,4',4',5,5,5',5'-octamethyl-2,2'-bi-1,3,2-dioxaborolane (299 mg, 1.18 mmol), P23 (300 mg, 0.785 mmol), [1,1'-bis(diphenylphosphino)ferrocene]dichloropalladium(II), dichloromethane complex (32.0 mg, 39.2 μmol), and oven-dried potassium acetate (308 mg, 3.14 mmol) in 1,4-dioxane (10 mL) was degassed by bubbling nitrogen through it for 5 minutes. The reaction vial was then sealed and heated at 100° C. in an aluminum block for 2 hours, whereupon it was allowed to cool to room temperature. 5-Bromo-2-methyl-2H-tetrazole (134 mg, 0.822 mmol), dichlorobis(triphenylphosphine)palladium(II) (27.5 mg, 39.2 μmol), and a degassed aqueous solution of sodium carbonate (2.0 M; 0.981 mL, 1.96 mmol) were added, and the reaction mixture was again degassed with bubbling nitrogen for 5 minutes. It was then stirred at 90° C. for 18 hours, cooled to room temperature, diluted with ethyl acetate, and filtered through diatomaceous earth. The organic layer of the filtrate was washed with saturated aqueous sodium chloride solution, dried over magnesium sulfate, filtered, and concentrated in vacuo; LCMS analysis indicated the presence of C68: LCMS m/z 386.3 [M+H]+. Silica gel chromatography (Gradient: 20% to 50% ethyl acetate in heptane) provided C68 as a light-yellow oil. Yield: 280 mg, 0.726 mmol, 92%. This batch of C68 was used in Examples 3 and 4 below.

Step 2. Synthesis of (2S)-7-methyl-6-(2-methyl-2H-tetrazol-5-yl)-3,4-dihydro-1H-spiro[1,8-naphthyridine-2,3'-pyrrolidine], dihydrochloride salt (P26)

A mixture of C68 (185 mg, 0.480 mmol) and a solution of hydrogen chloride in 2-propanol (1.25 M; 1.9 mL, 2.4 mmol) was heated to 50° C. for 1 hour. Concentration of the reaction mixture in vacuo provided P26 as a solid, which was used without additional purification. Yield: 170 mg, 0.47 mmol, 98%.

Preparation P27
[(2S)-1'-(tert-Butoxycarbonyl-7-methyl-3,4-dihydro-1H-spiro[1,8-napthyridine-2,3'-pyrrolidin]-6-yl]boronic acid (P27)

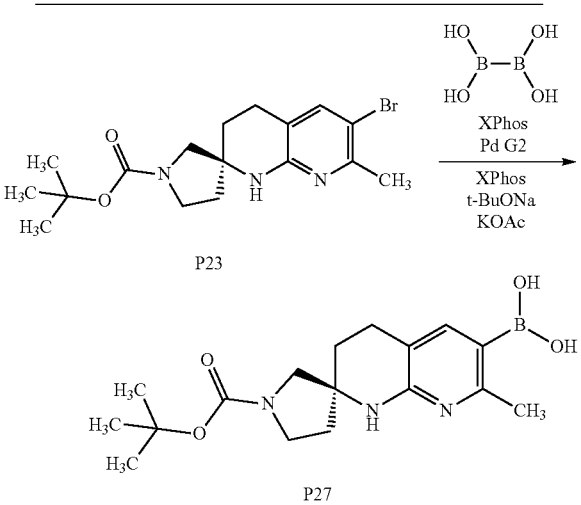

A reaction vessel containing a mixture of P23 (19.5 g, 51.0 mmol), potassium acetate (12.5 g, 127 mmol), sodium tert-butoxide (49.0 mg, 0.510 mmol), chloro(2-dicyclohexylphosphino-2',4',6'-triisopropyl-1,1'-biphenyl)[2-(2'-amino-1,1'-biphenyl)]palladium(II) [XPhos Pd G2; 401 mg, 0.510 mmol), and 2-dicyclohexylphosphino-2',4',6'-triisopropylbiphenyl (XPhos; 729 mg, 1.53 mmol) was purged with nitrogen. Methanol (200 mL), ethane-1,2-diol (20 mL), and tetrahydroxydiboron (11.4 g, 127 mmol) were then added, whereupon nitrogen was bubbled through the reaction mixture for 10 minutes. The reaction mixture was heated to an internal temperature of 50° C. for 2 hours, cooled to room temperature and then to 0° C., and adjusted to pH 14 by addition of aqueous sodium hydroxide solution (4 M; 80 mL) (Caution: gas evolution). The resulting mixture was stirred at room temperature for 30 minutes and filtered; the filtrate was concentrated in vacuo and extracted twice with tert-butyl methyl ether. The combined organic layers were then extracted with aqueous sodium hydroxide solution (2 M; 2×100 mL). All the aqueous layers were combined, and the stirring mixture was treated drop-wise with hydrochloric acid (4 M; approximately 20 mL) until solids precipitated (this occurred at a pH of approximately 9). After the mixture had been stirred at room temperature for an additional 30 minutes, it was extracted four times with ethyl acetate. The combined ethyl acetate layers were washed with saturated aqueous sodium chloride solution, dried over sodium sulfate, filtered, and concentrated in vacuo to provide P27 as a light-yellow powder. Yield: 12.5 g, 36.0 mmol, 71%. LCMS m/z 348.4 [M+H]$^+$. $^1$H NMR (400 MHz, methanol-d$_4$), characteristic peaks: δ 7.74 (br s, 1H), 3.46-3.35 (m, 2H), 2.92-2.72 (m, 2H), 2.48 (s, 3H), 2.12-1.83 (m, 4H), [1.47 (s) and 1.46 (s), total 9H].

mmol), additional [1,1'-bis(diphenylphosphino)ferrocene]dichloropalladium(II), dichloromethane complex (216 mg, 0.264 mmol), and aqueous sodium carbonate solution (2.0 M; 7.93 mL, 15.9 mmol). After this reaction mixture had been sparged with nitrogen, it was heated to 100° C. for 18 hours, at which time LCMS analysis indicated conversion to C69: LCMS m/z 382.4 [M+H]$^+$. The reaction mixture was cooled, partitioned between aqueous ammonium chloride solution and ethyl acetate, and then the entire mixture was filtered through a pad of diatomaceous earth. The filter pad was rinsed with both water and ethyl acetate, and the aqueous layer of the combined filtrate was extracted with ethyl acetate (2×30 mL). After all the organic layers had been combined, they were washed sequentially with water (100 mL) and saturated aqueous sodium chloride solution, dried over magnesium sulfate, filtered, and concentrated in vacuo. The residue (2.9 g) was dissolved in ethyl acetate (10 mL) and treated with SiliaMetS Thiol (SiliCycle, R51030B; 2 g); the resulting mixture was heated at reflux for 10 minutes and then cooled to room temperature. Filtration through a pad of diatomaceous earth provided a filtrate, which was concentrated under reduced pressure to afford C69 as a brown gum (2 g). This material was employed in the following step without additional purification.

Preparation P28

(2S)-7-Methyl-6-(pyrimidin-2-yl)-3,4-dihydro-1H-spiro[1,8-napthyridine-2,3'-pyrrolidine], dihydrochloride salt (P28)

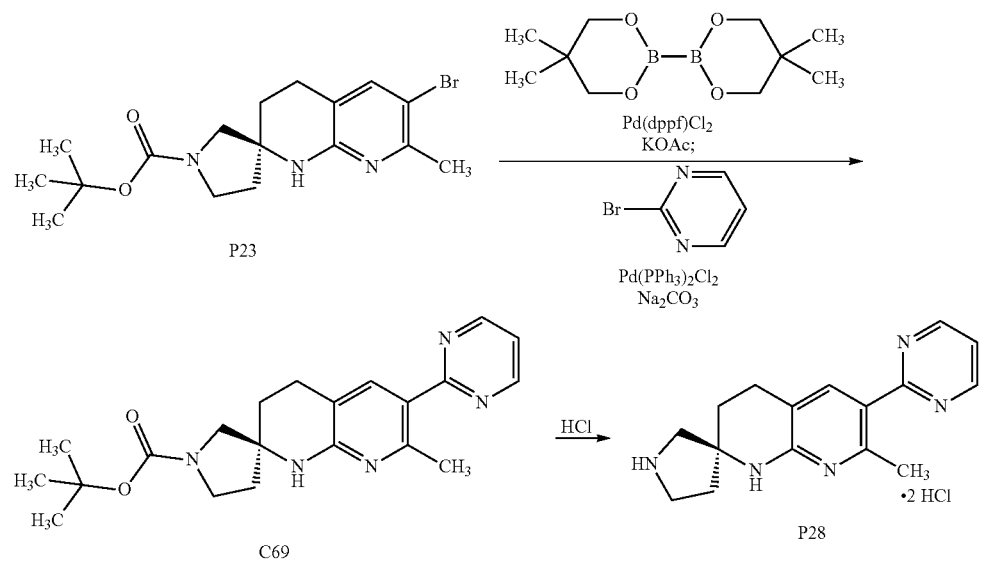

Step 1. Synthesis of tert-butyl (2S)-7-methyl-6-(pyrimidin-2-yl)-3,4-dihydro-1H-spiro[1,8-naphthyridine-2,3'-pyrrolidine]-1'-carboxylate (C69).

Nitrogen was bubbled through a mixture of oven-dried potassium acetate (2.07 g, 21.1 mmol), P23 (material from Preparations P23 and P24; 2.02 g, 5.28 mmol), 5,5,5',5'-tetramethyl-2,2'-bi-1,3,2-dioxaborinane (1.79 g, 7.92 mmol), and [1,1'-bis(diphenylphosphino)ferrocene]dichloropalladium(II), dichloromethane complex (216 mg, 0.264 mmol) in 1,4-dioxane (20 mL) for 5 minutes. The reaction mixture was then heated in a 105° C. aluminum block for 2 hours, whereupon it was allowed to cool to room temperature and then treated with 2-bromopyrimidine (840 mg, 5.28

Step 2. Synthesis of (2S)-7-methyl-6-(pyrimidin-2-yl)-3,4-dihydro-1H-spiro[1,8-naphthyridine-2,3'-pyrrolidine], dihydrochloride salt (P28)

A solution of hydrogen chloride was prepared by slow addition of acetyl chloride (1.50 mL, 21.1 mmol) to 2-propanol (4 mL). In a separate flask, C69 (from the previous step; 2 g; ≤5.28 mmol) was dissolved in a mixture of propan-2-yl acetate (15 mL) and 2-propanol (15 mL); this required heating at 50° C. Once a solution had been attained, the hydrogen chloride solution was slowly added to it, and the reaction mixture was heated at 50° C. for 2 hours. It was then allowed to cool slowly to room temperature while being stirred; stirring was continued at room temperature for 18 hours. The resulting solid was collected via vacuum filtration under nitrogen, providing P28 as a hygroscopic solid. Yield: 750 mg, 2.12 mmol, 40% over 2 steps. LCMS m/z 282.3 [M+H]$^+$. $^1$H NMR (400 MHz, methanol-d$_4$) δ 8.91 (d, J=4.9 Hz, 2H), 8.58 (s, 1H), 7.43 (t, J=4.9 Hz, 1H), 3.76-3.66 (m, 1H), 3.66-3.52 (m, 2H), 3.46 (d, component of AB quartet, J=12.5 Hz, 1H), 3.12-2.95 (m, 2H), 2.90 (s, 3H), 2.49-2.38 (m, 1H), 2.37-2.25 (m, 1H), 2.24-2.06 (m, 2H).

The indicated absolute stereochemistry was assigned on the basis of conversion of this lot of P28 to Example 14; the absolute stereochemistry of 14 was established via single-crystal X-ray analysis (see Example 14 below).

Preparation P29
tert-Butyl 4,7-dimethyl-1H-spiro[1,8-napthyridine-2,3'-pyrrolidin]-1'-carboxylate (P29)

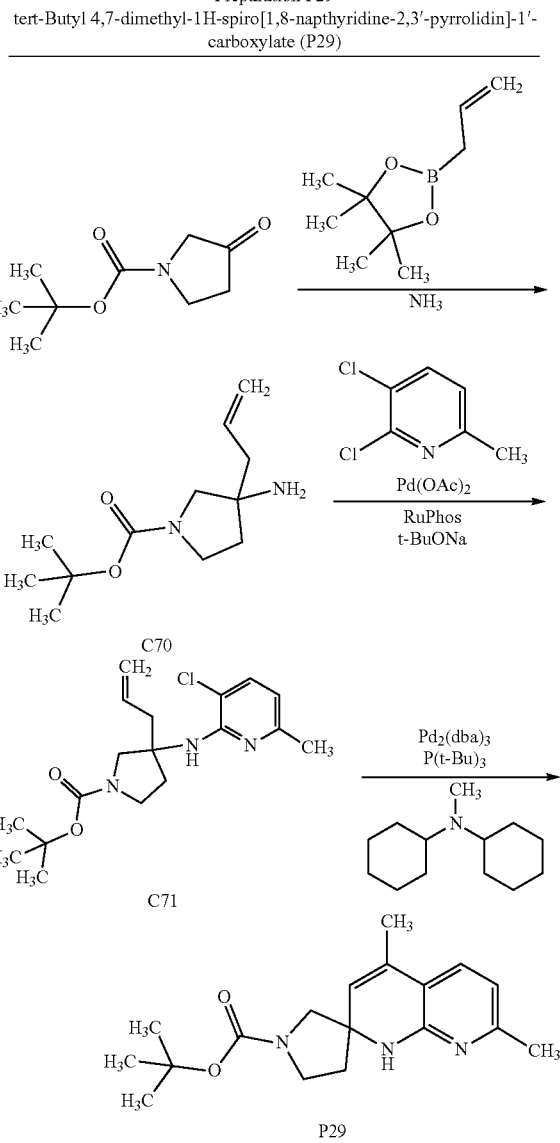

Step 1. Synthesis of tert-butyl 3-amino-3-(prop-2-en-1-yl)pyrrolidine-1-carboxylate (C70).

A mixture of tert-butyl 3-oxopyrrolidine-1-carboxylate (500 mg, 2.70 mmol) and a solution of ammonia in methanol (7 M; 3.9 mL, 27 mmol) was stirred at room temperature for 30 minutes. To this was then added, in a drop-wise manner, a solution of 4,4,5,5-tetramethyl-2-(prop-2-en-1-yl)-1,3,2-dioxaborolane (907 mg, 5.40 mmol) in methanol, and the reaction mixture was stirred at room temperature for 18 hours. Volatiles were removed in vacuo, and the residue was subjected to silica gel chromatography (Gradient: 0% to 10% methanol in dichloromethane) to provide C70. Yield: 200 mg, 0.884 mmol, 33%. $^1$H NMR (400 MHz, chloroform-d) δ 5.91-5.76 (m, 1H), 5.20 (m, 1H), 5.15 (br d, J=11 Hz, 1H), 3.53-3.38 (m, 2H), 3.32-3.08 (m, 2H), 2.28 (d, J=7.5 Hz, 2H), 1.89-1.79 (m, 1H), 1.73-1.63 (m, 1H), 1.46 (s, 9H).

Step 2. Synthesis of tert-butyl 3-[(3-chloro-6-methylpyridin-2-yl)amino]-3-(prop-2-en-1-yl)pyrrolidine-1-carboxylate (C71)

A vial containing a mixture of 2,3-dichloro-6-methylpyridine (100 mg, 0.617 mmol), C70 (168 mg, 0.742 mmol), palladium(II) acetate (6.93 mg, 30.9 µmol), 2-dicyclohexylphosphino-2',6'-diisopropoxybiphenyl (RuPhos; 28.8 mg, 61.7 µmol), and sodium tert-butoxide (119 mg, 1.24 mmol) in 1,4-dioxane (8 mL) was sparged with nitrogen, sealed, and heated at 80° C. overnight. LCMS analysis indicated conversion to C71: LCMS m/z 352.3 (chlorine isotope pattern observed) [M+H]$^+$, whereupon the reaction mixture was cooled to room temperature and partitioned between water and dichloromethane. The aqueous layer was extracted with dichloromethane, and the combined organic layers were washed with saturated aqueous sodium chloride solution, dried over magnesium sulfate, filtered, concentrated in vacuo, and subjected to silica gel chromatography (Gradient: 0% to 50% ethyl acetate in heptane) to provide C71 as an oil that solidified upon standing. Yield: 121 mg, 0.344 mmol, 56%. $^1$H NMR (400 MHz, chloroform-d) δ 7.29 (d, J=8.1 Hz, 1H), 6.42-6.34 (m, 1H), 5.82-5.68 (m, 1H), 5.11-5.03 (m, 1H), 5.03-4.93 (m, 1H), 3.79-3.69 (m, 1H), [3.62 (d, component of AB quartet, J=11.6 Hz), 3.56 (d, component of AB quartet, J=11.4 Hz), and 3.54-3.36 (m), total 3H], 2.95-2.83 (m, 1H), 2.76-2.63 (m, 1H), 2.45-2.28 (m, 1H), 2.34 (s, 3H), 2.08-1.96 (m, 1H), 1.50-1.41 (br s, 9H).

Step 3. Synthesis of tert-butyl 4,7-dimethyl-1H-spiro[1,8-naphthyridine-2,3'-pyrrolidine]-1'-carboxylate (P29)

A mixture of C71 (40 mg, 0.11 mmol), tris(dibenzylideneacetone)dipalladium(0) (5.20 mg, 5.68 µmol), N-cyclohexyl-N-methylcyclohexanamine (111 mg, 0.568 mmol), and tri-tert-butylphosphine (1.15 mg, 5.68 µmol) in N,N-dimethylformamide (1.0 mL) was degassed and then heated at 80° C. for 2 hours. The heat was increased to 120° C., and the reaction mixture was maintained at that temperature for 3 days. LCMS analysis indicated conversion to P29: LCMS m/z 316.3 [M+H]$^+$. After the reaction mixture had cooled to room temperature, it was partitioned between ethyl acetate and water, and the aqueous layer was extracted twice with ethyl acetate. The combined organic layers were washed with saturated aqueous sodium chloride solution, dried over magnesium sulfate, filtered, and concentrated in vacuo; silica gel chromatography (Gradient: 0% to 100% ethyl acetate in heptane) afforded P29. Yield: 30 mg, 95 µmol, 86%. $^1$H NMR (400 MHz, chloroform-d), characteristic peaks: δ 7.13 (d, J=7.5 Hz, 1H), 6.40 (d, J=7.5 Hz, 1H), 5.27 (br s, 1H), 5.06-4.99 (br s, 1H), 3.58-3.40 (m, 3H), 3.31-3.21 (m, 1H), 2.31 (s, 3H), [1.96 (s) and 1.96 (s), total 3H], [1.46 (s) and 1.44 (s), total 9H].

Preparation P30
tert-Butyl 1-benzyl-7-methyl-3,4-dihydro-1H-spiro[1,8-napthyridine-2,3'-pyrrolidin]-1'-carboxylate (P30)

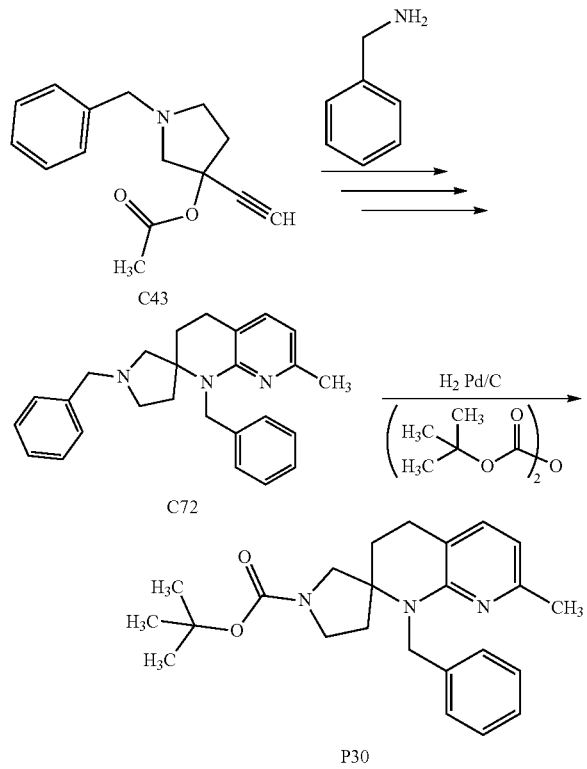

Step 1. Synthesis of 1,1'-dibenzyl-7-methyl-3,4-dihydro-1H-spiro[1,8-naphthyridine-2,3'-pyrrolidine] (C72)

Conversion of C43 to C72 was carried out using the method described for synthesis of C47 from C43 in Preparations P17 and P18, by utilizing 1-phenylmethanamine in place of 1-(4-methoxyphenyl)methanamine. Silica gel chromatography (Gradient: 0% to 10% methanol in dichloromethane) provided C72. Yield for cyclization step to provide C72: 580 mg, 1.51 mmol, 69%.

Step 2. Synthesis of tert-butyl 1-benzyl-7-methyl-3,4-dihydro-1H-spiro[1,8-naphthyridine-2,3'-pyrrolidine]-1'-carboxylate (P30)

A mixture of C72 (550 mg, 1.43 mmol), palladium on carbon (50 mg, 0.143 mmol), and di-tert-butyl dicarbonate (376 mg, 1.72 mmol) in methanol (20 mL) was hydrogenated overnight at 75 psi. The reaction mixture was filtered through diatomaceous earth, and the filtrate was concentrated in vacuo; silica gel chromatography (Gradient: 0% to 100% ethyl acetate in heptane) afforded P30 as a white semi-solid. Yield: 482 mg, 1.22 mmol, 85%. $^1$H NMR (400 MHz, chloroform-d) δ 7.29-7.07 (m, 6H, assumed; partially obscured by solvent peak), 6.39 (d, J=7.2 Hz, 1H), 5.15-4.99 (m, 1H), 4.97-4.78 (m, 1H), 3.58-3.19 (m, 4H), 2.87-2.71 (m, 2H), 2.31-2.16 (m, 1H), 2.24 (s, 3H), 2.07-1.95 (m, 1H), 1.92-1.79 (m, 1H), 1.75-1.63 (m, 1H), [1.45 (s) and 1.43 (s), total 9H].

Preparation of P31
6-[5-(Difluoromethyl)-1-methyl-1H-1,2,4-triazol-3-yl]-7-methyl-3,4-dihydro-1H-spiro[1,8-napthyridine-2,3'-pyrrolidine] (P31)

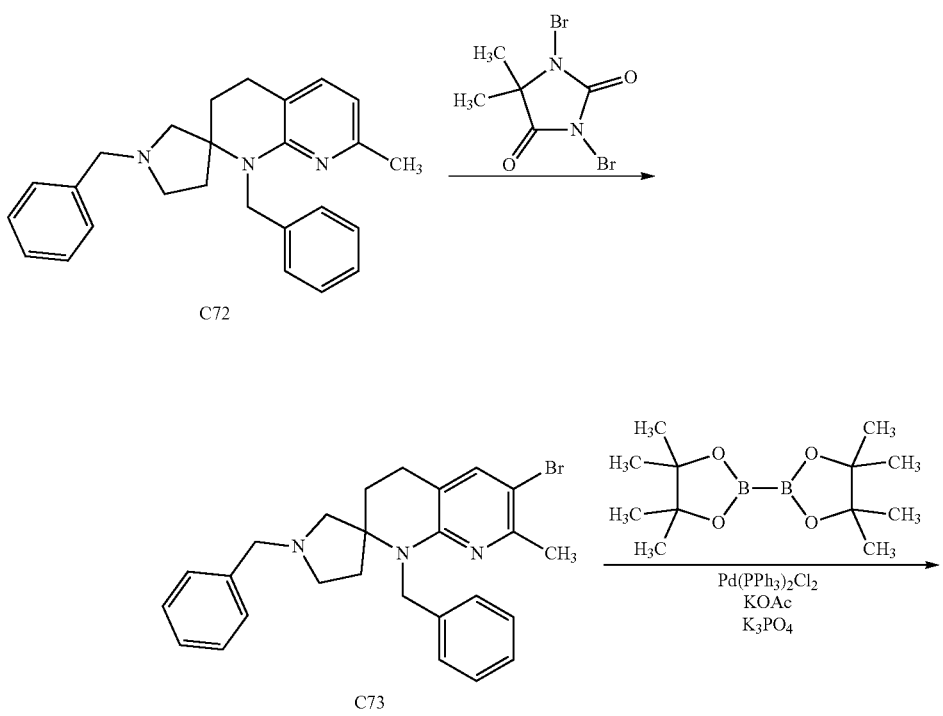

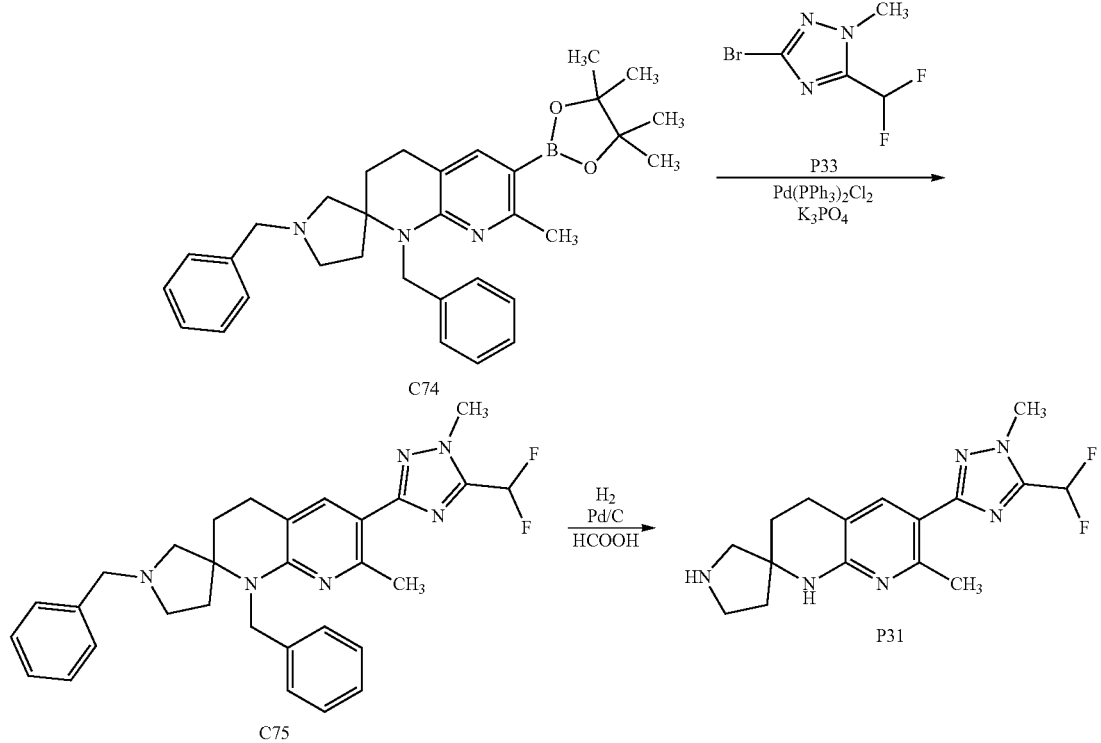

Step 1. Synthesis of 1,1'-dibenzyl-6-bromo-7-methyl-3,4-dihydro-1H-spiro[1,8-naphthyridine-2,3'-pyrrolidine] (C73)

1,3-Dibromo-5,5-dimethylimidazolidine-2,4-dione (532 mg, 1.86 mmol) was added in portions to a 0° C. solution of C72 (1.19 g, 3.10 mmol) in dichloromethane (16 mL). LCMS analysis after 1 hour indicated conversion to C73: LCMS m/z 462.2 (bromine isotope pattern observed) [M+H]$^+$. The reaction mixture was diluted with dichloromethane (20 mL), washed sequentially with saturated aqueous sodium sulfite solution, saturated aqueous sodium bicarbonate solution, and saturated aqueous sodium chloride solution, dried over magnesium sulfate, filtered, and concentrated in vacuo. Silica gel chromatography (Gradient: 0% to 50% ethyl acetate in heptane) afforded C73 as an oil. Yield: 980 mg, 2.12 mmol, 68%. $^1$H NMR (400 MHz, chloroform-d) δ 7.32-7.12 (m, 11H, assumed; partially obscured by solvent peak), 5.03 (AB quartet, $J_{AB}$=16.3 Hz, $\Delta v_{AB}$=26.6 Hz, 2H), 3.54 (AB quartet, $J_{AB}$=13.1 Hz, $\Delta v_{AB}$=41.8 Hz, 2H), 2.93 (d, J=10.2 Hz, 1H), 2.88 (ddd, J=8.5, 8.5, 3.4 Hz, 1H), 2.84-2.75 (m, 1H), 2.74-2.65 (m, 1H), 2.40-2.32 (m, 1H), 2.29 (s, 3H), 2.19 (d, J=10.2 Hz, 1H), 2.12 (ddd, J=13.4, 8.3, 8.3 Hz, 1H), 1.99 (ddd, J=13.7, 8.8, 5.2 Hz, 1H), 1.93-1.85 (m, 1H), 1.81 (ddd, J=13.4, 7.3, 3.5 Hz, 1H).

Step 2. Synthesis of 1,1'-dibenzyl-7-methyl-6-(4,4,5,5-tetramethyl-1,3,2-dioxaborolan-2-yl)-3,4-dihydro-1H-spiro[1,8-naphthyridine-2,3'-pyrrolidine] (C74)

A reaction vial was charged with 4,4,4',4',5,5,5',5'-octamethyl-2,2'-bi-1,3,2-dioxaborolane (148 mg, 0.583 mmol), C73 (180 mg, 0.389 mmol), [1,1'-bis(diphenylphosphino)ferrocene]dichloropalladium(II), dichloromethane complex (31.8 mg, 38.9 μmol), and oven-dried potassium acetate (153 mg, 1.56 mmol) in 1,4-dioxane (5 mL). Nitrogen was bubbled through the reaction mixture for 5 minutes, whereupon the vial was sealed and heated at 100° C. in an aluminum block for 2 hours. LCMS analysis indicated the presence of C74: LCMS m/z 510.4 [M+H]$^+$. After the reaction mixture had cooled to room temperature, it was diluted with ethyl acetate, and filtered through a pad of diatomaceous earth. The filtrate was concentrated in vacuo to provide C74, which was used directly in the following step.

Step 3. Synthesis of 1,1'-dibenzyl-6-[5-(difluoromethyl)-1-methyl-1H-1,2,4-triazol-3-yl]-7-methyl-3,4-dihydro-1H-spiro[1,8-naphthyridine-2,3'-pyrrolidine] (C75)

Dichlorobis(triphenylphosphine)palladium(II) (5.24 mg, 7.46 μmol), an aqueous solution of potassium phosphate (2.0 M; 0.466 mL, 0.932 mmol), and 3-bromo-5-(difluoromethyl)-1-methyl-1H-1,2,4-triazole (P33; 79.1 mg, 0.373 mmol) were added to a solution of C74 (from the previous step; 50.389 mmol) in tetrahydrofuran (5 mL). After the reaction mixture had been sparged with nitrogen, the reaction vessel was sealed and heated at 70° C. in an aluminum block for 1 hour. The temperature was then increased to 100° C., and heating was continued overnight. 3-Bromo-5-(difluoromethyl)-1-methyl-1H-1,2,4-triazole (P33; 79.1 mg, 0.373 mmol) was again added, and heating was carried out for an additional 6 hours, whereupon the reaction mixture was cooled and partitioned between ethyl acetate and water. The aqueous layer was extracted twice with ethyl acetate, and the combined organic layers were washed with saturated aqueous sodium chloride solution, dried over magnesium sulfate, filtered, and concentrated in vacuo. Silica gel chromatography (Gradient: 0% to 100% ethyl acetate in heptane) provided C75. Yield: 105 mg, 0.204 mmol, 52% over 2 steps. LCMS m/z 515.3 [M+H]$^+$. $^1$H NMR (400 MHz, chloroform-d) δ 7.69 (s, 1H), 7.33-7.19 (m, 9H, assumed; partially obscured by solvent peak), 7.18-7.12 (m, 1H), 6.85 (t, $J_{HF}$=52.6 Hz, 1H), 5.14 (AB quartet, $J_{AB}$=16.3 Hz, $\Delta v_{AB}$=17.6 Hz, 2H), 4.05 (s, 3H), 3.54 (AB quartet, $J_{AB}$=13.0 Hz, $\Delta v_{AB}$=38.8 Hz, 2H), 2.97 (d, J=10.2 Hz, 1H), 2.93-2.81 (m, 2H), 2.81-2.72 (m, 1H), 2.53 (s, 3H), 2.41-2.32 (m, 1H), 2.22 (d, J=10.2 Hz, 1H), 2.15 (ddd, J=13.5, 8.3, 8.2 Hz, 1H), 2.06-1.97 (m, 1H), 1.96-1.88 (m, 1H), 1.84 (ddd, J=13.4, 7.3, 3.4 Hz, 1H).

Step 4. Synthesis of 6-[5-(difluoromethyl)-1-methyl-1H-1,2,4-triazol-3-yl]-7-methyl-3,4-dihydro-1H-spiro[1,8-naphthyridine-2,3'-pyrrolidine] (P31)

Palladium on carbon (10%, wet with water; 20 mg) was added to a solution of C75 (105 mg, 0.204 mmol) in methanol (5 mL) containing a drop of formic acid, and the resulting mixture was hydrogenated overnight at room temperature and 70 psi. After filtration, the filtrate was concentrated in vacuo to provide P31 as a light-yellow solid. Yield: 63 mg, 0.19 mmol, 93%. LCMS m/z 335.2 [M+H]$^+$. $^1$H NMR (400 MHz, chloroform-d) δ 8.20 (s, 1H), 6.86 (t, $J_{HF}$=52.4 Hz, 1H), 4.10 (s, 3H), 3.78-3.51 (m, 3H), 3.41 (d, J=12.3 Hz, 1H), 2.99-2.85 (m, 2H), 2.83 (s, 3H), 2.29-2.19 (m, 2H), 2.19-2.01 (m, 2H).

Step 1. Synthesis of tert-butyl (2S)-6-[5-(difluoromethyl)-1-methyl-1H-1,2,4-triazol-3-yl]-7-methyl-3,4-dihydro-1H-spiro[1,8-naphthyridine-2,3'-pyrrolidine]-1'-carboxylate (C76)

Using the method described for synthesis of C68 from P23 in Alternate Preparation of P26, P23 (220 mg, 0.575 mmol) and 3-bromo-5-(difluoromethyl)-1-methyl-1H-1,2,4-triazole (P33; 128 mg, 0.604 mmol) were used to prepare C76. Silica gel chromatography (Gradient: 20% to 50% ethyl acetate in heptane) afforded C76 as a white solid. Yield: 110 mg, 0.253 mmol, 44%. LCMS m/z 435.4 [M+H]$^+$.

Step 2. Synthesis of (2S)-6-[5-(difluoromethyl)-1-methyl-1H-1,2,4-triazol-3-yl]-7-methyl-3,4-dihydro-1H-spiro[1,8-naphthyridine-2,3'-pyrrolidine], dihydrochloride salt (P32)

A mixture of C76 (110 mg, 0.253 mmol) in a solution of hydrogen chloride in 2-propanol (1.25 M, 1.0 mL, 1.2 mmol) was heated at 50° C. for 1 hour. LCMS analysis indicated formation of P32: LCMS m/z 335.3 [M+H]$^+$. Concentration in vacuo afforded P32 as a solid. Yield: 74 mg, 0.182 mmol, 72%.

Preparation P32
(2S)-6-[5-(Difluoromethyl)-1-methyl-1H-1,2,4-triazol-3-yl]-7-methyl-3,4-dihydro-1H-spiro[1,8-naphthyridine-2,3'-pyrrolidine], dihydrochloride salt (P32)

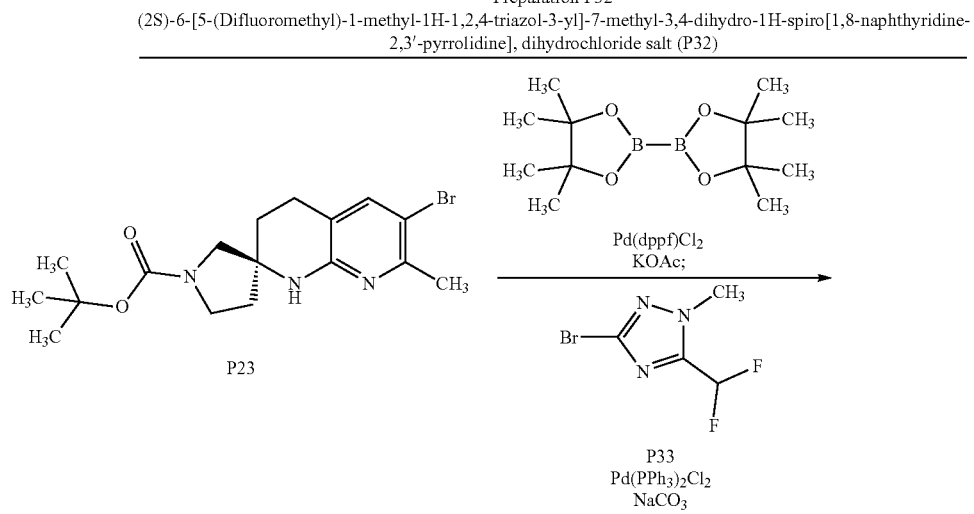

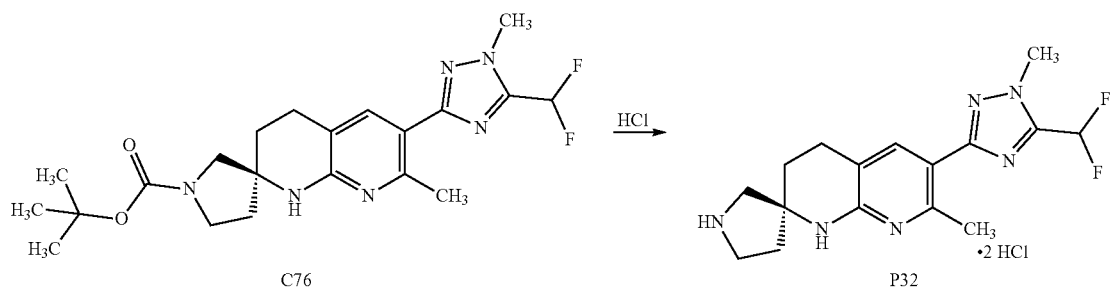

Preparation P33
3-Bromo-5-(difluoromethyl)-1-methyl-1H-1,2,4-triazole (P33)

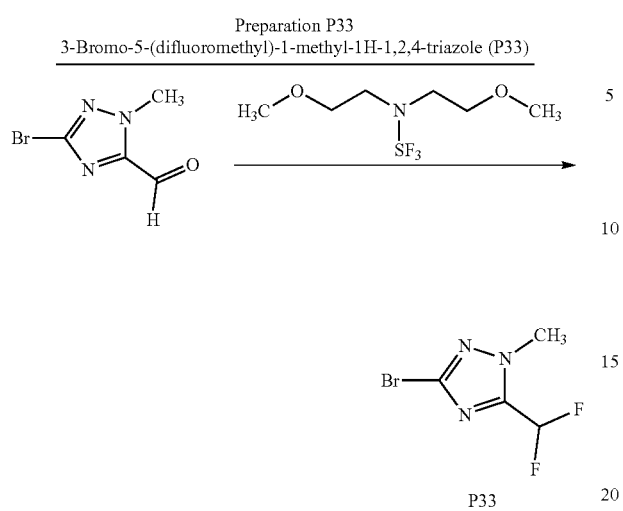

[Bis(2-methoxyethyl)amino]sulfur trifluoride (47.0 mL, 255 mmol) was added in a drop-wise manner to a 0° C. mixture of 3-bromo-1-methyl-1H-1,2,4-triazole-5-carbaldehyde (24.2 g, 127 mmol) in dichloromethane (400 mL); the reaction mixture was allowed to warm to 20° C. and stir at 20° C. for 16 hours. After drop-wise addition of aqueous sodium bicarbonate solution, the resulting mixture was extracted with dichloromethane (3×300 mL). The combined organic layers were washed with saturated aqueous sodium chloride solution, dried over sodium sulfate, filtered, and concentrated in vacuo. Chromatography on silica gel (Gradient: 50% to 70% dichloromethane in petroleum ether) afforded 3-bromo-5-(difluoromethyl)-1-methyl-1H-1,2,4-triazole (P33) as a light-yellow oil (17.7 g). This material was combined with the product of a similar reaction carried out using 3-bromo-1-methyl-1H-1,2,4-triazole-5-carbaldehyde (12.0 g, 63.2 mmol); concentration under reduced pressure provided P33 as a white solid. Combined yield: 25.2 g, 119 mmol, 63%. LCMS m/z 212 (bromine isotope pattern observed) [M+H]$^+$. $^1$H NMR (400 MHz, methanol-d$_4$) δ 7.06 (t, J$_{HF}$=52.2 Hz, 1H), 4.01 (s, 3H).

Examples 1 and 2
(2R)-2-(5-Chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 (1) and (2R)-2-(5-Chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 (2)

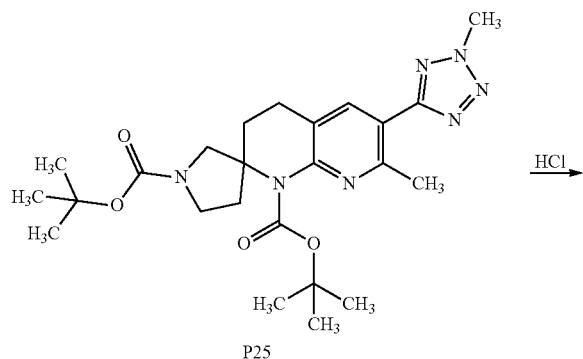

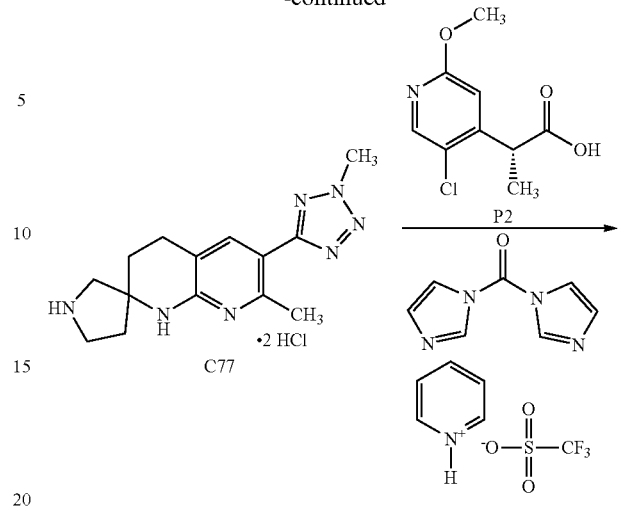

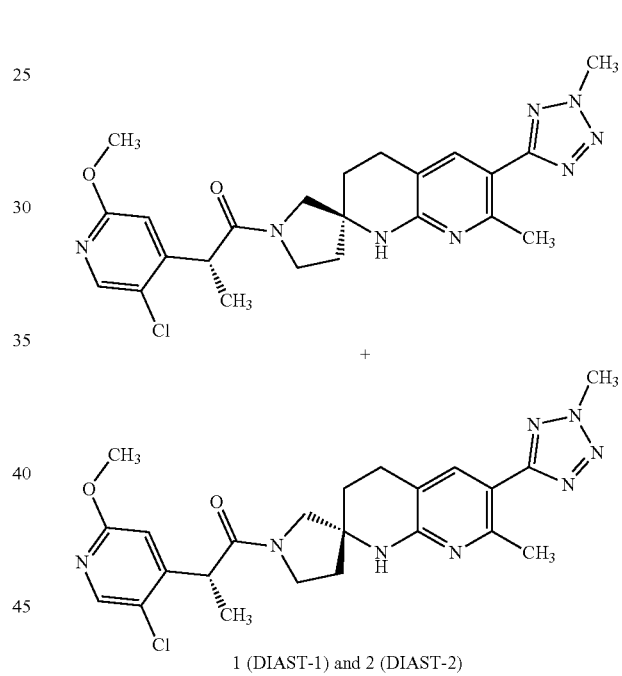

Step 1. Synthesis of 7-methyl-6-(2-methyl-2H-tetrazol-5-yl)-3,4-dihydro-1H-spiro[1,8-naphthyridine-2,3'-pyrrolidine], Dihydrochloride Salt (C77)

A solution of hydrogen chloride in 1,4-dioxane (4.0 M; 0.587 mL, 2.35 mmol) was added to a solution of P25 (285 mg, 0.587 mmol) in a mixture of dichloromethane (1 mL) and 1,1,1,3,3,3-hexafluoropropan-2-ol (1 mL). After the reaction mixture had been stirred at room temperature for 2 hours, LCMS analysis indicated the presence of C77: LCMS m/z 286.3 [M+H]$^+$. Removal of volatiles in vacuo afforded C77 as a white solid. Yield: 210 mg, 0.586 mmol, quantitative.

Step 2. Synthesis of (2R)-2-(5-chloro-2-methoxy-pyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 (1) and (2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 (2)

To a solution of P2 (65.7 mg, 0.305 mmol) in acetonitrile (1 mL) was added pyridinium trifluoromethanesulfonate (140 mg, 0.611 mmol), and the mixture was stirred until it was a solution. 1,1'-Carbonyldiimidazole (49.4 mg, 0.305 mmol) was added in one portion, and the reaction mixture was stirred at room temperature for 45 minutes, whereupon a solution of C77 (104 mg, 0.290 mmol) in acetonitrile (2 mL) was introduced. After the reaction mixture had been stirred at room temperature for 3 hours, it was diluted with aqueous ammonium chloride solution, and the resulting mixture was extracted three times with ethyl acetate. The combined organic layers were dried over magnesium sulfate, filtered, and concentrated in vacuo. Silica gel chromatography (Gradient: 20% to 100% ethyl acetate in heptane) afforded a mixture of 1 and 2 as a white solid (105 mg), LCMS m/z 483.3 (chlorine isotope pattern observed) [M+H]$^+$. Separation of the diastereomers was carried out via supercritical fluid chromatography [Column: Chiral Technologies Chiralpak IB, 21×250 mm, 5 μm; Mobile phase 85:15 carbon dioxide/(0.2% ammonium hydroxide in methanol); Flow rate: 75 mL/minute; Back pressure: 200 bar]; the first-eluting diastereomer was designated as 1 {(2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1}, and the second-eluting diastereomer as 2 {(2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2}.

1—Yield: 7.2 mg, 15 μmol, 5%. LCMS m/z 483.2 [M+H]$^+$. $^1$H NMR (400 MHz, methanol-d$_4$) δ [8.15 (s) and 8.14 (s), total 1H], [7.87 (s) and 7.83 (s), total 1H], [6.81 (s) and 6.75 (s), total 1H], [4.39 (s) and 4.39 (s), total 3H], [4.31 (q, J=6.8 Hz) and 4.22 (q, J=6.9 Hz), total 1H], 3.90 (s, 3H), [3.9-3.81 (m) and 3.76-3.52 (m), total 3H], [3.48 (d, component of AB quartet, J=12.3 Hz) and 3.35 (d, J=10.7 Hz), total 1H], [2.93-2.72 (m) and 2.6-2.46 (m), total 2H], [2.60 (s) and 2.58 (s), total 3H], 2.16-1.84 (m, 3H), 1.80-1.72 (m, 1H), [1.43 (d, J=6.8 Hz) and 1.42 (d, J=6.9 Hz), total 3H]. Retention time: 2.32 minutes [Analytical conditions. Column: Chiral Technologies Chiralpak IB, 4.6×100 mm, 5 μm; Mobile phase 3:2 carbon dioxide/(0.2% ammonium hydroxide in methanol); Flow rate: 1.5 mL/minute; Back pressure: 120 bar].

2—Yield: 7.9 mg, 16 μmol, 6%. LCMS m/z 483.2 [M+H]$^+$. Retention time: 2.53 minutes (Analytical conditions identical to those used for 1).

Examples 3 and 4
2-(6-Methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 (3) and 2-(6-Methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 (4)

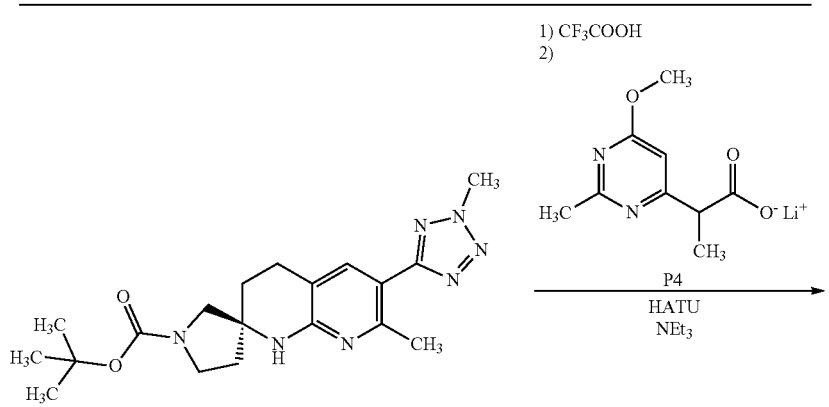

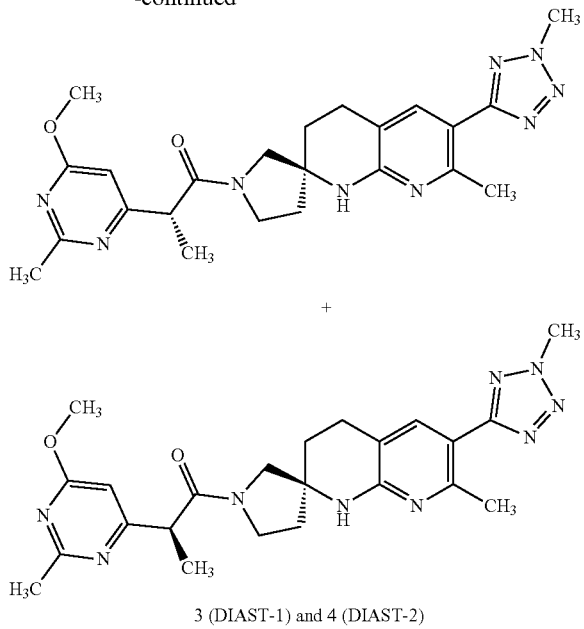

3 (DIAST-1) and 4 (DIAST-2)

Trifluoroacetic acid (2 mL) was added to a solution of C68 (280 mg, 0.726 mmol) in dichloromethane (10 mL), and the reaction mixture was stirred at room temperature for 2 hours. It was then concentrated in vacuo and evaporated twice with ethyl acetate to afford the deprotected material as a dark brown oil (200 mg), LCMS m/z 286.3 [M+H]$^+$. A portion of this oil (35 mg) and P4 (24.9 mg, 0.123 mmol) were dissolved in dichloromethane (3 mL) and treated with O-(7-azabenzotriazol-1-yl)-N,N,N',N'-tetramethyluronium hexafluorophosphate (HATU; 70.0 mg, 0.184 mmol) and triethylamine (51.3 µL, 0.368 mmol), followed by N,N-dimethylformamide (2 drops) to aid solubility. After the reaction mixture had been stirred at room temperature overnight, it was diluted with dichloromethane, washed sequentially with aqueous sodium bicarbonate solution and saturated aqueous sodium chloride solution, filtered, dried, and concentrated under reduced pressure. Separation of the component diastereomers was carried out using supercritical fluid chromatography [Column: Chiral Technologies Chiralpak IA, 21×250 mm, 5 µm; Mobile phase: 7:3 carbon dioxide/(0.5% ammonium hydroxide in methanol); Flow rate: 75 mL/minute; Back pressure: 120 bar]; the first-eluting diastereomer was designated as 3 {2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1} and the second-eluting diastereomer as 4 {2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2}.

3—Yield: 3.1 mg, 6.7 µmol, 5%. LCMS m/z 464.3 [M+H]$^+$. $^1$H NMR (400 MHz, methanol-d$_4$) δ [7.86 (s) and 7.85 (s), total 1H], [6.65 (s) and 6.61 (s), total 1H], [4.39 (s) and 4.39 (s), total 3H], [4.05 (q, J=7.0 Hz), 4.01-3.89 (m), 3.88-3.55 (m), 3.59 (s), and 3.53 (s), total 5H], [3.98 (s) and 3.96 (s), total 3H], 2.95-2.75 (m, 2H), [2.60 (s), 2.58 (s), and 2.55 (s), total 6H], 2.19-1.71 (m, 4H), [1.46 (d, J=7.1 Hz) and 1.44 (d, J=7.1 Hz), total 3H]. Retention time: 2.47 minutes [Analytical conditions. Column: Chiral Technologies Chiralpak IA, 4.6×100 mm, 5 µm; Mobile phase: 65:35 carbon dioxide/(methanol containing 0.5% ammonium hydroxide); Flow rate: 1.5 mL/minute; Back pressure: 120 bar].

4—Yield: 3.6 mg, 7.8 µmol, 6%. LCMS m/z 486.3 [M+Na$^+$]. Retention time: 2.92 minutes (Analytical conditions identical to those used for 3).

Alternate Synthesis of Examples 3 and 4
2-(6-Methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3′-pyrrolidin]-1′-yl]propan-1-one, DIAST-1 (3) and 2-(6-Methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3′-pyrrolidin]-1′-yl]propan-1-one, DIAST-2 (4)

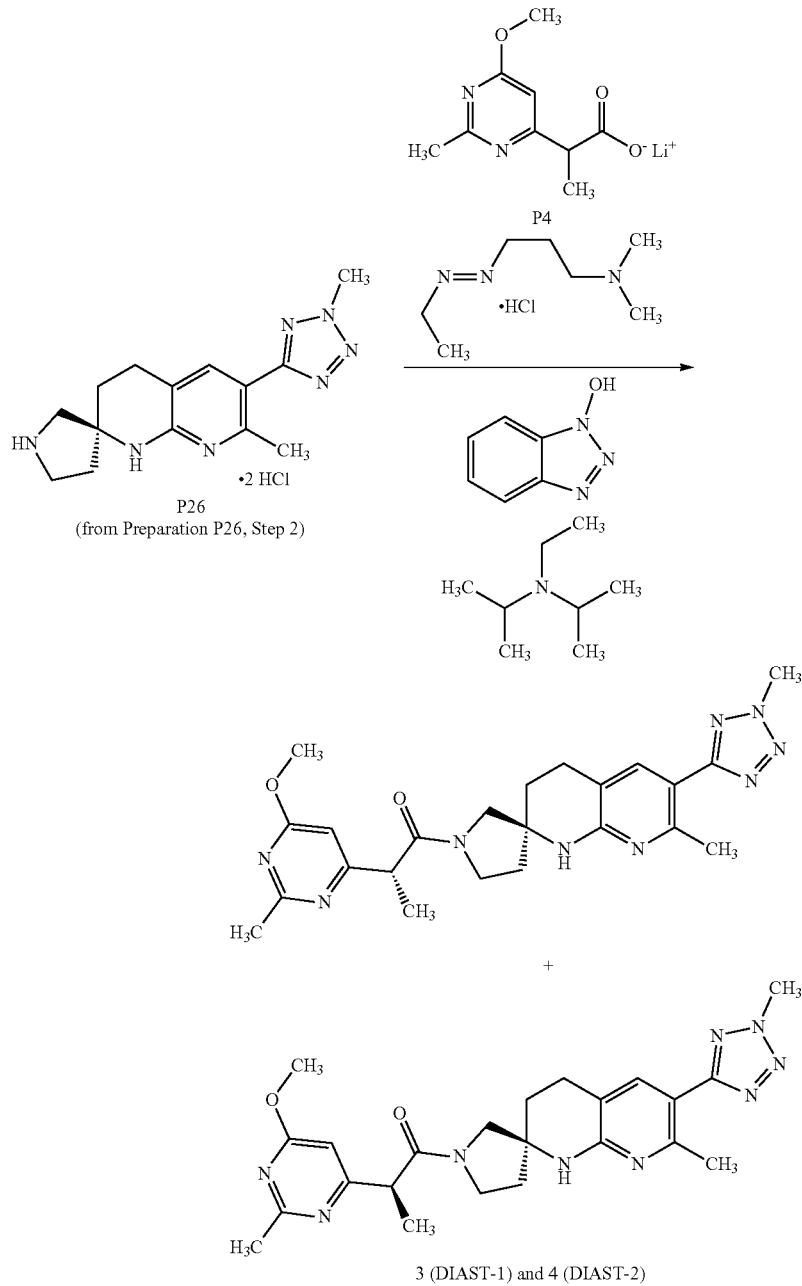

3 (DIAST-1) and 4 (DIAST-2)

A solution of P26 (material from Preparation P26; 105 mg, 0.293 mmol), P4 (69.0 mg, 0.352 mmol), 1-[3-(dimethylamino)propyl]-3-ethylcarbodiimide hydrochloride (EDCI; 169 mg, 0.882 mmol), 1H-benzotriazol-1-ol (119 mg, 0.881 mmol) and N,N-diisopropylethylamine (0.255 mL, 1.46 mmol) in N,N-dimethylformamide (3 mL) was stirred at 25° C. for 16 hours. The reaction mixture was then diluted with water (40 mL) and extracted with ethyl acetate (3×30 mL), and the combined organic layers were washed with saturated aqueous sodium chloride solution, dried over sodium sulfate, filtered, and concentrated in vacuo. Silica gel chromatography (Gradient: 0% to 10% methanol in dichloromethane) was followed by separation of the two diastereomers using supercritical fluid chromatography [Column: Chiral Technologies Chiralcel OJ, 30×250 mm, 5 µm; Mobile phase: 85:15 carbon dioxide/(2-propanol containing 0.2% propan-2-amine); Flow rate: 80 mL/minute; Back pressure: 100 bar]. The first-eluting diastereomer was designated as 3 {2-(6-methoxy-2-methylpyrimidin-4-yl)-1-[(2S)-7-methyl-6-(2-methyl-2H-tetrazol-5-yl)-3,4-dihydro- 1H-spiro[1,8-naphthyridine-2,3'-pyrrolidin]-1'-yl]propan-1-one, DIAST-1}, and the second-eluting diastereomer as 4 {2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2}.

3—Yield: 30 mg, 65 μmol, 22%. LCMS m/z 464.2 [M+H]$^+$. $^1$H NMR (400 MHz, methanol-d$_4$) δ [7.86 (s) and 7.84 (s), total 1H], [6.65 (s) and 6.61 (s), total 1H], [4.39 (s) and 4.39 (s), total 3H], [4.04 (q, J=7.0 Hz), 4.00-3.89 (m), 3.88-3.60 (m), 3.59 (s), and 3.53 (s), total 5H], [3.97 (s) and 3.96 (s), total 3H], [2.94-2.74 (m) and 2.67-2.59 (m), total 2H], [2.60 (s), 2.58 (s), and 2.55 (s), total 6H], [2.16-2.06 (m) and 2.06-1.71 (m), total 4H], [1.46 (d, J=7.1 Hz) and 1.44 (d, J=7.1 Hz), total 3H]. Retention time: 4.92 minutes (Analytical conditions. Column: Chiral Technologies Chiralcel OJ, 4.6×250 mm, 5 μm; Mobile phase A: carbon dioxide; Mobile phase B: 2-propanol containing 0.2% propan-2-amine; Gradient: 5% B for 1.00 minute, then 5% to 60% B over 8.00 minutes; Flow rate: 3.0 mL/minute; Back pressure: 120 bar).

4—Yield: 30 mg, 65 μmol, 22%. LCMS m/z 464.2 [M+H]$^+$. $^1$H NMR (400 MHz, methanol-d$_4$) δ 7.85 (s, 1H), [6.62 (s) and 6.59 (s), total 1H], [4.40 (s) and 4.39 (s), total 3H], [4.04 (q, J=7.1 Hz), 3.98-3.85 (m), 3.77-3.60 (m), 3.58 (d, component of AB quartet, J=10.6 Hz), and 3.55-3.48 (m), total 5H], [3.96 (s) and 3.91 (s), total 3H], 2.92-2.76 (m, 2H), [2.59 (s), 2.57 (s), 2.56 (s), and 2.37 (s), total 6H], [2.21-2.09 (m), 2.08-2.01 (m), and 2.01-1.78 (m), total 4H], [1.47 (d, J=6.9 Hz) and 1.42 (d, J=7.0 Hz), total 3H]. Retention time: 5.05 minutes (Analytical conditions identical to those used for 3).

Assignment of the two diastereomers as 3 and 4 was carried out on the basis of the similarity of the $^1$H NMR spectra of this first-eluting enantiomer (3) with the sample of 3 from Examples 3 and 4 above. Further support was provided by comparison of the chromatographic retention time for this batch of 3 with the products from Examples 3 and 4 above:

Retention time of 3 from Alternate Synthesis of Examples 3 and 4: 2.28 minutes
Retention time of 3 from Examples 3 and 4: 2.46 minutes
Retention time of 4 from Examples 3 and 4: 2.91 minutes These analyses were run using the same analytical method: [Column: Chiral Technologies Chiralpak IA, 4.6× 100 mm, 5 μm; Mobile phase: 65:35 carbon dioxide/(methanol containing 0.5% ammonium hydroxide); Flow rate: 1.5 mL/minute; Back pressure: 120 bar].

The biological activity (K$_i$) of the respective examples from these two experiments was also consistent with the given assignments (data from individual batches that are summarized in Table 2):

Example 3 from Examples 3 and 4: 0.36 nM
Example 3 from Alternate Synthesis of Examples 3 and 4: 1.2 nM
Example 4 from Examples 3 and 4: 25 nM
Example 4 from Alternate Synthesis of Examples 3 and 4: 34 nM Examples 5 and 6
2-[6-(Difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 (5) and 2-[6-(Difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 (6)

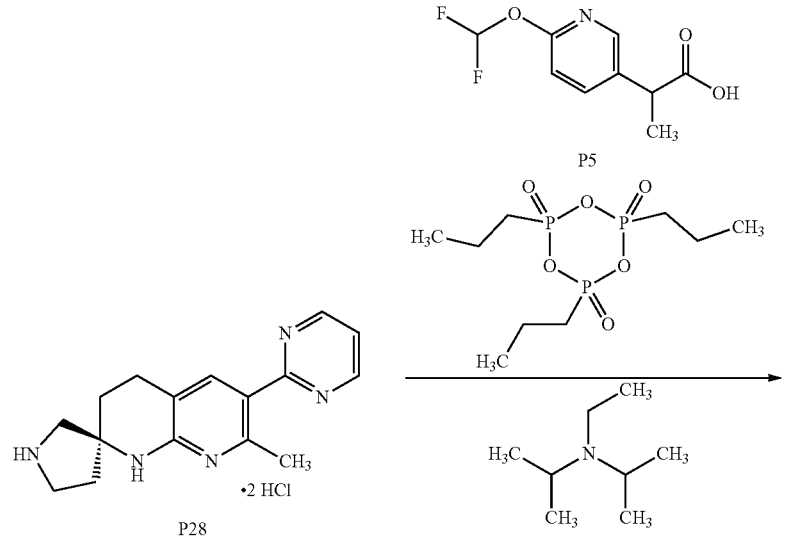

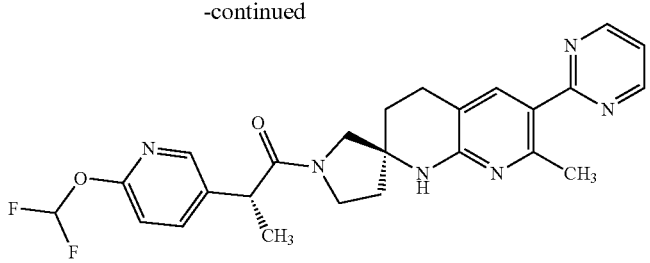

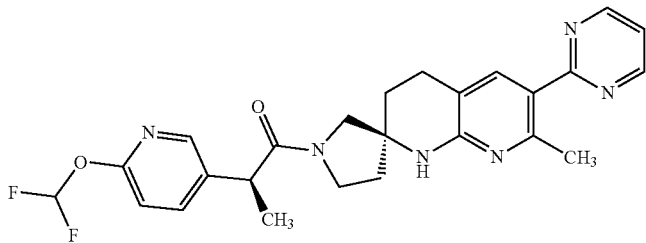

5 (DIAST-1) and 6 (DIAST-2)

A mixture of P28 (50 mg, 0.14 mmol), P5 (30.6 mg, 0.141 mmol), N,N-diisopropylethylamine (0.12 mL, 0.69 mmol), and 2,4,6-tripropyl-1,3,5,2,4,6-trioxatriphosphinane 2,4,6-trioxide (50% solution in ethyl acetate; 0.25 mL, 0.42 mmol) in dichloromethane (10 mL) was stirred at 25° C. for 16 hours, whereupon it was diluted with water (20 mL) and extracted with dichloromethane (2×20 mL). The combined organic layers were sequentially washed with aqueous sodium bicarbonate solution (30 mL) and saturated aqueous sodium chloride solution (30 mL), dried over sodium sulfate, filtered, and concentrated in vacuo. Chromatography on silica gel (Gradient: 0% to 10% methanol in dichloromethane) afforded a mixture of 5 and 6; these diastereomers were separated using reversed-phase HPLC (Column: Chiral Technologies Chiralpak IE; 50×250 mm; 10 μm; Mobile phase: 95:5 ethanol/acetonitrile; Flow rate: 60 mL/minute). The first-eluting diastereomer was designated as 5 {2-[6-(difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1} and the second-eluting diastereomer was designated as 6 {2-[6-(difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2}; both were isolated as white solids.

5—Yield: 10 mg, 21 μmol, 15%. LCMS m/z 481.3 [M+H]+. 1H NMR (400 MHz, methanol-$d_4$) δ [8.82 (d, J=4.9 Hz) and 8.81 (d, J=4.9 Hz), total 2H], [8.19 (d, J=2.5 Hz) and 8.12 (d, J=2.5 Hz), total 1H], 7.88-7.76 (m, 2H), [7.52 (t, $J_{HF}$=73.2 Hz) and 7.43 (t, $J_{HF}$=73.1 Hz), total 1H], [7.31 (t, J=4.9 Hz) and 7.31 (t, J=4.9 Hz), total 1H], [6.96 (d, J=8.5 Hz) and 6.89 (d, J=8.5 Hz), total 1H], [4.07 (q, J=6.9 Hz), 4.03-3.91 (m), 3.74-3.63 (m), 3.60 (d, component of AB quartet, J=12.1 Hz), 3.58-3.51 (m), 3.44 (d, J=12.4 Hz) and 3.40 (d, J=10.6 Hz), total 5H], 2.92-2.77 (m, 2H), [2.58 (s) and 2.54 (s), total 3H], [2.22-2.10 (m), 2.08-1.93 (m) and 1.93-1.77 (m), total 4H], [1.46 (d, J=6.9 Hz) and 1.42 (d, J=6.9 Hz), total 3H]. Retention time: 7.12 minutes (Analytical conditions. Column: Chiral Technologies Chiralpak AY-H; 4.6×250 mm; Mobile phase: 95:5:0.1 ethanol/acetonitrile/diethylamine; Flow rate: 0.6 mL/minute).

6—Yield: 9.8 mg, 20 μmol, 14%. LCMS m/z 481.3 [M+H]+. 1H NMR (400 MHz, methanol-$d_4$) δ [8.81 (d, J=4.9 Hz) and 8.80 (d, J=4.9 Hz), total 2H], [8.21 (d, J=2.5 Hz) and 8.16 (d, J=2.5 Hz), total 1H], 7.90-7.78 (m, 2H), [7.54 (t, $J_{HF}$=73.2 Hz) and 7.53 (t, $J_{HF}$=73.2 Hz), total 1H], [7.31 (t, J=4.9 Hz) and 7.30 (t, J=4.9 Hz), total 1H], [6.98 (d, J=8.5 Hz) and 6.96 (d, J=8.5 Hz), total 1H], [4.08 (q, J=6.9 Hz) and 4.00 (q, J=6.9 Hz), total 1H], [3.95-3.87 (m), 3.78-3.54 (m), 3.51 (AB quartet, $J_{AB}$=12.3 Hz, $\Delta v_{AB}$=33.2 Hz), and 3.39 (d, J=10.7 Hz), total 4H], [2.94-2.71 (m) and 2.62-2.49 (m), total 2H], [2.57 (s) and 2.54 (s), total 3H], [2.16-2.04 (m) and 2.02-1.84 (m), total 3H], 1.78-1.70 (m, 1H), [1.45 (d, J=7.0 Hz) and 1.42 (d, J=7.0 Hz), total 3H]. Retention time: 10.66 minutes (Analytical conditions identical to those used for 5).

Examples 7 and 8
1-[(2S)-7-Methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one, DIAST-1 (7) and
1-[(2S)-7-Methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one, DIAST-2 (8)

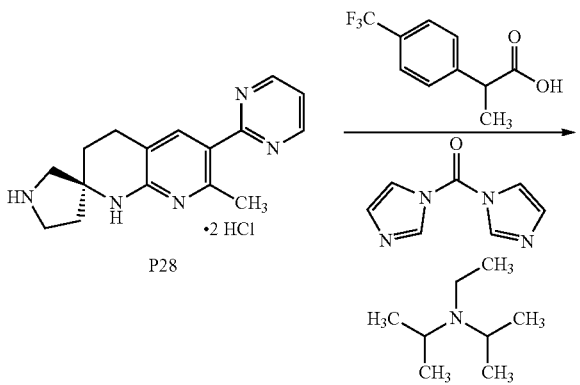

-continued

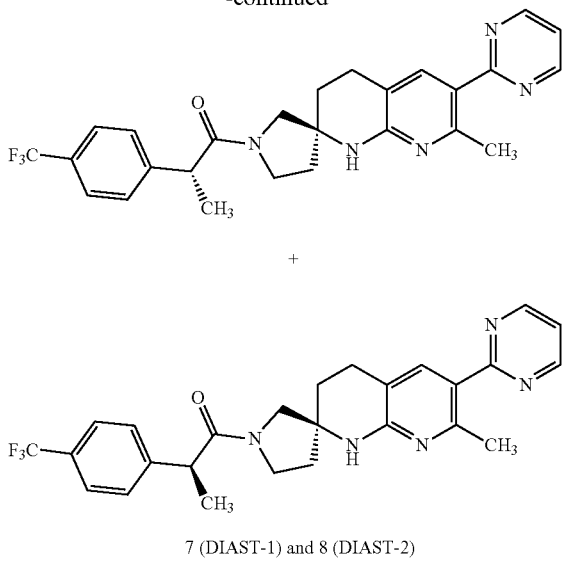

7 (DIAST-1) and 8 (DIAST-2)

1,1'-Carbonyldiimidazole (240 mg, 1.48 mmol) was added portion-wise to a solution of 2-[4-(trifluoromethyl)phenyl]propanoic acid (323 mg, 1.48 mmol) in acetonitrile (5 mL). After the reaction mixture had been stirred at room temperature for 45 minutes, a mixture of P28 (500 mg, 1.41 mmol) and N,N-diisopropylethylamine (0.504 mL, 2.89 mmol) in acetonitrile (2 mL) was added. Stirring was continued at room temperature for 18 hours, whereupon the reaction mixture was extracted with ethyl acetate. The combined organic layers were washed sequentially with saturated aqueous sodium bicarbonate solution and saturated aqueous sodium chloride solution, dried over magnesium sulfate, filtered, and concentrated in vacuo. The residue was separated into its component diastereomers via supercritical fluid chromatography {Column: Chiral Technologies Chiralcel OJ, 30×250 mm, 5 µm; Mobile phase 85:15 carbon dioxide/[methanol containing 0.2% (7 M ammonia in methanol)]; Flow rate: 80 mL/minute; Back pressure: 100 bar}. The first-eluting diastereomer was designated as 7 {1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one, DIAST-1} and the second-eluting diastereomer was designated as 8 {1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one, DIAST-2}; both were isolated as solids.

7—Yield: 250 mg, 0.519 mmol, 37%. LCMS m/z 482.4 [M+H]$^+$. $^1$H NMR (400 MHz, methanol-$d_4$) δ [8.80 (d, J=4.9 Hz) and 8.79 (d, J=4.9 Hz), total 2H], [7.83 (s) and 7.75 (s), total 1H], 7.68-7.62 (m, 2H), [7.54 (d, component of AB quartet, J=8.1 Hz) and 7.49 (d, component of AB quartet, J=8.1 Hz), total 2H], [7.28 (t, J=4.9 Hz) and 7.28 (t, J=4.9 Hz), total 1H], [4.10 (q, J=6.9 Hz) and 4.00 (q, J=6.9 Hz), total 1H], [3.92-3.83 (m) and 3.71 (ddd, J=12.5, 8.5, 6.2 Hz), total 1H], [3.62-3.46 (m), 3.46 (d, component of AB quartet, J=12.3 Hz), and 3.26 (d, J=10.7 Hz), total 3H], [2.91-2.75 (m), 2.68-2.58 (m), and 2.35-2.25 (m), total 2H], [2.56 (s) and 2.53 (s), total 3H], [2.13-1.99 (m) and 1.99-1.81 (m), total 3H], 1.66-1.58 (m, 1H), [1.45 (d, J=6.9 Hz) and 1.42 (d, J=6.9 Hz), total 3H]. Retention time: 4.28 minutes [Column: Chiral Technologies Chiralcel OJ, 4.6×250 mm, 5 µm; Mobile phase A: carbon dioxide; Mobile phase B: methanol containing 0.2% (7 M ammonia in methanol); Gradient: 5% B for 1.0 minute, then 5% to 60% B over 8.0 minutes; Flow rate: 3.0 mL/minute; Back pressure: 120 bar].

8—Yield: 260 mg, 0.540 mmol, 38%. LCMS m/z 482.4 [M+H]$^+$. $^1$H NMR (400 MHz, methanol-$d_4$) δ [8.80 (d, J=4.9 Hz) and 8.79 (d, J=4.9 Hz), total 2H], [7.82 (s) and 7.81 (s), total 1H], [7.64 (d, component of AB quartet, J=8.1 Hz) and 7.57 (d, component of AB quartet, J=8.2 Hz), total 2H], [7.52 (d, component of AB quartet, J=8.1 Hz) and 7.47 (d, component of AB quartet, J=8.2 Hz), total 2H], [7.29 (t, J=4.9 Hz) and 7.28 (t, J=4.9 Hz), total 1H], [4.09 (q, J=6.9 Hz) and 4.03 (q, J=6.9 Hz), total 1H], [3.96-3.87 (m) and 3.46-3.37 (m), total 1H], [3.73-3.63 (m), 3.52 (AB quartet, $J_{AB}$=12.3 Hz, $\Delta v_{AB}$=62.6 Hz), and 3.27 (d, J=10.6 Hz), total 3H]. 2.90-2.71 (m, 2H), [2.57 (s) and 2.53 (s), total 3H], [2.15-2.05 (m), 2.04-1.90 (m), and 1.89-1.70 (m), total 4H], [1.45 (d, J=6.9 Hz) and 1.43 (d, J=6.9 Hz), total 3H]. Retention time: 4.74 minutes (Analytical conditions identical to those used for 7).

Examples 9, 10, 11, and 12

1-[4,7-Dimethyl-3,4-dihydro-1H-spiro[1,8-naphthyridine-2,3'-pyrrolidin]-1'-yl)-2-(4-fluorophenyl)ethan-1-one, DIAST-1 (9),
1-[4,7-Dimethyl-3,4-dihydro-1H-spiro[1,8-naphthyridine-2,3'-pyrrolidin]-1'-yl)-2-(4-fluorophenyl)ethan-1-one, DIAST-2 (10),
1-[4,7-Dimethyl-3,4-dihydro-1H-spiro[1,8-naphthyridine-2,3'-pyrrolidin]-1'-yl)-2-(4-fluorophenyl)ethan-1-one, DIAST-3 (11), and
1-[4,7-Dimethyl-3,4-dihydro-1H-spiro[1,8-naphthyridine-2,3'-pyrrolidin]-1'-yl)-2-(4-fluorophenyl)ethan-1-one, DIAST-4 (12)

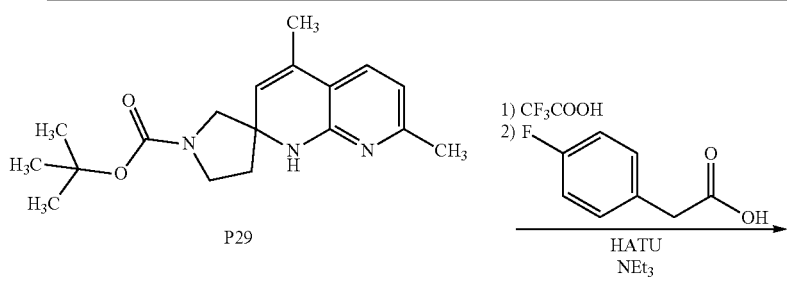

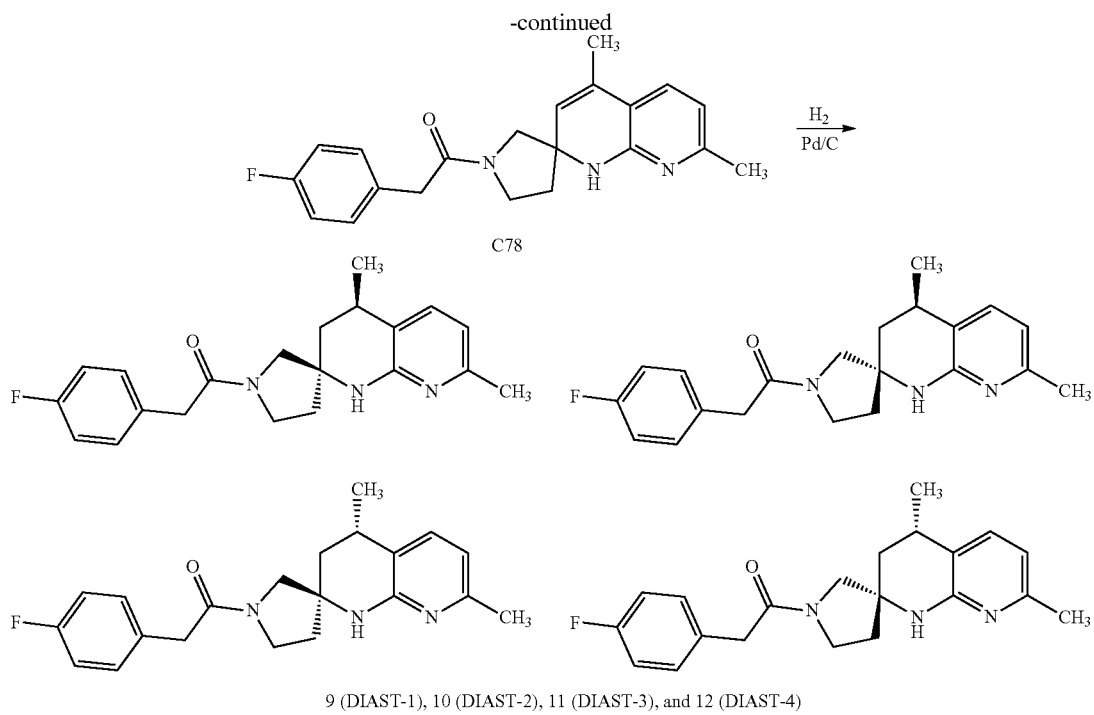

9 (DIAST-1), 10 (DIAST-2), 11 (DIAST-3), and 12 (DIAST-4)

Step 1. Synthesis of 1-(4,7-dimethyl-1H-spiro[1,8-naphthyridine-2,3'-pyrrolidin]-1'-yl)-2-(4-fluorophenyl)ethan-1-one (C78)

Trifluoroacetic acid (0.5 mL) was added to a solution of P29 (30 mg, 95 µmol) in dichloromethane (3 mL), and the reaction mixture was stirred at room temperature for 1 hour. After removal of volatiles via concentration in vacuo, the residue was coevaporated twice with ethyl acetate and heptane, then dissolved in dichloromethane (5 mL). To this solution were added triethylamine (13.3 µL, 95.4 µmol), (4-fluorophenyl)acetic acid (14.7 mg, 95.4 µmol), and O-(7-azabenzotriazol-1-yl)-N,N,N',N'-tetramethyluronium hexafluorophosphate (HATU; 36.2 mg, 95.2 µmol). After the reaction mixture had been stirred at room temperature for 1 hour, it was concentrated in vacuo and purified via chromatography on silica gel (Gradient: 0% to 10% methanol in dichloromethane), affording C78 as an off-white powder. Yield: 34 mg, quantitative. LCMS m/z 352.2 [M+H]+.

Step 2. Synthesis of 1-(4,7-dimethyl-3,4-dihydro-1H-spiro[1,8-naphthyridine-2,3'-pyrrolidin]-1'-yl)-2-(4-fluorophenyl)ethan-1-one, DIAST-1 (9), 1-(4,7-dimethyl-3,4-dihydro-1H-spiro[1,8-naphthyridine-2,3'-pyrrolidin]-1'-yl)-2-(4-fluorophenyl)ethan-1-one, DIAST-2 (10), 1-(4,7-dimethyl-3,4-dihydro-1H-spiro[1,8-naphthyridine-2,3'-pyrrolidin]-1'-yl)-2-(4-fluorophenyl)ethan-1-one, DIAST-3 (11), and 1-(4,7-dimethyl-3,4-dihydro-1H-spiro[1,8-naphthyridine-2,3'-pyrrolidin]-1'-yl)-2-(4-fluorophenyl)ethan-1-one, DIAST-4 (12)

A solution of C78 (22 mg, 63 µmol) in methanol (3 mL) was treated with palladium on carbon (10%; 5 mg) and hydrogenated overnight at 50 psi. The reaction mixture was then filtered, concentrated in vacuo, and subjected to supercritical fluid chromatography (Column: Chiral Technologies Chiralcel OJ-H, 5 µm; Mobile phase A: carbon dioxide; Mobile phase B: methanol containing 0.2% ammonium hydroxide; Gradient: 3% to 5% B; Flow rate: 75 mL/minute; Back pressure: 200 bar) to separate the four diastereomers. The first-eluting diastereomer was designated as 9 {1-(4,7-dimethyl-3,4-dihydro-1H-spiro[1,8-naphthyridine-2,3'-pyrrolidin]-1'-yl)-2-(4-fluorophenyl)ethan-1-one, DIAST-1}, the second-eluting as 10 {1-(4,7-dimethyl-3,4-dihydro-1H-spiro[1,8-naphthyridine-2,3'-pyrrolidin]-1'-yl)-2-(4-fluorophenyl)ethan-1-one, DIAST-2}, the third-eluting as 11 {1-(4,7-dimethyl-3,4-dihydro-1H-spiro[1,8-naphthyridine-2,3'-pyrrolidin]-1'-yl)-2-(4-fluorophenyl)ethan-1-one, DIAST-3}, and the fourth-eluting as 12 {1-(4,7-dimethyl-3,4-dihydro-1H-spiro[1,8-naphthyridine-2,3'-pyrrolidin]-1'-yl)-2-(4-fluorophenyl)ethan-1-one, DIAST-4}.

9—Yield: 1.2 mg, 3.4 µmol, 5%. LCMS m/z 354.3 [M+H]+. $^1$H NMR (400 MHz, chloroform-d) δ 7.31-7.21 (m, 2H, assumed; partially obscured by solvent peak), 7.21-7.16 (m, 1H), 7.05-6.94 (m, 2H), [6.48 (d, J=7.5 Hz) and 6.47 (d, J=7.5 Hz), total 1H], [3.77-3.52 (m) and 3.44 (d, component of AB quartet, J=12.1 Hz), total 4H], [3.62 (s) and 3.39 (s), total 2H], [2.90-2.77 (m) and 2.61-2.48 (m), total 1H], 2.33 (s, 3H), 2.13-2.03 (m, 1H), 2.02-1.94 (m, 1H), 1.89-1.74 (m, 1H), [1.33 (d, J=6.7 Hz) and 1.28 (d, J=6.7 Hz), total 3H]. Retention time: 2.77 minutes (Analytical conditions. Column: Chiral Technologies Chiralcel OJ-H, 4.6×100 mm, 5 µm; Mobile phase: 85:15 carbon dioxide/(methanol containing 0.2% ammonium hydroxide); Flow rate: 1.5 mL/minute; Back pressure: 120 bar).

10—Yield: 1.3 mg, 3.7 µmol, 6%. LCMS m/z 354.3 [M+H]+. $^1$H NMR (400 MHz, chloroform-d) δ 7.30-7.19 (m, 3H, assumed; partially obscured by solvent peak), 7.06-6.98 (m, 2H), [6.48 (d, J=7.4 Hz) and 6.47 (d, J=7.4 Hz), total 1H], [3.75-3.55 (m) and 3.50-3.40 (m), total 6H], 2.95-2.82 (m, 1H), 2.33 (s, 3H), [2.13-1.79 (m) and 1.74-1.66 (m, assumed; partially obscured by water peak), total 4H], 1.36-1.30 (m, 3H). Retention time: 2.92 minutes (Analytical conditions identical to those used for 9).

11—Yield: 1.3 mg, 3.7 μmol, 6%. LCMS m/z 354.3 [M+H]+. 1H NMR (400 MHz, chloroform-d) δ 7.29-7.21 (m, 2H, assumed; partially obscured by solvent peak), 7.21-7.15 (m, 1H), 7.05-6.93 (m, 2H), [6.48 (d, J=7.5 Hz) and 6.47 (d, J=7.5 Hz), total 1H], [3.74-3.52 (m) and 3.45 (d, component of AB quartet, J=12.0 Hz), total 4H], [3.62 (s) and 3.39 (s), total 2H], [2.90-2.78 (m) and 2.61-2.49 (m), total 1H], [2.33 (s) and 2.32 (s), total 3H], 2.10-2.04 (m, 1H), 2.00-1.94 (m, 1H), 1.88-1.74 (m, 1H), [1.32 (d, J=6.7 Hz) and 1.28 (d, J=6.7 Hz), total 3H]. Retention time: 3.48 minutes (Analytical conditions identical to those used for 9).

12—Yield: 2.1 mg, 5.9 μmol, 9%. LCMS m/z 354.3 [M+H]+. 1H NMR (400 MHz, chloroform-d) δ 7.29-7.20 (m, 3H, assumed; partially obscured by solvent peak), 7.06-6.98 (m, 2H), [6.48 (d, J=7.4 Hz) and 6.46 (d, J=7.4 Hz), total 1H], [3.74-3.55 (m) and 3.50-3.40 (m), total 6H], 2.95-2.82 (m, 1H), 2.32 (s, 3H), [2.12-1.78 (m) and 1.74-1.66 (m, assumed; partially obscured by water peak), total 4H], 1.36-1.30 (m, 3H). Retention time: 4.14 minutes (Analytical conditions identical to those used for 9).

By comparison of the 1H NMR data, 9 and 11 are enantiomers of one another. Similarly, 10 and 12 comprise a pair of enantiomers.

hours. It was then concentrated in vacuo and evaporated twice from ethyl acetate, providing the deprotected substrate as a dark brown oil (200 mg); a portion of this material was used in the subsequent coupling.

To a solution of P7 (36.4 mg, 0.183 mmol) in acetonitrile (3 mL) was added pyridinium trifluoromethanesulfonate (88.0 mg, 0.384 mmol), followed by 1,1'-carbonyldiimidazole (31.1 mg, 0.192 mmol). After this mixture had been stirred at room temperature for 45 minutes, a portion of the deprotected material from above (73 mg, 50.18 mmol), as a solution in acetonitrile (3 mL), was added, and the reaction mixture was stirred at room temperature overnight. It was then partitioned between dichloromethane and dilute aqueous ammonium chloride solution; the organic layer was washed with saturated aqueous sodium chloride solution, dried over sodium sulfate, filtered, and concentrated in vacuo. Silica gel chromatography (Gradient: 0% to 10% methanol in dichloromethane), followed by supercritical fluid chromatography [Column: Chiral Technologies Chiralpak IA, 21×250 mm, 5 μm; Mobile phase: 7:3 carbon dioxide/(0.5% ammonium hydroxide in methanol); Flow rate: 75 mL/minute; Back pressure: 120 bar] provided (2R)-2-(5-fluoro-2-methoxypyridin-4-yl)-1-[(2S)-7-methyl- Example 13
(2R)-2-(5-Fluoro-2-methoxypyridin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one (13)

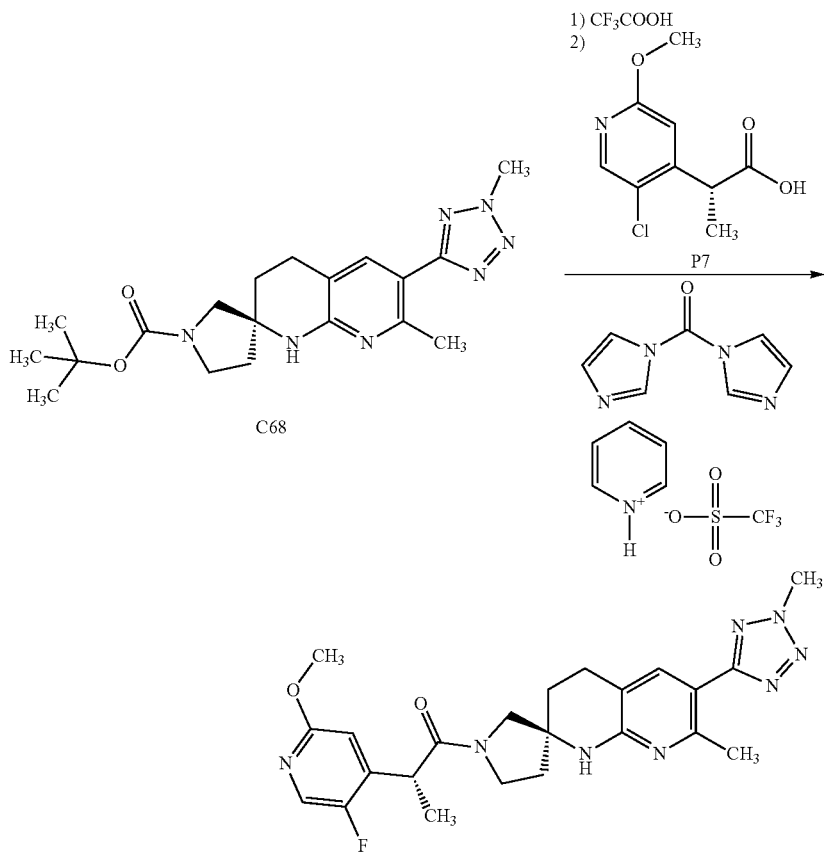

A solution of C68 (280 mg, 0.726 mmol) in dichloromethane (10 mL) was treated with trifluoroacetic acid (2 mL) and the reaction mixture was stirred at room temperature for 2 6-(2-methyl-2H-tetrazol-5-yl)-3,4-dihydro-1H-spiro[1,8-naphthyridine-2,3'-pyrrolidin]-1'-yl]propan-1-one (13). Yield: 13.6 mg, 29.1 μmol, approximately 16%. LCMS m/z 489.3 [M+Na$^+$]. Retention time: 2.6 minutes [Analytical conditions. Column: Chiral Technologies Chiralpak IA, 4.6× 100 mm, 5 μm; Mobile phase: 65:35 carbon dioxide/(methanol containing 0.5% ammonium hydroxide); Flow rate: 1.5 mL/minute; Back pressure: 120 bar].

Example 14
(2R)-2-(5-Fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (14)

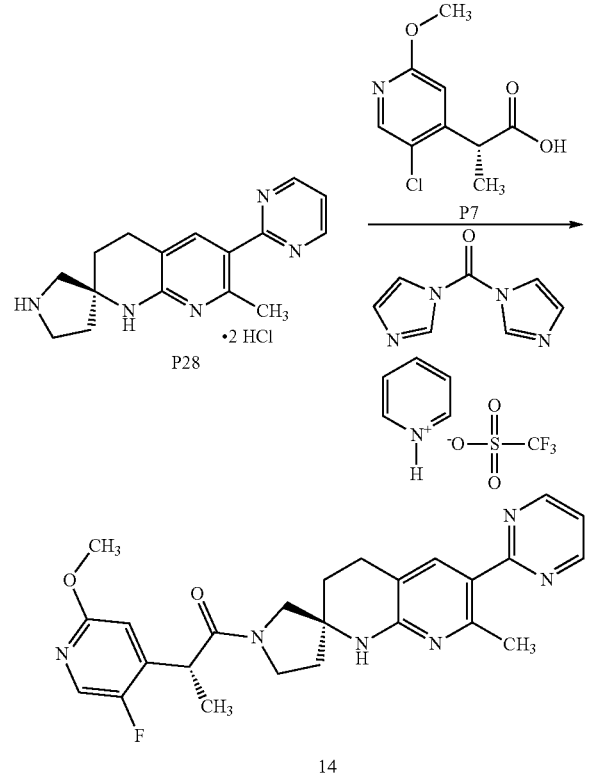

Pyridinium trifluoromethanesulfonate (1.02 g, 4.45 mmol) was added to a solution of P7 (material from Step 2 of Alternate Preparation (#1) of P7; 422 mg, 2.12 mmol) in acetonitrile (10 mL). To the resulting solution was added 1,1'-carbonyldiimidazole (360 mg, 2.22 mmol) in one portion, and the reaction mixture was allowed to stir at room temperature for 45 minutes, whereupon a solution of P28 (material from Step 2 of Preparation P28; 750 mg, 2.12 mmol) in acetonitrile (5 mL) was added in one portion. After the reaction had been stirred at room temperature for an additional 3 hours, it was diluted with saturated aqueous ammonium chloride solution and extracted three times with ethyl acetate. The combined organic layers were washed sequentially with saturated aqueous sodium bicarbonate solution and saturated aqueous sodium chloride solution, dried over magnesium sulfate, filtered, and concentrated in vacuo; silica gel chromatography (Gradient: 30% to 100% ethyl acetate in heptane) afforded (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (14) as a white solid.

The indicated absolute stereochemistry was assigned on the basis of a single crystal X-ray structure analysis carried out on 14 derived from crystallization of this lot (see below). Yield: 670 mg, 1.45 mmol, 68%. LCMS m/z 463.4 [M+H]$^+$.

$^1$H NMR (400 MHz, methanol-d$_4$) δ [8.81 (d, J=4.9 Hz) and 8.80 (d, J=4.9 Hz), total 2H], [7.99 (d, J=1.6 Hz) and 7.98 (d, J=1.7 Hz), total 1H], [7.84 (s) and 7.81 (s), total 1H], [7.30 (t, J=4.9 Hz) and 7.29 (t, J=4.9 Hz), total 1H], [6.78 (d, J=4.9 Hz) and 6.73 (d, J=4.9 Hz), total 1H], [4.27 (q, J=6.9 Hz) and 4.19 (q, J=6.9 Hz), total 1H], [3.93-3.83 (m) and 3.76-3.67 (m), total 1H], [3.88 (s) and 3.88 (s), total 3H], [3.67-3.57 (m), 3.53 (AB quartet, J$_{AB}$=12.3 Hz, Δν$_{AB}$=34.7 Hz), and 3.39 (d, component of AB quartet, J=10.6 Hz), total 3H], [2.94-2.72 (m) and 2.63-2.54 (m), total 2H], [2.57 (s) and 2.55 (s), total 3H], 2.15-1.83 (m, 3H), 1.83-1.74 (m, 1H), [1.45 (d, J=6.8 Hz) and 1.43 (d, J=6.8 Hz), total 3H].

Recrystallization from a 3:2 mixture of ethyl acetate and heptane provided material with a diastereomeric excess of 99.1%; further recrystallization from acetonitrile afforded the single crystal that was used for X-ray structural determination.

Single-Crystal X-Ray Structural Determination of 14

Single Crystal X-Ray Analysis

Data collection was performed on a Bruker D8 Quest diffractometer at room temperature. Data collection consisted of omega and phi scans.

The structure was solved by intrinsic phasing using SHELX software suite in the triclinic class group P1. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correctly assigned is 100%. The Hooft parameter is reported as 0.05 with an esd (estimated standard deviation) of (10) and the Parson's parameter is reported as 0.04 with an esd of (10).

The final R-index was 4.5%. A final difference Fourier revealed no missing or misplaced electron density.

Pertinent crystal, data collection, and refinement information is summarized in Table A.

Atomic coordinates, bond lengths, bond angles, and displacement parameters are listed in Tables B-D.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE A

Crystal data and structure refinement for 14.

| | |
|---|---|
| Empirical formula | $C_{25}H_{27}FN_6O_2$ |
| Formula weight | 462.52 |
| Temperature | 296(2) K |
| Wavelength | 1.54178 Å |
| Crystal system | Triclinic |
| Space group | P1 |
| Unit cell dimensions | a = 10.4754(9) Å   α = 81.768(5)° |
| | b = 10.5355(8) Å   β = 80.815(5)° |
| | c = 11.0180(8) Å   γ = 78.772(5)° |
| Volume | 1169.50(16) Å$^3$ |
| Z | 2 |
| Density (calculated) | 1.313 Mg/m$^3$ |
| Absorption coefficient | 0.754 mm$^{-1}$ |
| F(000) | 488 |
| Crystal size | 0.240 × 0.120 × 0.060 mm$^3$ |
| Theta range for data collection | 4.092 to 72.270° |
| Index ranges | −12 <= h <= 12, −12 <= k <= 12, |
| | −12 <=/<= 13 |
| Reflections collected | 21430 |
| Independent reflections | 7296 [R$_{int}$ = 0.0428] |
| Completeness to theta = 67.679° | 98.0% |
| Absorption correction | Empirical |
| Refinement method | Full-matrix least-squares on F$^2$ |
| Data/restraints/parameters | 7296/5/625 |
| Goodness-of-fit on F$^2$ | 1.062 |
| Final R indices [I > 2σ(I)] | R1 = 0.0446, wR2 = 0.1114 |
| R indices (all data) | R1 = 0.0527, wR2 = 0.1168 |
| Absolute structure parameter | 0.04(10) |
| Extinction coefficient | n/a |
| Largest diff. peak and hole | 0.148 and −0.173 e.Å$^{-3}$ |

TABLE B

Atomic coordinates (× 10$^4$) and equivalent isotropic displacement parameters (Å$^2$ × 10$^3$) for 14. U(eq) is defined as one-third of the trace of the orthogonalized U$^{ij}$ tensor.

| | x | y | z | U(eq) |
|---|---|---|---|---|
| F(1) | 1604(4) | 1726(3) | 11110(2) | 102(1) |
| F(2) | 8860(3) | 8452(2) | 3037(3) | 76(1) |
| N(1) | 512(3) | 5134(3) | 10290(3) | 59(1) |
| N(2) | 4192(3) | 1871(3) | 7816(3) | 53(1) |
| N(3) | 6543(3) | −105(3) | 8407(3) | 55(1) |
| N(4) | 6740(3) | −2336(3) | 8819(3) | 48(1) |
| N(5) | 6228(3) | −4410(3) | 12960(3) | 63(1) |
| N(6) | 7450(4) | −5741(3) | 11457(3) | 62(1) |
| N(7) | 9543(3) | 4968(3) | 3636(3) | 57(1) |
| N(8) | 6107(3) | 8985(3) | 5156(3) | 56(1) |
| N(9) | 3735(4) | 8607(3) | 7003(3) | 61(1) |
| N(10) | 3426(3) | 8380(3) | 9139(3) | 54(1) |
| N(11) | 3989(4) | 4172(4) | 11438(4) | 76(1) |
| N(12) | 2709(4) | 5861(4) | 12541(3) | 70(1) |
| O(1) | 344(3) | 6324(3) | 8383(3) | 70(1) |
| O(2) | 2839(3) | 2132(4) | 6383(3) | 81(1) |
| O(3) | 9449(4) | 3639(3) | 5483(3) | 82(1) |
| O(4) | 7448(3) | 10447(3) | 4814(3) | 85(1) |
| C(1) | 842(4) | 3963(5) | 10940(4) | 66(1) |
| C(2) | 644(4) | 5155(4) | 9077(4) | 51(1) |
| C(3) | 64(5) | 7451(5) | 9037(5) | 74(1) |
| C(4) | 1064(4) | 4063(4) | 8461(3) | 52(1) |
| C(5) | 1407(3) | 2868(4) | 9118(3) | 50(1) |
| C(6) | 1267(4) | 2874(4) | 10393(4) | 62(1) |
| C(7) | 1906(4) | 1639(4) | 8491(4) | 56(1) |
| C(8) | 788(5) | 1213(5) | 7997(5) | 81(1) |
| C(9) | 3017(4) | 1889(4) | 7485(3) | 55(1) |
| C(10) | 5293(4) | 2231(4) | 6912(3) | 58(1) |
| C(11) | 6370(4) | 2208(4) | 7686(4) | 62(1) |
| C(12) | 6095(4) | 1192(4) | 8798(3) | 51(1) |
| C(13) | 4592(4) | 1495(4) | 9059(4) | 52(1) |
| C(14) | 6749(4) | 1266(4) | 9916(4) | 59(1) |
| C(15) | 6407(4) | 229(4) | 10968(4) | 58(1) |
| C(16) | 6549(4) | −1081(4) | 10530(3) | 47(1) |
| C(17) | 6599(3) | −1203(3) | 9270(3) | 44(1) |
| C(18) | 6838(3) | −3450(4) | 9603(3) | 47(1) |

TABLE B-continued

Atomic coordinates (× 10$^4$) and equivalent isotropic displacement parameters (Å$^2$ × 10$^3$) for 14. U(eq) is defined as one-third of the trace of the orthogonalized U$^{ij}$ tensor.

| | x | y | z | U(eq) |
|---|---|---|---|---|
| C(19) | 6987(4) | −4662(4) | 8990(4) | 56(1) |
| C(20) | 6765(3) | −3431(4) | 10887(3) | 48(1) |
| C(21) | 6620(4) | −2218(4) | 11313(3) | 49(1) |
| C(22) | 6822(4) | −4606(4) | 11815(4) | 51(1) |
| C(23) | 6289(5) | −5453(5) | 13800(4) | 74(1) |
| C(24) | 6886(5) | −6666(5) | 13529(5) | 75(1) |
| C(25) | 7472(5) | −6771(4) | 12345(5) | 73(1) |
| C(26) | 9380(4) | 6193(4) | 3058(4) | 59(1) |
| C(27) | 9307(4) | 4845(4) | 4857(4) | 55(1) |
| C(28) | 9954(6) | 2552(5) | 4795(5) | 82(1) |
| C(29) | 8910(4) | 5881(4) | 5552(4) | 56(1) |
| C(30) | 8736(4) | 7139(4) | 4967(3) | 49(1) |
| C(31) | 9001(4) | 7242(4) | 3682(3) | 51(1) |
| C(32) | 8359(4) | 8302(4) | 5681(4) | 55(1) |
| C(33) | 9570(5) | 8903(5) | 5735(5) | 82(1) |
| C(34) | 7282(4) | 9328(4) | 5168(3) | 58(1) |
| C(35) | 5713(4) | 7727(4) | 5626(4) | 55(1) |
| C(36) | 4211(4) | 8059(4) | 5835(4) | 56(1) |
| C(37) | 3937(5) | 9134(5) | 4753(4) | 74(1) |
| C(38) | 5056(5) | 9880(4) | 4592(4) | 68(1) |
| C(39) | 3572(4) | 6886(5) | 5838(4) | 67(1) |
| C(40) | 3919(4) | 5864(4) | 6906(4) | 63(1) |
| C(41) | 3725(4) | 6453(4) | 8106(4) | 53(1) |
| C(42) | 3640(4) | 7792(4) | 8108(4) | 51(1) |
| C(43) | 3317(4) | 7643(4) | 10249(4) | 54(1) |
| C(44) | 3093(5) | 8399(5) | 11340(4) | 74(1) |
| C(45) | 3437(4) | 6291(4) | 10338(4) | 54(1) |
| C(46) | 3632(4) | 5729(4) | 9238(4) | 54(1) |
| C(47) | 3377(4) | 5399(4) | 11518(4) | 58(1) |
| C(48) | 3918(6) | 3351(6) | 12474(6) | 91(2) |
| C(49) | 3250(6) | 3723(6) | 13569(5) | 88(2) |
| C(50) | 2662(5) | 4994(6) | 13564(5) | 79(1) |

TABLE C

Bond lengths [Å] and angles [°] for 14.

| | |
|---|---|
| F(1)-C(6) | 1.364(5) |
| F(2)-C(31) | 1.361(4) |
| N(1)-C(2) | 1.319(5) |
| N(1)-C(1) | 1.348(5) |
| N(2)-C(9) | 1.335(5) |
| N(2)-C(10) | 1.471(5) |
| N(2)-C(13) | 1.473(5) |
| N(3)-C(17) | 1.387(5) |
| N(3)-C(12) | 1.458(5) |
| N(3)-H(3X) | 0.97(2) |
| N(4)-C(17) | 1.331(5) |
| N(4)-C(18) | 1.351(4) |
| N(5)-C(23) | 1.330(5) |
| N(5)-C(22) | 1.340(5) |
| N(6)-C(22) | 1.328(5) |
| N(6)-C(25) | 1.353(5) |
| N(7)-C(27) | 1.321(5) |
| N(7)-C(26) | 1.347(5) |
| N(8)-C(34) | 1.352(5) |
| N(8)-C(38) | 1.461(5) |
| N(8)-C(35) | 1.464(5) |
| N(9)-C(42) | 1.387(5) |
| N(9)-C(36) | 1.461(5) |
| N(9)-H(9X) | 0.95(2) |
| N(10)-C(42) | 1.338(5) |
| N(10)-C(43) | 1.353(5) |
| N(11)-C(48) | 1.331(6) |
| N(11)-C(47) | 1.335(6) |
| N(12)-C(47) | 1.331(6) |
| N(12)-C(50) | 1.346(6) |
| O(1)-C(2) | 1.362(5) |
| O(1)-C(3) | 1.435(5) |
| O(2)-C(9) | 1.241(5) |
| O(3)-C(27) | 1.349(5) |

TABLE C-continued

Bond lengths [Å] and angles [°] for 14.

| | |
|---|---|
| O(3)-C(28) | 1.432(6) |
| O(4)-C(34) | 1.224(5) |
| C(1)-C(6) | 1.339(6) |
| C(1)-H(1) | 0.9300 |
| C(2)-C(4) | 1.382(5) |
| C(3)-H(3A) | 0.9600 |
| C(3)-H(3B) | 0.9600 |
| C(3)-H(3C) | 0.9600 |
| C(4)-C(5) | 1.373(5) |
| C(4)-H(4) | 0.9300 |
| C(5)-C(6) | 1.390(5) |
| C(5)-C(7) | 1.518(6) |
| C(7)-C(9) | 1.509(6) |
| C(7)-C(8) | 1.532(6) |
| C(7)-H(7) | 0.9800 |
| C(8)-H(8A) | 0.9600 |
| C(8)-H(8B) | 0.9600 |
| C(8)-H(8C) | 0.9600 |
| C(10)-C(11) | 1.514(6) |
| C(10)-H(10A) | 0.9700 |
| C(10)-H(10B) | 0.9700 |
| C(11)-C(12) | 1.536(5) |
| C(11)-H(11A) | 0.9700 |
| C(11)-H(11B) | 0.9700 |
| C(12)-C(14) | 1.520(5) |
| C(12)-C(13) | 1.533(5) |
| C(13)-H(13A) | 0.9700 |
| C(13)-H(13B) | 0.9700 |
| C(14)-C(15) | 1.524(6) |
| C(14)-H(14A) | 0.9700 |
| C(14)-H(14B) | 0.9700 |
| C(15)-C(16) | 1.498(5) |
| C(15)-H(15A) | 0.9700 |
| C(15)-H(15B) | 0.9700 |
| C(16)-C(21) | 1.370(5) |
| C(16)-C(17) | 1.404(5) |
| C(18)-C(20) | 1.407(5) |
| C(18)-C(19) | 1.498(5) |
| C(19)-H(19A) | 0.9600 |
| C(19)-H(19B) | 0.9600 |
| C(19)-H(19C) | 0.9600 |
| C(20)-C(21) | 1.397(5) |
| C(20)-C(22) | 1.487(5) |
| C(21)-H(21) | 0.9300 |
| C(23)-C(24) | 1.361(7) |
| C(23)-H(23) | 0.9300 |
| C(24)-C(25) | 1.360(7) |
| C(24)-H(24) | 0.9300 |
| C(25)-H(25) | 0.9300 |
| C(26)-C(31) | 1.345(5) |
| C(26)-H(26) | 0.9300 |
| C(27)-C(29) | 1.382(6) |
| C(28)-H(28A) | 0.9600 |
| C(28)-H(28B) | 0.9600 |
| C(28)-H(28C) | 0.9600 |
| C(29)-C(30) | 1.380(5) |
| C(29)-H(29) | 0.9300 |
| C(30)-C(31) | 1.392(5) |
| C(30)-C(32) | 1.505(5) |
| C(32)-C(34) | 1.521(6) |
| C(32)-C(33) | 1.536(6) |
| C(32)-H(32) | 0.9800 |
| C(33)-H(33A) | 0.9600 |
| C(33)-H(33B) | 0.9600 |
| C(33)-H(33C) | 0.9600 |
| C(35)-C(36) | 1.531(6) |
| C(35)-H(35A) | 0.9700 |
| C(35)-H(35B) | 0.9700 |
| C(36)-C(39) | 1.514(6) |
| C(36)-C(37) | 1.543(6) |
| C(37)-C(38) | 1.508(7) |
| C(37)-H(37A) | 0.9700 |
| C(37)-H(37B) | 0.9700 |
| C(38)-H(38A) | 0.9700 |
| C(38)-H(38B) | 0.9700 |
| C(39)-C(40) | 1.516(6) |
| C(39)-H(39A) | 0.9700 |
| C(39)-H(39B) | 0.9700 |
| C(40)-C(41) | 1.507(6) |
| C(40)-H(40A) | 0.9700 |
| C(40)-H(40B) | 0.9700 |
| C(41)-C(46) | 1.365(5) |
| C(41)-C(42) | 1.397(5) |
| C(43)-C(45) | 1.396(6) |
| C(43)-C(44) | 1.499(6) |
| C(44)-H(44A) | 0.9600 |
| C(44)-H(44B) | 0.9600 |
| C(44)-H(44C) | 0.9600 |
| C(45)-C(46) | 1.393(6) |
| C(45)-C(47) | 1.491(6) |
| C(46)-H(46) | 0.9300 |
| C(48)-C(49) | 1.363(8) |
| C(48)-H(48) | 0.9300 |
| C(49)-C(50) | 1.360(8) |
| C(49)-H(49) | 0.9300 |
| C(50)-H(50) | 0.9300 |
| C(2)-N(1)-C(1) | 116.3(4) |
| C(9)-N(2)-C(10) | 121.6(3) |
| C(9)-N(2)-C(13) | 127.5(3) |
| C(10)-N(2)-C(13) | 110.9(3) |
| C(17)-N(3)-C(12) | 120.6(3) |
| C(17)-N(3)-H(3X) | 111(3) |
| C(12)-N(3)-H(3X) | 122(3) |
| C(17)-N(4)-C(18) | 119.2(3) |
| C(23)-N(5)-C(22) | 116.2(4) |
| C(22)-N(6)-C(25) | 115.6(4) |
| C(27)-N(7)-C(26) | 116.4(3) |
| C(34)-N(8)-C(38) | 121.4(3) |
| C(34)-N(8)-C(35) | 127.4(3) |
| C(38)-N(8)-C(35) | 111.1(4) |
| C(42)-N(9)-C(36) | 120.1(3) |
| C(42)-N(9)-H(9X) | 115(3) |
| C(36)-N(9)-H(9X) | 120(3) |
| C(42)-N(10)-C(43) | 118.8(3) |
| C(48)-N(11)-C(47) | 116.7(5) |
| C(47)-N(12)-C(50) | 115.7(4) |
| C(2)-O(1)-C(3) | 116.0(3) |
| C(27)-O(3)-C(28) | 118.2(3) |
| C(6)-C(1)-N(1) | 122.2(4) |
| C(6)-C(1)-H(1) | 118.9 |
| N(1)-C(1)-H(1) | 118.9 |
| N(1)-C(2)-O(1) | 118.2(3) |
| N(1)-C(2)-C(4) | 124.2(4) |
| O(1)-C(2)-C(4) | 117.6(3) |
| O(1)-C(3)-H(3A) | 109.5 |
| O(1)-C(3)-H(3B) | 109.5 |
| H(3A)-C(3)-H(3B) | 109.5 |
| O(1)-C(3)-H(3C) | 109.5 |
| H(3A)-C(3)-H(3C) | 109.5 |
| H(3B)-C(3)-H(3C) | 109.5 |
| C(5)-C(4)-C(2) | 119.7(4) |
| C(5)-C(4)-H(4) | 120.1 |
| C(2)-C(4)-H(4) | 120.1 |
| C(4)-C(5)-C(6) | 115.0(4) |
| C(4)-C(5)-C(7) | 122.2(3) |
| C(6)-C(5)-C(7) | 122.8(4) |
| C(1)-C(6)-F(1) | 118.9(4) |
| C(1)-C(6)-C(5) | 122.6(4) |
| F(1)-C(6)-C(5) | 118.5(4) |
| C(9)-C(7)-C(5) | 108.5(3) |
| C(9)-C(7)-C(8) | 112.5(4) |
| C(5)-C(7)-C(8) | 110.7(3) |
| C(9)-C(7)-H(7) | 108.4 |
| C(5)-C(7)-H(7) | 108.4 |
| C(8)-C(7)-H(7) | 108.4 |
| C(7)-C(8)-H(8A) | 109.5 |
| C(7)-C(8)-H(8B) | 109.5 |
| H(8A)-C(8)-H(8B) | 109.5 |
| C(7)-C(8)-H(8C) | 109.5 |
| H(8A)-C(8)-H(8C) | 109.5 |
| H(8B)-C(8)-H(8C) | 109.5 |
| O(2)-C(9)-N(2) | 120.8(4) |
| O(2)-C(9)-C(7) | 121.1(4) |
| N(2)-C(9)-C(7) | 118.1(3) |
| N(2)-C(10)-C(11) | 104.2(3) |
| N(2)-C(10)-H(10A) | 110.9 |

TABLE C-continued

Bond lengths [Å] and angles [°] for 14.

| | |
|---|---|
| C(11)-C(10)-H(10A) | 110.9 |
| N(2)-C(10)-H(10B) | 110.9 |
| C(11)-C(10)-H(10B) | 110.9 |
| H(10A)-C(10)-H(10B) | 108.9 |
| C(10)-C(11)-C(12) | 103.9(3) |
| C(10)-C(11)-H(11A) | 111.0 |
| C(12)-C(11)-H(11A) | 111.0 |
| C(10)-C(11)-H(11B) | 111.0 |
| C(12)-C(11)-H(11B) | 111.0 |
| H(11A)-C(11)-H(11B) | 109.0 |
| N(3)-C(12)-C(14) | 108.2(3) |
| N(3)-C(12)-C(13) | 110.9(3) |
| C(14)-C(12)-C(13) | 112.7(3) |
| N(3)-C(12)-C(11) | 108.7(3) |
| C(14)-C(12)-C(11) | 114.9(3) |
| C(13)-C(12)-C(11) | 101.4(3) |
| N(2)-C(13)-C(12) | 103.4(3) |
| N(2)-C(13)-H(13A) | 111.1 |
| C(12)-C(13)-H(13A) | 111.1 |
| N(2)-C(13)-H(13B) | 111.1 |
| C(12)-C(13)-H(13B) | 111.1 |
| H(13A)-C(13)-H(13B) | 109.1 |
| C(12)-C(14)-C(15) | 110.8(3) |
| C(12)-C(14)-H(14A) | 109.5 |
| C(15)-C(14)-H(14A) | 109.5 |
| C(12)-C(14)-H(14B) | 109.5 |
| C(15)-C(14)-H(14B) | 109.5 |
| H(14A)-C(14)-H(14B) | 108.1 |
| C(16)-C(15)-C(14) | 112.2(3) |
| C(16)-C(15)-H(15A) | 109.2 |
| C(14)-C(15)-H(15A) | 109.2 |
| C(16)-C(15)-H(15B) | 109.2 |
| C(14)-C(15)-H(15B) | 109.2 |
| H(15A)-C(15)-H(15B) | 107.9 |
| C(21)-C(16)-C(17) | 115.9(3) |
| C(21)-C(16)-C(15) | 123.1(3) |
| C(17)-C(16)-C(15) | 121.0(3) |
| N(4)-C(17)-N(3) | 115.9(3) |
| N(4)-C(17)-C(16) | 124.0(3) |
| N(3)-C(17)-C(16) | 120.0(3) |
| N(4)-C(18)-C(20) | 121.2(3) |
| N(4)-C(18)-C(19) | 114.4(3) |
| C(20)-C(18)-C(19) | 124.3(3) |
| C(18)-C(19)-H(19A) | 109.5 |
| C(18)-C(19)-H(19B) | 109.5 |
| H(19A)-C(19)-H(19B) | 109.5 |
| C(18)-C(19)-H(19C) | 109.5 |
| H(19A)-C(19)-H(19C) | 109.5 |
| H(19B)-C(19)-H(19C) | 109.5 |
| C(21)-C(20)-C(18) | 117.3(3) |
| C(21)-C(20)-C(22) | 118.0(3) |
| C(18)-C(20)-C(22) | 124.7(3) |
| C(16)-C(21)-C(20) | 122.3(3) |
| C(16)-C(21)-H(21) | 118.9 |
| C(20)-C(21)-H(21) | 118.9 |
| N(6)-C(22)-N(5) | 125.7(4) |
| N(6)-C(22)-C(20) | 118.4(3) |
| N(5)-C(22)-C(20) | 115.8(3) |
| N(5)-C(23)-C(24) | 123.0(5) |
| N(5)-C(23)-H(23) | 118.5 |
| C(24)-C(23)-H(23) | 118.5 |
| C(23)-C(24)-C(25) | 116.7(4) |
| C(23)-C(24)-H(24) | 121.6 |
| C(25)-C(24)-H(24) | 121.6 |
| N(6)-C(25)-C(24) | 122.7(4) |
| N(6)-C(25)-H(25) | 118.6 |
| C(24)-C(25)-H(25) | 118.6 |
| C(31)-C(26)-N(7) | 122.3(3) |
| C(31)-C(26)-H(26) | 118.9 |
| N(7)-C(26)-H(26) | 118.9 |
| N(7)-C(27)-O(3) | 118.8(4) |
| N(7)-C(27)-C(29) | 124.2(4) |
| O(3)-C(27)-C(29) | 117.0(3) |
| O(3)-C(28)-H(28A) | 109.5 |
| O(3)-C(28)-H(28B) | 109.5 |
| H(28A)-C(28)-H(28B) | 109.5 |
| O(3)-C(28)-H(28C) | 109.5 |
| H(28A)-C(28)-H(28C) | 109.5 |
| H(28B)-C(28)-H(28C) | 109.5 |
| C(30)-C(29)-C(27) | 119.8(4) |
| C(30)-C(29)-H(29) | 120.1 |
| C(27)-C(29)-H(29) | 120.1 |
| C(29)-C(30)-C(31) | 114.9(4) |
| C(29)-C(30)-C(32) | 121.9(3) |
| C(31)-C(30)-C(32) | 123.1(3) |
| C(26)-C(31)-F(2) | 119.1(3) |
| C(26)-C(31)-C(30) | 122.5(3) |
| F(2)-C(31)-C(30) | 118.4(3) |
| C(30)-C(32)-C(34) | 112.9(3) |
| C(30)-C(32)-C(33) | 110.5(4) |
| C(34)-C(32)-C(33) | 110.5(4) |
| C(30)-C(32)-H(32) | 107.5 |
| C(34)-C(32)-H(32) | 107.5 |
| C(33)-C(32)-H(32) | 107.5 |
| C(32)-C(33)-H(33A) | 109.5 |
| C(32)-C(33)-H(33B) | 109.5 |
| H(33A)-C(33)-H(33B) | 109.5 |
| C(32)-C(33)-H(33C) | 109.5 |
| H(33A)-C(33)-H(33C) | 109.5 |
| H(33B)-C(33)-H(33C) | 109.5 |
| O(4)-C(34)-N(8) | 120.4(4) |
| O(4)-C(34)-C(32) | 121.6(4) |
| N(8)-C(34)-C(32) | 118.0(3) |
| N(8)-C(35)-C(36) | 103.4(3) |
| N(8)-C(35)-H(35A) | 111.1 |
| C(36)-C(35)-H(35A) | 111.1 |
| N(8)-C(35)-H(35B) | 111.1 |
| C(36)-C(35)-H(35B) | 111.1 |
| H(35A)-C(35)-H(35B) | 109.0 |
| N(9)-C(36)-C(39) | 108.3(3) |
| N(9)-C(36)-C(35) | 111.3(3) |
| C(39)-C(36)-C(35) | 112.5(3) |
| N(9)-C(36)-C(37) | 109.0(3) |
| C(39)-C(36)-C(37) | 114.0(4) |
| C(35)-C(36)-C(37) | 101.5(3) |
| C(38)-C(37)-C(36) | 105.0(3) |
| C(38)-C(37)-H(37A) | 110.7 |
| C(36)-C(37)-H(37A) | 110.7 |
| C(38)-C(37)-H(37B) | 110.7 |
| C(36)-C(37)-H(37B) | 110.7 |
| H(37A)-C(37)-H(37B) | 108.8 |
| N(8)-C(38)-C(37) | 105.0(3) |
| N(8)-C(38)-H(38A) | 110.7 |
| C(37)-C(38)-H(38A) | 110.7 |
| N(8)-C(38)-H(38B) | 110.7 |
| C(37)-C(38)-H(38B) | 110.7 |
| H(38A)-C(38)-H(38B) | 108.8 |
| C(36)-C(39)-C(40) | 110.7(3) |
| C(36)-C(39)-H(39A) | 109.5 |
| C(40)-C(39)-H(39A) | 109.5 |
| C(36)-C(39)-H(39B) | 109.5 |
| C(40)-C(39)-H(39B) | 109.5 |
| H(39A)-C(39)-H(39B) | 108.1 |
| C(41)-C(40)-C(39) | 111.5(4) |
| C(41)-C(40)-H(40A) | 109.3 |
| C(39)-C(40)-H(40A) | 109.3 |
| C(41)-C(40)-H(40B) | 109.3 |
| C(39)-C(40)-H(40B) | 109.3 |
| H(40A)-C(40)-H(40B) | 108.0 |
| C(46)-C(41)-C(42) | 116.2(4) |
| C(46)-C(41)-C(40) | 122.9(4) |
| C(42)-C(41)-C(40) | 120.8(4) |
| N(10)-C(42)-N(9) | 115.7(3) |

TABLE C-continued

Bond lengths [Å] and angles [°] for 14.

| | |
|---|---|
| N(10)-C(42)-C(41) | 123.7(4) |
| N(9)-C(42)-C(41) | 120.5(3) |
| N(10)-C(43)-C(45) | 121.5(4) |
| N(10)-C(43)-C(44) | 114.3(3) |
| C(45)-C(43)-C(44) | 124.2(4) |
| C(43)-C(44)-H(44A) | 109.5 |
| C(43)-C(44)-H(44B) | 109.5 |
| H(44A)-C(44)-H(44B) | 109.5 |
| C(43)-C(44)-H(44C) | 109.5 |
| H(44A)-C(44)-H(44C) | 109.5 |
| H(44B)-C(44)-H(44C) | 109.5 |
| C(46)-C(45)-C(43) | 117.4(4) |
| C(46)-C(45)-C(47) | 117.4(4) |
| C(43)-C(45)-C(47) | 125.2(4) |
| C(41)-C(46)-C(45) | 122.2(4) |
| C(41)-C(46)-H(46) | 118.9 |
| C(45)-C(46)-H(46) | 118.9 |
| N(12)-C(47)-N(11) | 125.4(4) |
| N(12)-C(47)-C(45) | 118.8(4) |
| N(11)-C(47)-C(45) | 115.7(4) |
| N(11)-C(48)-C(49) | 122.5(5) |
| N(11)-C(48)-H(48) | 118.7 |
| C(49)-C(48)-H(48) | 118.7 |
| C(50)-C(49)-C(48) | 116.7(5) |
| C(50)-C(49)-H(49) | 121.7 |
| C(48)-C(49)-H(49) | 121.7 |
| N(12)-C(50)-C(49) | 123.0(5) |
| N(12)-C(50)-H(50) | 118.5 |
| C(49)-C(50)-H(50) | 118.5 |

Symmetry transformations used to generate equivalent atoms

TABLE D

Anisotropic displacement parameters ($Å^2 \times 10^3$) for 14.
The anisotropic displacement factor exponent takes the form:
$-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| F(1) | 159(3) | 72(2) | 54(2) | 5(1) | −6(2) | 14(2) |
| F(2) | 108(2) | 52(1) | 56(1) | 5(1) | −5(1) | 3(1) |
| N(1) | 57(2) | 61(2) | 54(2) | −18(2) | 1(2) | 0(2) |
| N(2) | 60(2) | 49(2) | 40(2) | −1(1) | −1(1) | 3(2) |
| N(3) | 70(2) | 43(2) | 43(2) | −2(1) | −3(2) | 3(2) |
| N(4) | 49(2) | 43(2) | 48(2) | −6(1) | −6(1) | 0(1) |
| N(5) | 68(2) | 52(2) | 60(2) | 5(2) | 1(2) | −4(2) |
| N(6) | 71(2) | 46(2) | 66(2) | 0(2) | −18(2) | −2(2) |
| N(7) | 61(2) | 52(2) | 54(2) | −14(2) | −5(2) | 4(2) |
| N(8) | 69(2) | 40(2) | 51(2) | 3(1) | −3(2) | 3(2) |
| N(9) | 74(2) | 44(2) | 58(2) | −11(2) | 0(2) | 0(2) |
| N(10) | 56(2) | 46(2) | 57(2) | −11(2) | 3(1) | −6(2) |
| N(11) | 80(3) | 60(2) | 82(3) | 11(2) | −18(2) | −5(2) |
| N(12) | 68(2) | 78(3) | 65(2) | 2(2) | −5(2) | −25(2) |
| O(1) | 84(2) | 50(2) | 69(2) | −6(2) | −13(2) | 4(2) |
| O(2) | 84(2) | 104(3) | 46(2) | −10(2) | −10(1) | 9(2) |
| O(3) | 121(3) | 47(2) | 69(2) | −1(2) | −5(2) | −2(2) |
| O(4) | 92(2) | 43(2) | 107(3) | −1(2) | 12(2) | −9(2) |
| C(1) | 75(2) | 72(3) | 45(2) | −14(2) | 2(2) | 1(2) |
| C(2) | 40(2) | 55(2) | 56(2) | −10(2) | −5(2) | −5(2) |
| C(3) | 72(3) | 55(3) | 93(3) | −14(2) | −13(2) | 1(2) |
| C(4) | 52(2) | 55(2) | 44(2) | −9(2) | −5(2) | −1(2) |
| C(5) | 42(2) | 56(2) | 48(2) | −10(2) | −4(2) | −4(2) |
| C(6) | 72(3) | 59(3) | 46(2) | −2(2) | −2(2) | 4(2) |
| C(7) | 59(2) | 50(2) | 55(2) | −8(2) | −7(2) | −1(2) |
| C(8) | 82(3) | 76(3) | 92(3) | −29(3) | −12(3) | −15(3) |
| C(9) | 65(3) | 47(2) | 47(2) | −12(2) | −5(2) | 10(2) |
| C(10) | 70(3) | 47(2) | 45(2) | 1(2) | 6(2) | 2(2) |
| C(11) | 69(3) | 47(2) | 62(2) | −2(2) | 8(2) | −12(2) |
| C(12) | 60(2) | 41(2) | 49(2) | −5(2) | −1(2) | −9(2) |
| C(13) | 67(2) | 44(2) | 39(2) | −2(2) | −3(2) | −2(2) |
| C(14) | 68(3) | 48(2) | 64(2) | −9(2) | −13(2) | −12(2) |
| C(15) | 73(3) | 51(2) | 50(2) | −8(2) | −16(2) | −4(2) |
| C(16) | 49(2) | 46(2) | 46(2) | −9(2) | −7(2) | −2(2) |
| C(17) | 43(2) | 42(2) | 44(2) | −6(2) | −5(2) | 0(2) |
| C(18) | 42(2) | 45(2) | 52(2) | −6(2) | −9(2) | −4(2) |

TABLE D-continued

Anisotropic displacement parameters ($Å^2 \times 10^3$) for 14.
The anisotropic displacement factor exponent takes the form:
$-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(19) | 62(2) | 49(2) | 58(2) | −10(2) | −10(2) | −5(2) |
| C(20) | 43(2) | 47(2) | 50(2) | −4(2) | −6(2) | −6(2) |
| C(21) | 48(2) | 51(2) | 46(2) | −3(2) | −9(2) | −3(2) |
| C(22) | 46(2) | 46(2) | 59(2) | −5(2) | −8(2) | −6(2) |
| C(23) | 85(3) | 62(3) | 66(3) | 12(2) | −1(2) | −13(2) |
| C(24) | 85(3) | 61(3) | 75(3) | 15(2) | −14(3) | −17(3) |
| C(25) | 81(3) | 43(2) | 94(4) | −2(2) | −29(3) | −2(2) |
| C(26) | 62(2) | 64(3) | 42(2) | −6(2) | −3(2) | 7(2) |
| C(27) | 56(2) | 48(2) | 57(2) | −6(2) | −5(2) | −2(2) |
| C(28) | 103(4) | 44(2) | 95(4) | −9(2) | −23(3) | 3(2) |
| C(29) | 64(2) | 50(2) | 46(2) | −4(2) | 2(2) | −4(2) |
| C(30) | 47(2) | 49(2) | 48(2) | −8(2) | −1(2) | −4(2) |
| C(31) | 56(2) | 45(2) | 45(2) | −1(2) | −4(2) | 5(2) |
| C(32) | 62(2) | 52(2) | 50(2) | −11(2) | 2(2) | −10(2) |
| C(33) | 85(3) | 77(3) | 90(3) | −21(3) | −9(3) | −25(3) |
| C(34) | 72(3) | 43(2) | 53(2) | −10(2) | 13(2) | −6(2) |
| C(35) | 61(2) | 45(2) | 53(2) | −8(2) | 1(2) | −4(2) |
| C(36) | 61(2) | 53(2) | 53(2) | −9(2) | −8(2) | 0(2) |
| C(37) | 78(3) | 76(3) | 60(3) | −6(2) | −20(2) | 11(3) |
| C(38) | 90(3) | 53(2) | 50(2) | 1(2) | −3(2) | 7(2) |
| C(39) | 61(2) | 70(3) | 72(3) | −25(2) | −12(2) | −4(2) |
| C(40) | 62(2) | 56(2) | 74(3) | −22(2) | 3(2) | −16(2) |
| C(41) | 44(2) | 49(2) | 65(2) | −14(2) | 2(2) | −7(2) |
| C(42) | 46(2) | 46(2) | 59(2) | −10(2) | 3(2) | −6(2) |
| C(43) | 46(2) | 54(2) | 60(2) | −10(2) | −1(2) | −7(2) |
| C(44) | 93(3) | 70(3) | 59(2) | −14(2) | 6(2) | −20(3) |
| C(45) | 41(2) | 54(2) | 66(2) | −4(2) | −3(2) | −10(2) |
| C(46) | 48(2) | 43(2) | 71(3) | −9(2) | 0(2) | −10(2) |
| C(47) | 47(2) | 62(2) | 66(3) | 2(2) | −8(2) | −15(2) |
| C(48) | 95(4) | 78(4) | 91(4) | 20(3) | −22(3) | −11(3) |
| C(49) | 88(4) | 91(4) | 82(4) | 25(3) | −26(3) | −25(3) |
| C(50) | 70(3) | 102(4) | 70(3) | −2(3) | −6(2) | −35(3) |

Thus, the absolute stereochemistry of compound Example 14 was determined by single crystal X-ray crystallography FIG. 1 is the obtained single crystal X-ray structure (ORTEP drawing) of the crystalline compound Example 14: (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one.

In some embodiments, the present invention provides a crystalline form of (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one. In some further embodiments, the crystalline form of (2R)-2-(5-Fluoro-2-methoxypyridin-4-yl)-1-[(2S)-7-methyl-6-(pyrimidin-2-yl)-3,4-dihydro-1 H-spiro[1,8-naphthyridine-2,3'-pyrrolidin]-1'-yl]propan-1-one is the one described (or as prepared) in Example 14.

Alternate Synthesis of Example 14
(2R)-2-(5-Fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (14)
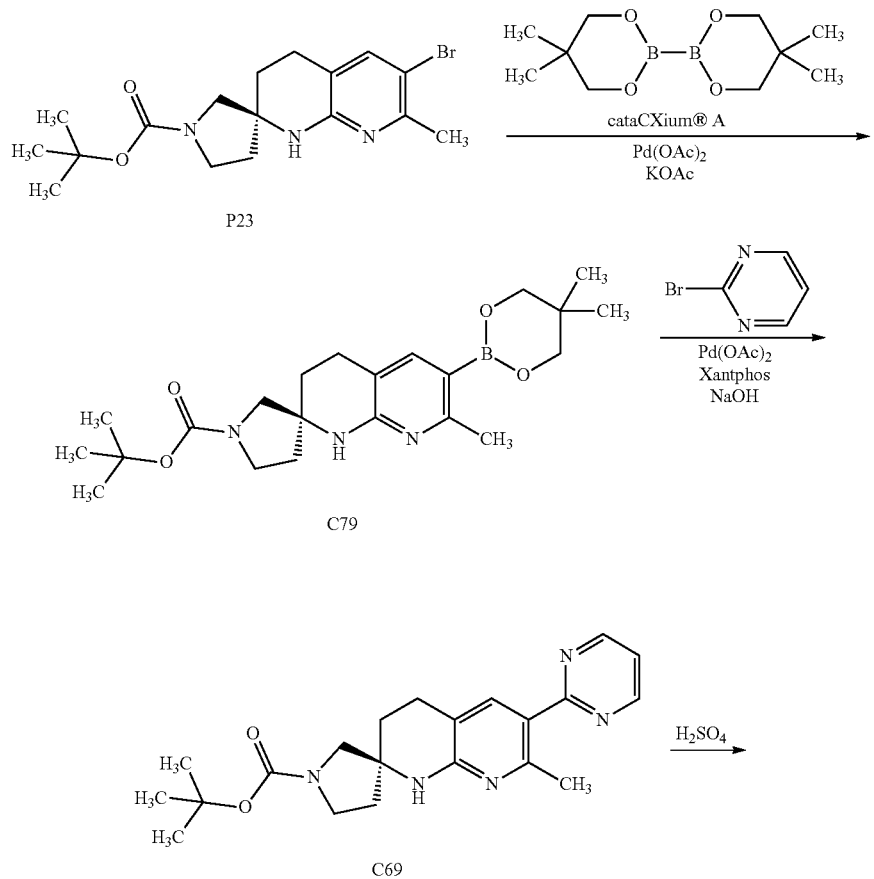
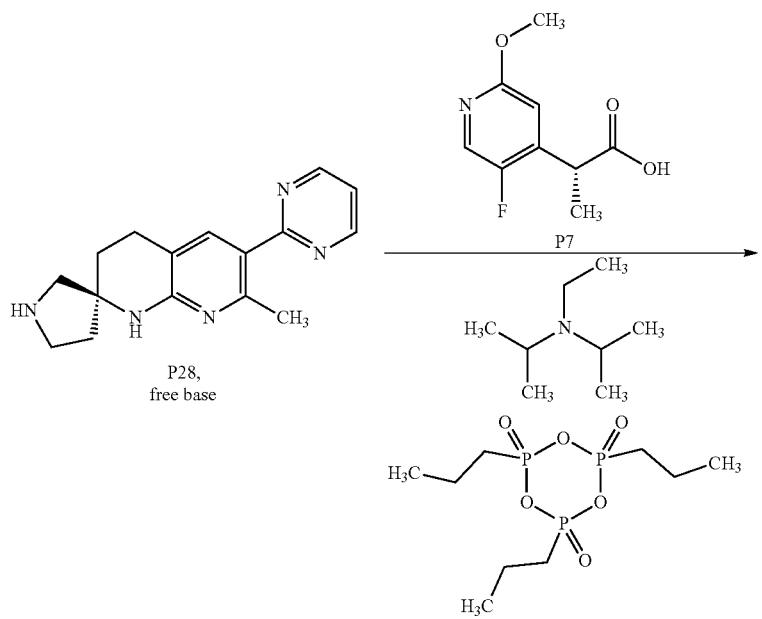

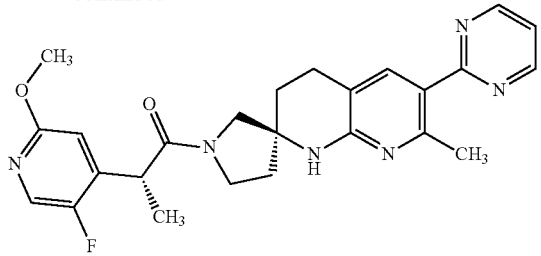

14

Step 1. Synthesis of tert-butyl (2S)-6-(5,5-dimethyl-1,3,2-dioxaborinan-2-yl)-7-methyl-3,4-dihydro-1H-spiro[1,8-naphthyridine-2,3'-pyrrolidine]-1'-carboxylate (C79)

Di(1-adamantyl)-n-butylphosphine (cataCXium® A; 2.21 g, 6.16 mmol), followed by palladium(II) acetate (0.461 mg, 2.05 mmol), was added to 2-methyltetrahydrofuran (170 mL); the catalyst mixture was sparged with argon for 10 to 20 minutes between each manipulation. The mixture was heated at reflux for 1 hour, then cooled to ≤50° C.

In a separate reactor, P23 (98.2% by mass; 80.0 g, 205 mmol), 5,5,5',5'-tetramethyl-2,2'-bi-1,3,2-dioxaborinane (60.3 g, 267 mmol), potassium acetate (97% by mass; 62.4 g, 617 mmol), and water (2.37 mL, 132 mmol) were added to 2-methyltetrahydrofuran (220 mL). The sides of the reactor were rinsed with 2-methyltetrahydrofuran (100 mL), and the resulting mixture was sparged with argon for approximately 1 hour. The catalyst mixture was then added via cannula, over less than 2 minutes, and the reaction mixture was heated to reflux at a rate of 1° C./minute. After 4 hours at reflux, it was cooled to 10° C., held at that temperature overnight, and rapidly treated drop-wise, over 15 minutes, with aqueous sodium hydroxide solution (1.0 M; 410 mL, 410 mmol). The internal temperature was maintained below 17° C. during the addition. The resulting mixture was warmed to 20° C., diluted with tert-butyl methyl ether (180 mL) and mixed well for 5 minutes, whereupon the aqueous layer was confirmed to be at pH 10. To the organic layer was added aqueous sodium hydroxide solution (1.0 M; 480 mL, 480 mmol) in four portions over 4 minutes; after stirring for 5 minutes, the organic layer was separated and similarly extracted with aqueous sodium hydroxide solution (1.0 M; 480 mL, 480 mmol). The combined sodium hydroxide extracts were mixed with toluene (240 mL), and treated portion-wise with hydrochloric acid (12.2 M; 62.3 mL, 760 mmol), at a rate that maintained the temperature below 30° C. The pH of the resulting mixture was 14; additional hydrochloric acid (12.2 M; 34 mL, 415 mmol) was added to adjust the pH to 10. After the mixture had been stirred for 5 minutes, the aqueous layer was extracted with toluene (2×240 mL), and the toluene layers were combined, affording C79 as a solution in toluene. The bulk of this material was used in the following step. Estimated yield: 73.2 g (by quantitative NMR), 176 mmol, 86% yield, as a solution in toluene.

Step 2. Synthesis of tert-butyl (2S)-7-methyl-6-(pyrimidin-2-yl)-3,4-dihydro-1H-spiro[1,8-naphthyridine-2,3'-pyrrolidine]-1'-carboxylate (C69)

To a solution of C79 in toluene (from the previous step; 509 mL, containing 72.7 g, 175 mmol, of C79) was added aqueous sodium hydroxide solution (1 M; 530 mL, 530 mmol) followed by 2-bromopyrimidine (39.0 g, 245 mmol). The resulting mixture was sparged with argon for 30 minutes, whereupon 4,5-bis(diphenylphosphino)-9,9-dimethylxanthene (Xantphos; 1.27 g, 2.19 mmol) and palladium(II) acetate (394 mg, 1.76 mmol) were added. After the reaction mixture had been heated at 50° C. for 3.5 hours, it was cooled to 20° C., allowed to stir overnight, and filtered. The filter cake was rinsed with toluene (150 mL), and the organic layer of the combined filtrates was washed with water by stirring for 5 minutes and then allowing the mixture to stand for 30 minutes; solids in the mixture were kept with the organic layer, which was subjected to short-path distillation at 100 mbar and 60° C. The mixture was distilled until approximately 275 mL remained, whereupon it was cooled to 20° C. at a rate of 1° C./minute. After the mixture had stirred for 30 minutes, during which time solids were noted, heptane (727 mL) was slowly added drop-wise, over 30 minutes. The resulting solution was stirred for 10 minutes, heated to 60° C. at a rate of 1° C./minute, and stirred at 60° C. for 90 minutes, whereupon it was cooled to 20° C. at a rate of 1° C./minute and allowed to stir for 3 days. Filtration, followed by rinsing of the solid cake twice with the filtrate and once with heptane (220 mL), provided C69 as a solid. Yield: 63.85 g, 167.4 mmol, 96%. HPLC purity: 99.4%. $^{1}$H NMR (600 MHz, DMSO-$d_6$) δ 8.80 (d, J=4.8 Hz, 2H), 7.90 (s, 1H), 7.27 (t, J=4.8 Hz, 1H), [7.25 (br s) and 7.24 (br s), total 1H], 3.56-3.49 (m, 1H), 3.37-3.30 (m, 1H), 3.28-3.21 (m, 2H), 2.80-2.73 (m, 1H), 2.73-2.65 (m, 1H), 2.59 (s, 3H), 1.99-1.84 (m, 2H), 1.82-1.69 (m, 2H), [1.41 (s) and 1.39 (s), total 9H].

Acquisition of Powder X-Ray Diffraction (PXRD) Data for Crystalline C69

A sample of C69 (prepared as described in Step 2 hereinabove) was submitted for Powder X-ray diffraction (PXRD) analysis and found to be a crystalline material.

Powder X-ray diffraction analysis was conducted using a Bruker AXS D8 Endeavor diffractometer equipped with a copper (Cu) radiation source. The divergence slit was set at 15 mm continuous illumination. Diffracted radiation was detected by a PSD-Lynx Eye detector, with the detector PSD opening set at 4.123 degrees. The X-ray tube voltage and amperage were set to 40 kV and 40 mA, respectively. In addition, the energy dispersive detector, a nickel filter was used. Data was collected in the Theta-Theta goniometer at the Cu wavelength from 3.0 to 40.0 degrees 2-Theta using a step size of 0.0100 degrees and a step time of 1.0 second. The antiscatter screen was set to a fixed distance of 1.5 mm. Samples were prepared by placing them in a silicon low background sample holder and rotated at 15 revolutions/min during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +/−0.2° 2-Theta (USP-941).

Figure 4:
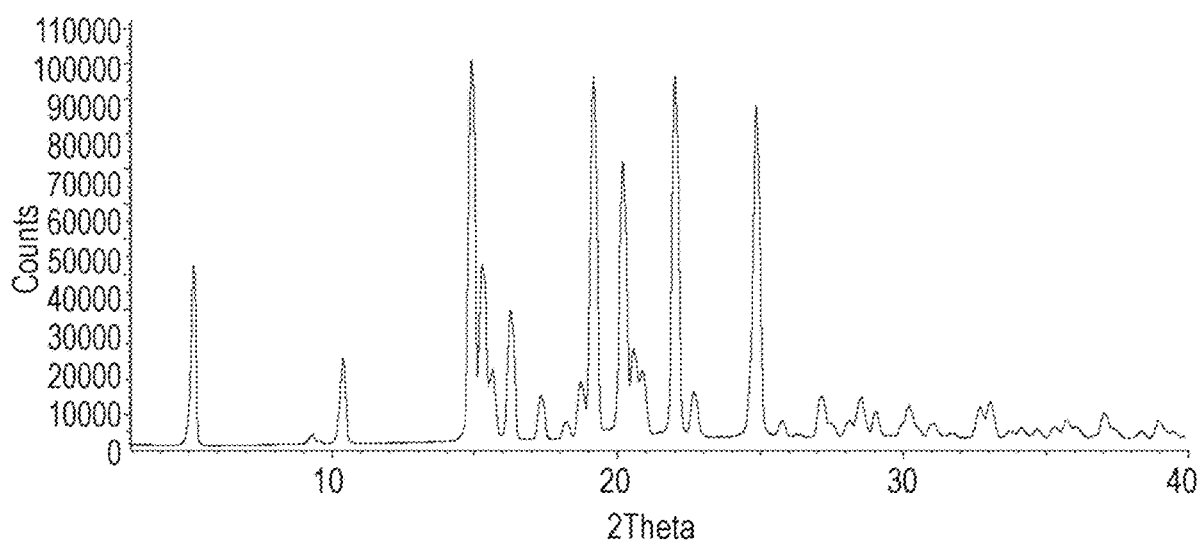
FIG. 4 shows an observed, representative powder X-ray diffraction pattern of a crystalline form of C69.

One representative diffraction pattern was observed for the crystalline form of C69 and is provided in FIG. 4. A list of diffraction peaks expressed in terms of the degree 2θ and relative intensities with a relative intensity of 3.0% of a PXRD from the sample of crystalline C69 are shown in Table X-C69 below.

TABLE X-C69

PXRD peak list for C69

| Angle (2-Theta) | Relative Intensity (%) |
|---|---|
| 5.2 | 47.3 |
| 10.4 | 22.3 |
| 14.9 | 100.0 |
| 15.3 | 46.0 |
| 15.7 | 18.7 |
| 16.3 | 33.9 |
| 17.4 | 11.5 |
| 18.2 | 4.6 |
| 18.7 | 14.8 |
| 19.2 | 95.0 |
| 20.2 | 72.6 |
| 20.6 | 23.2 |
| 20.9 | 17.5 |
| 22.0 | 95.1 |
| 22.7 | 11.8 |
| 24.9 | 87.3 |
| 25.8 | 4.0 |
| 27.1 | 10.8 |
| 28.2 | 4.2 |
| 28.5 | 10.5 |
| 29.0 | 6.6 |
| 30.2 | 8.3 |
| 31.0 | 3.4 |
| 32.7 | 8.5 |
| 33.1 | 9.4 |
| 35.8 | 4.6 |
| 37.1 | 6.7 |
| 39.0 | 4.6 |

In some embodiments, the present invention provide a compound that is tert-butyl (2S)-7-methyl-6-(pyrimidin-2-yl)-3,4-dihydro-1H-spiro[1,8-naphthyridine-2,3'-pyrrolidine]-1'-carboxylate or a salt thereof. In some embodiments, the present invention provide a compound that is tert-butyl (2S)-7-methyl-6-(pyrimidin-2-yl)-3,4-dihydro-1H-spiro[1,8-naphthyridine-2,3'-pyrrolidine]-1'-carboxylate. In some further embodiments, the present invention provide a crystalline form of tert-butyl (2S)-7-methyl-6-(pyrimidin-2-yl)-3,4-dihydro-1H-spiro[1,8-naphthyridine-2,3'-pyrrolidine]-1'-carboxylate. In some further embodiments, the crystalline form of tert-butyl (2S)-7-methyl-6-(pyrimidin-2-yl)-3,4-dihydro-1H-spiro[1,8-naphthyridine-2,3'-pyrrolidine]-1'-carboxylate exhibits a powder X-ray diffraction pattern comprising at least one characteristic peak, in terms of 2θ, as those listed in Table X-C69. In some embodiments, the crystalline form of tert-butyl (2S)-7-methyl-6-(pyrimidin-2-yl)-3,4-dihydro-1H-spiro[1,8-naphthyridine-2,3'-pyrrolidine]-1'-carboxylate exhibits a powder X-ray diffraction pattern comprising at least two characteristic peaks, in terms of 2θ, as those listed in Table X-C69. In some embodiments, the crystalline form of tert-butyl (2S)-7-methyl-6-(pyrimidin-2-yl)-3,4-dihydro-1H-spiro[1,8-naphthyridine-2,3'-pyrrolidine]-1'-carboxylate exhibits a powder X-ray diffraction pattern comprising at least three characteristic peaks, in terms of 2θ, as those listed in Table X-C69. In some embodiments, the crystalline form of tert-butyl (2S)-7-methyl-6-(pyrimidin-2-yl)-3,4-dihydro-1H-spiro[1,8-naphthyridine-2,3'-pyrrolidine]-1'-carboxylate exhibits a powder X-ray diffraction pattern comprising at least four (e.g. 4, 5, 6, 7, 8, 9, or 10) characteristic peaks, in terms of 2θ, as those listed in Table X-C69. In some embodiments, the crystalline form of tert-butyl (2S)-7-methyl-6-(pyrimidin-2-yl)-3,4-dihydro-1H-spiro[1,8-naphthyridine-2,3'-pyrrolidine]-1'-carboxylate exhibits a powder X-ray diffraction pattern substantially as shown in FIG. 4.

Step 3. Synthesis of (2S)-7-methyl-6-(pyrimidin-2-yl)-3,4-dihydro-1H-spiro[1,8-naphthyridine-2,3'-pyrrolidine] (P28, free base)

A solution of C69 (96% by mass; 50.0 g, 126 mmol) in water (100 mL) and 2-propanol (150 mL) was added over 10 minutes to an 80° C. mixture of water (150 mL) and concentrated sulfuric acid (14.5 mL, 272 mmol). After the reaction mixture had been stirred at 80° C. for 4 hours, it was cooled to 25° C. and was then subjected to short-path distillation at 120° C. and atmospheric pressure. When the mixture had been distilled to a volume of approximately 200 mL, the temperature was lowered to 50° C., activated carbon (Darco G-60; 10 g) was added, and stirring was continued for 1.5 hours at 50° C. The mixture was then cooled to 25° C. and filtered using a 10 μm filter. The filter cake was rinsed with water (100 mL), and the combined filtrates were diluted with 2-propanol (20 mL); the resulting mixture, of pH 0.86, was basified to the point of haziness that then cleared up, by addition of 6 M aqueous sodium hydroxide solution (approximately 75 mL). The resulting pH was 9.32. The mixture was treated drop-wise with additional 6 M aqueous sodium hydroxide solution (approximately 20 drops) to a pH of 9.6 to 9.7, at which point haziness persisted. Stirring was continued for 45 minutes, whereupon additional 6 M aqueous sodium hydroxide solution (to a total of approximately 80 mL, 480 mmol) was added, and stirring was continued at 20° C. for 30 minutes. The mixture was then heated to 50° C. at a rate of 1° C./minute, stirred for 1.5 hours, and cooled to 20° C. at a rate of 1° C./minute. After stirring for 1.5 hours, the mixture was filtered; the filter cake was rinsed with aqueous sodium hydroxide solution (1 M; 100 mL, 100 mmol), and dried overnight in vacuo at 50° C. to provide P28, free base. Yield: 30.87 g, 98.1% P28 via quantitative NMR, 108 mmol, 86%. $^1$H NMR (600 MHz, DMSO-d$_6$) δ 8.79 (d, J=4.8 Hz, 2H), 7.88 (s, 1H), 7.25 (t, J=4.8 Hz, 1H), 7.01 (s, 1H), 2.99 (ddd, J=11.0, 8.4, 6.4 Hz, 1H), 2.79 (ddd, J=10.9, 8.6, 5.6 Hz, 1H), 2.75-2.68 (m, 3H), 2.61 (d, J=11.3 Hz, 1H), 2.58 (s, 3H), 1.80-1.68 (m, 3H), 1.65 (ddd, J=12.7, 8.6, 6.4 Hz, 1H).

Acquisition of Powder X-ray Diffraction (PXRD) Data for Crystalline P28

A sample of P28 (prepared as described in Step 3 hereinabove) was submitted for Powder X-ray diffraction (PXRD) analysis and found to be a crystalline material.

Powder X-ray diffraction analysis was conducted using a Bruker AXS D8 Endeavor diffractometer equipped with a copper (Cu) radiation source. The divergence slit was set at 15 mm continuous illumination. Diffracted radiation was detected by a PSD-Lynx Eye detector, with the detector PSD opening set at 4.123 degrees. The X-ray tube voltage and amperage were set to 40 kV and 40 mA, respectively. In addition, the energy dispersive detector, a nickel filter was used. Data was collected in the Theta-Theta goniometer at the Cu wavelength from 3.0 to 40.0 degrees 2-Theta using a step size of 0.0100 degrees and a step time of 1.0 second. The antiscatter screen was set to a fixed distance of 1.5 mm. Samples were prepared by placing them in a silicon low background sample holder and rotated at 15 revolutions/min during collection. Data were collected using Bruker DIF-FRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of 3% were generally chosen. Typically, the peaks which were not resolved or were consistent with noise were not selected. A typical error associated with the peak position from PXRD stated in USP up to +/−0.2° 2-Theta (USP-941).

Figure 5:
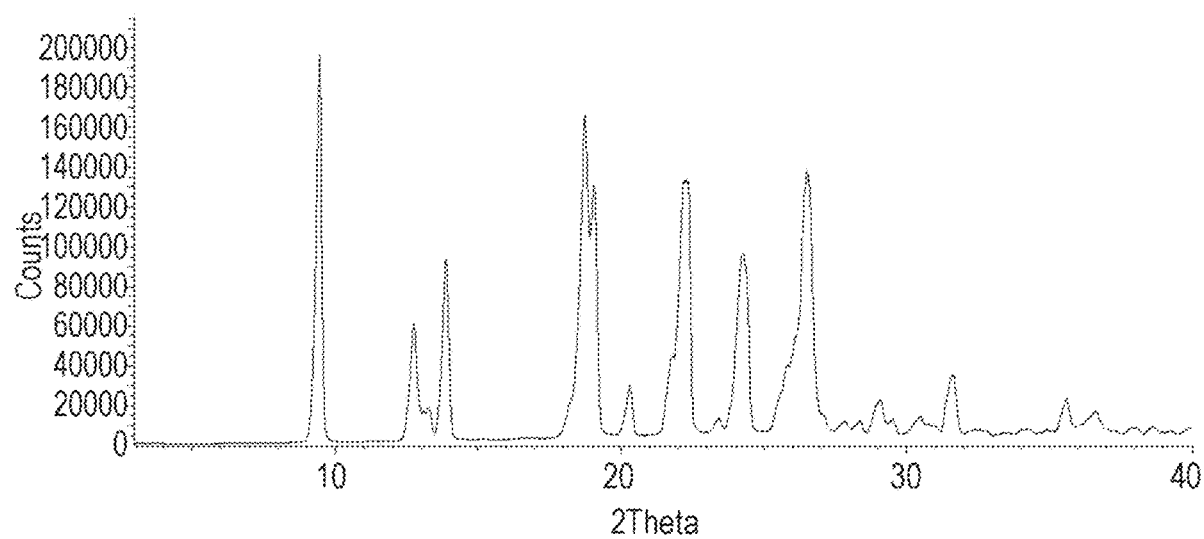
FIG. 5 shows an observed, representative powder X-ray diffraction pattern of a crystalline form of P28.
Figure 6:
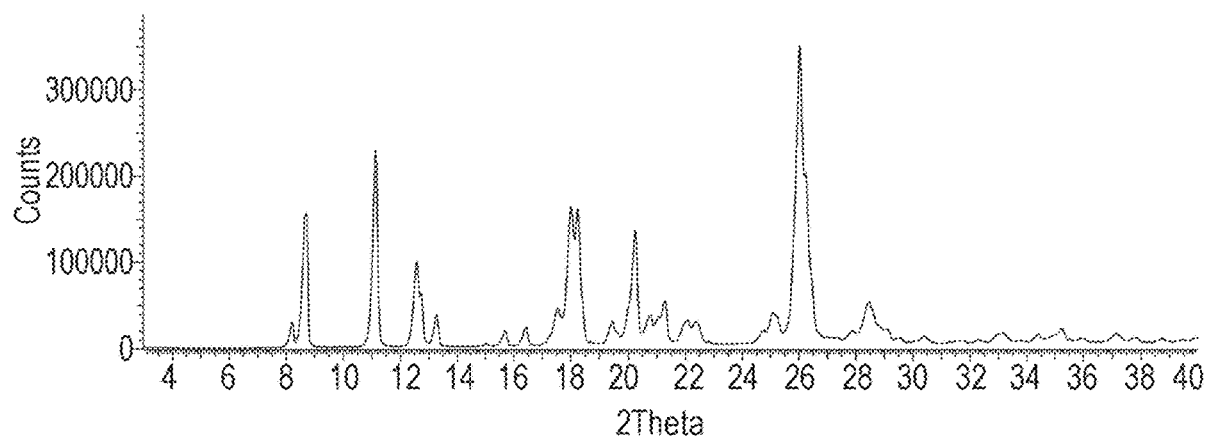
FIG. 6 shows an observed, representative powder X-ray diffraction pattern of a crystalline form of Example 14.

One representative diffraction pattern was observed for the crystalline form of P28 and is provided in FIG. 5. A list of diffraction peaks expressed in terms of the degree 2θ and relative intensities with a relative intensity of 3.0% of a PXRD from the sample of crystalline P28 are shown in Table X-P28 below.

TABLE X-P28

PXRD peak list for the crystalline from of P28

| Angle (2-Theta) | Relative Intensity (%) |
|---|---|
| 9.5 | 100 |
| 12.8 | 30.1 |
| 13.3 | 8.4 |
| 13.9 | 46.9 |
| 18.8 | 83.5 |
| 19.1 | 64.7 |
| 20.3 | 13.0 |
| 21.8 | 20.8 |
| 22.3 | 66.4 |
| 23.4 | 3.8 |
| 24.3 | 46.7 |
| 26.5 | 68.8 |
| 27.9 | 3.0 |
| 28.4 | 3.2 |
| 29.1 | 8.6 |
| 29.5 | 3.7 |
| 30.5 | 4.6 |
| 31.6 | 15.4 |
| 35.6 | 9.1 |
| 36.6 | 6.0 |

In some embodiments, the present invention provide a compound that is (2S)-7-methyl-6-(pyrimidin-2-yl)-3,4-dihydro-1H-spiro[1,8-naphthyridine-2,3'-pyrrolidine] or a salt thereof. In some embodiments, the present invention provide a compound that is (2S)-7-methyl-6-(pyrimidin-2-yl)-3,4-dihydro-1H-spiro[1,8-naphthyridine-2,3'-pyrrolidine]. In some further embodiments, the present invention provide a crystalline form of (2S)-7-methyl-6-(pyrimidin-2-yl)-3,4-dihydro-1H-spiro[1,8-naphthyridine-2,3'-pyrrolidine]. In some further embodiments, the crystalline form of (2S)-7-methyl-6-(pyrimidin-2-yl)-3,4-dihydro-1H-spiro[1,8-naphthyridine-2,3'-pyrrolidine] exhibits a powder X-ray diffraction pattern comprising at least one characteristic peak, in terms of 2θ, as those listed in Table X-P28.

In some embodiments, the crystalline form of (2S)-7-methyl-6-(pyrimidin-2-yl)-3,4-dihydro-1H-spiro[1,8-naphthyridine-2,3'-pyrrolidine] exhibits a powder X-ray diffraction pattern comprising at least two characteristic peaks, in terms of 2θ, as those listed in Table X-P28. In some embodiments, the crystalline form of (2S)-7-methyl-6-(pyrimidin-2-yl)-3,4-dihydro-1H-spiro[1,8-naphthyridine-2,3'-pyrrolidine] exhibits a powder X-ray diffraction pattern comprising at least three characteristic peaks, in terms of 2θ, as those listed in Table X-P28. In some embodiments, the crystalline form of (2S)-7-methyl-6-(pyrimidin-2-yl)-3,4-dihydro-1H-spiro[1,8-naphthyridine-2,3'-pyrrolidine] exhibits a powder X-ray diffraction pattern comprising at least four (e.g. 4, 5, 6, 7, 8, 9, or 10) characteristic peaks, in terms of 2θ, as those listed in Table X-P28. In some embodiments, the crystalline form of (2S)-7-methyl-6-(pyrimidin-2-yl)-3,4-dihydro-1H-spiro[1,8-naphthyridine-2,3'-pyrrolidine] exhibits a powder X-ray diffraction pattern substantially as shown in FIG. 5.

Step 4. Synthesis of (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (14)

A slurry of P7 (19.1 g, 95.9 mmol) in 2-methyltetrahydrofuran (200 mL) was treated with P28, free base (98.1% by mass, 25 g, 87.2 mmol) followed by N,N-diisopropylethylamine (19 mL, 110 mmol). 2,4,6-Tripropyl-1,3,5,2,4,6-trioxatriphosphinane 2,4,6-trioxide (50% solution by weight in ethyl acetate; 65 mL, 110 mmol) was added over 15 minutes, at a rate that maintained the internal reaction temperature below 30° C. After the reaction mixture had been stirred for 100 minutes, aqueous sodium bicarbonate solution (1.14 M; 250 mL, 285 mmol) was added (Caution: gas evolution) and stirring was continued for 10 minutes at 20° C. The resulting mixture was heated to 40° C., stirred for 30 minutes, and again treated with aqueous sodium bicarbonate solution (1.14 M; 125 mL, 142 mmol). After this mixture had been stirred for 80 minutes, water (75 mL) was added and stirring was continued for 10 minutes. The organic layer was subjected to distillation at 60° C. and 500 mbar, until the mixture had been reduced to 5 volumes. 2-Methyltetrahydrofuran (125 mL) was added, the temperature was adjusted to 45° C. to 50° C., and the mixture was filtered through diatomaceous earth. Additional 2-methyltetrahydrofuran (50 mL) was used to rinse the filter pad, and the combined filtrates were distilled at 60° C. and 500 mbar to approximately 3 volumes. The heat was increased to 80° C. until solids at the bottom of the reactor were released, then decreased to 50° C. The resulting material was treated at 50° C., over 15 minutes, with heptane (250 mL), and allowed to stir at 50° C. for 90 minutes. It was then cooled to 20° C. at a rate of 1° C./minute and allowed to stir for 3 days, whereupon it was diluted to a volume of 600 mL by addition of 10 mol % 2-methyltetrahydrofuran in heptane. Filtration provided a filter cake, which was rinsed with heptane (75 mL) and dried overnight at 50° C. in vacuo, affording (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (14) as a solid. Yield: 29.63 g, 64.06 mmol, 73%. HPLC purity: 100%. LCMS m/z 463.3 [M+H]$^+$. $^1$H NMR (600 MHz, DMSO-d$_6$) δ [8.81 (d, J=4.8 Hz) and 8.80 (d, J=4.7 Hz), total 2H], [8.12 (s) and 8.10 (s), total 1H], [7.90 (s) and 7.87

(s), total 1H], [7.33 (s) and 7.23 (s), total 1H], 7.30-7.26 (m, 1H), [6.75 (d, J=4.8 Hz) and 6.69 (d, J=4.8 Hz), total 1H], [4.15 (q, J=6.9 Hz) and 4.10 (q, J=6.9 Hz), total 1H], [3.83 (s) and 3.82 (s), total 3H], [3.78-3.71 (m), 3.61-3.49 (m), 3.47-3.41 (m), 3.42 (d, J=11.2 Hz), 3.32-3.28 (m, assumed; partially obscured by water peak), and 3.25 (d, J=10.4 Hz), total 4H], [2.80-2.65 (m) and 2.5-2.43 (m, assumed; partially obscured by solvent peak), total 2H], [2.59 (s) and 2.57 (s), total 3H], [2.03-1.94 (m) and 1.87-1.72 (m), total 3H], 1.67-1.60 (m, 1H), 1.36-1.30 (m, 3H).

Acquisition of Powder X-ray Diffraction (PXRD) Data for Crystalline Example 14

A sample of Example 14 (prepared substantially as described in this Alternate Synthesis method, except that in Step 4, the filtration through diatomaceous earth part was replace by treatment of the mixture with SiliaMetS® Thiol followed by filtration. SiliaMetS® Thiol: Silicycle Inc., Product number R51030B) was milled and submitted for Powder X-ray diffraction (PXRD) analysis and found to be a crystalline material (designated as Form I).

Powder X-ray diffraction analysis was conducted using a Bruker AXS D8 Endeavor diffractometer equipped with a copper (Cu) radiation source. The divergence slit was set at 15 mm continuous illumination. Diffracted radiation was detected by a PSD-Lynx Eye detector, with the detector PSD opening set at 4.123 degrees. The X-ray tube voltage and amperage were set to 40 kV and 40 mA, respectively. In addition, the energy dispersive detector, a nickel filter was used. Data was collected in the Theta-Theta goniometer at the Cu wavelength from 3.0 to 40.0 degrees 2-Theta using a step size of 0.0100 degrees and a step time of 1.0 second. The antiscatter screen was set to a fixed distance of 1.5 mm. Samples were prepared by placing them in a silicon low background sample holder and rotated at 15 revolutions/min during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of 3% were generally chosen. Typically, the peaks which were not resolved or were consistent with noise were not selected. A typical error associated with the peak position from PXRD stated in USP up to +/−0.2° 2-Theta (USP-941).

One representative diffraction pattern was observed for Form I of Example 14 and is provided in FIG. 1. A list of diffraction peaks expressed in terms of the degree 2θ and relative intensities with a relative intensity of 3.0% of a PXRD from the sample of crystalline Example 14 are shown in Table X1 below.

TABLE X1

| Angle (2-Theta) | Relative Intensity (%) |
| --- | --- |
| 8.2 | 8.6 |
| 8.7 | 45.6 |
| 11.1 | 65.9 |
| 12.6 | 28.7 |
| 12.7 | 17.8 |
| 13.3 | 10.6 |
| 15.7 | 5.0 |
| 16.4 | 6.3 |
| 17.5 | 12.1 |

TABLE X1-continued

| Angle (2-Theta) | Relative Intensity (%) |
| --- | --- |
| 18.0 | 46.3 |
| 18.2 | 45.7 |
| 19.4 | 7.6 |
| 20.3 | 38.0 |
| 20.8 | 9.9 |
| 21.1 | 9.2 |
| 21.3 | 14.6 |
| 22.1 | 7.9 |
| 22.4 | 7.5 |
| 24.8 | 4.6 |
| 25.1 | 10.2 |
| 26.0 | 100.0 |
| 26.3 | 57.0 |
| 27.9 | 4.2 |
| 28.5 | 14.0 |
| 28.8 | 6.1 |
| 29.1 | 4.8 |
| 33.1 | 3.4 |
| 35.2 | 4.7 |
| 37.1 | 3.0 |

In some embodiments, the present invention provides a crystalline form of (2R)-2-(5-Fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one. In some further embodiments, the present invention provides a crystalline form of (2R)-2-(5-Fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one that is designated as Form I.

In some embodiments, Form I (of Example 14) exhibits a powder X-ray diffraction pattern comprising at least one characteristic peak, in terms of 2θ, selected from at 8.7±0.2°; 11.1±0.2°; and 13.3±0.2°. In some embodiments, Form I exhibits a powder X-ray diffraction pattern comprising at least one characteristic peak, in terms of 2θ, at 8.7±0.2°. In some embodiments, Form I exhibits a powder X-ray diffraction pattern comprising at least one characteristic peak, in terms of 2θ, at 11.1±0.2°. In some embodiments, Form I exhibits a powder X-ray diffraction pattern comprising at least one characteristic peak, in terms of 2θ, at 13.3±0.2°. In some embodiments, Form I exhibits a powder X-ray diffraction pattern comprising at least two characteristic peaks, in terms of 2θ, selected from at 8.7±0.2°; 11.1±0.2°; and 13.3±0.2°. In some embodiments, Form I exhibits a powder X-ray diffraction pattern comprising two characteristic peaks, in terms of 2θ, selected from at 8.7±0.2°; and 11.1±0.2. In some embodiments, Form I exhibits a powder X-ray diffraction pattern comprising at least three characteristic peaks, in terms of 2θ, selected from at 8.7±0.2°; 11.1±0.2°; and 13.3±0.2°.

In some embodiments, Form I exhibits a powder X-ray diffraction pattern comprising at least two characteristic peaks, in terms of 2θ, selected from at 8.7±0.2°; 11.1±0.2°; and 26.0±0.2. In some embodiments, Form I exhibits a powder X-ray diffraction pattern comprising at least two characteristic peaks, in terms of 2θ, selected from at 8.7±0.2°; and 26.0±0.2°. In some embodiments, Form I exhibits a powder X-ray diffraction pattern comprising at least two characteristic peaks, in terms of 2θ, selected from at 11.1±0.2°; and 26.0±0.2°. In some embodiments, Form I exhibits a powder X-ray diffraction pattern comprising at least three characteristic peaks, in terms of 2θ, selected from at 8.7±0.2°; 11.1±0.2°; and 26.0±0.2°.

In some embodiments, Form I exhibits a powder X-ray diffraction pattern comprising at least two characteristic peaks, in terms of 2θ, as those listed in Table X1. In some embodiments, Form I exhibits a powder X-ray diffraction pattern comprising at least three characteristic peaks, in terms of 2θ, as those listed in Table X1. In some embodiments, Form I exhibits a powder X-ray diffraction pattern comprising at least four (e.g. 4, 5, 6, 7, 8, 9, or 10) characteristic peaks, in terms of 2θ, as those listed in Table X1.

In some embodiments, Form I exhibits a powder X-ray diffraction pattern substantially as shown in FIG. 1.

Example 15
(2R)-2-(5-Chloro-2-methoxypyridin-4-yl)-1-[(2S)-7-methyl-6-(pyrimidin-2-yl)-3,4-dihydro-1H-spiro[1,8-naphthyridine-2,3′-pyrrolidin]-1′-yl]propan-1-one (15)

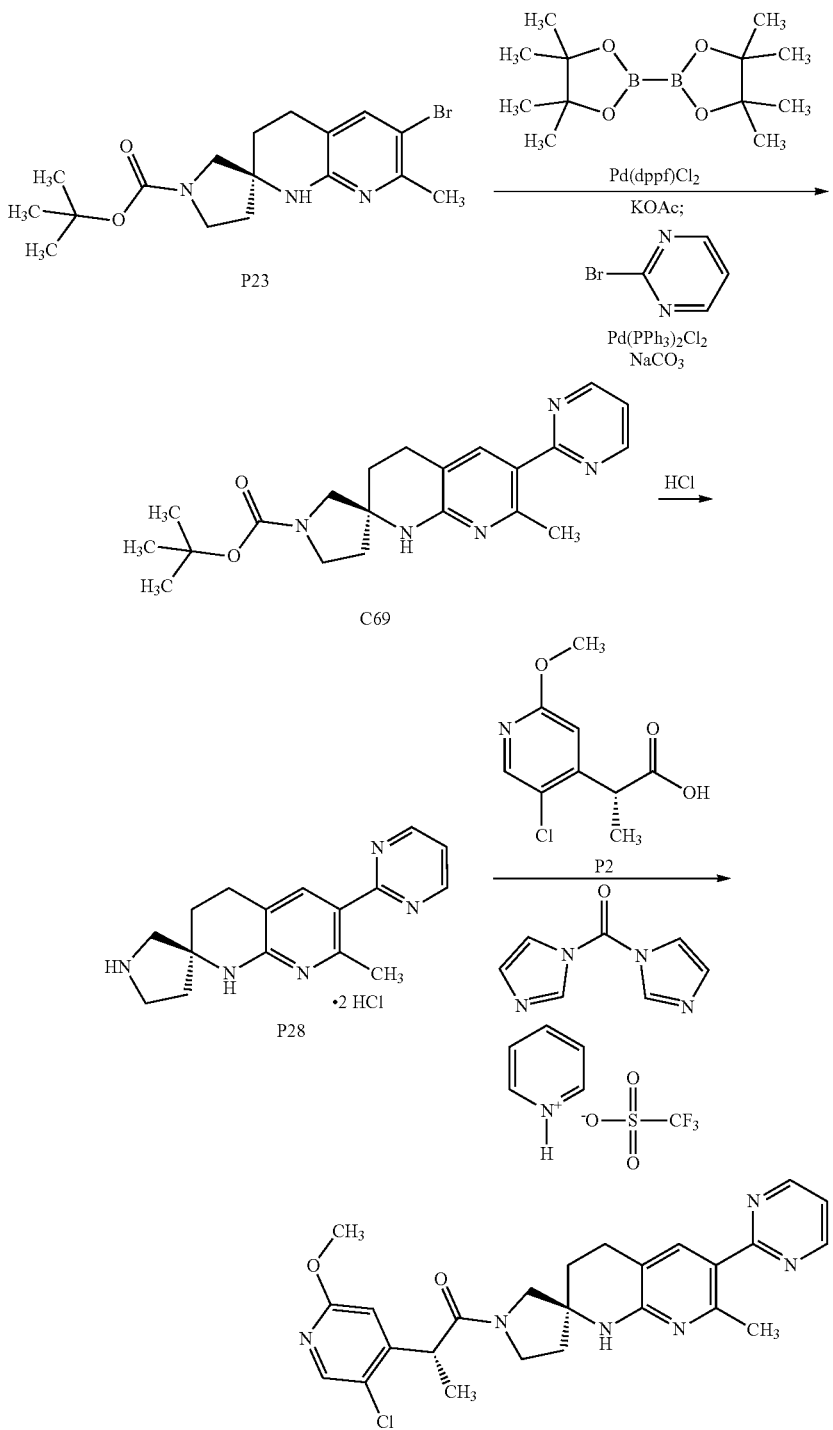

Step 1. Synthesis of tert-butyl (2S)-7-methyl-6-(pyrimidin-2-yl)-3,4-dihydro-1H-spiro[1,8-naphthyridine-2,3'-pyrrolidine]-1'-carboxylate (C69)

A mixture of 4,4,4',4',5,5,5',5'-octamethyl-2,2'-bi-1,3,2-dioxaborolane (249 mg, 0.981 mmol), P23 (250 mg, 0.654 mmol), bis(diphenylphosphino)ferrocene]dichloropalladium(II), dichloromethane complex (26.7 mg, 32.7 µmol), and oven-dried potassium acetate (257 mg, 2.62 mmol) in 1,4-dioxane (12 mL) was degassed by bubbling nitrogen through it for 5 minutes. After the reaction vial had been sealed, it was heated to 100° C. in an aluminum block for 2 hours, then allowed to cool to room temperature. 2-Bromopyrimidine (109 mg, 0.686 mmol), dichlorobis(triphenylphosphine)palladium(II) (22.9 mg, 32.6 µmol), and a degassed solution of aqueous sodium carbonate (2.0 M; 0.817 mL, 1.63 mmol) were then added to the reaction mixture, and it was heated at 90° C. for 18 hours. After cooling to room temperature, the reaction mixture was diluted with ethyl acetate and filtered through diatomaceous earth. The organic layer of the filtrate was washed with saturated aqueous sodium chloride solution, dried over magnesium sulfate, filtered, and concentrated in vacuo; chromatography on silica gel (Eluents: 20%, then 50%, then 100% ethyl acetate in heptane) provided C69 as a white solid. Yield: 55.0 mg, 0.144 mmol, 22%. LCMS m/z 382.3 [M+H]$^+$. $^1$H NMR (400 MHz, chloroform-d) δ 8.76 (d, J=4.8 Hz, 2H), 7.92 (s, 1H), 7.11 (t, J=4.9 Hz, 1H), 5.37 (br s, 1H), 3.62-3.26 (m, 4H), 2.88-2.76 (m, 2H), 2.68 (s, 3H), 2.06-1.77 (m, 4H), 1.46 (br s, 9H).

Step 2. Synthesis of (2S)-7-methyl-6-(pyrimidin-2-yl)-3,4-dihydro-1H-spiro[1,8-naphthyridine-2,3'-pyrrolidine], dihydrochloride salt (P28)

A solution of hydrogen chloride in 1,4-dioxane (4.0 M; 0.144 mL, 0.576 mmol) was added to a solution of C69 (55.0 mg, 0.144 mmol) in a mixture of dichloromethane (0.5 mL) and 1,1,1,3,3,3-hexafluoropropan-2-ol (0.5 mL), and the reaction mixture was stirred at room temperature for 2 hours, whereupon LCMS analysis indicated conversion to P28: LCMS m/z 282.3 [M+H]$^+$. The reaction mixture was concentrated in vacuo, providing P28 as a yellow gum. Yield: 50 mg, 0.141 mmol, 98%.

Step 3. Synthesis of (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (15)

Pyridinium trifluoromethanesulfonate (35.6 mg, 0.155 mmol) was added to a solution of P2 (16.7 mg, 77.4 µmol) in acetonitrile (1 mL). The resulting solution was treated with 1,1'-carbonyldiimidazole (12.6 mg, 77.7 µmol) in one portion, and the reaction mixture was stirred at room temperature for 45 minutes. A solution of P28 (25.0 mg, 70.6 µmol) in acetonitrile (2 mL) was then added in one portion, and stirring was continued at room temperature for 3 hours, whereupon the reaction mixture was diluted with aqueous ammonium chloride solution and extracted three times with ethyl acetate. The combined organic layers were dried over magnesium sulfate, filtered, and concentrated in vacuo. Purification via silica gel chromatography (Gradient: 20% to 100% ethyl acetate in heptane) followed by supercritical fluid chromatography (Column: Chiral Technologies Chiralcel OJ-H, 21×250 mm, 5 µm; Mobile phase 9:1 carbon dioxide/(methanol containing 0.2% ammonium hydroxide); Flow rate: 75 mL/minute; Back pressure: 150 bar) afforded (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (15). Yield: 5.9 mg, 12 µmol, 17%. LCMS m/z 479.3 (chlorine isotope pattern observed) [M+H]$^+$. $^1$H NMR (400 MHz, methanol-d$_4$) δ [8.81 (d, J=5.0 Hz) and 8.81 (d, J=5.0 Hz), total 2H], [8.15 (s) and 8.14 (s), total 1H], [7.85 (s) and 7.81 (s), total 1H], [7.31 (t, J=4.9 Hz) and 7.30 (t, J=4.9 Hz), total 1H], [6.81 (s) and 6.76 (s), total 1H], [4.32 (q, J=7.0 Hz) and 4.23 (q, J=6.9 Hz), total 1H], 3.91 (br s, 3H), [3.9-3.83 (m) and 3.76-3.52 (m), total 3H], [3.49 (d, J=12.2 Hz) and 3.38-3.3 (m, assumed; partially obscured by solvent peak), total 1H], [2.93-2.72 (m) and 2.56-2.47 (m), total 2H], [2.57 (s) and 2.56 (s), total 3H], [2.16-2.07 (m) and 2.05-1.84 (m), total 3H], 1.80-1.73 (m, 1H), [1.43 (d, J=6.9 Hz) and 1.42 (d, J=6.9 Hz), total 3H].

Alternate Step 3. Synthesis of (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (15) for X-Ray Crystal Structure Determination Pyridinium trifluoromethanesulfonate (112 mg, 0.487 mmol) was added to a solution of P2 (material from Preparations P2 and P3; 50.0 mg, 0.232 mmol) in acetonitrile (3 mL). The resulting solution was treated with 1,1'-carbonyldiimidazole (39.5 mg, 0.244 mmol) in one portion, and the reaction mixture was stirred at room temperature for 30 minutes. A solution of P28 (82.1 mg, 0.232 mmol) was then added in one portion; after 1 hour, a drop of water was added to provide a solution. After the reaction mixture had been stirred at room temperature for 2 hours, LCMS analysis indicated conversion to 15: LCMS m/z 479.3 (chlorine isotope pattern observed) [M+H]$^+$. The reaction mixture was then partitioned between ethyl acetate and aqueous sodium bicarbonate solution; the organic layer was washed sequentially with water and saturated aqueous sodium chloride solution, dried over magnesium sulfate, filtered, and concentrated in vacuo. Silica gel chromatography (Gradient: 0% to 10% methanol in dichloromethane) afforded (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one (15) as a solid. Yield: 102 mg, 0.213 mmol, 92%.

This material was dissolved in a mixture (approximately 12 mL) of 10% ethyl acetate in heptane by application of heat. The solution was allowed to cool and then stand, partially capped, at room temperature for 3 days. The resulting solid provided a crystal for X-ray structure determination (see below).

Single-Crystal X-Ray Structural Determination of 15

Single Crystal X-Ray Analysis

Data collection was performed on a Bruker D8 Venture diffractometer at room temperature. Data collection consisted of omega and phi scans. The micro-sized and multi-domain type of crystalline material used produced Theta diffraction above 0.90-0.94 Å resolution region.

The structure was solved by intrinsic phasing using SHELX software suite in the triclinic class space group P1. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correctly assigned is 100.0%. The Hooft parameter is reported as 0.04 with an esd (estimated standard deviation) of (3) and the Parson's parameter is reported as 0.05 with an esd of (3).

The final R-index was 6.9%. A final difference Fourier revealed no missing or misplaced electron density.

Pertinent crystal, data collection, and refinement information is summarized in Table E. Atomic coordinates, bond lengths, and displacement parameters are listed in Tables F-H.

SOFTWARE AND REFERENCES

See list provided above for Single-crystal X-ray structural determination of 14.

TABLE E

Crystal data and structure refinement for 15.

| | |
|---|---|
| Empirical formula | $C_{25}H_{27}ClN_6O_2$ |
| Formula weight | 478.97 |
| Temperature | 296(2) K |
| Wavelength | 1.54178 Å |
| Crystal system | Triclinic |
| Space group | P1 |
| Unit cell dimensions | a = 10.4965(18) Å   α = 81.230(9)° |
| | b = 10.6212(19) Å   β = 79.685(8)° |
| | c = 11.0122(12) Å   γ = 79.614(10)° |
| Volume | 1178.9(3) Å$^3$ |
| Z | 2 |
| Density (calculated) | 1.349 Mg/m$^3$ |
| Absorption coefficient | 1.722 mm$^{-1}$ |
| F(000) | 504 |
| Crystal size | 0.060 × 0.060 × 0.010 mm$^3$ |
| Theta range for data collection | 6.184 to 59.264° |
| Index ranges | −11 <= h <= 10, |
| | −11 <= k <= 11, |
| | −10 <=/<= 12 |
| Reflections collected | 4221 |
| Independent reflections | 3443 [R$_{int}$ = 0.0452] |
| Completeness to theta = 59.264° | 74.4% |
| Absorption correction | Empirical |
| Refinement method | Full-matrix least-squares on F$^2$ |
| Data/restraints/parameters | 3443/5/625 |
| Goodness-of-fit on F$^2$ | 1.015 |
| Final R indices [I > 2σ(I)] | R1 = 0.0683, wR2 = 0.1935 |
| R indices (all data) | R1 = 0.0784, wR2 = 0.2014 |
| Absolute structure parameter | 0.03(2) |
| Extinction coefficient | n/a |
| Largest diff. peak and hole | 0.260 and −0.298 e.Å$^{-3}$ |

TABLE F

Atomic coordinates (×10$^4$) and equivalent isotropic displacement parameters (Å$^2$ × 10$^3$) for 15. U(eq) is defined as one-third of the trace of the orthogonalized U$^{ij}$ tensor.

| | x | y | z | U(eq) |
|---|---|---|---|---|
| Cl(1) | 6162(5) | 4556(4) | 11470(4) | 125(2) |
| Cl(2) | 4027(3) | 11950(3) | 2739(3) | 86(1) |
| N(1) | 11100(10) | −1274(12) | 12928(11) | 78(3) |
| N(2) | 12296(10) | −2540(12) | 11435(11) | 80(3) |
| N(3) | 11631(8) | 868(10) | 8803(9) | 61(3) |
| N(4) | 11360(9) | 3087(10) | 8424(9) | 68(3) |
| N(5) | 9017(9) | 5024(10) | 7873(9) | 67(3) |
| N(6) | 5332(9) | 8256(11) | 10307(10) | 72(3) |
| N(7) | −1168(11) | 7183(13) | 11403(11) | 88(4) |
| N(8) | −2377(10) | 8821(12) | 12537(12) | 83(4) |
| N(9) | −1657(9) | 11396(11) | 9171(10) | 68(3) |
| N(10) | −1362(10) | 11712(11) | 7026(11) | 73(3) |
| N(11) | 1032(10) | 12150(10) | 5137(10) | 70(3) |
| N(12) | 4409(9) | 8180(11) | 3666(10) | 71(3) |
| O(1) | 7653(9) | 5298(12) | 6446(9) | 102(4) |
| O(2) | 5331(8) | 9404(9) | 8371(9) | 84(3) |
| O(3) | 2327(9) | 13665(9) | 4947(11) | 100(3) |
| O(4) | 4159(11) | 6908(9) | 5559(10) | 98(3) |
| C(1) | 11155(16) | −2308(19) | 13774(16) | 101(5) |
| C(2) | 11720(14) | −3506(16) | 13502(17) | 89(5) |
| C(3) | 12286(14) | −3571(13) | 12349(18) | 86(5) |
| C(4) | 11689(11) | −1436(14) | 11799(12) | 67(3) |
| C(5) | 11631(10) | −254(11) | 10866(11) | 62(3) |
| C(6) | 11710(9) | −233(11) | 9576(12) | 60(3) |
| C(7) | 11862(12) | −1425(13) | 8971(13) | 75(4) |
| C(8) | 11460(10) | 1989(12) | 9247(11) | 61(3) |
| C(9) | 11378(10) | 2074(12) | 10523(11) | 60(3) |
| C(10) | 11467(10) | 940(13) | 11319(12) | 62(3) |
| C(11) | 11182(12) | 3353(14) | 10987(11) | 73(4) |
| C(12) | 11518(12) | 4419(14) | 9962(13) | 76(4) |
| C(13) | 10902(10) | 4341(13) | 8816(12) | 65(3) |
| C(14) | 11176(13) | 5386(15) | 7705(14) | 84(4) |
| C(15) | 10092(11) | 5415(13) | 6946(11) | 71(4) |
| C(16) | 9390(13) | 4583(12) | 9082(11) | 64(3) |
| C(17) | 7821(13) | 5021(14) | 7545(11) | 72(4) |
| C(18) | 6709(11) | 4755(13) | 8557(13) | 72(3) |
| C(19) | 5586(14) | 4333(18) | 8079(17) | 101(5) |
| C(20) | 6199(11) | 5987(14) | 9216(12) | 68(3) |
| C(21) | 5946(10) | 7194(12) | 8450(12) | 64(3) |
| C(22) | 5527(10) | 8276(13) | 9099(13) | 65(3) |
| C(23) | 5014(14) | 10543(15) | 9005(16) | 89(4) |
| C(24) | 5559(12) | 7091(15) | 10974(13) | 81(4) |
| C(25) | 5945(12) | 5998(14) | 10461(13) | 75(4) |
| C(26) | −1245(16) | 6381(17) | 12445(16) | 95(5) |
| C(27) | −1873(15) | 6660(20) | 13529(17) | 95(5) |
| C(28) | −2410(14) | 7950(20) | 13559(15) | 95(5) |
| C(29) | −1732(11) | 8410(14) | 11493(12) | 68(3) |
| C(30) | −1664(10) | 9299(14) | 10335(13) | 72(4) |
| C(31) | −1749(10) | 10643(14) | 10277(12) | 68(3) |
| C(32) | −1946(13) | 11343(15) | 11388(15) | 88(4) |
| C(33) | −1446(11) | 10898(14) | 8114(13) | 72(4) |
| C(34) | −1396(11) | 9544(13) | 8072(12) | 67(3) |
| C(35) | −1483(10) | 8810(12) | 9214(12) | 62(3) |
| C(36) | −1180(13) | 9021(13) | 6858(13) | 78(4) |
| C(37) | −1550(12) | 10052(14) | 5801(13) | 77(4) |
| C(38) | −893(11) | 11211(14) | 5831(12) | 72(4) |
| C(39) | −1136(15) | 12299(16) | 4759(14) | 89(4) |
| C(40) | −50(13) | 13094(14) | 4635(13) | 80(4) |
| C(41) | 622(11) | 10909(11) | 5577(12) | 66(3) |
| C(42) | 2171(13) | 12537(13) | 5212(11) | 70(4) |
| C(43) | 3280(12) | 11502(13) | 5641(12) | 67(3) |
| C(44) | 4468(12) | 12138(18) | 5781(17) | 100(5) |
| C(45) | 3660(11) | 10362(12) | 4923(13) | 67(3) |
| C(46) | 3735(12) | 9103(15) | 5546(11) | 70(3) |
| C(47) | 4094(11) | 8102(14) | 4900(15) | 77(4) |
| C(48) | 4662(15) | 5801(14) | 4915(15) | 88(4) |
| C(49) | 4354(12) | 9371(14) | 3082(14) | 76(4) |
| C(50) | 3994(11) | 10478(13) | 3653(12) | 65(4) |

TABLE G

Bond lengths [Å] for 15.

| Bond | Length |
|---|---|
| Cl(1)-C(25) | 1.754(13) |
| Cl(2)-C(50) | 1.728(11) |
| N(1)-C(4) | 1.307(18) |
| N(1)-C(1) | 1.328(18) |
| N(2)-C(4) | 1.313(18) |
| N(2)-C(3) | 1.370(17) |
| N(3)-C(8) | 1.326(16) |
| N(3)-C(6) | 1.336(14) |
| N(4)-C(8) | 1.364(14) |
| N(4)-C(13) | 1.436(17) |
| N(4)-H(4X) | 0.99(3) |
| N(5)-C(17) | 1.367(17) |
| N(5)-C(16) | 1.441(16) |
| N(5)-C(15) | 1.454(14) |
| N(6)-C(22) | 1.307(17) |
| N(6)-C(24) | 1.344(17) |
| N(7)-C(26) | 1.320(18) |
| N(7)-C(29) | 1.340(18) |
| N(8)-C(29) | 1.319(19) |
| N(8)-C(28) | 1.342(19) |
| N(9)-C(33) | 1.317(19) |
| N(9)-C(31) | 1.350(16) |
| N(10)-C(33) | 1.366(16) |
| N(10)-C(38) | 1.464(19) |
| C(13)-C(14) | 1.545(17) |
| C(14)-C(15) | 1.52(2) |
| C(14)-H(14A) | 0.9700 |
| C(14)-H(14B) | 0.9700 |
| C(15)-H(15A) | 0.9700 |
| C(15)-H(15B) | 0.9700 |
| C(16)-H(16A) | 0.9700 |
| C(16)-H(16B) | 0.9700 |
| C(17)-C(18) | 1.498(17) |
| C(18)-C(19) | 1.53(2) |
| C(18)-C(20) | 1.56(2) |
| C(18)-H(18) | 0.9800 |
| C(19)-H(19A) | 0.9600 |
| C(19)-H(19B) | 0.9600 |
| C(19)-H(19C) | 0.9600 |
| C(20)-C(25) | 1.35(2) |
| C(20)-C(21) | 1.433(17) |
| C(21)-C(22) | 1.408(19) |
| C(21)-H(21) | 0.9300 |
| C(23)-H(23A) | 0.9600 |
| C(23)-H(23B) | 0.9600 |
| C(23)-H(23C) | 0.9600 |
| C(24)-C(25) | 1.33(2) |
| C(24)-H(24) | 0.9300 |
| C(26)-C(27) | 1.30(3) |
| C(26)-H(26) | 0.9300 |
| C(27)-C(28) | 1.39(2) |
| C(27)-H(27) | 0.9300 |
| C(28)-H(28) | 0.9300 |
| C(29)-C(30) | 1.465(18) |
| C(30)-C(35) | 1.38(2) |
| C(30)-C(31) | 1.407(19) |
| C(31)-C(32) | 1.49(2) |
| C(32)-H(32A) | 0.9600 |
| C(32)-H(32B) | 0.9600 |
| C(32)-H(32C) | 0.9600 |
| C(33)-C(34) | 1.44(2) |
| C(34)-C(35) | 1.372(17) |
| C(34)-C(36) | 1.49(2) |
| C(35)-H(35) | 0.9300 |
| C(36)-C(37) | 1.525(18) |
| C(36)-H(36A) | 0.9700 |
| C(36)-H(36B) | 0.9700 |
| C(37)-C(38) | 1.52(2) |
| C(37)-H(37A) | 0.9700 |
| C(37)-H(37B) | 0.9700 |
| C(38)-C(39) | 1.543(19) |
| C(38)-C(41) | 1.547(16) |
| C(39)-C(40) | 1.51(2) |
| C(39)-H(39A) | 0.9700 |
| C(39)-H(39B) | 0.9700 |
| C(40)-H(40A) | 0.9700 |
| C(40)-H(40B) | 0.9700 |
| C(41)-H(41A) | 0.9700 |
| C(41)-H(41B) | 0.9700 |
| C(42)-C(43) | 1.538(18) |
| C(43)-C(45) | 1.502(19) |
| C(43)-C(44) | 1.56(2) |
| C(43)-H(43) | 0.9800 |
| C(44)-H(44A) | 0.9600 |
| C(44)-H(44B) | 0.9600 |
| C(44)-H(44C) | 0.9600 |
| C(45)-C(50) | 1.372(18) |
| C(45)-C(46) | 1.403(18) |
| C(46)-C(47) | 1.33(2) |
| C(46)-H(46) | 0.9300 |
| C(48)-H(48A) | 0.9600 |
| C(48)-H(48B) | 0.9600 |
| C(48)-H(48C) | 0.9600 |
| C(49)-C(50) | 1.38(2) |
| C(49)-H(49) | 0.9300 |

Symmetry transformations used to generate equivalent atoms

TABLE H

Anisotropic displacement parameters ($Å^2 \times 10^3$) for 15.
The anisotropic displacement factor exponent takes the form:
$-2\pi^2[h^2 a^{*2} U^{11} + \ldots + 2 h k a^* b^* U^{12}]$.

|  | $U^{11}$ | $U^{22}$ | $U^{33}$ | $U^{23}$ | $U^{13}$ | $U^{12}$ |
|---|---|---|---|---|---|---|
| Cl(1) | 182(4) | 78(3) | 80(3) | 15(2) | 22(3) | 9(3) |
| Cl(2) | 99(2) | 68(2) | 76(2) | 14(2) | 0(2) | −10(2) |
| N(1) | 81(7) | 66(8) | 74(8) | 7(6) | 7(6) | −12(5) |
| N(2) | 78(6) | 60(8) | 93(8) | 7(6) | −13(6) | −2(6) |
| N(3) | 57(5) | 44(7) | 74(7) | 3(5) | −6(4) | 3(4) |
| N(4) | 78(6) | 53(7) | 58(6) | 6(5) | 0(5) | 2(5) |
| N(5) | 75(6) | 59(7) | 53(6) | 7(5) | 6(5) | 1(5) |
| N(6) | 76(6) | 63(8) | 69(8) | −1(6) | 4(5) | −10(5) |
| N(7) | 97(8) | 76(10) | 75(8) | 4(6) | 2(6) | 2(6) |
| N(8) | 72(6) | 86(10) | 88(9) | −1(7) | −2(6) | −28(6) |
| N(9) | 62(5) | 64(7) | 67(7) | −6(5) | 15(5) | −7(5) |
| N(10) | 82(6) | 48(7) | 76(7) | −3(5) | 15(5) | −4(5) |
| N(11) | 78(7) | 51(7) | 67(6) | 5(5) | 5(5) | −2(5) |
| N(12) | 83(7) | 63(8) | 56(7) | −8(5) | 8(5) | 2(5) |
| O(1) | 93(6) | 130(10) | 65(6) | 0(6) | −2(5) | 14(6) |
| O(2) | 96(6) | 53(6) | 89(6) | 4(5) | 2(5) | −3(5) |
| O(3) | 104(7) | 45(6) | 138(9) | −7(6) | 19(6) | −16(5) |
| O(4) | 137(8) | 41(6) | 104(7) | 7(5) | −3(6) | −9(5) |
| C(1) | 115(11) | 86(14) | 87(11) | 22(10) | 0(9) | −19(9) |
| C(2) | 89(9) | 72(13) | 97(12) | 36(10) | −12(8) | −29(8) |
| C(3) | 90(9) | 36(9) | 135(15) | 3(8) | −36(10) | −10(7) |
| C(4) | 61(7) | 59(9) | 69(9) | 10(6) | −2(6) | −6(6) |
| C(5) | 61(7) | 57(9) | 56(7) | 4(6) | 9(5) | −4(5) |
| C(6) | 48(6) | 42(8) | 84(9) | −1(6) | −4(6) | 2(5) |
| C(7) | 82(7) | 55(9) | 75(8) | 5(6) | −3(6) | 3(6) |
| C(8) | 55(6) | 51(9) | 64(8) | 13(6) | −1(5) | 4(5) |
| C(9) | 63(7) | 43(8) | 69(8) | 5(6) | −7(6) | −7(5) |
| C(10) | 59(6) | 62(9) | 63(7) | 0(6) | −14(6) | −4(6) |
| C(11) | 80(7) | 75(10) | 55(7) | 6(6) | −15(6) | 4(6) |
| C(12) | 83(8) | 58(9) | 85(9) | −8(7) | −10(7) | −8(6) |
| C(13) | 63(7) | 53(9) | 67(8) | 3(6) | 6(6) | −3(6) |
| C(14) | 87(9) | 55(9) | 93(10) | 3(7) | 22(8) | −12(7) |
| C(15) | 86(8) | 53(8) | 57(7) | 4(6) | 16(6) | 1(6) |
| C(16) | 75(7) | 43(7) | 63(7) | 4(5) | −5(6) | 1(5) |
| C(17) | 94(10) | 67(9) | 40(7) | 2(5) | 0(6) | 10(7) |
| C(18) | 74(7) | 54(9) | 81(9) | −1(6) | −9(7) | −1(6) |
| C(19) | 94(10) | 92(13) | 122(13) | −32(10) | −13(9) | −15(8) |
| C(20) | 58(6) | 66(9) | 70(9) | −2(6) | 4(6) | −5(5) |
| C(21) | 57(6) | 50(8) | 75(8) | −5(6) | 3(6) | 1(5) |
| C(22) | 55(6) | 59(9) | 74(9) | 8(6) | −10(6) | −5(5) |
| C(23) | 91(9) | 54(10) | 117(12) | 1(8) | −18(8) | −10(7) |
| C(24) | 82(8) | 79(12) | 65(8) | −12(7) | 22(7) | 3(7) |
| C(25) | 77(8) | 65(10) | 66(9) | 10(7) | 14(7) | −5(7) |
| C(26) | 115(11) | 78(13) | 79(11) | 14(9) | −8(9) | −8(8) |
| C(27) | 92(10) | 96(15) | 91(12) | 34(10) | −27(9) | −29(9) |
| C(28) | 98(10) | 115(16) | 74(10) | −15(9) | 7(8) | −42(10) |
| C(29) | 53(6) | 71(10) | 72(9) | 3(7) | 6(6) | −16(6) |
| C(30) | 53(7) | 72(10) | 78(9) | −4(7) | 18(6) | −4(6) |

TABLE H-continued

Anisotropic displacement parameters (Å² × 10³) for 15.
The anisotropic displacement factor exponent takes the form:
$-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(31) | 62(7) | 70(10) | 67(8) | −5(7) | 13(6) | −19(6) |
| C(32) | 85(8) | 72(10) | 101(11) | −10(8) | 17(8) | −23(7) |
| C(33) | 62(7) | 70(10) | 68(8) | 4(7) | 17(6) | −7(6) |
| C(34) | 59(7) | 60(9) | 78(9) | −12(6) | 3(6) | −6(6) |
| C(35) | 58(6) | 40(8) | 83(9) | −5(6) | 2(6) | −4(5) |
| C(36) | 83(8) | 57(9) | 87(9) | −7(7) | 12(7) | −20(6) |
| C(37) | 68(7) | 79(11) | 85(9) | −15(7) | −9(6) | −13(7) |
| C(38) | 65(7) | 70(10) | 70(8) | −2(7) | 7(6) | −2(6) |
| C(39) | 109(10) | 73(11) | 79(10) | −5(8) | −10(8) | −4(8) |
| C(40) | 97(9) | 57(9) | 71(8) | 2(6) | 4(7) | 5(7) |
| C(41) | 79(7) | 36(7) | 72(8) | −5(5) | 6(6) | −2(5) |
| C(42) | 88(9) | 54(9) | 58(7) | −6(6) | 25(6) | −16(7) |
| C(43) | 82(8) | 59(9) | 56(7) | −1(6) | −7(6) | −12(6) |
| C(44) | 104(10) | 85(13) | 112(12) | 5(9) | −21(9) | −26(9) |
| C(45) | 63(7) | 44(8) | 85(10) | −9(6) | 11(6) | −5(5) |
| C(46) | 76(7) | 76(11) | 45(7) | 8(6) | 2(6) | −4(7) |
| C(47) | 62(7) | 54(10) | 101(12) | 18(8) | −10(7) | 0(6) |
| C(48) | 119(11) | 41(9) | 98(10) | 12(7) | −17(8) | −11(7) |
| C(49) | 82(8) | 55(10) | 76(9) | 6(7) | 3(7) | 2(7) |
| C(50) | 65(7) | 58(9) | 63(8) | 17(6) | −1(6) | 15(6) |

Figure 2:
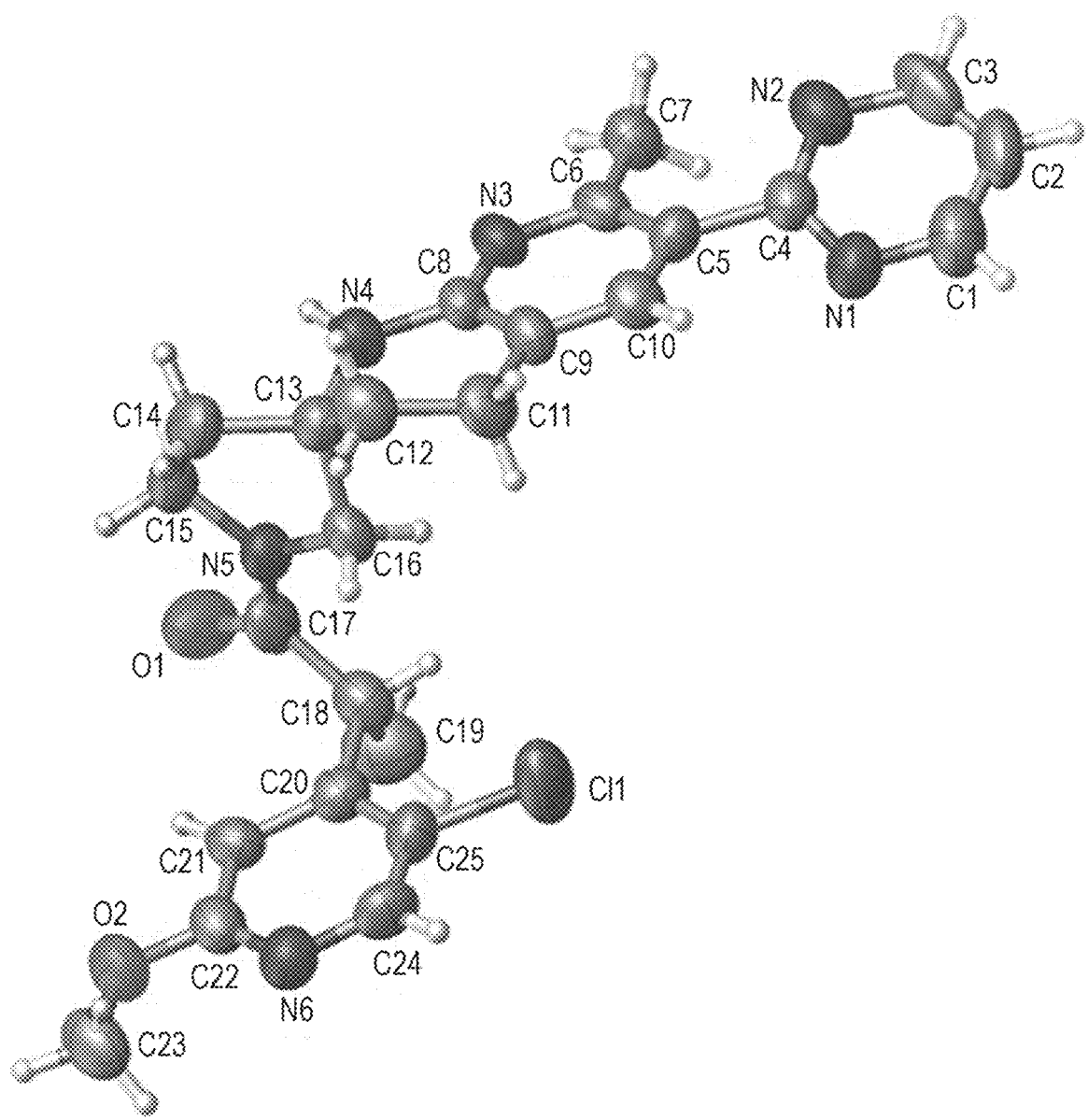
FIG. 2 shows an illustrative single crystal structure of compound Example 15.

Thus, the absolute stereochemistry of compound Example 15 was determined by single crystal X-ray crystallography FIG. 2 is the obtained single crystal X-ray structure (ORTEP drawing) of the crystalline compound Example 15: (2R)-2-(5-Chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one.

In some embodiments, the present invention provides a crystalline form of (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one. In some further embodiments, the crystalline form of (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one is the one described (or as prepared) in Example 15.

Examples 16 and 17
(2R)-2-(5-Fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1 (16) and (2R)-2-(5-Fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-2 (17)

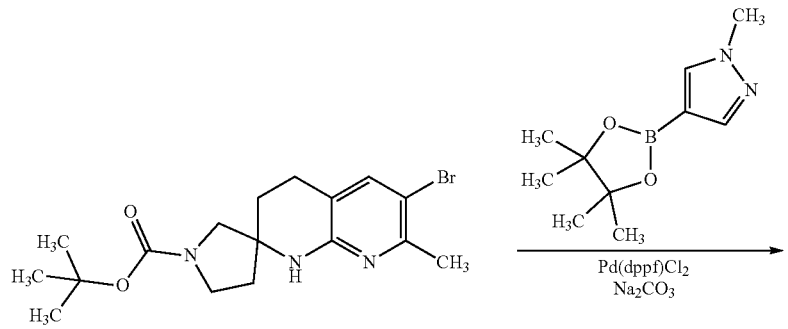

P22

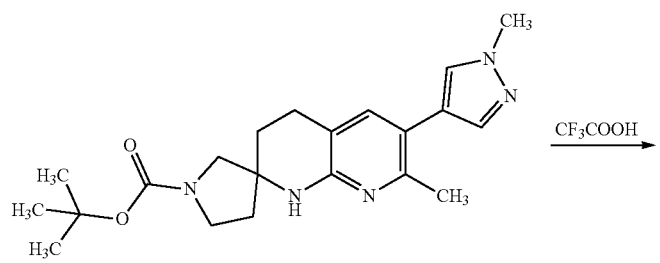

C80

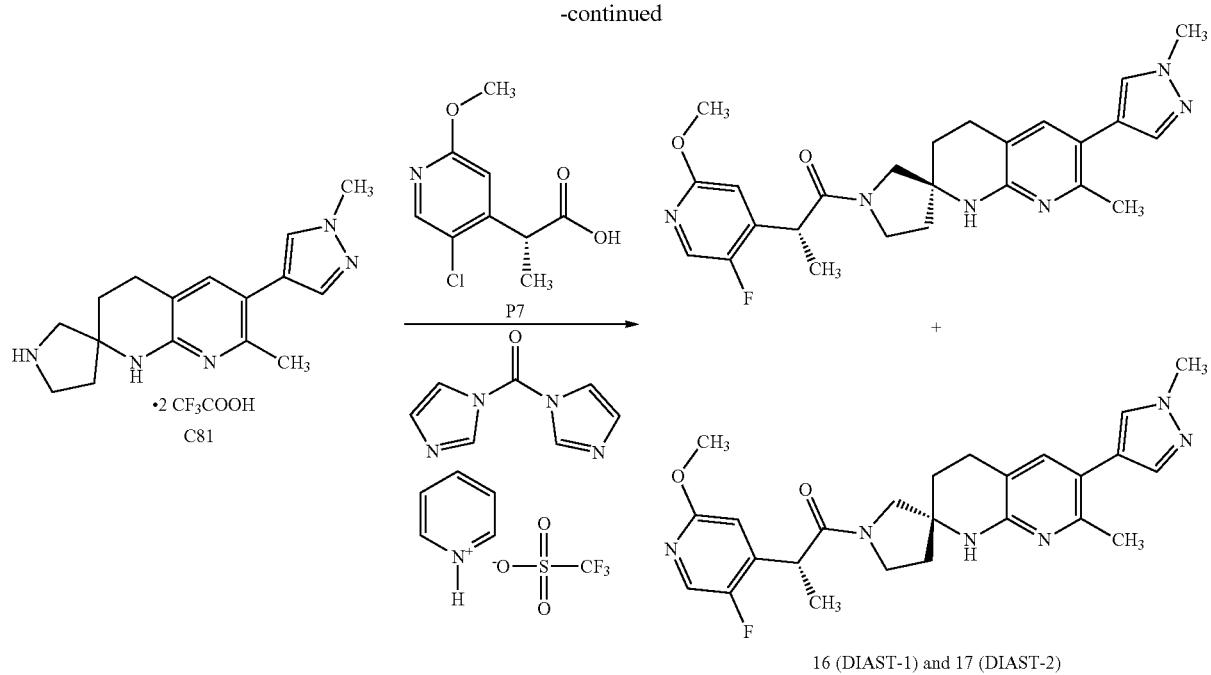

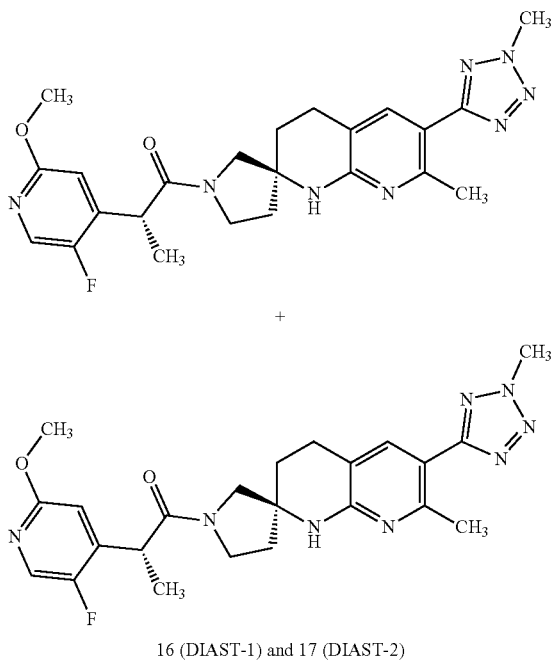

16 (DIAST-1) and 17 (DIAST-2)

Step 1. Synthesis of tert-butyl 7-methyl-6-(1-methyl-1H-pyrazol-4-yl)-3,4-dihydro-1H-spiro[1,8-naphthyridine-2,3'-pyrrolidine]-1'-carboxylate (C80)

A mixture of P22 (100 mg, 0.262 mmol), 1-methyl-4-(4,4,5,5-tetramethyl-1,3,2-dioxaborolan-2-yl)-1H-pyrazole (109 mg, 0.524 mmol), bis(diphenylphosphino)ferrocene] dichloropalladium(II), dichloromethane complex (10.7 mg, 13.1 µmol), and aqueous sodium carbonate solution (2.0 M; 0.33 mL, 0.66 mmol) in 1,4-dioxane (3 mL) was sparged with nitrogen. The reaction vial was sealed and heated to 80° C. overnight, whereupon LCMS analysis indicated conversion to C80: LCMS m/z 384.3 [M+H]$^+$. After the reaction mixture had cooled to room temperature, it was partitioned between ethyl acetate and water, and the aqueous layer was extracted twice with ethyl acetate. The combined organic layers were washed with saturated aqueous sodium chloride solution, dried over magnesium sulfate, filtered, and purified via silica gel chromatography (Gradient: 0% to 100% ethyl acetate in heptane) to afford C80 as a solid. Yield: 93 mg, 0.24 mmol, 92%. $^1$H NMR (400 MHz, chloroform-d), characteristic peaks: δ 7.52 (s, 1H), 7.36 (s, 1H), 7.19 (s, 1H), 3.95 (s, 3H), 3.62-3.26 (m, 4H), 2.85-2.68 (m, 2H), 2.41 (s, 3H), [1.47 (s) and 1.45 (s), total 9H].

Step 2. Synthesis of 7-methyl-6-(1-methyl-1H-pyrazol-4-yl)-3,4-dihydro-1H-spiro[1,8-naphthyridine-2,3'-pyrrolidine], bis(trifluoroacetate) salt (C81)

Trifluoroacetic acid (1.0 mL) was added to a solution of C80 (92 mg, 0.24 mmol) in dichloromethane (3 mL), and the reaction mixture was stirred at room temperature for 2 hours. It was then concentrated in vacuo, and the residue was coevaporated twice with ethyl acetate/heptane to afford C81 as a gum. Yield: 128 mg, assumed quantitative. LCMS m/z 284.2 [M+H]$^+$.

Step 3. Synthesis of (2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1 (16) and (2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-2 (17)

To a solution of P7 (23.9 mg, 0.120 mmol) in acetonitrile (1 mL) was added pyridinium trifluoromethanesulfonate (57.8 mg, 0.252 mmol), followed by 1,1'-carbonyldiimidazole (20.4 mg, 0.126 mmol). After the reaction mixture had stirred at room temperature for 45 minutes, a solution of C81 (34.0 mg, 66.5 μmol) in acetonitrile was added, and stirring was continued overnight at room temperature. LCMS analysis at this point indicated the presence of the coupling product: LCMS m/z 465.3 [M+H]$^+$. The reaction mixture was then partitioned between dichloromethane and dilute aqueous ammonium chloride solution; the organic layer was washed with saturated aqueous sodium chloride solution, dried over sodium sulfate, filtered, and concentrated in vacuo. Purification via silica gel chromatography (Gradient: 0% to 10% methanol in dichloromethane) was followed by supercritical fluid chromatography (Column: Phenomenex Lux Cellulose-1, 21×250 mm, 5 μm; Mobile phase: 4:1 carbon dioxide/(methanol containing 0.2% ammonium hydroxide); Flow rate: 75 mL/minute; Back pressure: 120 bar]. The first-eluting diastereomer was designated as 16 {(2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1}, and the second-eluting diastereomer as 17 {(2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-2}.

16—Yield: 7.3 mg, 15.7 μmol, 24%. LCMS m/z 465.5 [M+H]$^+$. $^1$H NMR (400 MHz, methanol-d$_4$) δ [7.99 (d, J=1.6 Hz) and 7.97 (d, J=1.7 Hz), total 1H], [7.67 (s) and 7.67 (s), total 1H], 7.55-7.52 (m, 1H), [7.29 (s) and 7.27 (s), total 1H], [6.78 (d, J=4.9 Hz) and 6.72 (d, J=4.9 Hz), total 1H], [4.27 (q, J=6.9 Hz) and 4.18 (q, J=6.9 Hz), total 1H], [3.92 (s) and 3.92 (s), total 3H], [3.88 (s) and 3.88 (s), total 3H], [3.88-3.83 (m), 3.75-3.56 (m), and 3.54 (d, component of AB quartet, J=12.1 Hz), total 3H], [3.45 (d, component of AB quartet, J=12.3 Hz) and 3.36 (d, J=10.6 Hz), total 1H], [2.89-2.70 (m) and 2.59-2.49 (m), total 2H], [2.37 (s) and 2.34 (s), total 3H], 2.13-1.81 (m, 3H), 1.80-1.71 (m, 1H), 1.47-1.40 (m, 3H). Retention time: 3.71 minutes [Analytical conditions. Column: Phenomenex Lux Cellulose-1, 4.6×100 mm, 5 μm; Mobile phase: 3:1 carbon dioxide/(methanol containing 0.2% ammonium hydroxide); Flow rate: 1.5 mL/minute; Back pressure: 200 bar].

17—Yield: 6.2 mg, 13.3 μmol, 20%. LCMS m/z 466.6 [M+H]$^+$. Retention time: 4.64 minutes (Analytical conditions identical to those used for 16).

Examples 18
(2R)-2-(5-Fluoro-2-methoxypyridin-4-yl)-1-{(2S)-7-methyl-6-[(4,6-$^2$H$_2$)pyrimidin-2-yl]-3,4-dihydro-1H-spiro[1,8-naphthyridine-2,3'-pyrrolidin]-1'-yl}propan-1-one (18)

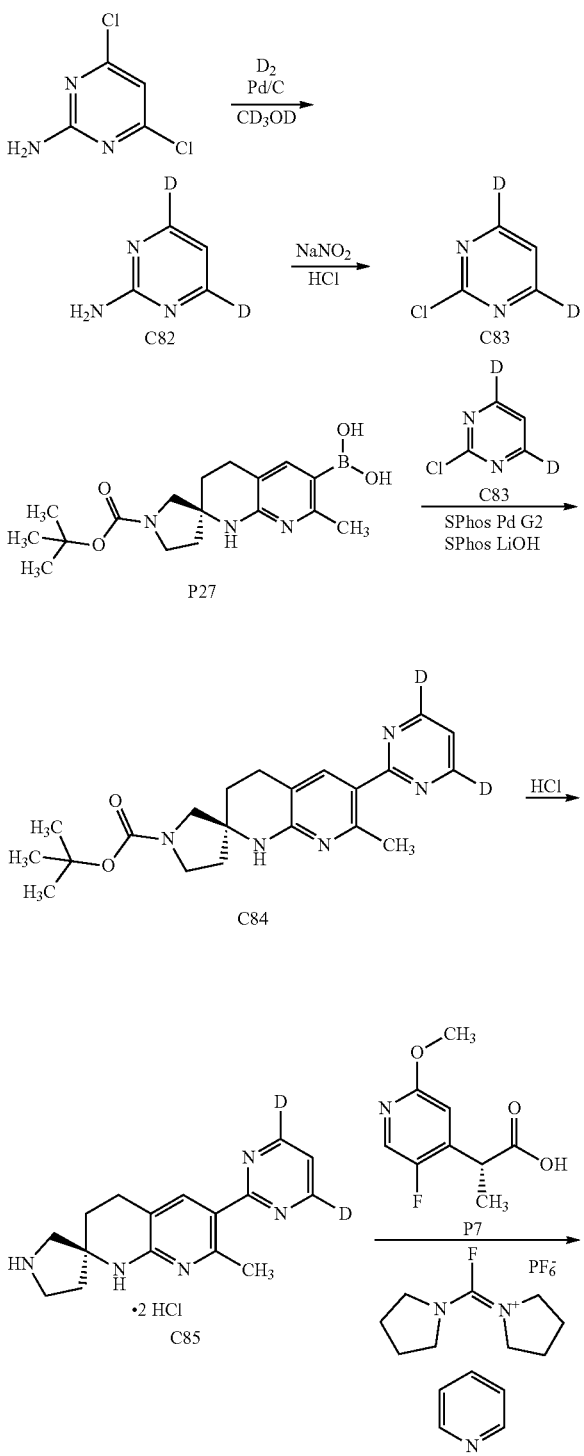

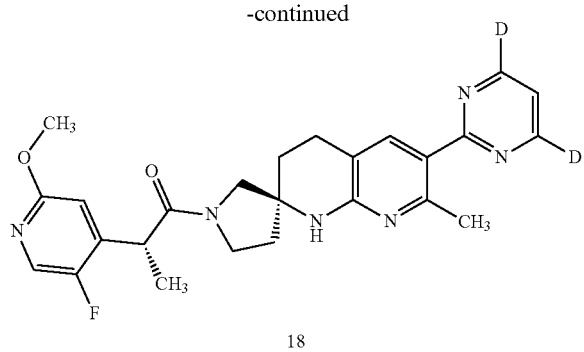

18

Step 1. Synthesis of (4,6-²H₂)pyrimidin-2-amine (C82)

To a solution of 4,6-dichloropyrimidin-2-amine (500 mg, 3.05 mmol) in methanol-d₄ (10 mL) were added palladium on carbon (100 mg) and triethylamine (1.3 mL, 9.3 mmol). The reaction mixture was stirred under deuterium gas at 20° C. for 6 hours, whereupon it was filtered to remove the catalyst. After the collected catalyst had been washed with methanol (2×10 mL), the combined filtrates were concentrated in vacuo, then subjected to silica gel chromatography (Gradient: 0% to 80% ethyl acetate in petroleum ether), affording C82 as a white solid. Yield: 210 mg, 2.16 mmol, 71%. LCMS m/z 98.2 [M+H]⁺. ¹H NMR (400 MHz, DMSO-d₆) δ 6.60-6.52 (br s, 2H), 6.53 (s, 1H).

Step 2. Synthesis of 2-chloro(4,6-²H₂)pyrimidine (C83)

Intermediate C82 (210 mg, 2.16 mmol) was added portion-wise to concentrated hydrochloric acid (0.7 mL) at 0° C., and the resulting mixture was stirred until it became homogeneous. The solution was then cooled to about −15° C., whereupon a cold solution of sodium nitrite (298 mg, 4.32 mmol) in water (0.5 mL) was added drop-wise over 1 hour, while the reaction temperature was maintained between −15° C. and −10° C. The reaction mixture was stirred for 1 hour, and the temperature was allowed to rise to about −5° C.; it was then carefully neutralized to a pH of 7 by addition of 30% aqueous sodium hydroxide solution, while the reaction temperature was maintained below 0° C. The resulting mixture was extracted with diethyl ether (3×5 mL), and the combined organic layers were washed with saturated aqueous sodium chloride solution (10 mL), dried over sodium sulfate, filtered, and concentrated in vacuo to afford C83 as a white solid. Yield: 115 mg, 0.987 mmol, 46%. ¹H NMR (400 MHz, DMSO-d₆) δ 7.60 (s, 1H).

Step 3. Synthesis of tert-butyl (2S)-7-methyl-6-[(4,6-²H₂)pyrimidin-2-yl]-3,4-dihydro-1H-spiro[1,8-naphthyridine-2,3'-pyrrolidine]-1'-carboxylate (C84)

A mixture of C83 (40 mg, 0.34 mmol), P27 (119 mg, 0.34 mmol), 2-dicyclohexylphosphino-2',6'-dimethoxybiphenyl (SPhos; 5.6 mg, 14 μmol), chloro(2-dicyclohexylphosphino-2',6'-dimethoxy-1,1'-biphenyl)[2-(2'-amino-1,1'-biphenyl)]palladium(II) (SPhos Pd G2; 4.9 mg, 6.8 μmol), and aqueous lithium hydroxide solution (2 M; 0.4 mL, 0.8 mmol) in tetrahydrofuran (5 mL) was purged with nitrogen for 3 minutes, whereupon the reaction mixture was stirred at 60° C. for 4 hours. It was then concentrated in vacuo; the residue was purified using chromatography on silica gel (Gradient: 0% to 50% ethyl acetate in petroleum ether) to provide C84 as a yellow solid. Yield: 116 mg, 0.302 mmol, 89%. LCMS m/z 384.3 [M+H]⁺. ¹H NMR (400 MHz, chloroform-d) δ [8.04 (s) and 8.01 (s), total 1H], 7.14 (s, 1H), 3.67-3.30 (m, 4H), 2.92-2.76 (m, 2H), [2.74 (s) and 2.73 (s), total 3H], 2.12-1.79 (m, 4H), [1.47 (s) and 1.46 (s), total 9H].

Step 4. Synthesis of (2S)-7-methyl-6-[(4,6-²H₂)pyrimidin-2-yl]-3,4-dihydro-1H-spiro[1,8-naphthyridine-2,3'-pyrrolidine], dihydrochloride salt (C85)

A solution of hydrogen chloride in 1,4-dioxane (4 M; 3 mL) was added to a solution of C84 (116 mg, 0.302 mmol) in dichloromethane (3 mL), and the reaction mixture was stirred at 20° C. for 2 hours. Concentration in vacuo afforded C85 as a yellow solid. Yield: 108 mg, 0.303 mmol, quantitative. LCMS m/z 284.2 [M+H]⁺. ¹H NMR (400 MHz, DMSO-d₆) δ 10.09-9.93 (br s, 1H), 9.82-9.67 (br s, 1H), 9.01 (s, 1H), 8.45 (s, 1H), 7.50 (s, 1H), 3.50-3.34 (m, 2H), 3.34-3.27 (m, 2H), 3.01-2.84 (m, 2H), 2.82 (s, 3H), 2.26-2.07 (m, 3H), 1.99-1.87 (m, 1H).

Step 5. Synthesis of (2R)-2-(5-fluoro-2-methoxypyridin-4-yl)-1-{(2S)-7-methyl-6-[(4,6-²H₂)pyrimidin-2-yl]-3,4-dihydro-1H-spiro[1,8-naphthyridine-2,3'-pyrrolidin]-1'-yl}propan-1-one (18)

A solution of C85 (80 mg, 0.22 mmol), P7 (45 mg, 0.23 mmol), fluoro-N,N,N',N'-bis(tetramethylene)formamidinium hexafluorophosphate (BTFFH; 85 mg, 0.27 mmol), and pyridine (71 mg, 0.890 mmol) in dichloromethane (10 mL) was stirred at 25° C. for 16 hours. After the reaction mixture had been poured into aqueous sodium bicarbonate solution (10 mL), it was extracted with ethyl acetate (2×20 mL); the combined organic layers were washed with saturated aqueous sodium chloride solution, dried over sodium sulfate, filtered, and concentrated in vacuo. Silica gel chromatography (Gradient: 0% to 10% methanol in dichloromethane) afforded (2R)-2-(5-fluoro-2-methoxypyridin-4-yl)-1-{(2S)-7-methyl-6-[(4,6-²H₂)pyrimidin-2-yl]-3,4-dihydro-1H-spiro[1,8-naphthyridine-2,3'-pyrrolidin]-1'-yl}propan-1-one (18) as a white solid. Yield: 27 mg, 58 μmol, 26%. LCMS m/z 465.3 [M+H]⁺. ¹H NMR (400 MHz, methanol-d₄) δ [8.00 (d, J=1.7 Hz) and 7.98 (d, J=1.7 Hz), total 1H], [7.85 (s) and 7.82 (s), total 1H], [7.31 (s) and 7.30 (s), total 1H], [6.78 (d, J=4.9 Hz) and 6.73 (d, J=4.9 Hz), total 1H], [4.28 (q, J=6.9 Hz) and 4.20 (q, J=6.9 Hz), total 1H], [3.93-3.85 (m), 3.77-3.67 (m), 3.67-3.57 (m), 3.53 (AB quartet, J_{AB}=12.2 Hz, Δν_{AB}=35.5 Hz), and 3.39 (d, J=10.6 Hz), total 4H], [3.89 (s) and 3.88 (s), total 3H], [2.95-2.75 (m) and 2.64-2.55 (m), total 2H], [2.58 (s) and 2.55 (s), total 3H], [2.16-2.06 (m) and 2.05-1.85 (m), total 3H], 1.84-1.75 (m, 1H), [1.45 (d, J=6.9 Hz) and 1.44 (d, J=6.9 Hz), total 3H].

Examples 19 and 20
2-(4-Fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-1 (19) and 2-(4-Fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-2 (20)
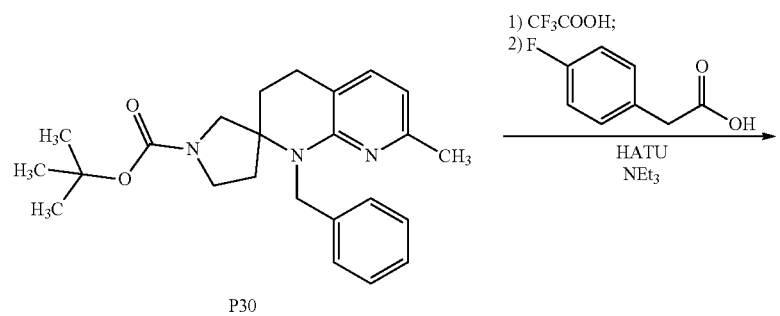
P30
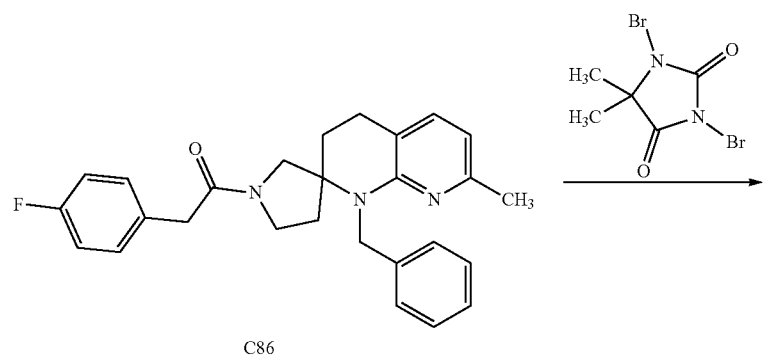
C86
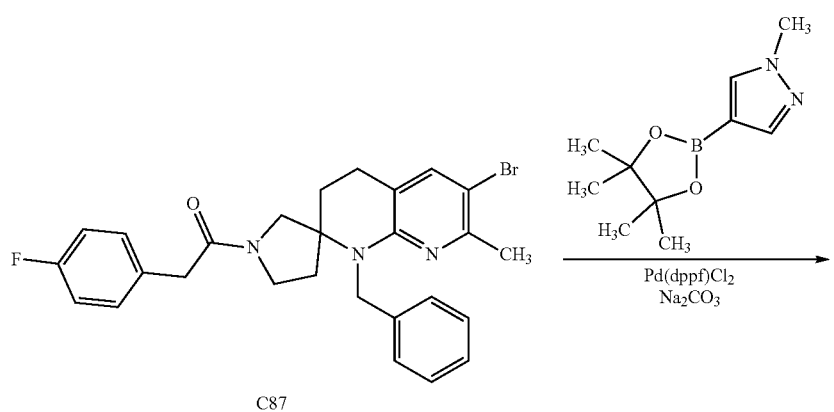
C87
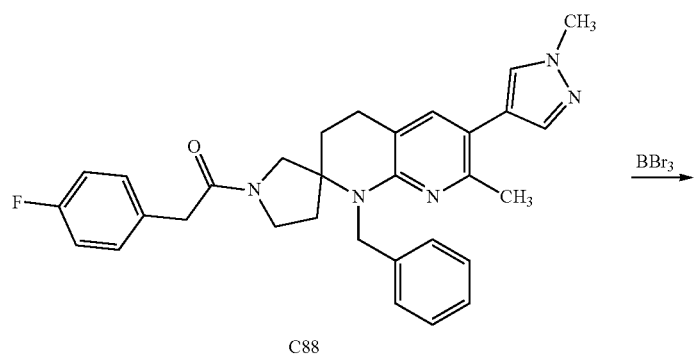
C88

-continued

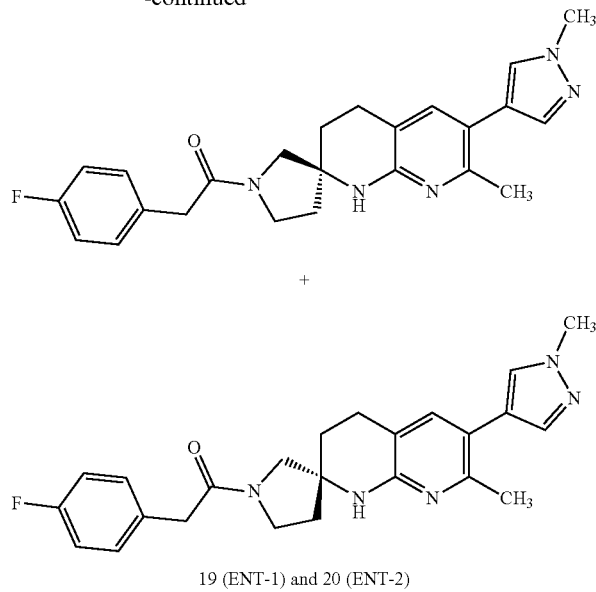

19 (ENT-1) and 20 (ENT-2)

Step 1. Synthesis of 1-(1-benzyl-7-methyl-3,4-dihydro-1H-spiro[1,8-naphthyridine-2,3'-pyrrolidin]-1'-yl)-2-(4-fluorophenyl)ethan-1-one (C86)

Trifluoroacetic acid (319 mg, 2.80 mmol) was added to a solution of P30 (110.0 mg, 0.280 mmol) in dichloromethane (4 mL), and the reaction mixture was stirred at room temperature for 2 hours. It was then concentrated in vacuo, coevaporated with ethyl acetate several times and dissolved in dichloromethane (4 mL). The resulting solution was treated with triethylamine (84.9 mg, 0.839 mmol), O-(7-azabenzotriazol-1-yl)-N,N,N',N'-tetramethyluronium hexafluorophosphate (HATU; 117 mg, 0.308 mmol), and (4-fluorophenyl)acetic acid (43.1 mg, 0.280 mmol) and stirred overnight at room temperature. After removal of solvent in vacuo, the residue was purified using silica gel chromatography (Gradient: 0% to 10% methanol in dichloromethane) to afford C86 as a light-tan solid. Yield: 120 mg, 0.279 mmol, quantitative. $^1$H NMR (400 MHz, chloroform-d) δ [7.31-7.13 (m), 7.13-7.06 (m), and 7.05-6.91 (m), total 10H], 6.44-6.38 (m, 1H), 5.11-4.97 (m, 1H), [4.88 (d, component of AB quartet, J=16.8 Hz) and 4.77 (d, component of AB quartet, J=16.7 Hz), total 1H], [3.71-3.60 (m), 3.59-3.37 (m), and 3.33-3.24 (m), total 6H], [2.83-2.69 (m) and 2.62-2.51 (m), total 2H], 2.35-2.17 (m, 1H), [2.24 (s) and 2.23 (s), total 3H], 2.01-1.68 (m, 3H).

Step 2. Synthesis of 1-(1-benzyl-6-bromo-7-methyl-3,4-dihydro-1H-spiro[1,8-naphthyridine-2,3'-pyrrolidin]-1'-yl)-2-(4-fluorophenyl)ethan-1-one (C87)

1,3-Dibromo-5,5-dimethylimidazolidine-2,4-dione (47.9 mg, 0.168 mmol) was added in several small portions to a 0° C. solution of C86 (120 mg, 0.279 mmol) in dichloromethane (5 mL). The reaction mixture was allowed to warm to room temperature; after 30 minutes, C87 was observed via LCMS analysis: LCMS m/z 508.3 (bromine isotope pattern observed) [M+H]$^+$. After 1 hour, the reaction mixture was concentrated in vacuo and subjected to chromatography on silica gel (Gradient: 0% to 100% ethyl acetate in heptane), providing C87. Yield: 65.0 mg, 0.128 mmol, 46%. $^1$H NMR (400 MHz, chloroform-d) δ [7.35-7.17 (m), 7.16-7.06 (m), and 7.05-6.91 (m), total 10H], [4.98 (d, component of AB quartet, J=16.7 Hz) and 4.98 (d, component of AB quartet, J=16.8 Hz), total 1H], [4.80 (d, component of AB quartet, J=16.8 Hz) and 4.72 (d, component of AB quartet, J=16.7 Hz), total 1H], [3.72-3.62 (m), 3.58-3.43 (m), and 3.33-3.24 (m), total 6H], [2.85-2.69 (m) and 2.62-2.48 (m), total 2H], 2.38-2.15 (m, 1H), [2.34 (s) and 2.32 (s), total 3H], 2.01-1.70 (m, 3H).

Step 3. Synthesis of 1-[1-benzyl-7-methyl-6-(1-methyl-1H-pyrazol-4-yl)-3,4-dihydro-1H-spiro[1,8-naphthyridine-2,3'-pyrrolidin]-1'-yl]-2-(4-fluorophenyl)ethan-1-one (C88)

A reaction vial was charged with C87 (65.0 mg, 0.128 mmol), 1-methyl-4-(4,4,5,5-tetramethyl-1,3,2-dioxaborolan-2-yl)-1H-pyrazole (33.1 mg, 0.159 mmol), [1,1'-bis(diphenylphosphino)ferrocene]dichloropalladium(II), dichloromethane complex (5.20 mg, 6.37 µmol), aqueous sodium carbonate solution (2.0 M; 0.127 mL, 0.254 mmol), and 1,4-dioxane (3 mL). After the vial had been purged with nitrogen, it was sealed and heated at 90° C. overnight, whereupon LCMS analysis indicated conversion to C88: LCMS m/z 510.4 [M+H]$^+$. The reaction mixture was then cooled to room temperature and partitioned between ethyl acetate and aqueous ammonium chloride solution. The aqueous layer was extracted twice with ethyl acetate, and the combined organic layers were washed with saturated aqueous sodium chloride solution, dried over magnesium sulfate, filtered, and concentrated in vacuo. Silica gel chromatography (Gradient: 0% to 10% methanol in dichloromethane) provided C88 as a solid. Yield: 65.0 mg, 0.128 mmol, quantitative.

Step 4. Synthesis of 2-(4-fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-1 (19) and 2-(4-fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-2 (20)

A solution of boron tribromide in dichloromethane (1.0 M; 0.765 mL, 0.765 mmol) was added to a −78° C. solution of C88 (65.0 mg, 0.128 mmol) in dichloromethane (3 mL), whereupon the reaction mixture was allowed to warm to room temperature and stir for 15 hours. It was then treated with methanol (0.5 mL) and concentrated in vacuo. Separation of the component enantiomers was carried out using supercritical fluid chromatography [Column: Chiral Technologies Chiralpak AS-H, 21×250 mm, 5 μm; Mobile phase: 83:7 carbon dioxide/(methanol containing 0.2% ammonium hydroxide); Flow rate: 75 mL/minute; Back pressure: 200 bar]. The first-eluting diastereomer was designated as 19 {2-(4-fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-1}, and the second-eluting diastereomer as 20 {2-(4-fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-2}.

19—Yield: 3.8 mg, 9.1 μmol, 7%. LCMS m/z 442.5 [M+Na$^+$]. Retention time: 2.88 minutes [Analytical conditions. Column: Chiral Technologies Chiralpak AS-H, 4.6× 100 mm, 5 μm; Mobile phase: 4:1 carbon dioxide/(methanol containing 0.2% ammonium hydroxide); Flow rate: 1.5 mL/minute; Back pressure: 200 bar].

20—Yield: 2.0 mg, 4.8 μmol, 4%. L-MS m/z 442.5 [M+Na$^+$]. Retention time: 4.01 minutes (Analytical conditions identical to those used for 19).

TABLE 1

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 21 | Example 18; P27, P7 | 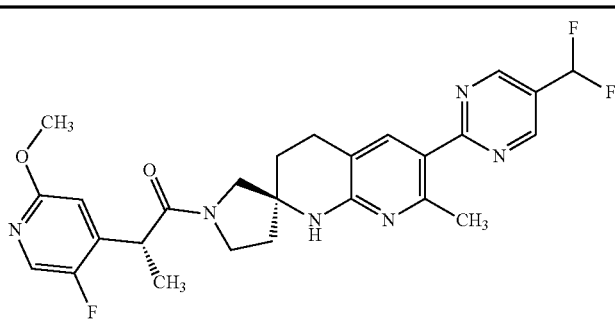 | 8.98-8.93 (m, 2H), [8.05 (s) and 8.02 (s), total 1H], [8.00 (d, J = 1.7 Hz) and 7.98 (d, J = 1.7 Hz), total 1H], 6.98 (br t, $J_{HF}$ = 55 Hz, 1H), [6.78 (d, J = 4.9 Hz) and 6.73 (d, J = 5.0 Hz), total 1H], [4.28 (q, J = 6.9 Hz) and 4.20 (q, J = 6.9 Hz), total 1H], [3.95-3.83 (m) and 3.77-3.67 (m), total 1H], [3.89 (s) and 3.88 (s), total 3H], 3.67-3.54 (m, 2H), [3.52-3.46 (m) and 3.43-3.37 (m), total 1H, assumed; partially obscured by solvent peak], [2.95-2.75 (m) and 2.7-2.53 (m), total 2H], [2.66 (s) and 2.63 (s), total 3H], 2.18-1.84 (m, 3H), 1.84-1.74 (m, 1H), [1.45 (d, J = 6.9 Hz) and 1.44 (d, J = 6.9 Hz), total 3H]; 513.3 |
| 22 | Example 18$^1$; P27, P7 | 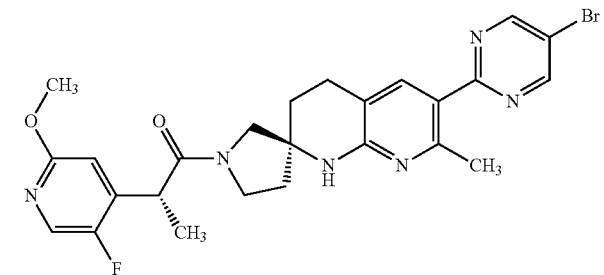 [SMILES: COc1cc([C@@H](C)C(=O)N2CC[C@@]3(CCc4cc(-c5ncc(Br)cn5)c(C)nc4N3)C2)c(F)cn1] | [8.88 (s) and 8.88 (s), total 2H], 8.01-7.94 (m, 2H), [6.78 (d, J = 4.9 Hz) and 6.73 (d, J = 4.9 Hz), total 1H], [4.27 (q, J = 6.9 Hz) and 4.19 (q, J = 6.9 Hz), total 1H], [3.94-3.84 (m), 3.77-3.67 (m), 3.65-3.57 (m), 3.64 (d, half of AB quartet, J = 10.9 Hz), 3.53 (AB quartet, $J_{AB}$ = 12.2 Hz, $\Delta v_{AB}$ = 36.4 Hz), and 3.39 (d, half of AB quartet, J = 10.7 Hz), total 4H], [3.88 (s) and 3.88 (s), total 3H], [2.93-2.74 (m) and 2.61-2.53 (m), total 2H], [2.62 (s) and 2.60 (s), total 3H], [2.15-2.06 (m) and 2.04-1.83 (m), total 3H], 1.83-1.74 (m, 1H), [1.45 (d, J = 6.9 Hz) and 1.44 (d, J = 6.9 Hz), total 3H]; 543.3 (bromine isotope pattern observed) |
| 23 | Alternate Synthesis of Examples 3 and 4$^{2,3}$; P17, P4 | 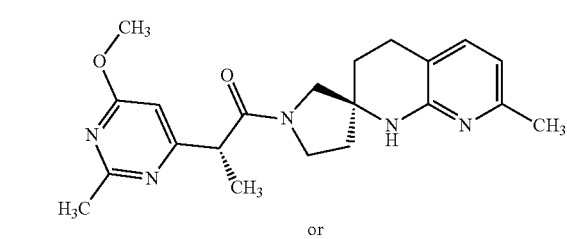 | 6.05 minutes$^4$; 382.3$^5$ | or

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
|  |  | 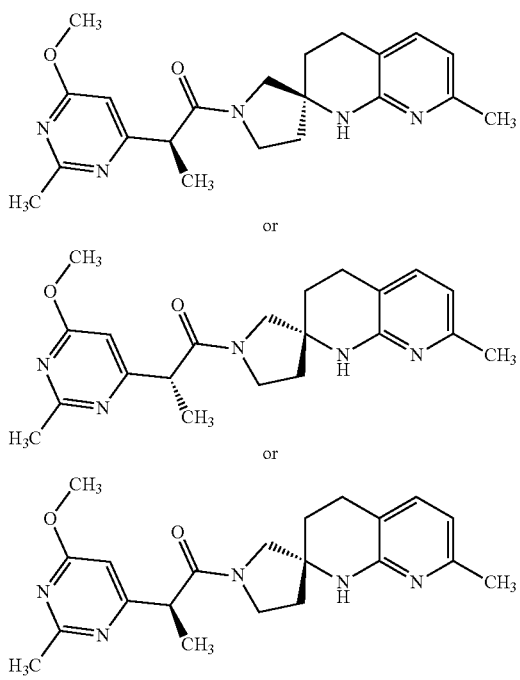 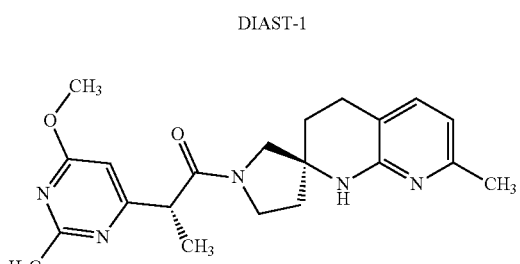 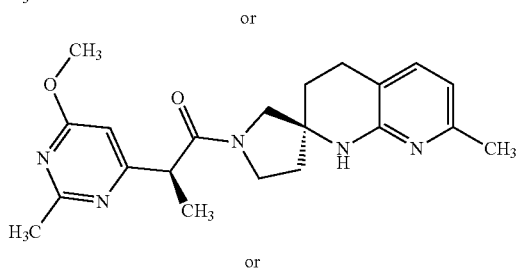<br>DIAST-1 |  |
| 24 | Alternate Synthesis of Examples 3 and 4[2,3]; P17, P4 | 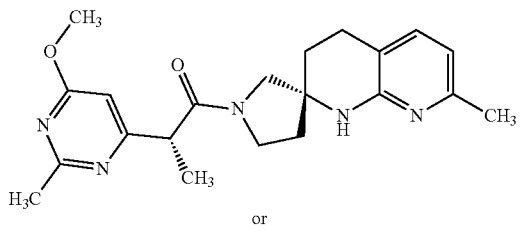 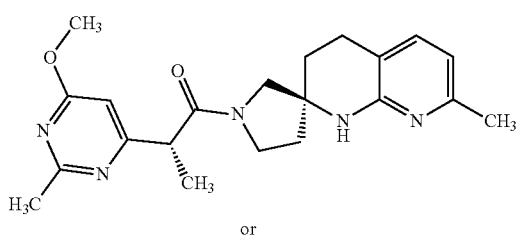 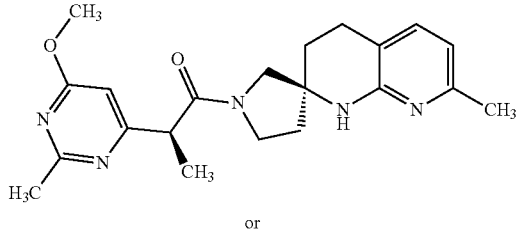 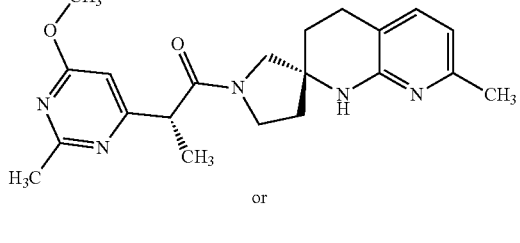 | 7.40 minutes[4]; 382.3[5] |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| | | 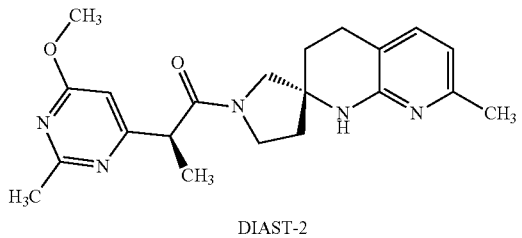<br>DIAST-2 | |
| 25 | Alternate Synthesis of Examples 3 and 4[2,3]; P17, P4 | 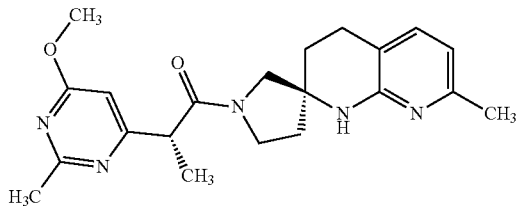<br>or<br>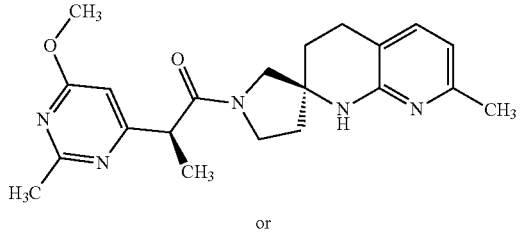<br>or<br>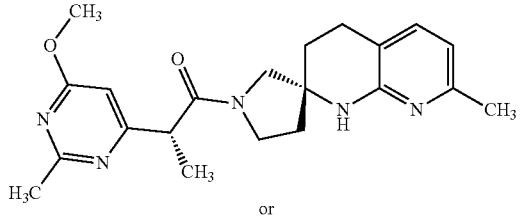<br>or<br>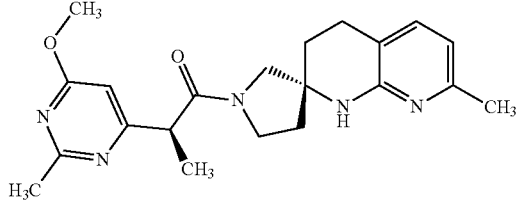<br>DIAST-3 | 5.49 minutes[6]; 382.3[5] |

TABLE 1-continued

Method of synthesis, structure, and physicochemical data for Examples 21-201.

| Example Number | Method of synthesis; Non-commercial starting materials | Structure | ¹H NMR (400 MHz, methanol-d₄) δ; Mass spectrum, observed ion m/z [M + H]⁺ or HPLC retention time; Mass spectrum m/z [M + H]⁺ (unless otherwise indicated) |
|---|---|---|---|
| 26 | Alternate Synthesis of Examples 3 and 4[2,3]; P17, P4 | 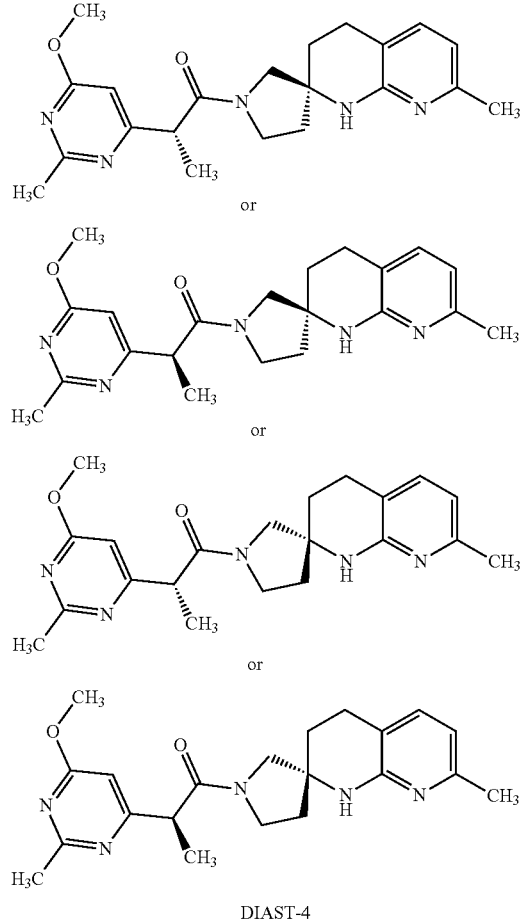<br>DIAST-4 | 6.23 minutes[6]; 382.3[5] |
| 27 | Examples 1 and 2[7]; P23, P7 | 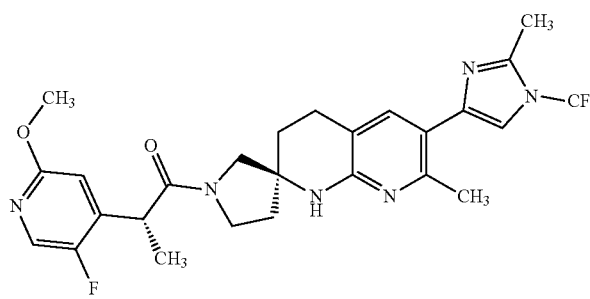 | [7.99 (d, J = 1.6 Hz) and 7.98 (d, J = 1.7 Hz), total 1H], [7.59 (s) and 7.55 (s), total 1H], 7.47 (s, 1H), [6.78 (d, J = 4.9 Hz) and 6.72 (d, J = 4.9 Hz), total 1H], [4.27 (q, J = 6.9 Hz) and 4.18 (q, J = 6.9 Hz), total 1H], [3.94-3.83 (m), 3.76-3.52 (m), 3.47 (d, half of AB quartet, J = 12.3 Hz), and 3.37 (d, half of AB quartet, J = 10.6 Hz), total 4H], [3.88 (s) and 3.88 (s), total 3H], [2.93-2.72 (m) and 2.62-2.50 (m), total 2H], 2.58 (br s, 3H), [2.44 (s) and 2.42 (s), total 3H], [2.16-2.04 (m) and 2.04-1.84 (m), total 3H], 1.82-1.73 (m, 1H), 1.47-1.40 (m, 3H); 533.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 28 | Example 13; P28, P8 | 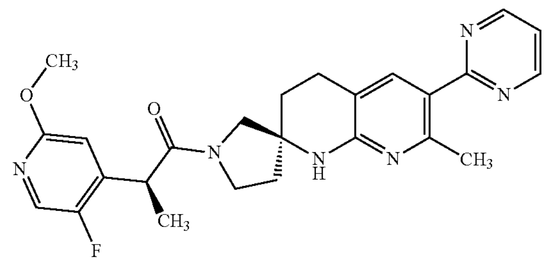 [SMILES: COc1cc([C@H](C)C(=O)N2CC[C@@]3(CCc4cc(-c5ncccn5)c(C)nc4N3)C2)c(F)cn1] | [8.85 (d, J = 4.9 Hz) and 8.84 (d, J = 4.9 Hz), total 2H], 8.12-8.06 (m, 1H), [7.99 (d, J = 1.6 Hz) and 7.88 (d, J = 1.7 Hz), total 1H], [7.35 (t, J = 4.9 Hz) and 7.35 (t, J = 4.9 Hz), total 1H], 6.77-6.73 (m, 1H), [4.27 (q, J = 6.9 Hz) and 4.19 (q, J = 6.9 Hz), total 1H], [3.98-3.89 (m) and 3.76-3.41 (m), total 4H], [3.88 (s) and 3.86 (s), total 3H], 2.99-2.82 (m, 2H), [2.68 (s) and 2.65 (s), total 3H], [2.26-2.17 (m), 2.15-1.98 (m), and 1.98-1.83 (m), total 4H], [1.47 (d, J = 6.9 Hz) and 1.44 (d, J = 6.9 Hz), total 3H]; 463.3 |
| 29 | Examples 1 and 2$^8$; P24, P7 | 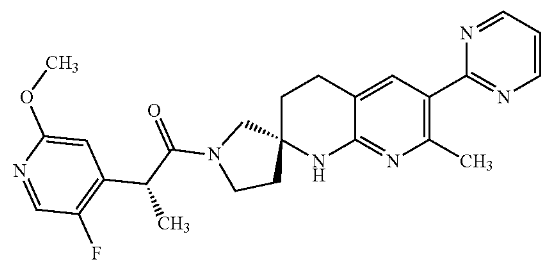 [SMILES: COc1cc([C@@H](C)C(=O)N2CC[C@]3(CCc4cc(-c5ncccn5)c(C)nc4N3)C2)c(F)cn1] | [8.82 (d, J = 4.9 Hz) and 8.81 (d, J = 4.9 Hz), total 2H], [7.98 (d, J = 1.7 Hz) and 7.88-7.84 (m), total 2H], [7.31 (t, J = 4.9 Hz) and 7.31 (t, J = 4.9 Hz), total 1H], 6.75 (d, J = 5.0 Hz, 1H), [4.27 (q, J = 6.9 Hz) and 4.18 (q, J = 6.9 Hz), total 1H], [3.98-3.89 (m), 3.75-3.61 (m), 3.58 (d, half of AB quartet, J = 12.2 Hz), 3.56-3.45 (m), and 3.39 (d, half of AB quartet, J = 10.5 Hz), total 4H], [3.88 (s) and 3.86 (s), total 3H], 2.94-2.76 (m, 2H), [2.58 (s) and 2.55 (s), total 3H], [2.20-2.11 (m), 2.10-1.94 (m), and 1.94-1.79 (m), total 4H], [1.47 (d, J = 6.9 Hz) and 1.43 (d, J = 6.9 Hz), total 3H]; 463.4 |
| 30 | Examples 1 and 2$^8$; P24, P8 | 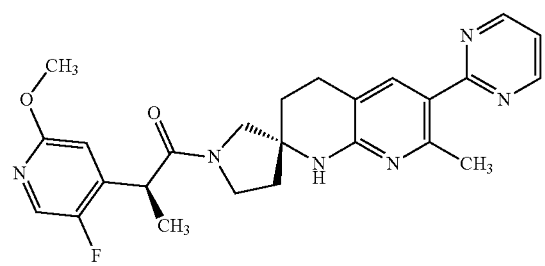 [SMILES: COc1cc([C@H](C)C(=O)N2CC[C@]3(CCc4cc(-c5ncccn5)c(C)nc4N3)C2)c(F)cn1] | [8.81 (d, J = 4.9 Hz) and 8.81 (d, J = 4.9 Hz), total 2H], [8.00 (d, J = 1.6 Hz) and 7.98 (d, J = 1.7 Hz), total 1H], [7.85 (s) and 7.82 (s), total 1H], [7.31 (t, J = 4.9 Hz) and 7.30 (t, J = 4.9 Hz), total 1H], [6.78 (d, J = 4.9 Hz) and 6.73 (d, J = 5.0 Hz), total 1H], [4.28 (q, J = 6.9 Hz) and 4.19 (q, J = 6.9 Hz), total 1H], [3.93-3.83 (m), 3.77-3.67 (m), 3.67-3.58 (m), 3.64 (d, half of AB quartet, J = 10.9 Hz), 3.53 (AB quartet, J$_{AB}$ = 12.1 Hz, Δν$_{AB}$ = 35.4 Hz), and 3.39 (d, half of AB quartet, J = 10.6 Hz), total 4H], [3.89 (s) and 3.88 (s), total 3H], [2.94-2.74 (m) and 2.64-2.56 (m), total 2H], [2.57 (s) and 2.55 (s), total 3H], 2.16-1.84 (m, 3H), 1.83-1.74 (m, 1H), [1.45 (d, J = 6.9 Hz) and 1.44 (d, J = 6.9 Hz), total 3H]; 463.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 31 | Alternate Synthesis of Examples 3 and 4[9,10,11]; C66, P4 | DIAST-1 | 7.86 (s, 1H), [6.62 (s) and 6.59 (s), total 1H], [4.40 (s) and 4.39 (s), total 3H], [4.04 (q, J = 7.0 Hz), 3.97-3.85 (m), and 3.78-3.48 (m), total 5H], [3.96 (s) and 3.91 (s), total 3H], 2.92-2.77 (m, 2H), [2.60 (s), 2.58 (s), 2.56 (s), and 2.37 (s), total 6H], [2.22-2.11 (m) and 2.09-2.01 (m), total 2H], 2.01-1.79 (m, 2H), [1.47 (d, J = 7.0 Hz) and 1.42 (d, J = 7.0 Hz), total 3H]; 464.4 |
| 32 | Alternate Synthesis of Examples 3 and 4[9,10,11]; C66, P4 | DIAST-2 | [7.85 (s) and 7.84 (s), total 1H], [6.65 (s) and 6.61 (s), total 1H], [4.39 (s) and 4.39 (s), total 3H], [4.04 (q, J = 7.1 Hz) and 4.00-3.93 (m), total 1H], [3.97 (s) and 3.96 (s), total 3H], [3.88-3.55 (m) and 3.53 (s), total 4H], [2.94-2.75 (m) and 2.66-2.58 (m), total 2H], [2.60 (s), 2.58 (s), and 2.55 (s), total 6H], [2.15-2.06 (m) and 2.04-1.71 (m), total 4H], [1.46 (d, J = 7.1 Hz) and 1.44 (d, J = 7.1 Hz), total 3H]; 464.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 33 | Example 14[12]; C44, P7 | 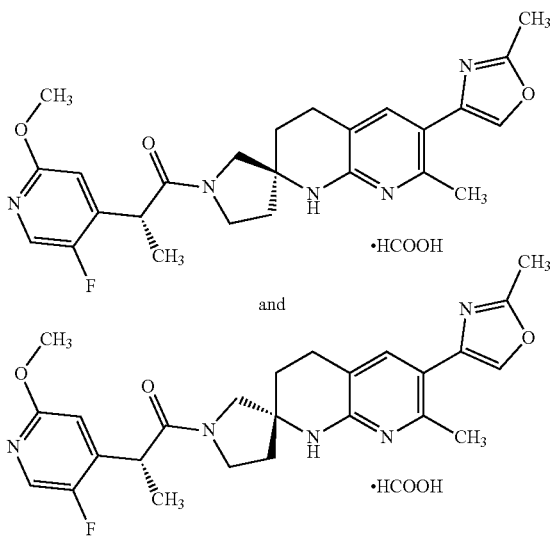 [SMILES: COc1cc([C@@H](C)C(=O)N2CC[C@]3(CCc4cc(-c5coc(C)n5)c(C)nc4N3)C2)c(F)cn1 ; COc1cc([C@@H](C)C(=O)N2CC[C@@]3(CCc4cc(-c5coc(C)n5)c(C)nc4N3)C2)c(F)cn1 ; "·HCOOH" ; "·HCOOH"] | [8.39 br (s) and 8.00-7.96 (m), total 2H], 7.86-7.82 (m, 1H), [7.62 (br s) and 7.59 (s), total 1H], 6.79-6.70 (m, 1H), [4.31-4.22 (m) and 4.22-4.12 (m), total 1H], [3.98-3.85 (m), 3.76-3.43 (m), and 3.41-3.33 (m), total 4H, assumed; partially obscured by solvent peak], [3.88 (s), 3.88 (s), 3.88 (s), and 3.85 (s), total 3H], [2.92-2.72 (m) and 2.62-2.49 (m), total 2H], [2.49 (s) and 2.49 (br s), total 3H], [2.42 (s), 2.41 (s), 2.39 (s) and 2.39 (s), total 3H], 2.20-1.72 (m, 4H), 1.49-1.39 (m, 3H); 466.2 |
| 34 | Examples 5 and 6[13]; P28 | 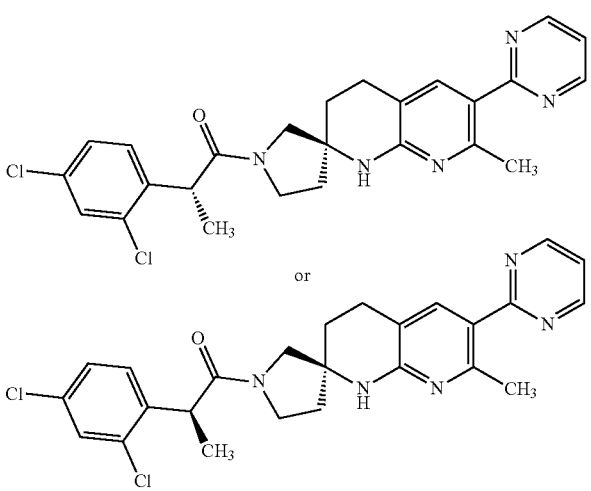

DIAST-1 | 8.84 (d, J = 4.9 Hz, 2H), [8.13 (br s) and 8.04 (br s), total 1H], 7.54-7.50 (m, 1H), 7.42-7.31 (m, 3H), [4.38 (q, J = 7.0 Hz) and 4.27 (q, J = 6.9 Hz), total 1H], [3.93-3.84 (m), 3.77-3.67 (m), 3.67-3.57 (m), 3.52 (d, component of AB quartet, J = 12.4 Hz), 3.50-3.41 (m), and 3.26 (d, J = 10.7 Hz), total 4H], [2.99-2.85 (m), 2.84-2.74 (m), and 2.56-2.44 (m), total 2H], 2.67 (s, 3H), [2.20-2.09 (m) and 2.07-1.89 (m), total 3H], 1.80-1.71 (m, 1H), [1.42 (d, J = 6.9 Hz) and 1.40 (d, J = 6.9 Hz), total 3H]; 482.0 (dichloro isotope pattern observed) |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 35 | Examples 5 and 6[13]; P28 | DIAST-2 | 8.86-8.83 (m, 2H), [8.10 (br s) and 8.07 (br s), total 1H], [7.54-7.50 (m) and 7.40-7.29 (m), total 4H], [4.36 (q, J = 6.9 Hz) and 4.25 (br q, J = 7 Hz), total 1H], [3.95-3.86 (m), 3.77-3.59 (m), 3.52 (d, component of AB quartet, J = 12.3 Hz), 3.38 (ddd, J = 10.7, 8.3, 5.5 Hz), and 3.27 (d, J = 10.6 Hz), total 4H], 2.98-2.76 (m, 2H), [2.69 (s) and 2.67 (s), total 3H], [2.25-2.15 (m), 2.13-1.97 (m), and 1.96-1.79 (m), total 4H], [1.43 (d, J = 6.9 Hz) and 1.38 (d, J = 6.9 Hz), total 3H]; 482.0 (dichloro isotope pattern observed) |
| 36 | Examples 5 and 6[14]; P28, P9 | DIAST-1 | [8.81 (d, J = 4.9 Hz) and 8.81 (d, J = 4.9 Hz), total 2H], [8.29 (br s) and 8.27 (br s), total 1H], [7.86 (s) and 7.80 (s), total 1H], [7.31 (t, J = 4.9 Hz) and 7.30 (t, J = 4.9 Hz), total 1H], [6.99 (t, J$_{HF}$ = 54.3 Hz) and 6.94 (t, J$_{HF}$ = 54.2 Hz), total 1H], [6.88 (s) and 6.81 (s), total 1H], [4.36 (q, J = 6.8 Hz) and 4.28 (q, J = 6.8 Hz), total 1H], 3.96 (s, 3H), [3.88-3.80 (m), 3.78-3.68 (m), 3.66-3.54 (m), 3.52-3.43 (m), and 3.27 (d, J = 10.9 Hz), total 4H], [2.93-2.81 (m), 2.79-2.68 (m), and 2.49-2.38 (m), total 2H], [2.57 (s) and 2.55 (s), total 3H], [2.16-2.05 (m) and 2.03-1.83 (m), total 3H], 1.76-1.68 (m, 1H), [1.45 (d, J = 6.7 Hz) and 1.44 (d, J = 6.8 Hz), total 3H]; 495.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 37 | Examples 5 and 6[14]; P28, P9 | 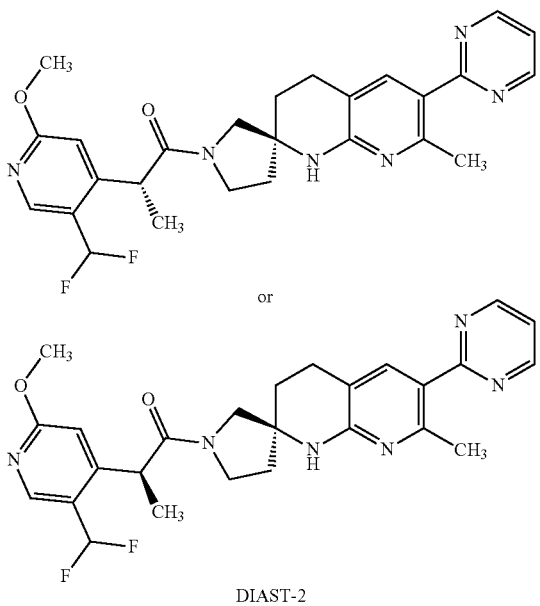 [SMILES: COc1cc([C@@H](C)C(=O)N2CC[C@@]3(CCc4cc(-c5ncccn5)c(C)nc4N3)C2)c(C(F)F)cn1 ; COc1cc([C@H](C)C(=O)N2CC[C@@]3(CCc4cc(-c5ncccn5)c(C)nc4N3)C2)c(C(F)F)cn1]  DIAST-2 | [8.81 (d, J = 4.9 Hz) and 8.81 (d, J = 4.9 Hz), total 2H], [8.28 (br s) and 8.14 (br s), total 1H], [7.85 (s) and 7.82 (s), total 1H], [7.31 (t, J = 4.9 Hz) and 7.31 (t, J = 4.9 Hz), total 1H], [6.98 (t, $J_{HF}$ = 54.2 Hz) and 6.87 (t, $J_{HF}$ = 54.2 Hz), total 1H], [6.84 (s) and 6.82 (s), total 1H], [4.36 (q, J = 6.8 Hz) and 4.25 (q, J = 6.8 Hz), total 1H], [3.95 (s) and 3.94 (s), total 3H], [3.94-3.84 (m), 3.76-3.65 (m), 3.64-3.55 (m), 3.48 (d, component of AB quartet, J = 12.1 Hz), 3.43-3.36 (m, assumed; partially obscured by solvent peak), and 3.25 (d, J = 10.7 Hz), total 4H], 2.92-2.74 (m, 2H), [2.58 (s) and 2.54 (s), total 3H], [2.19-1.91 (m) and 1.91-1.75 (m), total 4H], [1.47 (d, J = 6.8 Hz) and 1.42 (d, J = 6.8 Hz), total 3H]; 495.3 |
| 38 | Examples 5 and 6[15,16]; P28 | 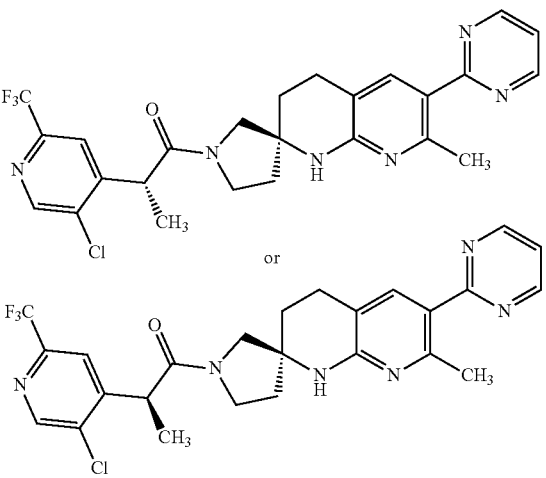  DIAST-1 | 8.85-8.80 (m, 2H), [8.75 (s) and 8.61 (s), total 1H], [8.31 (br s) and 7.93-7.82 (m), total 2H], [7.32 (t, J = 4.9 Hz) and 7.31 (t, J = 4.9 Hz), total 1H], [4.51 (q, J = 7.0 Hz) and 4.43 (q, J = 6.9 Hz), total 1H], [4.05-3.94 (m) and 3.81-3.46 (m), total 4H], 2.98-2.79 (m, 2H), [2.60 (s) and 2.55 (s), total 3H], 2.26-1.79 (m, 4H), [1.56 (d, J = 7.0 Hz) and 1.50 (d, J = 7.0 Hz), total 3H]; 517.2 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 39 | Examples 5 and 6[15,16]; P28 | 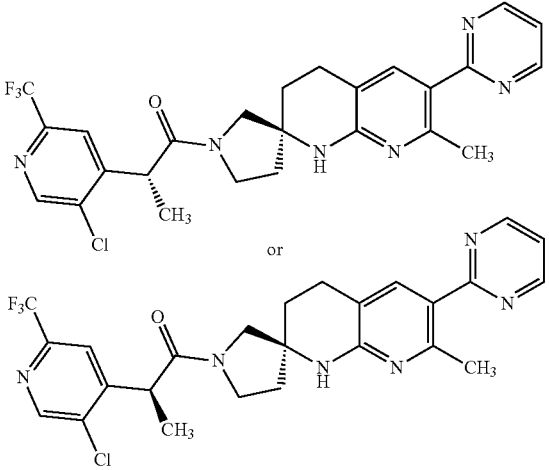<br>DIAST-2 | [8.82 (d, J = 4.9 Hz) and 8.81 (d, J = 4.9 Hz), total 2H], [8.75 (s) and 8.74 (s), total 1H], [8.36 (br s), 7.93-7.84 (m), and 7.82 (s), total 2H], [7.32 (t, J = 4.9 Hz) and 7.31 (t, J = 4.9 Hz), total 1H], [4.52 (q, J = 6.9 Hz) and 4.44 (q, J = 7.0 Hz), total 1H], [4.00-3.91 (m) and 3.81-3.48 (m), total 4H], [2.96-2.79 (m) and 2.73-2.60 (m), total 2H], [2.59 (s) and 2.57 (s), total 3H], [2.21-2.09 (m) and 2.08-1.80 (m), total 4H], [1.53 (d, J = 6.9 Hz) and 1.52 (d, J = 7.0 Hz), total 3H]; 517.2 |
| 40 | Examples 5 and 6[17,18]; P28 | 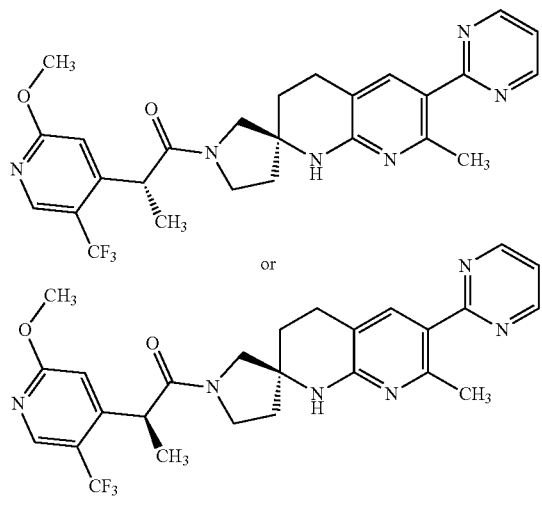<br>DIAST-1 | [8.81 (d, J = 4.9 Hz) and 8.81 (d, J = 4.9 Hz), total 2H], [8.49 (s) and 8.47 (s), total 1H], [7.86 (s) and 7.82 (s), total 1H], [7.31 (t, J = 4.9 Hz) and 7.30 (t, J = 4.9 Hz), total 1H], [6.96 (s) and 6.89 (s), total 1H], [4.25 (q, J = 6.8 Hz) and 4.17 (q, J = 6.8 Hz), total 1H], 3.99 (s, 3H), [3.88-3.79 (m) and 3.77-3.68 (m), total 1H], [3.67-3.56 (m), 3.51-3.39 (m), and 3.24 (d, J = 10.6 Hz), total 3H], [2.94-2.73 (m) and 2.56-2.45 (m), total 2H], [2.58 (s) and 2.55 (s), total 3H], [2.16-2.03 (m), 2.03-1.92 (m), and 1.92-1.84 (m), total 3H], 1.78-1.71 (m, 1H), [1.46 (d, J = 6.8 Hz) and 1.46 (d, J = 6.8 Hz), total 3H]; 513.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 41 | Examples 5 and 6[17,18]; P28 | DIAST-2 | [8.81 (d, J = 4.9 Hz) and 8.81 (d, J = 4.9 Hz), total 2H], [8.48 (s) and 8.34 (s), total 1H], [7.85 (s) and 7.82 (s), total 1H], [7.31 (t, J = 4.9 Hz) and 7.30 (t, J = 4.9 Hz), total 1H], [6.91 (s) and 6.89 (s), total 1H], [4.25 (q, J = 6.9 Hz) and 4.12 (q, J = 6.8 Hz), total 1H], [3.98 (s) and 3.97 (s), total 3H], [3.93-3.84 (m), 3.77-3.63 (m), 3.63-3.56 (m), 3.47 (d, component of AB quartet, J = 12.2 Hz), 3.40-3.3 (m, assumed; partially obscured by solvent peak), and 3.21 (d, J = 10.5 Hz), total 4H], 2.92-2.70 (m, 2H), [2.58 (s) and 2.54 (s), total 3H], [2.20-2.09 (m) and 2.09-1.76 (m), total 4H], [1.48 (d, J = 6.8 Hz) and 1.42 (d, J = 6.8 Hz), total 3H]; 513.3 |
| 42 | Examples 5 and 6[19]; P28 | DIAST-1 | [8.81 (d, J = 4.9 Hz) and 8.80 (d, J = 4.9 Hz), total 2H], [7.84 (s) and 7.78 (s), total 1H], [7.31 (t, J = 4.9 Hz) and 7.30 (t, J = 4.9 Hz), total 1H], 7.13-7.00 (m, 3H), [3.97-3.80 (m), 3.75-3.66 (m), 3.63-3.50 (m), 3.44 (d, component of AB quartet, J = 12.2 Hz), and 3.36-3.3 (m, assumed; partially obscured by solvent peak), total 5H], [3.87 (s) and 3.86 (s), total 3H], [2.90-2.81 (m), 2.74-2.64 (m), and 2.46-2.35 (m), total 2H], [2.56 (s) and 2.54 (s), total 3H], [2.14-2.02 (m) and 2.00-1.84 (m), total 3H], 1.69-1.62 (m, 1H), [1.38 (d, J = 6.9 Hz) and 1.36 (d, J = 6.9 Hz), total 3H]; 462.2 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 43 | Examples 5 and 6[19]; P28 | 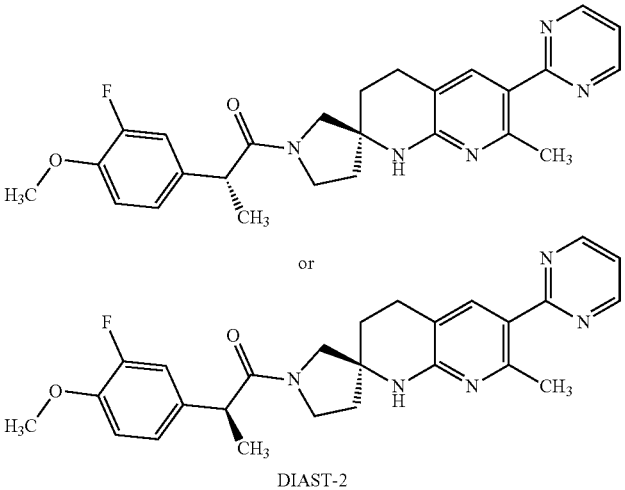 [SMILES: COc1ccc([C@@H](C)C(=O)N2CC[C@@]3(CCc4cc(-c5ncccn5)c(C)nc4N3)C2)cc1F ; COc1ccc([C@H](C)C(=O)N2CC[C@@]3(CCc4cc(-c5ncccn5)c(C)nc4N3)C2)cc1F] | [8.81 (d, J = 4.9 Hz) and 8.81 (d, J = 4.9 Hz), total 2H], [7.83 (br s) and 7.82 (br s), total 1H], [7.30 (t, J = 4.9 Hz) and 7.30 (t, J = 4.9 Hz), total 1H], 7.10-6.87 (m, 3H), [3.96-3.79 (m), 3.72-3.54 (m), 3.50-3.41 (m), and 3.34 (d, J = 10.8 Hz), total 5H], [3.86 (s) and 3.74 (s), total 3H], 2.91-2.74 (m, 2H), [2.57 (s) and 2.54 (s), total 3H], [2.17-1.91 (m) and 1.91-1.72 (m), total 4H], [1.39 (d, J = 6.9 Hz) and 1.36 (d, J = 6.9 Hz), total 3H]; 462.3 |
| 44 | Examples 5 and 6[20,21]; P28 | 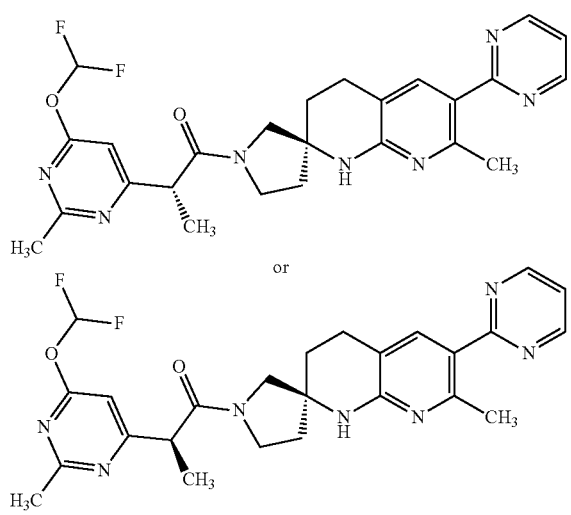 | 8.82 (br d, J = 4.9 Hz, 2H), [7.91 (s) and 7.90 (s), total 1H], [7.66 (t, $J_{HF}$ = 71.9 Hz) and 7.61 (t, $J_{HF}$ = 71.9 Hz), total 1H], [7.32 (t, J = 4.9 Hz) and 7.31 (t, J = 4.9 Hz), total 1H], [6.86 (s) and 6.82 (s), total 1H], [4.16 (q, J = 7.0 Hz) and 4.06 (q, J = 7.0 Hz), total 1H], [3.97-3.87 (m), 3.80-3.60 (m), and 3.55 (AB quartet, $J_{AB}$ = 12.3 Hz, $\Delta v_{AB}$ = 13.7 Hz), total 4H], 2.96-2.79 (m, 2H), 2.61 (s, 3H), [2.58 (s) and 2.45 (s), total 3H], 2.25-2.03 (m, 2H), 2.03-1.83 (m, 2H), [1.52 (d, J = 7.0 Hz) and 1.46 (d, J = 7.0 Hz), total 3H]; 496.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 45 | Examples 5 and 6[20,21]; P28 | 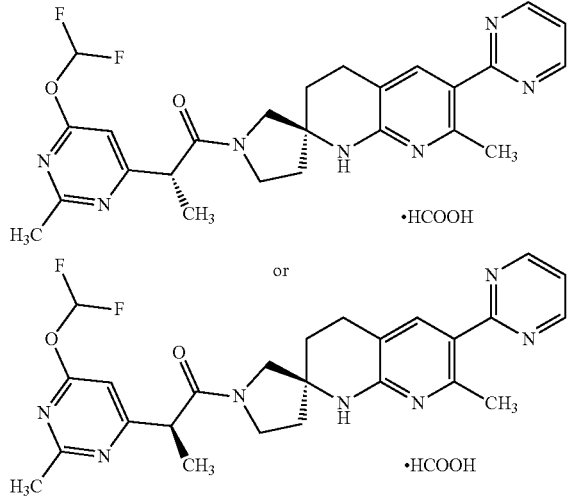DIAST-2 | [8.82 (d, J = 4.9 Hz) and 8.82 (d, J = 4.9 Hz), total 2H], 8.4-8.2 (br s, 1H), 7.97-7.87 (m, 1H), [7.67 (t, $J_{HF}$ = 71.9 Hz) and 7.66 (t, $J_{HF}$ = 71.9 Hz), total 1H], [7.32 (t, J = 4.9 Hz) and 7.31 (t, J = 4.9 Hz), total 1H], [6.88 (s) and 6.85 (s), total 1H], [4.16 (q, J = 7.1 Hz) and 4.10 (q, J = 7.0 Hz), total 1H], [3.92-3.51 (m), 3.65 (s) and 3.55 (br s), total 4H], [2.97-2.79 (m) and 2.76-2.6 (m), total 2H], [2.65 (s), 2.61 (s), 2.60 (s), and 2.59 (s), total 6H], [2.20-2.09 (m) and 2.08-1.76 (m), total 4H], 1.53-1.45 (m, 3H); 496.2 |
| 46 | Examples 5 and 6[22]; P28, P10 | 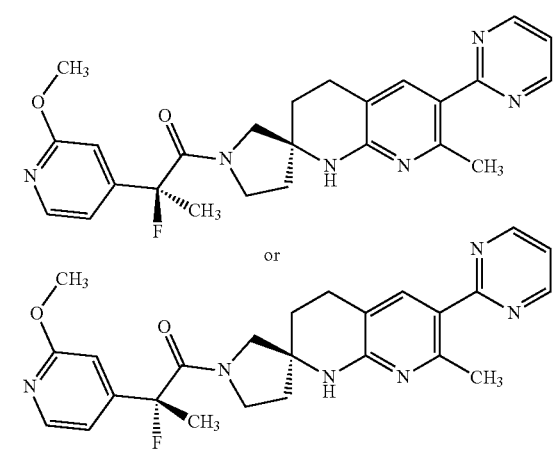DIAST-1 | 8.80 (d, J = 4.9 Hz, 2H), 8.20 (d, J = 5.4 Hz, 1H), [7.84 (s) and 7.73 (s), total 1H], 7.30 (t, J = 4.9 Hz, 1H), [7.02 (dd, J = 5.5, 1.6 Hz) and 6.99 (dd, J = 5.4, 1.6 Hz), total 1H], [6.86 (br s) and 6.81 (br s), total 1H], [3.94 (s) and 3.93 (s), total 3H], [3.72-3.43 (m) and 3.37-3.3 (m, assumed; partially obscured by solvent peak), total 4H], 2.92-2.77 (m), 2.65-2.56 (m), 2.15-1.87 (m), and 1.62-1.44 (m), total 6H], [2.56 (s) and 2.55 (s), total 3H], [1.83 (d, $J_{HF}$ = 23.4 Hz) and 1.80 (d, $J_{HF}$ = 23.4 Hz), total 3H]; 463.3 |

TABLE 1-continued

Method of synthesis, structure, and physicochemical data for Examples 21-201.

| Example Number | Method of synthesis; Non-commercial starting materials | Structure | 1H NMR (400 MHz, methanol-$d_4$) δ; Mass spectrum, observed ion m/z [M + H]+ or HPLC retention time; Mass spectrum m/z [M + H]+ (unless otherwise indicated) |
|---|---|---|---|
| 47 | Examples 5 and 6[22]; P28, P10 | DIAST-2 | 8.81 (d, J = 5.0 Hz, 2H), [8.18 (d, J = 5.4 Hz) and 8.04 (d, J = 5.4 Hz), total 1H], [7.84 (s) and 7.83 (s), total 1H], 7.33-7.27 (m, 1H), [7.01 (br d, J = 5.2 Hz) and 6.88 (br d, J = 5.4 Hz), total 1H], [6.85 (br s) and 6.74 (br s), total 1H], [4.05-3.43 (m) and 3.40-3.3 (m, assumed; partially obscured by solvent peak), total 4H], [3.93 (s) and 3.76 (s), total 3H], 2.90-2.65 (m, 2H), [2.57 (s) and 2.57 (s), total 3H], 2.09-1.75 (m, 4H), [1.84 (d, $J_{HF}$ = 23.1 Hz) and 1.79 (d, $J_{HF}$ = 23.4 Hz), total 3H]; 463.3 |
| 48 | Alternate Synthesis of Examples 3 and 4[23]; P28 | DIAST-1 | [8.81 (d, J = 4.9 Hz) and 8.80 (d, J = 4.9 Hz), total 2H], [7.84 (s) and 7.75 (s), total 1H], [7.45 (br d, J = 8.7 Hz) and 7.40 (br d, J = 8.7 Hz), total 2H], [7.30 (t, J = 4.9 Hz) and 7.30 (t, J = 4.9 Hz), total 1H], 7.28-7.24 (m, 2H), [4.05 (q, J = 6.9 Hz) and 3.96 (q, J = 6.9 Hz), total 1H], [3.92-3.84 (m), 3.71 (ddd, J = 12.5, 8.6, 5.8 Hz), 3.63-3.51 (m), and 3.45 (d, component of AB quartet, J = 12.3 Hz), total 4H], [2.93-2.78 (m), 2.69-2.60 (m), 2.35-2.24 (m), 2.14-2.02 (m), 2.00-1.84 (m), and 1.66-1.59 (m), total 6H], [2.56 (s) and 2.54 (s), total 3H], [1.43 (d, J = 6.9 Hz) and 1.40 (d, J = 6.9 Hz), total 3H]; 498.1 |
| 49 | Alternate Synthesis of Examples 3 and 4[23]; P28 | DIAST-2 | [8.81 (d, J = 4.9 Hz) and 8.81 (d, J = 4.9 Hz), total 2H], [7.84 (s) and 7.83 (s), total 1H], [7.43 (br d, J = 8.7 Hz) and 7.37 (br d, J = 8.7 Hz), total 2H], [7.31 (t, J = 4.9 Hz) and 7.30 (t, J = 4.9 Hz), total 1H], [7.25 (br d, J = 8.3 Hz) and 7.16 (br d, J = 8.3 Hz), total 2H], [4.04 (q, J = 6.9 Hz), 4.00-3.88 (m), 3.72-3.63 (m), 3.60 (br d, component of AB quartet, J = 12.3 Hz), 3.50-3.42 (m), 3.44 (d, component of AB quartet, J = 12.0 Hz), and 3.35-3.3 (m, assumed; largely obscured by solvent peak), total 5H], 2.92-2.74 (m, 2H), [2.57 (s) and 2.54 (s), total 3H], [2.17-2.08 (m), 2.06-1.92 (m), and 1.92-1.73 (m), total 4H], [1.44 (d, J = 6.9 Hz) and 1.41 (d, J = 6.9 Hz), total 3H]; 498.1 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 50 | Alternate Synthesis of Examples 3 and 4[24]; P28 | 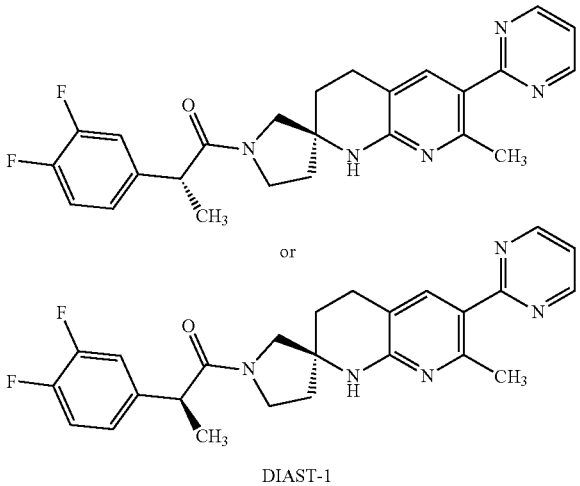 [SMILES: Cc1nc2c(cc1-c1ncccn1)CC[C@@]1(CCN(C(=O)[C@H](C)c3ccc(F)c(F)c3)C1)N2 ; Cc1nc2c(cc1-c1ncccn1)CC[C@@]1(CCN(C(=O)[C@@H](C)c3ccc(F)c(F)c3)C1)N2]<br>DIAST-1 | 8.84-8.78 (m, 2H), [7.88 (s) and 7.83 (s), total 1H], [7.35-7.19 (m) and 7.19-7.08 (m), total 4H], [4.01 (q, J = 7.0 Hz) and 3.94 (q, J = 6.8 Hz), total 1H], [3.92-3.84 (m), 3.77-3.67 (m), 3.66-3.52 (m), 3.46 (d, component of AB quartet, J = 12.3 Hz), and 3.38-3.3 (m, assumed; partially obscured by solvent peak), total 4H], [2.95-2.69 (m) and 2.56-2.44 (m), total 2H], [2.58 (s) and 2.56 (s), total 3H], 2.15-1.84 (m, 3H), 1.75-1.66 (m, 1H), [1.41 (d, J = 7.1 Hz) and 1.39 (d, J = 7.0 Hz), total 3H]; 450.2 |
| 51 | Alternate Synthesis of Examples 3 and 4[24]; P28 | 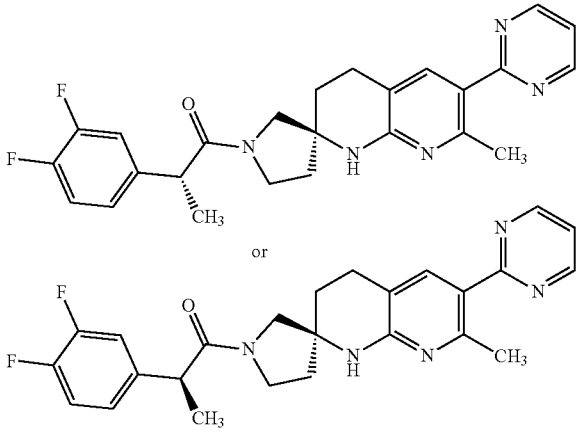<br>DIAST-2 | [8.82 (d, J = 4.8 Hz) and 8.81 (d, J = 4.9 Hz), total 2H], [7.85 (s) and 7.84 (s), total 1H], 7.33-7.28 (m, 1H), 7.28-7.02 (m, 3H), [4.01 (q, J = 6.9 Hz), 3.96-3.87 (m), 3.74-3.62 (m), 3.53-3.45 (m), 3.52 (AB quartet, $J_{AB}$ = 12.2 Hz, $\Delta v_{AB}$ = 57.6 Hz), and 3.36 (d, J = 10.6 Hz), total 5H], 2.92-2.75 (m, 2H), [2.58 (s) and 2.55 (s), total 3H], [2.18-2.09 (m), 2.07-1.92 (m), and 1.92-1.74 (m), total 4H], [1.42 (d, J = 6.9 Hz) and 1.38 (d, J = 6.8 Hz), total 3H]; 450.2 |
| 52 | Alternate Synthesis of Examples 3 and 4[25]; P28 | 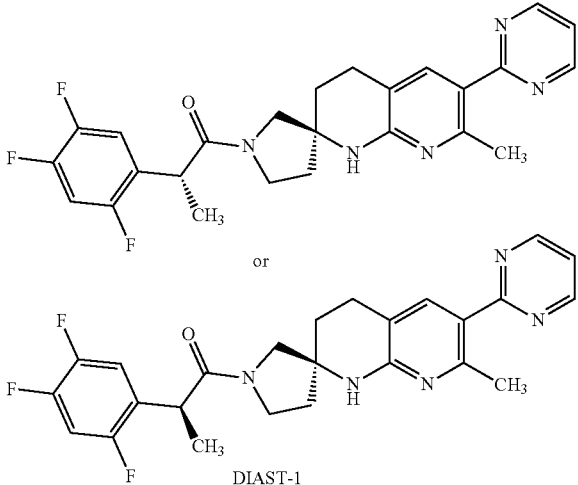<br>DIAST-1 | 8.83-8.79 (m, 2H), [7.84 (s) and 7.82 (s), total 1H], 7.38-7.25 (m, 2H), 7.25-7.15 (m, 1H), [4.28 (q, J = 6.7 Hz) and 4.20 (q, J = 6.9 Hz), total 1H], [3.93-3.84 (m), 3.76-3.55 (m), 3.52 (AB quartet, $J_{AB}$ = 12.2 Hz, $\Delta v_{AB}$ = 32.0 Hz), and 3.39 (d, J = 10.6 Hz), total 4H], [2.95-2.75 (m) and 2.67-2.55 (m), total 2H], [2.57 (s) and 2.55 (s), total 3H], 2.15-1.84 (m, 3H), 1.82-1.74 (m, 1H), [1.43 (d, J = 6.8 Hz) and 1.42 (d, J = 6.8 Hz), total 3H]; 468.2 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 53 | Alternate Synthesis of Examples 3 and 4[25]; P28 | (structure shown; DIAST-2) | 8.86-8.78 (m, 2H), [7.85 (s) and 7.83 (s), total 1H], [7.37-7.15 (m) and 7.08-6.97 (m), total 3H], [4.28 (q, J = 6.9 Hz) and 4.16 (q, J = 6.6 Hz), total 1H], [3.99-3.89 (m), 3.77-3.60 (m), 3.57-3.49 (m), 3.52 (AB quartet, $J_{AB}$ = 12.3 Hz, $\Delta v_{AB}$ = 45.4 Hz), and 3.37 (d, J = 10.6 Hz), total 4H], 2.93-2.75 (m, 2H), [2.58 (s) and 2.55 (s), total 3H], 2.21-1.76 (m, 4H), [1.45 (d, J = 6.9 Hz) and 1.39 (d, J = 6.9 Hz), total 3H]; 468.2 |
| 54 | Alternate Synthesis of Examples 3 and 4; P28 | (structure shown) | [8.82 (d, J = 4.9 Hz) and 8.81 (d, J = 4.9 Hz), total 2H], 7.86 (s, 1H), 7.34-7.28 (m, 1H), 7.13-7.00 (m, 2H), 3.90-3.59 (m, 3H), [3.75 (s), 3.70 (s), and 3.63 (s), total 2H], 3.58-3.46 (m, 1H), 2.96-2.77 (m, 2H), 2.58 (br s, 3H), 2.24-1.84 (m, 4H); 454.2 |
| 55 | Alternate Synthesis of Examples 3 and 4[26]; P28 | (structure shown; DIAST-1) | [8.82 (d, J = 4.9 Hz) and 8.81 (d, J = 4.9 Hz), total 2H], 7.87 (br s, 1H), [7.31 (t, J = 4.9 Hz) and 7.31 (t, J = 4.9 Hz), total 1H], [7.14 (dd, J = 8.9, 6.6 Hz) and 7.07 (dd, J = 8.8, 6.6 Hz), total 2H], 4.02 (q, J = 6.9 Hz), 3.98-3.88 (m), 3.77-3.62 (m), 3.59 (d, component of AB quartet, J = 12.2 Hz), 3.54 (ddd, J = 10.6, 8.4, 4.9 Hz), 3.44 (d, component of AB quartet, J = 12.3 Hz), and 3.40 (d, J = 10.7 Hz), total 5H], 2.92-2.79 (m, 2H), [2.58 (s) and 2.56 (s), total 3H], [2.20-2.10 (m), 2.08-1.93 (m), and 1.93-1.80 (m), total 4H], [1.43 (d, J = 6.9 Hz) and 1.38 (d, J = 6.9 Hz), total 3H]; 468.2 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 56 | Alternate Synthesis of Examples 3 and 4[26]; P28 | 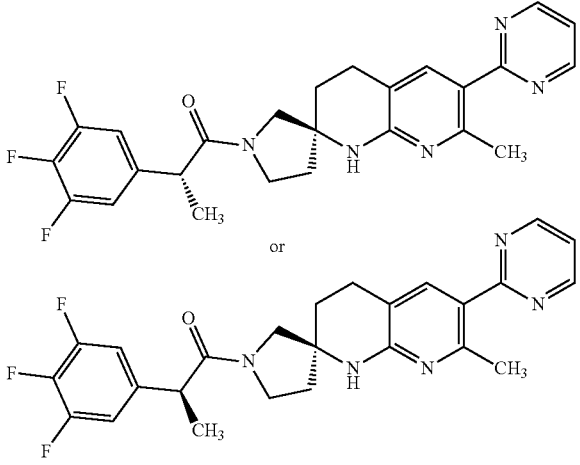 DIAST-2 | [8.82 (d, J = 4.9 Hz) and 8.81 (d, J = 4.9 Hz), total 2H], [7.88 (br s) and 7.85 (br s), total 1H], [7.31 (t, J = 4.9 Hz) and 7.31 (t, J = 4.9 Hz), total 1H], 7.19-7.10 (m, 2H), [4.02 (q, J = 6.9 Hz) and 3.96 (q, J = 6.9 Hz), total 1H], [3.92-3.84 (m), 3.77-3.57 (m), 3.52 (AB quartet, $J_{AB}$ = 12.4 Hz, $\Delta v_{AB}$ = 25.6 Hz), and 3.38 (d, J = 10.7 Hz), total 4H], [2.95-2.75 (m) and 2.68-2.58 (m), total 2H], [2.58 (s) and 2.56 (s), total 3H], [2.15-2.04 (m) and 2.03-1.85 (m), total 3H], 1.81-1.74 (m, 1H), [1.41 (d, J = 7.0 Hz) and 1.39 (d, J = 6.9 Hz), total 3H]; 468.2 |
| 57 | Alternate Synthesis of Examples 3 and 4[27,28]; P28 | 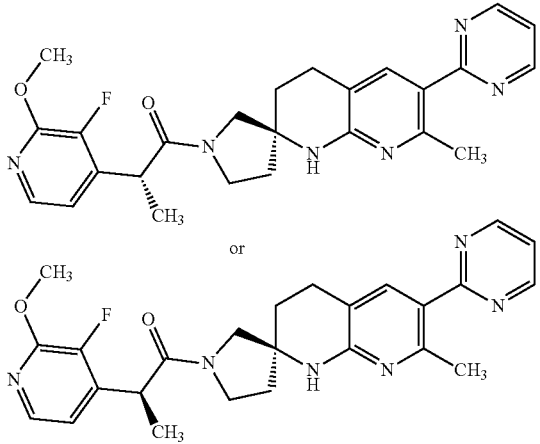 DIAST-1 | [8.81 (d, J = 4.9 Hz) and 8.81 (d, J = 4.9 Hz), total 2H], 7.89 (dd, J = 5.2, 5.2 Hz, 1H), [7.85 (br s) and 7.81 (br s), total 1H], [7.31 (t, J = 4.9 Hz) and 7.30 (t, J = 4.9 Hz), total 1H], [6.95 (dd, J = 5, 5 Hz) and 6.91 (dd, J = 5, 5 Hz), total 1H], [4.35 (q, J = 6.9 Hz) and 4.26 (q, J = 6.9 Hz), total 1H], [4.00 (s) and 3.99 (s), total 3H], [3.92-3.84 (m), 3.76-3.67 (m), 3.67-3.48 (m), 3.52 (AB quartet, $J_{AB}$ = 12.2 Hz, $\Delta v_{AB}$ = 38.4 Hz), and 3.42-3.3 (m, assumed; partially obscured by solvent peak), total 4H], [2.94-2.72 (m) and 2.64-2.50 (m), total 2H], [2.57 (s) and 2.55 (s), total 3H], [2.15-2.03 (m) and 2.03-1.84 (m), total 3H], 1.79-1.72 (m, 1H), [1.44 (d, J = 6.9 Hz) and 1.43 (d, J = 6.9 Hz), total 3H]; 463.2 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 58 | Alternate Synthesis of Examples 3 and 4[27,28]; P28 | (DIAST-2) | [8.81 (d, J = 4.9 Hz) and 8.81 (d, J = 4.9 Hz), total 2H], [7.89 (d, J = 5.3 Hz) and 7.87-7.82 (m), total 2H], 7.30 (t, J = 4.9 Hz, 1H), [6.92 (dd, J = 5, 5 Hz) and 6.88 (dd, J = 5, 5 Hz), total 1H], [4.34 (q, J = 7.0 Hz) and 4.23 (q, J = 6.9 Hz), total 1H], [3.99 (s) and 3.85 (s), total 3H], [3.98-3.88 (m), 3.79-3.61 (m), 3.52 (AB quartet, $J_{AB}$ = 12.1 Hz, $\Delta v_{AB}$ = 45.6 Hz), 3.48-3.40 (m), and 3.35-3.26 (m, assumed; largely obscured by solvent peak), total 4H], 2.92-2.74 (m, 2H), [2.58 (s) and 2.56 (s), total 3H], [2.20-2.10 (m) and 2.10-1.76 (m), total 4H], [1.45 (d, J = 6.9 Hz) and 1.41 (d, J = 6.9 Hz), total 3H]; 463.3 |
| 59 | Alternate Synthesis of Examples 3 and 4[29,30,31]; P28 | ·HCOOH (partial) (DIAST-1) | [8.83 (d, J = 4.9 Hz) and 8.82 (d, J = 4.9 Hz), total 2H], 8.36 (v br s, 0.5 H; assumed to be a partial formate salt), [8.25 (s) and 8.10 (s), total 1H], [7.88 (br s) and 7.87 (br s), total 1H], [7.51 (t, $J_{HF}$ = 72.6 Hz) and 7.49 (t, $J_{HF}$ = 72.6 Hz), total 1H], [7.32 (t, J = 4.9 Hz) and 7.31 (t, J = 4.9 Hz), total 1H], [7.00 (s) and 7.00 (s), total 1H], [4.37 (q, J = 6.9 Hz) and 4.29 (q, J = 6.9 Hz), total 1H], [4.00-3.91 (m), 3.79-3.53 (m), 3.51 (d, component of AB quartet, J = 12.4 Hz), and 3.47 (d, J = 10.6 Hz), total 4H], 2.96-2.77 (m, 2H), [2.59 (s) and 2.55 (s), total 3H], 2.23-1.80 (m, 4H), [1.50 (d, J = 7.0 Hz) and 1.44 (d, J = 6.9 Hz), total 3H]; 515.2 (chlorine isotope pattern observed) |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 60 | Alternate Synthesis of Examples 3 and 4[29,30,31]; P28 | (DIAST-2) | [8.82 (d, J = 4.9 Hz) and 8.82 (d, J = 4.9 Hz), total 2H], 8.30 (br s, 0.5 H; assumed to be a partial formate salt), [8.25 (s) and 8.24 (s), total 1H], [7.92 (br s) and 7.88 (br s), total 1H], [7.52 (t, $J_{HF}$ = 72.6 Hz) and 7.51 (t, $J_{HF}$ = 72.7 Hz), total 1H], [7.32 (t, J = 4.9 Hz) and 7.31 (t, J = 4.9 Hz), total 1H], [7.03 (s) and 6.99 (s), total 1H], [4.39 (q, J = 6.9 Hz) and 4.31 (q, J = 6.9 Hz), total 1H], [3.95-3.86 (m), 3.77-3.60 (m), 3.55 (AB quartet, $J_{AB}$ = 12.4 Hz, $\Delta v_{AB}$ = 13.5 Hz), and 3.46 (d, J = 10.6 Hz), total 4H], [2.96-2.78 (m) and 2.69-2.59 (m), total 2H], [2.60 (s) and 2.59 (s), total 3H], [2.19-2.09 (m) and 2.07-1.79 (m), total 4H], [1.48 (d, J = 6.9 Hz) and 1.47 (d, J = 6.9 Hz), total 3H]; 515.2 (chlorine isotope pattern observed) |
| 61 | Alternate Synthesis of Examples 3 and 4[32,31]; P28, P11 | (DIAST-1) | [8.82 (d, J = 4.9 Hz) and 8.81 (d, J = 4.9 Hz), total 2H], 8.40 (v br s, 0.5 H; assumed to be a partial formate salt), [7.86 (br s) and 7.85 (br s), total 1H], 7.31 (t, J = 4.9 Hz, 1H), [6.83 (t, $J_{HF}$ = 74.1 Hz) and 6.74 (t, $J_{HF}$ = 74.2 Hz), total 1H], [6.78-6.76 (m), 6.64-6.59 (m), and 6.47 (dd, J = 2, 2 Hz), total 2H], 6.70-6.67 (m, 1H), [3.96 (q, J = 7.0 Hz), 3.92-3.82 (m), 3.76-3.55 (m), 3.50-3.40 (m), 3.47 (d, component of AB quartet, J = 12.0 Hz), and 3.38 (d, J = 10.7 Hz), total 5H], [3.80 (s) and 3.69 (s), total 3H], 2.91-2.75 (m, 2H), [2.59 (s) and 2.55 (s), total 3H], [2.18-2.08 (m), 2.08-1.91 (m), and 1.91-1.73 (m), total 4H], [1.42 (d, J = 6.9 Hz) and 1.38 (d, J = 6.9 Hz), total 3H]; 510.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 62 | Alternate Synthesis of Examples 3 and 4[32,31]; P28, P11 | 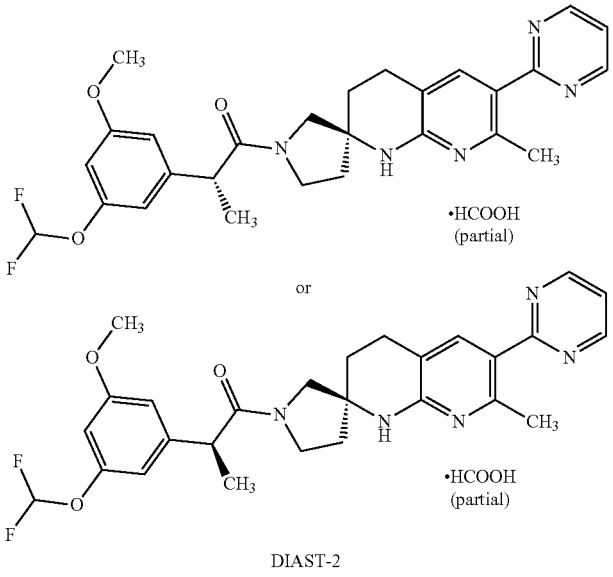 DIAST-2 | [8.81 (d, J = 4.9 Hz) and 8.81 (d, J = 4.9 Hz), total 2H], 8.42 (v br s, 0.5 H; assumed to be a partial formate salt), [7.87 (s) and 7.79 (s), total 1H], [7.31 (t, J = 4.9 Hz) and 7.30 (t, J = 4.9 Hz), total 1H], [6.84 (t, $J_{HF}$ = 74.2 Hz) and 6.82 (t, $J_{HF}$ = 74.1 Hz), total 1H], [6.80-6.77 (m) and 6.77-6.73 (m), total 1H], [6.73-6.70 (m) and 6.68-6.65 (m), total 1H], 6.63-6.60 (m, 1H), [3.97 (q, J = 6.8 Hz), 3.92-3.83 (m), 3.71 (ddd, J = 12.4, 8.5, 5.8 Hz), 3.64-3.50 (m), 3.46 (d, component of AB quartet, J = 12.2 Hz), and 3.35 (d, J = 10.8 Hz), total 5H], [3.81 (s) and 3.79 (s), total 3H], [2.94-2.78 (m), 2.74-2.63 (m), 2.43-2.32 (m), 2.15-2.02 (m), and 2.01-1.83 (m), total 5H], [2.57 (s) and 2.55 (s), total 3H], 1.70-1.62 (m, 1H), 1.45-1.35 (m, 3H); 510.3 |
| 63 | Alternate Synthesis of Examples 3 and 4[33,34,35]; P28 | 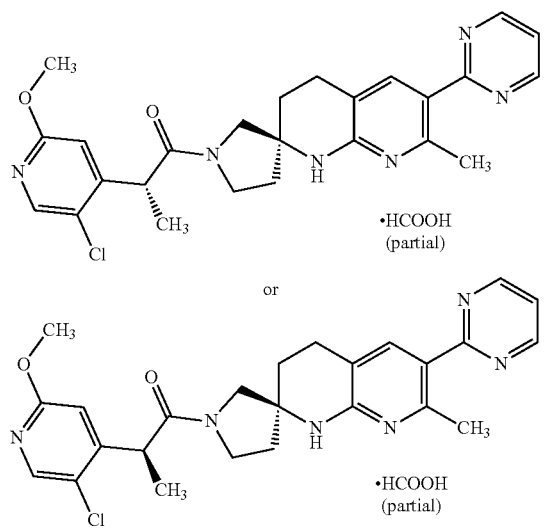 DIAST-1 | 8.84-8.80 (m, 2H), 8.40 (v br s, 0.5 H; assumed to be a partial formate salt), [8.35 (s) and 8.22 (s), total 1H], [7.87 (br s) and 7.86 (br s), total 1H], [7.32 (t, J = 4.9 Hz) and 7.31 (t, J = 4.9 Hz), total 1H], [7.19 (s) and 7.18 (s), total 1H], [4.41 (q, J = 7.0 Hz) and 4.33 (q, J = 6.9 Hz), total 1H], [4.02-3.92 (m) and 3.79-3.47 (m), total 4H], 2.96-2.77 (m, 2H), [2.59 (s) and 2.55 (s), total 3H], [2.24-2.15 (m), 2.15-2.04 (m), and 2.04-1.80 (m), total 4H], [1.52 (d, J = 7.0 Hz) and 1.46 (d, J = 6.9 Hz), total 3H]; 533.2 (chlorine isotope pattern observed) |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 64 | Alternate Synthesis of Examples 3 and 4[33,34,35]; P28 | 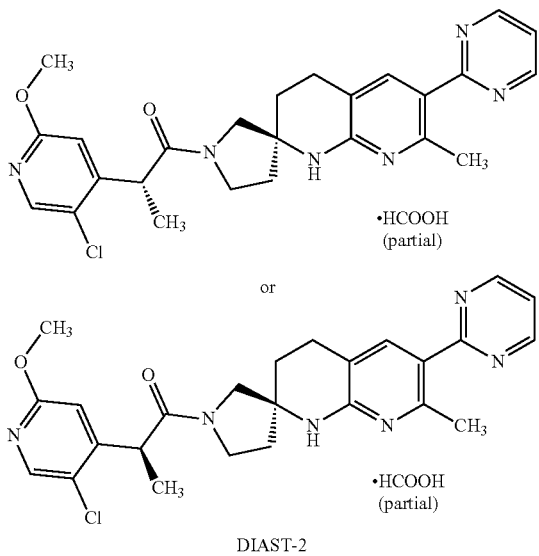 DIAST-2 | [8.82 (d, J = 4.9 Hz) and 8.82 (d, J = 4.9 Hz), total 2H], [8.36 (s) and 8.34 (s), total 1H], 8.29 (v br s, 0.75 H; assumed to be a partial formate salt), [7.93 (s) and 7.89 (s), total 1H], [7.32 (t, J = 4.9 Hz) and 7.32 (t, J = 4.9 Hz), total 1H], [7.22 (s) and 7.17 (s), total 1H], [4.43 (q, J = 6.9 Hz) and 4.35 (q, J = 6.9 Hz), total 1H], [3.97-3.88 (m), 3.77-3.60 (m), 3.60-3.52 (m), and 3.50 (d, component of AB quartet, J = 10.3 Hz), total 4H], [2.97-2.79 (m) and 2.72-2.60 (m), total 2H], [2.60 (s) and 2.59 (s), total 3H], [2.21-2.09 (m) and 2.09-1.80 (m), total 4H], [1.50 (d, J = 6.9 Hz) and 1.49 (d, J = 7.0 Hz), total 3H]; 533.2 (chlorine isotope pattern observed) |
| 65 | Alternate Synthesis of Examples 3 and 4[36,31]; C77 | 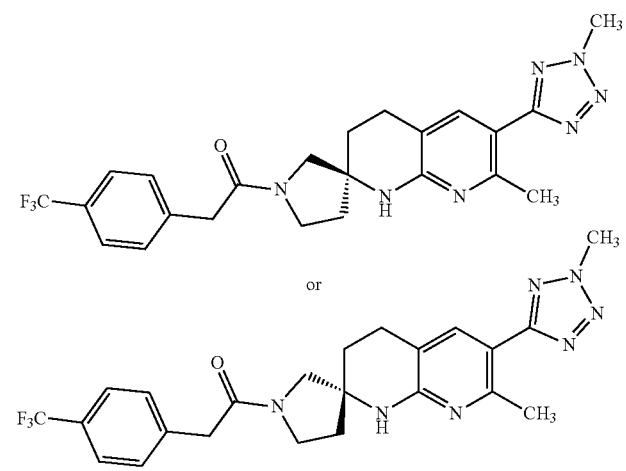 ENT-1 | [7.94 (s) and 7.91 (s), total 1H], [7.64 (d, J = 8.0 Hz) and 7.61 (d, J = 8.0 Hz), total 2H], [7.49 (d, J = 8.2 Hz) and 7.46 (d, J = 8.1 Hz), total 2H], [4.40 (s) and 4.40 (s), total 3H], [3.92-3.75 (m), 3.86 (s), 3.81 (s), 3.75-3.63 (m), 3.63 (s), and 3.55 (AB quartet, J$_{AB}$ = 12.2 Hz, Δν$_{AB}$ = 15.9 Hz), total 6H], 2.95-2.72 (m, 2H), 2.63 (br s, 3H), [2.24-2.00 (m) and 2.00-1.83 (m), total 4H]; 472.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 66 | Alternate Synthesis of Examples 3 and 4[36,31]; C77 | 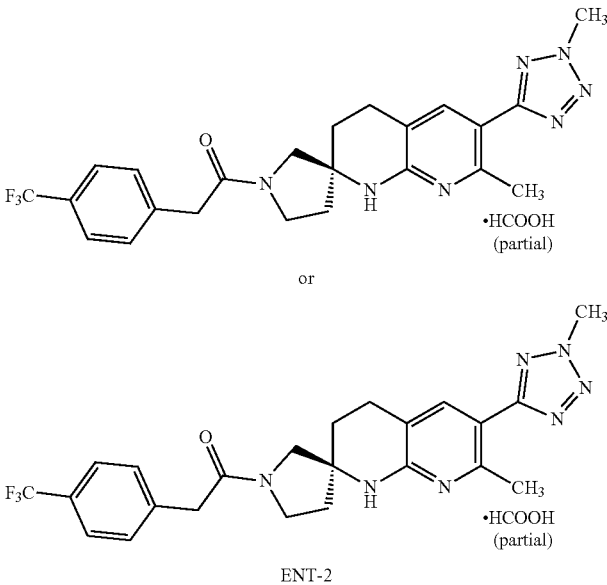 [SMILES: Cc1nc2c(cc1-c1nnn(C)n1)CC[C@@]1(CCN(C(=O)Cc3ccc(C(F)(F)F)cc3)C1)N2 ; "or" ; Cc1nc2c(cc1-c1nnn(C)n1)CC[C@@]1(CCN(C(=O)Cc3ccc(C(F)(F)F)cc3)C1)N2]<br>or<br>ENT-2 | 8.42 (br s, 0.8 H; assumed to be a partial formate salt), [7.88 (s) and 7.86 (s), total 1H], [7.64 (d, J = 8.1 Hz) and 7.60 (d, J = 8.1 Hz), total 2H], [7.49 (d, J = 8.1 Hz) and 7.46 (d, J = 8.1 Hz), total 2H], [4.40 (s) and 4.39 (s), total 3H], [3.91-3.75 (m), 3.85 (s), 3.81 (s), 3.75-3.62 (m), 3.61 (br s), and 3.53 (AB quartet, $J_{AB}$ = 12.2 Hz, $\Delta v_{AB}$ = 16.9 Hz), total 6H], 2.95-2.69 (m, 2H), 2.60 (s, 3H), [2.22-2.01 (m) and 2.01-1.81 (m), total 4H]; 472.3 |
| 67 | Example 18[37]; P27, P7 | 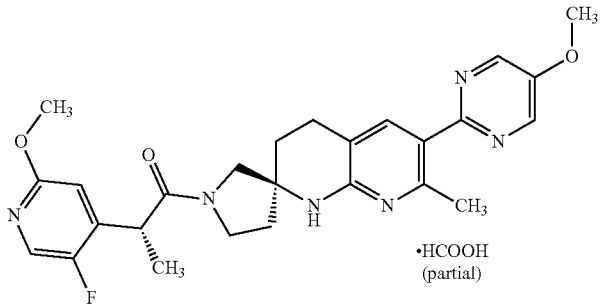 | [8.54 (s) and 8.54 (s), total 2H], 8.39 (v br s, 0.8 H; assumed to be a partial formate salt), [8.00 (d, J = 1.6 Hz) and 7.98 (d, J = 1.7 Hz), total 1H], [7.84 (s) and 7.79 (s), total 1H], [6.78 (d, J = 4.9 Hz) and 6.73 (d, J = 5.0 Hz), total 1H], [4.28 (q, J = 6.9 Hz) and 4.19 (q, J = 6.9 Hz), total 1H], [3.98 (s) and 3.98 (s), total 3H], [3.93-3.82 (m), 3.77-3.54 (m), 3.49 (d, component of AB quartet, J = 12.4 Hz), and 3.39 (d, J = 10.6 Hz), total 4H], [3.88 (s) and 3.88 (s), total 3H], [2.95-2.74 (m) and 2.64-2.50 (m), total 2H], [2.55 (s) and 2.54 (s), total 3H], [2.17-2.06 (m), 2.05-1.84 (m), and 1.84-1.75 (m), total 4H], [1.45 (d, J = 6.9 Hz) and 1.44 (d, J = 6.9 Hz), total 3H]; 493.3 |
| 68 | Example 67; P27, P7 | 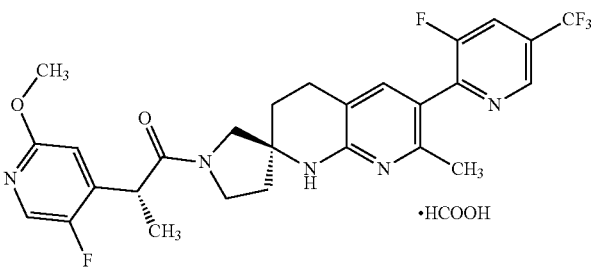 [SMILES: COc1cc([C@@H](C)C(=O)N2CC[C@@]3(CCc4cc(-c5ncc(C(F)(F)F)cc5F)c(C)nc4N3)C2)c(F)cn1 ; "·HCOOH"] | 8.78 (s, 1H), 8.51 (v br s, 1H), 8.11-8.04 (m, 1H), [8.00 (d, J = 1.7 Hz,) and 7.98 (d, J = 1.7 Hz), total 1H], [7.39 (br s) and 7.36 (br s), total 1H], [6.79 (d, J = 4.9 Hz) and 6.73 (d, J = 4.9 Hz), total 1H], [4.28 (q, J = 6.9 Hz) and 4.20 (q, J = 6.9 Hz), total 1H], [3.94-3.84 (m), 3.77-3.68 (m), 3.68-3.54 (m), 3.49 (d, component of AB quartet, J = 12.2 Hz), and 3.40 (d, J = 10.6 Hz), total 4H], [3.89 (s) and 3.88 (s), total 3H], [2.93-2.73 (m) and 2.64-2.52 (m), total 2H], [2.26 (s) and 2.23 (s), total 3H], [2.17-2.07 (m), 2.05-1.84 (m), and 1.83-1.75 (m), total 4H], [1.45 (d, J = 6.9 Hz) and 1.44 (d, J = 6.9 Hz), total 3H]; 548.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 69 | Example 67; P27, P7 | (structure with ·CF$_3$COOH salt) | 8.03-7.95 (m, 3H), [7.90 (s) and 7.87 (s), total 1H], [6.79 (d, J = 4.9 Hz) and 6.73 (d, J = 4.9 Hz), total 1H], 4.33-4.19 (m, 1H), [4.00-3.81 (m), 3.80-3.59 (m), and 3.44 (d, J = 11.0 Hz), total 4H], 3.88 (s, 3H), [3.07-2.87 (m) and 2.84-2.72 (m), total 2H], [2.47 (s) and 2.45 (s), total 3H], [2.33-2.19 (m) and 2.15-1.88 (m), total 4H], [1.46 (d, J = 6.9 Hz) and 1.46 (d, J = 6.9 Hz), total 3H]; 548.3 |
| 70 | Example 67; P27, P7 | (structure with ·HCOOH (partial)) | 8.55-8.52 (m, 1H), 8.50 (br s, 1H), 8.37 (v br s, 0.6 H; assumed to be a partial formate salt), [7.99 (d, J = 1.7 Hz) and 7.98 (d, J = 1.7 Hz), total 1H], [7.45 (s) and 7.41 (s), total 1H], [6.78 (d, J = 4.9 Hz) and 6.73 (d, J = 4.9 Hz), total 1H], [4.27 (q, J = 6.9 Hz) and 4.19 (q, J = 6.9 Hz), total 1H], [3.94-3.83 (m), 3.77-3.53 (m), 3.48 (d, component of AB quartet, J = 12.3 Hz), and 3.38 (d, J = 10.5 Hz), total 4H], [3.88 (s) and 3.88 (s), total 3H], [2.94-2.73 (m) and 2.64-2.52 (m), total 2H], [2.38 (s) and 2.36 (s), total 3H], 2.24-2.15 (m, 1H), [2.15-2.05 (m) and 2.04-1.83 (m), total 3H], 1.83-1.74 (m, 1H), [1.45 (d, J = 6.8 Hz) and 1.44 (d, J = 6.9 Hz), total 3H], 1.14-1.03 (m, 4H); 503.3 |
| 71 | Example 67; P27, P7 | (structure with ·HCOOH (partial)) | 9.01 (br s, 1H), 8.90 (s, 1H), 8.40 (v br s, 0.4 H; assumed to be a partial formate salt), [8.00 (d, J = 1.7 Hz) and 7.98 (d, J = 1.7 Hz), total 1H], [7.62 (s) and 7.59 (s), total 1H], [6.78 (d, J = 4.9 Hz) and 6.73 (d, J = 4.9 Hz), total 1H], [4.28 (q, J = 6.9 Hz) and 4.20 (q, J = 6.8 Hz), total 1H], [3.93-3.84 (m), 3.77-3.68 (m), 3.68-3.55 (m), 3.48 (d, component of AB quartet, J = 12.3 Hz), and 3.39 (d, J = 10.6 Hz), total 4H], [3.88 (s) and 3.88 (s), total 3H], [2.96-2.76 (m) and 2.66-2.55 (m), total 2H], [2.49 (s) and 2.47 (s), total 3H], [2.17-2.07 (m), 2.05-1.85 (m), and 1.84-1.74 (m), total 4H], [1.45 (d, J = 6.9 Hz) and 1.44 (d, J = 6.9 Hz), total 3H]; 531.3 |
| 72 | Example 67; P27, P7 | (structure) | 9.30 (s, 1H), 8.02-7.96 (m, 2H), [7.71 (s) and 7.69 (s), total 1H], [6.78 (d, J = 4.9 Hz) and 6.73 (d, J = 4.9 Hz), total 1H], [4.27 (q, J = 6.9 Hz) and 4.19 (q, J = 6.8 Hz), total 1H], [3.93-3.84 (m), 3.77-3.55 (m), 3.49 (d, component of AB quartet, J = 12.3 Hz), and 3.39 (d, J = 10.6 Hz), total 4H], [3.88 (s) and 3.88 (s), total 3H], [2.97-2.76 (m) and 2.66-2.53 (m), total 2H], [2.56 (s) and 2.54 (s), total 3H], [2.18-2.07 (m), 2.05-1.84 (m), and 1.84-1.75 (m), total 4H], [1.45 (d, J = 6.9 Hz) and 1.44 (d, J = 6.9 Hz), total 3H]; 531.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 73 | Alternate Synthesis of Examples 3 and 4; P28 | 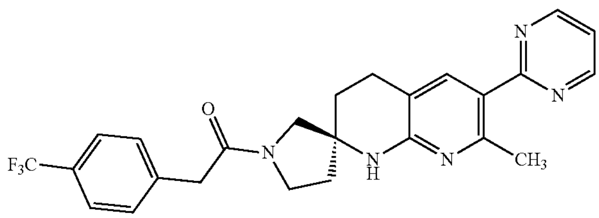 [SMILES: Cc1nc2c(cc1-c1ncccn1)CC[C@@]1(CCN(C(=O)Cc3ccc(C(F)(F)F)cc3)C1)N2] | [8.82 (d, J = 4.9 Hz) and 8.81 (d, J = 4.9 Hz), total 2H], [7.87 (s) and 7.85 (s), total 1H], [7.64 (d, J = 8.2 Hz) and 7.61 (d, J = 8.4 Hz), total 2H], [7.49 (d, J = 8.2 Hz) and 7.46 (d, J = 8.1 Hz), total 2H], [7.31 (t, J = 4.9 Hz) and 7.31 (t, J = 4.9 Hz), total 1H], [3.91-3.75 (m), 3.86 (s), 3.81 (s), 3.75-3.62 (m), 3.62 (s), and 3.54 (AB quartet, J$_{AB}$ = 12.2 Hz, Δv$_{AB}$ = 18.3 Hz), total 6H], 2.95-2.70 (m, 2H), 2.58 (s, 3H), 2.23-2.01 (m, 2H), 2.01-1.82 (m, 2H); 468.2 |
| 74 | 14$^{38}$ | 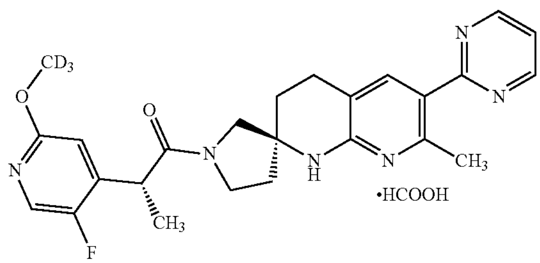 [SMILES: [2H]C([2H])([2H])Oc1cc([C@@H](C)C(=O)N2CC[C@@]3(CCc4cc(-c5ncccn5)c(C)nc4N3)C2)c(F)cn1 ; "·HCOOH"] | 8.82 (br d, J = 5 Hz, 2H), 8.6 (v br s, uncertain integration; assumed to be formate salt), [7.99 (d, J = 1.7 Hz) and 7.98 (d, J = 1.7 Hz), total 1H], [7.91 (s) and 7.86 (s), total 1H], [7.32 (t, J = 4.9 Hz) and 7.31 (t, J = 4.9 Hz), total 1H], [6.78 (d, J = 4.9 Hz) and 6.73 (d, J = 4.9 Hz), total 1H], [4.27 (q, J = 6.9 Hz) and 4.20 (q, J = 6.9 Hz), total 1H], [3.93-3.83 (m), 3.77-3.54 (m), 3.50 (d, component of AB quartet, J = 12.4 Hz), and 3.40 (d, J = 10.6 Hz), total 4H], [2.96-2.75 (m) and 2.66-2.53 (m), total 2H], [2.59 (s) and 2.58 (s), total 3H], [2.18-2.07 (m) and 2.05-1.85 (m), total 3H], 1.84-1.75 (m, 1H), [1.45 (d, J = 6.9 Hz) and 1.44 (d, J = 6.9 Hz), total 3H]; 466.3 |
| 75 | Alternate Synthesis of Examples 3 and 4$^{39}$; P28, P12 | or<br><br>DIAST-1 | [8.82 (d, J = 4.8 Hz) and 8.81 (d, J = 4.9 Hz), total 2H], [8.22-8.20 (m) and 8.11-8.08 (m), total 1H], 7.85 (br s, 1H), [7.31 (t, J = 4.9 Hz) and 7.31 (t, J = 4.9 Hz), total 1H], [7.21 (d, J = 4.7 Hz) and 7.20 (d, J = 4.7 Hz), total 1H], [4.38 (q, J = 7.0 Hz) and 4.30 (q, J = 7.0 Hz), total 1H], [4.03-3.92 (m), 3.77-3.54 (m), and 3.52-3.45 (m), total 4H], 2.96-2.77 (m, 2H), [2.58 (s) and 2.55 (s), total 3H], [2.24-2.14 (m), 2.14-1.95 (m), and 1.95-1.80 (m), total 4H], [1.53 (d, J = 6.9 Hz) and 1.48 (d, J = 6.9 Hz), total 3H]; 517.2 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 76 | Alternate Synthesis of Examples 3 and 4[39]; P28, P12 | 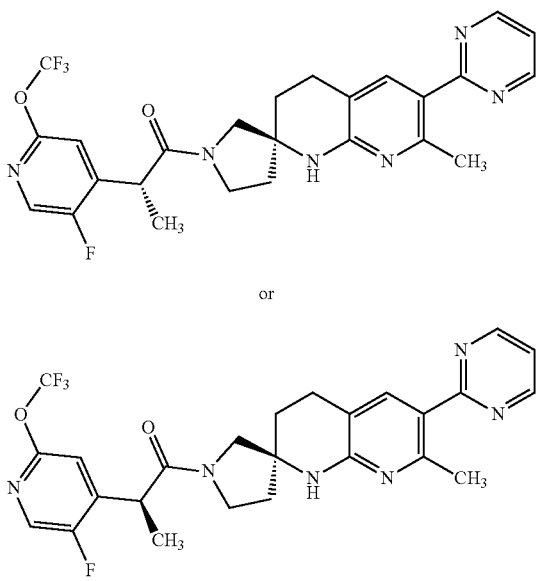 DIAST-2 | [8.82 (d, J = 4.9 Hz) and 8.81 (d, J = 4.9 Hz), total 2H], [8.23-8.21 (m) and 8.21-8.19 (m), total 1H], [7.85 (s) and 7.83 (s), total 1H], [7.31 (t, J = 4.9 Hz) and 7.30 (t, J = 4.9 Hz), total 1H], [7.24 (d, J = 4.7 Hz) and 7.20 (d, J = 4.7 Hz), total 1H], [4.39 (q, J = 7.0 Hz) and 4.32 (q, J = 6.9 Hz), total 1H], [3.97-3.88 (m) and 3.78-3.46 (m), total 4H], [2.95-2.78 (m) and 2.75-2.63 (m), total 2H], [2.58 (s) and 2.55 (s), total 3H], [2.19-2.07 (m) and 2.07-1.80 (m), total 4H], [1.51 (d, J = 6.9 Hz) and 1.49 (d, J = 6.9 Hz), total 3H]; 517.3 |
| 77 | Alternate Synthesis of Examples 3 and 4[40,31]; P28, P13 | 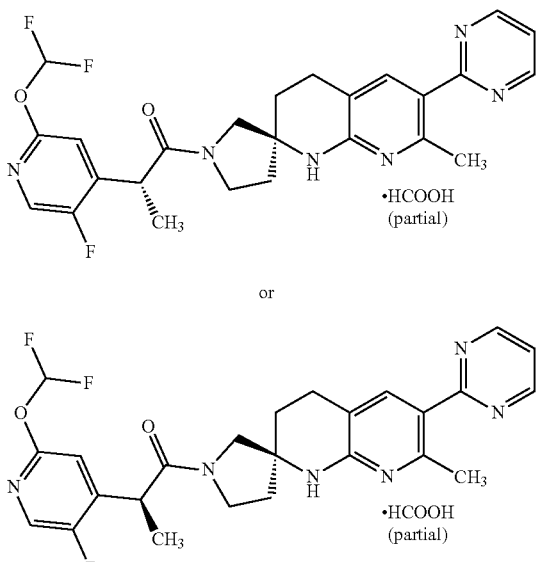 DIAST-1 | [8.83 (d, J = 4.9 Hz) and 8.82 (d, J = 4.9 Hz), total 2H], 8.33 (br s, 0.4 H; assumed to be a partial formate salt), [8.09 (d, J = 1.4 Hz) and 7.97 (d, J = 1.4 Hz), total 1H], [7.90 (s) and 7.88 (s), total 1H], [7.47 (t, $J_{HF}$ = 73.0 Hz) and 7.44 (t, $J_{HF}$ = 73.0 Hz), total 1H], [7.32 (t, J = 4.9 Hz) and 7.31 (t, J = 4.9 Hz), total 1H], [7.00 (d, J = 4.8 Hz) and 6.99 (d, J = 4.8 Hz), total 1H], [4.34 (q, J = 6.9 Hz) and 4.25 (q, J = 6.9 Hz), total 1H], [4.02-3.92 (m), 3.77-3.55 (m), 3.49 (d, component of AB quartet, J = 12.4 Hz), and 3.46 (d, component of AB quartet, J = 10.6 Hz), total 4H], 2.95-2.78 (m, 2H), [2.60 (s) and 2.56 (s), total 3H], [2.24-2.14 (m) and 2.14-1.81 (m), total 4H], [1.51 (d, J = 7.0 Hz) and 1.46 (d, J = 6.9 Hz), total 3H]; 499.2 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 78 | Alternate Synthesis of Examples 3 and 4[40,31]; P28, P13 | [structure: DIAST-2 or alternate, ·HCOOH salts] | [8.82 (d, J = 4.9 Hz) and 8.82 (d, J = 4.9 Hz), total 2H], 8.32 (br s, 1H), [8.11 (d, J = 1.4 Hz) and 8.09 (d, J = 1.4 Hz), total 1H], [7.91 (s) and 7.88 (s), total 1H], 7.47 (t, J$_{HF}$ = 73.0 Hz, 1H), [7.32 (t, J = 4.9 Hz) and 7.31 (t, J = 4.9 Hz), total 1H], [7.03 (d, J = 4.8 Hz) and 6.98 (d, J = 4.8 Hz), total 1H], [4.35 (q, J = 6.9 Hz) and 4.28 (q, J = 6.9 Hz), total 1H], [3.96-3.87 (m), 3.78-3.60 (m), 3.54 (AB quartet, J$_{AB}$ = 12.4 Hz, Δv$_{AB}$ = 19.8 Hz), and 3.47 (d, component of AB quartet, J = 10.6 Hz), total 4H], [2.96-2.79 (m) and 2.73-2.61 (m), total 2H], [2.60 (s) and 2.58 (s), total 3H], [2.19-2.08 (m) and 2.07-1.78 (m), total 4H], [1.49 (d, J = 6.9 Hz) and 1.48 (d, J = 6.9 Hz), total 3H]; 499.3 |
| 79 | Alternate Synthesis of Examples 3 and 4[41,42]; P28 | [structure: DIAST-1 or alternate] | 8.84-8.80 (m, 2H), [8.61 (br s) and 8.49 (br s), total 1H], [7.91 (d, J = 5.4 Hz) and 7.90 (d, J = 5.4 Hz), total 1H], 7.85 (br s, 1H), [7.32 (t, J = 4.9 Hz) and 7.31 (t, J = 4.9 Hz), total 1H], [4.46 (q, J = 7.0 Hz) and 4.39 (q, J = 6.9 Hz), total 1H], [4.04-3.95 (m), 3.75 (d, J = 10.6 Hz), 3.73-3.61 (m), 3.53 (AB quartet, J$_{AB}$ = 12.3 Hz, Δv$_{AB}$ = 39.4 Hz), and 3.52 (d, J = 10.5 Hz), total 4H], 2.96-2.76 (m, 2H), [2.58 (s) and 2.54 (s), total 3H], [2.23-2.14 (m), 2.14-1.96 (m), and 1.96-1.80 (m), total 4H], [1.56 (d, J = 7.0 Hz) and 1.51 (d, J = 7.0 Hz), total 3H]; 501.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 80 | Alternate Synthesis of Examples 3 and 4[41,42,31]; P28 | (structure shown; ·HCOOH (partial)) or (structure shown; ·HCOOH (partial)) DIAST-2 | [8.83 (d, J = 4.9 Hz) and 8.82 (d, J = 4.9 Hz), total 2H], [8.62 (br s) and 8.60 (br s), total 1H], 8.23 (v br s, 0.5 H; assumed to be a partial formate salt), 7.98-7.85 (m, 2H), [7.32 (t, J = 4.9 Hz) and 7.32 (t, J = 4.9 Hz), total 1H], [4.47 (q, J = 7.0 Hz) and 4.40 (q, J = 7.0 Hz), total 1H], [4.01-3.91 (m), 3.79-3.68 (m), and 3.68-3.49 (m), total 4H], [2.97-2.80 (m) and 2.77-2.66 (m), total 2H], [2.61 (s) and 2.59 (s), total 3H], [2.21-2.09 (m) and 2.09-1.79 (m), total 4H], [1.54 (d, J = 6.9 Hz) and 1.53 (d, J = 6.9 Hz), total 3H]; 501.2 |
| 81 | Synthesis of Examples 3 and 4[43,31]; P28, P14 | (structure shown; ·2 HCOOH) or (structure shown; ·2 HCOOH) DIAST-1 | [8.82 (d, J = 4.9 Hz) and 8.81 (d, J = 4.9 Hz), total 2H], 8.42 (br s, 2H), [7.93 (d, J = 1.8 Hz) and 7.92 (d, J = 1.8 Hz), total 1H], [7.90 (s) and 7.85 (s), total 1H], [7.31 (t, J = 4.9 Hz) and 7.31 (t, J = 4.9 Hz), total 1H], [6.54 (d, J = 4.8 Hz) and 6.50 (d, J = 4.8 Hz), total 1H], [4.24 (q, J = 6.9 Hz) and 4.15 (q, J = 6.8 Hz), total 1H], [3.93-3.84 (m), 3.78-3.68 (m), 3.67-3.52 (m), 3.51 (d, component of AB quartet, J = 12.2 Hz), and 3.36 (d, J = 10.8 Hz), total 4H], [3.04 (s) and 3.04 (s), total 6H], [2.95-2.82 (m), 2.82-2.71 (m), and 2.55-2.45 (m), total 2H], [2.59 (s) and 2.57 (s), total 3H], [2.19-2.06 (m), 2.04-1.94 (m), and 1.94-1.85 (m), total 3H], 1.81-1.71 (m, 1H), [1.44 (d, J = 6.9 Hz) and 1.44 (d, J = 6.9 Hz), total 3H]; 476.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 82 | Alternate Synthesis of Examples 3 and 4[43]; P28, P14 | 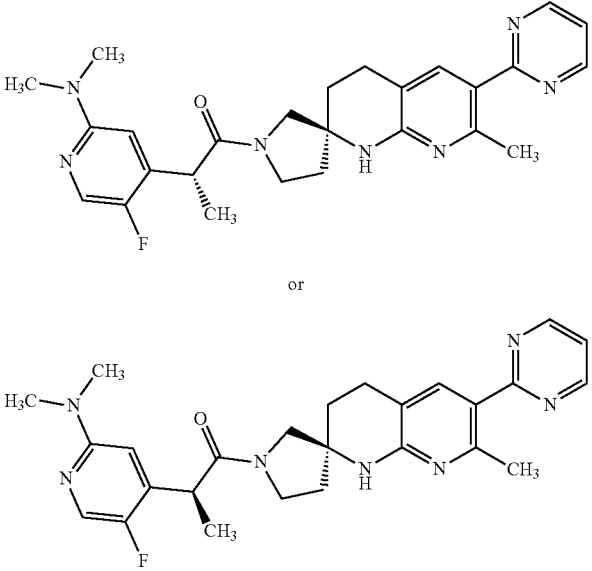<br>DIAST-2 | [8.82 (d, J = 4.9 Hz) and 8.81 (d, J = 4.9 Hz), total 2H], [7.92 (d, J = 1.8 Hz) and 7.79 (d, J = 1.9 Hz), total 1H], 7.84 (br s, 1H), [7.31 (t, J = 4.9 Hz) and 7.30 (t, J = 4.9 Hz), total 1H], 6.53 (d, J = 4.8 Hz, 1H), [4.23 (q, J = 6.9 Hz) and 4.14 (q, J = 6.9 Hz), total 1H], [3.97-3.88 (m), 3.73-3.63 (m), 3.54 (AB quartet, $J_{AB}$ = 12.2 Hz, $\Delta v_{AB}$ = 33.9 Hz), 3.51-3.43 (m), and 3.38 (d, J = 10.5 Hz), total 4H], [3.04 (s) and 3.02 (s), total 6H], 2.94-2.77 (m, 2H), [2.58 (s) and 2.55 (s), total 3H], [2.20-2.10 (m), 2.09-1.93 (m), and 1.93-1.76 (m), total 4H], [1.46 (d, J = 6.9 Hz) and 1.43 (d, J = 6.9 Hz), total 3H]; 476.3 |
| 83 | Alternate Synthesis of Examples 3 and 4[44,45]; P28 | 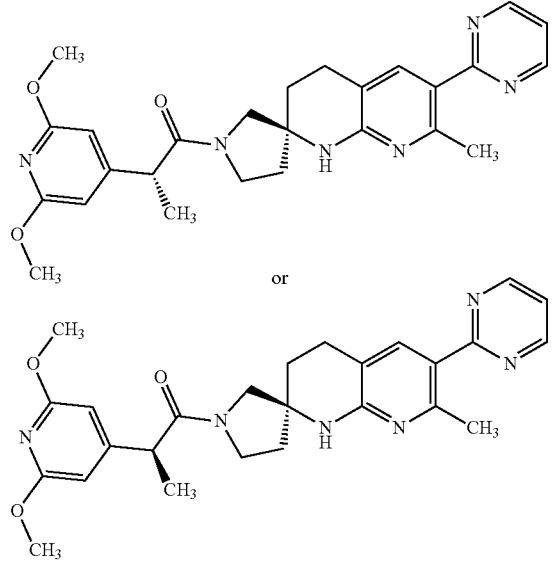<br>DIAST-1 | [8.81 (d, J = 4.9 Hz) and 8.81 (d, J = 4.9 Hz), total 2H], [7.89 (s) and 7.82 (s), total 1H], [7.31 (t, J = 4.9 Hz) and 7.31 (t, J = 4.9 Hz), total 1H], [6.30 (s) and 6.26 (s), total 2H], 3.95-3.80 (m, 1H), [3.90 (s) and 3.89 (s), total 6H], [3.75-3.65 (m), 3.64-3.49 (m), 3.46 (d, component of AB quartet, J = 12.3 Hz), and 3.35-3.3 (m, assumed; largely obscured by solvent peak), total 4H], [2.94-2.78 (m), 2.77-2.67 (m), and 2.50-2.39 (m), total 2H], [2.58 (s) and 2.56 (s), total 3H], [2.14-2.03 (m), 2.01-1.83 (m), and 1.74-1.67 (m), total 4H], 1.41-1.34 (m, 3H); 475.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 84 | Alternate Synthesis of Examples 3 and 4[44,45]; P28 | 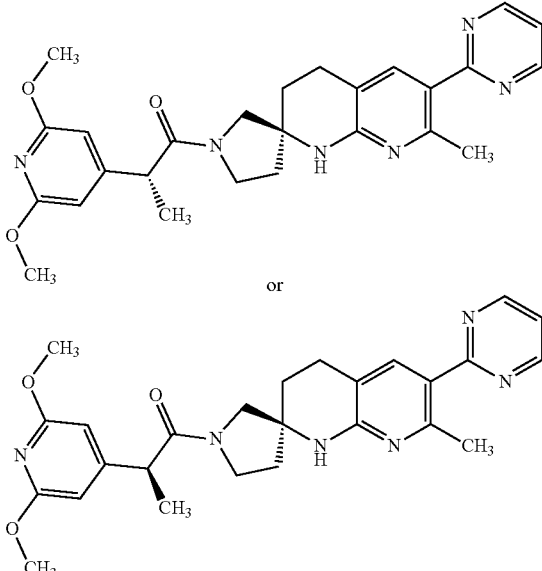 | [8.81 (d, J = 4.9 Hz) and 8.81 (d, J = 4.9 Hz), total 2H], [7.85 (s) and 7.84 (s), total 1H], 7.30 (t, J = 4.9 Hz, 1H), [6.27 (s) and 6.22 (s), total 2H], 3.95-3.78 (m, 1H), [3.89 (s) and 3.81 (s), total 6H], [3.73-3.54 (m), 3.50-3.39 (m), and 3.38-3.3 (m, assumed; partially obscured by solvent peak), total 4H], 2.91-2.76 (m, 2H), [2.57 (s) and 2.55 (s), total 3H], [2.16-1.91 (m) and 1.91-1.75 (m), total 4H], [1.39 (d, J = 6.9 Hz) and 1.36 (d, J = 6.9 Hz), total 3H]; 475.3 |
| 85 | Examples 5 and 6[46]; P28, P15 | 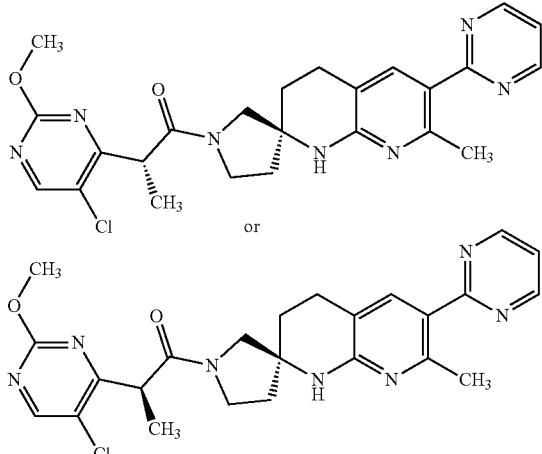 | [8.82 (d, J = 4.9 Hz) and 8.81 (d, J = 4.9 Hz), total 2H], [8.51 (s) and 8.40 (s), total 1H], [7.87 (br s) and 7.85 (br s), total 1H], [7.31 (t, J = 4.9 Hz) and 7.31 (t, J = 4.9 Hz), total 1H], [4.42 (q, J = 7.0 Hz) and 4.35 (q, J = 7.0 Hz), total 1H], 4.01 (s, 3H), [3.94-3.85 (m), 3.80-3.70 (m), 3.70-3.60 (m), 3.60-3.49 (m), and 3.44 (d, J = 10.5 Hz), total 4H], 2.96-2.78 (m, 2H), [2.59 (s) and 2.57 (s), total 3H], [2.25-2.16 (m), 2.15-1.96 (m), and 1.96-1.81 (m), total 4H], [1.56 (d, J = 7.0 Hz) and 1.50 (d, J = 6.9 Hz), total 3H]; 480.3 (chlorine isotope pattern observed) |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 86 | Examples 5 and 6[46]; P28, P15 | 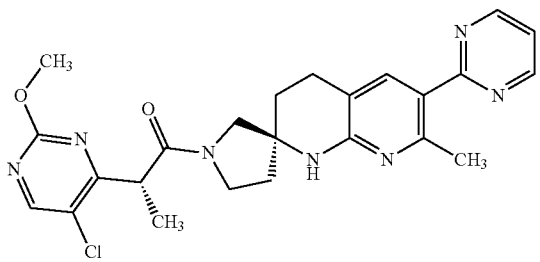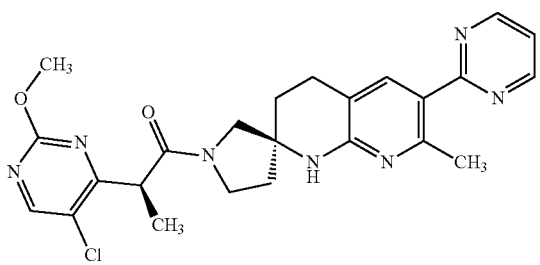DIAST-2 | [8.81 (d, J = 4.9 Hz) and 8.81 (d, J = 4.9 Hz), total 2H], [8.52 (s) and 8.50 (s), total 1H], [7.86 (br s) and 7.83 (br s), total 1H], [7.31 (t, J = 4.9 Hz) and 7.31 (t, J = 4.9 Hz), total 1H], [4.43 (q, J = 6.9 Hz) and 4.37 (q, J = 7.0 Hz), total 1H], 4.01 (s, 3H), [3.90-3.81 (m), 3.77-3.51 (m), and 3.44 (d, component of AB quartet, J = 10.6 Hz), total 4H], [2.95-2.78 (m) and 2.69-2.57 (m), total 2H], [2.58 (s) and 2.57 (s), total 3H], [2.20-2.09 (m) and 2.08-1.78 (m), total 4H], [1.53 (d, J = 6.9 Hz) and 1.52 (d, J = 6.9 Hz), total 3H]; 480.2 (chlorine isotope pattern observed) |
| 87 | Examples 3 and 4[47,48]; C72 | 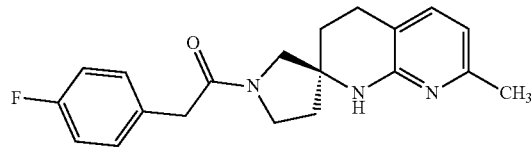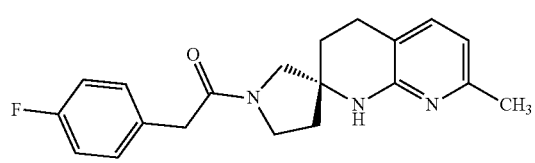ENT-1 | 1.82 minutes[49]; 362.5 [M + Na$^+$] |
| 88 | Examples 3 and 4[47,48]; C72 | 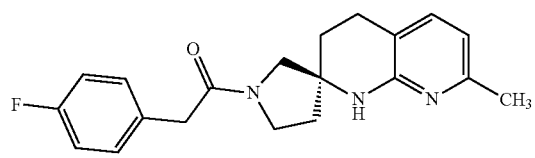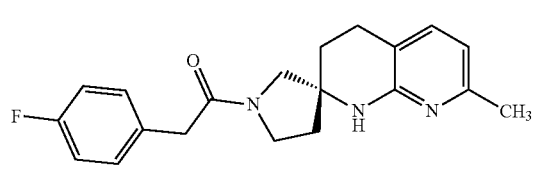ENT-2 | 2.33 minutes[49]; 362.5 [M + Na$^+$] |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 89 | Examples 3 and 4; C81 | 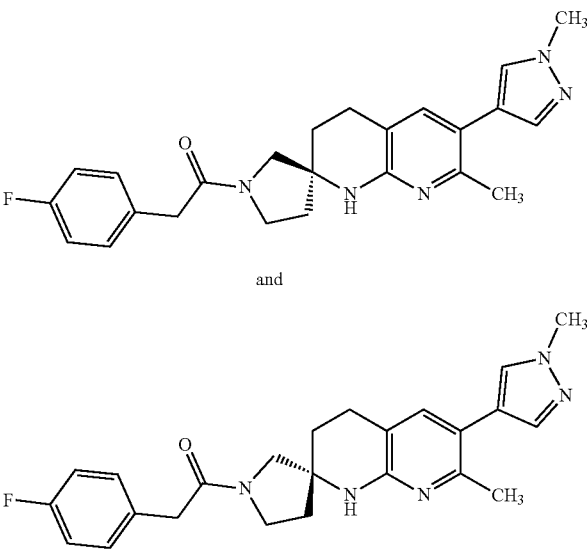 [SMILES: Cc1nc2c(cc1-c1cnn(C)c1)CC[C@@]1(CCN(C(=O)Cc3ccc(F)cc3)C1)N2 ; Cc1nc2c(cc1-c1cnn(C)c1)CC[C@]1(CCN(C(=O)Cc3ccc(F)cc3)C1)N2] and | 1.87 minutes[50]; 420.6 |
| 90 | Example 14[51]; C81 | 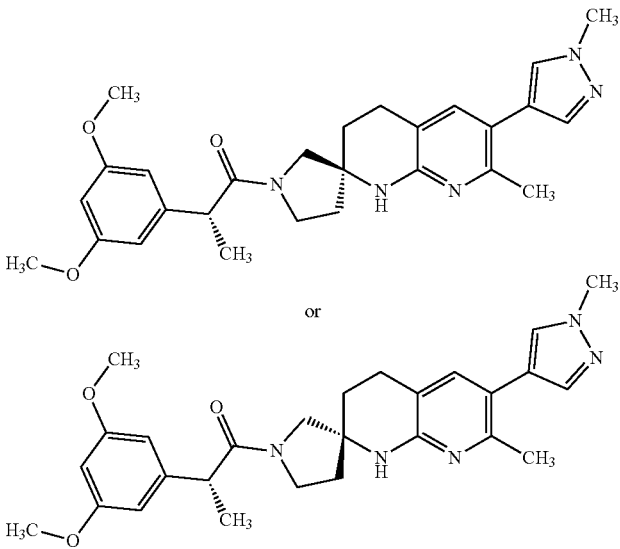 or<br>DIAST-1 | 2.41 minutes[52]; 498.5 [M + Na$^+$] |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 91 | Example 14[51]; C81 | DIAST-2 | 3.16 minutes[52]; 498.5 [M + Na$^+$] |
| 92 | Example 14[53,54]; C74, P7 | DIAST-1 | 2.68 minutes[55]; 534.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d4) δ; Mass spectrum, observed ion m/z [M + H]+ or HPLC retention time; Mass spectrum m/z [M + H]+ (unless otherwise indicated) |
|---|---|---|---|
| 93 | Example 14[53,54]; C74, P7 | 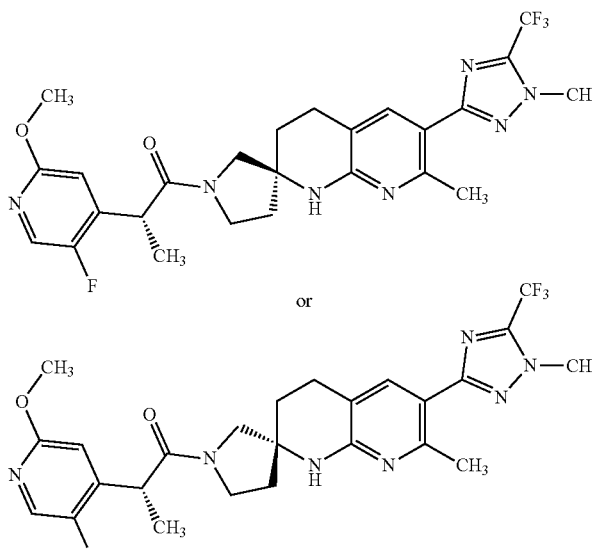 DIAST-2 | 2.92 minutes[55]; 534.4 |
| 94 | Example 14[53,56]; C74, P2 | 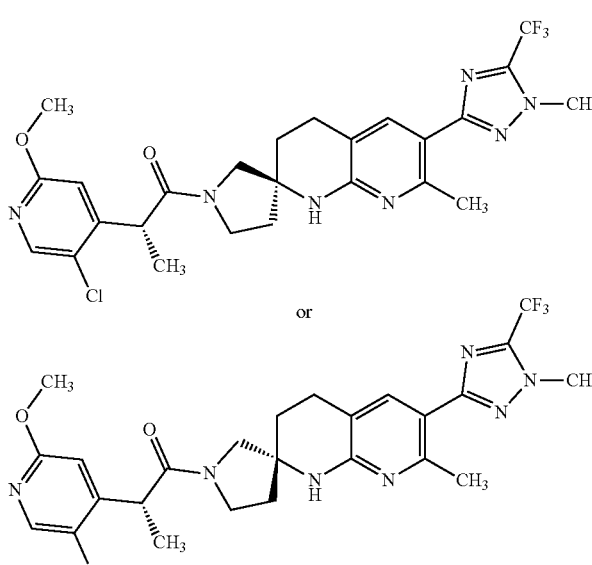 DIAST-1 | 2.22 minutes[57]; 550.6 (chlorine isotope pattern observed) |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 95 | Example 14[53,56]; C74, P2 | 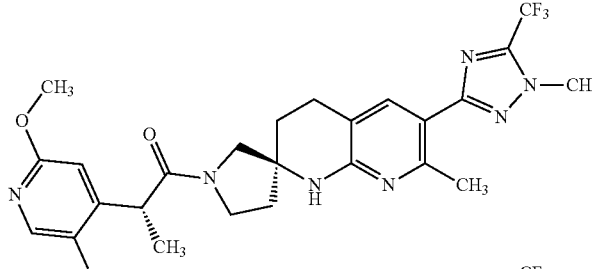 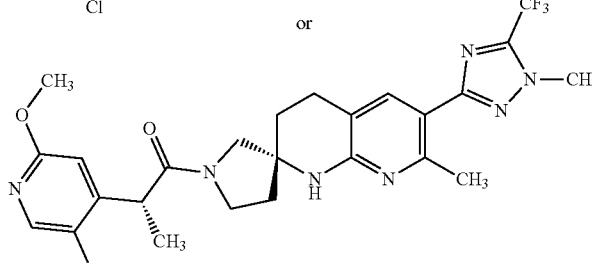 DIAST-2 | 2.69 minutes[57]; 550.6 |
| 96 | Example 13[58]; P17 | 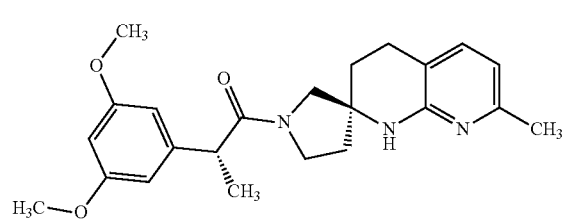 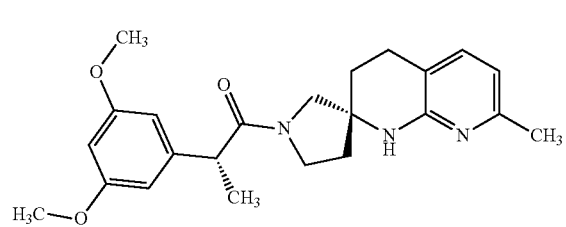 DIAST-1 | 1.60 minutes[59]; 418.4 [M + Na$^+$] |

TABLE 1-continued

Method of synthesis, structure, and physicochemical data for Examples 21-201.

| Example Number | Method of synthesis; Non-commercial starting materials | Structure | $^1$H NMR (400 MHz, methanol-d[4]) δ; Mass spectrum, observed ion m/z [M + H]+ or HPLC retention time; Mass spectrum m/z [M + H]+ (unless otherwise indicated) |
|---|---|---|---|
| 97 | Example 13[58]; P17 | DIAST-2 | 1.94 minutes[59]; 418.4 [M + Na+] |
| 98 | Example 13[60]; P17, P7 | DIAST-1 | 1.37 minutes[59]; 385.5 |
| 99 | Example 13[60]; P17, P7 | DIAST-2 | 1.81 minutes[59]; 407.4 [M + Na+] |

TABLE 1-continued

*Method of synthesis, structure, and physicochemical data for Examples 21-201.*

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 100 | Example 13[61]; P17, P2 | 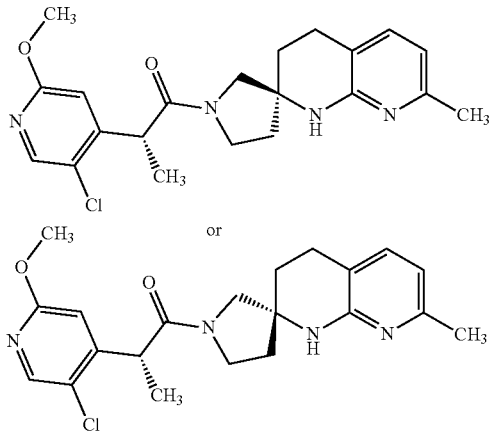DIAST-1 | 1.58 minutes[59]; 401.5 (chlorine isotope pattern observed) |
| 101 | Example 13[61]; P17, P2 | 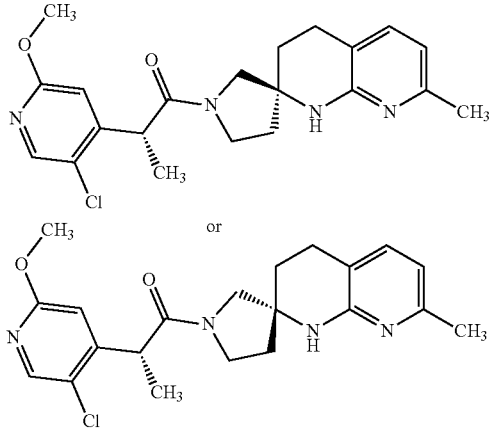DIAST-2 | 2.08 minutes[59]; 423.4 [M + Na$^+$] |
| 102 | Example 13[62,63]; P17, P7 | 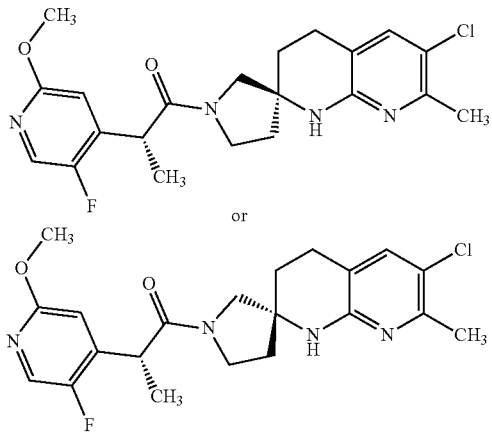DIAST-1 | 1.73 minutes[64]; 419.3 (chlorine isotope pattern observed) |

TABLE 1-continued

Method of synthesis, structure, and physicochemical data for Examples 21-201.

| Example Number | Method of synthesis; Non-commercial starting materials | Structure | ¹H NMR (400 MHz, methanol-d₄) δ; Mass spectrum, observed ion m/z [M + H]⁺ or HPLC retention time; Mass spectrum m/z [M + H]⁺ (unless otherwise indicated) |
|---|---|---|---|
| 103 | Example 13[62,63]; P17, P7 | 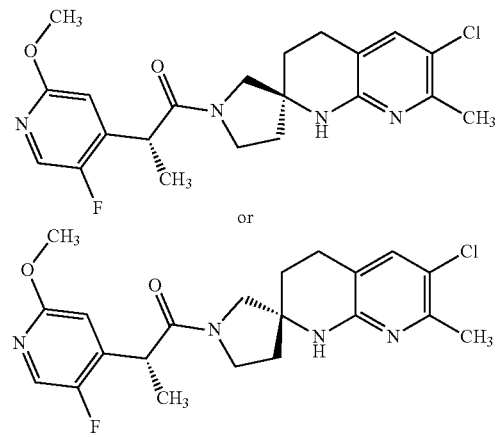 DIAST-2 | 2.57 minutes[64]; 419.3 (chlorine isotope pattern observed) |
| 104 | Example 14[65]; C81, P2 | 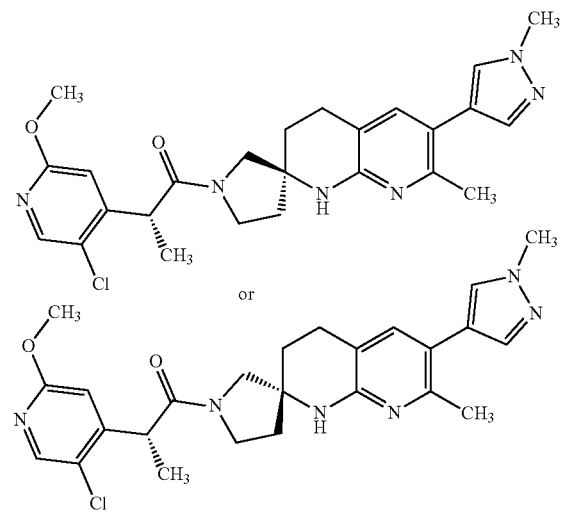 DIAST-1 | 3.07 minutes[66]; 483.5 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 105 | Example 14[65]; C81, P2 | 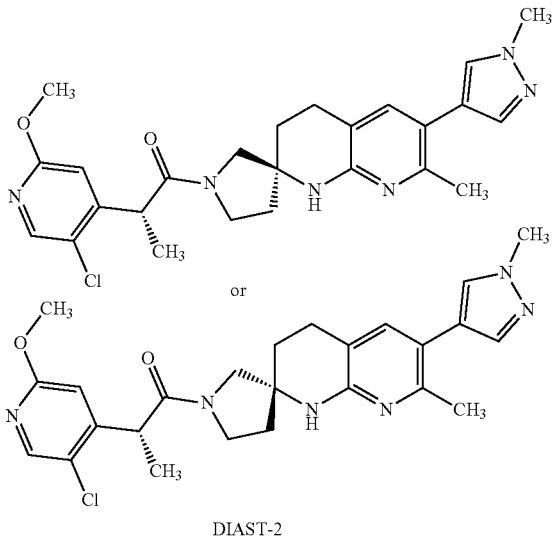<br>DIAST-2 | 3.85 minutes[66]; 483.5 |
| 106 | Example 3 and 4; P28 | 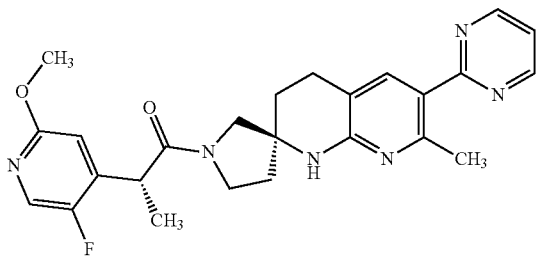 [SMILES: COc1cc([C@@H](C)C(=O)N2CC[C@@]3(CCc4cc(-c5ncccn5)c(C)nc4N3)C2)c(F)cn1] | 1.76 minutes[50]; 449.3 |
| 107 | Example 14[67]; P26, P5 | 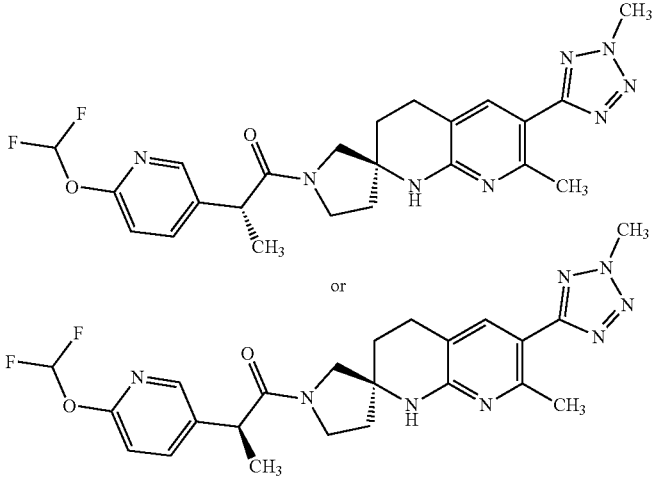<br>DIAST-1 | 3.72 minutes[68]; 485.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 108 | Example 14[67]; P26, P5 | 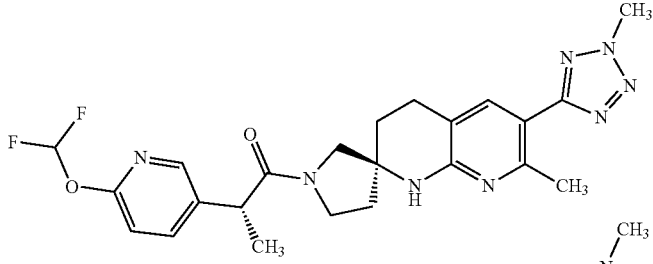<br>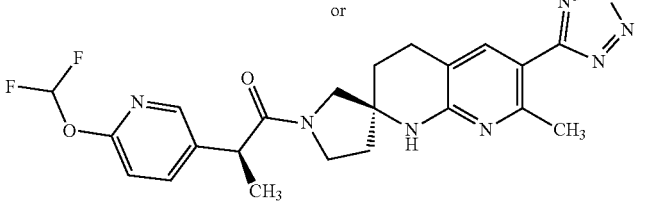<br>DIAST-2 | 4.2 minutes[68]; 485.3 |
| 109 | Example 14[69]; P26 | 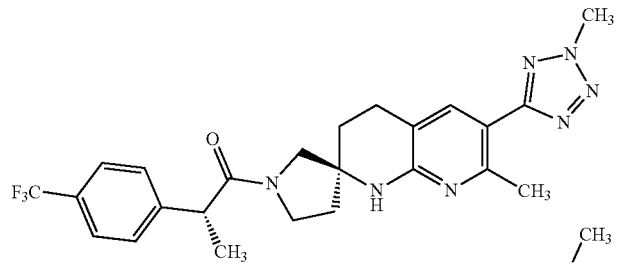<br>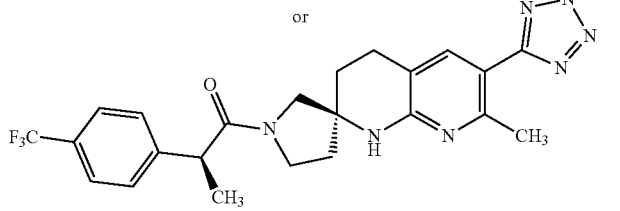<br>DIAST-1 | 3.72 minutes[70]; 486.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 110 | Example 14[69]; P26 | 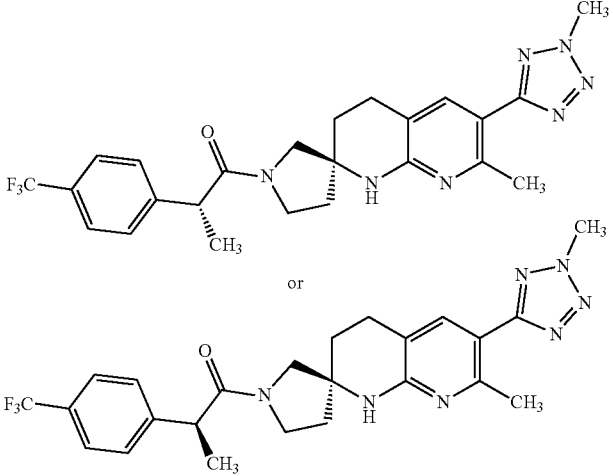<br>or<br>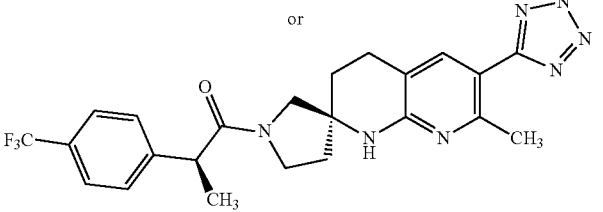<br>DIAST-2 | 3.80 minutes[70]; 486.3 |
| 111 | Example 1 and 2[71]; P23, P7 | 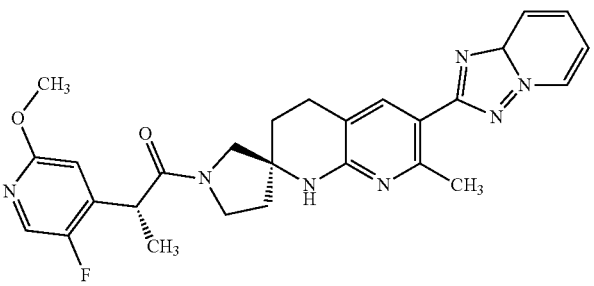 | 8.79-8.74 (m, 1H), [8.00 (d, J = 1.6 Hz) and 7.98 (d, J = 1.7 Hz), total 1H], [7.94 (s) and 7.91 (s), total 1H], 7.76-7.71 (m, 1H), 7.71-7.64 (m, 1H), 7.20-7.13 (m, 1H), [6.79 (d, J = 4.9 Hz) and 6.73 (d, J = 5.0 Hz), total 1H], [4.28 (q, J = 6.9 Hz) and 4.20 (q, J = 6.9 Hz), total 1H], [3.93-3.83 (m), 3.77-3.68 (m), 3.68-3.54 (m), 3.49 (d, component of AB quartet, J = 12.3 Hz), and 3.40 (d, J = 10.6 Hz), total 4H], [3.89 (s) and 3.88 (s), total 3H], [2.96-2.76 (m) and 2.66-2.54 (m), total 2H], [2.70 (s) and 2.67 (s), total 3H], [2.16-2.06 (m), 2.05-1.84 (m), and 1.84-1.75 (m), total 4H], [1.45 (d, J = 6.8 Hz) and 1.44 (d, J = 6.8 Hz), total 3H]; 502.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 112 | Example 14[72,73]; P21, P7 | 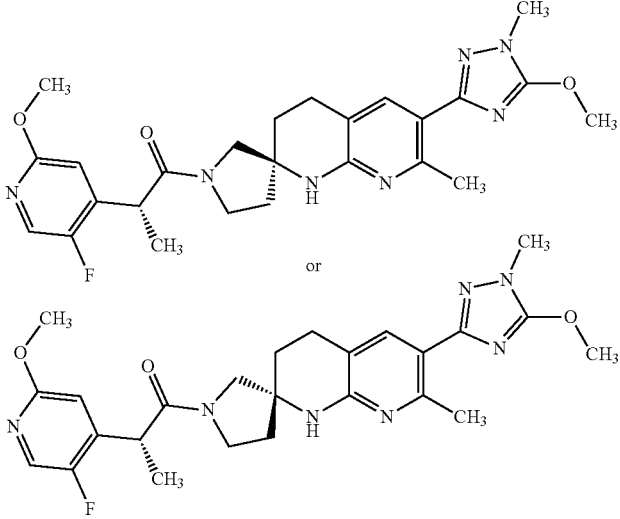 DIAST-1 | 2.91 minutes[74]; 496.4 |
| 113 | Example 14[72,73]; P21, P7 | 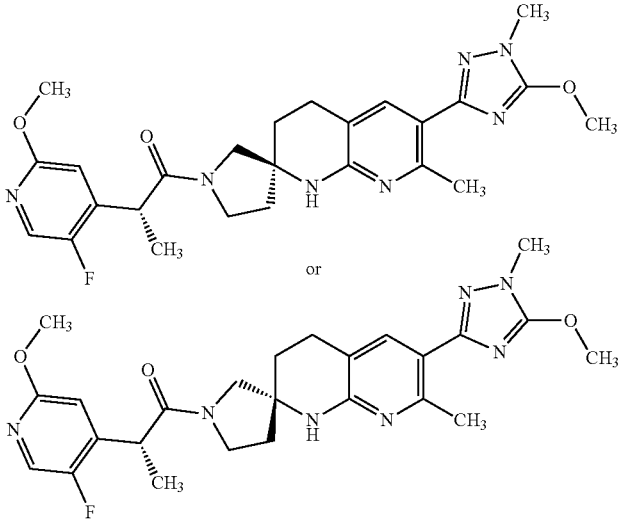 DIAST-2 | 3.17 minutes[74]; 496.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 114 | Example 14[72,75]; P21, P2 | 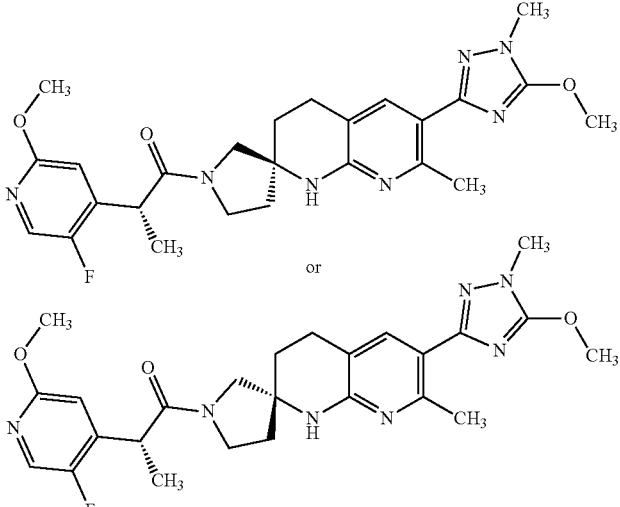 DIAST-1 | 2.06 minutes[76]; 512.3 |
| 115 | Example 14[72,75]; P21, P2 | 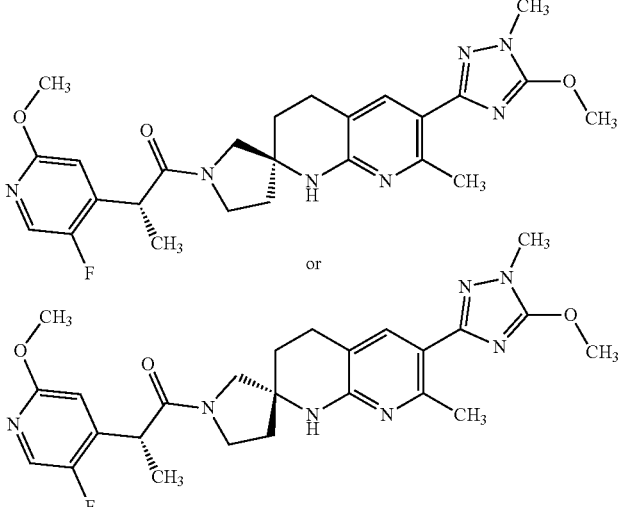 DIAST-2 | 2.29 minutes[76]; 512.3 |
| 116 | Example 14[77]; C77, P7 | 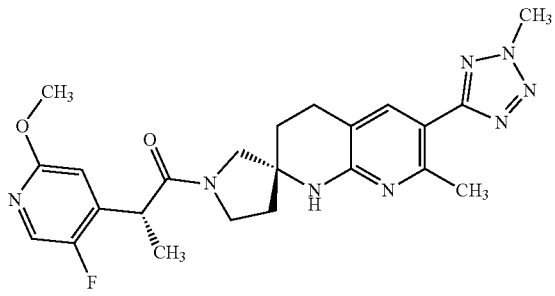 [SMILES: COc1cc([C@@H](C)C(=O)N2CC[C@]3(CCc4cc(-c5nnn(C)n5)c(C)nc4N3)C2)c(F)cn1] | 3.52 minutes[74]; 467.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 117 | Like Example 14[71]; P23, P2 | 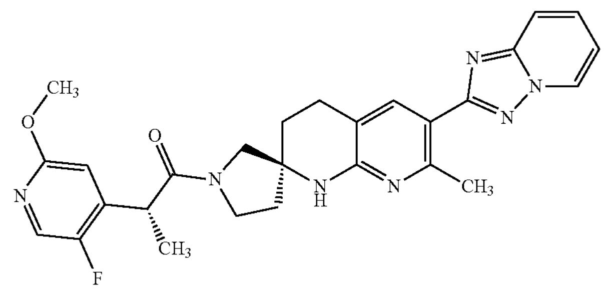 [SMILES: COc1cc([C@@H](C)C(=O)N2CC[C@@]3(CCc4cc(-c5nc6ccccn6n5)c(C)nc4N3)C2)c(F)cn1] | 8.80-8.74 (m, 1H), [8.15 (s) and 8.14 (s), total 1H], [7.94 (s) and 7.91 (s), total 1H], 7.77-7.72 (m, 1H), 7.71-7.65 (m, 1H), 7.20-7.15 (m, 1H), [6.81 (s) and 6.76 (s), total 1H], [4.32 (q, J = 6.9 Hz) and 4.23 (q, J = 6.9 Hz), total 1H], [3.93-3.83 (m), 3.77-3.67 (m), 3.67-3.53 (m), 3.50 (d, component of AB quartet, J = 12.2 Hz), and 3.36 (d, J = 10.6 Hz), total 4H], 3.91 (s, 3H), [2.97-2.74 (m) and 2.60-2.49 (m), total 2H], [2.70 (s) and 2.68 (s), total 3H], [2.17-2.07 (m), 2.05-1.85 (m), and 1.82-1.73 (m), total 4H], [1.44 (d, J = 6.9 Hz) and 1.42 (d, J = 6.9 Hz), total 3H]; 518.3 |
| 118 | Example 14[78]; P23, P7 | 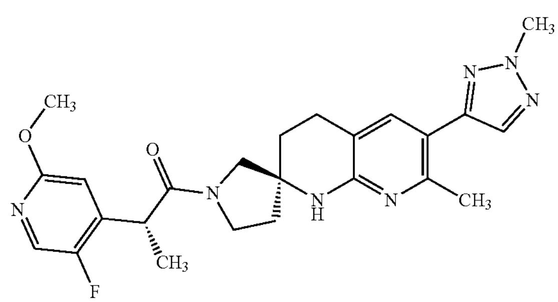 | 1.97 minutes[50]; 466.5 |
| 119 | Example 14[78]; P23, P2 | 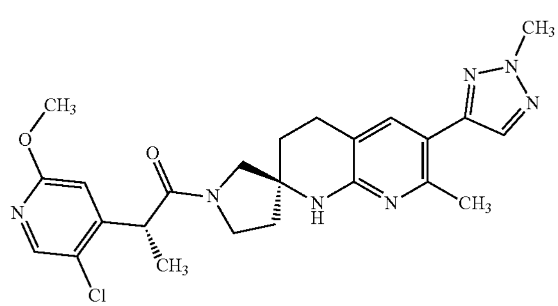 [SMILES: COc1cc([C@@H](C)C(=O)N2CC[C@@]3(CCc4cc(-c5cnn(C)n5)c(C)nc4N3)C2)c(Cl)cn1] | 2.10 minutes[50]; 482.5 (chlorine isotope pattern observed) |
| 120 | Like Example 14; P32, P2 | 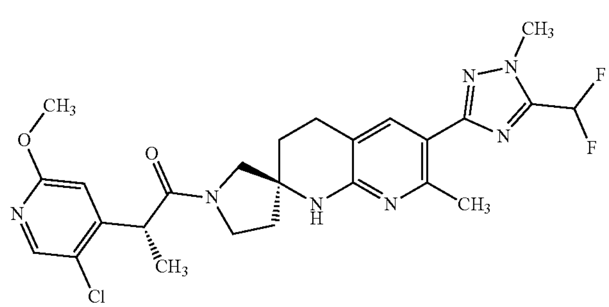 | 2.16 minutes[50]; 532.6 (chlorine isotope pattern observed) |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 121 | Like Example 14; P32 | 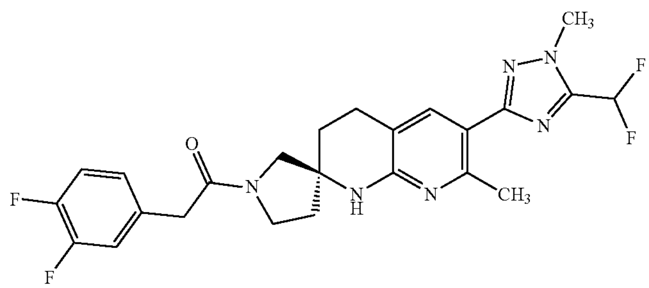 [SMILES: Cc1nc2c(cc1-c1nc(C(F)F)n(C)n1)CC[C@@]1(CCN(C(=O)Cc3ccc(F)c(F)c3)C1)N2] | 2.12 minutes[50]; 489.6 |
| 122 | Like Example 14; P32, P7 | 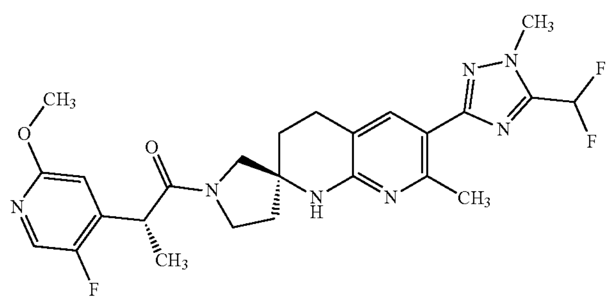 [SMILES: COc1cc([C@@H](C)C(=O)N2CC[C@@]3(CCc4cc(-c5nc(C(F)F)n(C)n5)c(C)nc4N3)C2)c(F)cn1] | 2.01 minutes[50]; 516.6 |
| 123 | Alternate Synthesis of Examples 3 and 4[79]; P32, P4 | DIAST-1 | 2.22 minutes[80]; 513.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 124 | Alternate Synthesis of Examples 3 and 4[79]; P32, P4 | DIAST-2 | 2.67 minutes[80]; 513.4 |
| 125 | Example 3 and 4[81,82]; C68 | DIAST-1 | 1.63 minutes[83]; 449.4 |

TABLE 1-continued

Method of synthesis, structure, and physicochemical data for Examples 21-201.

| Example Number | Method of synthesis; Non-commercial starting materials | Structure | ¹H NMR (400 MHz, methanol-d₄) δ; Mass spectrum, observed ion m/z [M + H]⁺ or HPLC retention time; Mass spectrum m/z [M + H]⁺ (unless otherwise indicated) |
|---|---|---|---|
| 126 | Example 3 and 4[81,82]; C68 | 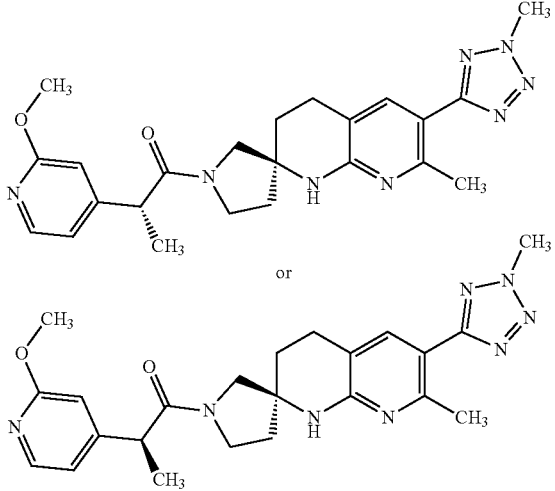 DIAST-2 | 1.87 minutes[83]; 449.3 |
| 127 | Examples 5 and 6[84,85]; P26 | 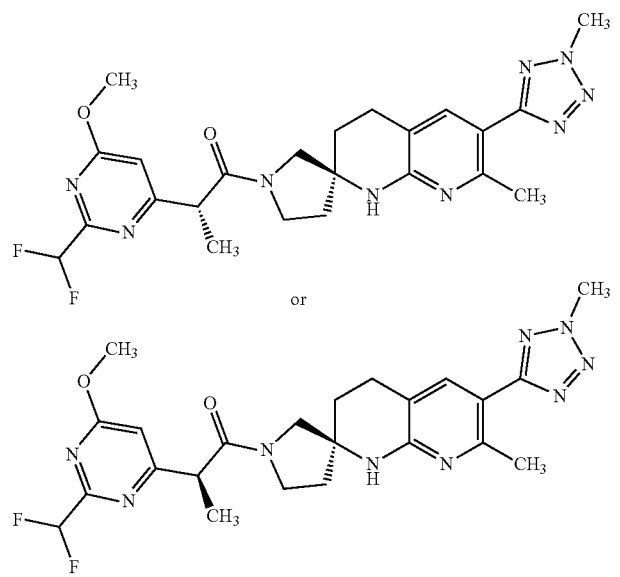 DIAST-1 | 1.96 minutes[86]; 500.4 |

TABLE 1-continued

Method of synthesis, structure, and physicochemical data for Examples 21-201.

| Example Number | Method of synthesis; Non-commercial starting materials | Structure | ¹H NMR (400 MHz, methanol-d₄) δ; Mass spectrum, observed ion m/z [M + H]⁺ or HPLC retention time; Mass spectrum m/z [M + H]⁺ (unless otherwise indicated) |
|---|---|---|---|
| 128 | Examples 5 and 6[84,85]; P26 | DIAST-2 | 2.15 minutes[86]; 500.4 |
| 129 | Examples 5 and 6[71,84,87]; P23 | DIAST-1 | 2.74 minutes[86]; 535.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 130 | Examples 5 and 6[71,84,87]; P23 | (structure shown; DIAST-2) | 3.33 minutes[86]; 535.4 |
| 131 | Example 14[88]; P23, P7 | (structure shown) | 2.16 minutes[89]; 469.4 |
| 132 | Examples 5 and 6[71,90,91]; P23 | (structure shown; DIAST-1) | 3.20 minutes[92]; 503.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 133 | Examples 5 and 6[71,90,91]; P23 | 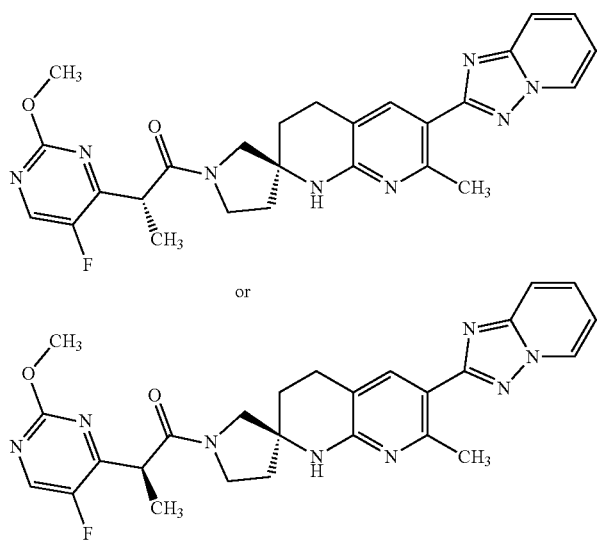 DIAST-2 | 3.58 minutes[92]; 503.4 |
| 134 | Examples 5 and 6[90,93]; P26 | 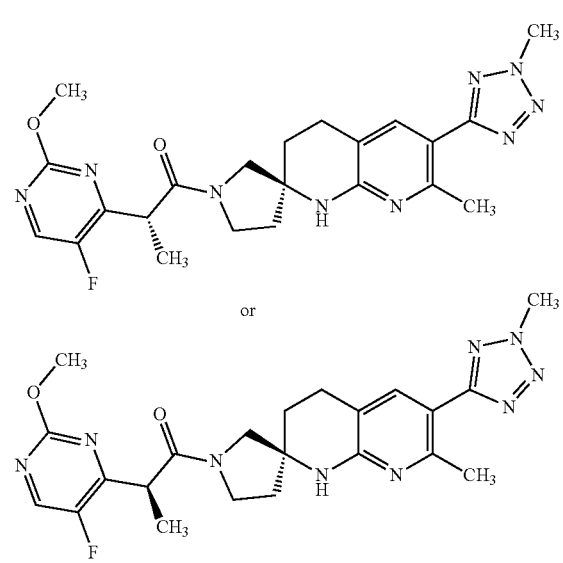 DIAST-1 | 2.40 minutes[94]; 468.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 135 | Examples 5 and 6[90,93]; P26 | (structure shown: DIAST-2) | 2.78 minutes[94]; 468.4 |
| 136 | Example 14[95,96]; P28 | (structure shown: DIAST-1) | 2.02 minutes[97]; 459.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 137 | Example 14[95,96]; P28 | 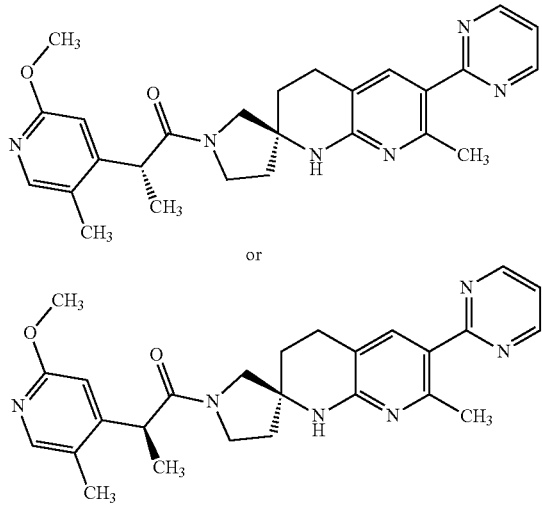 DIAST-2 | 2.32 minutes[97]; 459.4 |
| 138 | Example 1 and 2[98,99]; P27, P7 | 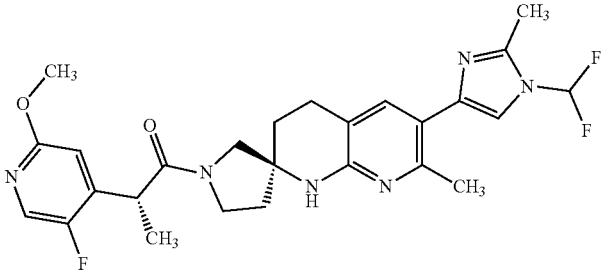 [SMILES: COc1cc([C@@H](C)C(=O)N2CC[C@@]3(CCc4cc(-c5cn(C(F)F)c(C)n5)c(C)nc4N3)C2)c(F)cn1] | 1.98 minutes[50]; 515.6 |
| 139 | Example 18[100]; P27, P7 | 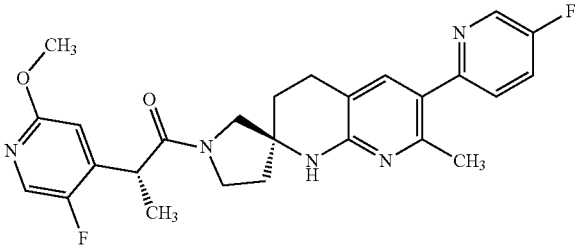 [SMILES: COc1cc([C@@H](C)C(=O)N2CC[C@@]3(CCc4cc(-c5ccc(F)cn5)c(C)nc4N3)C2)c(F)cn1] | 2.12 minutes[50]; 480.6 |
| 140 | Example 18[100]; P27, P7 | 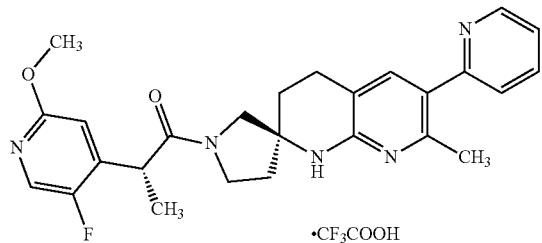 [SMILES: COc1cc([C@@H](C)C(=O)N2CC[C@@]3(CCc4cc(-c5ccccn5)c(C)nc4N3)C2)c(F)cn1 ; "·CF3COOH"] ·CF$_3$COOH | 1.77 minutes[50]; 462.6 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 141 | Example 18$^{100}$; P27, P7 | 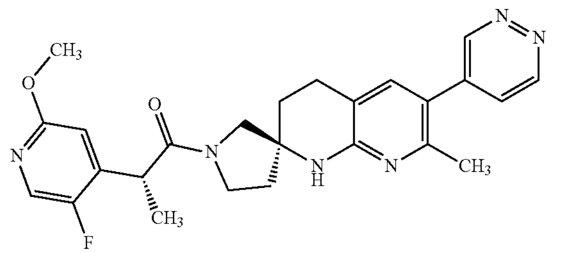 [SMILES: COc1cc([C@@H](C)C(=O)N2CC[C@@]3(CCc4cc(-c5ccnnc5)c(C)nc4N3)C2)c(F)cn1] | 1.70 minutes$^{50}$; 463.6 |
| 142 | Example 18$^{100}$; P27, P7 | 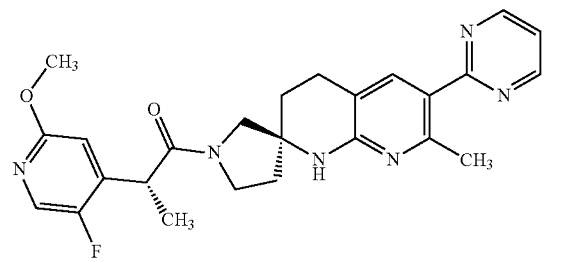 [SMILES: COc1cc([C@@H](C)C(=O)N2CC[C@@]3(CCc4cc(-c5ncccn5)c(C)nc4N3)C2)c(F)cn1] | 1.85 minutes$^{50}$; 463.6 |
| 143 | Example 18$^{101}$; P27, P7 | •CF$_3$COOH | 2.47 minutes$^{50}$; 531.6 |
| 144 | Example 18$^{100}$; P27, P7 | •CF$_3$COOH | 2.30 minutes$^{50}$; 497.5 |
| 145 | Example 18$^{101}$; P27, P7 | •CF$_3$COOH | 2.47 minutes$^{50}$; 531.5 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 146 | Example 18[101]; P27, P7 | 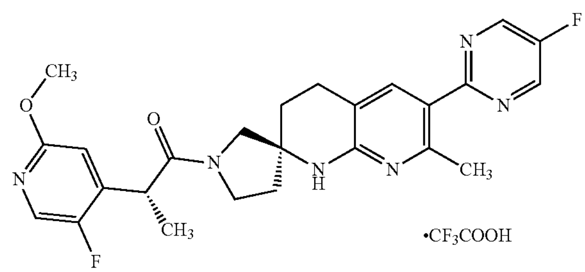 [SMILES: COc1cc([C@@H](C)C(=O)N2CC[C@@]3(CCc4cc(-c5ncc(F)cn5)c(C)nc4N3)C2)c(F)cn1 ; "·CF3COOH"] | 2.12 minutes[50]; 481.5 |
| 147 | Example 13[102]; P27, P7 | 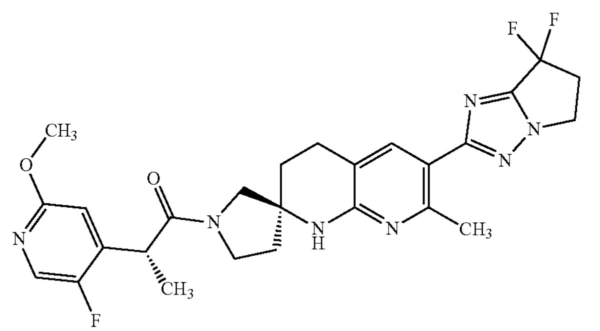 [SMILES: COc1cc([C@@H](C)C(=O)N2CC[C@@]3(CCc4cc(-c5nc6n(n5)CCC6(F)F)c(C)nc4N3)C2)c(F)cn1] | 2.20 minutes[50]; 528.6 |
| 148 | Alternate Synthesis of Examples 3 and 4[103,104]; P28, C29 | DIAST-1 | 3.20 minutes[68]; 481.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 149 | Alternate Synthesis of Examples 3 and 4[103,104]; P28, C29 | (structure shown, DIAST-2) | 3.61 minutes[68]; 481.3 |
| 150 | Example 18[100]; P27, P7 | (structure shown) | 2.03 minutes[50]; 468.5 |
| 151 | Example 18[100]; P27, P7 | (structure shown) | 1.84 minutes[50]; 477.5 |
| 152 | Example 18[105]; P27, P7 | (structure shown) | 2.04 minutes[50]; 544.6 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 153 | Example 18[100]; P27, P7 | 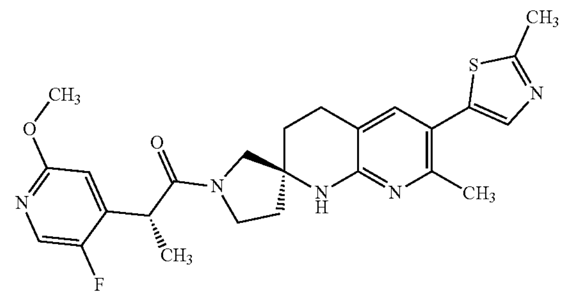 [SMILES: COc1cc([C@@H](C)C(=O)N2CC[C@@]3(CCc4cc(-c5cnc(C)s5)c(C)nc4N3)C2)c(F)cn1] | 2.04 minutes[50]; 482.5 |
| 154 | Example 18[100]; P27, P7 | 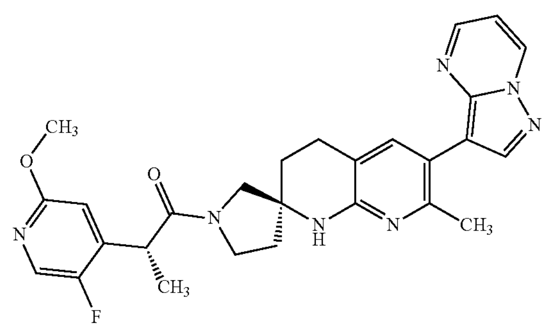 [SMILES: COc1cc([C@@H](C)C(=O)N2CC[C@@]3(CCc4cc(-c5cnn6cccnc56)c(C)nc4N3)C2)c(F)cn1] | 2.01 minutes[50]; 502.5 |
| 155 | Example 18[100]; P27, P7 | 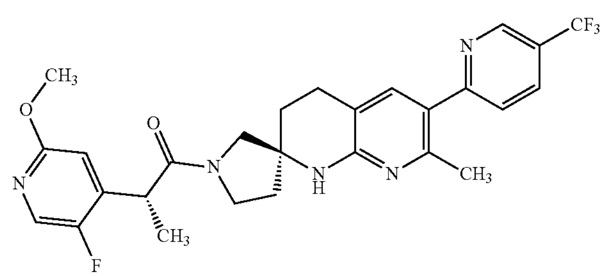 [SMILES: COc1cc([C@@H](C)C(=O)N2CC[C@@]3(CCc4cc(-c5ccc(C(F)(F)F)cn5)c(C)nc4N3)C2)c(F)cn1] | 2.43 minutes[50]; 530.5 |
| 156 | Example 18[100]; P27, P7 | 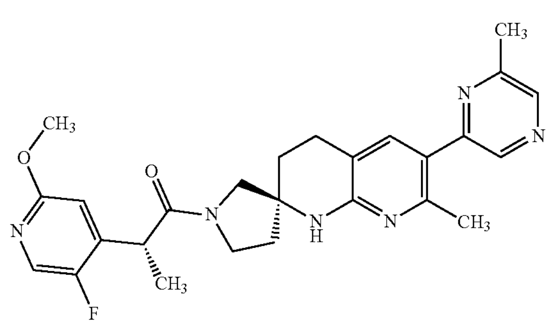 [SMILES: COc1cc([C@@H](C)C(=O)N2CC[C@@]3(CCc4cc(-c5cncc(C)n5)c(C)nc4N3)C2)c(F)cn1] | 1.96 minutes[50]; 477.5 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 157 | Example 18[100]; P27, P7 | 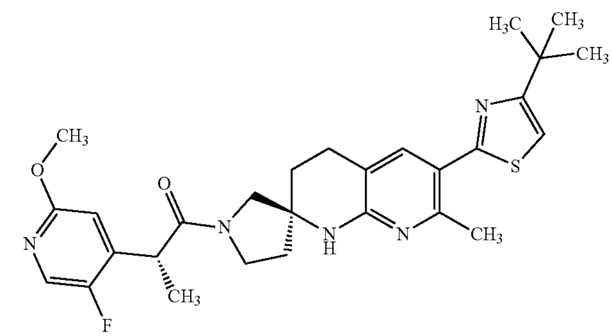 [SMILES: COc1cc([C@@H](C)C(=O)N2CC[C@@]3(CCc4cc(-c5nc(C(C)(C)C)cs5)c(C)nc4N3)C2)c(F)cn1] | 2.82 minutes[50]; 524.5 |
| 158 | Example 18[100]; P27, P7 | 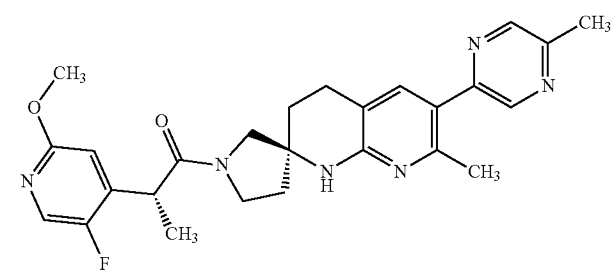 [SMILES: COc1cc([C@@H](C)C(=O)N2CC[C@@]3(CCc4cc(-c5cnc(C)cn5)c(C)nc4N3)C2)c(F)cn1] | 1.96 minutes[50]; 477.5 |
| 159 | Example 18[100]; P27, P7 | 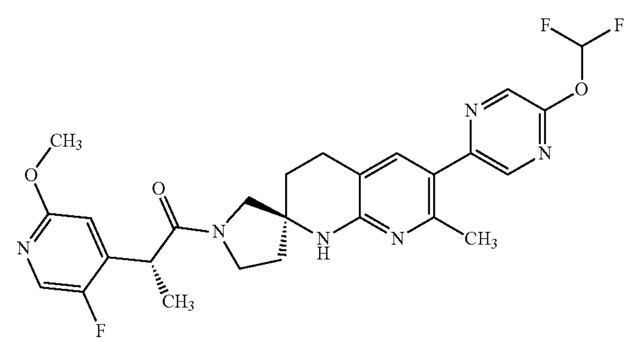 [SMILES: COc1cc([C@@H](C)C(=O)N2CC[C@@]3(CCc4cc(-c5cnc(OC(F)F)cn5)c(C)nc4N3)C2)c(F)cn1] | 2.44 minutes[50]; 528.5 |
| 160 | Example 18[100]; P27, P7 | 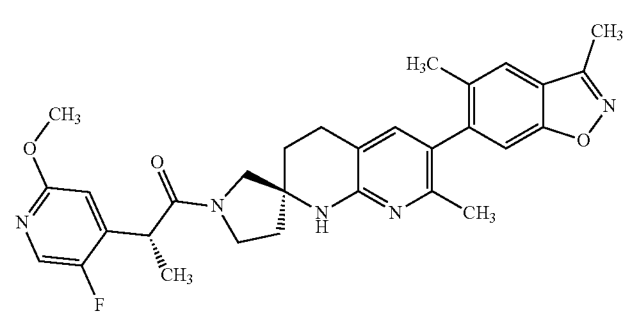 [SMILES: COc1cc([C@@H](C)C(=O)N2CC[C@@]3(CCc4cc(-c5cc6onc(C)c6cc5C)c(C)nc4N3)C2)c(F)cn1] | 2.48 minutes[50]; 530.6 |

TABLE 1-continued

Method of synthesis, structure, and physicochemical data for Examples 21-201.

| Example Number | Method of synthesis; Non-commercial starting materials | Structure | $^{1}$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 161 | Example 18[100]; P27, P7 | 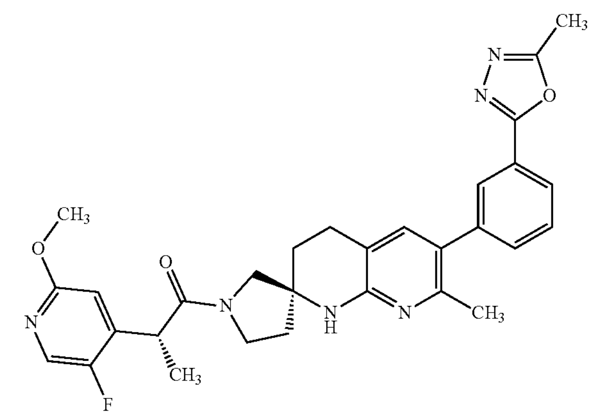 [SMILES: COc1cc([C@@H](C)C(=O)N2CC[C@@]3(CCc4cc(-c5cccc(-c6nnc(C)o6)c5)c(C)nc4N3)C2)c(F)cn1] | 2.23 minutes[50]; 543.6 |
| 162 | Example 18[100]; P27, P7 | 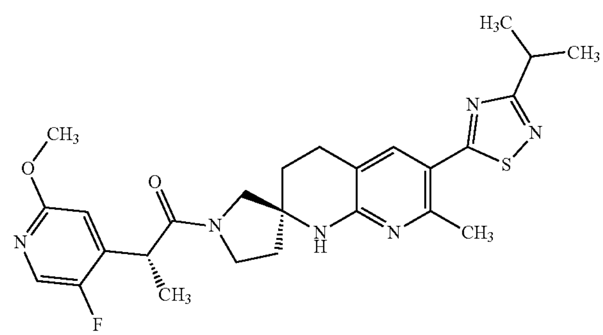 [SMILES: COc1cc([C@@H](C)C(=O)N2CC[C@@]3(CCc4cc(-c5nc(C(C)C)ns5)c(C)nc4N3)C2)c(F)cn1] | 2.54 minutes[50]; 511.5 |
| 163 | Example 18[100]; P27, P7 | 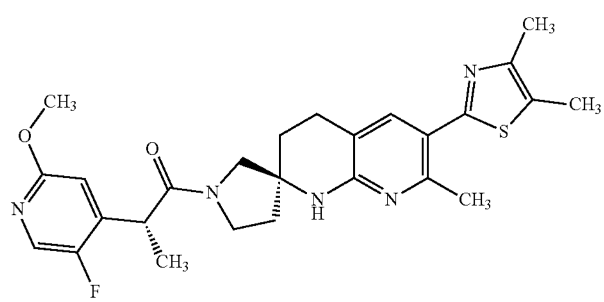 [SMILES: COc1cc([C@@H](C)C(=O)N2CC[C@@]3(CCc4cc(-c5nc(C)c(C)s5)c(C)nc4N3)C2)c(F)cn1] | 2.36 minutes[50]; 496.5 |
| 164 | Example 18[100]; P27, P7 | 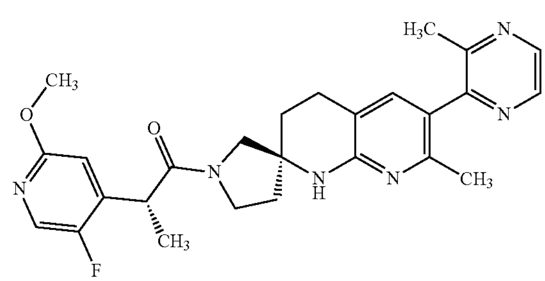 [SMILES: COc1cc([C@@H](C)C(=O)N2CC[C@@]3(CCc4cc(-c5nccnc5C)c(C)nc4N3)C2)c(F)cn1] | 1.87 minutes[50]; 477.5 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 165 | Example 18[100]; P27, P7 | 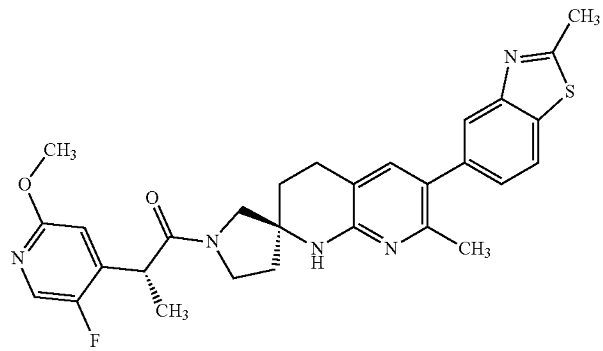 [SMILES: COc1cc([C@@H](C)C(=O)N2CC[C@@]3(CCc4cc(-c5ccc6sc(C)nc6c5)c(C)nc4N3)C2)c(F)cn1] | 2.41 minutes[50]; 532.5 |
| 166 | Example 18[100]; P27, P7 | 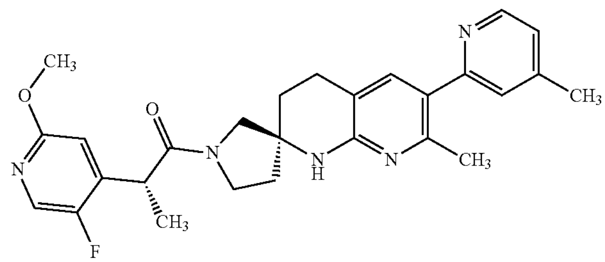 [SMILES: COc1cc([C@@H](C)C(=O)N2CC[C@@]3(CCc4cc(-c5cc(C)ccn5)c(C)nc4N3)C2)c(F)cn1] | 1.69 minutes[50]; 476.5 |
| 167 | Example 18[100]; P27, P7 | 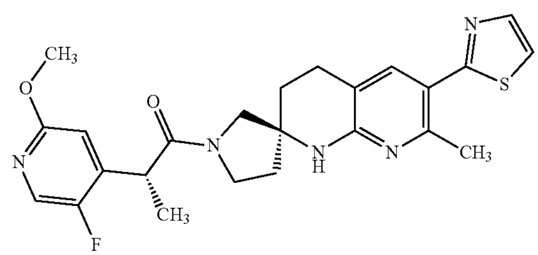 [SMILES: COc1cc([C@@H](C)C(=O)N2CC[C@@]3(CCc4cc(-c5nccs5)c(C)nc4N3)C2)c(F)cn1] | 2.08 minutes[50]; 468.5 |
| 168 | Example 18[100]; P27, P7 | 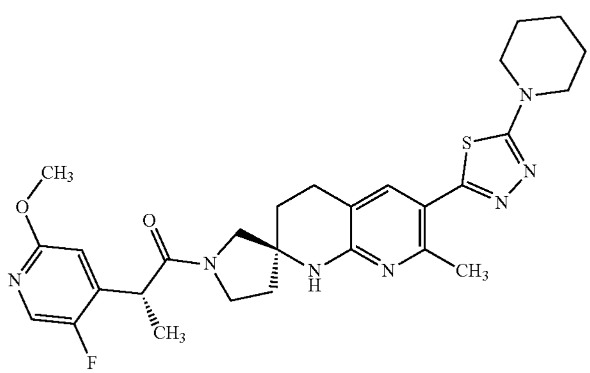 [SMILES: COc1cc([C@@H](C)C(=O)N2CC[C@@]3(CCc4cc(-c5nnc(N6CCCCC6)s5)c(C)nc4N3)C2)c(F)cn1] | 2.32 minutes[50]; 552.6 |

TABLE 1-continued

Method of synthesis, structure, and physicochemical data for Examples 21-201.

| Example Number | Method of synthesis; Non-commercial starting materials | Structure | 1H NMR (400 MHz, methanol-d4) δ; Mass spectrum, observed ion m/z [M + H]+ or HPLC retention time; Mass spectrum m/z [M + H]+ (unless otherwise indicated) |
|---|---|---|---|
| 169 | Example 18[100]; P27, P7 | 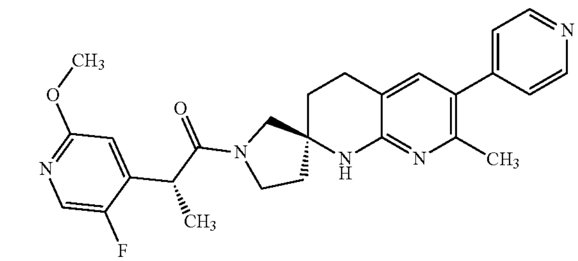 [SMILES: COc1cc([C@@H](C)C(=O)N2CC[C@@]3(CCc4cc(-c5ccncc5)c(C)nc4N3)C2)c(F)cn1] | 1.52 minutes[50]; 462.5 |
| 170 | Example 18[100]; P27, P7 | 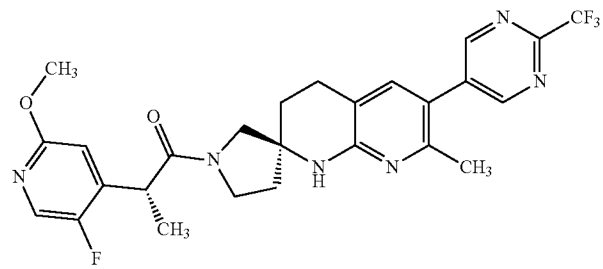 [SMILES: COc1cc([C@@H](C)C(=O)N2CC[C@@]3(CCc4cc(-c5cnc(C(F)(F)F)nc5)c(C)nc4N3)C2)c(F)cn1] | 2.27 minutes[50]; 531.5 |
| 171 | Example 18[100]; P27, P7 | 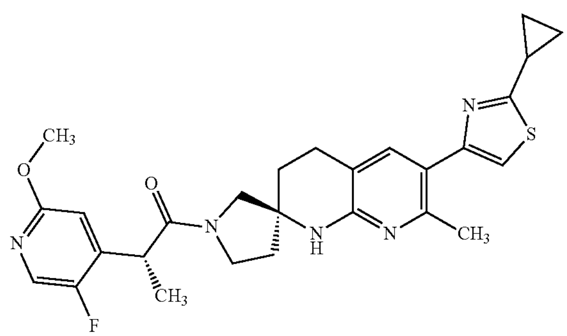 [SMILES: COc1cc([C@@H](C)C(=O)N2CC[C@@]3(CCc4cc(-c5csc(C6CC6)n5)c(C)nc4N3)C2)c(F)cn1] | 2.43 minutes[50]; 508.5 |
| 172 | Example 18[100]; P27, P7 | 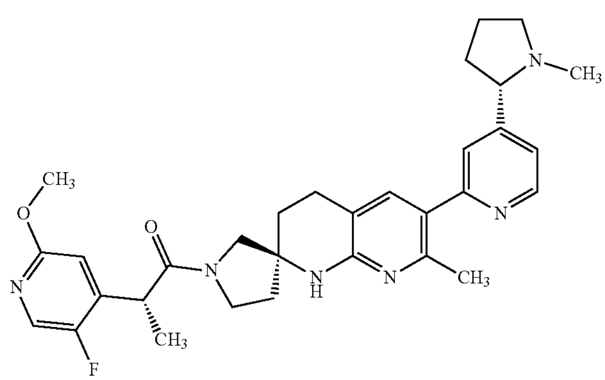 [SMILES: COc1cc([C@@H](C)C(=O)N2CC[C@@]3(CCc4cc(-c5cc([C@@H]6CCCN6C)ccn5)c(C)nc4N3)C2)c(F)cn1] | 2.27 minutes[50]; 544.5 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 173 | Example 18$^{100}$; P27, P7 | 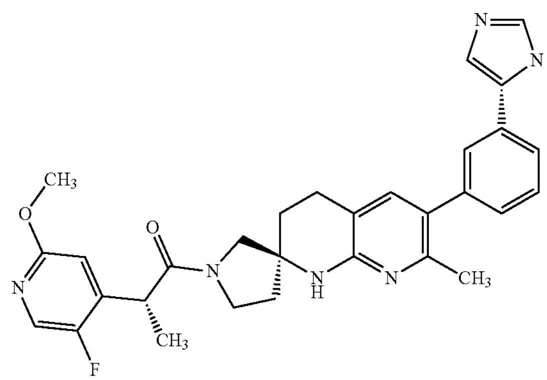 | 2.34 minutes$^{50}$; 528.5 |
| 174 | Example 18$^{100}$; P27, P7 | 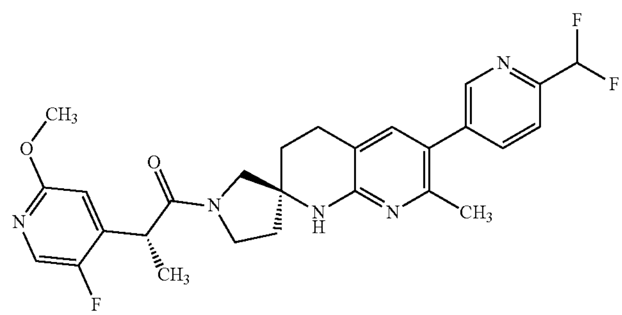 [SMILES: COc1cc([C@@H](C)C(=O)N2CC[C@@]3(CCc4cc(-c5ccc(C(F)F)nc5)c(C)nc4N3)C2)c(F)cn1] | 2.14 minutes$^{50}$; 512.4 |
| 175 | Example 18$^{100}$; P27, P7 | 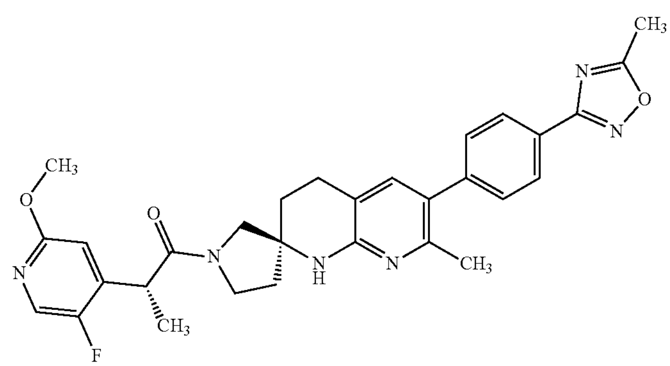 [SMILES: COc1cc([C@@H](C)C(=O)N2CC[C@@]3(CCc4cc(-c5ccc(-c6noc(C)n6)cc5)c(C)nc4N3)C2)c(F)cn1] | 2.41 minutes$^{50}$; 543.5 |
| 176 | Example 18$^{100}$; P27, P7 | 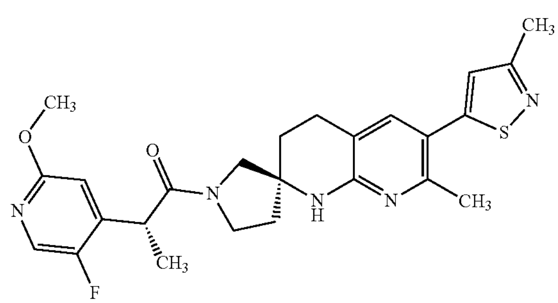 [SMILES: COc1cc([C@@H](C)C(=O)N2CC[C@@]3(CCc4cc(-c5cc(C)ns5)c(C)nc4N3)C2)c(F)cn1] | 2.13 minutes$^{50}$; 482.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 177 | Example 18[100]; P27, P7 | 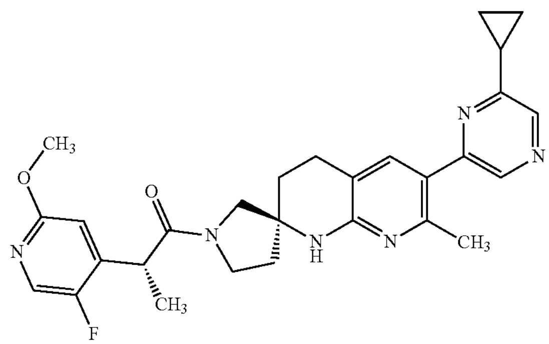 [SMILES: COc1cc([C@@H](C)C(=O)N2CC[C@@]3(CCc4cc(-c5cncc(C6CC6)n5)c(C)nc4N3)C2)c(F)cn1] | 2.25 minutes[50]; 503.5 |
| 178 | Example 18[100]; P27, P7 | 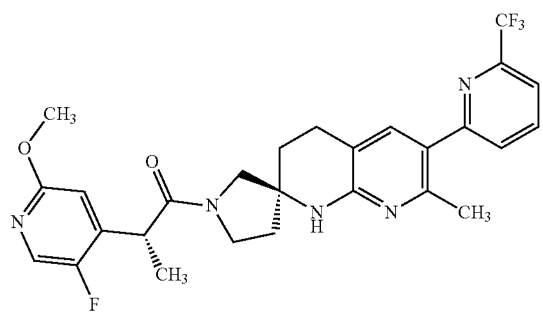 [SMILES: COc1cc([C@@H](C)C(=O)N2CC[C@@]3(CCc4cc(-c5cccc(C(F)(F)F)n5)c(C)nc4N3)C2)c(F)cn1] | 2.44 minutes[50]; 530.4 |
| 179 | Example 18[100]; P27, P7 | 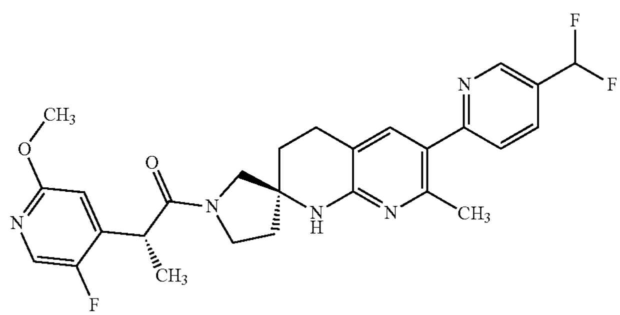 [SMILES: COc1cc([C@@H](C)C(=O)N2CC[C@@]3(CCc4cc(-c5ccc(C(F)F)cn5)c(C)nc4N3)C2)c(F)cn1] | 2.19 minutes[50]; 512.4 |
| 180 | Example 18[100]; P27, P7 | 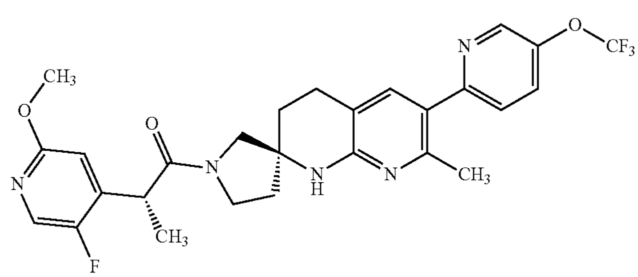 [SMILES: COc1cc([C@@H](C)C(=O)N2CC[C@@]3(CCc4cc(-c5ccc(OC(F)(F)F)cn5)c(C)nc4N3)C2)c(F)cn1] | 2.44 minutes[50]; 546.4 |

TABLE 1-continued

Method of synthesis, structure, and physicochemical data for Examples 21-201.

| Example Number | Method of synthesis; Non-commercial starting materials | Structure | ¹H NMR (400 MHz, methanol-d₄) δ; Mass spectrum, observed ion m/z [M + H]⁺ or HPLC retention time; Mass spectrum m/z [M + H]⁺ (unless otherwise indicated) |
|---|---|---|---|
| 181 | Example 18[100]; P27, P7 | 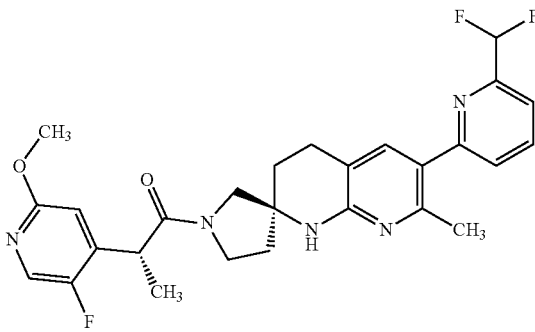 | 2.27 minutes[50]; 512.4 |
| 182 | Example 18[100]; P27, P7 | 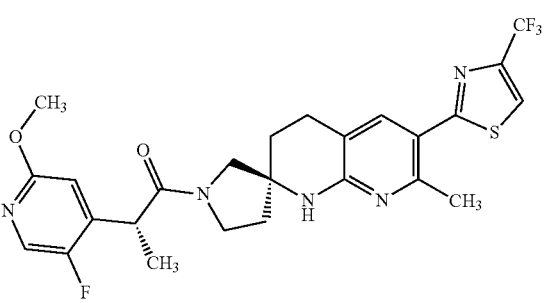 [SMILES: COc1cc([C@@H](C)C(=O)N2CC[C@@]3(CCc4cc(-c5nc(C(F)(F)F)cs5)c(C)nc4N3)C2)c(F)cn1] | 2.46 minutes[50]; 536.4 |
| 183 | Example 18[100]; P27, P7 | 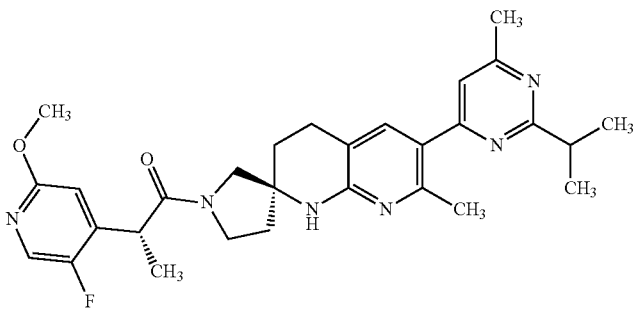 [SMILES: COc1cc([C@@H](C)C(=O)N2CC[C@@]3(CCc4cc(-c5cc(C)nc(C(C)C)n5)c(C)nc4N3)C2)c(F)cn1] | 2.14 minutes[50]; 519.5 |
| 184 | Example 18[100]; P27, P7 | 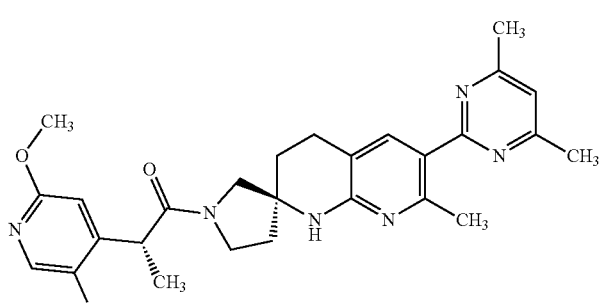 | 2.11 minutes[50]; 491.5 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 185 | Example 18[101]; P27, P7 | 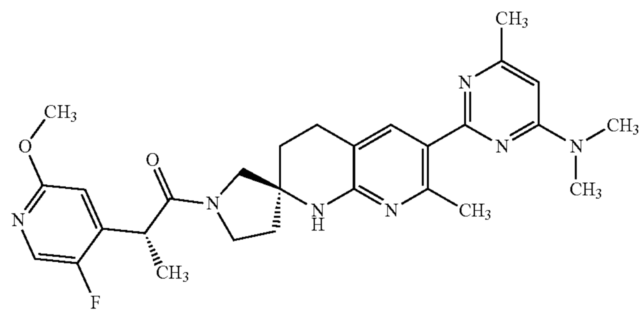 [SMILES: COc1cc([C@@H](C)C(=O)N2CC[C@@]3(CCc4cc(-c5nc(C)cc(N(C)C)n5)c(C)nc4N3)C2)c(F)cn1] | 2.68 minutes[50]; 574.5 |
| 186 | Example 18[100]; P27, P7 | 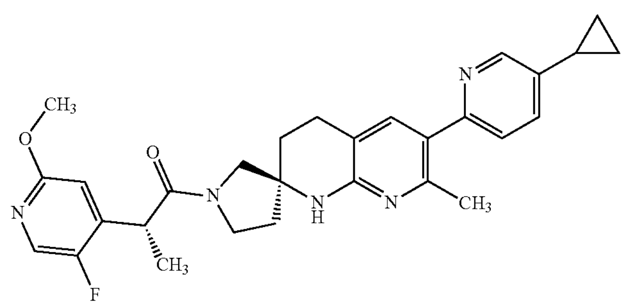 [SMILES: COc1cc([C@@H](C)C(=O)N2CC[C@@]3(CCc4cc(-c5ccc(C6CC6)cn5)c(C)nc4N3)C2)c(F)cn1] | 2.01 minutes[50]; 502.5 |
| 187 | Example 18[100]; P27, P7 | 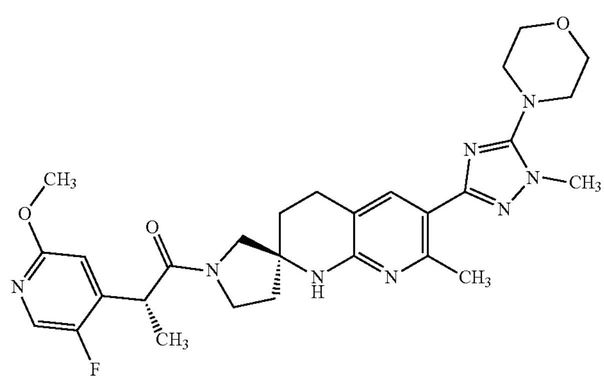 [SMILES: COc1cc([C@@H](C)C(=O)N2CC[C@@]3(CCc4cc(-c5nc(N6CCOCC6)n(C)n5)c(C)nc4N3)C2)c(F)cn1] | 2.00 minutes[50]; 551.5 |
| 188 | Example 18[106]; P27, P7 | 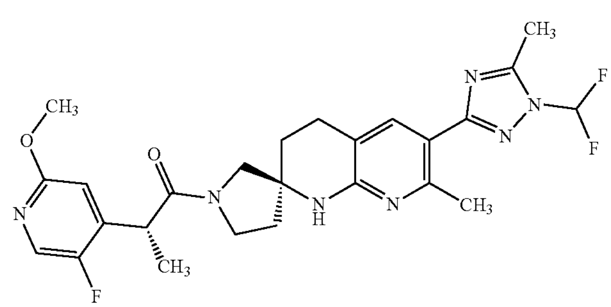 [SMILES: COc1cc([C@@H](C)C(=O)N2CC[C@@]3(CCc4cc(-c5nc(C)n(C(F)F)n5)c(C)nc4N3)C2)c(F)cn1] | 2.11 minutes[50]; 516.4 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 189 | Example 18[107]; P27, P7 | 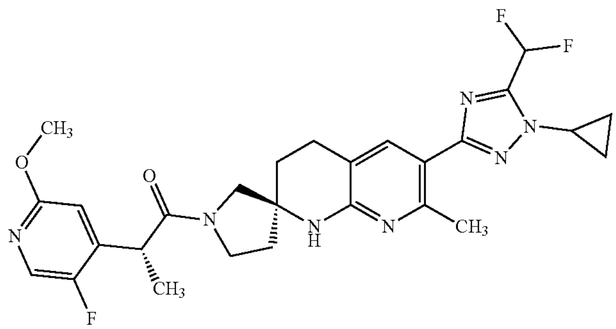 [SMILES: COc1cc([C@@H](C)C(=O)N2CC[C@@]3(CCc4cc(-c5nc(C(F)F)n(C6CC6)n5)c(C)nc4N3)C2)c(F)cn1] | 2.33 minutes[50]; 542.4 |
| 190 | Alternate Synthesis of Examples 3 and 4[108]; P28 | DIAST-1 | [8.81 (d, J = 4.9 Hz) and 8.81 (d, J = 4.9 Hz), total 2H], [7.84 (s) and 7.80 (s), total 1H], 7.45-7.31 (m, 1H), [7.31 (t, J = 4.9 Hz) and 7.30 (t, J = 4.9 Hz), total 1H], 7.03-6.94 (m, 2H), [4.27 (q, J = 7.0 Hz) and 4.16 (q, J = 6.9 Hz), total 1H], [3.91-3.82 (m), 3.76-3.67 (m), 3.64-3.48 (m), 3.46 (d, component of AB quartet, J = 12.4 Hz), and 3.3-3.26 (m, assumed; largely obscured by solvent peak), total 4H], [2.94-2.81 (m), 2.81-2.70 (m), and 2.53-2.43 (m), total 2H], [2.57 (s) and 2.55 (s), total 3H], [2.15-2.03 (m) and 2.01-1.84 (m), total 3H], 1.75-1.68 (m, 1H), [1.42 (d, J = 6.8 Hz) and 1.41 (d, J = 6.8 Hz), total 3H]; 450.1 |
| 191 | Alternate Synthesis of Examples 3 and 4[108]; P28 | DIAST-2 | 8.84-8.78 (m, 2H), [7.84 (s) and 7.83 (s), total 1H], 7.42-7.33 (m, 1H), 7.33-7.28 (m, 1H), [7.02-6.89 (m) and 6.82 (ddd, J = 10.6, 9.0, 2.6 Hz), total 2H], [4.26 (q, J = 6.9 Hz) and 4.14 (q, J = 6.9 Hz), total 1H], [3.96-3.87 (m), 3.74-3.64 (m), 3.62 (d, J = 10.6 Hz), 3.58 (d, component of AB quartet, J = 12.2 Hz), 3.50-3.39 (m), and 3.3-3.27 (m, assumed; partially obscured by solvent peak), total 4H], 2.92-2.74 (m, 2H), [2.57 (s) and 2.55 (s), total 3H], [2.20-2.10 (m), 2.08-1.92 (m), and 1.92-1.75 (m), total 4H], [1.44 (d, J = 6.9 Hz) and 1.39 (d, J = 6.9 Hz), total 3H]; 450.1 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 192 | Alternate Synthesis of Examples 3 and 4[109,110]; P28, P16 | 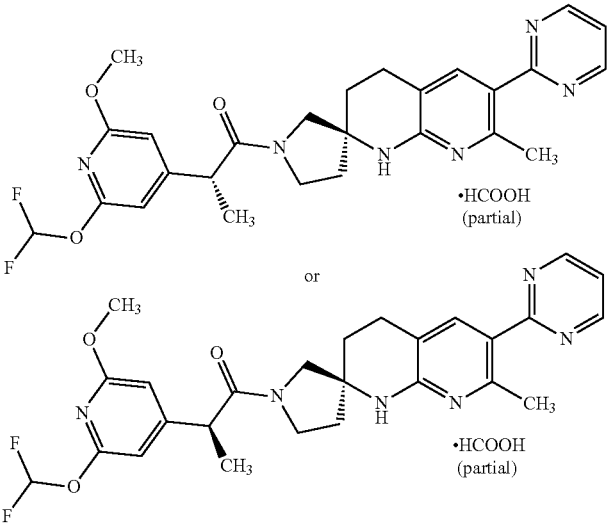<br>DIAST-1 | [8.81 (d, J = 4.9 Hz) and 8.81 (d, J = 4.9 Hz), total 2H], 8.34 (v br s, 0.25 H; assumed to be a partial formate salt), [7.89 (s) and 7.83 (s), total 1H], [7.54 (t, $J_{HF}$ = 73.2 Hz) and 7.53 (t, $J_{HF}$ = 73.2 Hz), total 1H], [7.31 (t, J = 4.9 Hz) and 7.31 (t, J = 4.9 Hz), total 1H], [6.58 (d, J = 1.2 Hz) and 6.54 (d, J = 1.2 Hz), total 1H], [6.51 (d, J = 1.2 Hz) and 6.46 (d, J = 1.2 Hz), total 1H], [4.01 (q, J = 6.9 Hz), 3.98-3.83 (m), 3.76-3.67 (m), 3.67-3.53 (m), 3.48 (d, component of AB quartet, J = 12.3 Hz), and 3.37-3.3 (m, assumed; partially obscured by solvent peak), total 5H], [3.90 (s) and 3.89 (s), total 3H], [2.95-2.71 (m) and 2.60-2.47 (m), total 2H], [2.58 (s) and 2.56 (s), total 3H], [2.14-2.04 (m) and 2.02-1.84 (m), total 3H], 1.78-1.71 (m, 1H), [1.41 (d, J = 7.0 Hz) and 1.39 (d, J = 6.9 Hz), total 3H]; 511.3 |
| 193 | Alternate Synthesis of Examples 3 and 4[109,110]; P28, P16 | 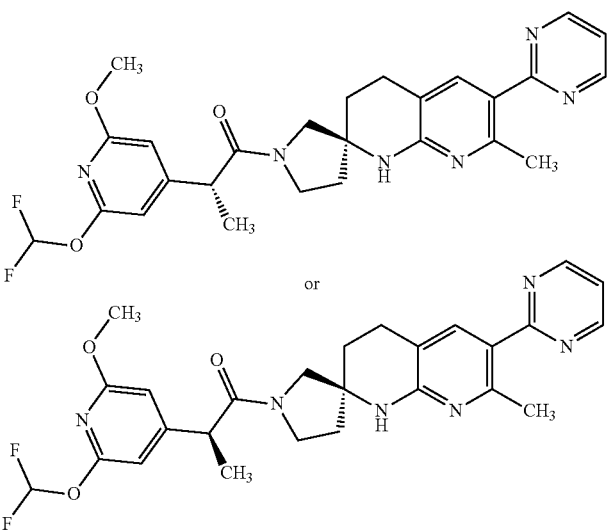<br>DIAST-2 | [8.82 (d, J = 4.9 Hz) and 8.81 (d, J = 4.9 Hz), total 2H], 7.88 (s, 1H), [7.53 (t, $J_{HF}$ = 73.3 Hz) and 7.45 (t, $J_{HF}$ = 73.2 Hz), total 1H], 7.31 (t, J = 4.9 Hz, 1H), [6.55 (d, J = 1.1 Hz) and 6.50 (d, J = 1.1 Hz), total 1H], [6.48 (d, J = 1.2 Hz) and 6.43 (d, J = 1.2 Hz), total 1H], [4.00 (q, J = 6.9 Hz), 3.96-3.86 (m), 3.75-3.62 (m), 3.60 (d, component of AB quartet, J = 12.5 Hz), 3.52-3.43 (m), and 3.37 (d, J = 10.7 Hz), total 5H], [3.89 (s) and 3.81 (s), total 3H], 2.93-2.78 (m, 2H), [2.59 (s) and 2.56 (s), total 3H], [2.18-2.09 (m), 2.08-1.92 (m), and 1.92-1.77 (m), total 4H], [1.42 (d, J = 6.9 Hz) and 1.38 (d, J = 6.9 Hz), total 3H]; 511.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 194 | Alternate Synthesis of Examples 3 and 4[111,112]; P28 | 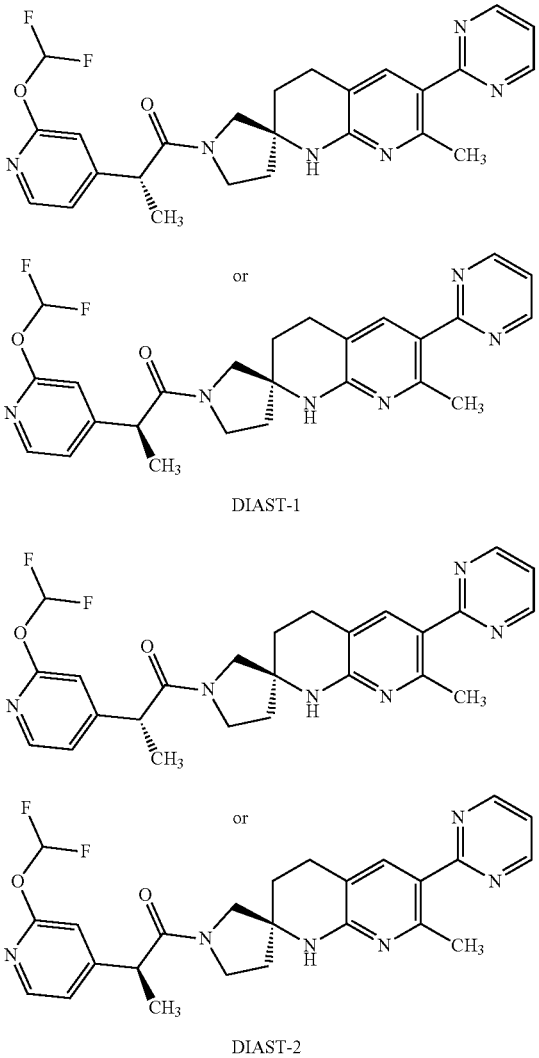DIAST-1 | [8.81 (d, J = 4.9 Hz) and 8.81 (d, J = 4.9 Hz), total 2H], [8.16 (d, J = 5.3 Hz) and 8.08 (d, J = 5.3 Hz), total 1H], [7.85 (s) and 7.83 (s), total 1H], [7.54 (t, $J_{HF}$ = 73.1 Hz) and 7.46 (t, $J_{HF}$ = 73.0 Hz), total 1H], [7.31 (t, J = 4.9 Hz) and 7.30 (t, J = 4.9 Hz), total 1H], [7.18 (dd, J = 5.3, 1.5 Hz) and 7.10 (dd, J = 5.3, 1.5 Hz), total 1H], [6.95 (br s) and 6.89 (br s), total 1H], [4.08 (q, J = 6.9 Hz) and 3.99 (q, J = 7.0 Hz), total 1H], [4.00-3.88 (m), 3.77-3.63 (m), 3.60 (d, component of AB quartet, J = 12.4 Hz), 3.53-3.43 (m), and 3.36 (d, J = 10.6 Hz), total 4H], 2.93-2.75 (m, 2H), [2.58 (s) and 2.55 (s), total 3H], [2.20-1.92 (m) and 1.92-1.76 (m), total 4H], [1.46 (d, J = 6.9 Hz) and 1.41 (d, J = 6.9 Hz), total 3H]; 481.2 |
| 195 | Alternate Synthesis of Examples 3 and 4[111,112]; P28 | 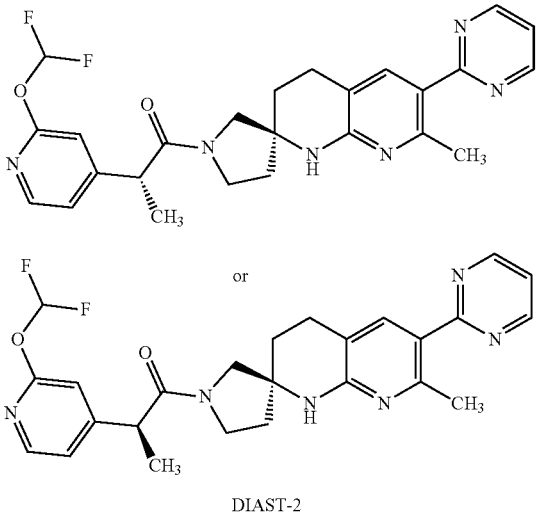DIAST-2 | [8.82 (d, J = 4.9 Hz) and 8.81 (d, J = 4.9 Hz), total 2H], 8.20-8.14 (m, 1H), [7.91 (s) and 7.85 (s), total 1H], [7.55 (t, $J_{HF}$ = 73.0 Hz) and 7.54 (t, $J_{HF}$ = 73.1 Hz), total 1H], [7.31 (t, J = 4.9 Hz) and 7.31 (t, J = 4.9 Hz), total 1H], [7.20 (dd, J = 5.3, 1.5 Hz) and 7.16 (dd, J = 5.3, 1.5 Hz), total 1H], [6.97 (br s) and 6.93 (br s), total 1H], [4.09 (q, J = 6.9 Hz) and 4.02 (q, J = 6.9 Hz), total 1H], [3.94-3.85 (m), 3.79-3.69 (m), 3.67 (d, component of AB quartet, J = 10.7 Hz), 3.65-3.55 (m), 3.57 (d, J = 12.0 Hz), 3.50 (d, component of AB quartet, J = 12.4 Hz), and 3.37-3.3 (m, assumed; partially obscured by solvent peak), total 4H], [2.95-2.72 (m) and 2.58-2.48 (m), total 2H], [2.59 (s) and 2.57 (s), total 3H], [2.16-2.05 (m) and 2.03-1.85 (m), total 3H], 1.79-1.71 (m, 1H), [1.45 (d, J = 7.0 Hz) and 1.43 (d, J = 6.9 Hz), total 3H]; 481.3 |
| 196 | Example 18; P27, P7 | 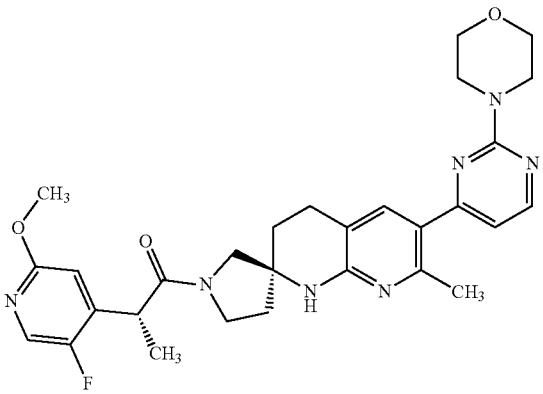 [SMILES: COc1cc([C@@H](C)C(=O)N2CC[C@@]3(CCc4cc(-c5ccnc(N6CCOCC6)n5)c(C)nc4N3)C2)c(F)cn1] | [8.32 (d, J = 5.1 Hz) and 8.31 (d, J = 5.1 Hz), total 1H], 8.04-7.95 (m, 1H), [7.55 (s) and 7.52 (s), total 1H], [6.79 (d, J = 4.9 Hz) and 6.73 (d, J = 4.8 Hz), total 1H], 6.76 (d, J = 5.2 Hz, 1H), [4.27 (q, J = 6.9 Hz) and 4.19 (q, J = 6.9 Hz), total 1H], [3.93-3.67 (m), 3.67-3.53 (m), 3.47 (d, component of AB quartet, J = 12.4 Hz), and 3.38 (d, J = 10.5 Hz), total 4H], [3.88 (s) and 3.88 (s), total 3H], 3.82-3.77 (m, 4H), 3.77-3.72 (m, 4H], [2.94-2.75 (m) and 2.65-2.52 (m), total 2H], [2.50 (br s) and 2.48 (br s), total 3H], [2.16-2.05 (m), 2.04-1.82 (m), and 1.82-1.73 (m), total 4H], [1.45 (d, J = 6.8 Hz) and 1.43 (d, J = 6.8 Hz), total 3H]; 548.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 197 | Example 18; P27, P7 | 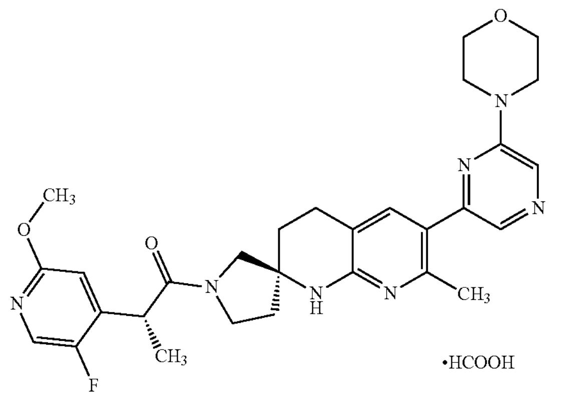 [SMILES: COc1cc([C@@H](C)C(=O)N2CC[C@@]3(CCc4cc(-c5cncc(N6CCOCC6)n5)c(C)nc4N3)C2)c(F)cn1 ; "·HCOOH"] | 8.23 (s, 1H), 8.07 (br s, 1H), [8.00 (d, J = 1.7 Hz) and 7.98 (d, J = 1.7 Hz), total 1H], [7.55 (s) and 7.52 (s), total 1H], [6.78 (d, J = 4.9 Hz) and 6.73 (d, J = 5.0 Hz), total 1H], [4.28 (q, J = 6.9 Hz) and 4.20 (q, J = 6.9 Hz), total 1H], [4.00 (s) and 4.00 (s), total 3H], [3.93-3.84 (m), 3.77-3.68 (m), 3.68-3.54 (m), 3.49 (d, component of AB quartet, J = 12.3 Hz), and 3.39 (d, J = 10.6 Hz), total 4H], [3.88 (s) and 3.88 (s), total 3H], [2.95-2.75 (m) and 2.66-2.55 (m), total 2H], [2.49 (s) and 2.47 (s), total 3H], [2.17-2.06 (m) and 2.05-1.84 (m), total 3H], 1.84-1.75 (m, 1H), [1.45 (d, J = 6.9 Hz) and 1.44 (d, J = 6.9 Hz), total 3H]; 493.3 |
| 198 | Example 18; P27, P7 | 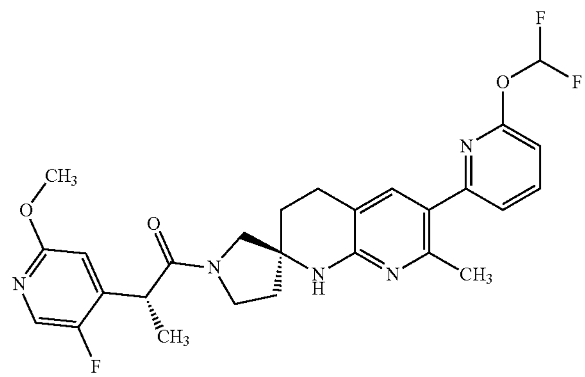 [SMILES: COc1cc([C@@H](C)C(=O)N2CC[C@@]3(CCc4cc(-c5cccc(OC(F)F)n5)c(C)nc4N3)C2)c(F)cn1] | [8.00 (d, J = 1.7 Hz) and 7.98 (d, J = 1.7 Hz), total 1H], 7.90-7.84 (m, 1H), [7.56 (t, $J_{HF}$ = 73.2 Hz) and 7.56 (t, $J_{HF}$ = 73.2 Hz), total 1H], [7.50 (s) and 7.47 (s), total 1H], 7.29 (d, J = 7.5 Hz, 1H), 6.85 (br d, J = 8 Hz, 1H), [6.78 (d, J = 4.9 Hz) and 6.73 (d, J = 4.9 Hz), total 1H], [4.28 (q, J = 6.9 Hz) and 4.19 (q, J = 6.9 Hz), total 1H], [3.93-3.84 (m), 3.76-3.67 (m), 3.67-3.53 (m), 3.48 (d, component of AB quartet, J = 12.3 Hz), 3.42-3.35 (m), and 3.39 (d, J = 10.5 Hz), total 4H], [3.89 (s) and 3.88 (s), total 3H], [2.94-2.74 (m) and 2.64-2.53 (m), total 2H], [2.44 (s) and 2.42 (s), total 3H], [2.15-2.05 (m), 2.04-1.83 (m), and 1.83-1.74 (m), total 4H], [1.45 (d, J = 6.9 Hz) and 1.44 (d, J = 6.9 Hz), total 3H]; 528.3 |
| 199 | Example 18; P27, P7 | 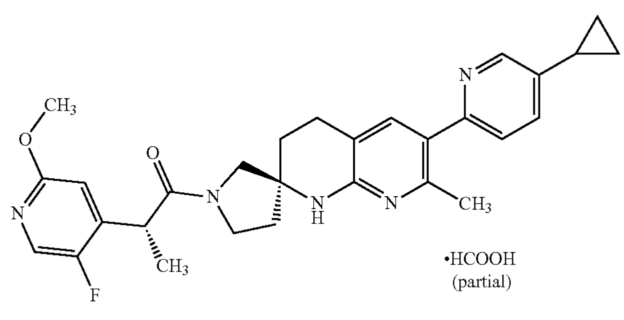 [SMILES: COc1cc([C@@H](C)C(=O)N2CC[C@@]3(CCc4cc(-c5ccc(C6CC6)cn5)c(C)nc4N3)C2)c(F)cn1] | 8.36 (v br s, 0.7 H; assumed to be a partial formate salt), [7.99 (d, J = 1.7 Hz) and 7.98 (d, J = 1.7 Hz), total 1H], 7.64 (d, component of AB quartet, J = 8.8 Hz, 1H), [7.50 (d, component of AB quartet, J = 8.8 Hz) and 7.50 (d, component of AB quartet, J = 8.8 Hz), total 1H], [7.44 (s) and 7.41 (s), total 1H], [6.78 (d, J = 4.9 Hz) and 6.73 (d, J = 4.9 Hz), total 1H], [4.28 (q, J = 6.9 Hz) and 4.19 (q, J = 6.9 Hz), total 1H], [3.94-3.83 (m), 3.77-3.68 (m), 3.67-3.53 (m), 3.48 (d, component of AB quartet, J = 12.2 Hz), and 3.39 (d, J = 10.6 Hz), total 4H], [3.88 (s) and 3.88 (s), total 3H], [2.94-2.74 (m) and 2.64-2.53 (m), total 2H], [2.36 (s) and 2.34 (s), total 3H], 2.34-2.24 (m, 1H), [2.16-2.06 (m) and 2.05-1.84 (m), total 3H], 1.83-1.74 (m, 1H), [1.45 (d, J = 6.9 Hz) and 1.44 (d, J = 6.9 Hz), total 3H], 1.24-1.09 (m, 4H); 503.3 |

TABLE 1-continued

Method of synthesis, structure, and physicochemical data for Examples 21-201.

| Example Number | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| 200 | Example 18; P27, P7 | (structure) | [8.99 (d, J = 5.0 Hz) and 8.98 (d, J = 5.0 Hz), total 1H], [8.07 (s) and 8.04 (s), total 1H], [8.00 (d, J = 1.7 Hz) and 7.98 (d, J = 1.7 Hz), total 1H], [7.51 (d, J = 5.0 Hz) and 7.50 (d, J = 5.0 Hz), total 1H], [6.78 (d, J = 4.9 Hz) and 6.75-6.72 (m), total 1H], [6.72 (t, $J_{HF}$ = 54.8 Hz) and 6.72 (t, $J_{HF}$ = 54.8 Hz), total 1H], [4.28 (q, J = 6.9 Hz) and 4.20 (q, J = 6.9 Hz), total 1H], [3.94-3.84 (m), 3.77-3.54 (m), 3.49 (d, component of AB quartet, J = 12.4 Hz), 3.42-3.35 (m), and 3.40 (d, J = 10.6 Hz), total 4H], [3.88 (s) and 3.88 (s), total 3H], [2.95-2.76 (m) and 2.66-2.54 (m), total 2H], [2.66 (s) and 2.64 (s), total 3H], [2.17-2.06 (m), 2.05-1.83 (m), and 1.83-1.75 (m), total 4H], [1.45 (d, J = 6.9 Hz) and 1.44 (d, J = 6.9 Hz), total 3H]; 513.3 |
| 201 | Example 18; P27, P7 | (structure) | 8.33 (br s, 1H), [8.13 (s) and 8.11 (s), total 1H], 7.98 (br s, 1H), [6.77 (d, J = 4.9 Hz) and 6.73 (d, J = 4.9 Hz), total 1H], 4.32-4.17 (m, 1H), [3.97-3.83 (m), 3.80 (d, J = 11.0 Hz), 3.77-3.56 (m), and 3.43 (d, J = 11.0 Hz), total 4H], 3.88 (s, 3H), [3.06-2.87 (m) and 2.81-2.70 (m), total 2H], [2.78 (s) and 2.76 (s), total 3H], [2.31-2.16 (m) and 2.12-1.93 (m), total 3H], 1.93-1.86 (m, 1H), 1.45 (br d, J = 6.9 Hz, 3H); 536.2 |

1. Reaction of 5-bromo-2-iodopyrimidine with P27 was effected using [1,1'-bis(diphenylphosphino)ferrocene]dichloropalladium(II) and sodium carbonate, to afford the requisite tert-butyl (2S)-6-(5-bromopyrimidin-2-yl)-7-methyl-3,4-dihydro-1H-spiro[1,8-naphthyridine-2,3'-pyrrolidine]-1'-carboxylate.

2. Deprotection of P17 with hydrogen chloride in 2-propanol provided the requisite 7-methyl-3,4-dihydro-1H-spiro[1,8-naphthyridine-2,3'-pyrrolidine].

3. Separation of the product into its four component diastereomers was carried out via supercritical fluid chromatography, as follows: An initial separation was carried out [Column: Chiral Technologies Chiralcel OJ, 30×250 mm, 5 μm; Mobile phase: 9:1 carbon dioxide/(2-propanol containing 0.2% 1-aminopropan-2-ol); Flow rate: 80 mL/minute; Back pressure: 100 bar] to provide a first-eluting mixture (Pdt1) and a second-eluting mixture (Pdt2). Retention time for Pdt1: 3.80 minutes [Analytical conditions. Column: Chiral Technologies Chiralcel OJ, 4.6×250 mm, 5 μm; Mobile phase A: carbon dioxide; Mobile phase B: 2-propanol containing 0.2% 1-aminopropan-2-ol; Gradient: 5% B for 1.00 minute, then 5% to 60% B over 8.00 minutes; Flow rate: 3.0 mL/minute; Back pressure: 120 bar]. Retention time for Pdt2: 4.08 minutes (Analytical conditions identical to those used for Pdt1).

Pdt1 was then separated {Column: Phenomenex Lux Amylose-1, 30×250 mm, 5 μm; Mobile phase: 3:2 carbon dioxide/[(1:1 acetonitrile:methanol) containing 0.2% (7 M ammonia in methanol)]; Flow rate: 80 mL/minute; Back pressure: 100 bar}. The first-eluting diastereomer was designated as Example 23, and the second-eluting diastereomer as Example 24.

Pdt2 was separated {Column: Phenomenex Lux Amylose-1, 30×250 mm, 5 μm; Mobile phase: 7:3 carbon dioxide/[ethanol containing 0.2% (7 M ammonia in methanol)]; Flow rate: 80 mL/minute; Back pressure: 100 bar} to provide first-eluting diastereomer Example 25 and second-eluting diastereomer Example 26.

4. Analytical conditions. Column: Phenomenex Lux Amylose-1, 4.6×250 mm, 5 μm; Mobile phase A: carbon dioxide; Mobile phase B: (1:1 acetonitrile/methanol) containing 0.2% (7 M ammonia in methanol); Gradient: 5% B for 1.00 minute, then 5% to 60% B over 8.00 minutes; Flow rate: 3.0 mL/minute; Back pressure: 120 bar.

5. This LCMS data was derived from analysis of the reaction mixture.

6. Analytical conditions. Column: Phenomenex Lux Amylose-1, 4.6×250 mm, 5 μm; Mobile phase A: carbon dioxide; Mobile phase B: ethanol containing 0.2% (7 M ammonia in methanol)]; Gradient: 5% B for 1.00 minute, then 5% to 60% B over 8.00 minutes; Flow rate: 3.0 mL/minute; Back pressure: 120 bar.

7. The requisite tert-butyl (2S)-7-methyl-6-[2-methyl-1-(trifluoromethyl)-1H-imidazol-4-yl]-3,4-dihydro-1H-spiro

[1,8-naphthyridine-2,3'-pyrrolidine]-1'-carboxylate was synthesized from P23 using the method described in Preparation P28 for synthesis of C69; 4-iodo-2-methyl-1-(trifluoromethyl)-1H-imidazole was used in place of 2-bromopyrimidine.

8. [(2R)-1'-(tert-Butoxycarbonyl)-7-methyl-3,4-dihydro-1H-spiro[1,8-naphthyridine-2,3'-pyrrolidin]-6-yl]boronic acid was prepared from P24 using the method described in Preparation P27. Subsequent conversion to the requisite tert-butyl (2R)-7-methyl-6-(pyrimidin-2-yl)-3,4-dihydro-1H-spiro[1,8-naphthyridine-2,3'-pyrrolidine]-1'-carboxylate was carried out in the same manner that C84 was synthesized from P27 in Example 18.

9. Deprotection of C66 with hydrogen chloride in dichloromethane provided the requisite (2R)-7-methyl-6-(2-methyl-2H-tetrazol-5-yl)-3,4-dihydro-1H-spiro[1,8-naphthyridine-2,3'-pyrrolidine].

10. The product was separated into its component diastereomers using supercritical fluid chromatography [Column: Chiral Technologies Chiralcel OJ-H, 30×250 mm, 5 μm; Mobile phase: 4:1 carbon dioxide/(methanol containing 0.2% ammonium hydroxide); Flow rate: 80 mL/minute; Back pressure: 120 bar]. The first-eluting diastereomer was designated as Example 31, and the second-eluting diastereomer as Example 32. On analytical supercritical fluid chromatography [Column: Chiral Technologies Chiralcel OJ-H, 4.6×250 mm, 5 μm; Mobile phase A: carbon dioxide; Mobile phase B: methanol containing 0.2% (7 M ammonia in methanol); Gradient: 5% B for 1.00 minute, then 5% to 60% B over 8.00 minutes; Flow rate: 3.0 mL/minute; Back pressure: 120 bar], Example 31 exhibited a retention time of 4.22 minutes. Example 32 had a retention time of 4.48 minutes under the same conditions.

11. From comparison of the $^1$H NMR spectra, Example 31 is the enantiomer of Example 4, and Example 32 is the enantiomer of Example 3.

12. Conversion of C44 to 1'-benzyl-7-methyl-6-(2-methyl-1,3-oxazol-4-yl)-3,4-dihydro-1H-spiro[1,8-naphthyridine-2,3'-pyrrolidine] was carried out using the method described for synthesis of C48 in Preparations P17 and P18, except that 2-chloro-3-iodo-6-methyl-5-(2-methyl-1,3-oxazol-4-yl)pyridine was used in place of C40. Subsequent hydrogenation provided the requisite 7-methyl-6-(2-methyl-1,3-oxazol-4-yl)-3,4-dihydro-1H-spiro[1,8-naphthyridine-2,3'-pyrrolidine].

13. The product was separated into its component diastereomers using supercritical fluid chromatography [Column: Chiral Technologies Chiralcel OJ-H, 20×250 mm, 5 μm; Mobile phase: 78:22 carbon dioxide/(methanol containing 0.2% ammonium hydroxide); Flow rate: 50 mL/minute]. The first-eluting diastereomer was designated as Example 34, and the second-eluting diastereomer as Example 35. On analytical supercritical fluid chromatography [Column: Chiral Technologies Chiralcel OJ-3R, 3.0×150 mm, 3 μm; Mobile phase: 3:1 carbon dioxide/(methanol containing 0.1% diethylamine); Flow rate: 2.5 mL/minute], Example 34 exhibited a retention time of 2.63 minutes. Example 35 had a retention time of 3.36 minutes under the same conditions.

14. The product was separated into its component diastereomers using HPLC (Column: Chiral Technologies Chiralpak AD, 50×250 mm, 10 μm; Mobile phase: 95:5:0.1 ethanol/acetonitrile/diethylamine; Flow rate: 60 mL/minute). The first-eluting diastereomer was designated as Example 36, and the second-eluting diastereomer as Example 37. On analytical HPLC (Column: Chiral Technologies Chiralpak AD-H, 4.6×150 mm, 5 μm; Mobile phase: 95:5:0.1 ethanol/acetonitrile/diethylamine; Flow rate: 0.8 mL/minute), Example 36 exhibited a retention time of 5.04 minutes. Example 37 had a retention time of 7.89 minutes under the same conditions.

15. Conversion of 5-chloro-4-iodo-2-(trifluoromethyl)pyridine to the requisite 2-[5-chloro-2-(trifluoromethyl)pyridin-4-yl]propanoic acid was carried out using the method described in Preparation P5. LCMS m/z 254.0 (chlorine isotope pattern observed) [M+H]$^+$. $^1$H NMR (400 MHz, methanol-d$_4$) δ 8.72 (s, 1H), 7.83 (s, 1H), 4.27 (q, J=7.3 Hz, 1H), 1.57 (d, J=7.3 Hz, 3H).

16. The product was separated into its component diastereomers using HPLC (Column: Chiral Technologies Chiralpak AY, 50×250 mm, 10 μm; Mobile phase: 60:40:0.1 hexane/ethanol/diethylamine; Flow rate: 60 mL/minute). The first-eluting diastereomer was designated as Example 38, and the second-eluting diastereomer as Example 39. On analytical HPLC (Column: Chiral Technologies Chiralpak AD-H, 4.6×150 mm, 5 μm; Mobile phase: methanol; Flow rate: 1.0 mL/minute), Example 38 exhibited a retention time of 3.53 minutes. Example 39 had a retention time of 5.46 minutes under the same conditions.

17. Conversion of 4-iodo-2-methoxy-5-(trifluoromethyl)pyridine to the requisite 2-[2-methoxy-5-(trifluoromethyl)pyridin-4-yl]propanoic acid was carried out using the method described in Preparation P5. LCMS m/z 250.1 [M+H]$^+$. $^1$H NMR (400 MHz, chloroform-d) δ 8.46 (s, 1H), 6.88 (s, 1H), 4.10 (q, J=7.1 Hz, 1H), 4.00 (s, 3H), 1.54 (d, J=7.0 Hz, 3H).

18. The product was separated into its component diastereomers using HPLC (Column: Chiral Technologies Chiralpak IA, 50×250 mm, 10 μm; Mobile phase: 70:30:0.1 hexane/ethanol/diethylamine; Flow rate: 60 mL/minute). The first-eluting diastereomer was designated as Example 40, and the second-eluting diastereomer as Example 41. On analytical HPLC (Column: Chiral Technologies Chiralpak IA-3, 4.6×250 mm, 3 μm; Mobile phase: 70:30:0.1 hexane/ethanol/diethylamine; Flow rate: 1.0 mL/minute), Example 40 exhibited a retention time of 6.49 minutes. Example 41 had a retention time of 8.39 minutes under the same conditions.

19. The product was separated into its component diastereomers using supercritical fluid chromatography [Column: Chiral Technologies Chiralcel OJ-H, 20×250 mm, 5 μm; Mobile phase: 7:3 carbon dioxide/(methanol containing 0.2% ammonium hydroxide); Flow rate: 50 mL/minute]. The first-eluting diastereomer was designated as Example 42, and the second-eluting diastereomer as Example 43. On analytical supercritical fluid chromatography [Column: Chiral Technologies Chiralcel OJ-3R, 3.0×150 mm, 3 μm; Mobile phase: 7:3 carbon dioxide/(methanol containing 0.1% diethylamine); Flow rate: 2.5 mL/minute], Example 42 exhibited a retention time of 1.81 minutes. Example 43 had a retention time of 2.54 minutes under the same conditions.

20. 6-Chloro-2-methylpyrimidin-4-ol was converted to 4-chloro-6-(difluoromethoxy)-2-methylpyrimidine using the method described in Preparation P11, Step 1. This material was then used to prepare the requisite lithium 2-[6-(difluoromethoxy)-2-methylpyrimidin-4-yl]propanoate according to the method provided in Preparation P4. LCMS m/z 233.1 [M+H]$^+$. $^1$H NMR (400 MHz, methanol-d$_4$) δ 7.62 (t, J$_{HF}$=72.1 Hz, 1H), 6.83 (s, 1H), 3.70 (q, J=7.2 Hz, 1H), 2.58 (s, 3H), 1.48 (d, J=7.2 Hz, 3H).

21. The product was separated into its component diastereomers using HPLC (Column: Chiral Technologies Chiralpak IA 4.6 cm×25 mm; Mobile phase: ethanol; Flow rate: 1 mL/minute). The first-eluting diastereomer was designated as Example 44, and the second-eluting diastereomer as Example 45. Each of these diastereomers was subjected to a final purification via reversed-phase HPLC (Column: Nouryon Kromasil 100-5 C18, 21.5×100 mm, 5 μm; Mobile phase A: water containing 0.1% formic acid; Mobile phase B: acetonitrile; Gradient: 20% to 40% B). On analytical HPLC (Column: Column: Chiral Technologies Chiralpak IA, 4.6×250 mm; Mobile phase: ethanol; Flow rate: 1.0 mL/minute), Example 44 exhibited a retention time of 9.78 minutes. Example 45 had a retention time of 13.69 minutes under the same conditions.

22. The product was separated into its component diastereomers using supercritical fluid chromatography (Column: Chiral Technologies Chiralcel OJ-H, 20×250 mm, 5 μm; Mobile phase: 72:28 carbon dioxide/ethanol; Flow rate: 50 mL/minute). The first-eluting diastereomer was designated as Example 46, and the second-eluting diastereomer as Example 47. On analytical supercritical fluid chromatography [Column: Chiral Technologies Chiralcel OJ-3R, 3.0× 150 mm, 3 μm; Mobile phase: 3:1 carbon dioxide/(methanol containing 0.1% diethylamine); Flow rate: 2.5 mL/minute], Example 46 exhibited a retention time of 1.62 minutes. Example 47 had a retention time of 2.77 minutes under the same conditions.

23. The product was separated into its component diastereomers using supercritical fluid chromatography [Column: Chiral Technologies Chiralcel OJ-H, 20×250 mm, 5 μm; Mobile phase: 88:12 carbon dioxide/(methanol containing 0.2% ammonium hydroxide); Flow rate: 50 mL/minute]. The first-eluting diastereomer was designated as Example 48, and the second-eluting diastereomer as Example 49. On analytical supercritical fluid chromatography [Column: Chiral Technologies Chiralcel OJ-3R, 3.0×150 mm, 3 μm; Mobile phase: 4:1 carbon dioxide/(methanol containing 0.1% diethylamine); Flow rate: 2.0 mL/minute], Example 48 exhibited a retention time of 2.43 minutes. Example 49 had a retention time of 3.04 minutes under the same conditions.

24. The product was separated into its component diastereomers using supercritical fluid chromatography [Column: Chiral Technologies Chiralcel OJ-H, 20×250 mm, 5 μm; Mobile phase: 84:16 carbon dioxide/(methanol containing 0.2% ammonium hydroxide); Flow rate: 50 mL/minute]. The first-eluting diastereomer was designated as Example 50, and the second-eluting diastereomer as Example 51. On analytical supercritical fluid chromatography [Column: Chiral Technologies Chiralcel OJ-3R, 3.0×150 mm, 3 μm; Mobile phase: 3:1 carbon dioxide/(methanol containing 0.1% diethylamine); Flow rate: 2.5 mL/minute], Example 50 exhibited a retention time of 1.77 minutes. Example 51 had a retention time of 2.16 minutes under the same conditions.

25. The product was separated into its component diastereomers using supercritical fluid chromatography [Column: Chiral Technologies Chiralcel OJ-H, 20×250 mm, 5 μm; Mobile phase: 86:14 carbon dioxide/(methanol containing 0.2% ammonium hydroxide); Flow rate: 50 mL/minute]. The first-eluting diastereomer was designated as Example 52, and the second-eluting diastereomer as Example 53. On analytical supercritical fluid chromatography (Column: Chiral Technologies Chiralcel OJ-3R, 3.0×150 mm, 3 μm; Mobile phase: 4:1 carbon dioxide/(methanol containing 0.1% diethylamine); Flow rate: 2.0 mL/minute), Example 52 exhibited a retention time of 2.24 minutes. Example 53 had a retention time of 2.58 minutes under the same conditions.

26. The product was separated into its component diastereomers using HPLC (Column: Chiral Technologies Chiralpak IG, 25×250 mm, 10 μm; Mobile phase: ethanol; Flow rate: 30 mL/minute). The first-eluting diastereomer was designated as Example 55, and the second-eluting diastereomer as Example 56. On analytical HPLC (Column: Chiral Technologies Chiralpak IG-3, 4.6×150 mm, 3 μm; Mobile phase: ethanol; Flow rate: 0.5 mL/minute), Example 55 exhibited a retention time of 9.79 minutes. Example 56 had a retention time of 12.37 minutes under the same conditions.

27. Conversion of 3-fluoro-4-iodo-2-methoxypyridine to the requisite 2-(3-fluoro-2-methoxypyridin-4-yl)propanoic acid was carried out using the method described in Preparation P5. LCMS m/z 200.1 [M+H]$^+$. $^1$H NMR (400 MHz, chloroform-d) δ 7.89 (d, J=5.3 Hz, 1H), 6.83 (dd, J=5, 5 Hz, 1H), 4.09 (q, J=7.2 Hz, 1H), 4.02 (s, 3H), 1.52 (d, J=7.4 Hz, 3H).

28. The product was separated into its component diastereomers using supercritical fluid chromatography [Column: Chiral Technologies Chiralcel OJ-H, 20×250 mm, 5 μm; Mobile phase: 4:1 carbon dioxide/(methanol containing 0.2% ammonium hydroxide); Flow rate: 50 mL/minute]. The first-eluting diastereomer was designated as Example 57, and the second-eluting diastereomer as Example 58. On analytical supercritical fluid chromatography [Column: Chiral Technologies Chiralcel OJ-3R, 3.0×150 mm, 3 μm; Mobile phase: 3:1 carbon dioxide/(methanol containing 0.1% diethylamine); Flow rate: 2.5 mL/minute], Example 57 exhibited a retention time of 1.77 minutes. Example 58 had a retention time of 2.92 minutes under the same conditions.

29. Conversion of 5-chloro-4-iodopyridin-2-ol to the requisite 2-[5-chloro-2-(difluoromethoxy)pyridin-4-yl]propanoic acid was carried out using the method described in Preparation P5. LCMS m/z 252.1 (chlorine isotope pattern observed) [M+H]$^+$. $^1$H NMR (400 MHz, methanol-d$_4$) δ 8.21 (s, 1H), 7.50 (t, $J_{HF}$=72.8 Hz, 1H), 7.01 (s, 1H), 4.13 (q, J=7.2 Hz, 1H), 1.52 (d, J=7.2 Hz, 3H).

30. The product was separated into its component diastereomers using HPLC (Column: Chiral Technologies Chiralpak AD, 50×250 mm, 10 μm; Mobile phase: 70:30:0.1 methanol/acetonitrile/diethylamine; Flow rate: 50 mL/minute). The first-eluting diastereomer was designated as Example 59, and the second-eluting diastereomer as Example 60. On analytical HPLC (Column: Chiral Technologies Chiralpak AD-H, 4.6×150 mm, 5 μm; Mobile phase: 4:1 methanol/acetonitrile; Flow rate: 1.0 mL/minute), Example 59 exhibited a retention time of 3.16 minutes. Example 60 had a retention time of 6.23 minutes under the same conditions.

31. A final purification was carried out using reversed-phase C18 chromatography (Mobile phase A: water containing 0.1% formic acid; Mobile phase B: acetonitrile; Gradient: 0% to 50% B).

32. The product was separated into its component diastereomers using HPLC (Column: Chiral Technologies Chiralpak AY, 50×250 mm, 10 μm; Mobile phase: 70:30:0.1 hexane/ethanol/diethylamine; Flow rate: 60 mL/minute). The first-eluting diastereomer was designated as Example 61, and the second-eluting diastereomer as Example 62. On analytical HPLC (Column: Chiral Technologies Chiralpak AY-3, 4.6×150 mm, 3 μm; Mobile phase: 70:30:0.1 hexane/ethanol/diethylamine; Flow rate: 1.0 mL/minute), Example 61 exhibited a retention time of 4.41 minutes. Example 62 had a retention time of 5.60 minutes under the same conditions.

33. Reaction of 5-chloro-4-iodopyridin-2-ol with 1-trifluoromethyl-1,2-benziodoxol-3-(1H)-one in nitromethane at 100° C. provided 5-chloro-4-iodo-2-(trifluoromethoxy)pyridine. This material was converted to the requisite 2-[5-chloro-2-(trifluoromethoxy)pyridin-4-yl]propanoic acid using the method described in Preparation P5. LCMS m/z 270.0 (chlorine isotope pattern observed) [M+H]⁺. ¹H NMR (400 MHz, methanol-d₄) δ 8.32 (s, 1H), 7.20 (s, 1H), 4.17 (q, J=7.3 Hz, 1H), 1.54 (d, J=7.3 Hz, 3H).

34. The product was separated into its component diastereomers using HPLC (Column: Chiral Technologies Chiralpak AD, 50×250 mm, 10 μm; Mobile phase: 100:0.1 methanol/diethylamine; Flow rate: 60 mL/minute). The first-eluting diastereomer was designated as Example 63, and the second-eluting diastereomer as Example 64. On analytical HPLC (Column: Chiral Technologies Chiralpak AD-H, 4.6× 250 mm, 5 μm; Mobile phase: 100:0.1 methanol/diethylamine; Flow rate: 1.0 mL/minute), Example 63 exhibited a retention time of 7.22 minutes. Example 64 had a retention time of 10.44 minutes under the same conditions.

35. A final purification was carried out using reversed-phase C18 chromatography (Mobile phase A: water containing 0.1% formic acid; Mobile phase B: acetonitrile; Gradient: 0% to 40% B).

36. The product was separated into its component enantiomers using supercritical fluid chromatography [Column: Chiral Technologies Chiralpak AD-H, 20×250 mm, 5 μm; Mobile phase: 64:36 carbon dioxide/(methanol containing 0.2% ammonium hydroxide); Flow rate: 50 mL/minute]. The first-eluting enantiomer was designated as Example 65, and the second-eluting enantiomer as Example 66. On analytical supercritical fluid chromatography [Column: Chiral Technologies Chiralpak AD-3R, 3.0×150 mm, 3 μm; Mobile phase: 65:35 carbon dioxide/(methanol containing 0.1% diethylamine); Flow rate: 2.0 mL/minute], Example 65 exhibited a retention time of 1.32 minutes. Example 66 had a retention time of 1.79 minutes under the same conditions.

37. The bromo-heterocyclic reactant (2-bromo-5-methoxypyrimidine) was used, rather than the chloro derivative.

38. Demethylation of Example 14 was carried out with trimethylsilyl iodide in acetonitrile at reflux, to provide (2R)-2-(5-fluoro-2-hydroxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one. This material was reacted with iodo(²H₃)methane and potassium carbonate in N,N-dimethylformamide to afford Example 74.

39. The product was separated into its component diastereomers using supercritical fluid chromatography [Column: Chiral Technologies Chiralpak IG-H, 20×250 mm, 5 μm; Mobile phase: 54:46 carbon dioxide/(methanol containing 0.2% ammonium hydroxide); Flow rate: 45 mL/minute]. The first-eluting diastereomer was designated as Example 75, and the second-eluting diastereomer as Example 76. On analytical supercritical fluid chromatography [Column: Chiral Technologies Chiralpak IG-3R, 3.0×150 mm, 3 μm; Mobile phase: 1:1 carbon dioxide/(methanol containing 0.1% diethylamine); Flow rate: 1.5 mL/minute], Example 75 exhibited a retention time of 1.93 minutes. Example 76 had a retention time of 2.99 minutes under the same conditions.

40. The product was separated into its component diastereomers using HPLC (Column: Chiral Technologies Chiralpak AD, 50×250 mm, 10 μm; Mobile phase: 70/30/0.1 methanol/acetonitrile/diethylamine; Flow rate: 60 mL/minute). The first-eluting diastereomer was designated as Example 77, and the second-eluting diastereomer as Example 78. On analytical HPLC (Column: Chiral Technologies Chiralpak AD-3, 4.6×250 mm, 3 μm; Mobile phase: 70/30/0.1 methanol/acetonitrile/diethylamine; Flow rate: 1.0 mL/minute), Example 77 exhibited a retention time of 2.58 minutes. Example 78 had a retention time of 4.41 minutes under the same conditions.

41. Conversion of 5-fluoro-4-iodo-2-(trifluoromethyl)pyridine to the requisite 2-[5-fluoro-2-(trifluoromethyl)pyridin-4-yl]propanoic acid was carried out using the method described in Preparation P5. LCMS m/z 238.1 [M+H]⁺. ¹H NMR (400 MHz, chloroform-d) δ 8.55 (s, 1H), 7.70 (d, J=5.4 Hz, 1H), 4.14 (q, J=7.3 Hz, 1H), 1.61 (d, J=7.3 Hz, 3H).

42. The product was separated into its component diastereomers using supercritical fluid chromatography [Column: Chiral Technologies Chiralpak IG-H, 20×250 mm, 5 μm; Mobile phase: 54:46 carbon dioxide/(methanol containing 0.2% ammonium hydroxide); Flow rate: 45 mL/minute]. The first-eluting diastereomer was designated as Example 79, and the second-eluting diastereomer as Example 80. On analytical supercritical fluid chromatography [Column: Chiral Technologies Chiralpak IG-3R, 3.0×150 mm, 3 μm; Mobile phase: 1:1 carbon dioxide/(methanol containing 0.1% diethylamine); Flow rate: 1.5 mL/minute], Example 79 exhibited a retention time of 1.97 minutes. Example 80 had a retention time of 3.41 minutes under the same conditions.

43. The product was separated into its component diastereomers using supercritical fluid chromatography [Column: Chiral Technologies Chiralcel OJ-H, 20×250 mm, 5 μm; Mobile phase: 86:14 carbon dioxide/(methanol containing 0.2% ammonium hydroxide); Flow rate: 50 mL/minute]. The first-eluting diastereomer was designated as Example 81, and the second-eluting diastereomer as Example 82. On analytical supercritical fluid chromatography [Column: Chiral Technologies Chiralcel OJ-3R, 3.0×150 mm, 3 μm; Mobile phase: 3:1 carbon dioxide/(methanol containing 0.1% diethylamine); Flow rate: 2.5 mL/minute], Example 81 exhibited a retention time of 1.55 minutes. Example 82 had a retention time of 1.79 minutes under the same conditions.

44. 2,6-Dimethoxy-4-methylpyridine was converted to the requisite 2-(2,6-dimethoxypyridin-4-yl)propanoic acid using the method described in Preparation P1. LCMS m/z 212.1 [M+H]⁺. ¹H NMR (400 MHz, chloroform-d) δ 6.26 (s, 2H), 3.90 (s, 6H), 3.63 (q, J=7.2 Hz, 1H), 1.47 (d, J=7.1 Hz, 3H).

45. The product was separated into its component diastereomers using supercritical fluid chromatography [Column: Chiral Technologies Chiralcel OJ-H, 20×250 mm, 5 μm; Mobile phase: 86:14 carbon dioxide/(methanol containing 0.2% ammonium hydroxide); Flow rate: 50 mL/minute]. The first-eluting diastereomer was designated as Example 83, and the second-eluting diastereomer as Example 84. On analytical supercritical fluid chromatography [Column: Chiral Technologies Chiralcel OJ-3R, 3.0×150 mm, 3 μm; Mobile phase: 3:1 carbon dioxide/(methanol containing 0.1% diethylamine); Flow rate: 2.5 mL/minute], Example 83 exhibited a retention time of 1.75 minutes. Example 84 had a retention time of 2.11 minutes under the same conditions.

46. The product was separated into its component diastereomers using supercritical fluid chromatography [Column: Chiral Technologies Chiralcel OD-H, 20×250 mm, 5 μm; Mobile phase: 68:32 carbon dioxide/(methanol containing 0.2% ammonium hydroxide); Flow rate: 50 mL/minute]. The first-eluting diastereomer was designated as Example 85, and the second-eluting diastereomer as Example 86. On analytical supercritical fluid chromatography [Column: Chiral Technologies ChiralCel OD-3R, 3.0×150 mm, 3 μm; Mobile phase: 7:3 carbon dioxide/(methanol containing 0.1% diethylamine); Flow rate: 2.0 mL/minute], Example 85 exhibited a retention time of 1.70 minutes. Example 86 had a retention time of 2.14 minutes under the same conditions.

47. Hydrogenation of C72 over palladium hydroxide provided the requisite 7-methyl-3,4-dihydro-1H-spiro[1,8-naphthyridine-2,3'-pyrrolidine].

48. The product was separated into its component enantiomers using supercritical fluid chromatography [Column: Chiral Technologies Chiralcel OJ-H, 21×250 mm, 5 μm; Mobile phase: 9:1 carbon dioxide/(methanol containing 0.2% ammonium hydroxide); Flow rate: 75 mL/minute; Back pressure: 200 bar]. The first-eluting enantiomer was designated as Example 87, and the second-eluting enantiomer as Example 88.

49. Conditions for analytical HPLC. Column: Phenomenex Lux Cellulose-3, 4.6×100 mm, 5 μm; Mobile phase: 4:1 carbon dioxide/(methanol containing 0.2% ammonium hydroxide); Flow rate: 1.5 mL/minute; Back pressure: 200 bar.

50. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes, then 95% B for 1.0 minute; Flow rate: 2 mL/minute.

51. The product was separated into its component diastereomers using supercritical fluid chromatography [Column: Chiral Technologies Chiralcel OD-H, 21×250 mm, 5 μm; Mobile phase: 3:1 carbon dioxide/(methanol containing 0.2% ammonium hydroxide); Flow rate: 75 mL/minute; Back pressure: 200 bar]. The first-eluting diastereomer was designated as Example 90, and the second-eluting diastereomer as Example 91.

52. Conditions for analytical HPLC. Column: Phenomenex Lux Cellulose-1, 4.6×100 mm, 5 μm; Mobile phase: 3:2 carbon dioxide/(methanol containing 0.2% ammonium hydroxide); Flow rate: 1.5 mL/minute; Back pressure: 200 bar.

53. Conversion of C74 to the requisite 7-methyl-6-[1-methyl-5-(trifluoromethyl)-1H-1,2,4-triazol-3-yl]-3,4-dihydro-1H-spiro[1,8-naphthyridine-2,3'-pyrrolidine] was carried out using the method described for synthesis of P31 from C74 in Preparation P31.

54. The product was separated into its component diastereomers using supercritical fluid chromatography [Column: Chiral Technologies Chiralpak IB, 21×250 mm, 5 μm; Mobile phase: 9:1 carbon dioxide/(methanol containing 0.2% ammonium hydroxide); Flow rate: 75 mL/minute; Back pressure: 200 bar]. The first-eluting diastereomer was designated as Example 92, and the second-eluting diastereomer as Example 93.

55. Conditions for analytical HPLC. Column: Chiral Technologies Chiralpak IB, 4.6×100 mm, 5 μm; Mobile phase: 85:15 carbon dioxide/(methanol containing 0.2% ammonium hydroxide); Flow rate: 1.5 mL/minute; Back pressure: 200 bar.

56. The product was separated into its component diastereomers using supercritical fluid chromatography [Column: Phenomenex Lux Cellulose-1, 21×250 mm, 5 μm; Mobile phase: 3:1 carbon dioxide/(methanol containing 0.2% ammonium hydroxide); Flow rate: 75 mL/minute; Back pressure: 120 bar]. The first-eluting diastereomer was designated as Example 94, and the second-eluting diastereomer as Example 95.

57. Conditions for analytical HPLC. Column: Phenomenex Lux Cellulose-1, 4.6×100 mm, 5 μm; Mobile phase: 7:3 carbon dioxide/(methanol containing 0.2% ammonium hydroxide); Flow rate: 1.5 mL/minute; Back pressure: 200 bar.

58. The product was separated into its component diastereomers using supercritical fluid chromatography [Column: Chiral Technologies Chiralcel OJ-H, 21×250 mm, 5 μm; Mobile phase: 92:8 carbon dioxide/(methanol containing 0.2% ammonium hydroxide); Flow rate: 75 mL/minute; Back pressure: 200 bar]. The first-eluting diastereomer was designated as Example 96, and the second-eluting diastereomer as Example 97.

59. Conditions for analytical HPLC. Column: Phenomenex Lux Cellulose-3, 4.6×100 mm, 5 μm; Mobile phase: 4:1 carbon dioxide/(methanol containing 0.2% ammonium hydroxide); Flow rate: 1.5 mL/minute; Back pressure: 120 bar.

60. The product was separated into its component diastereomers using supercritical fluid chromatography [Column: Chiral Technologies Chiralcel OJ-H, 21×250 mm, 5 μm; Mobile phase: 92:8 carbon dioxide/(methanol containing 0.2% ammonium hydroxide); Flow rate: 75 mL/minute; Back pressure: 200 bar]. The first-eluting diastereomer was designated as Example 98, and the second-eluting diastereomer as Example 99.

61. The product was separated into its component diastereomers using supercritical fluid chromatography [Column: Chiral Technologies Chiralcel OJ-H, 21×250 mm, 5 μm; Mobile phase: 92:8 carbon dioxide/(methanol containing 0.2% ammonium hydroxide); Flow rate: 75 mL/minute; Back pressure: 200 bar]. The first-eluting diastereomer was designated as Example 100, and the second-eluting diastereomer as Example 101.

62. Reaction of P17 with 1,3-dichloro-5,5-dimethylimidazolidine-2,4-dione afforded the requisite tert-butyl 6-chloro-7-methyl-3,4-dihydro-1H-spiro[1,8-naphthyridine-2,3'-pyrrolidine]-1'-carboxylate.

63. The product was separated into its component diastereomers using supercritical fluid chromatography [Column: Chiral Technologies Chiralcel OJ-H, 21×250 mm, 5 μm; Mobile phase: 4:1 carbon dioxide/(methanol containing 0.2% ammonium hydroxide); Flow rate: 75 mL/minute; Back pressure: 120 bar]. The first-eluting diastereomer was designated as Example 102, and the second-eluting diastereomer as Example 103.

64. Conditions for analytical HPLC. Column: Chiral Technologies Chiralcel OJ-H, 4.6×100 mm, 5 μm; Mobile phase: 7:3 carbon dioxide/(methanol containing 0.2% ammonium hydroxide); Flow rate: 1.5 mL/minute; Back pressure: 120 bar.

65. The product was separated into its component diastereomers using supercritical fluid chromatography [Column: Phenomenex Lux Cellulose-1, 21×250 mm, 5 μm; Mobile phase: 4:1 carbon dioxide/(methanol containing 0.2% ammonium hydroxide); Flow rate: 75 mL/minute; Back pressure: 120 bar]. The first-eluting diastereomer was designated as Example 104, and the second-eluting diastereomer as Example 105.

66. Conditions for analytical HPLC. Column: Phenomenex Lux Cellulose-1, 4.6×100 mm, 5 μm; Mobile phase: 65:35 carbon dioxide/(methanol containing 0.2% ammonium hydroxide); Flow rate: 1.5 mL/minute; Back pressure: 200 bar.

67. The product was separated into its component diastereomers using supercritical fluid chromatography [Column: Chiral Technologies Chiralpak AS-H, 21×250 mm, 5 μm; Mobile phase: 9:1 carbon dioxide/(methanol containing 0.2% ammonium hydroxide); Flow rate: 75 mL/minute; Back pressure: 120 bar]. The first-eluting diastereomer was designated as Example 107, and the second-eluting diastereomer as Example 108.

68. Conditions for analytical HPLC. Column: Chiral Technologies Chiralpak AS-H, 4.6×100 mm, 5 μm; Mobile phase: 85:15 carbon dioxide/(methanol containing 0.2% ammonium hydroxide); Flow rate: 1.5 mL/minute; Back pressure: 120 bar.

69. The product was separated into its component diastereomers using supercritical fluid chromatography [Column: Chiral Technologies Chiralpak IB, 21×250 mm, 5 μm; Mobile phase: 85:15 carbon dioxide/(methanol containing 0.2% ammonium hydroxide); Flow rate: 75 mL/minute; Back pressure: 120 bar]. The first-eluting diastereomer was designated as Example 109, and the second-eluting diastereomer as Example 110.

70. Conditions for analytical HPLC. Column: Chiral Technologies Chiralpak IB, 4.6×100 mm, 5 μm; Mobile phase: 4:1 carbon dioxide/(methanol containing 0.2% ammonium hydroxide); Flow rate: 1.5 mL/minute; Back pressure: 120 bar.

71. Conversion of P23 to the requisite (2S)-7-methyl-6-([1,2,4]triazolo[1,5-a]pyridin-2-yl)-3,4-dihydro-1H-spiro[1,8-naphthyridine-2,3'-pyrrolidine], dihydrochloride salt was carried out using the method described in Alternate Preparation of P26; in this case, 2-bromo[1,2,4]triazolo[1,5-a]pyridine was used in place of 5-bromo-2-methyl-2H-tetrazole.

72. Conversion of P21 to the requisite 6-(5-methoxy-1-methyl-1H-1,2,4-triazol-3-yl)-7-methyl-3,4-dihydro-1H-spiro[1,8-naphthyridine-2,3'-pyrrolidine], dihydrochloride salt was carried out using the method described in Alternate Preparation of P26; in this case, 3-bromo-5-methoxy-1-methyl-1H-1,2,4-triazole was used in place of 5-bromo-2-methyl-2H-tetrazole.

73. The product was separated into its component diastereomers using supercritical fluid chromatography [Column: Chiral Technologies Chiralpak IB, 21×250 mm, 5 μm; Mobile phase: 85:15 carbon dioxide/(methanol containing 0.2% ammonium hydroxide); Flow rate: 75 mL/minute; Back pressure: 200 bar]. The first-eluting diastereomer was designated as Example 112, and the second-eluting diastereomer as Example 113.

74. Conditions for analytical HPLC. Column: Chiral Technologies Chiralpak IB, 4.6×100 mm, 5 μm; Mobile phase: 3:1 carbon dioxide/(methanol containing 0.2% ammonium hydroxide); Flow rate: 1.5 mL/minute; Back pressure: 120 bar.

75. The product was separated into its component diastereomers using supercritical fluid chromatography [Column: Chiral Technologies Chiralpak IB, 21×250 mm, 5 μm; Mobile phase: 4:1 carbon dioxide/(methanol containing 0.2% ammonium hydroxide); Flow rate: 75 mL/minute; Back pressure: 200 bar]. The first-eluting diastereomer was designated as Example 114, and the second-eluting diastereomer as Example 115.

76. Conditions for analytical HPLC. Column: Chiral Technologies Chiralpak IB, 4.6×100 mm, 5 μm; Mobile phase: 3:2 carbon dioxide/(methanol containing 0.2% ammonium hydroxide); Flow rate: 1.5 mL/minute; Back pressure: 120 bar.

77. The product was separated into its component diastereomers using supercritical fluid chromatography [Column: Chiral Technologies Chiralpak IB, 21×250 mm, 5 μm; Mobile phase: 85:15 carbon dioxide/(methanol containing 0.2% ammonium hydroxide); Flow rate: 75 mL/minute; Back pressure: 200 bar]. The first-eluting diastereomer was Example 13, and the second-eluting diastereomer was designated as Example 116. Example 13 exhibited a retention time of 3.26 minutes. Example 116 had a retention time of 3.52 minutes under the same conditions (see footnote 74).

78. Conversion of P23 to the requisite (2S)-7-methyl-6-(2-methyl-2H-1,2,3-triazol-4-yl)-3,4-dihydro-1H-spiro[1,8-naphthyridine-2,3'-pyrrolidine], dihydrochloride salt was carried out using the method described in Alternate Preparation of P26; in this case, 4-bromo-2-methyl-2H-1,2,3-triazole was used in place of 5-bromo-2-methyl-2H-tetrazole.

79. The product was separated into its component diastereomers using supercritical fluid chromatography [Column: Chiral Technologies Chiralpak IA, 21×250 mm, 5 μm; Mobile phase: 4:1 carbon dioxide/(methanol containing 0.2% ammonium hydroxide); Flow rate: 75 mL/minute; Back pressure: 150 bar]. The first-eluting diastereomer was designated as Example 123, and the second-eluting diastereomer as Example 124.

80. Conditions for analytical HPLC. Column: Chiral Technologies Chiralpak IA, 4.6×100 mm, 5 μm; Mobile phase: 3:1 carbon dioxide/(methanol containing 0.2% ammonium hydroxide); Flow rate: 1.5 mL/minute; Back pressure: 200 bar.

81. Methyl (2-methoxypyridin-4-yl)acetate was converted to the requisite 2-(2-methoxypyridin-4-yl)propanoic acid using the method described in Preparation P1. LCMS m/z 182.1 [M+H]$^+$. $^1$H NMR (400 MHz, DMSO-d$_6$) δ 12.53 (br s, 1H), 8.09 (d, J=5.3 Hz, 1H), 6.90 (d, J=5.3 Hz, 1H), 6.71 (s, 1H), 3.83 (s, 3H), 3.69 (q, J=7.1 Hz, 1H), 1.34 (d, J=7.1 Hz, 3H).

82. The product was separated into its component diastereomers using supercritical fluid chromatography [Column: Chiral Technologies Chiralcel OJ-H, 21×250 mm, 5 μm; Mobile phase: 3:1 carbon dioxide/(methanol containing 0.2% ammonium hydroxide); Flow rate: 75 mL/minute; Back pressure: 120 bar]. The first-eluting diastereomer was designated as Example 125, and the second-eluting diastereomer as Example 126.

83. Conditions for analytical HPLC. Column: Chiral Technologies Chiralcel OJ-H, 4.6×100 mm, 5 μm; Mobile phase: 3:2 carbon dioxide/(methanol containing 0.2% ammonium hydroxide); Flow rate: 1.5 mL/minute; Back pressure: 120 bar.

84. 2,4-Dichloro-6-methoxypyrimidine was converted to dimethyl (2-chloro-6-methoxypyrimidin-4-yl)(methyl)propanedioate according to the method described in Step 1 of Preparation P4. This material was then used to synthesize the requisite lithium 2-[2-(difluoromethyl)-6-methoxypyrimidin-4-yl]propanoate using the method described in Preparation P9. LCMS m/z 233.1 [M+H]$^+$. $^1$H NMR (400 MHz, methanol-d$_4$) δ 6.91 (s, 1H), 6.54 (t, J$_{HF}$=54.7 Hz, 1H), 4.01 (s, 3H), 3.71 (q, J=7.2 Hz, 1H), 1.48 (d, J=7.2 Hz, 3H).

85. The product was separated into its component diastereomers using supercritical fluid chromatography [Column: Chiral Technologies Chiralpak IA, 21×250 mm, 5 μm; Mobile phase: 7:3 carbon dioxide/(methanol containing 0.2% ammonium hydroxide); Flow rate: 75 mL/minute; Back pressure: 120 bar]. The first-eluting diastereomer was designated as Example 127, and the second-eluting diastereomer as Example 128.

86. Conditions for analytical HPLC. Column: Chiral Technologies Chiralpak IA, 4.6×100 mm, 5 μm; Mobile phase: 3:2 carbon dioxide/(methanol containing 0.2% ammonium hydroxide); Flow rate: 1.5 mL/minute; Back pressure: 120 bar.

87. The product was separated into its component diastereomers using supercritical fluid chromatography [Column:

Chiral Technologies Chiralpak IA, 21×250 mm, 5 µm; Mobile phase: 3:2 carbon dioxide/(methanol containing 0.2% ammonium hydroxide); Flow rate: 75 mL/minute; Back pressure: 120 bar]. The first-eluting diastereomer was designated as Example 129, and the second-eluting diastereomer as Example 130.

88. Using the method reported by D. W. C. MacMillan et al., *J. Amer. Chem. Soc.* 2016, 138, 8084-8087, P23 was reacted with 4-bromotetrahydro-2H-pyran, in the presence of photocatalyst [Ir{dF(CF$_3$)ppy}$_2$(dtbpy)]PF$_6$, to provide tert-butyl (2S)-7-methyl-6-(oxan-4-yl)-3,4-dihydro-1H-spiro[1,8-naphthyridine-2,3'-pyrrolidine]-1'-carboxylate. Deprotection with hydrogen chloride afforded the requisite (2S)-7-methyl-6-(oxan-4-yl)-3,4-dihydro-1H-spiro[1,8-naphthyridine-2,3'-pyrrolidine], dihydrochloride salt.

89. Conditions for analytical HPLC. Column: Chiral Technologies Chiralpak IA, 4.6×100 mm, 5 µm; Mobile phase: 65:35 carbon dioxide/(methanol containing 0.2% ammonium hydroxide); Flow rate: 1.5 mL/minute; Back pressure: 120 bar.

90. Conversion of 4-chloro-5-fluoro-2-methoxypyrimidine to the requisite 2-(5-fluoro-2-methoxypyrimidin-4-yl)propanoic acid was carried out using the method described in Preparation P4. The final acid was contaminated with 4-ethyl-5-fluoro-2-methoxypyrimidine. LCMS m/z 201.1 [M+H]$^+$. $^1$H NMR (400 MHz, DMSO-d$_6$), product peaks only: δ 8.32 (s, 1H), 3.85 (s, 3H), 3.56 (q, J=7.3 Hz, 1H), 1.34 (d, J=7.3 Hz, 3H).

91. The product was separated into its component diastereomers using supercritical fluid chromatography [Column: Chiral Technologies Chiralcel OJ-H, 21×250 mm, 5 µm; Mobile phase: 4:1 carbon dioxide/(methanol containing 0.2% ammonium hydroxide); Flow rate: 75 mL/minute; Back pressure: 120 bar]. The first-eluting diastereomer was designated as Example 132, and the second-eluting diastereomer as Example 133.

92. Conditions for analytical HPLC. Column: Chiral Technologies Chiralcel OJ-H, 4.6×100 mm, 5 µm; Mobile phase: 3:1 carbon dioxide/(methanol containing 0.2% ammonium hydroxide); Back pressure: 120 bar.

93. The product was separated into its component diastereomers using supercritical fluid chromatography [Column: Chiral Technologies Chiralpak AS-H, 21×250 mm, 5 µm; Mobile phase: 85:15 carbon dioxide/(methanol containing 0.2% ammonium hydroxide); Flow rate: 75 mL/minute; Back pressure: 120 bar]. The first-eluting diastereomer was designated as Example 134, and the second-eluting diastereomer as Example 135.

94. Conditions for analytical HPLC. Column: Chiral Technologies Chiralpak AS-H, 4.6×100 mm, 5 µm; Mobile phase: 4:1 carbon dioxide/(methanol containing 0.2% ammonium hydroxide); Flow rate: 1.5 mL/minute; Back pressure: 120 bar.

95. Conversion of 2-methoxy-4,5-dimethylpyridine to the requisite 2-(2-methoxy-5-methylpyridin-4-yl)propanoic acid was carried out using the method described in Preparation P1. LCMS m/z 196.1 [M+H]$^+$. $^1$H NMR (400 MHz, methanol-d$_4$) δ 7.89 (br s, 1H), 6.69 (s, 1H), 3.90 (q, J=7.1 Hz, 1H), 3.86 (s, 3H), 2.26 (br s, 3H), 1.44 (d, J=7.2 Hz, 3H).

96. The product was separated into its component diastereomers using supercritical fluid chromatography [Column: Chiral Technologies Chiralpak IA, 5 µm; Mobile phase: 1:1 carbon dioxide/(methanol containing 0.2% ammonium hydroxide); Flow rate: 75 mL/minute; Back pressure: 120 bar]. The first-eluting diastereomer was designated as Example 136, and the second-eluting diastereomer as Example 137.

97. Conditions for analytical HPLC. Column: Chiral Technologies Chiralpak IA, 4.6×100 mm, 5 µm; Mobile phase: 1:1 carbon dioxide/(methanol containing 0.2% ammonium hydroxide); Flow rate: 1.5 mL/minute; Back pressure: 120 bar.

98. Reaction of P27 with 1-(difluoromethyl)-4-iodo-2-methyl-1H-imidazole, using the method reported for conversion of P27 to C84 in Example 18, provided the requisite tert-butyl (2S)-6-[1-(difluoromethyl)-2-methyl-1H-imidazol-4-yl]-7-methyl-3,4-dihydro-1H-spiro[1,8-naphthyridine-2,3'-pyrrolidine]-1'-carboxylate.

99. The requisite 1-(difluoromethyl)-4-iodo-2-methyl-1H-imidazole was prepared from 4-iodo-2-methyl-1H-imidazole using the method described for synthesis of C5 in Preparation P5.

100. The appropriate bromo-substituted heteroaromatic reactant was used in the palladium coupling.

101. The appropriate chloro-substituted heteroaromatic reactant was used in the palladium coupling.

102. Reaction of 3,5-dibromo-1H-1,2,4-triazole with 4-bromobut-1-ene in the presence of potassium carbonate provided 3,5-dibromo-1-(but-3-en-1-yl)-1H-1,2,4-triazole; this material was cyclized to 2-bromo-7-methylidene-6,7-dihydro-5H-pyrrolo[1,2-b][1,2,4]triazole using 2-dicyclohexylphosphino-2',6'-dimethoxybiphenyl (SPhos), chloro(2-dicyclohexylphosphino-2',6'-dimethoxy-1,1'-biphenyl)[2-(2'-amino-1,1'-biphenyl)]palladium(II) (SPhos Pd G2), and triethylamine at elevated temperature. Subsequent ozonolysis to the ketone was followed by reaction with (diethylamino)sulfur trifluoride to afford the requisite 2-bromo-7,7-difluoro-6,7-dihydro-5H-pyrrolo[1,2-b][1,2,4]triazole.

103. Conversion of C29 to the requisite 2-fluoro-2-(5-fluoro-2-methoxypyridin-4-yl)propanoic acid was carried out using the method described in steps 5 and 6 of Preparation P10. LCMS m/z 218.1 [M+H]$^+$. $^1$H NMR (400 MHz, methanol-d$_4$) δ 8.01 (d, J=2.6 Hz, 1H), 6.92 (d, J=5.0 Hz, 1H), 3.90 (s, 3H), 1.91 (br d, J$_{HF}$=23.1 Hz, 3H).

104. The product was separated into its component diastereomers using supercritical fluid chromatography [Column: Chiral Technologies Chiralpak AS-H, 21×250 mm, 5 µm; Mobile phase: 9:1 carbon dioxide/(methanol containing 0.2% ammonium hydroxide); Flow rate: 75 mL/minute; Back pressure: 120 bar]. The first-eluting diastereomer was designated as Example 148, and the second-eluting diastereomer as Example 149.

105. 3-Bromobenzohydrazide was acylated with acetyl chloride in the presence of triethylamine, and then cyclized by reaction with p-toluenesulfonyl chloride and triethylamine to afford the requisite 2-bromo-6-(5-methyl-1,3,4-oxadiazol-2-yl)pyridine.

106. Iodination of 5-methyl-1H-1,2,4-triazole with N-iodosuccinimide in N,N-dimethylformamide at elevated temperature afforded 3-iodo-5-methyl-1H-1,2,4-triazole; this material was converted to the requisite 1-(difluoromethyl)-3-iodo-5-methyl-1H-1,2,4-triazole using the method described for synthesis of C31 from C30 in Preparation P13.

107. Reaction of 3,5-dibromo-1H-1,2,4-triazole with cyclopropylboronic acid in the presence of copper(II) acetate, 2,2'-bipyridine, and sodium carbonate in 1,2-dichloroethane at 70° C. provided 3,5-dibromo-1-cyclopropyl-1H-1,2,4-triazole. Lithium-halogen exchange was then effected using n-butyllithium (1.1 equivalents) at −78° C., and the resulting anion was reacted with N,N-dimethylformamide to afford 3-bromo-1-cyclopropyl-1H-1,2,4-triazole-5-carbaldehyde. This was reacted with [bis(2-methoxyethyl)amino]

sulfur trifluoride in dichloromethane to give the requisite 3-bromo-1-cyclopropyl-5-(difluoromethyl)-1H-1,2,4-triazole.

108. The product was separated into its component diastereomers using supercritical fluid chromatography [Column: Chiral Technologies Chiralcel OJ-H, 20×250 mm, 5 µm; Mobile phase: 86:14 carbon dioxide/(methanol containing 0.2% ammonium hydroxide); Flow rate: 50 mL/minute]. The first-eluting diastereomer was designated as Example 190, and the second-eluting diastereomer as Example 191. On analytical supercritical fluid chromatography [Column: Chiral Technologies Chiralcel OJ-3R, 3.0×150 mm, 3 µm; Mobile phase: 4:1 carbon dioxide/(methanol containing 0.1% diethylamine); Flow rate: 2.0 mL/minute], Example 190 exhibited a retention time of 2.70 minutes. Example 191 had a retention time of 3.33 minutes under the same conditions.

109. The product was separated into its component diastereomers using HPLC (Column: Chiral Technologies Chiralcel OD, 25×250 mm, 10 µm; Mobile phase: 4:1 hexane/ethanol; Flow rate: 25 mL/minute). The first-eluting diastereomer was designated as Example 192, and the second-eluting diastereomer as Example 193. On analytical HPLC (Column: Chiral Technologies Chiralcel OD-H, 4.6×150 mm, 5 µm; Mobile phase: 85:15 hexane/ethanol; Flow rate: 1.0 mL/minute), Example 192 exhibited a retention time of 6.20 minutes. Example 193 had a retention time of 7.06 minutes under the same conditions.

110. A final purification was carried out using reversed-phase C18 chromatography (Mobile phase A: water containing 0.1% formic acid; Mobile phase B: acetonitrile; Gradient: 0% to 45% B).

111. Using the method described for synthesis of P13 from C30 in Preparation P13, methyl 2-(2-hydroxypyridin-4-yl)propanoate was converted to the requisite 2-[2-(difluoromethoxy)pyridin-4-yl]propanoic acid. LCMS m/z 218.0 [M+H]$^+$. $^1$H NMR (400 MHz, methanol-d$_4$) δ 8.14 (br d, J=5.3 Hz, 1H), 7.53 (t, J$_{HF}$=73.1 Hz, 1H), 7.16 (dd, J=5.3, 1.5 Hz, 1H), 6.93-6.91 (m, 1H), 3.80 (q, J=7.2 Hz, 1H), 1.48 (d, J=7.2 Hz, 3H).

112. The product was separated into its component diastereomers using HPLC (Column: Chiral Technologies Chiralpak IG, 50×250 mm, 10 µm; Mobile phase: 4:1 ethanol/acetonitrile; Flow rate: 30 mL/minute). The first-eluting diastereomer was designated as Example 194, and the second-eluting diastereomer as Example 195. On analytical HPLC (Column: Chiral Technologies Chiralpak IG, 4.6×150 mm, 5 µm; Mobile phase: 4:1 ethanol/acetonitrile; Flow rate: 0.5 mL/minute), Example 194 exhibited a retention time of 6.48 minutes. Example 195 had a retention time of 8.08 minutes under the same conditions.

Example AA. In Vitro Binding Affinity Assay Using hMC4R

The binding affinity of test compounds at the α-melanocyte-stimulating hormone receptor (hMC4R) was assessed using a radioligand competition binding assay. Recombinant Chinese hamster ovaries (CHO) cells stably expressing hMC4R (PerkinElmer #ES-191-C) were used for competitive binding. hMC4R membranes were grown in Dulbecco's Modified Essential Medium and Ham's F-12 Medium (DMEM/F12), 10% heat inactivated fetal bovine serum (FBS), 0.4 mg/mL Geneticin and 2 mM L-glutamine. Cell membranes were bulked and frozen until the assay was performed.

Compounds were solubilized in 100% dimethyl sulfoxide (DMSO) to a concentration of 30 mM. A 10-point intermediate dilution series using half log dilutions was created in 100% DMSO with a top concentration of 0.03 mM. The serially diluted compounds were spotted as 1 µL/well, in 96-well Costar 3363 plates. The final compound range in the assay was 300 nM to 0.01 nM with a final DMSO concentration of 1%. Control wells, containing 1 µL of 2 mM (2 µM final) alpha-melanocyte stimulating hormone (α-MSH-Tocris #2584) was added to the non-specific binding wells and 1 µL 100% DMSO for the total binding control wells. This was followed by the addition of 80 µL of assay buffer [25 mM HEPES, 5 mM MgCl$_2$, 2.5 mM CaCl$_2$, 150 mM NaCl, Complete EDTA-free Protease Inhibitor Tablet (Thermo Scientific #11873580001) and 0.25% BSA]. 10 µL of [$^{125}$I]-(NIe4, D-Phe7)-α-MSH (PerkinElmer #NEX3520) was added to all wells at 10-fold the final concentration of 0.5 nM. The radioligand concentration used was below the equilibrium dissociation constant (K$_d$) of 2.59 nM. The exact concentration of radioligand used for each experiment was determined by liquid scintillation counting and adjusted if necessary.

Frozen hMC4R cell membranes were thawed and Dounce homogenized. Homogenates were resuspended in assay buffer to a concentration of 2 µg per well. The competition binding reaction was initiated by the addition of 10 µL MC4R membrane solution to the assay-ready plates containing test compound and [$^{125}$I]-(NIe4, D-Phe7)-α-MSH. The plates were incubated for 2 hours at room temperature. Assay samples were then rapidly filtered through Unifilter-96 GF/B PEI coated filter plates using a filter plate harvester (PerkinElmer) and rinsed with ice-cold wash buffer [25 mM (4-(2-hydroxyethyl)-1-piperazineethanesulfonic acid (HEPES), 1 mM MgCl$_2$, 2.5 mM CaCl$_2$, and 500 mM NaCl]. Filter plates were dried overnight at room temperature. Plates were then bottom-sealed prior to the addition of 50 µL/well Ultima Gold XR scintillation fluid (PerkinElmer 6013111). Plates were then top-sealed, incubated for 60 minutes at room temperature and then the amount of radioactivity present was determined by liquid scintillation counting on a Microbeta Trilux (PerkinElmer #2450-0060).

The raw data (expressed as counts per minute) were analyzed using ActivityBase (IDBS Data Management Software). The percent effect at each concentration of compound was calculated by ActivityBase based on the values for the uninhibited wells (total binding controls) and fully inhibited wells (non-specific binding controls) on each assay plate. A concentration required for 50% inhibition (IC$_{50}$) value was determined from these data using a 4-parameter logistic model. Equilibrium dissociation constant for inhibitor of ligand and receptor interaction (Ki) values were then calculated from the IC$_{50}$ values using the Cheng-Prusoff equation: K$_i$=IC$_{50}$/(1+([L]/K$_d$)), where [L] is the concentration of the radioligand used in the experiment and K$_d$ is the affinity of the radioligand (determined in separate saturation experiments).

Example BB. Functional In Vitro MC4R Antagonist Potency Assay

The functional in vitro antagonist potency for test compounds was determined by monitoring intracellular cyclic adenosine monophosphate (cAMP) levels in Chinese hamster ovary (CHO-) cells stably expressing the human Melanocortin-4 receptor (MC4R). Following agonist activation, human MC4R associates with the G-protein complex causing the Ga subunit to exchange bound GDP for GTP, followed by dissociation of the Gα-GTP complex. The activated Gα subunit can couple to downstream effectors to regulate the levels of second messengers or cAMP within the cell. Thereby, determination of intracellular cAMP levels allows for pharmacological characterization. Intracellular cAMP levels are quantitated using a homogenous assay utilizing the Homogeneous Time-Resolved Fluorescence (HTRF) technology from CisBio. The method is a competitive immunoassay between native cAMP produced by cells and the cAMP labelled with the acceptor dye, d2. The two entities then compete for binding to a monoclonal anti-cAMP antibody labeled with cryptate. The specific signal is inversely proportional to the concentration of cAMP in the cells.

Test compounds were solubilized to 30 mM in 100% dimethyl sulfoxide (DMSO) and stored. An 11-point dilution series using 1 in 3 162-fold serial dilutions was created in 100% DMSO with a top concentration of 800 μM. The serially diluted compound was spotted into a 384-well plate (Greiner, Cat No. 781280) at 40 nL/well with duplicate points at each concentration, and then diluted 1 in 1000 with 40 μL assay buffer containing HBSS, 20 mM HEPES (Invitrogen), 0.1% BSA, and 250 μM IBMX (Sigma Aldrich) to create an intermediate plate at 2× final assay concentration (FAC). The final compound concentration range in the assay was 400 nM to 4 μM, with a final DMSO concentration of 0.1%.

In-house generated CHO- cells stably expressing the Gs-coupled human MC4R receptor were plated in 384-well assay plates (Corning, Cat No. 3570) in 50 μL/well of Ham's F-12 containing 10% heat inactivated FBS, 1× penicillin/streptomycin, 1 mM Glutamax (Invitrogen) at a density of 2,500 cells per well and incubated at 37° C. (95% $O_2$: 5% $CO_2$) overnight, with micro-clime lids (Labcyte, Cat No. LLS-0310). On day of assay, media was removed from the assay plate through gentle flicking and blotting plate on a paper towel and replaced with 5 μL of 2× antagonist compound in assay buffer (HBSS, 20 mM HEPES, 0.1% BSA, 250 μM IBMX) and 0.1% DMSO. Cells were incubated with compound for 30 minutes at 37° C. (95% $O_2$: 5% $CO_2$) before addition of 5 μL $EC_{80}$ agonist stimulation (200 nM α-melanocyte stimulating hormone, αMSH, Bachem) and another 30-minute incubation at 37° C. (95% $O_2$: 5% $CO_2$). Intracellular cAMP levels were quantified as per Cisbio's protocol (5 uL of D2 and then 5 uL Cryptate, incubated for 1-2 hours at room temperature). Samples were measured on an Envision plate reader (PerkinElmer Life and Analytical Sciences; excitation, 320 nm; emission, 665 nm/620 nm).

Data were analyzed using the ratio of fluorescence intensity at 620 and 665 nm for each well, extrapolated from the cAMP standard curve to express data as nM cAMP for each well. Data expressed as nM cAMP were then normalized to control wells using Activity Base (IDBS). Zero percent effect (ZPE) was defined as nM of cAMP generated from ECao agonist stimulation (200 nM αMSH). In the absence of an antagonist control compound, one hundred percent effect (HPE) was defined as nM of cAMP generated from assay buffer/vehicle only. The concentration and % effect values for each compound were plotted by Activity Base using a four-parameter logistic dose response equation, and the concentration required for 50% inhibition ($IC_{50}$) was determined. Equilibrium dissociation constant ($K_b$) values were then calculated according to the Leff-Dougall equation: $K_b=[IC_{50}]/((2+([A]/[EC_{50}])^n)^{1/n}-1)$, wherein A is the concentration of the agonist challenged used in the experiment (200 nM) and n=the slope.

Table 2 lists biological activities (K; values, see Example AA; and $K_b$ values, see Example BB) and compound names for Examples 1-201.

TABLE 2

| Example Number | $K_i$ (nM) geometric mean | Count used ($K_i$) | $K_b$ (nM) Antagonist geometric mean | Count used ($K_b$) | Compound Name |
|---|---|---|---|---|---|
| 1 | 0.21 | 3 | 0.049 | 6 | (2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 |
| 2 | 4.5 | 2 | 1.2 | 4 | (2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 |
| 3 | 0.54 | 3 | 0.25 | 5 | 2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 |
| 4 | 30 | 3 | 13 | 2 | 2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 |
| 5 | >200 | 1 | ND$^a$ | ND | 2-[6-(difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 6 | 0.44 | 3 | 8.5 | 3 | 2-[6-(difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 7 | 0.62 | 3 | 8.1 | 4 | 1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one, DIAST-1 |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
|---|---|---|---|---|---|
| 8 | 76 | 1 | >95 | 1 | 1-[(2S)-7-methyl-6-(pyrimidin-2-yl)-3,4-dihydro-1H-spiro[1,8-naphthyridne-2,3'-pyrrolidin]-1'-yl]-2-[4-(trifluoromethyl)phenyl]propan-1-one, DIAST-2 |
| 9 | 380 | 2 | ND | ND | 1-(4,7-dimethyl-3,4-dihydro-1H-spiro[1,8-naphthyridine-2,3'-pyrrolidin]-1'-yl)-2-(4-fluorophenyl)ethan-1-one, DIAST-1 |
| 10 | 440 | 2 | ND | ND | 1-(4,7-dimethyl-3,4-dihydro-1H-spiro[1,8-naphthyridine-2,3'-pyrrolidin]-1'-yl)-2-(4-fluorophenyl)ethan-1-one, DIAST-2 |
| 11 | >2200 | 1 | ND | ND | 1-(4,7-dimethyl-3,4-dihydro-1H-spiro[1,8-naphthyridine-2,3'-pyrrolidin]-1'-yl)-2-(4-fluorophenyl)ethan-1-one, DIAST-3 |
| 12 | >2200 | 1 | ND | ND | 1-(4,7-dimethyl-3,4-dihydro-1H-spiro[1,8-naphthyridine-2,3'-pyrrolidin]-1'-yl)-2-(4-fluorophenyl)ethan-1-one, DIAST-4 |
| 13 | 0.60 | 8 | 0.16 | 4 | (2R)-2-(5-fluoro-2-methoxypyridin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one |
| 14 | 0.46 | 12 | 0.72 | 11 | (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one |
| 15 | 0.25 | 3 | 0.051 | 6 | (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one |
| 16 | 0.36 | 3 | 0.88 | 3 | (2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1 |
| 17 | 69 | 2 | >64 | 4 | (2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-2 |
| 18 | 0.18 | 1 | 0.55 | 2 | (2R)-2-(5-fluoro-2-methoxypyridin-4-yl)-1-{(2S)-7-methyl-6-[(4,6-$^2$H$_2$)pyrimidin-2-yl]-3,4-dihydro-1H-spiro[1,8-naphthyridine-2,3'-pyrrolidin]-1'-yl}propan-1-one |
| 19 | >220 | 1 | ND | ND | 2-(4-fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-1 |
| 20 | 0.60 | 3 | ND | ND | 2-(4-fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one, ENT-2 |
| 21 | 2.2 | 2 | 20 | 3 | (2R)-1-{(2S)-6-[5-(difluoromethyl)pyrimidin-2-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 22 | 2 | 2 | ND | ND | (2R)-1-[(2S)-6-(5-bromopyrimidin-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 23 | 21 | 1 | 24 | 2 | 2-(6-methoxy-2-methylpyrimidin-4-yl)-1-(7-methyl-3,4-dihydro-1H-spiro[1,8-naphthyridine-2,3'-pyrrolidin]-1'-yl)propan-1-one, DIAST-1 |
| 24 | 77 | 1 | >97 | 1 | 2-(6-methoxy-2-methylpyrimidin-4-yl)-1-(7-methyl-3,4-dihydro-1H-spiro[1,8-naphthyridine-2,3'-pyrrolidin]-1'-yl)propan-1-one, DIAST-2 |
| 25 | 220 | 1 | >97 | 1 | 2-(6-methoxy-2-methylpyrimidin-4-yl)-1-(7-methyl-3,4-dihydro-1H-spiro[1,8-naphthyridine-2,3'-pyrrolidin]-1'-yl)propan-1-one, DIAST-3 |
| 26 | 210 | 1 | >97 | 1 | 2-(6-methoxy-2-methylpyrimidin-4-yl)-1-(7-methyl-3,4-dihydro-1H-spiro[1,8-naphthyridine-2,3'-pyrrolidin]-1'-yl)propan-1-one, DIAST-4 |
| 27 | 2 | 3 | 4.6 | 3 | (2R)-2-(5-fluoro-2-methoxypyridin-4-yl)-1-{(2S)-7-methyl-6-[2-methyl-1-(trifluoromethyl)-1H-imidazol-4-yl]-3,4-dihydro-1H-spiro[1,8-naphthyridine-2,3'-pyrrolidin]-1'-yl}propan-1-one |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
|---|---|---|---|---|---|
| 28 | 160 | 2 | >97 | 1 | (2S)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one |
| 29 | 11 | 1 | 12 | 2 | (2R)-2-(5-fluoro-2-methoxypyridin-4-yl)-1-[(2R)-7-methyl-6-(pyrimidin-2-yl)-3,4-dihydro-1H-spiro[1,8-naphthyridine-2,3'-pyrrolidin]-1'-yl]propan-1-one |
| 30 | >250 | 1 | >54 | 1 | (2S)-2-(5-fluoro-2-methoxypyridin-4-yl)-1-[(2R)-7-methyl-6-(pyrimidin-2-yl)-3,4-dihydro-1H-spiro[1,8-naphthyridine-2,3'-pyrrolidin]-1'-yl]propan-1-one |
| 31 | >250 | 1 | ND | ND | 2-(6-methoxy-2-methylpyrimidin-4-yl)-1-[(2R)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 |
| 32 | >250 | 1 | ND | ND | 2-(6-methoxy-2-methylpyrimidin-4-yl)-1-[(2R)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 |
| 33 | 2.6 | 3 | 3.2 | 3 | (2R)-2-(5-fluoro-2-methoxypyridin-4-yl)-1-[7-methyl-6-(2-methyl-1,3-oxazol-4-yl)-3,4-dihydro-1H-spiro[1,8-naphthyridine-2,3'-pyrrolidin]-1'-yl]propan-1-one, formate salt |
| 34 | 0.90 | 3 | 4.2 | 4 | 2-(2,4-dichlorophenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 35 | 82 | 1 | >95 | 1 | 2-(2,4-dichlorophenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 36 | 0.52 | 3 | 0.19 | 3 | 2-[5-(difluoromethyl)-2-methoxypyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 37 | 180 | 1 | ND | ND | 2-[5-(difluoromethyl)-2-methoxypyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 38 | >200 | 1 | ND | ND | 2-[5-chloro-2-(trifluoromethyl)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 39 | 4.9 | 3 | 23 | 3 | 2-[5-chloro-2-(trifluoromethyl)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 40 | 150 | 1 | ND | ND | 2-[2-methoxy-5-(trifluoromethyl)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 41 | 0.53 | 3 | 0.12 | 3 | 2-[2-methoxy-5-(trifluoromethyl)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 42 | 1.9 | 2 | 9.4 | 2 | 2-(3-fluoro-4-methoxyphenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 43 | 43 | 1 | ND | ND | 2-(3-fluoro-4-methoxyphenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 44 | 54 | 1 | ND | ND | 2-[6-(difluoromethoxy)-2-methylpyrimidin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 45 | 0.95 | 2 | 0.76 | 2 | 2-[6-(difluoromethoxy)-2-methylpyrimidin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, formate salt, DIAST-2 |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
| --- | --- | --- | --- | --- | --- |
| 46 | 3.5 | 2 | 7.2 | 2 | 2-fluoro-2-(2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 47 | 20 | 1 | ND | ND | 2-fluoro-2-(2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 48 | 0.36 | 3 | 1.8 | 4 | 1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethoxy)phenyl]propan-1-one, DIAST-1 |
| 49 | 64 | 1 | >95 | 1 | 1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethoxy)phenyl]propan-1-one, DIAST-2 |
| 50 | 0.81 | 3 | 2.9 | 4 | 2-(3,4-difluorophenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 51 | 120 | 1 | >110 | 1 | 2-(3,4-difluorophenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 52 | 0.68 | 3 | 2.6 | 4 | 1-[(2S)-7-methyl-6-(pyrimidin-2-yl)-3,4-dihydro-1H-spiro[1,8-naphthyridine-2,3'-pyrrolidin]-1'-yl]-2-(2,4,5-trifluorophenyl)propan-1-one, DIAST-1 |
| 53 | 54 | 1 | >95 | 1 | 1-[(2S)-7-methyl-6-(pyrimidin-2-yl)-3,4-dihydro-1H-spiro[1,8-naphthyridine-2,3'-pyrrolidin]-1'-yl]-2-(2,4,5-trifluorophenyl)propan-1-one, DIAST-2 |
| 54 | 0.93 | 3 | 4.1 | 4 | 1-[(2S)-7-methyl-6-(pyrimidin-2-yl)-3,4-dihydro-1H-spiro[1,8-naphthyridine-2,3'-pyrrolidin]-1'-yl]-2-(3,4,5-trifluorophenyl)ethan-1-one |
| 55 | 58 | 1 | >95 | 1 | 1-[(2S)-7-methyl-6-(pyrimidin-2-yl)-3,4-dihydro-1H-spiro[1,8-naphthyridine-2,3'-pyrrolidin]-1'-yl]-2-(3,4,5-trifluorophenyl)propan-1-one, DIAST-1 |
| 56 | 0.51 | 3 | 0.80 | 4 | 1-[(2S)-7-methyl-6-(pyrimidin-2-yl)-3,4-dihydro-1H-spiro[1,8-naphthyridine-2,3'-pyrrolidin]-1'-yl]-2-(3,4,5-trifluorophenyl)propan-1-one, DIAST-2 |
| 57 | 2.5 | 3 | 12 | 4 | 2-(3-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 58 | 190 | 2 | >62 | 1 | 2-(3-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 59 | 99 | 1 | ND | ND | 2-[5-chloro-2-(difluoromethoxy)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-1 |
| 60 | 0.54 | 3 | 0.18 | 3 | 2-[5-chloro-2-(difluoromethoxy)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-2 |
| 61 | 40 | 1 | ND | ND | 2-[3-(difluoromethoxy)-5-methoxyphenyl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-1 |
| 62 | 0.15 | 2 | 0.080 | 2 | 2-[3-(difluoromethoxy)-5-methoxyphenyl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-2 |
| 63 | 94 | 1 | ND | ND | 2-[5-chloro-2-(trifluoromethoxy)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-1 |
| 64 | 1 | 3 | 5.1 | 3 | 2-[5-chloro-2-(trifluoromethoxy)pyridin-4-yl]-1-[(2S)-7-methyl-6-(pyrimidin-2-yl)-3,4-dihydro- |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
| --- | --- | --- | --- | --- | --- |
| 65 | 1.7 | 2 | 10 | 2 | 1H-spiro[1,8-naphthyridine-2,3'-pyrrolidin]-1'-yl]propan-1-one, partial formate salt, DIAST-2 1-[7-methyl-6-(2-methyl-2H-tetrazol-5-yl)-3,4-dihydro-1H-spiro[1,8-naphthyridine-2,3'-pyrrolidin]-1'-yl]-2-[4-(trifluoromethyl)phenyl]ethan-1-one, ENT-1 |
| 66 | 250 | 1 | ND | ND | 1-[7-methyl-6-(2-methyl-2H-tetrazol-5-yl)-3,4-dihydro-1H-spiro[1,8-naphthyridine-2,3'-pyrrolidin]-1'-yl]-2-[4-(trifluoromethyl)phenyl]ethan-1-one, partial formate salt, ENT-2 |
| 67 | 2.5 | 2 | 14 | 2 | (2R)-2-(5-fluoro-2-methoxypyridin-4-yl)-1-[(2S)-6-(5-methoxypyrimidin-2-yl)-7-methyl-3,4-dihydro-1H-spiro[1,8-naphthyridine-2,3'-pyrrolidin]-1'-yl]propan-1-one, partial formate salt |
| 68 | 35 | 1 | ND | ND | (2R)-2-(5-fluoro-2-methoxypyridin-4-yl)-1-{(2S)-6-[3-fluoro-5-(trifluoromethyl)pyridin-2-yl]-7-methyl-3,4-dihydro-1H-spiro[1,8-naphthyridine-2,3'-pyrrolidin]-1'-yl}propan-1-one, formate salt |
| 69 | 5.1 | 1 | ND | ND | (2R)-2-(5-fluoro-2-methoxypyridin-4-yl)-1-{(2S)-6-[3-fluoro-6-(trifluoromethyl)pyridin-2-yl]-7-methyl-3,4-dihydro-1H-spiro[1,8-naphthyridine-2,3'-pyrrolidin]-1'-yl}propan-1-one, trifluoroacetate salt |
| 70 | 40 | 1 | ND | ND | (2R)-1-[(2S)-6-(5-cyclopropylpyrazin-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one, partial formate salt |
| 71 | 49 | 1 | ND | ND | (2R)-2-(5-fluoro-2-methoxypyridin-4-yl)-1-{(2S)-7-methyl-6-[5-(trifluoromethyl)pyrazin-2-yl]-3,4-dihydro-1H-spiro[1,8-naphthyridine-2,3'-pyrrolidin]-1'-yl}propan-1-one, partial formate salt |
| 72 | 3.3 | 1 | ND | ND | (2R)-2-(5-fluoro-2-methoxypyridin-4-yl)-1-{(2S)-7-methyl-6-[6-(trifluoromethyl)pyrimidin-4-yl]-3,4-dihydro-1H-spiro[1,8-naphthyridine-2,3'-pyrrolidin]-1'-yl}propan-1-one |
| 73 | 2.7 | 2 | 17 | 2 | 1-[(2S)-7-methyl-6-(pyrimidin-2-yl)-3,4-dihydro-1H-spiro[1,8-naphthyridine-2,3'-pyrrolidin]-1 yl]-2-[4-(trifluoromethyl)phenyl]ethan-1-one |
| 74 | 1.3 | 3 | 0.60 | 2 | (2R)-2-{5-fluoro-2-[($^2$H$_3$)methyloxy]pyridin-4-yl}-1-[(2S)-7-methyl-6-(pyrimidin-2-yl)-3,4-dihydro-1H-spiro[1,8-naphthyridine-2,3'-pyrrolidin]-1'-yl]propan-1-one, formate salt |
| 75 | 180 | 1 | ND | ND | 2-[5-fluoro-2-(trifluoromethoxy)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 76 | 2.2 | 3 | 9 | 3 | 2-[5-fluoro-2-(trifluoromethoxy)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 77 | 84 | 1 | ND | ND | 2-[2-(difluoromethoxy)-5-fluoropyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-1 |
| 78 | 0.62 | 3 | 1.2 | 3 | 2-[2-(difluoromethoxy)-5-fluoropyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, formate salt, DIAST-2 |
| 79 | >250 | 1 | ND | ND | 2-[5-fluoro-2-(trifluoromethyl)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 80 | 8 | 3 | 28 | 3 | 2-[5-fluoro-2-(trifluoromethyl)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-2 |
| 81 | 6.6 | 1 | ND | ND | 2-[2-(dimethylamino)-5-fluoropyridin-4-yl]-1-[(2S)-7-methyl-6-(pyrimidin-2-yl)-3,4-dihydro- |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
| --- | --- | --- | --- | --- | --- |
| 82 | 120 | 1 | ND | ND | 1H-spiro[1,8-naphthyridine-2,3'-pyrrolidin]-1'-yl]propan-1-one, bis(formate) salt, DIAST-1 |
| 83 | 0.67 | 3 | 0.54 | 3 | 2-[2-(dimethylamino)-5-fluoropyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 84 | 52 | 1 | ND | ND | 2-(2,6-dimethoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 85 | >250 | 1 | ND | ND | 2-(2,6-dimethoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 86 | 2.3 | 1 | ND | ND | 2-(5-chloro-2-methoxypyrimidin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 87 | 48 | 4 | ND | ND | 2-(5-chloro-2-methoxypyrimidin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 88 | >2200 | 1 | ND | ND | 2-(4-fluorophenyl)-1-(7-methyl-3,4-dihydro-1H-spiro[1,8-naphthyridine-2,3'-pyrrolidin]-1'-yl)ethan-1-one, ENT-1 |
| 89 | 1.7 | 2 | >40 | 2 | 2-(4-fluorophenyl)-1-(7-methyl-3,4-dihydro-1H-spiro[1,8-naphthyridine-2,3'-pyrrolidin]-1'-yl)ethan-1-one, ENT-2 |
| 90 | 0.044 | 2 | 0.40 | 2 | 2-(4-fluorophenyl)-1-[7-methyl-6-(1-methyl-1H-pyrazol-4-yl)-3,4-dihydro-1H-spiro[1,8-naphthyridine-2,3'-pyrrolidin]-1'-yl]ethan-1-one |
| 91 | 17 | 1 | ND | ND | (2R)-2-(3,5-dimethoxyphenyl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1 |
| 92 | 0.45 | 5 | 0.16 | 3 | (2R)-2-(3,5-dimethoxyphenyl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-2 |
| 93 | 16 | 2 | 4.1 | 2 | (2R)-2-(5-fluoro-2-methoxypyridin-4-yl)-1-{7-methyl-6-[1-methyl-5-(trifluoromethyl)-1H-1,2,4-triazol-3-yl]-3,4-dihydro-1H-spiro[1,8-naphthyridine-2,3'-pyrrolidin]-1'-yl}propan-1-one, DIAST-1 |
| 94 | 1.2 | 4 | 0.12 | 3 | (2R)-2-(5-fluoro-2-methoxypyridin-4-yl)-1-{7-methyl-6-[1-methyl-5-(trifluoromethyl)-1H-1,2,4-triazol-3-yl]-3,4-dihydro-1H-spiro[1,8-naphthyridine-2,3'-pyrrolidin]-1'-yl}propan-1-one, DIAST-2 |
| 95 | 86 | 3 | 7.5 | 1 | (2R)-2-(5-chloro-2-methoxypyridin-4-yl)-1-{7-methyl-6-[1-methyl-5-(trifluoromethyl)-1H-1,2,4-triazol-3-yl]-3,4-dihydro-1H-spiro[1,8-naphthyridine-2,3'-pyrrolidin]-1'-yl}propan-1-one, DIAST-1 |
| 96 | 4.1 | 3 | 11 | 3 | (2R)-2-(5-chloro-2-methoxypyridin-4-yl)-1-{7-methyl-6-[1-methyl-5-(trifluoromethyl)-1H-1,2,4-triazol-3-yl]-3,4-dihydro-1H-spiro[1,8-naphthyridine-2,3'-pyrrolidin]-1'-yl}propan-1-one, DIAST-2 |
| 97 | 100 | 2 | ND | ND | (2R)-2-(3,5-dimethoxyphenyl)-1-(7-methyl-3,4-dihydro-1H-spiro[1,8-naphthyridine-2,3'-pyrrolidin]-1'-yl)propan-1-one, DIAST-1 |
| 98 | 2.8 | 3 | 19 | 3 | (2R)-2-(3,5-dimethoxyphenyl)-1-(7-methyl-3,4-dihydro-1H-spiro[1,8-naphthyridine-2,3'-pyrrolidin]-1'-yl)propan-1-one, DIAST-2 |
| 99 | 81 | 2 | ND | ND | (2R)-2-(5-fluoro-2-methoxypyridin-4-yl)-1-(7-methyl-3,4-dihydro-1H-spiro[1,8-naphthyridine-2,3'-pyrrolidin]-1'-yl)propan-1-one, DIAST-1 |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
|---|---|---|---|---|---|
| 100 | 1.1 | 4 | 5.5 | 3 | (2R)-2-(5-chloro-2-methoxypyridin-4-yl)-1-(7-methyl-3,4-dihydro-1H-spiro[1,8-naphthyridine-2,3'-pyrrolidin]-1'-yl)propan-1-one, DIAST-1 |
| 101 | 110 | 2 | ND | ND | (2R)-2-(5-chloro-2-methoxypyridin-4-yl)-1-(7-methyl-3,4-dihydro-1H-spiro[1,8-naphthyridine-2,3'-pyrrolidin]-1'-yl)propan-1-one, DIAST-2 |
| 102 | 110 | 2 | >92 | 1 | (2R)-1-(6-chloro-7-methyl-3,4-dihydro-1H-spiro[1,8-naphthyridine-2,3'-pyrrolidin]-1'-yl)-2-(5-fluoro-2-methoxypyridin-4-yl)propan-1-one, DIAST-1 |
| 103 | >250 | 1 | >92 | 1 | (2R)-1-(6-chloro-7-methyl-3,4-dihydro-1H-spiro[1,8-naphthyridine-2,3'-pyrrolidin]-1'-yl)-2-(5-fluoro-2-methoxypyridin-4-yl)propan-1-one, DIAST-2 |
| 104 | 0.48 | 3 | 0.060 | 3 | (2R)-2-(5-chloro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1 |
| 105 | 54 | 2 | 16 | 4 | (2R)-2-(5-chloro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-2 |
| 106 | 3.5 | 2 | 6.3 | 2 | 2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]ethan-1-one |
| 107 | 57 | 2 | ND | ND | 2-[6-(difluoromethoxy)pyridin-3-yl]-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 |
| 108 | 1.2 | 2 | 7.1 | 2 | 2-[6-(difluoromethoxy)pyridin-3-yl]-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 |
| 109 | 0.73 | 2 | 5.8 | 2 | 1-[(2S)-7-methyl-6-(2-methyl-2H-tetrazol-5-yl)-3,4-dihydro-1H-spiro[1,8-naphthyridine-2,3'-pyrrolidin]-1'-yl]-2-[4-(trifluoromethyl)phenyl]propan-1-one, DIAST-1 |
| 110 | 29 | 2 | ND | ND | 1-[(2S)-7-methyl-6-(2-methyl-2H-tetrazol-5-yl)-3,4-dihydro-1H-spiro[1,8-naphthyridine-2,3'-pyrrolidin]-1'-yl]-2-[4-(trifluoromethyl)phenyl]propan-1-one, DIAST-2 |
| 111 | 0.25 | 3 | 0.47 | 5 | (2R)-2-(5-fluoro-2-methoxypyridin-4-yl)-1-[(2S)-7-methyl-6-([1,2,4]triazolo[1,5-a]pyridin-2-yl)-3,4-dihydro-1H-spiro[1,8-naphthyridine-2,3'-pyrrolidin]-1'-yl]propan-1-one |
| 112 | 0.78 | 3 | 2 | 6 | (2R)-2-(5-fluoro-2-methoxypyridin-4-yl)-1-[6-(5-methoxy-1-methyl-1H-1,2,4-triazol-3-yl)-7-methyl-3,4-dihydro-1H-spiro[1,8-naphthyridine-2,3'-pyrrolidin]-1'-yl]propan-1-one, DIAST-1 |
| 113 | 17 | 1 | 8 | 4 | (2R)-2-(5-fluoro-2-methoxypyridin-4-yl)-1-[6-(5-methoxy-1-methyl-1H-1,2,4-triazol-3-yl)-7-methyl-3,4-dihydro-1H-spiro[1,8-naphthyridine-2,3'-pyrrolidin]-1'-yl]propan-1-one, DIAST-2 |
| 114 | 0.48 | 3 | 0.25 | 6 | (2R)-2-(5-chloro-2-methoxypyridin-4-yl)-1-[6-(5-methoxy-1-methyl-1H-1,2,4-triazol-3-yl)-7-methyl-3,4-dihydro-1H-spiro[1,8-naphthyridine-2,3'-pyrrolidin]-1'-yl]propan-1-one, DIAST-1 |
| 115 | 31 | 2 | 3.5 | 4 | (2R)-2-(5-chloro-2-methoxypyridin-4-yl)-1-[6-(5-methoxy-1-methyl-1H-1,2,4-triazol-3-yl)-7-methyl-3,4-dihydro-1H-spiro[1,8-naphthyridine-2,3'-pyrrolidin]-1'-yl]propan-1-one, DIAST-2 |
| 116 | 7.1 | 2 | 1.7 | 6 | (2R)-2-(5-fluoro-2-methoxypyridin-4-yl)-1-[(2R)-7-methyl-6-(2-methyl-2H-tetrazol-5-yl)-3,4-dihydro-1H-spiro[1,8-naphthyridine-2,3'-pyrrolidin]-1'-yl]propan-1-one |
| 117 | 0.28 | 3 | 0.070 | 4 | (2R)-2-(5-chloro-2-methoxypyridin-4-yl)-1-[(2S)-7-methyl-6-([1,2,4]triazolo[1,5-a]pyridin-2-yl)-3,4-dihydro-1H-spiro[1,8-naphthyridine-2,3'-pyrrolidin]-1'-yl]propan-1-one |
| 118 | 0.83 | 4 | 0.93 | 4 | (2R)-2-(5-fluoro-2-methoxypyridin-4-yl)-1-[(2S)-7-methyl-6-(2-methyl-2H-1,2,3-triazol-4-yl)-3,4- |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
|---|---|---|---|---|---|
| 119 | >17 | 2 | >1.1 | 5 | dihydro-1H-spiro[1,8-naphthyridine-2,3'-pyrrolidin]-1'-yl)propan-1-one (2R)-2-(5-chloro-2-methoxypyridin-4-yl)-1-[(2S)-7-methyl-6-(2-methyl-2H-1,2,3-triazol-4-yl)-3,4-dihydro-1H-spiro[1,8-naphthyridine-2,3'-pyrrolidin]-1'-yl]propan-1-one |
| 120 | 0.40 | 3 | 0.080 | 4 | (2R)-2-(5-chloro-2-methoxypyridin-4-yl)-1-{(2S)-6-[5-(difluoromethyl)-1-methyl-1H-1,2,4-triazol-3-yl]-7-methyl-3,4-dihydro-1H-spiro[1,8-naphthyridine-2,3'-pyrrolidin]-1'-yl}propan-1-one |
| 121 | 0.49 | 3 | 4 | 4 | 1-{(2S)-6-[5-(difluoromethyl)-1-methyl-1H-1,2,4-triazol-3-yl]-7-methyl-3,4-dihydro-1H-spiro[1,8-naphthyridine-2,3'-pyrrolidin]-1'-yl}-2-(3,4-difluorophenyl)ethan-1-one |
| 122 | 0.49 | 3 | 0.11 | 4 | (2R)-1-{(2S)-6-[5-(difluoromethyl)-1-methyl-1H-1,2,4-triazol-3-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 123 | 0.22 | 2 | 0.50 | 2 | 1-{(2S)-6-[5-(difluoromethyl)-1-methyl-1H-1,2,4-triazol-3-yl]-7-methyl-3,4-dihydro-1H-spiro[1,8-naphthyridine-2,3'-pyrrolidin]-1'-yl}-2-(6-methoxy-2-methylpyrimidin-4-yl)propan-1-one, DIAST-1 |
| 124 | 6.7 | 1 | 0.81 | 5 | 1-{(2S)-6-[5-(difluoromethyl)-1-methyl-1H-1,2,4-triazol-3-yl]-7-methyl-3,4-dihydro-1H-spiro[1,8-naphthyridine-2,3'-pyrrolidin]-1'-yl}-2-(6-methoxy-2-methylpyrimidin-4-yl)propan-1-one, DIAST-2 |
| 125 | 3.4 | 1 | 5.1 | 3 | 2-(2-methoxypyridin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 |
| 126 | 140 | 2 | ND | ND | 2-(2-methoxypyridin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 |
| 127 | 0.97 | 1 | 1.1 | 2 | 2-[2-(difluoromethyl)-6-methoxypyrimidin-4-yl]-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 |
| 128 | 10 | 3 | 3.8 | 4 | 2-[2-(difluoromethyl)-6-methoxypyrimidin-4-yl]-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 |
| 129 | 0.44 | 4 | 1.5 | 4 | 2-[2-(difluoromethyl)-6-methoxypyrimidin-4-yl]-1-[(2S)-7-methyl-6-([1,2,4]triazolo[1,5-a]pyridin-2-yl)-3,4-dihydro-1H-spiro[1,8-naphthyridine-2,3'-pyrrolidin]-1'-yl]propan-1-one, DIAST-1 |
| 130 | 5.9 | 4 | 9 | 2 | 2-[2-(difluoromethyl)-6-methoxypyrimidin-4-yl]-1-[(2S)-7-methyl-6-([1,2,4]triazolo[1,5-a]pyridin-2-yl)-3,4-dihydro-1H-spiro[1,8-naphthyridine-2,3'-pyrrolidin]-1'-yl]propan-1-one, DIAST-2 |
| 131 | 5.8 | 3 | 16 | 5 | (2R)-2-(5-fluoro-2-methoxypyridin-4-yl)-1-[(2S)-7-methyl-6-(oxan-4-yl)-3,4-dihydro-1H-spiro[1,8-naphthyridine-2,3'-pyrrolidin]-1'-yl]propan-1-one |
| 132 | 3.4 | 2 | 35 | 3 | 2-(5-fluoro-2-methoxypyrimidin-4-yl)-1-[(2S)-7-methyl-6-([1,2,4]triazolo[1,5-a]pyridin-2-yl)-3,4-dihydro-1H-spiro[1,8-naphthyridine-2,3'-pyrrolidin]-1'-yl]propan-1-one, DIAST-1 |
| 133 | 63 | 1 | ND | ND | 2-(5-fluoro-2-methoxypyrimidin-4-yl)-1-[(2S)-7-methyl-6-([1,2,4]triazolo[1,5-a]pyridin-2-yl)-3,4-dihydro-1H-spiro[1,8-naphthyridine-2,3'-pyrrolidin]-1'-yl]propan-1-one, DIAST-2 |
| 134 | 220 | 2 | >97 | 1 | 2-(5-fluoro-2-methoxypyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1 |
| 135 | 3.8 | 2 | 10 | 3 | 2-(5-fluoro-2-methoxypyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-2 |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
|---|---|---|---|---|---|
| 136 | 1.4 | 3 | 0.16 | 3 | 2-(2-methoxy-5-methylpyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 137 | 59 | 1 | 19 | 2 | 2-(2-methoxy-5-methylpyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 138 | 0.90 | 2 | 0.44 | 4 | (2R)-1-{(2S)-6-[1-(difluoromethyl)-2-methyl-1H-imidazol-4-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 139 | 13 | 2 | 21 | 2 | (2R)-2-(5-fluoro-2-methoxypyridin-4-yl)-1-[(2S)-6-(5-fluoropyridin-2-yl)-7-methyl-3,4-dihydro-1H-spiro[1,8-naphthyridine-2,3'-pyrrolidin]-1'-yl]propan-1-one |
| 140 | 6.3 | 2 | 19 | 2 | (2R)-2-(5-fluoro-2-methoxypyridin-4-yl)-1-[(2S)-7-methyl-6-(pyridin-2-yl)-3,4-dihydro-1H-spiro[1,8-naphthyridine-2,3'-pyrrolidin]-1'-yl]propan-1-one, trifluoroacetate salt |
| 141 | 14 | 2 | 29 | 2 | (2R)-2-(5-fluoro-2-methoxypyridin-4-yl)-1-[(2S)-7-methyl-6-(pyridazin-4-yl)-3,4-dihydro-1H-spiro[1,8-naphthyridine-2,3'-pyrrolidin]-1'-yl]propan-1-one |
| 142 | 1.8 | 2 | 3.6 | 2 | (2R)-2-(5-fluoro-2-methoxypyridin-4-yl)-1-[(2S)-7-methyl-6-(pyrazin-2-yl)-3,4-dihydro-1H-spiro[1,8-naphthyridine-2,3'-pyrrolidin]-1'-yl]propan-1-one |
| 143 | 1.3 | 3 | 2.6 | 3 | (2R)-2-(5-fluoro-2-methoxypyridin-4-yl)-1-{(2S)-7-methyl-6-[4-(trifluoromethyl)pyrimidin-2-yl]-3,4-dihydro-1H-spiro[1,8-naphthyridine-2,3'-pyrrolidin]-1'-yl}propan-1-one, trifluoroacetate salt |
| 144 | 2 | 3 | 8.5 | 3 | (2R)-1-[(2S)-6-(5-chloropyrimidin-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one, trifluoroacetate salt |
| 145 | 8.7 | 3 | 54 | 2 | (2R)-2-(5-fluoro-2-methoxypyridin-4-yl)-1-{(2S)-7-methyl-6-[5-(trifluoromethyl)pyrimidin-2-yl]-3,4-dihydro-1H-spiro[1,8-naphthyridine-2,3'-pyrrolidin]-1'-yl}propan-1-one, trifluoroacetate salt |
| 146 | 1.2 | 3 | 1.2 | 3 | (2R)-2-(5-fluoro-2-methoxypyridin-4-yl)-1-[(2S)-6-(5-fluoropyrimidin-2-yl)-7-methyl-3,4-dihydro-1H-spiro[1,8-naphthyridine-2,3'-pyrrolidin]-1'-yl]propan-1-one, trifluoroacetate salt |
| 147 | 0.62 | 2 | 0.57 | 2 | (2R)-1-[(2S)-6-(7,7-difluoro-6,7-dihydro-5H-pyrrolo[12-b][1,2,4]triazol-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 148 | 12 | 1 | 19 | 3 | 2-fluoro-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 149 | 1.8 | 2 | 7.9 | 2 | 2-fluoro-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 150 | 3.9 | 2 | 9 | 2 | (2R)-2-(5-fluoro-2-methoxypyridin-4-yl)-1-[(2S)-7-methyl-6-(1,2-thiazol-4-yl)-3,4-dihydro-1H-spiro[1,8-naphthyridine-2,3'-pyrrolidin]-1'-yl]propan-1-one |
| 151 | 23 | 2 | 40 | 2 | (2R)-2-(5-fluoro-2-methoxypyridin-4-yl)-1-[(2S)-7-methyl-6-(2-methylpyrimidin-5-yl)-3,4-dihydro-1H-spiro[1,8-naphthyridine-2,3'-pyrrolidin]-1'-yl]propan-1-one |
| 152 | 2.5 | 1 | ND | ND | (2R)-2-(5-fluoro-2-methoxypyridin-4-yl)-1-{(2S)-7-methyl-6-[6-(5-methyl-1,3,4-oxadiazol-2-yl)pyridin-2-yl]-3,4-dihydro-1H-spiro[1,8-naphthyridine-2,3'-pyrrolidin]-1'-yl}propan-1-one |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
| --- | --- | --- | --- | --- | --- |
| 153 | 3.3 | 2 | 15 | 2 | (2R)-2-(5-fluoro-2-methoxypyridin-4-yl)-1-[(2S)-7-methyl-6-(2-methyl-1,3-thiazol-5-yl)-3,4-dihydro-1H-spiro[1,8-naphthyridine-2,3'-pyrrolidin]-1'-yl]propan-1-one |
| 154 | 0.72 | 2 | 9.5 | 2 | (2R)-2-(5-fluoro-2-methoxypyridin-4-yl)-1-[(2S)-7-methyl-6-(pyrazolo[1,5-a]pyrimidin-3-yl)-3,4-dihydro-1H-spiro[1,8-naphthyridine-2,3'-pyrrolidin]-1'-yl]propan-1-one |
| 155 | 27 | 1 | ND | ND | (2R)-2-(5-fluoro-2-methoxypyridin-4-yl)-1-{(2S)-7-methyl-6-[5-(trifluoromethyl)pyridin-2-yl]-3,4-dihydro-1H-spiro[1,8-naphthyridine-2,3'-pyrrolidin]-1'-yl}propan-1-one |
| 156 | 5.9 | 2 | 20 | 2 | (2R)-2-(5-fluoro-2-methoxypyridin-4-yl)-1-[(2S)-7-methyl-6-(6-methylpyrazin-2-yl)-3,4-dihydro-1H-spiro[1,8-naphthyridine-2,3'-pyrrolidin]-1'-yl]propan-1-one |
| 157 | 15 | 1 | ND | ND | (2R)-1-[(2S)-6-(4-tert-butyl-1,3-thiazol-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 158 | 3.2 | 2 | 23 | 2 | (2R)-2-(5-fluoro-2-methoxypyridin-4-yl)-1-[(2S)-7-methyl-6-(5-methylpyrazin-2-yl)-3,4-dihydro-1H-spiro[1,8-naphthyridine-2,3'-pyrrolidin]-1'-yl]propan-1-one |
| 159 | 18 | 1 | ND | ND | (2R)-1-{(2S)-6-[6-(difluoromethoxy)pyridin-3-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 160 | 200 | 1 | ND | ND | (2R)-1-[(2S)-6-(3,5-dimethyl-1,2-benzoxazol-6-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 161 | 47 | 1 | ND | ND | (2R)-2-(5-fluoro-2-methoxypyridin-4-yl)-1-{(2S)-7-methyl-6-[3-(5-methyl-1,3,4-oxadiazol-2-yl)phenyl]-3,4-dihydro-1H-spiro[1,8-naphthyridine-2,3'-pyrrolidin]-1'-yl}propan-1-one |
| 162 | 8.2 | 1 | ND | ND | (2R)-2-(5-fluoro-2-methoxypyridin-4-yl)-1-{(2S)-7-methyl-6-[3-(propan-2-yl)-1,2,4-thiadiazol-5-yl]-3,4-dihydro-1H-spiro[1,8-naphthyridine-2,3'-pyrrolidin]-1'-yl}propan-1-one |
| 163 | 2.8 | 1 | ND | ND | (2R)-1-[(2S)-6-(4,5-dimethyl-1,3-thiazol-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 164 | 18 | 2 | >57 | 1 | (2R)-2-(5-fluoro-2-methoxypyridin-4-yl)-1-[(2S)-7-methyl-6-(3-methylpyrazin-2-yl)-3,4-dihydro-1H-spiro[1,8-naphthyridine-2,3'-pyrrolidin]-1'-yl]propan-1-one |
| 165 | 81 | 1 | ND | ND | (2R)-2-(5-fluoro-2-methoxypyridin-4-yl)-1-[(2S)-7-methyl-6-(2-methyl-1,3-benzothiazol-5-yl)-3,4-dihydro-1H-spiro[1,8-naphthyridine-2,3'-pyrrolidin]-1'-yl]propan-1-one |
| 166 | 8.2 | 1 | ND | ND | (2R)-2-(5-fluoro-2-methoxypyridin-4-yl)-1-[(2S)-7-methyl-6-(4-methylpyridin-2-yl)-3,4-dihydro-1H-spiro[1,8-naphthyridine-2,3'-pyrrolidin]-1'-yl]propan-1-one |
| 167 | 5.4 | 1 | ND | ND | (2R)-2-(5-fluoro-2-methoxypyridin-4-yl)-1-[(2S)-7-methyl-6-(1,3-thiazol-2-yl)-3,4-dihydro-1H-spiro[1,8-naphthyridine-2,3'-pyrrolidin]-1'-yl]propan-1-one |
| 168 | 86 | 1 | ND | ND | (2R)-2-(5-fluoro-2-methoxypyridin-4-yl)-1-{(2S)-7-methyl-6-[5-(piperidin-1-yl)-1,3,4-thiadiazol-2-yl]-3,4-dihydro-1H-spiro[1,8-naphthyridine-2,3'-pyrrolidin]-1'-yl}propan-1-one |
| 169 | 7.6 | 1 | ND | ND | (2R)-2-(5-fluoro-2-methoxypyridin-4-yl)-1-[(2S)-7-methyl-6-(pyridin-4-yl)-3,4-dihydro-1H-spiro[1,8-naphthyridine-2,3'-pyrrolidin]-1'-yl]propan-1-one |
| 170 | 43 | 1 | ND | ND | (2R)-2-(5-fluoro-2-methoxypyridin-4-yl)-1-{(2S)-7-methyl-6-[2-(trifluoromethyl)pyrimidin-5-yl]-3,4-dihydro-1H-spiro[1,8-naphthyridine-2,3'-pyrrolidin]-1'-yl}propan-1-one |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
| --- | --- | --- | --- | --- | --- |
| 171 | 3.6 | 1 | ND | ND | (2R)-1-[(2S)-6-(2-cyclopropyl-1,3-thiazol-4-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 172 | >250 | 1 | ND | ND | (2R)-2-(5-fluoro-2-methoxypyridin-4-yl)-1-[(2S)-7-methyl-6-{5-[(2S)-1-methylpyrrolidin-2-yl]pyridin-3-yl}-3,4-dihydro-1H-spiro[1,8-naphthyridine-2,3'-pyrrolidin]-1'-yl]propan-1-one |
| 173 | 85 | 1 | ND | ND | (2R)-2-(5-fluoro-2-methoxypyridin-4-yl)-1-{(2S)-7-methyl-6-[3-(1,3-oxazol-5-yl)phenyl]-3,4-dihydro-1H-spiro[1,8-naphthyridine-2,3'-pyrrolidin]-1'-yl}propan-1-one |
| 174 | 26 | 1 | ND | ND | (2R)-1-{(2S)-6-[6-(difluoromethyl)pyridin-3-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 175 | 45 | 1 | ND | ND | (2R)-2-(5-fluoro-2-methoxypyridin-4-yl)-1-{(2S)-7-methyl-6-[4-(5-methyl-1,2,4-oxadiazol-3-yl)phenyl]-3,4-dihydro-1H-spiro[1,8-naphthyridine-2,3'-pyrrolidin]-1'-yl}propan-1-one |
| 176 | 26 | 1 | ND | ND | (2R)-2-(5-fluoro-2-methoxypyridin-4-yl)-1-[(2S)-7-methyl-6-(3-methyl-1,2-thiazol-5-yl)-3,4-dihydro-1H-spiro[1,8-naphthyridine-2,3'-pyrrolidin]-1'-yl]propan-1-one |
| 177 | 59 | 1 | ND | ND | (2R)-1-[(2S)-6-(6-cyclopropylpyrazin-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 178 | 4.7 | 1 | ND | ND | (2R)-2-(5-fluoro-2-methoxypyridin-4-yl)-1-{(2S)-7-methyl-6-[6-(trifluoromethyl)pyridin-2-yl]-3,4-dihydro-1H-spiro[1,8-naphthyridine-2,3'-pyrrolidin]-1'-yl}propan-1-one |
| 179 | 21 | 1 | ND | ND | (2R)-1-{(2S)-6-[5-(difluoromethyl)pyridin-2-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 180 | 21 | 1 | ND | ND | (2R)-2-(5-fluoro-2-methoxypyridin-4-yl)-1-{(2S)-7-methyl-6-[5-(trifluoromethoxy)pyridin-2-yl]-3,4-dihydro-1H-spiro[1,8-naphthyridine-2,3'-pyrrolidin]-1'-yl}propan-1-one |
| 181 | 2.4 | 2 | 14 | 2 | (2R)-1-{(2S)-6-[6-(difluoromethyl)pyridin-2-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 182 | 12 | 1 | ND | ND | (2R)-2-(5-fluoro-2-methoxypyridin-4-yl)-1-{(2S)-7-methyl-6-[4-(trifluoromethyl)-1,3-thiazol-2-yl]-3,4-dihydro-1H-spiro[1,8-naphthyridine-2,3'-pyrrolidin]-1'-yl}propan-1-one |
| 183 | 4 | 1 | ND | ND | (2R)-2-(5-fluoro-2-methoxypyridin-4-yl)-1-{(2S)-7-methyl-6-[6-methyl-2-(propan-2-yl)pyrimidin-4-yl]-3,4-dihydro-1H-spiro[1,8-naphthyridine-2,3'-pyrrolidin]-1'-yl}propan-1-one |
| 184 | 6.3 | 1 | ND | ND | (2R)-1-[(2S)-6-(4,6-dimethylpyrimidin-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 185 | 5.5 | 1 | ND | ND | (2R)-1-{(2S)-6-[4-(dimethylamino)-6-(trifluoromethyl)pyrimidin-2-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 186 | 19 | 1 | ND | ND | (2R)-1-[(2S)-6-(5-cyclopropylpyridin-2-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one |
| 187 | 5.5 | 1 | ND | ND | (2R)-2-(5-fluoro-2-methoxypyridin-4-yl)-1-{(2S)-7-methyl-6-[1-methyl-5-(morpholin-4-yl)-1H-1,2,4-triazol-3-yl]-3,4-dihydro-1H-spiro[1,8-naphthyridine-2,3'-pyrrolidin]-1'-yl}propan-1-one |
| 188 | 0.41 | 2 | 0.086 | 2 | (2R)-1-{(2S)-6-[1-(difluoromethyl)-5-methyl-1H-1,2,4-triazol-3-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |

TABLE 2-continued

Biological activity and Compound name for Examples 1-201.

| Example Number | $K_i$ (nM) geometric mean | Count used ($K_i$) | $K_b$ (nM) Antagonist geometric mean | Count used ($K_b$) | Compound Name |
|---|---|---|---|---|---|
| 189 | 1.3 | 2 | 4.3 | 2 | (2R)-1-{(2S)-6-[1-cyclopropyl-5-(difluoromethyl)-1H-1,2,4-triazol-3-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 190 | 2.3 | 3 | 5.9 | 4 | 2-(2,4-difluorophenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 191 | 230 | 1 | >94 | 1 | 2-(2,4-difluorophenyl)-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 192 | 0.27 | 2 | ND | ND | 2-[2-(difluoromethoxy)-6-methoxypyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, partial formate salt, DIAST-1 |
| 193 | 28 | 1 | ND | ND | 2-[2-(difluoromethoxy)-6-methoxypyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 194 | 92 | 1 | ND | ND | 2-[2-(difluoromethoxy)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-1 |
| 195 | 1.2 | 3 | 3.5 | 3 | 2-[2-(difluoromethoxy)pyridin-4-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2 |
| 196 | 8.1 | 1 | ND | ND | (2R)-2-(5-fluoro-2-methoxypyridin-4-yl)-1-{(2S)-7-methyl-6-[2-(morpholin-4-yl)pyrimidin-4-yl]-3,4-dihydro-1H-spiro[1,8-naphthyridine-2,3'-pyrrolidin]-1'-yl}propan-1-one |
| 197 | 18 | 2 | 33 | 2 | (2R)-2-(5-fluoro-2-methoxypyridin-4-yl)-1-[(2S)-6-(6-methoxypyrazin-2-yl)-7-methyl-3,4-dihydro-1H-spiro[1,8-naphthyridine-2,3'-pyrrolidin]-1'-yl]propan-1-one, formate salt |
| 198 | 2.5 | 2 | 8.3 | 2 | (2R)-1-{(2S)-6-[6-(difluoromethoxy)pyridin-2-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 199 | 15 | 2 | >54 | 1 | (2R)-1-[(2S)-6-(6-cyclopropylpyridazin-3-yl)-7-methyl-3,4-dihydro-1H-spiro[1,8-naphthyridine-2,3'-pyrrolidin]-1'-yl]-2-(5-fluoro-2-methoxypyridin-4-yl)propan-1-one, partial formate salt |
| 200 | 0.82 | 2 | 0.59 | 2 | (2R)-1-{(2S)-6-[4-(difluoromethyl)pyrimidin-2-yl]-7-methyl-3,4-dihydro-1H-spiro[1,8-naphthyridine-2,3'-pyrrolidin]-1'-yl}-2-(5-fluoro-2-methoxypyridin-4-yl)propan-1-one |
| 201 | 110 | 1 | ND | ND | (2R)-2-(5-fluoro-2-methoxypyridin-4-yl)-1-{(2S)-7-methyl-6-[5-(trifluoromethyl)-1,3-thiazol-2-yl]-3,4-dihydro-1H-spiro[1,8-naphthyridine-2,3'-pyrrolidin]-1'-yl}propan-1-one |

$^a$ND: Not determined

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of Formula I:

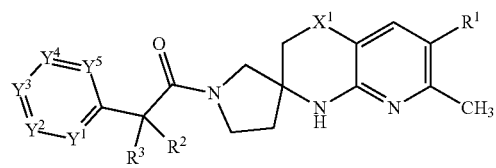

or a pharmaceutically acceptable salt thereof, wherein:
- R¹ is H, halogen, $C_{1-4}$ alkyl, $C_{1-4}$ haloalkyl, $C_{3-6}$ cycloalkyl, 4- to 7-membered heterocycloalkyl, phenyl, or $R^{1a}$, wherein each of the $C_{3-6}$ cycloalkyl and 4- to 7-membered heterocycloalkyl optionally substituted with 1, 2, 3, or 4 independently selected $C_{1-4}$ alkyl, and wherein the phenyl is optionally substituted with 1, 2, 3, or 4 independently selected $R^B$, wherein each $R^B$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or $R^{B1}$; or two adjacent $R^B$ together with the two ring-forming atoms of the phenyl to which they are attached form a fused 5- or 6-membered heteroaryl, each of which each is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;
- $R^{1a}$ is 5- or 6-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, —N($C_{1-4}$ alkyl)$_2$, $R^{A1}$, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy; or two adjacent $R^A$ together with the two ring-forming atoms of the 5- or 6-membered heteroaryl to which they are attached form a fused benzene ring or a fused 5- or 6-membered heteroaryl or a fused 5- or 6-membered heterocycloalkyl or a fused 5- or 6-membered cycloalkyl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;
- $R^{A1}$ is 5- or 6-membered heteroaryl or 5- or 6-membered heterocycloalkyl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;
- $R^{B1}$ is 5- or 6-membered heteroaryl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy;
- $X^1$ is $C(R^X)_2$, wherein each $R^X$ is independently H or $C_{1-4}$ alkyl;
- each of $R^2$ and $R^3$ is independently H, halogen, $C_{1-4}$ alkyl, $C_{1-4}$ hydroxyalkyl, $C_{1-4}$ haloalkyl, ($C_{1-4}$ alkoxy)-$C_{1-4}$ alkyl-, $C_{3-4}$ cycloalkyl, or ($C_{3-4}$ cycloalkyl)-$C_{1-4}$ alkyl, wherein each of $C_{3-4}$ cycloalkyl and ($C_{3-4}$ cycloalkyl)-$C_{1-4}$ alkyl- is optionally substituted with 1, 2, 3, 4, or 5 substituents each independently selected from halogen, —OH, $C_{1-4}$ alkyl, $C_{1-4}$ haloalkyl, $C_{1-4}$ alkoxy, and $C_{1-4}$ haloalkoxy;
- or $R^2$ and $R^3$ together with the carbon atom to which they are attached form $C_{3-6}$ cycloalkyl optionally substituted with 1, 2, 3, 4, or 5 substituents each independently selected from halogen, —OH, $C_{1-4}$ alkyl, $C_{1-4}$ haloalkyl, $C_{1-4}$ alkoxy, and $C_{1-4}$ haloalkoxy;
- each of $Y^1$, $Y^2$, $Y^3$, $Y^4$, and $Y^5$ is independently $CR^4$ or N, provided that no more than 3 of $Y^1$, $Y^2$, $Y^3$, $Y^4$, and $Y^5$ are N; and
- each $R^4$ is independently H, halogen, —OH, —CN, $C_{1-4}$ alkyl, $C_{1-4}$ haloalkyl, $C_{1-4}$ alkoxy, $C_{1-4}$ haloalkoxy, —N($C_{1-2}$ alkyl)$_2$, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

2. The compound or pharmaceutically acceptable salt of claim 1 wherein the compound is a compound of Formula Ia:

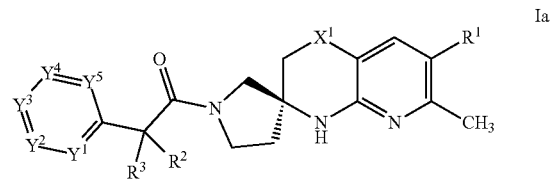

or a pharmaceutically acceptable salt thereof.

3. The compound or pharmaceutically acceptable salt of claim 1 wherein the compound is a compound of Formula II:

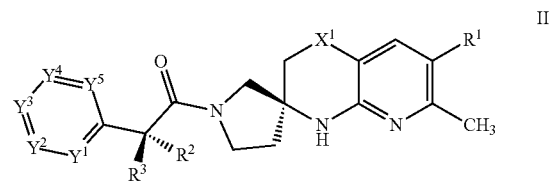

or a pharmaceutically acceptable salt thereof.

4. The compound or pharmaceutically acceptable salt of claim 1 wherein the compound is a compound of Formula III:

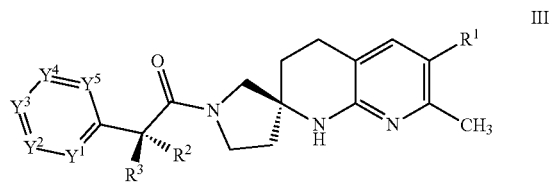

or a pharmaceutically acceptable salt thereof.

5. The compound or pharmaceutically acceptable salt of claim 1 wherein:
- R¹ is $R^{1a}$; and
- $R^{1a}$ is 6-membered heteroaryl optionally substituted with 1, 2, 3, or 4 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, $C_{3-4}$ cycloalkyl, or ($C_{3-4}$ cycloalkyl)-$C_{1-4}$ alkyl-, wherein each of the $C_{1-4}$ alkyl, $C_{3-4}$ cycloalkyl, and ($C_{3-4}$ cycloalkyl)-$C_{1-4}$ alkyl- is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy; or two adjacent $R^A$ together with the two ring-atoms of the 6-membered heteroaryl to which they are attached form a fused benzene ring or a fused 5- or 6-membered heteroaryl, each of which is optionally substituted with 1, 2, or 3 substituents each independently selected from halogen, —OH, —CN, $C_{1-4}$ alkyl, $C_{1-4}$ haloalkyl, $C_{1-4}$ alkoxy, and $C_{1-4}$ haloalkoxy.

6. The compound or pharmaceutically acceptable salt of claim 5 wherein $R^{1a}$ is pyrimidinyl optionally substituted with 1, 2, or 3 independently selected $R^A$, wherein each $R^A$ is halogen, —OH, —CN, $C_{1-4}$ alkyl, $C_{1-4}$ haloalkyl, $C_{1-4}$ alkoxy, $C_{1-4}$ haloalkoxy, or $C_{3-4}$ cycloalkyl.

7. The compound or pharmaceutically acceptable salt of claim 6 wherein $R^{1a}$ is pyrimidin-2-yl.

8. The compound or pharmaceutically acceptable salt of claim 1 wherein $X^1$ is $CH_2$.

9. The compound or pharmaceutically acceptable salt of claim 1 wherein each of $R^2$ and $R^3$ is independently H, F, or $C_{1-4}$ alkyl.

10. The compound or pharmaceutically acceptable salt of claim 9 wherein $R^2$ is methyl and $R^3$ is H.

11. The compound or pharmaceutically acceptable salt of claim 1 wherein $Y^3$ is N, and each of $Y^1$, $Y^2$, $Y^4$, and $Y^5$ is independently $CR^4$.

12. The compound or pharmaceutically acceptable salt of claim 1 wherein each $R^4$ is independently H, halogen, or $C_{1-2}$ alkoxy.

13. A compound selected from:
    (2R)-2-(5-chloro-2-methoxypyridin-4-yl)-1-[7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1;
    2-(6-methoxy-2-methylpyrimidin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one, DIAST-1;
    2-[6-(difluoromethoxy)pyridin-3-yl]-1-[(2S)-7-methyl-6-(pyrimidin-2-yl)-3,4-dihydro-1H-spiro[1,8-naphthyridine-2,3'-pyrrolidin]-1'-yl]propan-1-one, DIAST-2;
    1-[(2S)-7-methyl-6-(pyrimidin-2-yl)-3,4-dihydro-1H-spiro[1,8-naphthyridine-2,3'-pyrrolidin]-1'-yl]-2-[4-(trifluoromethyl)phenyl]propan-1-one, DIAST-1;
    1-(4,7-dimethyl-3,4-dihydro-1H-spiro[1,8-naphthyridine-2,3'-pyrrolidin]-1'-yl)-2-(4-fluorophenyl)ethan-1-one, DIAST-1;
    (2R)-2-(5-fluoro-2-methoxypyridin-4-yl)-1-[(2S)-7-methyl-6-(2-methyl-2H-tetrazol-5-yl)-3,4-dihydro-1H-spiro[1,8-naphthyridine-2,3'-pyrrolidin]-1'-yl]propan-1-one;
    (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one;
    (2R)-2-(5-chloro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one;
    (2R)-2-(5-fluoro-2-methoxypyridin-4-yl)-1-[7-methyl-6-(1-methyl-1H-pyrazol-4-yl)-3,4-dihydro-1H-spiro[1,8-naphthyridine-2,3'-pyrrolidin]-1'-yl]propan-1-one, DIAST-1; and
    (2R)-2-(5-fluoro-2-methoxypyridin-4-yl)-1-{(2S)-7-methyl-6-[(4,6-$^2H_2$)pyrimidin-2-yl]-3,4-dihydro-1H-spiro[1,8-naphthyridine-2,3'-pyrrolidin]-1'-yl}propan-1-one,
or pharmaceutically acceptable salt thereof.

14. A compound that is (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one, or pharmaceutically acceptable salt thereof.

15. A compound that is (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one.

16. A compound of claim 1 that is a crystalline form of (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one.

17. The compound of claim 14 that is the pharmaceutically acceptable salt of (2R)-2-(5-fluoro-2-methoxypyridin-4-yl)-1-[(2S)-7-methyl-6-(pyrimidin-2-yl)-3,4-dihydro-1H-spiro[1,8-naphthyridine-2,3'-pyrrolidin]-1'-yl]propan-1-one.

18. A pharmaceutical composition comprising (a) the compound of claim 17; and (b) a pharmaceutically acceptable carrier.

19. A pharmaceutical composition comprising (a) the compound of claim 14; and (b) a pharmaceutically acceptable carrier.

20. A pharmaceutical composition comprising (a) the compound of claim 15; and (b) a pharmaceutically acceptable carrier.

* * * * *